US009758527B2

(12) United States Patent
Yang et al.

(10) Patent No.: US 9,758,527 B2
(45) Date of Patent: Sep. 12, 2017

(54) CYCLOHEXENE DERIVATIVE, PREPARATION METHOD THEREFOR, AND PHARMACEUTICAL COMPOSITION FOR PREVENTING OR TREATING METABOLIC DISEASES, CONTAINING SAME AS ACTIVE INGREDIENT

(71) Applicant: HYUNDAI PHARM CO., LTD., Chungcheongnam-do (KR)

(72) Inventors: Jin Yang, Yongin-si (KR); Jinwoong Kim, Gyeonggi-do (KR); Han Kyu Lee, Hwaseong-si (KR); Jae Hyun Kim, Yongin-si (KR); Chang Mo Son, Suwon-si (KR); Kyu Hwan Lee, Ansan-si (KR); Jeongun Hwang, Gyeonggi-do (KR); Hyung-Ho Choi, Suwon-si (KR); Daehoon Kim, Seoul (KR); Jaekeol Rhee, Hwaseong-si (KR)

(73) Assignee: HYUNDAI PHARM CO., LTD. (KR)

( * ) Notice: Subject to any disclaimer, the term of this patent is extended or adjusted under 35 U.S.C. 154(b) by 0 days.

(21) Appl. No.: 15/307,719

(22) PCT Filed: May 1, 2015

(86) PCT No.: PCT/KR2015/004449
§ 371 (c)(1),
(2) Date: Oct. 28, 2016

(87) PCT Pub. No.: WO2015/167309
PCT Pub. Date: Nov. 5, 2015

(65) Prior Publication Data
US 2017/0114072 A1    Apr. 27, 2017

(30) Foreign Application Priority Data

May 2, 2014 (KR) ........................ 10-2014-0053535
Apr. 30, 2015 (KR) ........................ 10-2015-0062119

(51) Int. Cl.
| | | |
|---|---|---|
| C07D 491/113 | (2006.01) |
| C07D 211/22 | (2006.01) |
| C07D 401/04 | (2006.01) |
| C07D 401/12 | (2006.01) |
| C07D 401/14 | (2006.01) |
| C07D 405/14 | (2006.01) |
| C07D 413/04 | (2006.01) |
| C07D 413/14 | (2006.01) |
| C07D 487/10 | (2006.01) |

(52) U.S. Cl.
CPC ........ *C07D 491/113* (2013.01); *C07D 211/22* (2013.01); *C07D 401/04* (2013.01); *C07D 401/12* (2013.01); *C07D 401/14* (2013.01); *C07D 405/14* (2013.01); *C07D 413/04* (2013.01); *C07D 413/14* (2013.01); *C07D 487/10* (2013.01)

(58) Field of Classification Search
CPC C07D 491/113; C07D 211/22; C07D 401/04; C07D 401/12; C07D 401/14; C07D 405/14; C07D 413/04; C07D 413/14; C07D 487/10
See application file for complete search history.

(56) References Cited

FOREIGN PATENT DOCUMENTS

| | | |
|---|---|---|
| WO | WO 91/03243 A1 | 3/1991 |
| WO | WO 2004/065380 A1 | 8/2004 |
| WO | WO 2005/007647 A1 | 1/2005 |
| WO | WO 2005/007658 A2 | 1/2005 |
| WO | WO 2008/025798 A1 | 3/2008 |
| WO | WO 2008/070692 A2 | 6/2008 |
| WO | WO 2008/083238 A | 7/2008 |
| WO | WO 2009/106565 A1 | 9/2009 |
| WO | WO 2013/187646 A1 | 12/2013 |

OTHER PUBLICATIONS

Search Report for International Application No. PCT/KR2015/004449 (mailed Aug. 21, 2015).
Written Opinion for International Application No. PCT/KR2015/004449 (mailed Aug. 21, 2015).
Overton et al., "Deorphanization of a G protein-coupled receptor for oleoylethanolamide and its use in the discovery of small molecule hypophagic agents," *Cell Metabolism*, 3(3):167-175 (Mar. 2006).
Soga et al., "Lysophosphatidylcholine enhances glucose-dependent insulin secretion via an orphan G-protein-coupled receptor," *Biochem Biophys Res Commun*, 326(4):744-751 (Jan. 2005).

*Primary Examiner* — Kahsay Habte
(74) *Attorney, Agent, or Firm* — Merchant & Gould P.C.

(57) ABSTRACT

The present invention relates to: a cyclohexene derivative; a preparation method therefor; and a pharmaceutical composition for preventing or treating metabolic diseases, containing the same as an active ingredient. The cyclohexene derivative according to the present invention increases the intracellular activity of cyclic adenosine monophosphate (cAMP) by activating G protein-coupled receptor 119 (GPR-119) and simultaneously exhibits weight loss and hypoglycemic effects by inducing the release of glucagon-like peptide-1 (GLP-1), which is a neuroendocrine protein, and thus can be useful as a pharmaceutical composition for preventing or treating metabolic diseases such as obesity, type 1 diabetes, type 2 diabetes, inadequate glucose tolerance, insulin resistance, hyperglycemia, hyperlipidemia, hypertriglyceridemia, hypercholesterolemia, dyslipidemia and syndrome X.

8 Claims, 2 Drawing Sheets

[Figure 1]
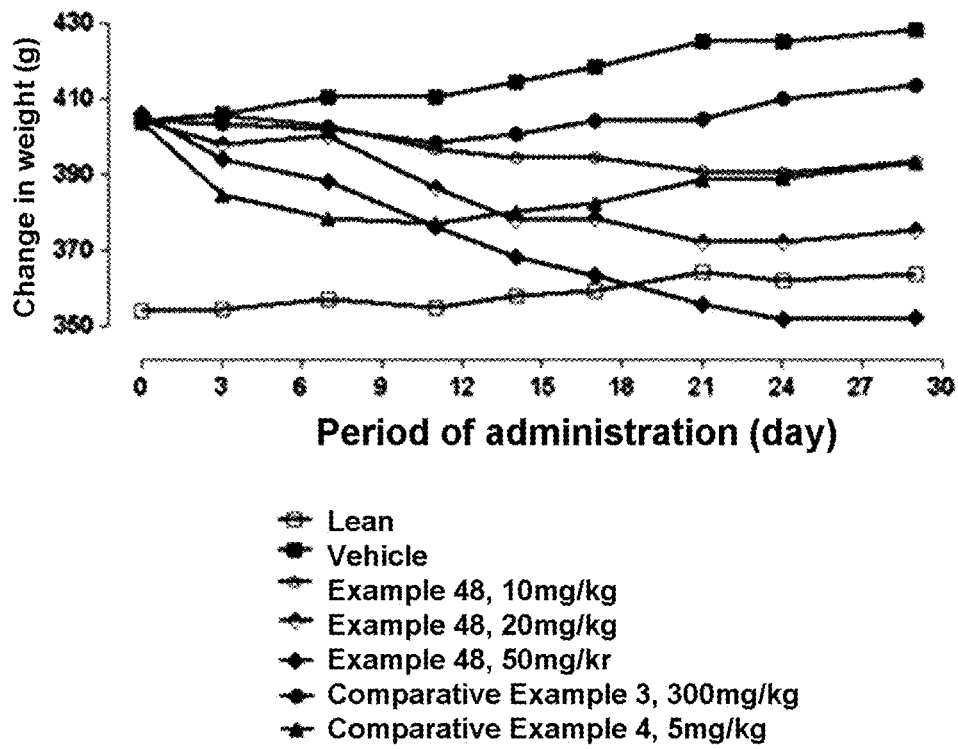
[Figure 2a]
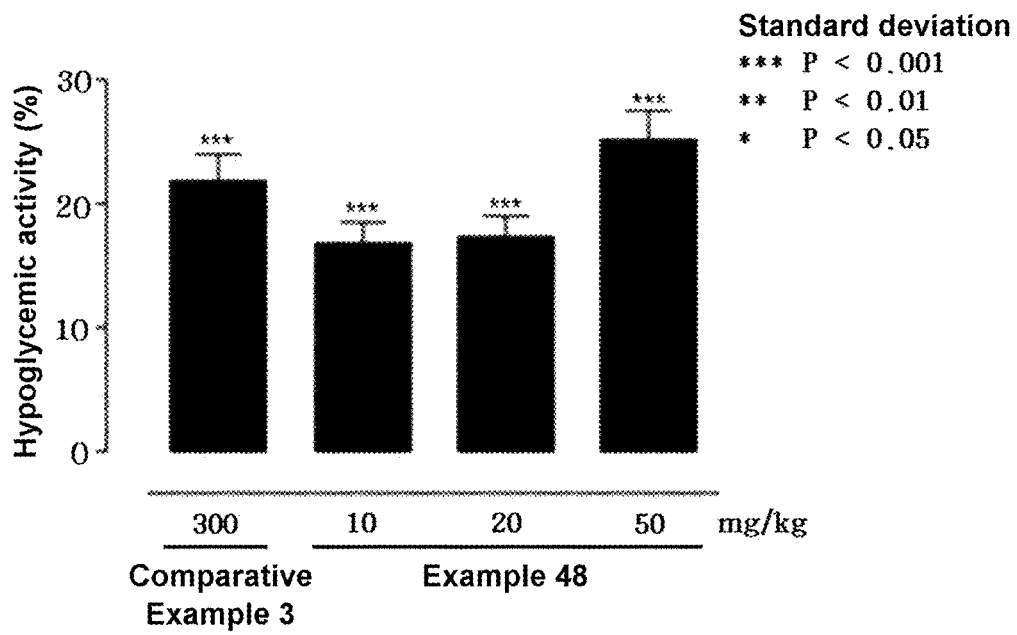

[Figure 2b]
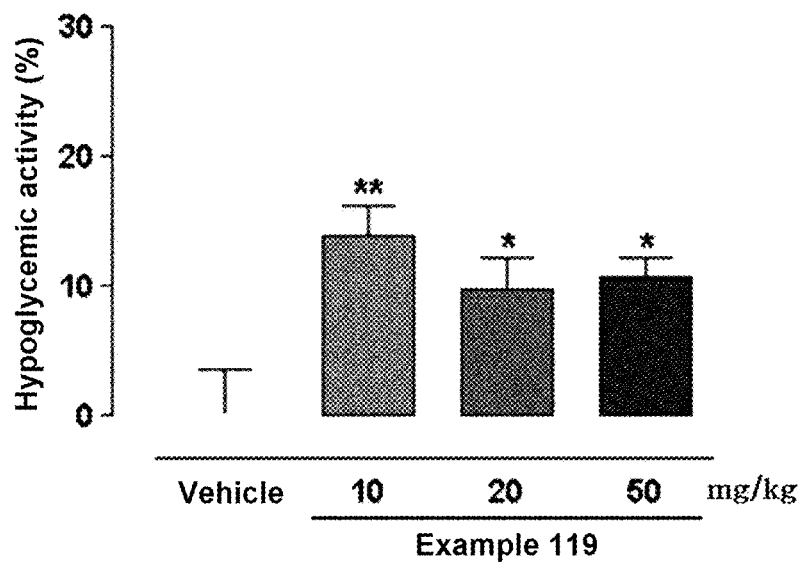
[Figure 3]
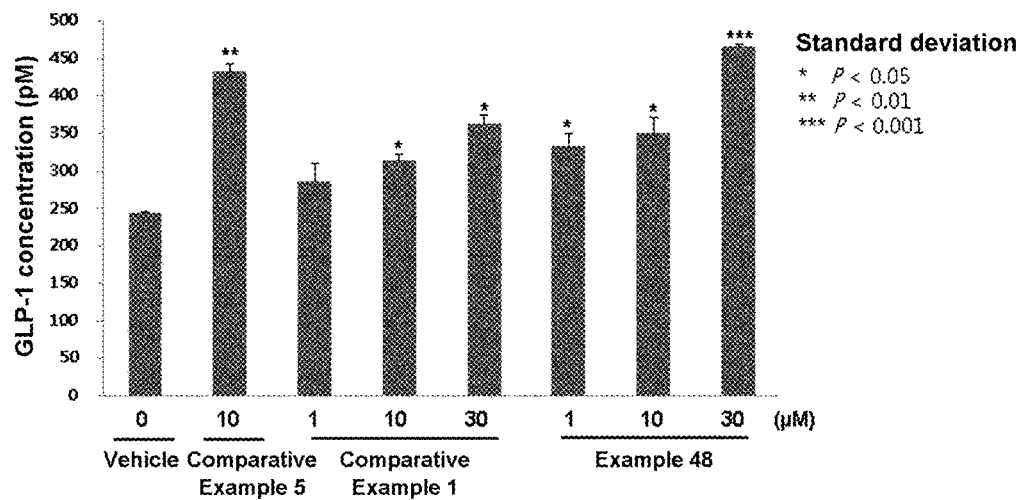

CYCLOHEXENE DERIVATIVE, PREPARATION METHOD THEREFOR, AND PHARMACEUTICAL COMPOSITION FOR PREVENTING OR TREATING METABOLIC DISEASES, CONTAINING SAME AS ACTIVE INGREDIENT

This application is a U.S. National Stage Application under 35 U.S.C. §371 of International Patent Application No. PCT/KR2015/004449 filed 1 May 2015, which claims the benefit of priority to Korean Patent Application No. 10-2015-0062119 filed 30 Apr. 2015 and Korean Patent Application No. 10-2014-0053535 filed 2 May 2014, the disclosures of all of which are hereby incorporated by reference in their entireties. The International Application was published in Korean on 5 Nov. 2015 as WO 2015/167309.

TECHNICAL FIELD

The present invention relates to a cyclohexene derivative, or an optical isomer or pharmaceutically acceptable salt thereof, a preparation method thereof, and a pharmaceutical composition for preventing or treating metabolic disease comprising the same as an active ingredient.

BACKGROUND ART

Metabolic diseases are disorders that are caused due to the abnormal metabolisms in separate organs from the human body, and thus include generic types of diseases caused by impaired metabolisms resulting from the in vivo imbalance of saccharides, lipids, proteins, vitamins, minerals, moisture, etc. In particular, metabolic diseases caused due to the weakening of immunity and the lack of nutrition supply account for over 99% of the adult diseases. Most adult diseases are caused by the nutritional imbalance caused by inadequate food intake, the lack of exercise, etc.

Representative examples of the metabolic diseases include obesity, type 1 diabetes, type 2 diabetes, inadequate glucose tolerance, insulin resistance, hyperglycemia, hyperlipidemia, hypertriglyceridemia, hypercholesterolemia, dyslipidemia, syndrome X, etc. When the metabolic diseases cause fat accumulation in the body, insulin resistance occurs in which insulin that is a hormone which moves glucose from the blood into the liver and muscles is not normally produced or its functions decline, thereby causing an increase in blood glucose level and arteriosclerosis, which leads to the onset of the adult diseases.

As a representative example of the metabolic diseases, diabetes mellitus is a serious metabolic disease from which over one hundred million people suffer all over the world. There are over 12,000,000 diabetic patients in the U.S. and approximately 600,000 new patients have been diagnosed with the diabetes mellitus each year. All people who do not have the same cause of diabetes but have suffered from the diabetes mellitus commonly produce an excessive amount of glucose in the liver, and have no activity to move glucose into cells in which the glucose is used as a main fuel for the body. People who do not suffer from diabetes mellitus depend on insulin hormones produced in the pancreas so that the glucose moves from the blood into cells of the body. However, people suffering from the diabetes neither produce insulin nor efficiently use the insulin produced thereby, and thus cannot move the glucose into their cells. Therefore, residual glucose that does not move into the cells may accumulate in blood, causing a disease referred to as hyperglycemia and leading to serious health problems over time.

Also, diabetes mellitus is a metabolic or vascular syndrome, or a syndrome associated with neuropathic factors. In general, the metabolic syndrome characterized by hyperglycemia include changes in carbohydrate, fat and protein metabolisms caused since insulin secretion is lacking or significantly decreased, or insulin exists but has no effects. The vascular syndrome results from abnormal blood vessels which cause cardiovascular, retinal and renal complications. Dysfunction in the peripheral and autonomic nervous systems is also a part of the diabetic syndrome. In addition, diabetes has been reported to be associated with the onset of renal disease, ocular disease and neurologic problems. The renal disease (nephropathy) develops when a "filtration mechanism" in the kidney is damaged, and an excessive amount of proteins leak into the urine, resulting in impaired kidney function. Also, diabetes mellitus is a provoking cause of inducing damage to the posterior retina of an eye, and increases the risk of developing cataract and glaucoma.

More specifically, the diabetes mellitus may be classified into two clinical syndromes; type 1 and 2 diabetes mellitus. Type 1 diabetes mellitus known as insulin-dependent diabetes mellitus (IDDM) is caused by autoimmune destruction of pancreatic β-cells producing insulin, and requires regular administration of exogenous insulin. Type 2 diabetes mellitus known as non-insulin-dependent diabetes mellitus (NIDDM) appears to develop due to its loss of an ability to properly regulate a blood glucose level. The type 2 diabetes mellitus is characterized by a disorder developed in people suffering from the type 2 diabetes mellitus who are deficient in insulin secretion or exhibit insulin resistance, that is, hardly have insulin or cannot effectively take use of insulin.

In the prior art, the current therapy against diabetes mellitus encompasses insulin, insulin secretagogues, glucose-lowering effectors, peroxisome proliferator-activated receptor (PPAR) activators, etc. However, there are problems associated with currently available therapies, including hypoglycaemia, weight gain, a decreased responsiveness to treatment over time, gastrointestinal dysfunction, and edema.

Accordingly, research has been conducted in various fields to introduce a more effective new therapy into the market. One specific target is G protein-coupled receptor 119 (GPR-119).

GPR-119 is one of G-protein-coupled receptors (GPCRs) that are mainly expressed in pancreatic, small intestinal, rectal and adipose tissues. When a ligand or agonist binds to the receptor, the receptor is structurally changed, and coupled to G-protein to catalyze reactions of secondary messengers in cells or organs.

GPR-119 receptors and isoforms thereof are found in mammalian species including humans, rats, mice, hamsters, chimpanzees, rhesus monkeys, cattle, and dogs. In particular, it is known that the expression of GPR-119 in pancreatic β-cells indicates that the GPR-119 receptors exert an effect on the insulin secretion. The activation of GPR-119 stimulates a cyclic adenosine monophosphate (cAMP) single pathway in which the intracellular activity of cAMP as a secondary messenger is enhanced in these cells. The stimulation of cAMP is involved in a variety of cellular reactions, such as expression of enzymes or genes, etc., and the stimulation of cAMP in the β-cells is induced through the activation of GPR-119. Also, gastric inhibitory polypeptides (GIPs), glucagon-like peptide-1 (GLP-1), peptide YY (PYY), and the like cause an insulin secretion action through the G-protein-coupled receptor in the β-cells. Incretins such as the GIP and GLP-1 are gut hormones that strongly stimulate the insulin secretion in a blood glucose level-dependent manner after meals.

GPR-119 activators are effective in improvements in β-cell functions and β-cell groups. The activation of GPR-119 stimulates the insulin secretion in vitro and in vivo (rodents) in a glucose-dependent manner. The finding of potent GPR-119 activators may reduce a level of plasma glucose to promote blood glucose control without the risk of developing hypoglycemia.

In recent years, it was shown that the GPR-119 activators efficiently reduce a blood glucose level in diabetic rodents without the risk of developing hypoglycemia. It was confirmed that the secretion of both insulin and incretin induced by the GPR-119 activators is dependent on the GPR-119 receptors in GPR-119-knockout animals. Also, it was shown that the GPR-119 activators induce weight loss in Sprague Dawley rats by reducing the food intake.

Non-patent document 1 discloses that the activation of GPR-119 induce cAMP to induce secretion of glucose-dependent glucagon-like peptide-1 (GLP-1) and insulin (T. Soga et al., Biochem. Biophy. Res. Commu. 326, (2005), 744-751). It was found that GLP-1 mediates its action through GLP-1R that is a certain G protein-coupled receptor (GPCR), regulates glucose homeostasis, stimulates glucose-dependent insulin secretion, and increases a mass of pancreatic β-cells. Also, it was found that GLP-1 slows down a gastric emptying rate and improves satiety.

However, the existing GLP-1 peptide activators have a negative effect on effectiveness due to deficiency in bioavailability when administered orally. Therefore, there is a demand for development of GPR-119 activators that exhibit excellent oral bioavailability and induce the secretion of GLP-1 into the blood as well.

As one example of the research results, it was proven that the GPR-119 activators disclosed in Patent Documents 1-2 and Non-patent Document 2 cause an acute decline in food intake after chronic administration, resulting in reduced body weight in rats. Also, Patent Document 3 discloses the therapeutic agents for treating metabolic diseases using trisubstituted pyrimidine derivatives with the growing interest in trisubstituted heteroaryl derivatives. Further, Patent Document 4 discloses the therapeutic agents for treating diabetes mellitus using aryl, heteroaryl or heterocyclyl derivatives, characterized in that the therapeutic agents activate IC-GPCR2 or GPR-119 as therapeutic agents for type 1 diabetes mellitus associated with insulin resistance. However, there are no known compounds having a cyclohexene backbone and use thereof for treating metabolic diseases.

Accordingly, the present inventors have conducted research on activators of GPR-119, and found that a cyclohexene derivative according to the present invention, or an optical isomer or pharmaceutically acceptable salt thereof activates G protein-coupled receptor 119 (GPR-119) to enhance the intracellular activity of cyclic adenosine monophosphate (cAMP), and induces the release of glucagon-like peptide-1 (GLP-1), which is a neuroendocrine protein, to simultaneously exhibit weight-loss and hypoglycemic effects, and thus is useful for pharmaceutical compositions for preventing or treating metabolic diseases such as obesity, type 1 diabetes, type 2 diabetes, inadequate glucose tolerance, insulin resistance, hyperglycemia, hyperlipidemia, hypertriglyceridemia, hypercholesterolemia, dyslipidemia and syndrome X. Therefore, the present invention has been completed based on these facts.

PRIOR ART DOCUMENT

Patent Document

1. WO 2005/007647
2. WO 2005/007658
3. WO 2004/065380
4. WO 2008/083238

Non-Patent Document

1. T. Soga et al., Biochem. Biophy. Res. Commu. 326, (2005), 744-751
2. Overton, H. A. et al., Cell metabolism, 3, (2006), 167-175

DISCLOSURE

Technical Problem

An aspect of the present invention may provide a cyclohexene derivative, or an optical isomer or pharmaceutically acceptable salt thereof.

Another aspect of the present invention may provide a method for preparing the cyclohexene derivative.

Still another aspect of the present invention may provide a pharmaceutical composition for preventing or treating metabolic diseases, which includes the cyclohexene derivative as an active ingredient.

Yet another aspect of the present invention may provide a G protein-coupled receptor 119 (GPR-119) activator including the cyclohexene derivative as an active ingredient.

Yet another aspect of the present invention may provide a health functional food for preventing or improving metabolic diseases, which includes the cyclohexene derivative as an active ingredient.

Technical Solution

To solve the above problems, the present invention provides a compound represented by the following Formula 1, or an optical isomer or pharmaceutically acceptable salt thereof.

[Formula 1]

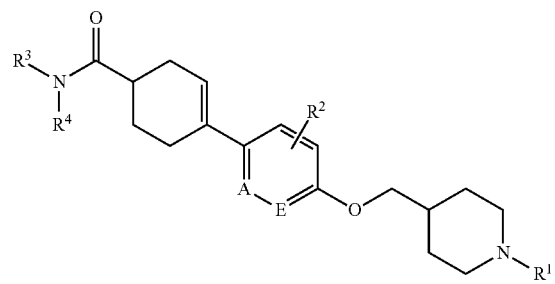

In Formula 1, $R^1$ is —H, —OH, a $C_{1-10}$ linear or branched alkyl, a $C_{1-10}$ linear or branched alkoxy, a $C_{1-10}$ linear or branched alkoxycarbonyl, or an unsubstituted or substituted 5- to 10-membered heteroaryl containing one or more heteroatoms selected from the group consisting of N, O, and S, wherein:

the substituted 5- to 10-membered heteroaryl is a 5- to 10-membered heteroaryl substituted with one or more $C_{1-10}$ linear or branched alkyl;

$R^2$ is —H, —OH, a halogen, a $C_{1-10}$ linear or branched alkyl, or a $C_{1-10}$ linear or branched alkoxy;

$R^3$ is —H, a $C_{1-10}$ linear or branched alkyl which is not substituted or substituted with one or more —OH or a halogen, a $C_{1-10}$ linear or branched alkoxy, a $C_{1-10}$ linear or branched alkoxy $C_{1-10}$ linear or branched alkyl, an unsubstituted $C_{3-10}$ cycloalkyl, an unsubstituted 5- to 10-membered heteroaryl $C_{1-10}$ linear or branched alkyl containing one or more heteroatoms selected from the group consisting of N, O, and S, —$(CH_2)_nNR^5R^6$, —$(CH_2)_mC(=O)OR^7$, or —$(CH_2)_pC(=O)NR^8R^9$, wherein:

$R^5$ and $R^6$ are each independently —H, -Boc

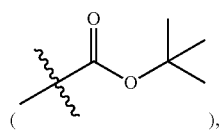, or a $C_{1-5}$ linear or branched alkyl, $R^7$ is —H, or a $C_{1-5}$ linear or branched alkyl, and $R^8$ and $R^9$ may be taken together with a nitrogen atom to which they are attached to form an unsubstituted or substituted 5- to 10-membered heterocycloalkyl containing one or more heteroatoms selected from the group consisting of N, O, and S, wherein:

the substituted 5- to 10-membered heterocycloalkyl is a 5- to 10-membered heterocycloalkyl substituted with one or more substituents selected from the group consisting of —CN, a $C_{1-5}$ linear or branched alkyl, a $C_{1-5}$ linear or branched alkoxy, and —$C(=O)NR^{10}R^{11}$, wherein $R^{10}$ and $R^{11}$ are each independently —H, or a $C_{1-5}$ linear or branched alkyl;

n, m, and p are each independently an integer ranging from 1 to 10;

$R^4$ is —H, a $C_{1-10}$ linear or branched alkyl which is not substituted or substituted with one or more —OH, or a $C_{1-10}$ linear or branched alkoxy;

provided that $R^3$ and $R^4$ may be taken together with a nitrogen atom to which they are attached to form an unsubstituted 3- to 10-membered heterocycloakenyl containing one or more heteroatoms selected from the group consisting of N, O, and S, or an unsubstituted, substituted or fused 3- to 10-membered heterocycloalkyl containing one or more heteroatoms selected from the group consisting of N, O, and S, wherein:

the substituted 3- to 10-membered heterocycloalkyl is a 3- to 10-membered heterocycloalkyl substituted with one or more substituents selected from the group consisting of —OH, —CN, =O, a halogen, a $C_{1-5}$ linear or branched alkyl which is not substituted or substituted with one or more —OH, a $C_{1-5}$ linear or branched alkoxy, an unsubstituted $C_{3-10}$ cycloalkyl $C_{1-5}$ linear or branched alkyl, an unsubstituted $C_{3-10}$ cycloalkyl, an unsubstituted 3- to 10-membered heterocycloalkyl containing one or more heteroatoms selected from the group consisting of N, O, and S, —$C(=O)NR^{12}R^{13}$, —$NR^{14}R^{15}$, and =$NR^{16}$; or substituted in a spiro fashion with a $C_{5-10}$ cycloakenyl fused with an unsubstituted $C_{6-10}$ aryl, or a 3- to 10-membered heterocycloalkyl which is not substituted or substituted with one or more -Boc

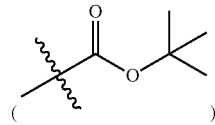

and contains one or more heteroatoms selected from the group consisting of N, O, and S, $R^{12}$, $R^{13}$, $R^{14}$, and $R^{15}$ are each independently —H, or a $C_{1-5}$ linear or branched alkyl, and $R^{16}$ is —H, —OH, or a $C_{1-5}$ linear or branched alkoxy, provided that the fused 3- to 10-membered heterocycloalkyl is a 3- to 10-membered heterocycloalkyl fused with an unsubstituted $C_{6-10}$ aryl, and the substitution and fusion may occur at the same time in the case of the unsubstituted, substituted or fused 3- to 10-membered heterocycloalkyl; and A and E are each independently —CH=, or —N=.

Also, as shown in the following Scheme 1, the present invention provides a method for preparing the compound represented by Formula 1, which includes:

reacting a compound represented by Formula 2 with a compound represented by Formula 3 to prepare a compound represented by Formula 4 (Step 1);

reacting the compound represented by Formula 4 prepared in Step 1 with a compound represented by Formula 5 to prepare a compound represented by Formula 6 (Step 2);

reacting the compound represented by Formula 6 prepared in Step 2 with a base to prepare a compound represented by Formula 7 (Step 3); and reacting the compound represented by Formula 7 prepared in Step 3 with a compound represented by Formula 8 to obtain the compound represented by Formula 1 (Step 4).

[Scheme 1]

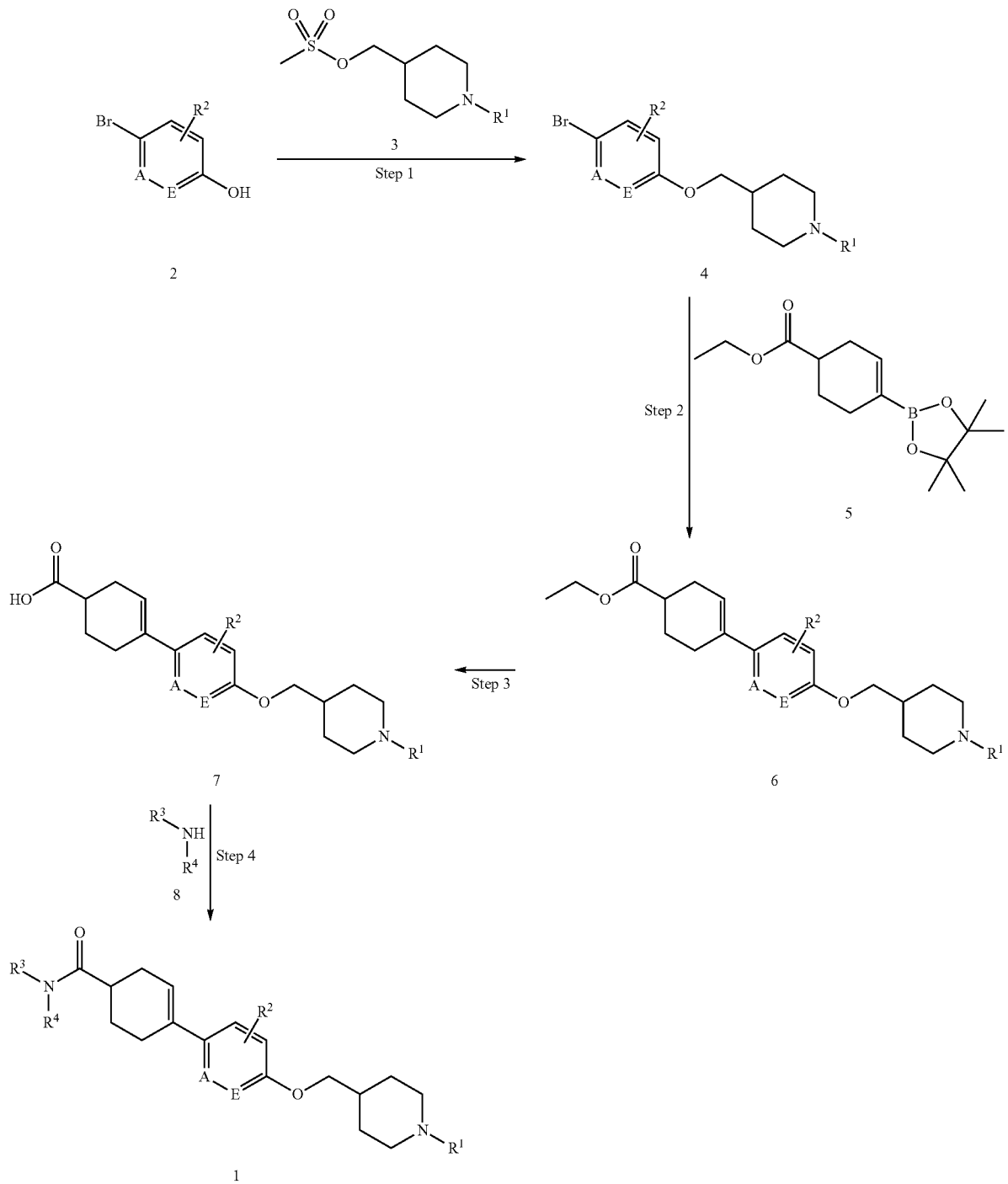

In Scheme 1, $R^1$, $R^2$, $R^3$, $R^4$, A, and E are as defined in Formula 1.

In addition, the present invention provides a pharmaceutical composition for preventing or treating metabolic diseases, which includes the compound represented by Formula 1, or an optical isomer or pharmaceutically acceptable salt thereof as an active ingredient.

Also, the present invention provides a G protein-coupled receptor 119 (GPR-119) activator including the compound represented by Formula 1, or the optical isomer or pharmaceutically acceptable salt thereof as an active ingredient.

Further, the present invention provides a health functional food for preventing or improving metabolic diseases, which includes the compound represented by Formula 1, or the optical isomer or pharmaceutically acceptable salt thereof as an active ingredient.

Advantageous Effects

The cyclohexene derivative according to the present invention, or the optical isomer or pharmaceutically acceptable salt thereof activates G protein-coupled receptor 119 (GPR-119) to enhance the intracellular activity of cyclic adenosine monophosphate (cAMP), and simultaneously induces the release of glucagon-like peptide-1 (GLP-1), which is a neuroendocrine protein, to simultaneously exhibit weight-loss and hypoglycemic effects, and thus can be useful for pharmaceutical compositions for preventing or treating metabolic diseases such as obesity, type 1 diabetes, type 2 diabetes, inadequate glucose tolerance, insulin resistance, hyperglycemia, hyperlipidemia, hypertriglyceridemia, hypercholesterolemia, dyslipidemia, syndrome X, etc.

DESCRIPTION OF DRAWINGS

FIG. 1 is a graph determining the changes in weights of rats after compounds of Example 48 and Comparative Examples 3 and 4 according to the present invention are administered to a diet-induced obesity (DIO) rat model for 4 weeks (In FIG. 1, the term "untreated group (Vehicle)" represents an untreated group in a high-fat DIO rat model; and the term "Lean" represents an untreated group in a normal SD rat model rather than a disease model).

FIG. 2A is a graph for evaluating hypoglycemic effects over time when glucose is administered at the end of the 4-week period of administration of the compounds of Example 48 and Comparative Example 3 according to the present invention in the DIO rat model, and after 30 minutes of administration of the compounds of Example 48 and Comparative Example 3.

FIG. 2B is a graph for evaluating hypoglycemic effects over time when glucose is administered at the end of the 4-week period of administration of the compound of Example 119 according to the present invention in the DIO rat model, and after 30 minutes of administration of the compound of Example 119.

FIG. 3 is graphs plotted for amounts of secreted glucagon-like peptide-1 (GLP-1) when NCI-H716 cells that are human enterocytes are treated with the compounds of Comparative Examples 1 and 5 and Example 48 according to the present invention.

BEST MODE

Hereinafter, the present invention will be described in detail.

The present invention provides a compound represented by the following Formula 1, or an optical isomer or pharmaceutically acceptable salt thereof.

[Formula 1]

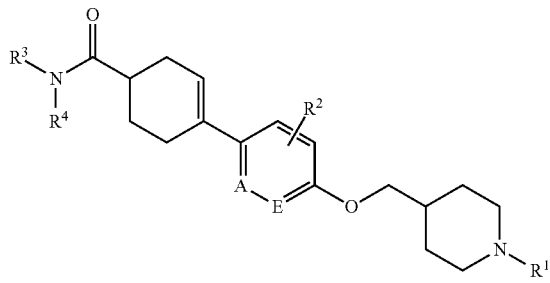

In Formula 1, $R^1$ is —H, —OH, a $C_{1-10}$ linear or branched alkyl, a $C_{1-10}$ linear or branched alkoxy, a $C_{1-10}$ linear or branched alkoxycarbonyl, or an unsubstituted or substituted 5- to 10-membered heteroaryl containing one or more heteroatoms selected from the group consisting of N, O, and S, wherein:

the substituted 5- to 10-membered heteroaryl is a 5- to 10-membered heteroaryl substituted with one or more $C_{1-10}$ linear or branched alkyl;

$R^2$ is —H, —OH, a halogen, a $C_{1-10}$ linear or branched alkyl, or a $C_{1-10}$ linear or branched alkoxy;

$R^3$ is —H, a $C_{1-10}$ linear or branched alkyl which is not substituted or substituted with one or more —OH or a halogen, a $C_{1-10}$ linear or branched alkoxy, a $C_{1-10}$ linear or branched alkoxy $C_{1-10}$ linear or branched alkyl, an unsubstituted $C_{3-10}$ cycloalkyl, an unsubstituted 5- to 10-membered heteroaryl $C_{1-10}$ linear or branched alkyl containing one or more heteroatoms selected from the group consisting of N, O, and S, —$(CH_2)_n NR^5 R^6$, —$(CH_2)_m C(=O)OR^7$, or —$(CH_2)_p C(=O)NR^8 R^9$, wherein:

$R^5$ and $R^6$ are each independently —H, -Boc

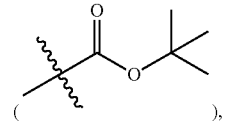

or a $C_{1-5}$ linear or branched alkyl, $R^7$ is —H, or a $C_{1-5}$ linear or branched alkyl, and $R^8$ and $R^9$ may be taken together with a nitrogen atom to which they are attached to form an unsubstituted or substituted 5- to 10-membered heterocycloalkyl containing one or more heteroatoms selected from the group consisting of N, O, and S, wherein:

the substituted 5- to 10-membered heterocycloalkyl is a 5- to 10-membered heterocycloalkyl substituted with one or more substituents selected from the group consisting of —CN, a $C_{1-5}$ linear or branched alkyl, a $C_{1-5}$ linear or branched alkoxy, and —$C(=O)NR^{10}R^{11}$, and $R^{10}$ and $R^{11}$ are each independently —H, or a $C_{1-5}$ linear or branched alkyl, n, m, and p are each independently an integer ranging from 1 to 10;

$R^4$ is —H, a $C_{1-10}$ linear or branched alkyl which is not substituted or substituted with one or more —OH, or a $C_{1-10}$ linear or branched alkoxy;

provided that $R^3$ and $R^4$ may be taken together with a nitrogen atom to which they are attached to form an unsubstituted 3- to 10-membered heterocycloakenyl containing one or more heteroatoms selected from the group consisting of N, O, and S, or an unsubstituted, substituted or fused 3- to 10-membered heterocycloalkyl containing one or more heteroatoms selected from the group consisting of N, O, and S, wherein:

the substituted 3- to 10-membered heterocycloalkyl is a 3- to 10-membered heterocycloalkyl substituted with one or more substituents selected from the group consisting of —OH, —CN, =O, a halogen, a $C_{1-5}$ linear or branched alkyl which is not substituted or substituted with one or more —OH, a $C_{1-5}$ linear or branched alkoxy, an unsubstituted $C_{3-10}$ cycloalkyl $C_{1-5}$ linear or branched alkyl, an unsubstituted $C_{3-10}$ cycloalkyl, an unsubstituted 3- to 10-membered heterocycloalkyl containing one or more heteroatoms selected from the group consisting of N, O, and S, —$C(=O)$ NR$^{12}$R$^{13}$, —NR$^{14}$R$^{15}$, and =NR$^{16}$; or substituted in a spiro fashion with a C$_{5-10}$ cycloakenyl fused with an unsubstituted C$_{6-10}$ aryl, or a 3- to 10-membered heterocycloalkyl which is not substituted or substituted with one or more -Boc

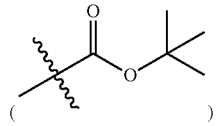 [SMILES: *C(=O)OC(C)(C)C]

and contains one or more heteroatoms selected from the group consisting of N, O, and S, R$^{12}$, R$^{13}$, R$^{14}$, and R$^{15}$ are each independently —H, or a C$_{1-5}$ linear or branched alkyl, and R$^{16}$ is —H, —OH, or a C$_{1-5}$ linear or branched alkoxy, provided that the fused 3- to 10-membered heterocycloalkyl is a 3- to 10-membered heterocycloalkyl fused with an unsubstituted C$_{6-10}$ aryl, and the substitution and fusion may occur at the same time in the case of the unsubstituted, substituted or fused 3- to 10-membered heterocycloalkyl; and A and E are each independently —CH=, or —N=.

Preferably, R$^{1}$ is a C$_{1-10}$ linear or branched alkoxycarbonyl, or an unsubstituted or substituted 5- to 10-membered heteroaryl containing one or more heteroatoms selected from the group consisting of N, O, and S, wherein:

the substituted 5- to 10-membered heteroaryl is a 5- to 10-membered heteroaryl substituted with one or more C$_{1-10}$ linear or branched alkyl;

R$^{2}$ is —H or a halogen;

R$^{3}$ is a C$_{1-10}$ linear or branched alkyl which is not substituted or substituted with one or more —OH or a halogen, a C$_{1-10}$ linear or branched alkoxy, a C$_{1-10}$ linear or branched alkoxy C$_{1-10}$ linear or branched alkyl, an unsubstituted C$_{3-10}$ cycloalkyl, an unsubstituted 5- to 10-membered heteroaryl C$_{1-10}$ linear or branched alkyl containing one or more heteroatoms selected from the group consisting of N, O, and S, —(CH$_{2}$)$_{n}$NR$^{5}$R$^{6}$, —(CH$_{2}$)$_{m}$C(=O)OR$^{7}$, or —(CH$_{2}$)$_{p}$C(=O)NR$^{8}$R$^{9}$, wherein:

R$^{5}$ and R$^{6}$ are each independently —H or -Boc


R$^{7}$ is —H, or a C$_{1-5}$ linear or branched alkyl, and

R$^{8}$ and R$^{9}$ may be taken together with a nitrogen atom to which they are attached to form an unsubstituted or substituted 5- to 10-membered heterocycloalkyl containing one or more heteroatoms selected from the group consisting of N, O, and S, wherein:

the substituted 5- to 10-membered heterocycloalkyl is a 5- to 10-membered heterocycloalkyl substituted with one or more substituents selected from the group consisting of —CN and —C(=O)NR$^{10}$R$^{11}$, and R$^{10}$ and R$^{11}$ are each independently —H, n, m, and p is each independently an integer ranging from 1 to 5;

R$^{4}$ is —H, or a C$_{1-10}$ linear or branched alkyl which is not substituted or substituted with one or more —OH;

provided that R$^{3}$ and R$^{4}$ may be taken together with a nitrogen atom to which they are attached to form an unsubstituted 3- to 10-membered heterocycloakenyl containing one or more heteroatoms selected from the group consisting of N, O, and S, or an unsubstituted, substituted or fused 3- to 10-membered heterocycloalkyl containing one or more heteroatoms selected from the group consisting of N, O, and S, wherein:

the substituted 3- to 10-membered heterocycloalkyl is a 3- to 10-membered heterocycloalkyl substituted with one or more substituents selected from the group consisting of —OH, —CN, =O, a halogen, a C$_{1-5}$ linear or branched alkyl which is not substituted or substituted with one or more —OH, an unsubstituted C$_{3-10}$ cycloalkyl C$_{1-5}$ linear or branched alkyl, an unsubstituted C$_{3-10}$ cycloalkyl, an unsubstituted 3- to 10-membered heterocycloalkyl containing one or more heteroatoms selected from the group consisting of N, O, and S, —C(=O)NR$^{12}$R$^{13}$, —NR$^{14}$R$^{15}$, and =NR$^{16}$; or substituted in a spiro fashion with a C$_{5-10}$ cycloakenyl fused with an unsubstituted C$_{6-10}$ aryl, or a 3- to 10-membered heterocycloalkyl which is not substituted or substituted with one or more -Boc

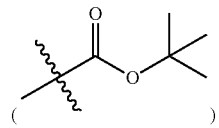 [SMILES: *C(=O)OC(C)(C)C]

and contains one or more heteroatoms selected from the group consisting of N, O, and S, R$^{12}$, R$^{13}$, R$^{14}$, and R$^{15}$ are each independently —H, or a C$_{1-5}$ linear or branched alkyl, and R$^{16}$ is —OH, or a C$_{1-5}$ linear or branched alkoxy, provided that the fused 3- to 10-membered heterocycloalkyl is a 3- to 10-membered heterocycloalkyl fused with an unsubstituted C$_{6-10}$ aryl, and the substitution and fusion may occur at the same time in the case of the unsubstituted, substituted or fused 3- to 10-membered heterocycloalkyl; and A and E are each independently —CH=, or —N=.

More preferably,

R$^{1}$ is

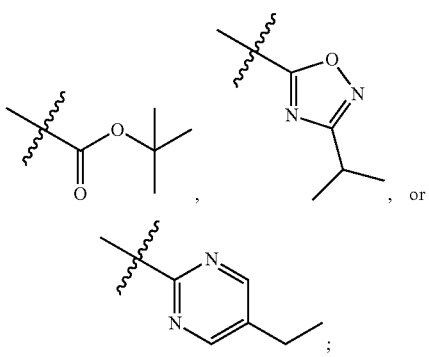

$R^2$ is —H or —F;
$R^3$ is
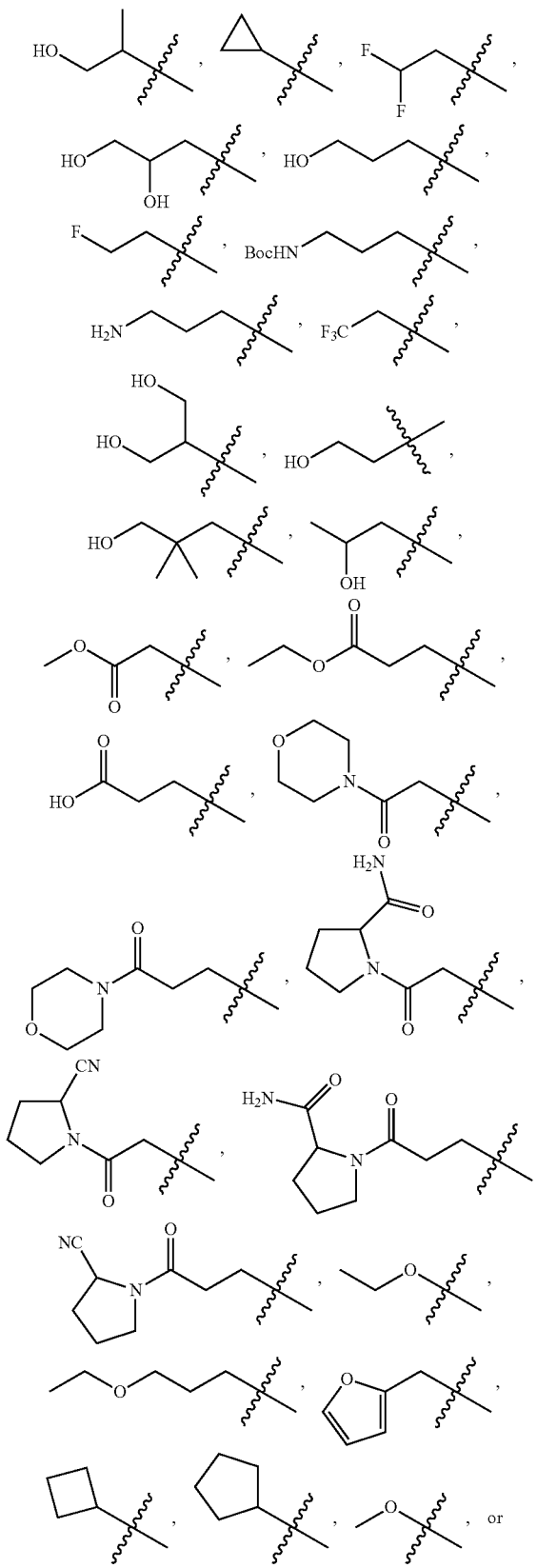
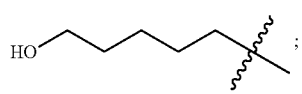
$R^4$ is —H, methyl, ethyl, or
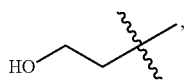
provided that $R^3$ and $R^4$ may be taken together with a nitrogen atom to which they are attached to form
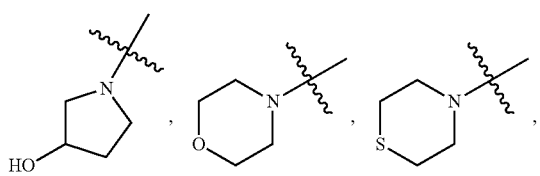
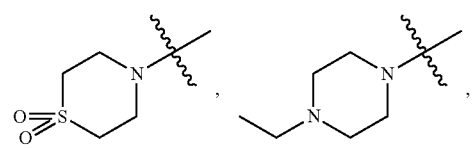
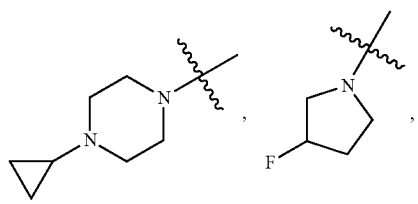
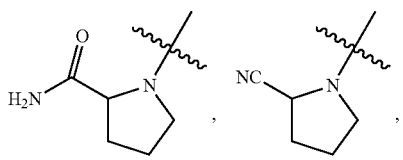
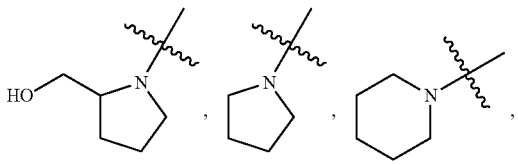
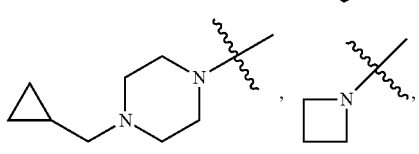
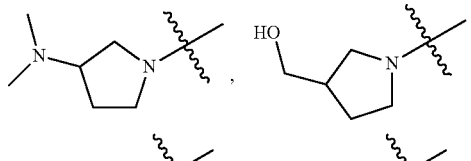
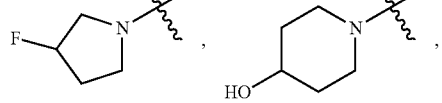

-continued

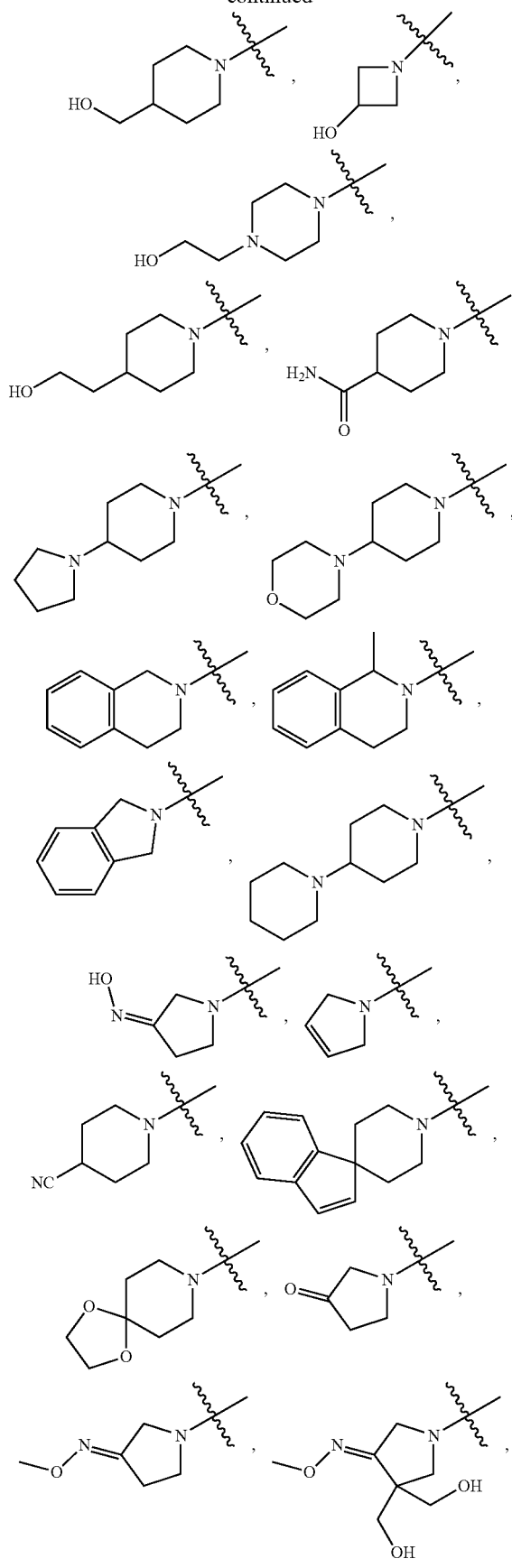

-continued

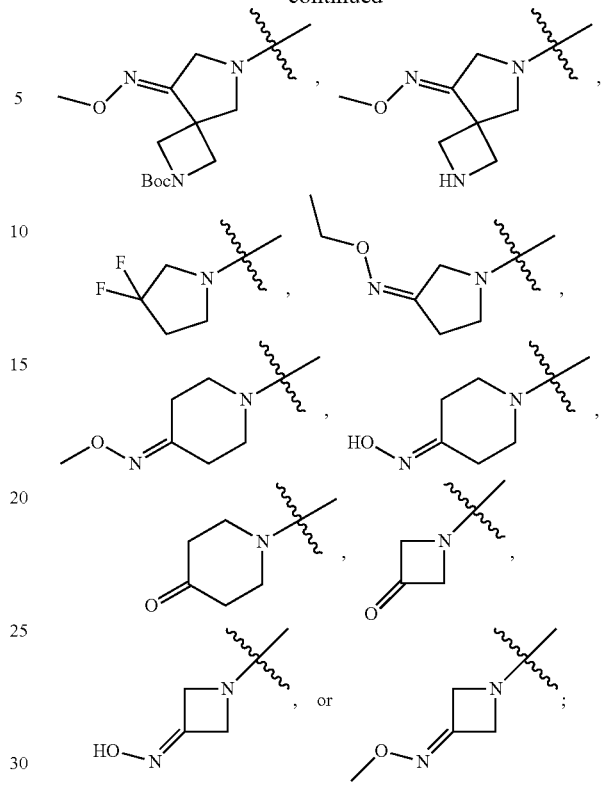

and

A and E are each independently —CH═, or —N═.

Preferred examples of the compound represented by Formula 1 according to the present invention may include the following compounds:

(1) tert-butyl 4-((4-(4-((R)-1-hydroxypropan-2-ylcarbamoyl)cyclohex-1-enyl)phenoxy)methyl)piperidine-1-carboxylate;

(2) tert-butyl 4-((4-(4-(cyclopropylcarbamoyl)cyclohex-1-enyl)phenoxy)methyl)piperidine-1-carboxylate;

(3) tert-butyl 4-((4-(4-(2,2-difluoroethylcarbamoyl)cyclohex-1-enyl)phenoxy)methyl)piperidine-1-carboxylate;

(4) tert-butyl 4-((4-(4-((R)-2,3-dihydroxypropylcarbamoyl)cyclohex-1-enyl)phenoxy)methyl)piperidine-1-carboxylate;

(5) tert-butyl 4-((4-(4-((R)-3-hydroxypyrrolidine-1-carbonyl)cyclohex-1-enyl)phenoxy)methyl)piperidine-1-carboxylate;

(6) tert-butyl 4-((4-(4-((3-hydroxypropyl)(methyl)carbamoyl)cyclohex-1-enyl)phenoxy)methyl)piperidine-1-carboxylate;

(7) tert-butyl 4-((4-(4-(morpholine-4-carbonyl)cyclohex-1-enyl)phenoxy)methyl)piperidine-1-carboxylate;

(8) 4-(4-((1-(5-ethylpyrimidin-2-yl)piperidin-4-yl)methoxy)phenyl)-N-((R)-1-hydroxypropan-2-yl)cyclohex-3-enecarboxamide;

(9) 4-(4-((1-(5-ethylpyrimidin-2-yl)piperidin-4-yl)methoxy)phenyl)-N-(3-hydroxypropyl)cyclohex-3-enecarboxamide;

(10) tert-butyl 4-((6-(4-((R)-2,3-dihydroxypropylcarbamoyl)cyclohex-1-enyl)pyridin-3-yloxy)methyl)piperidine-1-carboxylate;

(11) tert-butyl 4-((6-(4-((S)-1-hydroxypropan-2-ylcarbamoyl)cyclohex-1-enyl)pyridin-3-yloxy)methyl)piperidine-1-carboxylate;

(12) N-((R)-2,3-dihydroxypropyl)-4-(4-((1-(5-ethylpyrimidin-2-yl)piperidin-4-yl)methoxy)phenyl)cyclohex-3-enecarboxamide;
(13) (4-(4-((1-(5-ethylpyrimidin-2-yl)piperidin-4-yl)methoxy)phenyl)cyclohex-3-enyl)(morpholino)methanone;
(14) tert-butyl 4-((6-(4-(1,3-dihydroxypropan-2-ylcarbamoyl)cyclohex-1-enyl)pyridin-3-yloxy)methyl)piperidine-1-carboxylate;
(15) N-(1,3-dihydroxypropan-2-yl)-4-(4-((1-(5-ethylpyrimidin-2-yl)piperidin-4-yl)methoxy)phenyl)cyclohex-3-enecarboxamide;
(16) (4-(4-((1-(5-ethylpyrimidin-2-yl)piperidin-4-yl)methoxy)phenyl)cyclohex-3-enyl)((R)-3-hydroxypyrrolidin-1-yl)methanone;
(17) N-((R)-2,3-dihydroxypropyl)-4-(4-((1-(3-isopropyl-1,2,4-oxadiazol-5-yl)piperidin-4-yl)methoxy)phenyl)cyclohex-3-enecarboxamide;
(18) N-((S)-2,3-dihydroxypropyl)-4-(4-((1-(3-isopropyl-1,2,4-oxadiazol-5-yl)piperidin-4-yl)methoxy)phenyl)cyclohex-3-enecarboxamide;
(19) N-((S)-1-hydroxypropan-2-yl)-4-(4-((1-(3-isopropyl-1,2,4-oxadiazol-5-yl)piperidin-4-yl)methoxy)phenyl)cyclohex-3-enecarboxamide;
(20) N-((R)-1-hydroxypropan-2-yl)-4-(4-((1-(3-isopropyl-1,2,4-oxadiazol-5-yl)piperidin-4-yl)methoxy)phenyl)cyclohex-3-enecarboxamide;
(21) 4-(4-((1-(5-ethylpyrimidin-2-yl)piperidin-4-yl)methoxy)phenyl)-N-(2-hydroxyethyl)-N-methylcyclohex-3-enecarboxamide;
(22) N-(3-hydroxy-2,2- dimethylpropyl)-4-(4-((1-(3-isopropyl-1,2,4-oxadiazol-5-yl)piperidin-4-yl)methoxy)phenyl)cyclohex-3-enecarboxamide;
(23) N-(1,3-dihydroxypropan-2-yl)-4-(4-((1-(3-isopropyl-1,2,4-oxadiazol-5-yl)piperidin-4-yl)methoxy)phenyl)cyclohex-3-enecarboxamide;
(24) tert-butyl 4-((5-(4-((S)-1-hydroxypropan-2-ylcarbamoyl)cyclohex-1-enyl)pyridin-2-yloxy)methyl)piperidine-1-carboxylate;
(25) tert-butyl 4-((5-(4-((R)-1-hydroxypropan-2-ylcarbamoyl)cyclohex-1-enyl)pyridin-2-yloxy)methyl)piperidine-1-carboxylate;
(26) tert-butyl 4-((5-(4-((S)-2-hydroxypropylcarbamoyl)cyclohex-1-enyl)pyridin-2-yloxy)methyl)piperidine-1-carboxylate;
(27) tert-butyl 4-((5-(4-((R)-2-hydroxypropylcarbamoyl)cyclohex-1-enyl)pyridin-2-yloxy)methyl)piperidine-1-carboxylate;
(28) N-((R)-2-hydroxypropyl)-4-(4-((1-(3-isopropyl-1,2,4-oxadiazol-5-yl)piperidin-4-yl)methoxy)phenyl)cyclohex-3-enecarboxamide;
(29) N-((S)-2-hydroxypropyl)-4-(4-((1-(3-isopropyl-1,2,4-oxadiazol-5-yl)piperidin-4-yl)methoxy)phenyl)cyclohex-3-enecarboxamide;
(30) 4-(4-((1-(5-ethylpyrimidin-2-yl)piperidin-4-yl)methoxy)phenyl)-N-((R)-2-hydroxypropyl)cyclohex-3-enecarboxamide;
(31) N-(2-hydroxyethyl)-4-(4-((1-(3-isopropyl-1,2,4-oxadiazol-5-yl)piperidin-4-yl)methoxy)phenyl)cyclohex-3-enecarboxamide;
(32) tert-butyl 4-((5-(4-((R)-2,3-dihydroxypropylcarbamoyl)cyclohex-1-enyl)pyridin-2-yloxy)methyl)piperidine-1-carboxylate;
(33) tert-butyl 4-((5-(4-((S)-2,3-dihydroxypropylcarbamoyl)cyclohex-1-enyl)pyridin-2-yloxy)methyl)piperidine-1-carboxylate;
(34) N-(2-hydroxyethyl)-4-(4-((1-(3-isopropyl-1,2,4-oxadiazol-5-yl)piperidin-4-yl)methoxy)phenyl)-N-methylcyclohex-3-enecarboxamide;
(35) N-ethyl-N-(2-hydroxyethyl)-4-(4-((1-(3-isopropyl-1,2,4-oxadiazol-5-yl)piperidin-4-yl)methoxy)phenyl)cyclohex-3-enecarboxamide;
(36) N-((R)-1-hydroxypropan-2-yl)-4-(5-((1-(3-isopropyl-1,2,4-oxadiazol-5-yl)piperidin-4-yl)methoxy)pyridin-2-yl)cyclohex-3-enecarboxamide;
(37) N-((S)-1-hydroxypropan-2-yl)-4-(5-((1-(3-isopropyl-1,2,4-oxadiazol-5-yl)piperidin-4-yl)methoxy)pyridin-2-yl)cyclohex-3-enecarboxamide;
(38) N-((R)-2-hydroxypropyl)-4-(5-((1-(3-isopropyl-1,2,4-oxadiazol-5-yl)piperidin-4-yl)methoxy)pyridin-2-yl)cyclohex-3-enecarboxamide;
(39) N-((S)-2-hydroxypropyl)-4-(5-((1-(3-isopropyl-1,2,4-oxadiazol-5-yl)piperidin-4-yl)methoxy)pyridin-2-yl)cyclohex-3-enecarboxamide;
(40) N-((R)-2,3-dihydroxypropyl)-4-(5-((1-(3-isopropyl-1,2,4-oxadiazol-5-yl)piperidin-4-yl)methoxy)pyridin-2-yl)cyclohex-3-enecarboxamide;
(41) N-((S)-2,3-dihydroxypropyl)-4-(5-((1-(3-isopropyl-1,2,4-oxadiazol-5-yl)piperidin-4-yl)methoxy)pyridin-2-yl)cyclohex-3-enecarboxamide;
(42) tert-butyl 4-((5-(4-((S)-3-hydroxypyrrolidine-1-carbonyl)cyclohex-1-enyl)pyridin-2-yloxy)methyl)piperidine-1-carboxylate;
(43) tert-butyl 4-((5-(4-((R)-3-hydroxypyrrolidine-1-carbonyl)cyclohex-1-enyl)pyridin-2-yloxy)methyl)piperidine-1-carboxylate;
(44) tert-butyl 4-((2-fluoro-4-(4-((S)-3-hydroxypyrrolidine-1-carbonyl)cyclohex-1-enyl)phenoxy)methyl)piperidine-1-carboxylate;
(45) tert-butyl 4-((2-fluoro-4-(4-((R)-3-hydroxypyrrolidine-1-carbonyl)cyclohex-1-enyl)phenoxy)methyl)piperidine-1-carboxylate;
(46) N-(1,3-dihydroxypropan-2-yl)-4-(5-((1-(3-isopropyl-1,2,4-oxadiazol-5-yl)piperidin-4-yl)methoxy)pyridin-2-yl)cyclohex-3-enecarboxamide;
(47) N-(3-hydroxy-2,2-dimethylpropyl)-4-(5-((1-(3-isopropyl-1,2,4-oxadiazol-5-yl)piperidin-4-yl)methoxy)pyridin-2-yl)cyclohex-3-enecarboxamide;
(48) ((R)-3-hydroxypyrrolidin-1-yl)(4-(4-((1-(3-isopropyl-1,2,4-oxadiazol-5-yl)piperidin-4-yl)methoxy)phenyl)cyclohex-3-enyl)methanone;
(49) ((S)-3-hydroxypyrrolidin-1-yl)(4-(4-((1-(3-isopropyl-1,2,4-oxadiazol-5-yl)piperidin-4-yl)methoxy)phenyl)cyclohex-3-enyl)methanone;
(50) N-(2,2-difluoroethyl)-4-(4-((1-(5-ethylpyrimidin-2-yl)piperidin-4-yl)methoxy)phenyl)cyclohex-3-enecarboxamide;
(51) N-(2,2-difluoroethyl)-4-(4-((1-(3-isopropyl-1,2,4-oxadiazol-5-yl)piperidin-4-yl)methoxy)phenyl)cyclohex-3-enecarboxamide;
(52) (4-(4-((1-(3-isopropyl-1,2,4-oxadiazol-5-yl)piperidin-4-yl)methoxy)phenyl)cyclohex-3-enyl)(pyrrolidin-1-yl)methanone;
(53) ((S)-3-fluoropyrrolidin-1-yl)(4-(4-((1-(3-isopropyl-1,2,4-oxadiazol-5-yl)piperidin-4-yl)methoxy)phenyl)cyclohex-3-enyl)methanone;
(54) ((R)-3-fluoropyrrolidin-1-yl)(4-(4-((1-(3-isopropyl-1,2,4-oxadiazol-5-yl)piperidin-4-yl)methoxy)phenyl)cyclohex-3-enyl)methanone;
(55) (4-ethylpiperazin-1-yl)(4-(4-((1-(5-ethylpyrimidin-2-yl)piperidin-4-yl)methoxy)phenyl)cyclohex-3-enyl)methanone;

(56) (4-(4-((1-(3-isopropyl-1,2,4-oxadiazol-5-yl)piperidin-4-yl)methoxy)phenyl)cyclohex-3-enyl)(piperidin-1-yl)methanone;
(57) tert-butyl 4-((2-fluoro-4-(4-((S)-3-fluoropyrrolidine-1-carbonyl)cyclohex-1-enyl)phenoxy)methyl)piperidine-1-carboxylate;
(58) tert-butyl 4-((2-fluoro-4-(4-((R)-3-fluoropyrrolidine-1-carbonyl)cyclohex-1-enyl)phenoxy)methyl)piperidine-1-carboxylate;
(59) tert-butyl 4-((2-fluoro-4-(4-((S)-1-hydroxypropan-2-ylcarbamoyl)cyclohex-1-enyl)phenoxy)methyl)piperidine-1-carboxylate;
(60) tert-butyl 4-((2-fluoro-4-(4-((R)-1-hydroxypropan-2-ylcarbamoyl)cyclohex-1-enyl)phenoxy)methyl)piperidine-1-carboxylate;
(61) tert-butyl 4-((2-fluoro-4-(4-((S)-2-hydroxypropylcarbamoyl)cyclohex-1-enyl)phenoxy)methyl)piperidine-1-carboxylate;
(62) tert-butyl 4-((2-fluoro-4-(4-((R)-2-hydroxypropylcarbamoyl)cyclohex-1-enyl)phenoxy)methyl)piperidine-1-carboxylate;
(63) tert-butyl 4-((4-(4-((S)-2,3-dihydroxypropylcarbamoyl)cyclohex-1-enyl)-2-fluorophenoxy)methyl)piperidine-1-carboxylate;
(64) tert-butyl 4-((4-(4-((R)-2,3-dihydroxypropylcarbamoyl)cyclohex-1-enyl)-2-fluorophenoxy)methyl)piperidine-1-carboxylate;
(65) azetidin-1-yl(4-(4-((1-(3-isopropyl-1,2,4-oxadiazol-5-yl)piperidin-4-yl)methoxy)phenyl)cyclohex-3-enyl)methanone;
(66) (4-(4-((1-(3-isopropyl-1,2,4-oxadiazol-5-yl)piperidin-4-yl)methoxy)phenyl)cyclohex-3-enyl)(morpholino)methanone;
(67) tert-butyl 4-((4-(4-(1,3-dihydroxypropan-2-ylcarbamoyl)cyclohex-1-enyl)-2-fluorophenoxy)methyl)piperidine-1-carboxylate;
(68) tert-butyl 4-((5-(4-(1,3-dihydroxypropan-2-ylcarbamoyl)cyclohex-1-enyl)pyridin-2-yloxy)methyl)piperidine-1-carboxylate;
(69) tert-butyl 4-((2-fluoro-4-(4-(morpholine-4-carbonyl)cyclohex-1-enyl)phenoxy)methyl)piperidine-1-carboxylate;
(70) tert-butyl 4-((5-(4-(morpholine-4-carbonyl)cyclohex-1-enyl)pyridin-2-yloxy)methyl)piperidine-1-carboxylate;
(71) tert-butyl 4-((2-fluoro-4-(4-(thiomorpholine-4-carbonyl)cyclohex-1-enyl)phenoxy)methyl)piperidine-1-carboxylate;
(72) tert-butyl 4-((5-(4-(thiomorpholine-4-carbonyl)cyclohex-1-enyl)pyridin-2-yloxy)methyl)piperidine-1-carboxylate;
(73) tert-butyl 4-((2-fluoro-4-(4-(thiomorpholine-1,1-dioxide-4-carbonyl)cyclohex-1-enyl)phenoxy)methyl)piperidine-1-carboxylate;
(74) (4-(4-((1-(3-isopropyl-1,2,4-oxadiazol-5-yl)piperidin-4-yl)methoxy)phenyl)cyclohex-3-enyl)(thiomorpholino)methanone;
(75) N-(2-fluoroethyl)-4-(4-((1-(3-isopropyl-1,2,4-oxadiazol-5-yl)piperidin-4-yl)methoxy)phenyl)cyclohex-3-enecarboxamide;
(76) tert-butyl 3-(4-(4-((1-(3-isopropyl-1,2,4-oxadiazol-5-yl)piperidin-4-yl)methoxy)phenyl)-N-methylcyclohex-3-enecarboxamido)propylcarbamate;
(77) N-(3-aminopropyl)-4-(4-((1-(3-isopropyl-1,2,4-oxadiazol-5-yl)piperidin-4-yl)methoxy)phenyl)-N-methylcyclohex-3-enecarboxamide;
(78) 4-(4-((1-(3-isopropyl-1,2,4-oxadiazol-5-yl)piperidin-4-yl)methoxy)phenyl)-N-(2,2,2-trifluoroethyl)cyclohex-3-enecarboxamide;
(79) (4-ethylpiperazin-1-yl)(4-(4-((1-(3-isopropyl-1,2,4-oxadiazol-5-yl)piperidin-4-yl)methoxy)phenyl)cyclohex-3-enyl)methanone;
(80) N-(1,3-dihydroxypropan-2-yl)-4-(3-fluoro-4-((1-(3-isopropyl-1,2,4-oxadiazol-5-yl)piperidin-4-yl)methoxy)phenyl)cyclohex-3-enecarboxamide;
(81) 4-(3-fluoro-4-((1-(3-isopropyl-1,2,4-oxadiazol-5-yl)piperidin-4-yl)methoxy)phenyl)-N-(2-hydroxyethyl)-N-methylcyclohex-3-enecarboxamide;
(82) tert-butyl 4-((2-fluoro-4-(4-(3-hydroxy-2,2-dimethylpropylcarbamoyl)cyclohex-1-enyl)phenoxy)methyl)piperidine-1-carboxylate;
(83) 4-(3-fluoro-4-((1-(3-isopropyl-1,2,4-oxadiazol-5-yl)piperidin-4-yl)methoxy)phenyl)-N-((S)-1-hydroxypropan-2-yl)cyclohex-3-enecarboxamide;
(84) 4-(3-fluoro-4-((1-(3-isopropyl-1,2,4-oxadiazol-5-yl)piperidin-4-yl)methoxy)phenyl)-N-((R)-1-hydroxypropan-2-yl)cyclohex-3-enecarboxamide;
(85) tert-butyl 4-((4-(4-(2,2-difluoroethylcarbamoyl)cyclohex-1-enyl)-2-fluorophenoxy)methyl)piperidine-1-carboxylate;
(86) tert-butyl 4-((5-(4-(2,2,2-trifluoroethylcarbamoyl)cyclohex-1-enyl)pyridin-2-yloxy)methyl)piperidine-1-carboxylate;
(87) tert-butyl 4-((5-(4-(2,2-difluoroethylcarbamoyl)cyclohex-1-enyl)pyridin-2-yloxy)methyl)piperidine-1-carboxylate;
(88) tert-butyl 4-((5-(4-(2-fluoroethylcarbamoyl)cyclohex-1-enyl)pyridin-2-yloxy)methyl)piperidine-1-carboxylate;
(89) (4-cyclopropylpiperazin-1-yl)(4-(4-((1-(3-isopropyl-1,2,4-oxadiazol-5-yl)piperidin-4-yl)methoxy)phenyl)cyclohex-3-enyl)methanone;
(90) tert-butyl 4-((5-(4-((R)-3-fluoropyrrolidine-1-carbonyl)cyclohex-1-enyl)pyridin-2-yloxy)methyl)piperidine-1-carboxylate;
(91) tert-butyl 4-((5-(4-((S)-3-fluoropyrrolidine-1-carbonyl)cyclohex-1-enyl)pyridin-2-yloxy)methyl)piperidine-1-carboxylate;
(92) 4-(3-fluoro-4-((1-(3-isopropyl-1,2,4-oxadiazol-5-yl)piperidin-4-yl)methoxy)phenyl)-N-(2,2,2-trifluoroethyl)cyclohex-3-enecarboxamide;
(93) N-(2,2-difluoroethyl)-4-(3-fluoro-4-((1-(3-isopropyl-1,2,4-oxadiazol-5-yl)piperidin-4-yl)methoxy)phenyl)cyclohex-3-enecarboxamide;
(94) 4-(3-fluoro-4-((1-(3-isopropyl-1,2,4-oxadiazol-5-yl)piperidin-4-yl)methoxy)phenyl)-N-(2-fluoroethyl)cyclohex-3-enecarboxamide;
(95) (4-(3-fluoro-4-((1-(3-isopropyl-1,2,4-oxadiazol-5-yl)piperidin-4-yl)methoxy)phenyl)cyclohex-3-enyl)((S)-3-fluoropyrrolidin-1-yl)methanone;
(96) (4-(3-fluoro-4-((1-(3-isopropyl-1,2,4-oxadiazol-5-yl)piperidin-4-yl)methoxy)phenyl)cyclohex-3-enyl)((R)-3-fluoropyrrolidin-1-yl)methanone;
(97) (4-(3-fluoro-4-((1-(3-isopropyl-1,2,4-oxadiazol-5-yl)piperidin-4-yl)methoxy)phenyl)cyclohex-3-enyl)(morpholino)methanone;
(98) (4-(3-fluoro-4-((1-(3-isopropyl-1,2,4-oxadiazol-5-yl)piperidin-4-yl)methoxy)phenyl)cyclohex-3-enyl)(thiomorpholino)methanone;
(99) N-(2,2-difluoroethyl)-4-(5-((1-(3-isopropyl-1,2,4-oxadiazol-5-yl)piperidin-4-yl)methoxy)pyridin-2-yl)cyclohex-3-enecarboxamide;

(100) (4-(5-((1-(3-isopropyl-1,2,4-oxadiazol-5-yl)piperidin-4-yl)methoxy)pyridin-2-yl)cyclohex-3-enyl)(morpholino)methanone;
(101) ((R)-3-fluoropyrrolidin-1-yl)(4-(5-((1-(3-isopropyl-1,2,4-oxadiazol-5-yl)piperidin-4-yl)methoxy)pyridin-2-yl)cyclohex-3-enyl)methanone;
(102) ((S)-3-fluoropyrrolidin-1-yl)(4-(5-((1-(3-isopropyl-1,2,4-oxadiazol-5-yl)piperidin-4-yl)methoxy)pyridin-2-yl)cyclohex-3-enyl)methanone;
(103) 4-(4-((1-(5-ethylpyrimidin-2-yl)piperidin-4-yl)methoxy)phenyl)-N-(2,2,2-trifluoroethyl)cyclohex-3-enecarboxamide;
(104) 4-(4-((1-(5-ethylpyrimidin-2-yl)piperidin-4-yl)methoxy)phenyl)-N-(2-fluoroethyl)cyclohex-3-enecarboxamide;
(105) (2 S)-1-(4-(4-((1-(5-ethylpyrimidin-2-yl)piperidin-4-yl)methoxy)phenyl)cyclohex-3-enecarbonyl)pyrrolidine-2-carboxamide;
(106) (2 S)-1-(4-(4-((1-(5-ethylpyrimidin-2-yl)piperidin-4-yl)methoxy)phenyl)cyclohex-3-enecarbonyl)pyrrolidine-2-carbonitrile;
(107) tert-butyl 4-((4-(4-((S)-2-carbamoylpyrrolidine-1-carbonyl)cyclohex-1-enyl)-2-fluorophenoxy)methyl)piperidine-1-carboxylate;
(108) (2S)-1-(4-(3-fluoro-4-((1-(3-isopropyl-1,2,4-oxadiazol-5-yl)piperidin-4-yl)methoxy)phenyl)cyclohex-3-enecarbonyl)pyrrolidine-2-carboxamide;
(109) (methyl 2-(4-(3-fluoro-4-((1-(3-isopropyl-1,2,4-oxadiazol-5-yl)piperidin-4-yl)methoxy)phenyl)cyclohex-3-enecarboxamido)acetate;
(110) ethyl 3-(4-(3-fluoro-4-((1-(3-isopropyl-1,2,4-oxadiazol-5-yl)piperidin-4-yl)methoxy)phenyl)cyclohex-3-enecarboxamido)propanoate;
(111) 3-(4-(3-fluoro-4-((1-(3-isopropyl-1,2,4-oxadiazol-5-yl)piperidin-4-yl)methoxy)phenyl)cyclohex-3-enecarboxamido)propanoic acid;
(112) 4-(3-fluoro-4-((1-(3-isopropyl-1,2,4-oxadiazol-5-yl)piperidin-4-yl)methoxy)phenyl)-N-(2-morpholino-2-oxoethyl)cyclohex-3-enecarboxamide;
(113) 4-(3-fluoro-4-((1-(3-isopropyl-1,2,4-oxadiazol-5-yl)piperidin-4-yl)methoxy)phenyl)-N-(3-morpholino-3-oxopropyl)cyclohex-3-enecarboxamide;
(114) tert-butyl 4-((4-(4-((S)-2-cyanopyrrolidine-1-carbonyl)cyclohex-1-enyl)-2-fluorophenoxy)methyl)piperidine-1-carboxylate;
(115) (2S)-1-(4-(3-fluoro-4-((1-(3-isopropyl-1,2,4-oxadiazol-5-yl)piperidin-4-yl)methoxy)phenyl)cyclohex-3-enecarbonyl)pyrrolidine-2-carbonitrile;
(116) (2R)-1-(4-(3-fluoro-4-((1-(3-isopropyl-1,2,4-oxadiazol-5-yl)piperidin-4-yl)methoxy)phenyl)cyclohex-3-enecarbonyl)pyrrolidine-2-carboxamide;
(117) (2R)-1-(4-(3-fluoro-4-((1-(3-isopropyl-1,2,4-oxadiazol-5-yl)piperidin-4-yl)methoxy)phenyl)cyclohex-3-enecarbonyl)pyrrolidine-2-carbonitrile;
(118) (4-(4-((1-(5-ethylpyrimidin-2-yl)piperidin-4-yl)methoxy)phenyl)cyclohex-3-enyl)((R)-2-(hydroxymethyl)pyrrolidin-1-yl)methanone;
(119) (4-(4-((1-(5-ethylpyrimidin-2-yl)piperidin-4-yl)methoxy)phenyl)cyclohex-3-enyl)((S)-2-(hydroxymethyl)pyrrolidin-1-yl)methanone;
(120) 4-(3-fluoro-4-((1-(3-isopropyl-1,2,4-oxadiazol-5-yl)piperidin-4-yl)methoxy)phenyl)-N-(2-hydroxyethyl)cyclohex-3-enecarboxamide;
(121) (2R)-1-(2-(4-(3-fluoro-4-((1-(3-isopropyl-1,2,4-oxadiazol-5-yl)piperidin-4-yl)methoxy)phenyl)cyclohex-3-enecarboxamido)acetyl)pyrrolidine-2-carboxamide;
(122) N-(2-((R)-2-cyanopyrrolidin-1-yl)-2-oxoethyl)-4-(3-fluoro-4-((1-(3-isopropyl-1,2,4-oxadiazol-5-yl)piperidin-4-yl)methoxy)phenyl)cyclohex-3-enecarboxamide;
(123) (4-cyclopropylpiperazin-1-yl)(4-(4-((1-(5-ethylpyrimidin-2-yl)piperidin-4-yl)methoxy)phenyl)cyclohex-3-enyl)methanone;
(124) (4-(cyclopropylmethyl)piperazin-1-yl)(4-(4-((1-(5-ethylpyrimidin-2-yl)piperidin-4-yl)methoxy)phenyl)cyclohex-3-enyl)methanone;
(125) tert-butyl 4-((3-fluoro-4-(4-((S)-2-hydroxypropylcarbamoyl)cyclohex-1-enyl)phenoxy)methyl)piperidine-1-carboxylate;
(126) tert-butyl 4-((3-fluoro-4-(4-((R)-2-hydroxypropylcarbamoyl)cyclohex-1-enyl)phenoxy)methyl)piperidine-1-carboxylate;
(127) 4-(4-((1-(5-ethylpyrimidin-2-yl)piperidin-4-yl)methoxy)phenyl)-N-((S)-1-hydroxypropan-2-yl)cyclohex-3-enecarboxamide;
(128) N-((S)-2,3-dihydroxypropyl)-4-(4-((1-(5-ethylpyrimidin-2-yl)piperidin-4-yl)methoxy)phenyl)cyclohex-3-enecarboxamide;
(129) tert-butyl 4-((3-fluoro-4-(4-((R)-1-hydroxypropan-2-ylcarbamoyl)cyclohex-1-enyl)phenoxy)methyl)piperidine-1-carboxylate;
(130) tert-butyl 4-((3-fluoro-4-(4-((S)-1-hydroxypropan-2-ylcarbamoyl)cyclohex-1-enyl)phenoxy)methyl)piperidine-1-carboxylate;
(131) tert-butyl 4-((4-(4-((R)-2,3-dihydroxypropylcarbamoyl)cyclohex-1-enyl)-3-fluorophenoxy)methyl)piperidine-1-carboxylate;
(132) tert-butyl 4-((4-(4-((S)-2,3-dihydroxypropylcarbamoyl)cyclohex-1-enyl)-3-fluorophenoxy)methyl)piperidine-1-carboxylate;
(133) (2S)-1-(2-(4-(3-fluoro-4-((1-(3-isopropyl-1,2,4-oxadiazol-5-yl)piperidin-4-yl)methoxy)phenyl)cyclohex-3-enecarboxamido)acetyl)pyrrolidine-2-carboxamide;
(134) (2S)-1-(3-(4-(3-fluoro-4-((1-(3-isopropyl-1,2,4-oxadiazol-5-yl)piperidin-4-yl)methoxy)phenyl)cyclohex-3-enecarboxamido)propanoyl)pyrrolidine-2-carboxamide;
(135) (4-(4-((1-(5-ethylpyrimidin-2-yl)piperidin-4-yl)methoxy)phenyl)cyclohex-3-enyl)((S)-3-hydroxypyrrolidin-1-yl)methanone;
(136) 4-(4-((1-(5-ethylpyrimidin-2-yl)piperidin-4-yl)methoxy)phenyl)-N-((S)-2-hydroxypropyl)cyclohex-3-enecarboxamide;
(137) tert-butyl 4-((4-(4-(cyclopropylcarbamoyl)cyclohex-1-enyl)-3-fluorophenoxy)methyl)piperidine-1-carboxylate;
(138) tert-butyl 4-((3-fluoro-4-(4-(2-fluoroethylcarbamoyl)cyclohex-1-enyl)phenoxy)methyl)piperidine-1-carboxylate;
(139) N-(2-((S)-2-cyanopyrrolidin-1-yl)-2-oxoethyl)-4-(3-fluoro-4-((1-(3-isopropyl-1,2,4-oxadiazol-5-yl)piperidin-4-yl)methoxy)phenyl)cyclohex-3-enecarboxamide;
(140) N-(3-((S)-2-cyanopyrrolidin-1-yl)-3-oxopropyl)-4-(3-fluoro-4-((1-(3-isopropyl-1,2,4-oxadiazol-5-yl)piperidin-4-yl)methoxy)phenyl)cyclohex-3-enecarboxamide;
(141) tert-butyl 4-((4-(4-(2,2-difluoroethylcarbamoyl)cyclohex-1-enyl)-3-fluorophenoxy)methyl)piperidine-1-carboxylate;
(142) tert-butyl 4-((3-fluoro-4-(4-(2,2,2-trifluoroethylcarbamoyl)cyclohex-1-enyl)phenoxy)methyl)piperidine-1-carboxylate;
(143) ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone;

(144) ((S)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone;

(145) ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone hydrochloride;

(146) ((S)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone hydrochloride;

(147) ((R)-2-(hydroxymethyl)pyrrolidin-1-yl)(4-(4-((1-(3-isopropyl-1,2,4-oxadiazol-5-yl)piperidin-4-yl)methoxy)phenyl)cyclohex-3-enyl)methanone;

(148) ((S)-2-(hydroxymethyl)pyrrolidin-1-yl)(4-(4-((1-(3-isopropyl-1,2,4-oxadiazol-5-yl)piperidin-4-yl)methoxy)phenyl)cyclohex-3-enyl)methanone;

(149) ((R)-3-(hydroxymethyl)pyrrolidin-1-yl)(4-(4-((1-(3-isopropyl-1,2,4-oxadiazol-5-yl)piperidin-4-yl)methoxy)phenyl)cyclohex-3-enyl)methanone;

(150) ((S)-3-(hydroxymethyl)pyrrolidin-1-yl)(4-(4-((1-(3-isopropyl-1,2,4-oxadiazol-5-yl)piperidin-4-yl)methoxy)phenyl)cyclohex-3-enyl)methanone;

(151) (4-(4-((1-(5-ethylpyrimidin-2-yl)piperidin-4-yl)methoxy)phenyl)cyclohex-3-enyl)((R)-2-(hydroxymethyl)pyrrolidin-1-yl)methanone hydrochloride;

(152) (4-(4-((1-(5-ethylpyrimidin-2-yl)piperidin-4-yl)methoxy)phenyl)cyclohex-3-enyl)((S)-3-(hydroxymethyl)pyrrolidin-1-yl)methanone;

(153) (4-(4-((1-(5-ethylpyrimidin-2-yl)piperidin-4-yl)methoxy)phenyl)cyclohex-3-enyl)((R)-3-(hydroxymethyl)pyrrolidin-1-yl)methanone;

(154) ((S)-3-(dimethylamino)pyrrolidin-1-yl)(4-(4-((1-(5-ethylpyrimidin-2-yl)piperidin-4-yl)methoxy)phenyl)cyclohex-3-enyl)methanone;

(155) ((R)-3-(dimethylamino)pyrrolidin-1-yl)(4-(4-((1-(5-ethylpyrimidin-2-yl)piperidin-4-yl)methoxy)phenyl)cyclohex-3-enyl)methanone;

(156) ((S)-3-(dimethylamino)pyrrolidin-1-yl)(4-(4-((1-(5-ethylpyrimidin-2-yl)piperidin-4-yl)methoxy)phenyl)cyclohex-3-enyl)methanone hydrochloride;

(157) ((R)-3-(dimethylamino)pyrrolidin-1-yl)(4-(4-((1-(5-ethylpyrimidin-2-yl)piperidin-4-yl)methoxy)phenyl)cyclohex-3-enyl)methanone hydrochloride;

(158) (4-(4-((1-(5-ethylpyrimidin-2-yl)piperidin-4-yl)methoxy)phenyl)cyclohex-3-enyl)((S)-3-(hydroxymethyl)pyrrolidin-1-yl)methanone hydrochloride;

(159) (4-(4-((1-(5-ethylpyrimidin-2-yl)piperidin-4-yl)methoxy)phenyl)cyclohex-3-enyl)((R)-3-(hydroxymethyl)pyrrolidin-1-yl)methanone hydrochloride;

(160) (4-(4-((1-(5-ethylpyrimidin-2-yl)piperidin-4-yl)methoxy)phenyl)cyclohex-3-enyl)((S)-3-fluoropyrrolidin-1-yl)methanone;

(161) (4-(4-((1-(5-ethylpyrimidin-2-yl)piperidin-4-yl)methoxy)phenyl)cyclohex-3-enyl)((S)-3-fluoropyrrolidin-1-yl)methanone hydrochloride;

(162) (4-(4-((1-(5-ethylpyrimidin-2-yl)piperidin-4-yl)methoxy)phenyl)cyclohex-3-enyl)(pyrrolidin-1-yl)methanone;

(163) (4-(4-((1-(5-ethylpyrimidin-2-yl)piperidin-4-yl)methoxy)phenyl)cyclohex-3-enyl)(piperidin-1-yl)methanone;

(164) (4-(4-((1-(5-ethylpyrimidin-2-yl)piperidin-4-yl)methoxy)phenyl)cyclohex-3-enyl)(4-hydroxypiperidin-1-yl)methanone;

(165) (4-(4-((1-(5-ethylpyrimidin-2-yl)piperidin-4-yl)methoxy)phenyl)cyclohex-3-enyl)(4-(hydroxymethyl)piperidin-1-yl)methanone;

(166) (4-(4-((1-(5-ethylpyrimidin-2-yl)piperidin-4-yl)methoxy)phenyl)cyclohex-3-enyl)(pyrrolidin-1-yl)methanone hydrochloride;

(167) (4-(4-((1-(5-ethylpyrimidin-2-yl)piperidin-4-yl)methoxy)phenyl)cyclohex-3-enyl)(piperidin-1-yl)methanone hydrochloride;

(168) (4-(4-((1-(5-ethylpyrimidin-2-yl)piperidin-4-yl)methoxy)phenyl)cyclohex-3-enyl)(4-hydroxypiperidin-1-yl)methanone hydrochloride;

(169) (4-(4-((1-(5-ethylpyrimidin-2-yl)piperidin-4-yl)methoxy)phenyl)cyclohex-3-enyl)(4-(hydroxymethyl)piperidin-1-yl)methanone hydrochloride;

(170) azetidin-1-yl(4-(4-((1-(5-ethylpyrimidin-2-yl)piperidin-4-yl)methoxy)phenyl)cyclohex-3-enyl)methanone;

(171) (4-(4-((1-(5-ethylpyrimidin-2-yl)piperidin-4-yl)methoxy)phenyl)cyclohex-3-enyl)(3-hydroxyazetidin-1-yl)methanone;

(172) (4-(4-((1-(5-ethylpyrimidin-2-yl)piperidin-4-yl)methoxy)phenyl)cyclohex-3-enyl)(4-(2-hydroxyethyl)piperazin-1-yl)methanone;

(173) (4-(4-((1-(5-ethylpyrimidin-2-yl)piperidin-4-yl)methoxy)phenyl)cyclohex-3-enyl)(4-(2-hydroxyethyl)piperidin-1-yl)methanone;

(174) N-ethoxy-4-(4-((1-(5-ethylpyrimidin-2-yl)piperidin-4-yl)methoxy)phenyl)cyclohex-3-enecarboxamide;

(175) N-ethyl-4-(4-((1-(5-ethylpyrimidin-2-yl)piperidin-4-yl)methoxy)phenyl)-N-(2-hydroxyethyl)cyclohex-3-enecarboxamide;

(176) 4-(4-((1-(5-ethylpyrimidin-2-yl)piperidin-4-yl)methoxy)phenyl)-N-(2-hydroxyethyl)cyclohex-3-enecarboxamide;

(177) 4-(4-((1-(5-ethylpyrimidin-2-yl)piperidin-4-yl)methoxy)phenyl)-N-(3-hydroxy-2,2-dimethylpropyl)cyclohex-3-enecarboxamide;

(178) 1-(4-(4-((1-(5-ethylpyrimidin-2-yl)piperidin-4-yl)methoxy)phenyl)cyclohex-3-enecarbonyl)piperidine-4-carboxamide;

(179) 4-(4-((1-(5-ethylpyrimidin-2-yl)piperidin-4-yl)methoxy)phenyl)-N-(3-methoxypropyl)cyclohex-3-enecarboxamide;

(180) 4-(4-((1-(5-ethylpyrimidin-2-yl)piperidin-4-yl)methoxy)phenyl)-N-(furan-2-ylmethyl)cyclohex-3-enecarboxamide;

(181) 4-(4-((1-(5-ethylpyrimidin-2-yl)piperidin-4-yl)methoxy)phenyl)-N,N-bis(2-hydroxyethyl)cyclohex-3-enecarboxamide;

(182) (4-hydroxypiperidin-1-yl)(4-(4-((1-(3-isopropyl-1,2,4-oxadiazol-5-yl)piperidin-4-yl)methoxy)phenyl)cyclohex-3-enyl)methanone;

(183) (4-(hydroxymethyl)piperidin-1-yl)(4-(4-((1-(3-isopropyl-1,2,4-oxadiazol-5-yl)piperidin-4-yl)methoxy)phenyl)cyclohex-3-enyl)methanone;

(184) N-cyclopropyl-4-(4-((1-(3-isopropyl-1,2,4-oxadiazol-5-yl)piperidin-4-yl)methoxy)phenyl)cyclohex-3-enecarboxamide;

(185) N-(3-hydroxypropyl)-4-(4-((1-(3-isopropyl-1,2,4-oxadiazol-5-yl)piperidin-4-yl)methoxy)phenyl)cyclohex-3-enecarboxamide;

(186) (4-(2-hydroxyethyl)piperidin-1-yl)(4-(4-((1-(3-isopropyl-1,2,4-oxadiazol-5-yl)piperidin-4-yl)methoxy)phenyl)cyclohex-3-enyl)methanone;

(187) (4-(2-hydroxyethyl)piperazin-1-yl)(4-(4-((1-(3-isopropyl-1,2,4-oxadiazol-5-yl)piperidin-4-yl)methoxy)phenyl)cyclohex-3-enyl)methanone;

(188) 4-(4-((1-(3-isopropyl-1,2,4-oxadiazol-5-yl)piperidin-4-yl)methoxy)phenyl)-N-(methoxymethyl)cyclohex-3-enecarboxamide;

(189) N-cyclopropyl-4-(4-((1-(5-ethylpyrimidin-2-yl)piperidin-4-yl)methoxy)phenyl)cyclohex-3-enecarboxamide;
(190) tert-butyl 4-((4-(4-(2-hydroxyethylcarbamoyl)cyclohex-1-enyl)phenoxy)methyl)piperidine-1-carboxylate;
(191) tert-butyl 4-((4-(4-(3-hydroxy-2,2-dimethylpropylcarbamoyl)cyclohex-1-enyl)phenoxy)methyl)piperidine-1-carboxylate;
(192) tert-butyl 4-((4-(4-(methoxymethylcarbamoyl)cyclohex-1-enyl)phenoxy)methyl)piperidine-1-carboxylate;
(193) tert-butyl 4-((4-(4-(4-(pyrrolidin-1-yl)piperidine-1-carbonyl)cyclohex-1-enyl)phenoxy)methyl)piperidine-1-carboxylate;
(194) tert-butyl 4-((4-(4-(cyclobutylcarbamoyl)cyclohex-1-enyl)phenoxy)methyl)piperidine-1-carboxylate;
(195) tert-butyl 4-((4-(4-(cyclopentylcarbamoyl)cyclohex-1-enyl)phenoxy)methyl)piperidine-1-carboxylate;
(196) tert-butyl 4-((4-(4-(4-morpholinopiperidine-1-carbonyl)cyclohex-1-enyl)phenoxy)methyl)piperidine-1-carboxylate;
(197) 4-(4-((1-(5-ethylpyrimidin-2-yl)piperidin-4-yl)methoxy)phenyl)-N-methoxy-N-methylcyclohex-3-enecarboxamide;
(198) 4-(4-((1-(5-ethylpyrimidin-2-yl)piperidin-4-yl)methoxy)phenyl)-N-methoxycyclohex-3-enecarboxamide;
(199) tert-butyl 4-((4-(4-(ethyl(2-hydroxyethyl)carbamoyl)cyclohex-1-enyl)phenoxy)methyl)piperidine-1-carboxylate;
(200) tert-butyl 4-((4-(4-(4-(2-hydroxyethyl)piperidine-1-carbonyl)cyclohex-1-enyl)phenoxy)methyl)piperidine-1-carboxylate;
(201) tert-butyl 4-((4-(4-(4-(2-hydroxyethyl)piperazine-1-carbonyl)cyclohex-1-enyl)phenoxy)methyl)piperidine-1-carboxylate;
(202) tert-butyl 4-((4-(4-(pyrrolidine-1-carbonyl)cyclohex-1-enyl)phenoxy)methyl)piperidine-1-carboxylate;
(203) tert-butyl 4-((4-(4-(4-ethylpiperazine-1-carbonyl)cyclohex-1-enyl)phenoxy)methyl)piperidine-1-carboxylate;
(204) tert-butyl 4-((4-(4-(piperidine-1-carbonyl)cyclohex-1-enyl)phenoxy)methyl)piperidine-1-carboxylate;
(205) tert-butyl 4-((4-(4-(3-ethoxypropylcarbamoyl)cyclohex-1-enyl)phenoxy)methyl)piperidine-1-carboxylate;
(206) tert-butyl 4-((4-(4-(bis(2-hydroxyethyl)carbamoyl)cyclohex-1-enyl)phenoxy)methyl)piperidine-1-carboxylate;
(207) 1-(4-(4-((1-(3-isopropyl-1,2,4-oxadiazol-5-yl)piperidin-4-yl)methoxy)phenyl)cyclohex-3-enecarbonyl)piperidine-4-carboxamide;
(208) (4-(4-((1-(3-isopropyl-1,2,4-oxadiazol-5-yl)piperidin-4-yl)methoxy)phenyl)cyclohex-3-enyl)(4-(pyrrolidin-1-yl)piperidin-1-yl)methanone;
(209) (4-(4-((1-(3-isopropyl-1,2,4-oxadiazol-5-yl)piperidin-4-yl)methoxy)phenyl)cyclohex-3-enyl)(4-morpholinopiperidin-1-yl)methanone;
(210) N-cyclopentyl-4-(4-((1-(3-isopropyl-1,2,4-oxadiazol-5-yl)piperidin-4-yl)methoxy)phenyl)cyclohex-3-enecarboxamide;
(211) N-cyclobutyl-4-(4-((1-(3-isopropyl-1,2,4-oxadiazol-5-yl)piperidin-4-yl)methoxy)phenyl)cyclohex-3-enecarboxamide;
(212) (3,4-dihydroisoquinolin-2(1H)-yl)(4-(4-((1-(3-isopropyl-1,2,4-oxadiazol-5-yl)piperidin-4-yl)methoxy)phenyl)cyclohex-3-enyl)methanone;
(213) (4-(4-((1-(3-isopropyl-1,2,4-oxadiazol-5-yl)piperidin-4-yl)methoxy)phenyl)cyclohex-3-enyl)(1-methyl-3,4-dihydroisoquinolin-2(1H)-yl)methanone;
(214) isoindolin-2-yl(4-(4-((1-(3-isopropyl-1,2,4-oxadiazol-5-yl)piperidin-4-yl)methoxy)phenyl)cyclohex-3-enyl)methanone;
(215) 1,4'-bipiperidin-1'-yl(4-(4-((1-(3-isopropyl-1,2,4-oxadiazol-5-yl)piperidin-4-yl)methoxy)phenyl)cyclohex-3-enyl)methanone;
(216) tert-butyl 4-((4-(4-(1,4'-bipiperidine-1'-carbonyl)cyclohex-1-enyl)phenoxy)methyl)piperidine-1-carboxylate;
(217) (4-(4-((1-(5-ethylpyrimidin-2-yl)piperidin-4-yl)methoxy)phenyl)cyclohex-3-enyl)(3-(hydroxyimino)pyrrolidin-1-yl)methanone;
(218) (4-(4-((1-(5-ethylpyrimidin-2-yl)piperidin-4-yl)methoxy)phenyl)cyclohex-3-enyl)(4-(pyrrolidin-1-yl)piperidin-1-yl)methanone;
(219) 1,4'-bipiperidin-1'-yl(4-(4-((1-(5-ethylpyrimidin-2-yl)piperidin-4-yl)methoxy)phenyl)cyclohex-3-enyl)methanone;
(220) (4-(4-((1-(5-ethylpyrimidin-2-yl)piperidin-4-yl)methoxy)phenyl)cyclohex-3-enyl)(4-morpholinopiperidin-1-yl)methanone;
(221) tert-butyl 4-((4-(4-(furan-2-ylmethylcarbamoyl)cyclohex-1-enyl)phenoxy)methyl)piperidine-1-carboxylate;
(222) tert-butyl 4-((4-(4-(methoxycarbamoyl)cyclohex-1-enyl)phenoxy)methyl)piperidine-1-carboxylate;
(223) tert-butyl 4-((4-(4-(methoxy(methyl)carbamoyl)cyclohex-1-enyl)phenoxy)methyl)piperidine-1-carboxylate;
(224) tert-butyl 4-((4-(4-(2, 5-dihydro-1H-pyrrole-1-carbonyl)cyclohex-1-enyl)phenoxy)methyl)piperidine-1-carboxylate;
(225) tert-butyl 4-((4-(4-(4-hydroxypiperidine-1-carbonyl)cyclohex-1-enyl)phenoxy)methyl)piperidine-1-carboxylate;
(226) tert-butyl 4-((4-(4-(4-(hydroxymethyl)piperidine-1-carbonyl)cyclohex-1-enyl)phenoxy)methyl)piperidine-1-carboxylate;
(227) 1-(4-(4-((1-(5-ethylpyrimidin-2-yl)piperidin-4-yl)methoxy)phenyl)cyclohex-3-enecarbonyl)piperidine-4-carbonitrile;
(228) (4-(4-((1-(5-ethylpyrimidin-2-yl)piperidin-4-yl)methoxy)phenyl)cyclohex-3-enyl)(spiro[indene-1,4'-piperidin]-1'-yl)methanone;
(229) (4-(4-((1-(5-ethylpyrimidin-2-yl)piperidin-4-yl)methoxy)phenyl)cyclohex-3-enyl)(1,4-dioxa-8-azaspiro[4.5]decan-8-yl)methanone;
(230) N-cyclopentyl-4-(4-((1-(5-ethylpyrimidin-2-yl)piperidin-4-yl)methoxy)phenyl)cyclohex-3-enecarboxamide;
(231) N-cyclobutyl-4-(4-((1-(5-ethylpyrimidin-2-yl)piperidin-4-yl)methoxy)phenyl)cyclohex-3-enecarboxamide;
(232) (3,4-dihydroisoquinolin-2(1H)-yl)(4-(4-((1-(5-ethylpyrimidin-2-yl)piperidin-4-yl)methoxy)phenyl)cyclohex-3-enyl)methanone;
(233) tert-butyl 4-((4-(4-(5-hydroxypentylcarbamoyl)cyclohex-1-enyl)phenoxy)methyl)piperidine-1-carboxylate;
(234) 4-(4-((1-(5-ethylpyrimidin-2-yl)piperidin-4-yl)methoxy)phenyl)-N-(5-hydroxypentyl)cyclohex-3-enecarboxamide;
(235) (2,5-dihydro-1H-pyrrol-1-yl)(4-(4-((1-(5-ethylpyrimidin-2-yl)piperidin-4-yl)methoxy)phenyl)cyclohex-3-enyl)methanone;
(236) tert-butyl 4-((4-(4-((2-hydroxyethyl)(methyl)carbamoyl)cyclohex-1-enyl)phenoxy)methyl)piperidine-1-carboxylate;
(237) tert-butyl 4-((4-(4-(1,3-dihydroxypropan-2-ylcarbamoyl)cyclohex-1-enyl)phenoxy)methyl)piperidine-1-carboxylate;
(238) tert-butyl 4-((4-(4-(3-hydroxypropylcarbamoyl)cyclohex-1-enyl)phenoxy)methyl)piperidine-1-carboxylate;

(239) tert-butyl 4-((4-(4-(1,2,3,4-tetrahydroisoquinoline-2-carbonyl)cyclohex-1-enyl)phenoxy)methyl)piperidine-1-carboxylate;
(240) tert-butyl 4-((4-(4-(isoindoline-2-carbonyl)cyclohex-1-enyl)phenoxy)methyl)piperidine-1-carboxylate;
(241) (4-(4-((1-(5-ethylpyrimidin-2-yl)piperidin-4-yl)methoxy)phenyl)cyclohex-3-enyl)(isoindolin-2-yl)methanone;
(242) 4-(4-((1-(5-ethylpyrimidin-2-yl)piperidin-4-yl)methoxy)phenyl)-N-(3-hydroxypropyl)-N-methylcyclohex-3-enecarboxamide;
(243) N-(3-hydroxypropyl)-4-(4-((1-(3-isopropyl-1,2,4-oxadiazol-5-yl)piperidin-4-yl)methoxy)phenyl)-N-methylcyclohex-3-enecarboxamide;
(244) N-(furan-2-ylmethyl)-4-(4-((1-(3-isopropyl-1,2,4-oxadiazol-5-yl)piperidin-4-yl)methoxy)phenyl)cyclohex-3-enecarboxamide;
(245) N-(3-ethoxypropyl)-4-(4-((1-(3-isopropyl-1,2,4-oxadiazol-5-yl)piperidin-4-yl)methoxy)phenyl)cyclohex-3-enecarboxamide;
(246) 4-(4-((1-(3-isopropyl-1,2,4-oxadiazol-5-yl)piperidin-4-yl)methoxy)phenyl)-N-methoxycyclohex-3-enecarboxamide;
(247) 4-(4-((1-(3-isopropyl-1,2,4-oxadiazol-5-yl)piperidin-4-yl)methoxy)phenyl)-N-methoxy-N-methylcyclohex-3-enecarboxamide;
(248) N,N-bis(2-hydroxyethyl)-4-(4-((1-(3-isopropyl-1,2,4-oxadiazol-5-yl)piperidin-4-yl)methoxy)phenyl)cyclohex-3-enecarboxamide;
(249) 1-(4-(4-((1-(3-isopropyl-1,2,4-oxadiazol-5-yl)piperidin-4-yl)methoxy)phenyl)cyclohex-3-enecarbonyl)piperidine-4-carboxamide;
(250) 1-(4-(4-((1-(5-ethylpyrimidin-2-yl)piperidin-4-yl)methoxy)phenyl)cyclohex-3-enecarbonyl)pyrrolidin-3-one;
(251) 1-(4-(4-((1-(3-isopropyl-1,2,4-oxadiazol-5-yl)piperidin-4-yl)methoxy)phenyl)cyclohex-3-enecarbonyl)piperidine-4-carboxamide;
(252) 1-(4-(4-((1-(3-isopropyl-1,2,4-oxadiazol-5-yl)piperidin-4-yl)methoxy)phenyl)cyclohex-3-enecarbonyl)piperidine-4-carboxamide;
(253) (Z)-(3,3-bis(hydroxymethyl)-4-(methoxyimino)pyrrolidin-1-yl)(4-(4-((1-(5-ethylpyrimidin-2-yl)piperidin-4-yl)methoxy)phenyl)cyclohex-3-enyl)methanone;
(254) (Z)-tert-butyl 6-(4-(4-((1-(5-ethylpyrimidin-2-yl)piperidin-4-yl)methoxy)phenyl)cyclohex-3-enecarbonyl)-8-(methoxyimino)-2,6-diazaspiro[3.4]octane-2-carboxylate;
(255) (Z)-(4-(4-((1-(5-ethylpyrimidin-2-yl)piperidin-4-yl)methoxy)phenyl)cyclohex-3-enyl)(8-(methoxyimino)-2,6-diazaspiro[3.4]octan-6-yl)methanone hydrochloride;
(256) tert-butyl 4-((4-(4-(4-(cyclopropylmethyl)piperazine-1-carbonyl)cyclohex-1-enyl)phenoxy)methyl)piperidine-1-carboxylate;
(257) tert-butyl 4-((4-(4-(3,3-difluoropyrrolidine-1-carbonyl)cyclohex-1-enyl)phenoxy)methyl)piperidine-1-carboxylate;
(258) (3,3-difluoropyrrolidin-1-yl)(4-(4-((1-(5-ethylpyrimidin-2-yl)piperidin-4-yl)methoxy)phenyl)cyclohex-3-enyl)methanone;
(259) (3,3-difluoropyrrolidin-1-yl)(4-(4-((1-(3-isopropyl-1,2,4-oxadiazol-5-yl)piperidin-4-yl)methoxy)phenyl)cyclohex-3-enyl)methanone;
(260) N-(5-hydroxypentyl)-4-(4-((1-(3-isopropyl-1,2,4-oxadiazol-5-yl)piperidin-4-yl)methoxy)phenyl)cyclohex-3-enecarboxamide;
(261) tert-butyl 4-((4-(4-(2,2,2-trifluoroethylcarbamoyl)cyclohex-1-enyl)phenoxy)methyl)piperidine-1-carboxylate;
(262) tert-butyl 4-((4-(4-(4-cyanocyclohexanecarbonyl)cyclohex-1-enyl)phenoxy)methyl)piperidine-1-carboxylate;
(263) tert-butyl 4-((4-(4-(1,4-dioxa-8-azaspiro[4.5]decane-8-carbonyl)cyclohex-1-enyl)phenoxy)methyl)piperidine-1-carboxylate;
(264) tert-butyl 4-((4-(4-(spiro[indene-1,4'-piperidin]-1'-yl-carbonyl)cyclohex-1-enyl)phenoxy)methyl)piperidine-1-carboxylate;
(265) tert-butyl 4-((4-(4-(3-oxopyrrolidine-1-carbonyl)cyclohex-1-enyl)phenoxy)methyl)piperidine-1-carboxylate;
(266) 1-(4-(4-((1-(3-isopropyl-1,2,4-oxadiazol-5-yl)piperidin-4-yl)methoxy)phenyl)cyclohex-3-enecarbonyl)piperidine-4-carbonitrile;
(267) (4-(4-((1-(3-isopropyl-1,2,4-oxadiazol-5-yl)piperidin-4-yl)methoxy)phenyl)cyclohex-3-enyl)(1,4-dioxa-8-azaspiro[4.5]decan-8-yl)methanone;
(268) (2,3-dihydrospiro[indene-1,4'-piperidin]-1'-yl)(4-(4-((1-(3-isopropyl-1,2,4-oxadiazol-5-yl)piperidin-4-yl)methoxy)phenyl)cyclohex-3-enyl)methanone;
(269) (3-(ethoxyimino)pyrrolidin-1-yl)(4-(4-((1-(5-ethylpyrimidin-2-yl)piperidin-4-yl)methoxy)phenyl)cyclohex-3-enyl)methanone;
(270) tert-butyl 4-((4-(4-(4-(methoxyimino)piperidine-1-carbonyl)cyclohex-1-enyl)phenoxy)methyl)piperidine-1-carboxylate;
(271) tert-butyl 4-((4-(4-(4-(hydroxyimino)piperidine-1-carbonyl)cyclohex-1-enyl)phenoxy)methyl)piperidine-1-carboxylate;
(272) tert-butyl 4-((4-(4-(4-oxopiperidine-1-carbonyl)cyclohex-1-enyl)phenoxy)methyl)piperidine-1-carboxylate;
(273) tert-butyl 4-((4-(4-(3-(methoxyimino)pyrrolidine-1-carbonyl)cyclohex-1-enyl)phenoxy)methyl)piperidine-1-carboxylate;
(274) 1-(4-(4-((1-(5-ethylpyrimidin-2-yl)piperidin-4-yl)methoxy)phenyl)cyclohex-3-enecarbonyl)piperidin-4-one;
(275) 1-(4-(4-((1-(3-isopropyl-1,2,4-oxadiazol-5-yl)piperidin-4-yl)methoxy)phenyl)cyclohex-3-enecarbonyl)piperidin-4-one;
(276) (4-(hydroxyimino)piperidin-1-yl)(4-(4-((1-(3-isopropyl-1,2,4-oxadiazol-5-yl)piperidin-4-yl)methoxy)phenyl)cyclohex-3-enyl)methanone;
(277) (4-(4-((1-(5-ethylpyrimidin-2-yl)piperidin-4-yl)methoxy)phenyl)cyclohex-3-enyl)(4-(hydroxyimino)piperidin-1-yl)methanone;
(278) (4-(4-((1-(3-isopropyl-1,2,4-oxadiazol-5-yl)piperidin-4-yl)methoxy)phenyl)cyclohex-3-enyl)(4-(methoxyimino)piperidin-1-yl)methanone;
(279) (4-(4-((1-(3-isopropyl-1,2,4-oxadiazol-5-yl)piperidin-4-yl)methoxy)phenyl)cyclohex-3-enyl)(4-(methoxyimino)piperidin-1-yl)methanone;
(280) tert-butyl 4-((4-(4-(3-oxoazetidine-1-carbonyl)cyclohex-1-enyl)phenoxy)methyl)piperidine-1-carboxylate;
(281) tert-butyl 4-((4-(4-(3-(hydroxyimino)azetidine-1-carbonyl)cyclohex-1-enyl)phenoxy)methyl)piperidine-1-carboxylate;
(282) tert-butyl 4-((4-(4-(3-(methoxyimino)azetidine-1-carbonyl)cyclohex-1-enyl)phenoxy)methyl)piperidine-1-carboxylate;
(283) 1-(4-(4-((1-(5-ethylpyrimidin-2-yl)piperidin-4-yl)methoxy)phenyl)cyclohex-3-enecarbonyl)azetidin-3-one;
(284) 1-(4-(4-((1-(3-isopropyl-1,2,4-oxadiazol-5-yl)piperidin-4-yl)methoxy)phenyl)cyclohex-3-enecarbonyl)azetidin-3-one;

(285) (3-(hydroxyimino)azetidin-1-yl)(4-(4-((1-(3-isopropyl-1,2,4-oxadiazol-5-yl)piperidin-4-yl)methoxy)phenyl)cyclohex-3-enyl)methanone;
(286) (4-(4-((1-(3-isopropyl-1,2,4-oxadiazol-5-yl)piperidin-4-yl)methoxy)phenyl)cyclohex-3-enyl)(3-(methoxyimino)azetidin-1-yl)methanone;
(287) (4-(4-((1-(5-ethylpyrimidin-2-yl)piperidin-4-yl)methoxy)phenyl)cyclohex-3-enyl)(3-(methoxyimino)azetidin-1-yl)methanone;
(288) tert-butyl 4-((4-(4-(3-hydroxyazetidine-1-carbonyl)cyclohex-1-enyl)phenoxy)methyl)piperidine-1-carboxylate; and
(289) (3-hydroxyazetidin-1-yl)(4-(4-((1-(3-isopropyl-1,2,4-oxadiazol-5-yl)piperidin-4-yl)methoxy)phenyl)cyclohex-3-enyl)methanone;

The compound represented by Formula 1 according to the present invention may be used in the form of a pharmaceutically acceptable salt, and an acid addition salt formed by a pharmaceutically acceptable free acid is useful as the salt. The acid addition salt may be obtained from inorganic acids such as hydrochloric acid, nitric acid, phosphoric acid, sulfuric acid, hydrobromic acid, hydriodic acid, nitrous acid, or phosphorous acid, non-toxic organic acids such as aliphatic mono- and di-carboxylates, phenyl-substituted alkanoates, hydroxy alkanoates, and alkandioates, aromatic acids, aliphatic and aromatic sulfonic acids, and organic acids such as acetic acid, benzoic acid, citric acid, lactic acid, maleic acid, gluconic acid, methanesulfonic acid, 4-toluenesulfonic acid, tartaric acid, and fumaric acid. Such a pharmaceutically innocuous salt includes sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycolate, malate, tartrate, methanesulfonate, propanesulfonate, naphthalene-1-sulfonate, naphthalene-2-sulfonate, or mandelate.

The acid addition salt according to the present invention may be prepared using a conventional method, for example, prepared by dissolving the compound represented by Formula 1 in an organic solvent, for example, methanol, ethanol, acetone, methylenechloride, acetonitrile, etc., adding an organic or inorganic acid and filtering and drying the resulting precipitate, or by distilling a solvent and an excessive amount of an acid under reduced pressure and drying the resulting distillate, or prepared under an organic solvent.

In addition to the compound represented by Formula 1 and the pharmaceutically acceptable salt thereof, the present invention also encompasses all types of solvates, hydrates, optical isomers and the like which may be prepared from the compound of Formula 1 and the pharmaceutically acceptable salt thereof.

In addition, as shown in the following Scheme 1, the present invention provides a method for preparing the compound represented by Formula 1, which includes:
reacting a compound represented by Formula 2 with a compound represented by Formula 3 to prepare a compound represented by Formula 4 (Step 1);
reacting the compound represented by Formula 4 prepared in Step 1 with a compound represented by Formula 5 to prepare a compound represented by Formula 6 (Step 2);
reacting the compound represented by Formula 6 prepared in Step 2 with a base to prepare a compound represented by Formula 7 (Step 3); and
reacting the compound represented by Formula 7 prepared in Step 3 with a compound represented by Formula 8 to obtain the compound represented by Formula 1 (Step 4).

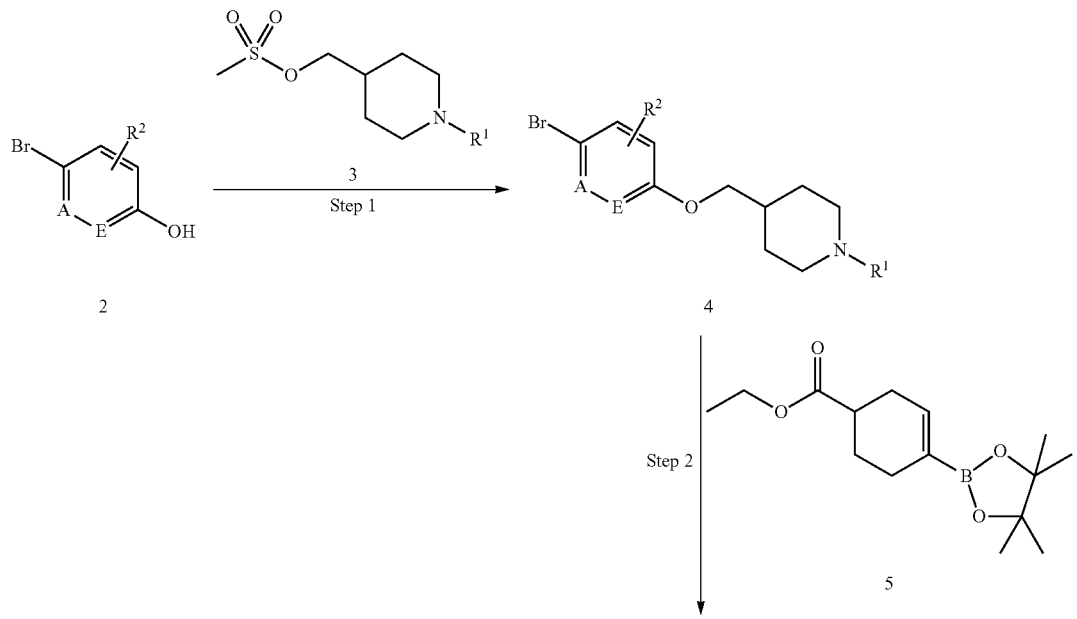

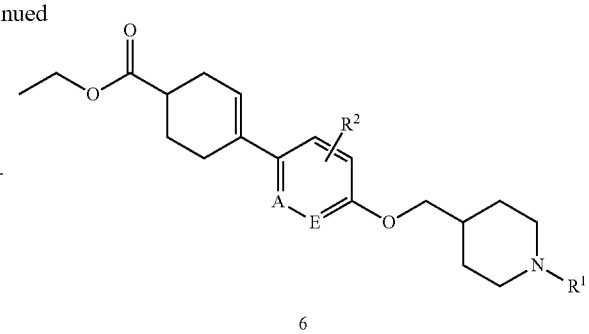

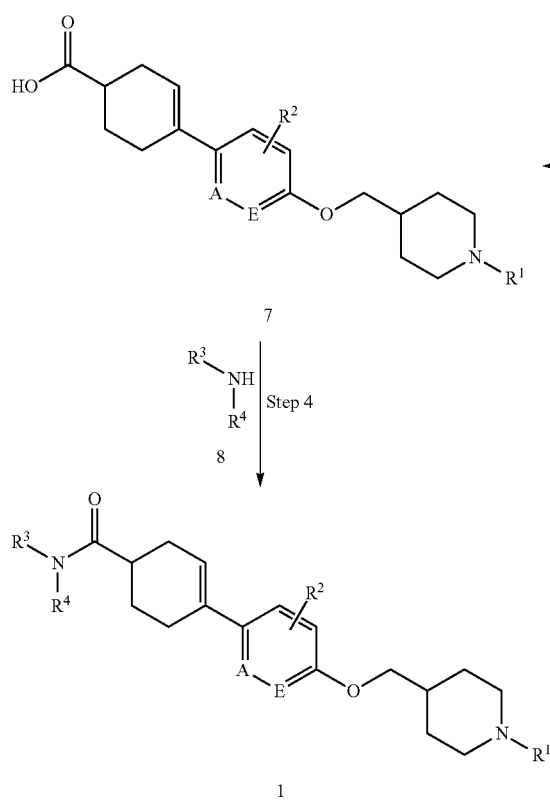

In Scheme 1, $R^1$, $R^2$, $R^3$, $R^4$, A, and E are as defined in Formula 1.

Hereinafter, respective steps of the method for preparing the compound represented by Formula 1 according to the present invention will be described in detail.

In the method for preparing the compound represented by Formula 1 according to the present invention, Step 1 includes performing a coupling reaction between a compound represented by Formula 2 and a compound represented by Formula 3 to obtain a compound represented by Formula 4.

In this case, dimethylformamide (DMF), tetrahydrofuran (THF), dichloromethane (DCM), toluene, acetonitrile, and the like may be used as the reaction solvent. Preferably, dimethylformamide (DMF) may be used.

Also, cesium carbonate ($Cs_2CO_3$), potassium hydroxide (KOH), sodium hydroxide (NaOH), lithium hydroxide (LiOH), and the like may be used as the base. Preferably, cesium carbonate ($Cs_2CO_3$) may be used.

In addition, the reaction is preferably carried out at a reaction temperature ranging from 0° C. to a boiling point of a solvent, and the reaction time is not particularly limited, but the reaction is preferably carried out for 0.5 to 10 hours.

In the method for preparing the compound represented by Formula 1 according to the present invention, Step 2 includes reacting the compound represented by Formula 4 prepared in Step 1 with a compound represented by Formula 5 in the presence of a base to obtain a compound represented by Formula 6. More specifically, Step 2 includes performing a Suzuki coupling reaction between the compound represented by Formula 4 prepared in Step 1 and a boronate compound represented by Formula 5 to obtain a compound represented by Formula 6.

In this case, at least one organic solvent selected from the group consisting of dioxane, ethanol, tetrahydrofuran (THF), diethylether, diphenylether, diisopropylether (DIPE), dimethylformamide (DMF), dimethylacetamide (DMA), dimethyl sulfoxide (DMSO), dichloromethane (DCM), chlorobenzene, toluene, and benzene may be mixed with water to form a solvent mixture, which may be used as the reaction solvent.

Also, cesium carbonate ($Cs_2CO_3$), potassium hydroxide (KOH), sodium hydroxide (NaOH), lithium hydroxide (LiOH), and the like may be used as the base. Preferably, cesium carbonate ($Cs_2CO_3$) may be used.

In addition, the reaction is preferably carried out at a reaction temperature ranging from 0° C. to a boiling point of the solvent, and a reaction time is not particularly limited, but the reaction is preferably carried out for 0.5 to 10 hours.

In the method for preparing the compound represented by Formula 1 according to the present invention, Step 3 includes reacting the compound represented by Formula 6 prepared in Step 2 with a base to prepare a compound represented by Formula 7.

In this case, at least one organic solvent selected from the group consisting of dioxane, ethanol, tetrahydrofuran (THF), diethylether, diphenylether, diisopropylether (DIPE), dimethylformamide (DMF), dimethylacetamide (DMA), dimethyl sulfoxide (DMSO), dichloromethane (DCM), chlorobenzene, toluene, and benzene may be mixed with water to form a solvent mixture, which may be used as the reaction solvent.

Also, cesium carbonate ($Cs_2CO_3$), potassium hydroxide (KOH), sodium hydroxide (NaOH), lithium hydroxide (LiOH), and the like may be used as the base. Preferably, lithium hydroxide (LiOH) may be used.

In addition, the reaction is preferably carried out at a reaction temperature ranging from 0° C. to a boiling point of the solvent, and the reaction time is not particularly limited, but the reaction is preferably carried out for 0.5 to 10 hours.

In the method for preparing the compound represented by Formula 1 according to the present invention, Step 4 includes reacting the compound represented by Formula 7 prepared in Step 3 with a compound represented by Formula 8 to obtain the compound represented by Formula 1.

In this case, at least one organic solvent selected from the group consisting of dioxane, ethanol, tetrahydrofuran (THF), diethylether, diphenylether, diisopropylether (DIPE), dimethylformamide (DMF), dimethylacetamide (DMA), dimethyl sulfoxide (DMSO), dichloromethane (DCM), chlorobenzene, toluene, and benzene may be mixed with water to form a solvent mixture, which may be used as the reaction solvent.

Also, the reaction is preferably carried out at a reaction temperature ranging from 0° C. to a boiling point of the solvent, and the reaction time is not particularly limited, but the reaction is preferably carried out for 0.5 to 10 hours.

Also, the present invention provides a pharmaceutical composition for preventing or treating metabolic diseases, which includes the compound represented by Formula 1 or the optical isomer or pharmaceutically acceptable salt thereof as an active ingredient.

The pharmaceutical composition according to the present invention activates G protein-coupled receptor 119 (GPR-119) to enhance the intracellular activity of cyclic adenosine monophosphate (cAMP), and induces the release of glucagon-like peptide-1 (GLP-1) that is a neuroendocrine protein.

In this case, the GPR-119 is a G-protein-coupled receptor (GPCR) mainly expressed in insulin-secreting cells of the pancreas. Thus, a GPR-119 expression profile has potential usefulness in treating various metabolic diseases including obesity and diabetes.

Further, the present invention provides a GPR-119 activator including the compound represented by Formula 1 or the optical isomer or pharmaceutically acceptable salt thereof as an active ingredient.

In this regard, an experiment is performed to evaluate a level of cAMP activation in response to stimulation of the GPR-119 receptor by the compound according to the present invention. As a result, it is confirmed that almost all the example compounds according to the present invention activate cAMP by 50% ($EC_{50}$) when present at a low concentration of 200 nM or less, indicating that the example compounds has an excellent effect of activation (see Table 2 for Experimental Example 1).

Also, an oral glucose tolerance test (OGTT) is performed on the compound according to the present invention. As a result, it is revealed that all the example compounds according to the present invention have a superior hypoglycemic effect, compared to GPR-119 activators (Comparative Examples 1 and 2) known in the prior art, and thus have a remarkably effective effect of activating GPR-119 in vivo (see Table 3 for Experimental Example 2).

In addition, an experiment is performed to simultaneously evaluate the weight-loss and hypoglycemic effects of the compound represented by Formula 1 according to the present invention or the optical isomer or pharmaceutically acceptable salt thereof. As a result, it is confirmed that the compound according to the present invention has a steady weight-loss effect for a 4-week period of oral administration (see FIG. 1 for Experimental Example 3). At the end of the 4-week administration, the compound according to the present invention is administered, and 2 g/kg of glucose is orally administered after 30 minutes so as to evaluate a hypoglycemic effect. As a result, it is revealed that the compound according to the present invention exhibits a remarkably excellent hypoglycemic effect (see FIG. 2 for Experimental Example 3). Accordingly, it can be seen that the compound according to the present invention simultaneously exhibits the weight-loss and hypoglycemic effects during the period of administration.

Additionally, an experiment is performed to evaluate an ability of the compound according to the present invention to induce secretion of GLP-1. As a result, it is revealed that the compound according to the present invention has an excellent effect of inducing the GLP-1 secretion (see FIG. 3 for Experimental Example 4).

Further, an acute toxicity test is performed on the compound according to the present invention in rats with cataract (Ihara's cataract rats; ICRs). As a result, it can be seen that the compound of the present invention has an $LD_{50}$ value of 2 g/kg or more in female ICR rats, indicating that the compound exhibits very low toxicity (see Experimental Example 5).

Therefore, the cyclohexene derivative according to the present invention, or the optical isomer or pharmaceutically acceptable salt thereof has a very excellent effect of activating cAMP as a GPR-119 activator, and also simultaneously exhibits the weight-loss and hypoglycemic effects, and thus may be useful for a pharmaceutical composition for preventing or treating metabolic diseases such as obesity, type 1 diabetes, type 2 diabetes, inadequate glucose tolerance, insulin resistance, hyperglycemia, hyperlipidemia, hypertriglyceridemia, hypercholesterolemia, dyslipidemia, syndrome X, etc.

For clinical administration, the compound represented by Formula 1 according to the present invention may be administered in the form of various oral and parenteral formulations. When the compound is prepared into formulations, the formulations are prepared using a filler, an extender, a binder, a wetting agent, a disintegrating agent, a diluent or vehicle (e.g., a surfactant), etc.

Solid formulations for oral administration include tablets, pills, powders, granules, capsules, troche, and the like. In this case, the solid formulations are prepared by mixing one or more of the compounds of the present invention with one or more vehicles such as starch, calcium carbonate, sucrose, lactose, gelatin, etc. In addition to simple vehicles, lubricants such as magnesium stearate and talc may also be used herein. Liquid formulations for oral administration include suspensions, solutions for internal use, emulsions, or syrups. In addition to simple diluents generally used herein, for example, water and liquid paraffin, the liquid formulations may include various vehicles, for example, wetting agents, sweetening agents, aromatics, preservatives, etc.

Preparations for parenteral administration include sterile aqueous solutions, non-aqueous solvents, suspensions, emulsions, lyophilized formulations, suppositories, etc. Propylene glycol, polyethylene glycol, vegetable oils such as olive oil, injectable esters such as ethylolate, and the like may be used as the non-aqueous solvents and suspensions. Witepsol, macrogol, Tween 61, cacao butter, laurin butter, glycerol, gelatin, and the like may be used as base materials for suppositories.

Also, the effective dose of the compound according to the present invention administered into the human body may vary according to the age, weight and sex of a patient, a mode of administration, the general physical conditions, and the severity of a disease. In general, the daily dose of the compound is in a range of approximately 0.001 to 100 mg/kg, preferably in a range of 0.01 to 35 mg/kg. In the case of an adult patient weighing 70 kg, the dose of the compound according to the present invention is generally in a range of 0.07 to 7,000 mg/day, preferably in a range of 0.7 to 2,500 mg/day, and may also administered once a day or multiple times in divided doses at certain intervals by a medical judgment of a general physician or pharmacist.

Further, the present invention provides a health functional food for preventing or improving metabolic diseases, which includes the compound represented by Formula 1 or the optical isomer or pharmaceutically acceptable salt thereof as an active ingredient.

MODE FOR INVENTION

Hereinafter, the present invention will be described in detail with reference to examples and experimental examples thereof.

However, it should be understood that the examples and experimental examples are given by way of illustration of the present invention only, and are not intended to limit the scope of the present invention.

Preparative Example 1

Preparation of ethyl 4-(trifluoromethylsulfonyloxy)cyclohex-3-enecarboxylate

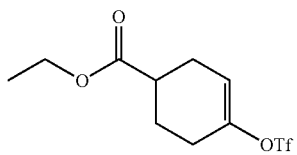 [SMILES: CCOC(=O)C1CC=C(OS(=O)(=O)C(F)(F)F)CC1]

136 μl of lithium hexamethyldisilazide (LiHMDS) was dissolved in 100 μl of THF in a 1,000 μl flask while stirring under nitrogen. After the resulting mixture was cooled to a temperature of 5° C., 17.8 g of ethyl 4-oxocyclohexanecarboxylate was slowly added dropwise, and the mixture was then stirred for 5 minutes. 41 g of 1,1,1-trifluoro-N-phenyl-N-(trifluoromethylsulfonyl)methanesulfonamide was slowly added dropwise, and then stirred for 2 hours. After the reaction was terminated, 300 μl of distilled water was slowly added, and the resulting mixture was extracted with 500 μl of ethyl acetate, washed with 100 μl of brine, dried with anhydrous magnesium sulfate, concentrated, and then isolated by silica column chromatography to obtain the title compound.

$^1$H NMR (400, CDCl$_3$): 3.69 (3H, s), 3.40 (4H, m), 3.20 (1H, m), 2.57 (2H, d), 2.48 (3H, m), 2.27 (2H, d), 1.47 (9H, s), 1.06 (3H, d)

Preparative Example 2

Preparation of ethyl 4-(4,4,5,5-tetramethyl-1,3,2-dioxaborolan-2-yl)cyclohex-3-enecarboxylate

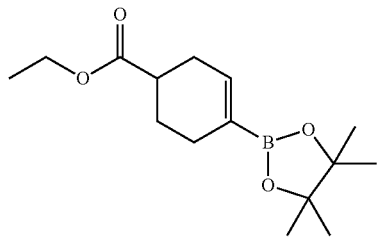 [SMILES: CCOC(=O)C1CC=C(B2OC(C)(C)C(C)(C)O2)CC1]

48.9 g of ethyl 4-(trifluoromethyl sulfonyloxy)cyclohex-3-enecarboxylate was dissolved in 300 μl of 1.4-dioxane in a 1,000 μl flask while stirring under nitrogen. 41 g of bis(pinacolate)diboron, 9 g of tetrakis(triphenylphosphine) palladium, and 32 g of potassium acetate were sequentially added dropwise thereto, and the resulting mixture was then stirred for 5 minutes. The mixture was gradually heated to a temperature of 90° C., and then stirred for 4 hours. After the reaction was terminated, the reaction mixture was cooled to room temperature. Then, 300 μl of hexane was added thereto, and filtered through celite. 300 μl of distilled water was slowly added thereto, and the reaction mixture was extracted with 500 μl of ethyl acetate, washed with 100 μl of brine, dried with anhydrous magnesium sulfate, concentrated, and then isolated by silica column chromatography to obtain the title compound.

$^1$H NMR (400, CDCl$_3$): 6.56 (1H, s), 4.16 (3H, q), 2.52 (1H, m), 2.40 (6H, m), 1.63 (2H, m), 1.29 (15H, m)

Preparative Example 3

Preparation of (1-(5-ethylpyrimidin-2-yl)piperidin-4-yl)methanol

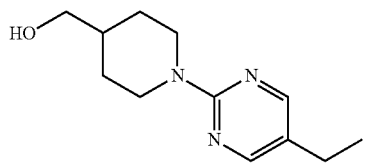 [SMILES: CCc1cnc(N2CCC(CO)CC2)nc1]

6.3 g of Piperidin-4-yl methanol was dissolved in 100 μl of DMF in a 250 μl flask, and then stirred under nitrogen. 13 μl of N,N-diisopropylethylamine was added dropwise thereto, and 5.2 g of 2-chloro-5-ethylpyrimidine was then added dropwise. The resulting mixture was gradually heated to a temperature of 60° C., and then stirred for 4 hours. After the reaction was terminated, the reaction mixture was slowly cooled to room temperature. Then, 100 μl of distilled water was slowly added thereto, and the reaction mixture was extracted with 300 μl of ethyl acetate, washed with 50 μl of brine, dried with anhydrous magnesium sulfate, and then concentrated to prepare the title compound.

$^1$H NMR (400, CDCl$_3$): 8.21 (2H, s), 4.80 (2H, d), 3.54 (2H, d), 2.94 (2H, m), 2.48 (2H, m), 1.86 (2H, m), 1.81 (1H, s), 1.26 (2H, m), 1.20 (3H, m)

Preparative Example 4

Preparation of (1-(5-ethylpyrimidin-2-yl)piperidin-4-yl)methyl methanesulfonate

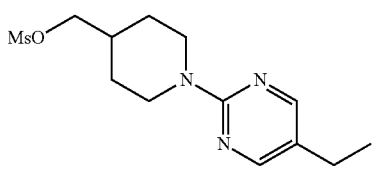 [SMILES: CCc1cnc(N2CCC(COS(C)(=O)=O)CC2)nc1]

11.4 g of (1-(5-ethylpyrimidin-2-yl)piperidin-4-yl)methanol was dissolved in 100 µl of dichloromethane in a 250 µl flask, and then stirred under nitrogen. 10 µl of triethylamine was added dropwise thereto, 4.2 µl of methanesulfonyl chloride was slowly added dropwise at 5° C., and the resulting mixture was then stirred for 30 minutes. When the reaction was terminated, 50 µl of distilled water was slowly added, and the reaction mixture was extracted with 20 µl of dichloromethane, washed with 100 µl of brine, dried with anhydrous magnesium sulfate, and then concentrated to obtain the title compound as a solid from diethyl ether.

$^1$H NMR (400, CDCl$_3$): 8.18 (2H, s), 4.77 (2H, d), 4.10 (2H, d), 3.04 (3H, m), 2.84 (2H, m), 2.46 (2H, m), 2.07 (1H, m), 1.86 (2H, d), 1.27 (2H, m), 1.19 (3H, m)

Preparative Example 5

Preparation of (1-(3-isopropyl-1,2,4-oxadiazol-5-yl)piperidin-4-yl)methanol

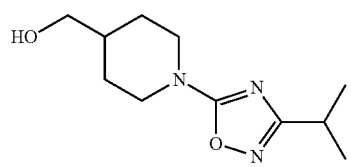 [SMILES: CC(C)c1noc(N2CCC(CO)CC2)n1]

300 g of piperidin-4-yl methanol was added to an acetonitrile/water mixture (400 µl/400 µl), and dissolved in a 1,000 µl flask while stirring under nitrogen. 330 g of sodium bicarbonate and 302 g of cyanogen bromide were added thereto, and then heated at reflux for 12 hours or more. When the reaction was completed, 100 µl of distilled water was slowly added thereto, and the resulting reaction mixture was extracted three times with 100 µl of dichloromethane, dried with anhydrous magnesium sulfate, and then concentrated. Residues were added to 2,000 µl of ethyl acetate, dissolved while stirring. Then, 175 g of N-hydroxyisobutyramide was added thereto, and 1,700 µl of a 1 M zinc chloride solution was slowly added dropwise, and the resulting mixture was then stirred for 12 hours or more. When the reaction was terminated, the resulting solids were filtered, and washed with 2,000 µl of diethyl ether. The resulting solids were added to 1,000 µl of ethanol, and dissolved while stirring, and 1,000 µl of a 4 N HCl aqueous solution was added dropwise thereto, and then heated at reflux for 4 hours or more. When the reaction was completed, the resulting reaction mixture was distilled under reduced pressure to remove ethanol, and the pH of the reaction mixture was then made basic with sodium bicarbonate. Then, the mixture was extracted three times with 1,000 µl of ethyl acetate. The extracted solution was dried with anhydrous magnesium sulfate, concentrated, and then isolated by silica column chromatography to obtain the title compound.

$^1$H NMR (400, CDCl$_3$): 4.24 (2H, d), 3.86 (2H, d), 3.15 (2H, m), 2.91 (1H, m), 1.91 (2H, m), 1.48 (2H, m), 1.43 (1H, m), 1.32 (6H, d)

Preparative Example 6

Preparation of (1-(3-isopropyl-1,2,4-oxadiazol-5-yl)piperidin-4-yl)methyl methanesulfonate

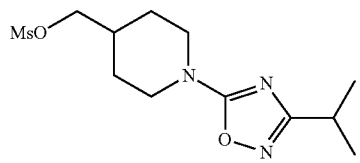 [SMILES: CC(C)c1noc(N2CCC(COS(C)(=O)=O)CC2)n1]

The title compound was prepared in the same manner as in <Preparative Example 4>, except that (1-(3-isopropyl-1,2,4-oxadiazol-5-yl)piperidin-4-yl)methanol was used instead of the (1-(5-ethylpyrimidin-2-yl)piperidin-4-yl) methyl methanesulfonate.

$^1$H NMR (400, CDCl$_3$): 4.24 (2H, d), 3.86 (2H, d), 3.15 (2H, m), 3.04 (3H, m), 2.91 (1H, m), 1.91 (2H, m), 1.48 (2H, m), 1.32 (6H, d)

Preparative Example 7

Preparation of tert-butyl 4-((methylsulfonyloxy)methyl)piperidine-1-carboxylate

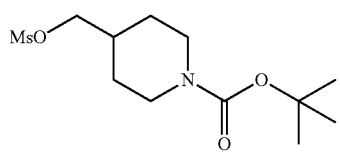 [SMILES: CC(C)(C)OC(=O)N1CCC(COS(C)(=O)=O)CC1]

The title compound was prepared in the same manner as in <Preparative Example 4>, except that tert-butyl 4-(hydroxymethyl)piperidine-1-carboxylate was used instead of the (1-(5-ethylpyrimidin-2-yl)piperidin-4-yl)methyl methanesulfonate.

$^1$H NMR (400, CDCl$_3$): 4.20 (2H, m), 4.04 (2H, d), 2.99 (3H, s), 2.70 (2H, m), 1.90 (1H, m), 1.70 (2H, m), 1.43 (9H, s), 1.10 (2H, m)

Preparative Example 8

Preparation of 2-(4-((4-bromophenoxy)methyl)piperidin-1-yl)-5-ethylpyrimidine

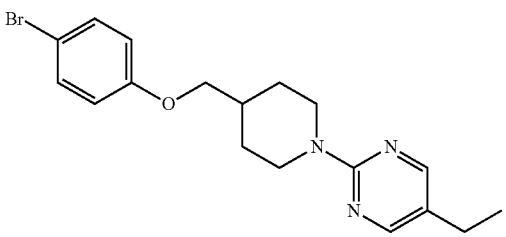 [SMILES: CCc1cnc(N2CCC(COc3ccc(Br)cc3)CC2)nc1]

50 g of (1-(5-ethylpyrimidin-2-yl)piperidin-4-yl)methyl methanesulfonate was dissolved in 300 µl of DMF in a 1,000 µl flask, and then stirred under nitrogen. 110 g of cesium carbonate was added dropwise thereto, and 30 g of 4-bromophenol was also added dropwise. The resulting mixture was stirred at 60° C. for 5 hours. When the reaction was terminated, the mixture was slowly cooled to room temperature. Solids formed by slowly adding 500 µl of distilled water at 0° C. were filtered, and then dried to obtain the title compound as a solid.

$^1$H NMR (400, CDCl$_3$): 8.21 (2H, s), 7.32 (2H, d), 6.85 (2H, d), 4.80 (2H, d), 3.54 (2H, m), 2.48 (2H, m), 1.86 (2H, d), 1.81 (1H, m), 1.26 (2H, m), 1.20 (3H, m)

Preparative Example 9

Preparation of 5-(4-((4-bromophenoxy)methyl)piperidin-1-yl)-3-isopropyl-1,2,4-oxadiazole

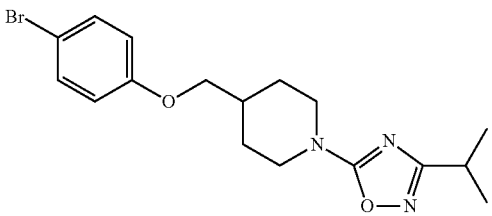

The title compound was prepared in the same manner as in <Preparative Example 8>, except that (1-(3-isopropyl-1,2,4-oxadiazol-5-yl)piperidin-4-yl)methyl methanesulfonate was used instead of the (1-(5-ethylpyrimidin-2-yl)piperidin-4-yl)methyl methanesulfonate.

$^1$H NMR (400, CDCl$_3$): 7.32 (2H, d), 6.85 (2H, d), 4.24 (2H, d), 3.86 (2H, d), 3.15 (1H, m), 1.91 (2H, m), 1.48 (2H, m), 1.32 (6H, d)

Preparative Example 10

Preparation of tert-butyl 4-((4-bromophenoxy)methyl)piperidine-1-carboxylate

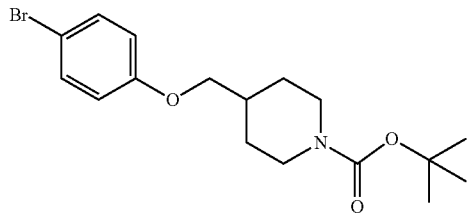 [SMILES: CC(C)(C)OC(=O)N1CCC(COc2ccc(Br)nc2)CC1]

The title compound was prepared in the same manner as in <Preparative Example 8>, except that tert-butyl 4-((methylsulfonyloxy)methyl)piperidine-1-carboxylate was used instead of the (1-(5-ethylpyrimidin-2-yl)piperidin-4-yl)methyl methanesulfonate.

$^1$H NMR (400, CDCl$_3$): 7.32 (2H, d), 6.85 (2H, d), 4.15 (2H, d), 3.86 (2H, d), 2.78 (2H, m), 2.12 (1H, m), 1.87 (9H, s), 1.32 (2H, m)

Preparative Example 11

Preparation of tert-butyl 4-((6-bromopyridin-3-yloxy)methyl)piperidine-1-carboxylate

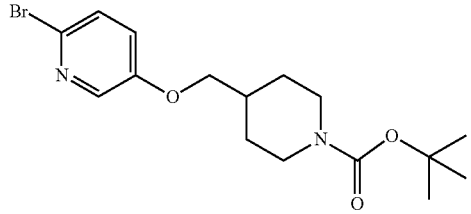

The title compound was prepared in the same manner as in <Preparative Example 8>, except that tert-butyl 4-((methylsulfonyloxy)methyl)piperidine-1-carboxylate was used instead of the (1-(5-ethylpyrimidin-2-yl)piperidin-4-yl)methyl methanesulfonate, and 2-bromo-5-hydroxypyridine was used instead of the 4-bromophenol.

$^1$H NMR (400, CDCl$_3$): 8.21 (1H, s), 7.38 (1H, d), 7.15 (1H, d), 4.15 (2H, d), 3.85 (2H, d), 2.78 (2H, m), 2.12 (1H, m), 1.87 (2H, m), 1.48 (9H, s), 1.32 (2H, m)

Preparative Example 12

Preparation of tert-butyl 4-((5-bromopyridin-2-yloxy)methyl)piperidine-1-carboxylate

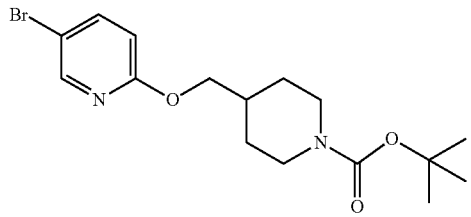 [SMILES: CC(C)(C)OC(=O)N1CCC(COc2ccc(Br)cn2)CC1]

6.6 g of tert-butyl 4-(hydroxymethyl)piperidine-1-carboxylate was dissolved in 100 µl of DMF in a 250 µl flask, and then stirred under nitrogen. 1.85 g of sodium hydride was added dropwise at 5° C., and the temperature was slowly raised to room temperature. After 4 hours, 50 µl of distilled water was slowly added at 0° C., and resulting solids were filtered and dried. The resulting solids were re-crystallized in hexane to obtain the title compound $^1$H NMR (400, CDCl$_3$): 8.14 (1H, s), 7.63 (1H, d), 6.71 (1H, d), 4.15 (2H, d), 3.85 (2H, d), 2.78 (2H, m), 2.12 (1H, m), 1.87 (2H, m), 1.48 (9H, s), 1.32 (2H, m)

Preparative Example 13

Preparation of 5-(4-((6-chloropyridin-3-yloxy)methyl)piperidin-1-yl)-3-isopropyl-1,2,4-oxadiazole

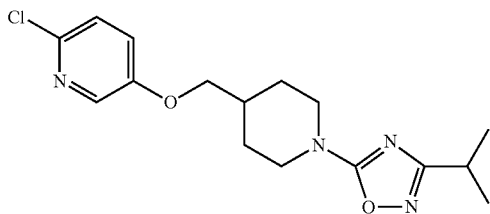

The title compound was prepared in the same manner as in <Preparative Example 8>, except that (1-(3-isopropyl-1,2,4-oxadiazol-5-yl)piperidin-4-yl)methyl methanesulfonate was used instead of the (1-(5-ethylpyrimidin-2-yl)piperidin-4-yl)methyl methanesulfonate, and 2-chloro-5-hydroxypyridine was used instead of the 4-bromophenol.

$^1$H NMR (400, CDCl$_3$): 8.21 (1H, s), 7.38 (1H, d), 7.15 (1H, d), 4.24 (2H, d), 3.86 (2H, d), 3.15 (2H, m), 2.91 (1H, m), 1.48 (2H, m), 1.32 (6H, d)

Preparative Example 14

Preparation of tert-butyl 4-((4-bromo-2-fluorophenoxy)methyl)piperidine-1-carboxylate

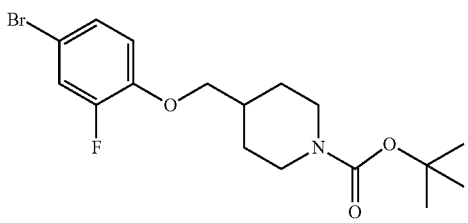 [SMILES: CC(C)(C)OC(=O)N1CCC(COc2ccc(Br)cc2F)CC1]

The title compound was prepared in the same manner as in <Preparative Example 8>, except that tert-butyl 4-((methylsulfonyloxy)methyl)piperidine-1-carboxylate was used instead of the (1-(5-ethylpyrimidin-2-yl)piperidin-4-yl)methyl methanesulfonate, and 2-fluoro-4-bromophenol was used instead of the 4-bromophenol.

$^1$H NMR (400, CDCl$_3$): 7.13 (1H, s), 7.08 (1H, d), 6.89 (1H, m), 4.15 (2H, d), 3.85 (2H, d), 2.78 (2H, m), 2.12 (1H, m), 1.87 (2H, m), 1.48 (9H, s), 1.32 (2H, m)

Preparative Example 15

Preparation of tert-butyl 4-((4-bromo-3-fluorophenoxy)methyl)piperidine-1-carboxylate

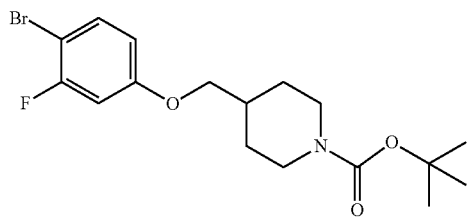 [SMILES: CC(C)(C)OC(=O)N1CCC(COc2ccc(Br)c(F)c2)CC1]

The title compound was prepared in the same manner as in <Preparative Example 8>, except that tert-butyl 4-((methylsulfonyloxy)methyl)piperidine-1-carboxylate was used instead of the (1-(5-ethylpyrimidin-2-yl)piperidin-4-yl)methyl methanesulfonate, and 3-fluoro-4-bromophenol was used instead of the 4-bromophenol.

$^1$H NMR (400, CDCl$_3$): 7.13 (1H, s), 6.65 (1H, d), 6.59 (1H, m), 4.15 (2H, d), 3.85 (2H, d), 2.78 (2H, m), 2.12 (1H, m), 1.87 (2H, m), 1.48 (9H, s), 1.32 (2H, m)

Preparative Example 16

Preparation of 5-(4-((4-bromo-2-fluorophenoxy)methyl)piperidin-1-yl)-3-isopropyl-1,2,4-oxadiazole

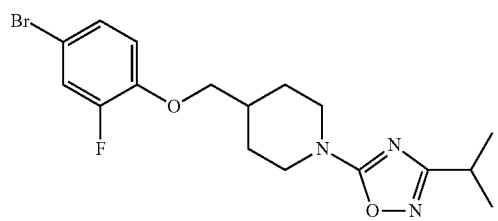 [SMILES: CC(C)c1noc(N2CCC(COc3ccc(Br)cc3F)CC2)n1]

The title compound was prepared in the same manner as in <Preparative Example 8>, except that (1-(3-isopropyl-1,2,4-oxadiazol-5-yl)piperidin-4-yl)methyl methanesulfonate was used instead of the (1-(5-ethylpyrimidin-2-yl)piperidin-4-yl)methyl methanesulfonate, and 2-fluoro-4-bromophenol was used instead of the 4-bromophenol.

$^1$H NMR (400, CDCl$_3$): 7.13 (1H, s), 7.08 (1H, d), 6.89 (1H, m), 4.24 (2H, d), 3.86 (2H, d), 3.15 (2H, m), 2.91 (1H, m), 1.91 (2H, m), 1.48 (2H, s), 1.32 (6H, d)

Preparative Example 17

Preparation of tert-butyl 4-((4-(4-(ethoxycarbonyl)cyclohex-1-enyl)phenoxy)methyl)piperidine-1-carboxylate

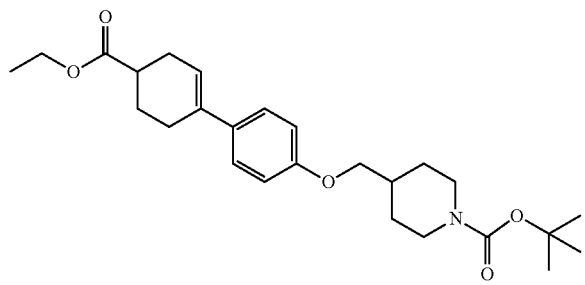 [SMILES: CCOC(=O)C1CC=C(c2ccc(OCC3CCN(C(=O)OC(C)(C)C)CC3)cc2)CC1]

5 g of tert-butyl 4-((4-bromophenoxy)methyl)piperidine-1-carboxylate was dissolved in a tetrahydrofuran/water/ethanol mixture (100 μl/20 μl/10 μl) in a 500 μl flask, and stirred under nitrogen. 550 mg of (1,1'-bis(diphenylphosphino)ferrocene)palladium(II) dichloride, 11 g of cesium carbonate, and 4.2 g of ethyl 4-(4,4,5,5-tetramethyl-1,3,2-dioxaborolan-2-yl)cyclohex-3-enecarboxylate were sequentially added dropwise thereto. The resulting mixture was gradually heated to a temperature of 80° C., and then stirred for 5 hours. After the reaction was terminated, the reaction mixture was slowly cooled to room temperature, 100 μl of distilled water was slowly added thereto, and the reaction mixture was filtered through celite. The filtrate was extracted with 300 μl of ethyl acetate, washed with 100 μl of brine, dried with anhydrous magnesium sulfate, concentrated, and then isolated by silica column chromatography to prepare the title compound.

$^1$H NMR (400, CDCl$_3$): 7.32 (2H, d), 6.85 (2H, d), 6.02 (1H, s), 4.10 (2H, m), 4.15 (2H, d), 3.85 (2H, d), 2.61 (1H, m), 2.47 (4H, m), 2.21 (2H, m), 1.98 (1H, m), 1.86 (2H, m), 1.61 (9H, s), 1.31 (2H, m), 1.20 (3H, m)

Preparative Example 18

Preparation of 4-(4-((1-(tert-butoxycarbonyl)piperidin-4-yl)methoxy)phenyl)cyclohex-3-enecarboxyilc acid

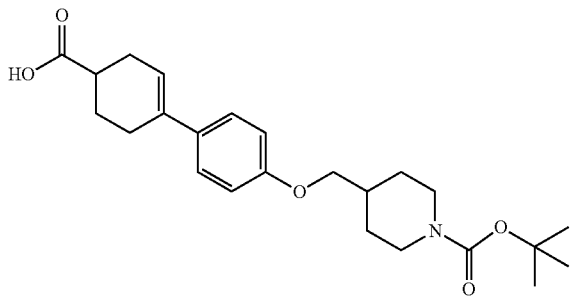 [SMILES: CC(C)(C)OC(=O)N1CCC(COc2ccc(C3=CCC(C(=O)O)CC3)cc2)CC1]

3.2 g of tert-butyl 4-((4-(4-(ethoxycarbonyl)cyclohex-1-enyl)phenoxy)methyl)piperidine-1-carboxylate was dissolved in a tetrahydrofuran/water/ethanol mixture (100 μl/50 μl/10 μl) in a 250 μl flask, and stirred under nitrogen. 2.4 g of lithium hydroxide monohydrate was added dropwise thereto, and then reacted at room temperature for 18 hours. After the reaction was terminated, the pH of the resulting reaction mixture was adjusted to pH 1 to 2 using concentrated HCl. The resulting solids were filtered, and dried to prepare the desired title compound.

$^1$H NMR (400, CDCl$_3$): 7.32 (2H, d), 6.85 (2H, d), 6.02 (1H, s), 4.15 (2H, m), 3.85 (2H, d), 2.61 (1H, m), 2.47 (4H, m), 2.21 (2H, m), 1.98 (1H, m), 1.86 (2H, m), 1.61 (9H, s), 1.31 (2H, m)

Preparative Example 19

Preparation of ethyl 4-(4-((1-(5-ethylpyrimidin-2-yl)piperidin-4-yl)methoxy)phenyl)cyclohex-3-enecarboxylate

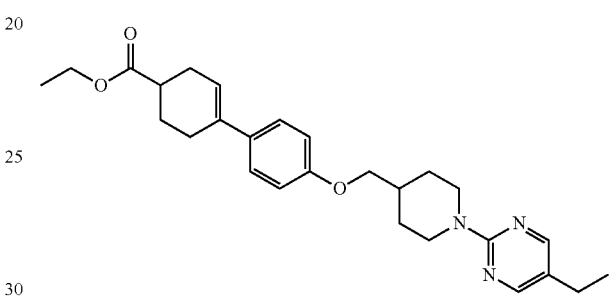

The title compound was prepared in the same manner as in <Preparative Example 17>, except that 2-(4-((4-bromophenoxy)methyl)piperidin-1-yl)-5-ethylpyrimidine was used instead of the tert-butyl 4-((4-bromophenoxy)methyl)piperidine-1-carboxylate.

$^1$H NMR (400, CDCl$_3$): 8.21 (2H, s), 7.32 (2H, d), 6.85 (2H, d), 6.02 (1H, s), 4.80 (2H, d), 4.19 (2H, m), 3.54 (2H, d), 2.94 (2H, m), 2.61 (1H, m), 2.48 (2H, m), 2.47 (4H, m), 2.21 (2H, m), 1.86 (2H, d), 1.81 (1H, m), 1.29 (3H, m), 1.26 (2H, m), 1.20 (3H, m)

Preparative Example 20

Preparation of 4-(4-((1-(5-ethylpyrimidin-2-yl)piperidin-4-yl)methoxy)phenyl)cyclohex-3-enecarboxyilc acid

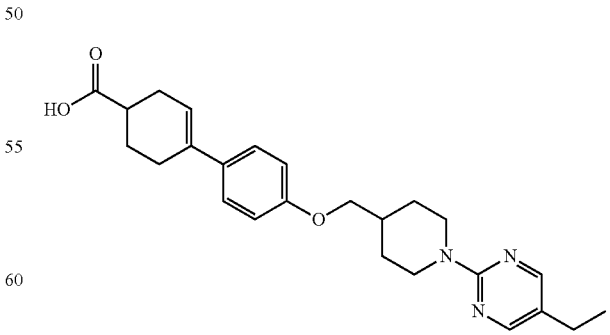

The title compound was prepared in the same manner as in <Preparative Example 18>, except that ethyl 4-(4-((1-(5-ethylpyrimidin-2-yl)piperidin-4-yl)methoxy)phenyl)cyclohex-3-enecarboxylate was used instead of the tert-butyl 4-((4-(4-(ethoxycarbonyl)cyclohex-1-enyl)phenoxy)methyl)piperidine-1-carboxylate.

¹H NMR (400, CDCl₃): 8.21 (2H, s), 7.32 (2H, d), 6.85 (2H, d), 6.02 (1H, s), 4.80 (2H, d), 3.54 (2H, m), 2.94 (2H, m), 2.61 (1H, m), 2.48 (2H, m), 2.47 (4H, m), 2.21 (2H, m), 1.86 (2H, d), 1.81 (1H, m), 1.26 (2H, m), 1.20 (3H, m)

Preparative Example 21

Preparation of ethyl 4-(4-((1-(3-isopropyl-1,2,4-oxadiazol-5-yl)piperidin-4-yl)methoxy)phenyl)cyclohex-3-enecarboxylate

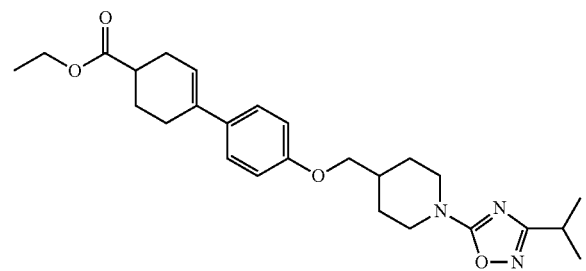 [SMILES: CCOC(=O)C1CC=C(c2ccc(OCC3CCN(c4nc(C(C)C)no4)CC3)cc2)CC1]

The title compound was prepared in the same manner as in <Preparative Example 17>, except that 5-(4-((4-bromophenoxy)methyl)piperidin-1-yl)-3-isopropyl-1,2,4-oxadiazole was used instead of the tert-butyl 4-((4-bromophenoxy)methyl)piperidine-1-carboxylate.

¹H NMR (400, CDCl₃): 7.32 (2H, d), 6.85 (2H, d), 6.02 (1H, s), 4.24 (2H, d), 4.19 (2H, m), 3.86 (2H, d), 3.15 (2H, m), 2.91 (1H, m), 2.61 (1H, m), 2.47 (4H, m), 2.21 (2H, m), 1.91 (2H, m), 1.48 (2H, m), 1.32 (6H, d), 1.29 (3H, m)

Preparative Example 22

Preparation of 4-(4-((1-(3-isopropyl-1,2,4-oxadiazol-5-yl)piperidin-4-yl)methoxy)phenyl)cyclohex-3-enecarboxyilc acid

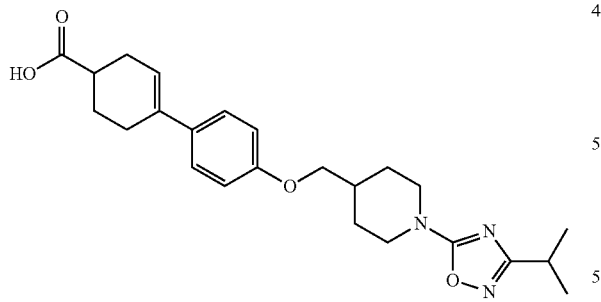

The title compound was prepared in the same manner as in <Preparative Example 18>, except that ethyl 4-(4-((1-(3-isopropyl-1,2,4-oxadiazol-5-yl)piperidin-4-yl)methoxy)phenyl)cyclohex-3-enecarboxylate was used instead of the tert-butyl 4-((4-(4-(ethoxycarbonyl)cyclohex-1-enyl)phenoxy)methyl)piperidine-1-carboxylate.

¹H NMR (400, CDCl₃): 7.32 (2H, d), 6.85 (2H, d), 6.02 (1H, s), 4.24 (2H, d), 3.86 (2H, d), 3.15 (2H, m), 2.91 (1H, m), 2.61 (1H, m), 2.47 (4H, m), 2.21 (2H, m), 1.91 (2H, m), 1.48 (2H, m), 1.32 (6H, d)

Preparative Example 23

Preparation of tert-butyl 4-((6-(4-(ethoxycarbonyl)cyclohex-1-enyl)pyridin-3-yloxy)methyl)piperidine-1-carboxylate

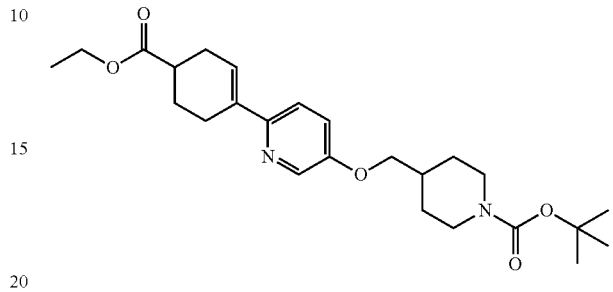

The title compound was prepared in the same manner as in <Preparative Example 17>, except that tert-butyl 4-((6-bromopyridin-3-yloxy)methyl)piperidine-1-carboxylate was used instead of the tert-butyl 4-((4-bromophenoxy)methyl)piperidine-1-carboxylate.

¹H NMR (400, CDCl₃): 8.21 (1H, s), 7.38 (1H, d), 7.15 (1H, d), 6.02 (1H, s), 4.19 (2H, m), 4.15 (2H, d), 3.85 (2H, d), 2.78 (2H, m), 2.61 (1H, m), 2.47 (4H, m), 2.21 (2H, m), 2.12 (1H, m), 1.87 (2H, m), 1.48 (9H, s), 1.32 (2H, m), 1.29 (3H, m)

Preparative Example 24

Preparation of 4-(5-((1-(tert-butoxycarbonyl)piperidin-4-yl)methoxy)pyridin-2-yl)cyclohex-3-enecarboxyilc acid

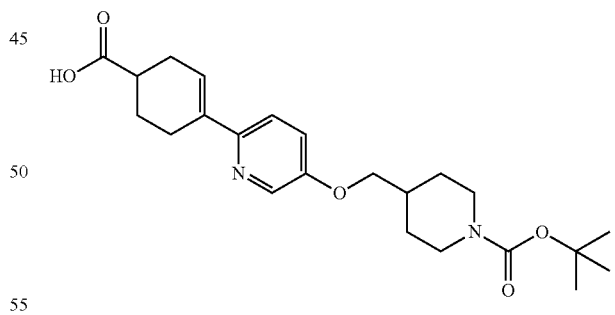

The title compound was prepared in the same manner as in <Preparative Example 18>, except that tert-butyl 4-((6-(4-(ethoxycarbonyl)cyclohex-1-enyl)pyridin-3-yloxy)methyl)piperidine-1-carboxylate was used instead of the tert-butyl 4-((4-(4-(ethoxycarbonyl)cyclohex-1-enyl)phenoxy)methyl)piperidine-1-carboxylate.

¹H NMR (400, CDCl₃): 8.21 (1H, s), 7.38 (1H, d), 7.15 (1H, d), 6.02 (1H, s), 4.15 (2H, m), 3.85 (2H, d), 2.78 (2H, m), 2.61 (1H, m), 2.47 (4H, m), 2.21 (2H, m), 2.12 (1H, m), 1.87 (2H, m), 1.48 (9H, s), 1.32 (2H, m)

Preparative Example 25

Preparation of ethyl 4-(5-((1-(3-isopropyl-1,2,4-oxadiazol-5-yl)piperidin-4-yl)methoxy)pyridin-2-yl)cyclohex-3-enecarboxylate

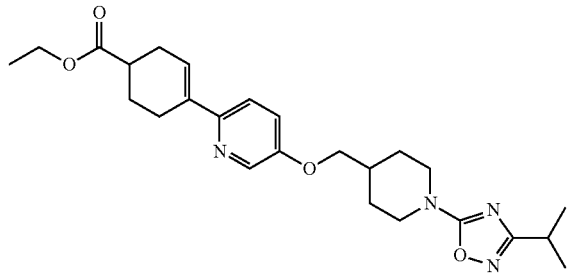

The title compound was prepared in the same manner as in <Preparative Example 17>, except that 5-(4-((6-chloropyridin-3-yloxy)methyl)piperidin-1-yl)-3-isopropyl-1,2,4-oxadiazole was used instead of the tert-butyl 4-((4-bromophenoxy)methyl)piperidine-1-carboxylate.

¹H NMR (400, CDCl₃): 8.21 (1H, s), 7.38 (1H, d), 7.15 (1H, d), 6.02 (1H, s), 4.24 (2H, m), 4.19 (2H, m), 3.86 (2H, d), 3.15 (2H, m), 2.91 (1H, m), 2.61 (1H, m), 2.47 (4H, m), 2.21 (2H, m), 1.91 (2H, m), 1.48 (2H, m), 1.32 (6H, d), 1.29 (3H, m)

Preparative Example 26

Preparation of 4-(5-((1-(3-isopropyl-1,2,4-oxadiazol-5-yl)piperidin-4-yl)methoxy)pyridin-2-yl)cyclohex-3-enecarboxyilc acid

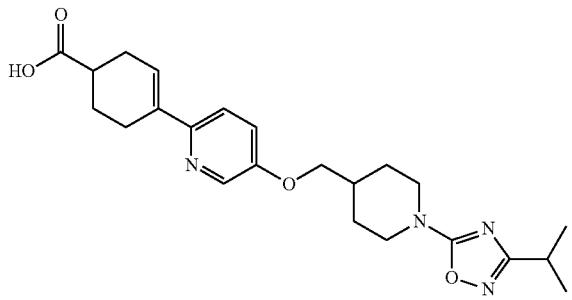 [SMILES: CC(C)c1noc(N2CCC(COc3ccc(C4=CCC(C(=O)O)CC4)cc3)CC2)n1]

The title compound was prepared in the same manner as in <Preparative Example 18>, except that 4-(5-((1-(3-isopropyl-1,2,4-oxadiazol-5-yl)piperidin-4-yl)methoxy)pyridin-2-yl)cyclohex-3-enecarboxyilc acid was used instead of the tert-butyl 4-((4-(4-(ethoxycarbonyl)cyclohex-1-enyl)phenoxy)methyl)piperidine-1-carboxylate.

¹H NMR (400, CDCl₃): 8.21 (1H, s), 7.38 (1H, d), 7.15 (1H, d), 6.02 (1H, s), 4.24 (2H, d), 3.86 (2H, d), 3.15 (2H, m), 2.91 (1H, m), 2.61 (1H, m), 2.47 (4H, m), 2.21 (2H, m), 1.91 (2H, m), 1.48 (2H, m), 1.32 (6H, d)

Preparative Example 27

Preparation of tert-butyl 4-((5-(4-(ethoxycarbonyl)cyclohex-1-enyl)pyridin-2-yloxy)methyl)piperidine-1-carboxylate

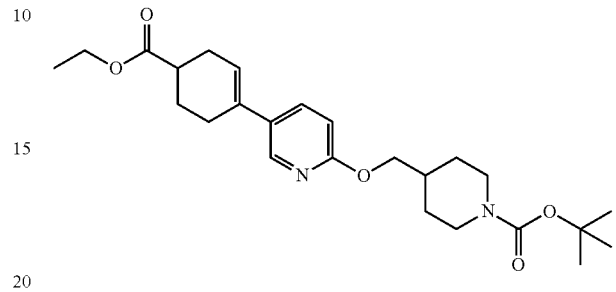

The title compound was prepared in the same manner as in <Preparative Example 17>, except that tert-butyl 4-((5-bromopyridin-2-yloxy)methyl)piperidine-1-carboxylate was used instead of the tert-butyl 4-((4-bromophenoxy)methyl)piperidine-1-carboxylate.

¹H NMR (400, CDCl₃): 8.14 (1H, s), 7.63 (1H, d), 6.71 (1H, d), 6.02 (1H, s), 4.19 (2H, m), 4.15 (2H, d), 3.85 (2H, d), 2.78 (2H, m), 2.61 (1H, m), 2.47 (4H, m), 2.21 (2H, m), 2.12 (1H, m), 1.87 (2H, m), 1.48 (9H, s), 1.32 (2H, m), 1.29 (3H, m)

Preparative Example 28

Preparation of 4-(6-((1-(tert-butoxycarbonyl)piperidin-4-yl)methoxy)pyridin-3-yl)cyclohex-3-enecarboxyilc acid

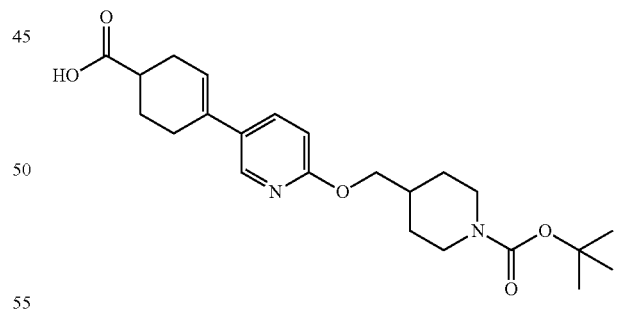

The title compound was prepared in the same manner as in <Preparative Example 18>, except that tert-butyl 4-((5-(4-(ethoxycarbonyl)cyclohex-1-enyl)pyridin-2-yloxy)methyl)piperidine-1-carboxylate was used instead of the tert-butyl 4-((4-(4-(ethoxycarbonyl)cyclohex-1-enyl)phenoxy)methyl)piperidine-1-carboxylate.

¹H NMR (400, CDCl₃): 8.14 (1H, s), 7.63 (1H, d), 6.71 (1H, d), 6.02 (1H, s), 4.15 (2H, d), 3.85 (2H, d), 2.78 (2H, m), 2.61 (1H, m), 2.47 (4H, m), 2.21 (2H, m), 2.12 (1H, m), 1.87 (2H, m), 1.48 (9H, s), 1.32 (2H, m)

Preparative Example 29

Preparation of tert-butyl 4-((4-(4-(ethoxycarbonyl)cyclohex-1-enyl)-2-fluorophenoxy)methyl)piperidine-1-carboxylate

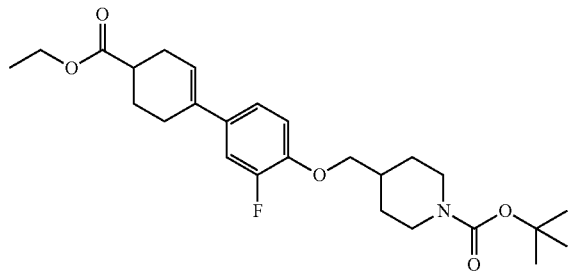 [SMILES: CCOC(=O)C1CC=C(c2ccc(OCC3CCN(C(=O)OC(C)(C)C)CC3)c(F)c2)CC1]

The title compound was prepared in the same manner as in <Preparative Example 17>, except that tert-butyl 4-((4-bromo-2-fluorophenoxy)methyl)piperidine-1-carboxylate was used instead of the tert-butyl 4-((4-bromophenoxy)methyl)piperidine-1-carboxylate.

$^1$H NMR (400, CDCl$_3$): 7.13 (1H, d), 7.08 (1H, d), 6.89 (1H, m), 6.02 (1H, s), 4.19 (2H, m), 4.15 (2H, d), 3.85 (2H, d), 2.78 (2H, m), 2.61 (1H, m), 2.47 (4H, m), 2.21 (2H, m), 2.12 (1H, m), 1.87 (2H, m), 1.48 (9H, s), 1.32 (2H, m), 1.29 (3H, m)

Preparative Example 30

Preparation of 4-(4-((1-(tert-butoxycarbonyl)piperidin-4-yl)methoxy)-3-fluorophenyl)cyclohex-3-enecarboxyilc acid

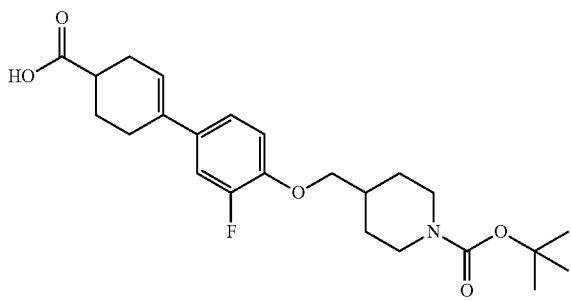 [SMILES: CC(C)(C)OC(=O)N1CCC(COc2ccc(C3=CCC(C(=O)O)CC3)cc2F)CC1]

The title compound was prepared in the same manner as in <Preparative Example 18>, except that tert-butyl 4-((4-(4-(ethoxycarbonyl)cyclohex-1-enyl)-2-fluorophenoxy)methyl)piperidine-1-carboxylate was used instead of the tert-butyl 4-((4-(4-(ethoxycarbonyl)cyclohex-1-enyl)phenoxy)methyl)piperidine-1-carboxylate.

$^1$H NMR (400, CDCl$_3$): 7.13 (1H, d), 7.08 (1H, d), 6.89 (1H, m), 6.02 (1H, s), 4.15 (2H, m), 3.85 (2H, d), 2.78 (2H, m), 2.61 (1H, m), 2.47 (4H, m), 2.21 (2H, m), 2.12 (1H, m), 1.87 (2H, m), 1.48 (9H, s), 1.32 (2H, m)

Preparative Example 31

Preparation of ethyl 4-(3-fluoro-4-((1-(3-isopropyl-1,2,4-oxadiazol-5-yl)piperidin-4-yl)methoxy)phenyl)cyclohex-3-enecarboxylate

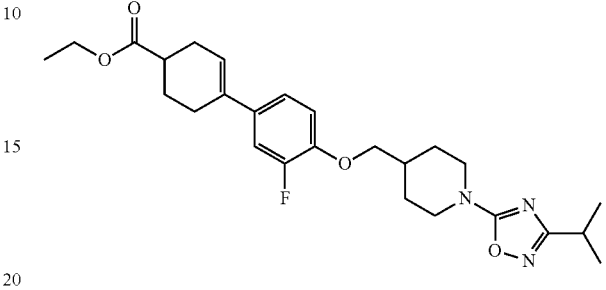

The title compound was prepared in the same manner as in <Preparative Example 17>, except that 5-(4-((4-bromo-2-fluorophenoxy)methyl)piperidin-1-yl)-3-isopropyl-1,2,4-oxadiazole was used instead of the tert-butyl 4-((4-bromophenoxy)methyl)piperidine-1-carboxylate.

$^1$H NMR (400, CDCl$_3$): 7.13 (1H, d), 7.08 (1H, d), 6.89 (1H, m), 6.02 (1H, s), 4.24 (2H, d), 4.19 (2H, m), 3.86 (2H, d), 3.15 (2H, m), 2.91 (1H, m), 2.61 (1H, m), 2.47 (4H, m), 2.21 (2H, m), 1.91 (2H, m), 1.48 (2H, m), 1.32 (6H, d), 1.29 (3H, m)

Preparative Example 32

Preparation of 4-(3-fluoro-4-((1-(3-isopropyl-1,2,4-oxadiazol-5-yl)piperidin-4-yl)methoxy)phenyl)cyclohex-3-enecarboxyilc acid

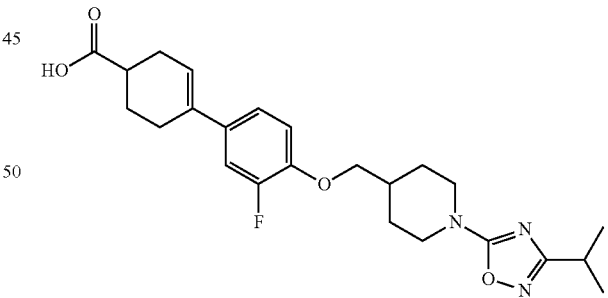

The title compound was prepared in the same manner as in <Preparative Example 18>, except that ethyl 4-(3-fluoro-4-((1-(3-isopropyl-1,2,4-oxadiazol-5-yl)piperidin-4-yl)methoxy)phenyl)cyclohex-3-enecarboxylate was used instead of the tert-butyl 4-((4-(4-(ethoxycarbonyl)cyclohex-1-enyl)phenoxy)methyl)piperidine-1-carboxylate.

$^1$H NMR (400, CDCl$_3$): 7.13 (1H, d), 7.08 (1H, d), 6.89 (1H, m), 6.02 (1H, s), 4.24 (2H, d), 3.86 (2H, d), 3.15 (2H, m), 2.91 (1H, m), 2.61 (1H, m), 2.47 (4H, m), 2.21 (2H, m), 1.91 (2H, m), 1.48 (2H, m), 1.32 (6H, d)

Preparative Example 33

Preparation of tert-butyl 4-((4-(4-(ethoxycarbonyl)cyclohex-1-enyl)-3-fluorophenoxy)methyl)piperidine-1-carboxylate

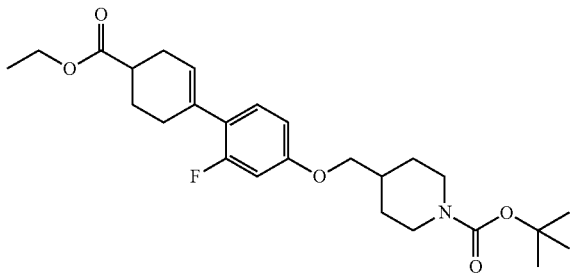 [SMILES: CCOC(=O)C1CC=C(c2ccc(OCC3CCN(C(=O)OC(C)(C)C)CC3)cc2F)CC1]

The title compound was prepared in the same manner as in <Preparative Example 17>, except that tert-butyl 4-((4-bromo-3-fluorophenoxy)methyl)piperidine-1-carboxylate was used instead of the tert-butyl 4-((4-bromophenoxy)methyl)piperidine-1-carboxylate.

$^1$H NMR (400, CDCl$_3$): 7.13 (1H, m), 6.65 (1H, d), 6.59 (1H, d), 6.02 (1H, s), 4.19 (2H, m), 4.15 (2H, d), 3.85 (2H, d), 2.78 (2H, m), 2.61 (1H, m), 2.47 (4H, m), 2.21 (2H, m), 2.12 (1H, m), 1.87 (2H, m), 1.48 (9H, s), 1.32 (2H, m), 1.29 (3H, m)

Preparative Example 34

Preparation of 4-(4-((1-(tert-butoxycarbonyl)piperidin-4-yl)methoxy)-2-fluorophenyl)cyclohex-3-enecarboxyilc acid

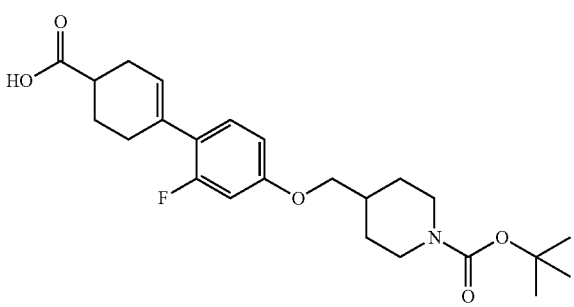 [SMILES: CC(C)(C)OC(=O)N1CCC(COc2ccc(C3=CCC(C(=O)O)CC3)c(F)c2)CC1]

The title compound was prepared in the same manner as in <Preparative Example 18>, except that tert-butyl 4-((4-(4-(ethoxycarbonyl)cyclohex-1-enyl)-3-fluorophenoxy)methyl)piperidine-1-carboxylate was used instead of the tert-butyl 4-((4-(4-(ethoxycarbonyl)cyclohex-1-enyl)phenoxy)methyl)piperidine-1-carboxylate.

$^1$H NMR (400, CDCl$_3$): 7.13 (1H, m), 6.65 (1H, d), 6.59 (1H, d), 6.02 (1H, s), 4.15 (2H, d), 3.85 (2H, d), 2.78 (2H, m), 2.61 (1H, m), 2.47 (4H, m), 2.21 (2H, m), 2.12 (1H, m), 1.87 (2H, m), 1.48 (9H, s), 1.32 (2H, m)

Example 1

Preparation of tert-butyl 4-((4-(4-((R)-1-hydroxypropan-2-ylcarbamoyl)cyclohex-1-enyl)phenoxy)methyl)piperidine-1-carboxylate

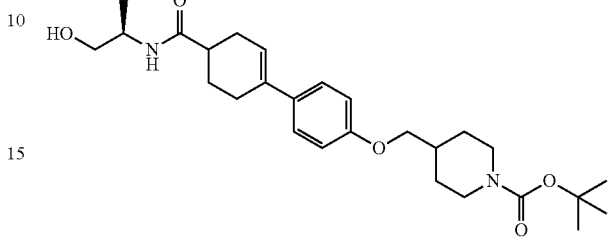

200 mg of 4-(4-((1-(tert-butoxycarbonyl)piperidin-4-yl)methoxy)phenyl)cyclohex-3-enecarboxyilc acid was dissolved in 20 µl of DMF in a 100 µl flask, and stirred under nitrogen. 140 mg of EDCI and 110 mg of HOBt were sequentially added dropwise thereto, and the resulting mixture was then additionally stirred for 10 minutes. 72 mg of (R)-2-amino-1-propanol was added dropwise thereto, and the mixture was then stirred at room temperature for 5 hours. After the reaction was terminated, 50 µl of distilled water was slowly added at 0° C., and the resulting solids were filtered, and dried to obtain a desired compound as a white solid (Amount obtained: 167 mg/Yield: 73%).

$^1$H NMR (400, CDCl$_3$): 7.31 (2H, d), 6.85 (2H, d), 6.05 (1H, s), 5.75 (1H, d) 4.15 (3H, m), 3.85 (2H, d), 3.72 (1H, m), 3.52 (1H, m), 2.78 (2H, m), 2.50 (5H, m), 2.12 (1H, m), 1.95 (1H, m), 1.88 (2H, m), 1.52 (9H, s), 1.30 (2H, m), 1.25 (3H, d)

Example 2

Preparation of tert-butyl 4-((4-(4-(cyclopropylcarbamoyl)cyclohex-1-enyl)phenoxy)methyl)piperidine-1-carboxylate

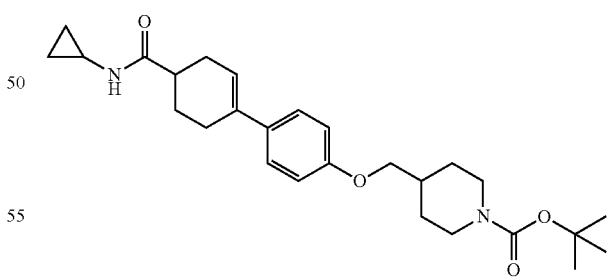

The title compound was prepared in the same manner as in <Example 1>, except that cyclopropylamine is used instead of the (R)-2-amino-1-propanol (Amount obtained: 180 mg/Yield: 80%).

$^1$H NMR (400, CDCl$_3$): 7.31 (2H, d), 6.86 (2H, d), 6.05 (1H, s), 5.75 (1H, d), 4.15 (3H, m), 3.81 (2H, d), 2.78 (3H, m), 3.45 (5H, m), 2.08 (2H, m), 1.98 (1H, m), 1.82 (2H, m), 1.52 (9H, s), 1.28 (2H, m), 0.78 (2H, d), 0.55 (2H, m)

Example 3

Preparation of tert-butyl 4-((4-(4-(2,2-difluoroethyl-carbamoyl)cyclohex-1-enyl)phenoxy)methyl)piperidine-1-carboxylate

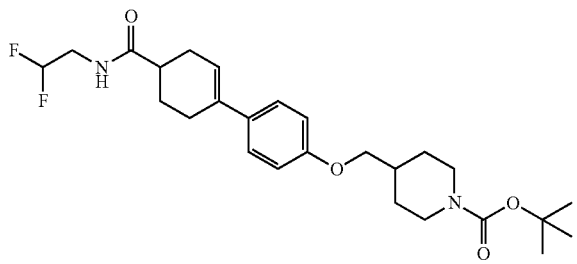 [SMILES: CC(C)(C)OC(=O)N1CCC(COc2ccc(C3=CCC(C(=O)NCC(F)F)CC3)cc2)CC1]

The title compound was prepared in the same manner as in <Example 1>, except that 2,2-difluoroethylamine was used instead of the (R)-2-amino-1-propanol (Amount obtained: 120 mg/Yield: 72%)

$^1$H NMR (400, CDCl$_3$): 7.31 (2H, d), 6.85 (2H, d), 6.05 (1H, s), 5.87 (1H, m), 4.15 (2H, m), 3.85 (2H, d), 3.68 (2H, m), 2.78 (2H, m), 2.50 (5H, m), 2.12 (1H, m), 1.85 (4H, m), 1.52 (9H, s), 1.30 (2H, m)

Example 4

Preparation of tert-butyl 4-((4-(4-((R)-2,3-dihydroxypropylcarbamoyl)cyclohex-1-enyl)phenoxy)methyl)piperidine-1-carboxylate

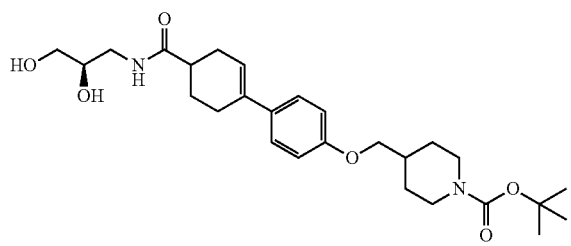

The title compound was prepared in the same manner as in <Example 1>, except that (R)-3-amino-1,2-propanediol was used instead of the (R)-2-amino-1-propanol (Amount obtained: 132 mg/Yield: 68%).

$^1$H NMR (400, CDCl$_3$): 7.32 (2H, d), 6.82 (2H, d), 6.04 (2H, s), 4.18 (2H, m), 3.85 (3H, m), 3.52 (4H, m), 2.98 (2H, m), 2.78 (2H, m), 2.52 (5H, m), 2.12 (1H, m), 1.95 (1H, m), 1.88 (2H, m), 1.52 (9H, s), 1.30 (2H, m)

Example 5

Preparation of tert-butyl 4-((4-(4-((R)-3-hydroxy-pyrrolidine-1-carbonyl)cyclohex-1-enyl)phenoxy)methyl)piperidine-1-carboxylate

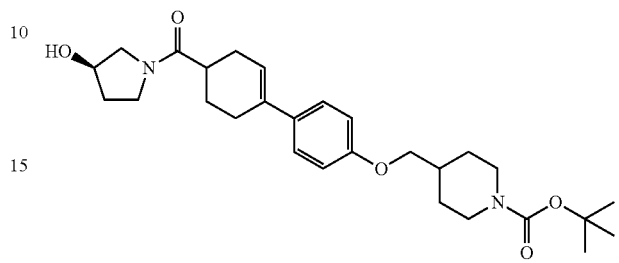

The title compound was prepared in the same manner as in <Example 1>, except that (R)-(+)-3-pyrrolidinol was used instead of the (R)-2-amino-1-propanol (Amount obtained: 130 mg/Yield: 56%).

$^1$H NMR (400, CDCl$_3$): 7.31 (2H, d), 6.85 (2H, d), 6.05 (1H, s), 4.60 (1H, d), 4.15 (2H, m), 3.85 (2H, d), 3.62 (4H, m), 2.72 (3H, m), 2.58 (3H, m), 2.34 (1H, m), 1.98 (8H, m), 1.52 (9H, s), 1.30 (2H, m)

Example 6

Preparation of tert-butyl 4-((4-(4-((3-hydroxypropyl)(methyl)carbamoyl)cyclohex-1-enyl)phenoxy)methyl)piperidine-1-carboxylate

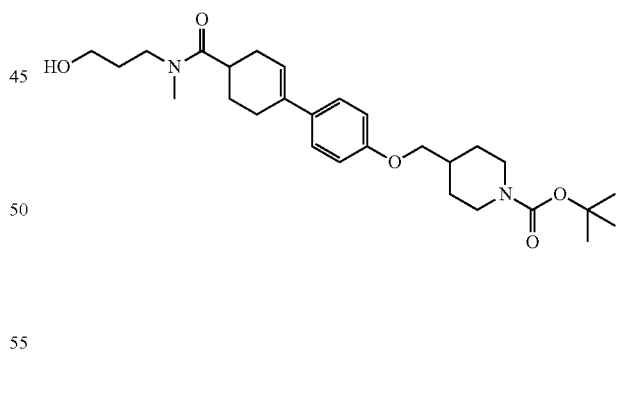

The title compound was prepared in the same manner as in <Example 1>, except that 3-(methylamino)-1-propanol was used instead of the (R)-2-amino-1-propanol (Amount obtained: 110 mg/Yield: 58%).

$^1$H NMR (400, CDCl$_3$): 7.32 (2H, d), 6.87 (2H, d), 6.05 (1H, s), 4.18 (2H, m), 3.95 (1H, m), 3.82 (2H, m), 3.62 (2H, m), 3.54 (2H, m), 3.12 (3H, s), 2.78 (3H, m), 2.50 (3H, m), 2.32 (1H, m), 1.95 (6H, m), 1.78 (2H, m), 1.52 (9H, s), 1.28 (2H, m)

Example 7

Preparation of tert-butyl 4-((4-(4-(morpholine-4-carbonyl)cyclohex-1-enyl)phenoxy)methyl)piperidine-1-carboxylate

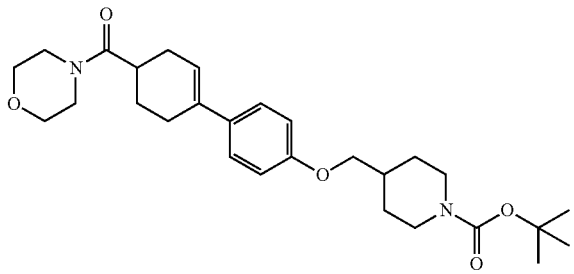 [SMILES: CC(C)(C)OC(=O)N1CCC(COc2ccc(C3=CCC(C(=O)N4CCOCC4)CC3)cc2)CC1]

The title compound was prepared in the same manner as in <Example 1>, except that morpholine was used instead of the (R)-2-amino-1-propanol (Amount obtained: 200 mg/Yield: 80%).

$^1$H NMR (400, CDCl$_3$): 7.31 (2H, d), 6.85 (2H, d), 6.05 (1H, s), 4.17 (2H, m), 3.83 (2H, m), 3.72 (4H, m), 3.58 (4H, m), 2.79 (3H, m), 2.59 (3H, m), 2.31 (1H, m), 2.02 (3H, m), 1.89 (2H, m), 1.52 (9H, s), 1.33 (2H, m).

Example 8

Preparation of 4-(4-((1-(5-ethylpyrimidin-2-yl)piperidin-4-yl)methoxy)phenyl)-N-((R)-1-hydroxypropan-2-yl)cyclohex-3-enecarboxamide

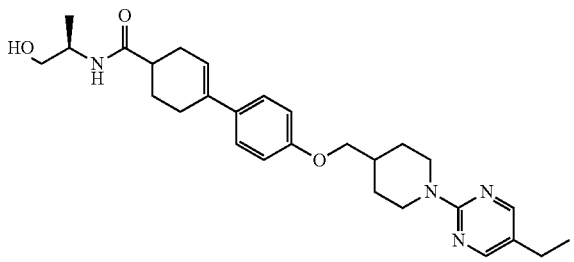 [SMILES: CCc1cnc(N2CCC(COc3ccc(C4=CCC(C(=O)N[C@H](C)CO)CC4)cc3)CC2)nc1]

250 mg of 4-(4-((1-(5-ethylpyrimidin-2-yl)piperidin-4-yl)methoxy)phenyl)cyclohex-3-enecarboxyilc acid was dissolved in 20 μl of DMF in a 100 μl flask, and stirred under nitrogen. 140 mg of EDCI and 110 mg of HOBt were sequentially added dropwise thereto, and the resulting mixture was additionally stirred for 10 minutes. 0.1 μl of (R)-2-amino-1-propanol was added dropwise thereto, and the mixture was then stirred at room temperature for 5 hours. After the reaction was terminated, 50 μl of distilled water was slowly added at 0° C., and the resulting solids were filtered, and dried to obtain a desired compound as a white solid (Amount obtained: 230 mg/Yield: 82%).

$^1$H NMR (400, CDCl$_3$): 8.19 (2H, s), 7.31 (2H, d), 6.85 (2H, d), 6.03 (1H, s), 5.75 (1H, d), 4.79 (2H, d), 4.15 (1H, m), 3.85 (2H, m), 3.72 (1H, m), 3.58 (1H, m), 2.94 (2H, t), 2.82 (1H, m), 2.48 (7H, m), 2.14 (2H, m), 1.88 (3H, m), 1.38 (2H, m), 1.23 (3H, t)

Example 9

Preparation of 4-(4-((1-(5-ethylpyrimidin-2-yl)piperidin-4-yl)methoxy)phenyl)-N-(3-hydroxypropyl)cyclohex-3-enecarboxamide

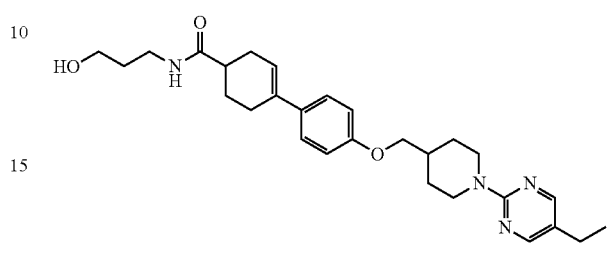

The title compound was prepared in the same manner as in <Example 8>, except that 3-amino-1-propanol was used instead of the (R)-2-amino-1-propanol (Amount obtained: 220 mg/Yield: 79%).

$^1$H NMR (400, CDCl$_3$): 8.19 (2H, s), 7.31 (2H, d), 6.85 (2H, d), 6.05 (1H, s), 5.95 (1H, t), 4.75 (2H, d), 3.85 (2H, d), 3.68 (2H, m), 3.48 (2H, m), 3.14 (1H, m), 2.94 (2H, m), 2.42 (7H, m), 2.12 (2H, m), 1.98 (3H, m), 1.72 (2H, m), 1.38 (2H, m), 1.21 (3H, t)

Example 10

Preparation of tert-butyl 4-((6-(4-((R)-2,3-dihydroxypropylcarbamoyl)cyclohex-1-enyl)pyridin-3-yloxy)methyl)piperidine-1-carboxylate

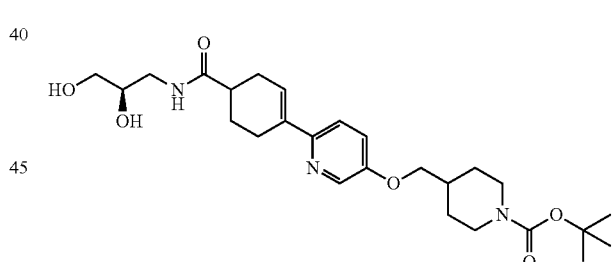

200 mg of 4-(5-((1-(tert-butoxycarbonyl)piperidin-4-yl)methoxy)pyridin-2-yl)cyclohex-3-enecarboxyilc acid was dissolved in 25 μl of DMF, and stirred. 140 mg of EDCI and 110 mg of HOBt were sequentially added dropwise thereto, and the resulting mixture was then additionally stirred for 10 minutes. 0.15 μl of (R)-3-amino-1,2-propanediol was added dropwise thereto, and the mixture was stirred at room temperature for 3 hours. When the reaction was terminated, 50 μl of distilled water was slowly added at 0° C., and the resulting solids were filtered, and dried to obtain a desired compound as a white solid (Amount obtained: 160 mg/Yield: 68%).

$^1$H NMR (400, CDCl$_3$): 8.22 (1H, s), 7.33 (1H, d), 7.18 (1H, d), 6.52 (1H, s), 6.28 (1H, m), 4.18 (2H, m), 3.85 (2H, d), 3.68 (1H, m), 3.72 (3H, m), 2.52 (4H, m), 2.18 (1H, m), 1.92 (4H, m), 1.34 (9H, s), 1.30 (2H, m)

Example 11

Preparation of tert-butyl 4-((6-(4-((S)-1-hydroxypropan-2-ylcarbamoyl)cyclohex-1-enyl)pyridin-3-yloxy)methyl)piperidine-1-carboxylate

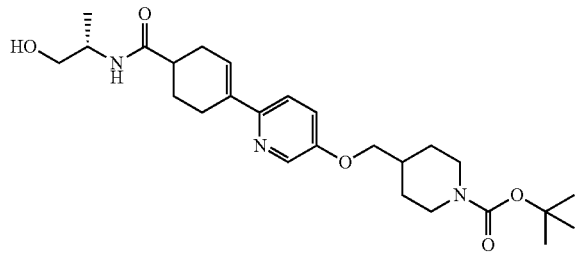 [SMILES: C[C@@H](CO)NC(=O)C1CC=C(c2ccc(OCC3CCN(C(=O)OC(C)(C)C)CC3)cn2)CC1]

The title compound was prepared in the same manner as in <Example 10>, except that (S)-2-amino-1-propanol was used instead of the (R)-3-amino-1,2-propanediol (Amount obtained: 155 mg/Yield: 70%).

$^1$H NMR (400, CDCl$_3$): 8.24 (1H, s), 7.33 (1H, d), 7.16 (1H, d), 6.54 (1H, s), 5.78 (1H, m), 4.18 (3H, m), 3.87 (2H, d), 3.64 (2H, m), 2.72 (3H, m), 2.52 (4H, m), 2.14 (1H, m), 1.84 (4H, m), 1.68 (1H, m), 1.48 (9H, s), 1.31 (2H, m), 1.20 (3H, d)

Example 12

Preparation of N-((R)-2,3-dihydroxypropyl)-4-(4-((1-(5-ethylpyrimidin-2-yl)piperidin-4-yl)methoxy)phenyl)cyclohex-3-enecarboxamide

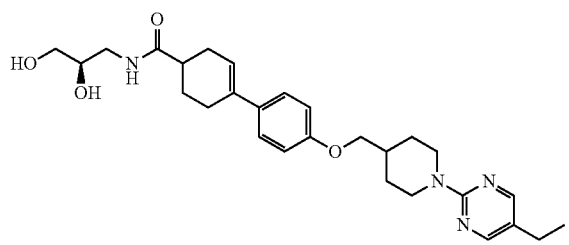

The title compound was prepared in the same manner as in <Example 8>, except that (R)-3-amino-1,2-propanediol was used instead of the (R)-2-amino-1-propanol (Amount obtained: 200 mg/Yield: 85%).

$^1$H NMR (400, DMSO-$d_6$): 8.23 (2H, s), 7.81 (1H, m), 7.33 (2H, d), 6.86 (2H, d), 6.05 (1H, s), 4.73 (1H, m), 4.67 (2H, d), 4.49 (1H, t), 3.85 (2H, d), 3.32 (4H, m), 2.88 (2H, t), 2.42 (7H, m), 1.98 (5H, m), 1.62 (2H, m), 1.18 (4H, m)

Example 13

Preparation of (4-(4-((1-(5-ethylpyrimidin-2-yl)piperidin-4-yl)methoxy)phenyl)cyclohex-3-enyl)(morpholino)methanone

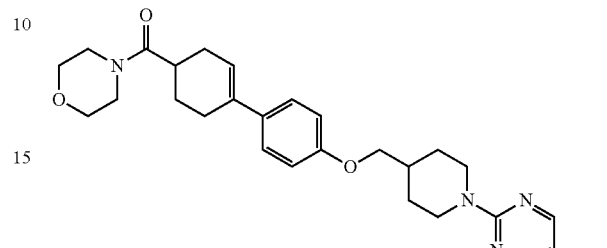

The title compound was prepared in the same manner as in <Example 8>, except that morpholine was used instead of the (R)-2-amino-1-propanol (Amount obtained: 175 mg/Yield: 65%).

$^1$H NMR (400, CDCl$_3$): 8.19 (2H, s), 7.33 (2H, d), 6.87 (2H, d), 6.06 (1H, s), 4.80 (2H, d), 3.85 (2H, d), 3.72 (6H, d), 3.58 (2H, m), 2.96 (2H, t), 2.78 (1H, m), 2.52 (7H, m), 2.28 (1H, m), 1.98 (5H, m), 1.38 (2H, m), 1.21 (3H, t)

Example 14

Preparation of tert-butyl 4-((6-(4-(1,3-dihydroxypropan-2-ylcarbamoyl)cyclohex-1-enyl)pyridin-3-yloxy)methyl)piperidine-1-carboxylate

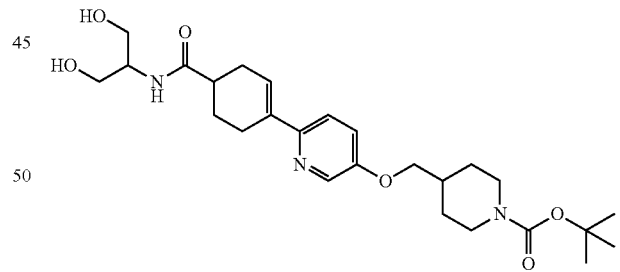

The title compound was prepared in the same manner as in <Example 10>, except that 2-amino-1,3-propanediol was used instead of the (R)-3-amino-1,2-propanediol (Amount obtained: 195 mg/Yield: 85%).

$^1$H NMR (400, CDCl$_3$): 8.22 (1H, s), 7.32 (1H, d), 7.16 (1H, d), 6.49 (2H, m), 4.17 (2H, m), 4.03 (1H, m), 3.89 (6H, m), 2.76 (3H, m), 2.52 (4H, m), 2.15 (1H, m), 1.99 (3H, m), 1.84 (2H, m), 1.67 (1H, m), 1.48 (9H, s), 1.34 (2H, m)

Example 15

Preparation of N-(1,3-dihydroxypropan-2-yl)-4-(4-((1-(5-ethylpyrimidin-2-yl)piperidin-4-yl)methoxy)phenyl)cyclohex-3-enecarboxamide

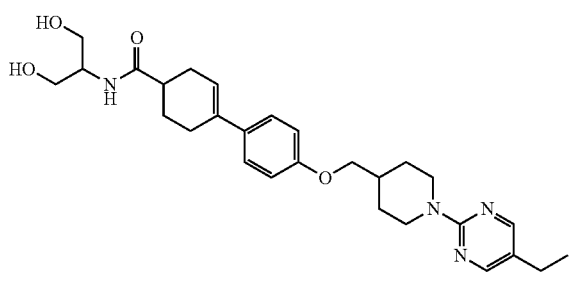 [SMILES: CCc1cnc(N2CCC(COc3ccc(C4=CCC(C(=O)NC(CO)CO)CC4)cc3)CC2)nc1]

The title compound was prepared in the same manner as in <Example 8>, except that 2-amino-1,3-propanediol was used instead of the (R)-2-amino-1-propanol (Amount obtained: 165 mg/Yield: 72%).

$^1$H NMR (400, DMSO-$_{d6}$): 8.22 (2H, s), 7.50 (1H, d), 7.33 (2H, d), 6.88 (2H, d), 4.63 (4H, m), 3.84 (2H, d), 3.73 (1H, m), 2.86 (2H, t), 2.43 (2H, m), 2.36 (2H, m), 1.98 (5H, m), 1.21 (7H, m), 1.98 (5H, m)

Example 16

Preparation of (4-(4-((1-(5-ethylpyrimidin-2-yl)piperidin-4-yl)methoxy)phenyl)cyclohex-3-enyl)((R)-3-hydroxypyrrolidin-1-yl)methanone

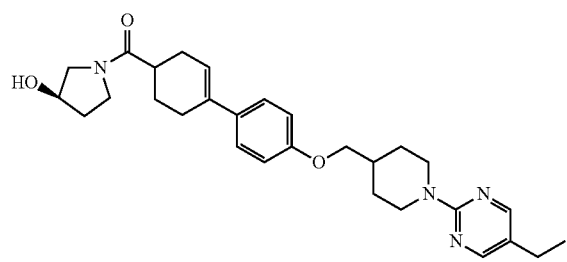 [SMILES: CCc1cnc(N2CCC(COc3ccc(C4=CCC(C(=O)N5CC[C@@H](O)C5)CC4)cc3)CC2)nc1]

The title compound was prepared in the same manner as in <Example 8>, except that (R)-(+)-3-pyrrolidinol was used instead of the (R)-2-amino-1-propanol (Amount obtained: 165 mg/Yield: 72%).

$^1$H NMR (400, CDCl$_3$): 8.19 (2H, s), 7.33 (2H, d), 6.87 (2H, d), 6.07 (1H, s), 4.80 (2H, d), 4.55 (1H, d), 3.85 (2H, d), 4.55 (5H, m), 2.93 (2H, t), 2.48 (8H, m), 2.05 (7H, m), 1.61 (2H, m), 1.38 (2H, m), 1.18 (3H, m)

Example 17

Preparation of N-((R)-2,3-dihydroxypropyl)-4-(4-((1-(3-isopropyl-1,2,4-oxadiazol-5-yl)piperidin-4-yl)methoxy)phenyl)cyclohex-3-enecarboxamide

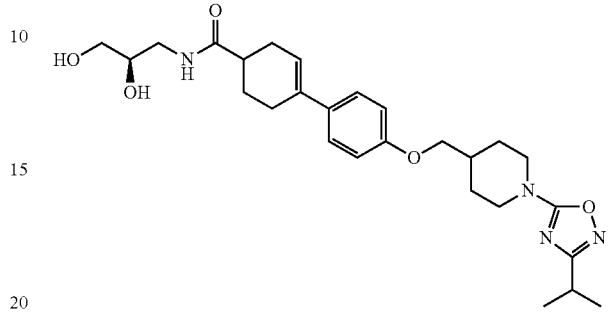

200 mg of 4-(4-((1-(3-isopropyl-1,2,4-oxadiazol-5-yl)piperidin-4-yl)methoxy)phenyl)cyclohex-3-enecarboxyilc acid was dissolved in 25 μl of DMF, and stirred. 140 mg of EDCI and 110 mg of HOBt were sequentially added dropwise thereto, and the resulting mixture was then additionally stirred for 10 minutes. 0.15 μl of (R)-3-amino-1,2-propanediol was added dropwise thereto, and the mixture was stirred at room temperature for 3 hours. After the reaction was terminated, 50 μl of distilled water was slowly added at 0° C., and the resulting solids were filtered, and dried to obtain a desired compound as a white solid (Amount obtained: 187 mg/Yield: 83%).

$^1$H NMR (400, CDCl$_3$): 7.32 (2H, d), 6.86 (2H, d), 6.15 (1H, t), 6.03 (1H, s), 4.23 (2H, d), 3.85 (2H, d), 3.80 (1H, m), 3.58 (2H, m), 3.48 (2H, m), 3.14 (4H, m), 2.92 (1H, m), 2.49 (5H, m), 2.09 (2H, m), 1.94 (3H, m), 1.43 (2H, m), 1.30 (6H, d)

Example 18

Preparation of N-((S)-2,3-dihydroxypropyl)-4-(4-((1-(3-isopropyl-1,2,4-oxadiazol-5-yl)piperidin-4-yl)methoxy)phenyl)cyclohex-3-enecarboxamide

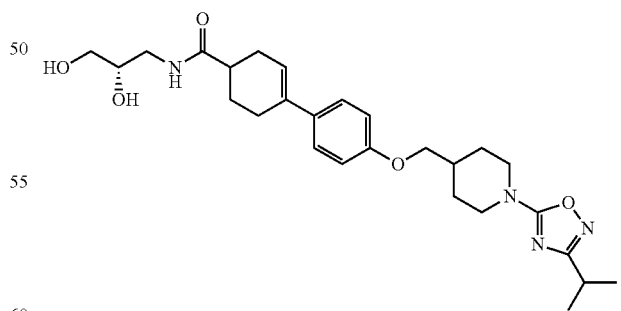

The title compound was prepared in the same manner as in <Example 17>, except that (S)-3-amino-1,2-propanediol was used instead of the (R)-3-amino-1,2-propanediol (Amount obtained: 155 mg/Yield: 70%).

$^1$H NMR (400, CDCl$_3$): 7.32 (2H, d), 6.83 (2H, d), 6.21 (1H, t), 6.03 (1H, s), 4.20 (2H, d), 3.85 (2H, d), 3.80 (1H, m), 3.58 (2H, m), 3.48 (2H, m), 3.14 (4H, m), 2.92 (1H, m), 2.49 (5H, m), 2.09 (2H, m), 1.94 (3H, m), 1.43 (2H, m), 1.30 (6H, d)

Example 19

Preparation of N-((S)-1-hydroxypropan-2-yl)-4-(4-((1-(3-isopropyl-1,2,4-oxadiazol-5-yl)piperidin-4-yl)methoxy)phenyl)cyclohex-3-enecarboxamide

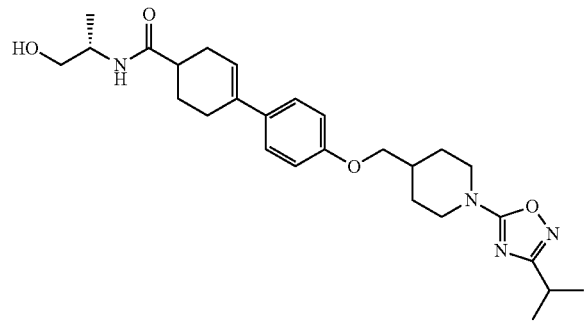 [SMILES: CC(C)c1noc(N2CCC(COc3ccc(C4=CCC(C(=O)N[C@@H](C)CO)CC4)cc3)CC2)n1]

The title compound was prepared in the same manner as in <Example 17>, except that (S)-2-amino-1-propanol was used instead of the (R)-3-amino-1,2-propanediol (Amount obtained: 130 mg/Yield: 62%).

¹H NMR (400, CDCl₃): 7.33 (2H, d), 6.84 (2H, d), 6.04 (1H, s), 5.74 (1H, s), 4.23 (2H, d), 4.14 (1H, s), 3.84 (2H, d), 3.73 (1H, m), 3.69 (1H, m), 3.14 (2H, m), 2.91 (1H, m), 2.53 (5H, m), 2.08 (3H, m), 1.94 (3H, m), 1.47 (2H, m), 1.30 (6H, d), 1.20 (3H, m)

Example 20

Preparation of N-((R)-1-hydroxypropan-2-yl)-4-(4-((1-(3-isopropyl-1,2,4-oxadiazol-5-yl)piperidin-4-yl)methoxy)phenyl)cyclohex-3-enecarboxamide

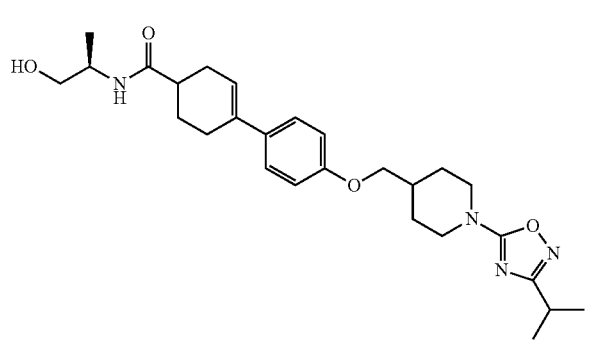 [SMILES: CC(C)c1noc(N2CCC(COc3ccc(C4=CCC(C(=O)N[C@H](C)CO)CC4)cc3)CC2)n1]

The title compound was prepared in the same manner as in <Example 17>, except that (R)-2-amino-1-propanol was used instead of the (R)-3-amino-1,2-propanediol (Amount obtained: 150 mg/Yield: 71%).

¹H NMR (400, CDCl₃): 7.33 (2H, d), 6.84 (2H, d), 6.04 (1H, s), 5.74 (1H, s), 4.23 (2H, d), 4.14 (1H, s), 3.84 (2H, d), 3.73 (1H, m), 3.69 (1H, m), 3.14 (2H, m), 2.91 (1H, m), 2.53 (5H, m), 2.08 (3H, m), 1.94 (3H, m), 1.47 (2H, m), 1.30 (6H, d), 1.20 (3H, m)

Example 21

Preparation of 4-(4-((1-(5-ethylpyrimidin-2-yl)piperidin-4-yl)methoxy)phenyl)-N-(2-hydroxyethyl)-N-methylcyclohex-3-enecarboxamide

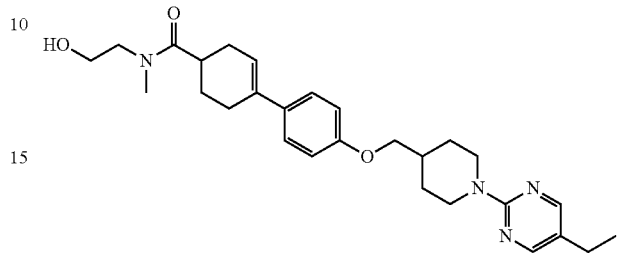

The title compound was prepared in the same manner as in <Example 8>, except that 2-(methylamino)ethanol was used instead of the (R)-2-amino-1-propanol (Amount obtained: 187 mg/Yield: 81%).

¹H NMR (400, CDCl₃): 8.19 (2H, s), 7.34 (2H, d), 6.87 (2H, d), 6.07 (1H, s), 4.80 (2H, d), 3.85 (4H, m), 3.63 (2H, m), 3.18 (3H, s), 2.96 (2H, t), 2.89 (1H, m), 2.48 (5H, m), 2.06 (5H, m), 1.38 (2H, m), 1.21 (3H, m)

Example 22

Preparation of N-(3-hydroxy-2,2-dimethylpropyl)-4-(4-((1-(3-isopropyl-1,2,4-oxadiazol-5-yl)piperidin-4-yl)methoxy)phenyl)cyclohex-3-enecarboxamide

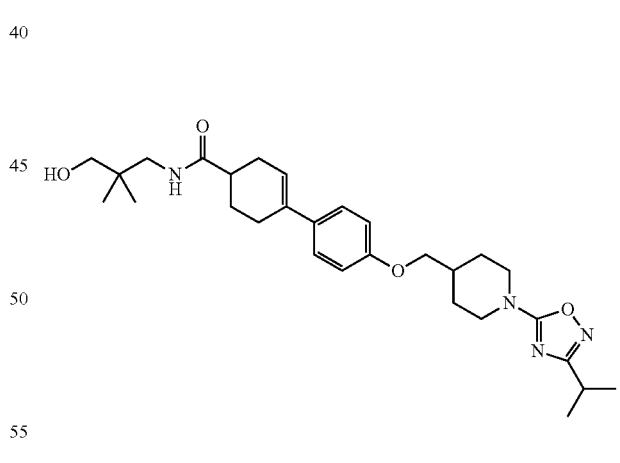

The title compound was prepared in the same manner as in <Example 17>, except that 3-amino-2,2-dimethylpropan-1-ol was used instead of the (R)-3-amino-1,2-propanediol (Amount obtained: 195 mg/Yield: 89%).

¹H NMR (400, MeOD): 7.65 (1H, s), 7.31 (2H, d), 6.85 (2H, d), 6.02 (1H, s), 4.18 (2H, d), 3.87 (2H, d), 3.15 (6H, m), 2.86 (1H, m), 2.46 (5H, m), 2.04 (5H, m), 1.48 (2H, m), 1.28 (6H, d), 0.89 (6H, s)

Example 23

Preparation of N-(1,3-dihydroxypropan-2-yl)-4-(4-((1-(3-isopropyl-1,2,4-oxadiazol-5-yl)piperidin-4-yl)methoxy)phenyl)cyclohex-3-enecarboxamide

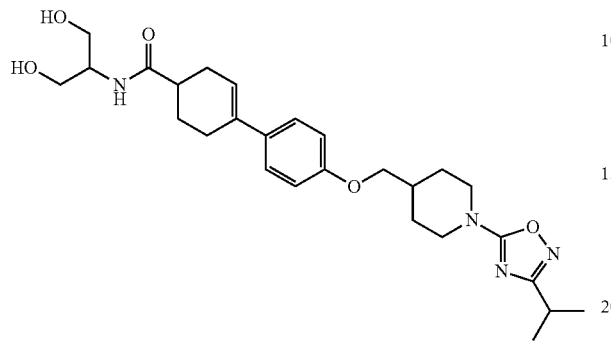

The title compound was prepared in the same manner as in <Example 17>, except that 2-amino-1.3-propanediol was used instead of the (R)-3-amino-1,2-propanediol (Amount obtained: 175 mg/Yield: 79%).

¹H NMR (400, MeOD): 7.27 (3H, d), 6.85 (2H, d), 6.02 (1H, s), 4.18 (2H, d), 3.87 (6H, d), 3.18 (3H, m), 2.86 (1H, m), 2.46 (5H, m), 2.04 (5H, m), 1.48 (2H, m), 1.28 (6H, d)

Example 24

Preparation of tert-butyl 4-((5-(4-((S)-1-hydroxy-propan-2-ylcarbamoyl)cyclohex-1-enyl)pyridin-2-yloxy)methyl)piperidine-1-carboxylate

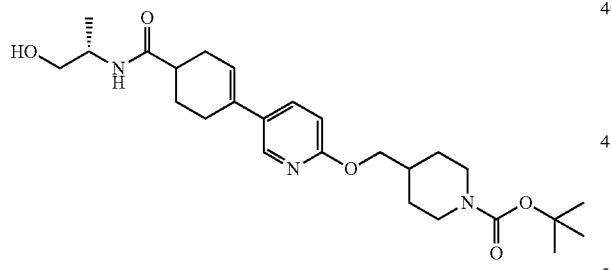

300 mg of 4-(6-((1-(tert-butoxycarbonyl)piperidin-4-yl)methoxy)pyridin-3-yl)cyclohex-3-enecarboxyilc acid was dissolved in 25 µl of DMF, and stirred. 210 mg of EDCI and 165 mg of HOBt were sequentially added dropwise thereto, and the resulting mixture was then additionally stirred for 10 minutes. 120 mg of (S)-2-amino-1-propanol was added dropwise thereto, and the mixture was stirred at room temperature for 5 hours. After the reaction was terminated, 50 µl of distilled water was slowly added at 0° C., and the resulting solids were filtered, and dried to obtain a desired compound as a white solid (Amount obtained: 235 mg/Yield: 84%).

¹H NMR (400, CDCl₃): 8.14 (1H, s), 7.62 (1H, d), 6.70 (1H, d), 6.04 (1H, s), 5.76 (1H, d) 4.16 (5H, m), 4.15 (2H, m), 2.79 (3H, m), 2.50 (5H, m), 2.13 (1H, m), 1.98 (5H, m), 1.48 (9H, s), 1.30 (2H, m), 1.20 (3H, d)

Example 25

Preparation of tert-butyl 4-((5-(4-((R)-1-hydroxy-propan-2-ylcarbamoyl)cyclohex-1-enyl)pyridin-2-yloxy)methyl)piperidine-1-carboxylate

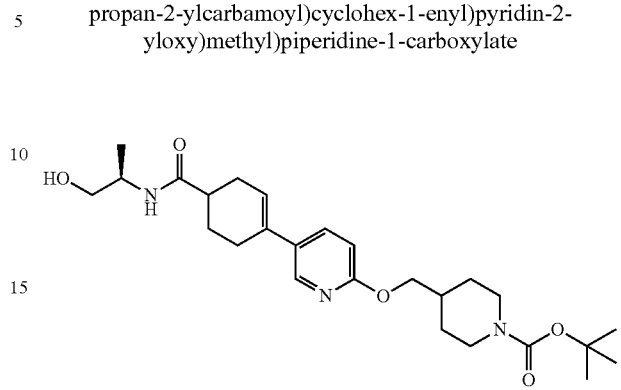

The title compound was prepared in the same manner as in <Example 24>, except that (R)-2-amino-1-propanol was used instead of the (S)-2-amino-1-propanol (Amount obtained: 140 mg/Yield: 62%).

¹H NMR (400, CDCl₃): 8.14 (1H, s), 7.62 (1H, d), 6.70 (1H, d), 6.04 (1H, s), 5.76 (1H, d) 4.16 (5H, m), 4.15 (2H, m), 2.79 (3H, m), 2.50 (5H, m), 2.13 (1H, m), 1.98 (5H, m), 1.48 (9H, s), 1.30 (2H, m), 1.20 (3H, d)

Example 26

Preparation of tert-butyl 4-((5-(4-((S)-2-hydroxy-propylcarbamoyl)cyclohex-1-enyl)pyridin-2-yloxy)methyl)piperidine-1-carboxylate

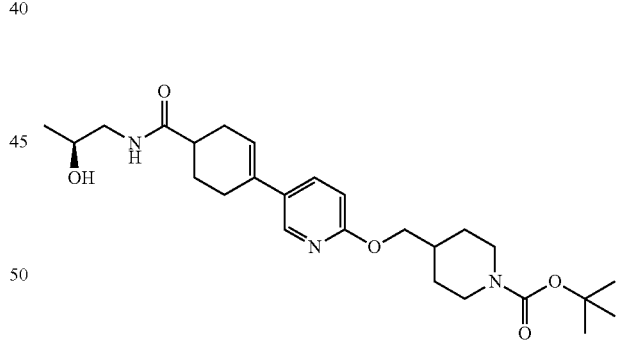

The title compound was prepared in the same manner as in <Example 24>, except that (S)-1-amino-2-propanol was used instead of the (S)-2-amino-1-propanol (Amount obtained: 155 mg/Yield: 67%).

¹H NMR (400, CDCl₃): 8.14 (1H, s), 7.61 (1H, d), 6.70 (1H, d), 6.05 (2H, s), 4.16 (4H, m), 3.97 (1H, m), 3.35 (2H, m), 2.79 (2H, m), 2.51 (6H, m), 2.14 (1H, m), 1.98 (4H, m), 1.48 (9H, s), 1.30 (2H, m), 1.21 (3H, d)

Example 27

Preparation of tert-butyl 4-((5-(4-((R)-2-hydroxy-propylcarbamoyl)cyclohex-1-enyl)pyridin-2-yloxy)methyl)piperidine-1-carboxylate

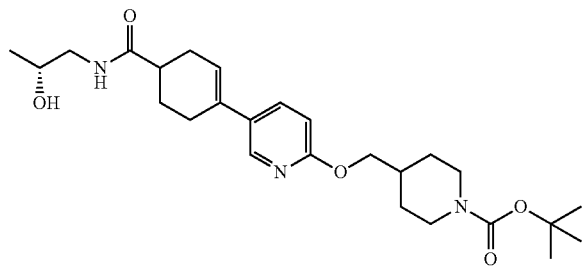 [SMILES: C[C@@H](O)CNC(=O)C1CC=C(c2ccc(OCC3CCN(C(=O)OC(C)(C)C)CC3)nc2)CC1]

The title compound was prepared in the same manner as in <Example 24>, except that (R)-1-amino-2-propanol was used instead of the (S)-2-amino-1-propanol (Amount obtained: 150 mg/Yield: 65%).

$^1$H NMR (400, CDCl$_3$): 8.14 (1H, s), 7.61 (1H, d), 6.70 (1H, d), 6.05 (2H, s), 4.16 (4H, m), 3.97 (1H, m), 3.35 (2H, m), 2.79 (2H, m), 2.51 (6H, m), 2.14 (1H, m), 1.98 (4H, m), 1.48 (9H, s), 1.30 (2H, m), 1.21 (3H, d)

Example 28

Preparation of N-((R)-2-hydroxypropyl)-4-(4-((1-(3-isopropyl-1,2,4-oxadiazol-5-yl)piperidin-4-yl)methoxy)phenyl)cyclohex-3-enecarboxamide

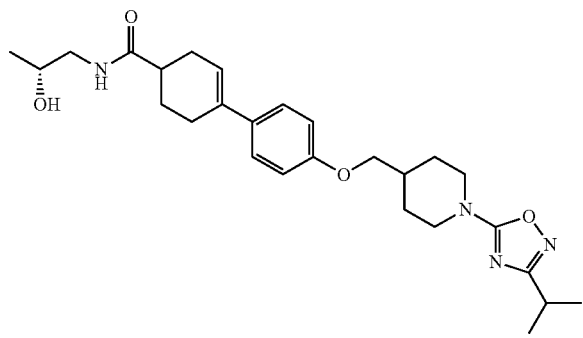 [SMILES: CC(C)c1noc(N2CCC(COc3ccc(C4=CCC(C(=O)NC[C@@H](C)O)CC4)cc3)CC2)n1]

The title compound was prepared in the same manner as in <Example 17>, except that (R)-1-amino-2-propanol was used instead of the (R)-3-amino-1,2-propanediol (Amount obtained: 100 mg/Yield: 43%).

$^1$H NMR (400, CDCl$_3$): 7.53 (2H, d), 6.86 (2H, d), 6.04 (2H, s), 4.23 (1H, m), 3.90 (2H, d), 3.50 (1H, m), 3.17 (3H, m), 2.91 (1H, m), 2.14 (2H, m), 1.94 (3H, m), 1.50 (2H, m), 1.32 (6H, d), 1.21 (3H, d)

Example 29

Preparation of N-((S)-2-hydroxypropyl)-4-(4-((1-(3-isopropyl-1,2,4-oxadiazol-5-yl)piperidin-4-yl)methoxy)phenyl)cyclohex-3-enecarboxamide

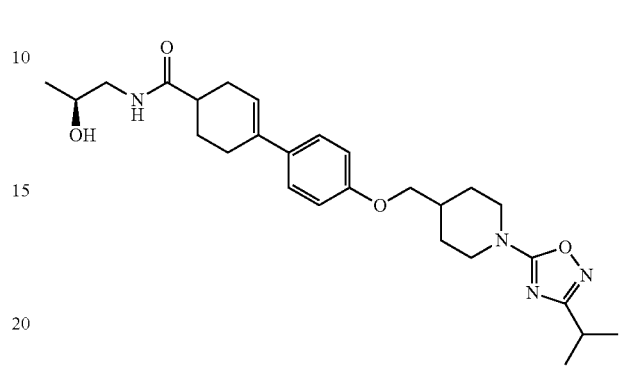

The title compound was prepared in the same manner as in <Example 17>, except that (S)-1-amino-2-propanol was used instead of the (R)-3-amino-1,2-propanediol (Amount obtained: 143 mg/Yield: 62%).

$^1$H NMR (400, CDCl$_3$): 7.53 (2H, d), 6.86 (2H, d), 6.04 (2H, s), 4.23 (1H, m), 3.90 (2H, d), 3.50 (1H, m), 3.17 (3H, m), 2.91 (1H, m), 2.14 (2H, m), 1.94 (3H, m), 1.50 (2H, m), 1.32 (6H, d), 1.21 (3H, d)

Example 30

Preparation of 4-(4-((1-(5-ethylpyrimidin-2-yl)piperidin-4-yl)methoxy)phenyl)-N-((R)-2-hydroxypropyl)cyclohex-3-enecarboxamide

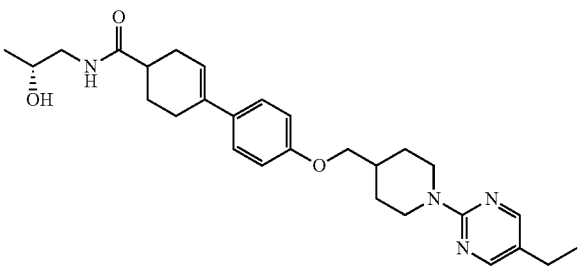 [SMILES: CCc1cnc(N2CCC(COc3ccc(C4=CCC(C(=O)NC[C@@H](C)O)CC4)cc3)CC2)nc1]

The title compound was prepared in the same manner as in <Example 8>, except that (R)-1-amino-2-propanol was used instead of the (R)-2-amino-1-propanol (Amount obtained: 180 mg/Yield: 79%).

$^1$H NMR (400, CDCl$_3$): 8.19 (2H, s), 7.32 (2H, d), 6.87 (2H, d), 6.04 (2H, s), 4.80 (2H, d), 3.96 (1H, m), 3.85 (2H, d), 3.52 (1H, m), 3.20 (1H, m), 2.92 (2H, t), 2.53 (8H, m), 2.13 (2H, m), 1.96 (3H, m), 1.38 (2H, m), 1.28 (6H, m)

Example 31

Preparation of N-(2-hydroxyethyl)-4-(4-((1-(3-isopropyl-1,2,4-oxadiazol-5-yl)piperidin-4-yl)methoxy)phenyl)cyclohex-3-enecarboxamide

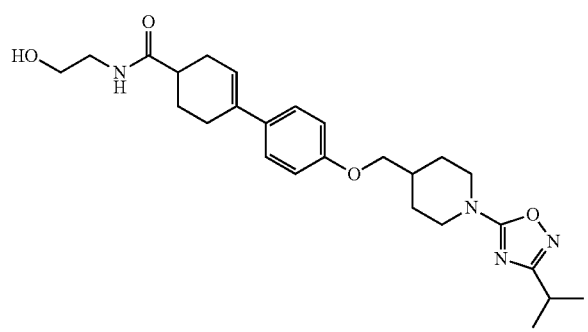

The title compound was prepared in the same manner as in <Example 17>, except that 2-aminoethanol was used instead of the (R)-3-amino-1,2-propanediol (Amount obtained: 220 mg/Yield: 94%).

$^1$H NMR (400, CDCl$_3$): 7.33 (2H, d), 6.86 (2H, d), 6.07 (2H, m), 4.23 (2H, m), 3.86 (2H, d), 3.79 (1H, m), 3.51 (1H, m), 3.15 (2H, m), 2.95 (1H, m), 2.51 (1H, m), 2.46 (4H, m), 2.06 (5H, m), 1.50 (2H, m), 1.30 (6H, d)

Example 32

Preparation of tert-butyl 4-((5-(4-((R)-2,3-dihydroxypropylcarbamoyl)cyclohex-1-enyl)pyridin-2-yloxy)methyl)piperidine-1-carboxylate The title compound was prepared in the same manner as in <Example 24>, except that (R)-3-amino-1,2-propanediol was used instead of the (S)-2-amino-1-propanol (Amount obtained: 176 mg/Yield: 80%).

$^1$H NMR (400, CDCl$_3$): 8.14 (1H, s), 7.62 (1H, d), 6.71 (1H, d), 6.06 (2H, m), 5.32 (5H, m), 3.80 (1H, m), 3.58 (2H, m), 3.46 (2H, m), 2.93 (1H, m), 2.78 (2H, m), 2.50 (5H, m), 1.98 (5H, s), 1.49 (9H, m), 1.27 (2H, m)

Example 33

Preparation of tert-butyl 4-((5-(4-((S)-2,3-dihydroxypropylcarbamoyl)cyclohex-1-enyl)pyridin-2-yloxy)methyl)piperidine-1-carboxylate The title compound was prepared in the same manner as in <Example 24>, except that (S)-3-amino-1,2-propanediol was used instead of the (S)-2-amino-1-propanol (Amount obtained: 200 mg/Yield: 87%).

$^1$H NMR (400, CDCl$_3$): 8.14 (1H, s), 7.62 (1H, d), 6.71 (1H, d), 6.06 (2H, m), 5.32 (5H, m), 3.80 (1H, m), 3.58 (2H, m), 3.46 (2H, m), 2.93 (1H, m), 2.78 (2H, m), 2.50 (5H, m), 1.98 (5H, s), 1.49 (9H, m), 1.27 (2H, m)

Example 34

Preparation of N-(2-hydroxyethyl)-4-(4-((1-(3-isopropyl-1,2,4-oxadiazol-5-yl)piperidin-4-yl)methoxy)phenyl)-N-methylcyclohex-3-enecarboxamide

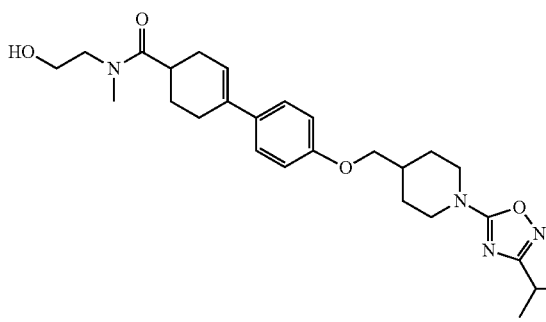

The title compound was prepared in the same manner as in <Example 17>, except that 2-(methylamino)ethanol was used instead of the (R)-3-amino-1,2-propanediol (Amount obtained: 190 mg/Yield: 82%).

¹H NMR (400, CDCl₃): 7.34 (2H, d), 6.86 (2H, d), 6.07 (2H, m), 4.23 (2H, m), 3.86 (4H, m), 3.63 (2H, m), 3.18 (3H, s), 3.15 (2H, m), 2.92 (2H, m), 2.50 (4H, m), 2.03 (5H, m), 1.92 (2H, m), 1.30 (6H, m)

Example 35

Preparation of N-ethyl-N-(2-hydroxyethyl)-4-(4-((1-(3-isopropyl-1,2,4-oxadiazol-5-yl)piperidin-4-yl)methoxy)phenyl)cyclohex-3-enecarboxamide

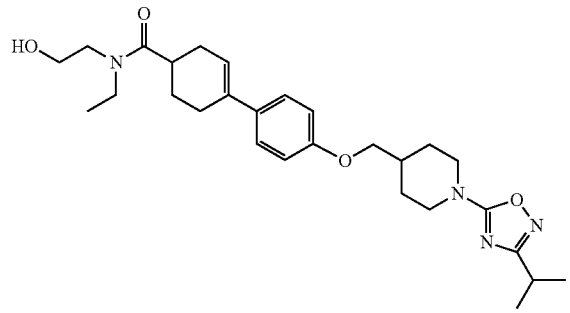 [SMILES: CCN(CCO)C(=O)C1CC=C(c2ccc(OCC3CCN(c4nc(C(C)C)no4)CC3)cc2)CC1]

The title compound was prepared in the same manner as in <Example 17>, except that 2-(ethyllamino)ethanol was used instead of the (R)-3-amino-1,2-propanediol (Amount obtained: 184 mg/Yield: 80%).

¹H NMR (400, CDCl₃): 7.34 (2H, d), 6.87 (2H, d), 6.08 (1H, m), 4.24 (2H, m), 3.86 (4H, m), 3.59 (2H, m), 3.49 (2H, m), 3.11 (2H, m), 2.94 (1H, m), 2.59 (5H, m), 1.98 (5H, m), 1.51 (2H, m), 1.31 (6H, m), 1.14 (3H, m)

Example 36

Preparation of N-((R)-1-hydroxypropan-2-yl)-4-(5-((1-(3-isopropyl-1,2,4-oxadiazol-5-yl)piperidin-4-yl)methoxy)pyridin-2-yl)cyclohex-3-enecarboxamide 300 mg of 4-(5-((1-(3-isopropyl-1,2,4-oxadiazol-5-yl)piperidin-4-yl)methoxy)pyridin-2-yl)cyclohex-3-enecarboxylic acid was dissolved in 25 µl of DMF, and stirred. 210 mg of EDCI and 165 mg of HOBt were sequentially added dropwise thereto, and the resulting mixture was then additionally stirred for 10 minutes. 120 mg of (R)-2-amino-1-propanol was added dropwise thereto, and the mixture was then stirred at room temperature for 5 hours. After the reaction was terminated, 50 µl of distilled water was slowly added at 0° C., and the resulting solids were filtered, and dried to obtain a desired compound as a white solid (Amount obtained: 280 mg/Yield: 82%).

¹H NMR (400, CDCl₃): 8.25 (1H, s), 7.35 (1H, d), 7.15 (1H, d), 6.57 (1H, m), 5.82 (1H, m), 4.25 (2H, d), 4.13 (1H, m), 3.90 (2H, d), 3.70 (2H, m), 3.14 (2H, m), 2.94 (1H, m), 2.53 (5H, m), 2.03 (5H, m), 1.50 (2H, m), 1.32 (6H, d), 1.20 (3H, d)

Example 37

Preparation of N-((S)-1-hydroxypropan-2-yl)-4-(5-((1-(3-isopropyl-1,2,4-oxadiazol-5-yl)piperidin-4-yl)methoxy)pyridin-2-yl)cyclohex-3-enecarboxamide The title compound was prepared in the same manner as in <Example 36>, except that (S)-2-amino-1-propanol was used instead of the (R)-2-amino-1-propanol (Amount obtained: 160 mg/Yield: 70%).

¹H NMR (400, CDCl₃): 8.25 (1H, s), 7.35 (1H, d), 7.15 (1H, d), 6.57 (1H, m), 5.82 (1H, m), 4.25 (2H, d), 4.13 (1H, m), 3.90 (2H, d), 3.70 (2H, m), 3.14 (2H, m), 2.94 (1H, m), 2.53 (5H, m), 2.03 (5H, m), 1.50 (2H, m), 1.32 (6H, d), 1.20 (3H, d)

Example 38

Preparation of N-((R)-2-hydroxypropyl)-4-(5-((1-(3-isopropyl-1,2,4-oxadiazol-5-yl)piperidin-4-yl)methoxy)pyridin-2-yl)cyclohex-3-enecarboxamide

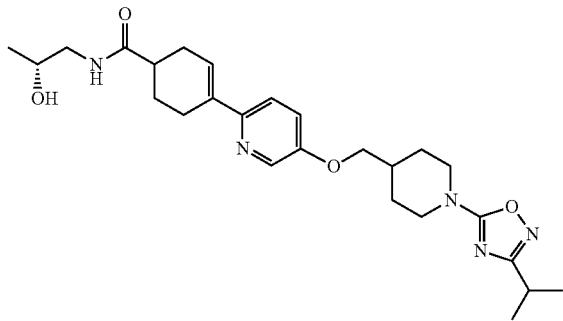 [SMILES: CC(C)c1noc(N2CCC(COc3ccc(C4=CCC(C(=O)NC[C@@H](C)O)CC4)nc3)CC2)n1]

The title compound was prepared in the same manner as in <Example 36>, except that (R)-1-amino-2-propanol was used instead of the (R)-2-amino-1-propanol (Amount obtained: 180 mg/Yield: 81%).

$^1$H NMR (400, CDCl$_3$): 8.24 (1H, s), 7.34 (1H, d), 7.17 (1H, d), 6.54 (1H, m), 6.12 (1H, m), 4.25 (2H, d), 3.96 (1H, m), 3.90 (2H, d), 3.51 (1H, m), 3.16 (3H, m), 2.93 (1H, m), 2.51 (5H, m), 2.03 (5H, m), 1.49 (2H, m), 1.31 (6H, d), 1.21 (3H, d)

Example 39

Preparation of N-((S)-2-hydroxypropyl)-4-(5-((1-(3-isopropyl-1,2,4-oxadiazol-5-yl)piperidin-4-yl)methoxy)pyridin-2-yl)cyclohex-3-enecarboxamide

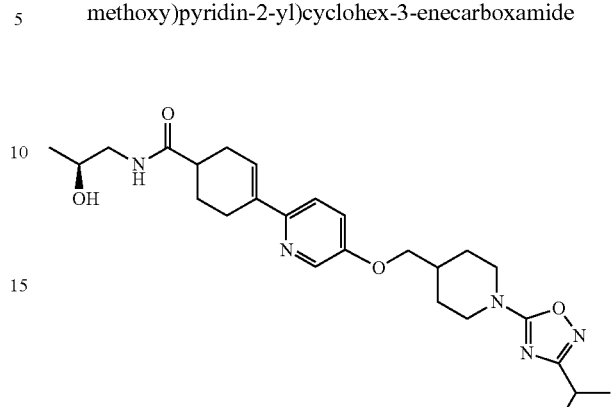

The title compound was prepared in the same manner as in <Example 36>, except that (S)-1-amino-2-propanol was used instead of the (R)-2-amino-1-propanol (Amount obtained: 185 mg/Yield: 76%).

$^1$H NMR (400, CDCl$_3$): 8.24 (1H, s), 7.34 (1H, d), 7.17 (1H, d), 6.54 (1H, m), 6.12 (1H, m), 4.25 (2H, d), 3.96 (1H, m), 3.90 (2H, d), 3.51 (1H, m), 3.16 (3H, m), 2.93 (1H, m), 2.51 (5H, m), 2.03 (5H, m), 1.49 (2H, m), 1.31 (6H, d), 1.21 (3H, d)

Example 40

Preparation of N-((R)-2,3-dihydroxypropyl)-4-(5-((1-(3-isopropyl-1,2,4-oxadiazol-5-yl)piperidin-4-yl)methoxy)pyridin-2-yl)cyclohex-3-enecarboxamide

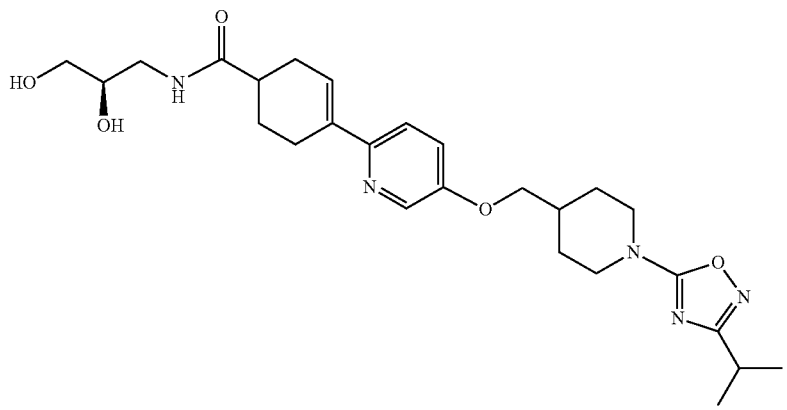 [SMILES: CC(C)c1noc(N2CCC(COc3ccc(C4=CCC(C(=O)NC[C@@H](O)CO)CC4)nc3)CC2)n1]

The title compound was prepared in the same manner as in <Example 36>, except that (R)-3-amino-1,2-propanediol was used instead of the (R)-2-amino-1-propanol (Amount obtained: 160 mg/Yield: 71%).

$^1$H NMR (400, CDCl$_3$): 8.24 (1H, s), 7.34 (1H, d), 7.17 (1H, d), 6.52 (1H, m), 6.16 (1H, m), 4.25 (2H, d), 3.90 (2H, d), 3.81 (1H, m), 3.59 (3H, m), 3.15 (3H, m), 2.93 (1H, m), 2.51 (5H, m), 2.09 (5H, m), 1.53 (2H, m), 1.31 (6H, d)

Example 41

Preparation of N-((S)-2,3-dihydroxypropyl)-4-(5-((1-(3-isopropyl-1,2,4-oxadiazol-5-yl)piperidin-4-yl)methoxy)pyridin-2-yl)cyclohex-3-enecarboxamide

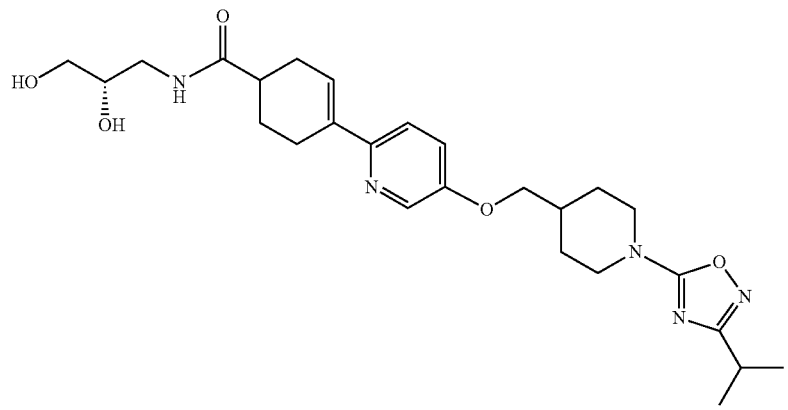 [SMILES: CC(C)c1noc(N2CCC(COc3ccc(C4=CCC(C(=O)NC[C@H](O)CO)CC4)nc3)CC2)n1]

The title compound was prepared in the same manner as in <Example 36>, except that (S)-3-amino-1,2-propanediol was used instead of the (R)-2-amino-1-propanol (Amount obtained: 176 mg/Yield: 77%).

$^1$H NMR (400, CDCl$_3$): 8.24 (1H, s), 7.34 (1H, d), 7.17 (1H, d), 6.52 (1H, m), 6.16 (1H, m), 4.25 (2H, d), 3.90 (2H, d), 3.81 (1H, m), 3.59 (3H, m), 3.15 (3H, m), 2.93 (1H, m), 2.51 (5H, m), 2.09 (5H, m), 1.53 (2H, m), 1.31 (6H, d)

Example 42

Preparation of tert-butyl 4-((5-(4-((S)-3-hydroxy-pyrrolidine-1-carbonyl)cyclohex-1-enyl)pyridin-2-yloxy)methyl)piperidine-1-carboxylate

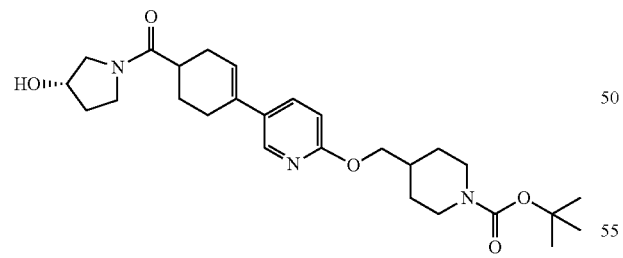

The title compound was prepared in the same manner as in <Example 24>, except that (S)-(−)-3-pyrrolidinol was used instead of the (S)-2-amino-1-propanol (Amount obtained: 145 mg/Yield: 65%).

$^1$H NMR (400, CDCl$_3$): 8.14 (1H, s), 7.63 (1H, d), 6.70 (1H, d), 6.07 (1H, s), 4.58 (1H, d), 4.16 (4H, m), 3.76 (4H, m), 2.75 (7H, m), 1.98 (8H, m), 1.52 (9H, m), 1.29 (2H, m)

Example 43

Preparation of tert-butyl 4-((5-(4-((R)-3-hydroxy-pyrrolidine-1-carbonyl)cyclohex-1-enyl)pyridin-2-yloxy)methyl)piperidine-1-carboxylate

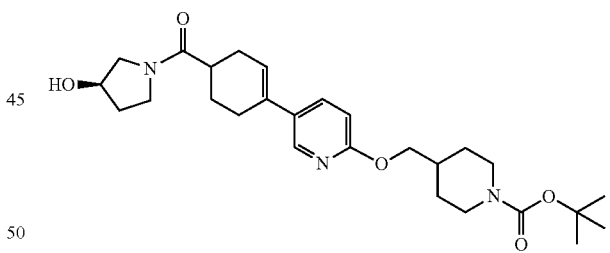

The title compound was prepared in the same manner as in <Example 24>, except that (R)-(+)-3-pyrrolidinol was used instead of the (S)-2-amino-1-propanol (Amount obtained: 162 mg/Yield: 70%).

$^1$H NMR (400, CDCl$_3$): 8.14 (1H, s), 7.63 (1H, d), 6.70 (1H, d), 6.07 (1H, s), 4.58 (1H, d), 4.16 (4H, m), 3.76 (4H, m), 2.75 (7H, m), 1.98 (8H, m), 1.52 (9H, m), 1.29 (2H, m)

Example 44

Preparation of tert-butyl 4-((2-fluoro-4-(4-((S)-3-hydroxypyrrolidine-1-carbonyl)cyclohex-1-enyl)phenoxy)methyl)piperidine-1-carboxylate

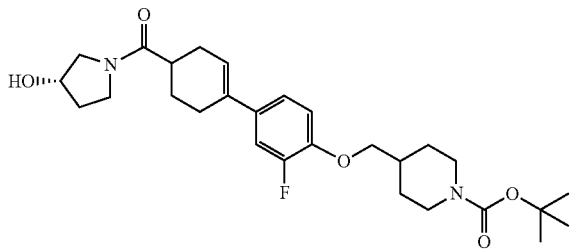 [SMILES: CC(C)(C)OC(=O)N1CCC(COc2ccc(C3=CCC(C(=O)N4CC[C@H](O)C4)CC3)cc2F)CC1]

300 mg of 4-(4-((1-(tert-butoxycarbonyl)piperidin-4-yl)methoxy)-3-fluorophenyl)cyclohex-3-enecarboxyilc acid was dissolved in 25 µl of DMF, and stirred. 210 mg of EDCI and 165 mg of HOBt were sequentially added dropwise thereto, and the resulting mixture was then additionally stirred for 10 minutes. 100 mg of (S)-(−)-3-pyrrolidinol was added dropwise thereto, and the mixture was stirred at room temperature for 12 hours. After the reaction was terminated, 50 µl of distilled water was slowly added at 0° C., and the resulting solids were filtered, and dried to obtain a desired compound as a white solid (Amount obtained: 195 mg/Yield: 58%).

$^1$H NMR (400, CDCl$_3$): 7.28 (2H, m), 6.91 (1H, t), 6.10 (1H, s), 4.58 (1H, d), 4.16 (4H, m), 3.88 (2H, d), 3.69 (4H, m), 2.75 (7H, m), 1.98 (8H, m), 1.52 (9H, m), 1.30 (2H, m)

Example 45

Preparation of tert-butyl 4-((2-fluoro-4-(4-((R)-3-hydroxypyrrolidine-1-carbonyl)cyclohex-1-enyl)phenoxy)methyl)piperidine-1-carboxylate

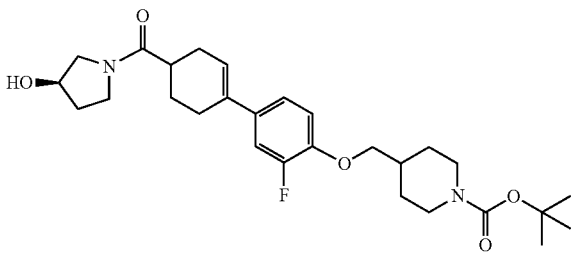 [SMILES: CC(C)(C)OC(=O)N1CCC(COc2ccc(C3=CCC(C(=O)N4CC[C@@H](O)C4)CC3)cc2F)CC1]

The title compound was prepared in the same manner as in <Example 44>, except that (R)-(+)-3-pyrrolidinol was used instead of the (S)-(−)-3-pyrrolidinol (Amount obtained: 120 mg/Yield: 52%).

$^1$H NMR (400, CDCl$_3$): 7.28 (2H, m), 6.91 (1H, t), 6.10 (1H, s), 4.58 (1H, d), 4.16 (4H, m), 3.88 (2H, d), 3.69 (4H, m), 2.75 (7H, m), 1.98 (8H, m), 1.52 (9H, m), 1.30 (2H, m)

Example 46

Preparation of N-(1,3-dihydroxypropan-2-yl)-4-(5-((1-(3-isopropyl-1,2,4-oxadiazol-5-yl)piperidin-4-yl)methoxy)pyridin-2-yl)cyclohex-3-enecarboxamide

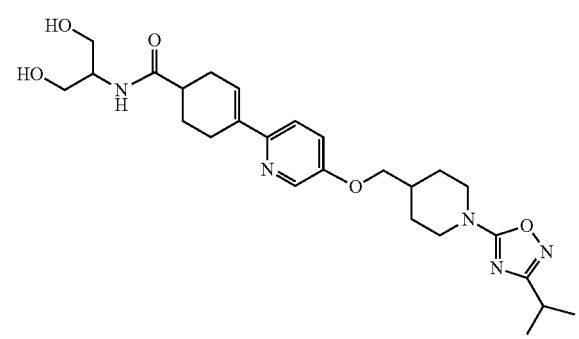 [SMILES: CC(C)c1noc(N2CCC(COc3ccc(C4=CCC(C(=O)NC(CO)CO)CC4)nc3)CC2)n1]

The title compound was prepared in the same manner as in <Example 36>, except that 2-amino-1,3-propanediol was used instead of the (R)-2-amino-1-propanol (Amount obtained: 185 mg/Yield: 52%).

$^1$H NMR (400, CDCl$_3$): 8.23 (1H, s), 7.34 (1H, d), 7.16 (1H, d), 6.48 (2H, m), 4.25 (2H, d), 4.03 (1H, m), 3.90 (2H, d), 3.81 (4H, m), 3.12 (2H, m), 2.94 (1H, m), 2.56 (1H, m), 2.49 (5H, m), 2.11 (3H, m), 1.98 (2H, m), 1.45 (2H, m), 1.30 (6H, d)

Example 47

Preparation of N-(3-hydroxy-2,2-dimethylpropyl)-4-(5-((1-(3-isopropyl-1,2,4-oxadiazol-5-yl)piperidin-4-yl)methoxy)pyridin-2-yl)cyclohex-3-enecarboxamide

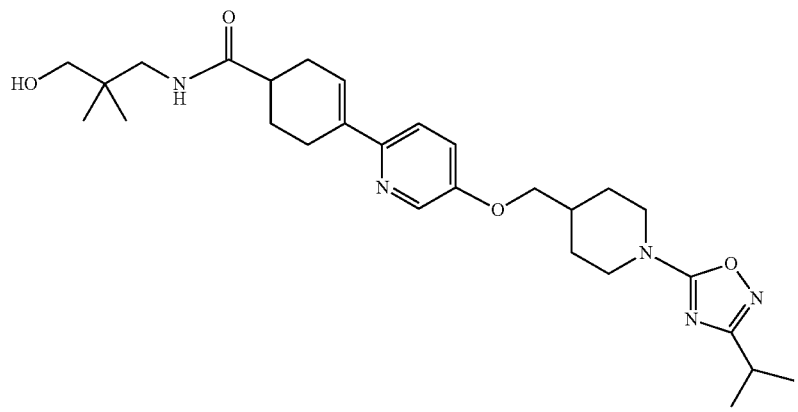 [SMILES: CC(C)c1noc(N2CCC(COc3ccc(C4=CCC(C(=O)NCC(C)(C)CO)CC4)nc3)CC2)n1]

The title compound was prepared in the same manner as in <Example 36>, except that 3-amino-2,2-dimethylpropan-1-ol was used instead of the (R)-2-amino-1-propanol (Amount obtained: 150 mg/Yield: 65%).

$^1$H NMR (400, CDCl$_3$): 8.25 (1H, s), 7.34 (1H, d), 7.17 (1H, d), 6.55 (1H, m), 6.05 (1H, m), 4.25 (2H, d), 3.90 (2H, d), 3.15 (6H, m), 2.93 (1H, m), 2.71 (1H, m), 2.47 (4H, m), 2.14 (2H, m), 1.98 (3H, m), 1.51 (2H, m), 1.31 (6H, m), 0.90 (6H, s)

Example 48

Preparation of ((R)-3-hydroxypyrrolidin-1-yl)(4-(4-((1-(3-isopropyl-1,2,4-oxadiazol-5-yl)piperidin-4-yl)methoxy)phenyl)cyclohex-3-enyl)methanone

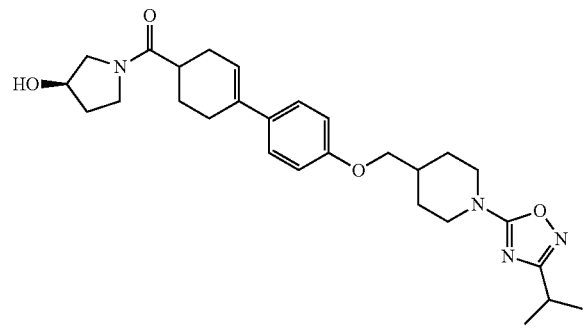 [SMILES: CC(C)c1noc(N2CCC(COc3ccc(C4=CCC(C(=O)N5CC[C@@H](O)C5)CC4)cc3)CC2)n1]

The title compound was prepared in the same manner as in <Example 17>, except that (R)-(+)-3-pyrrolidinol was used instead of the (R)-3-amino-1,2-propanediol (Amount obtained: 175 mg/Yield: 77%).

$^1$H NMR (400, CDCl$_3$): 7.33 (2H, d), 6.86 (2H, d), 6.07 (1H, m), 4.53 (1H, m), 4.23 (2H, d), 3.85 (2H, d), 3.68 (4H, m), 3.11 (2H, m), 2.90 (1H, m), 2.52 (6H, m), 1.99 (7H, m), 1.43 (2H, m), 1.29 (6H, d)

Example 49

Preparation of ((S)-3-hydroxypyrrolidin-1-yl)(4-(4-((1-(3-isopropyl-1,2,4-oxadiazol-5-yl)piperidin-4-yl)methoxy)phenyl)cyclohex-3-enyl)methanone

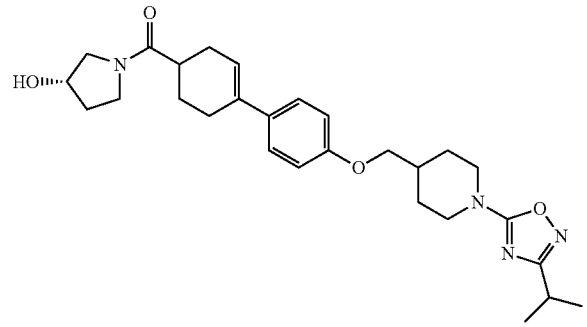 [SMILES: CC(C)c1noc(N2CCC(COc3ccc(C4=CCC(C(=O)N5CC[C@H](O)C5)CC4)cc3)CC2)n1]

The title compound was prepared in the same manner as in <Example 17>, except that (S)-(−)-3-pyrrolidinol was used instead of the (R)-3-amino-1,2-propanediol (Amount obtained: 120 mg/Yield: 52%).

$^1$H NMR (400, CDCl$_3$): 7.33 (2H, d), 6.86 (2H, d), 6.07 (1H, m), 4.53 (1H, m), 4.23 (2H, d), 3.85 (2H, d), 3.68 (4H, m), 3.11 (2H, m), 2.90 (1H, m), 2.52 (6H, m), 1.99 (7H, m), 1.43 (2H, m), 1.29 (6H, d)

Example 50

Preparation of N-(2,2-difluoroethyl)-4-(4-((1-(5-ethylpyrimidin-2-yl)piperidin-4-yl)methoxy)phenyl)cyclohex-3-enecarboxamide

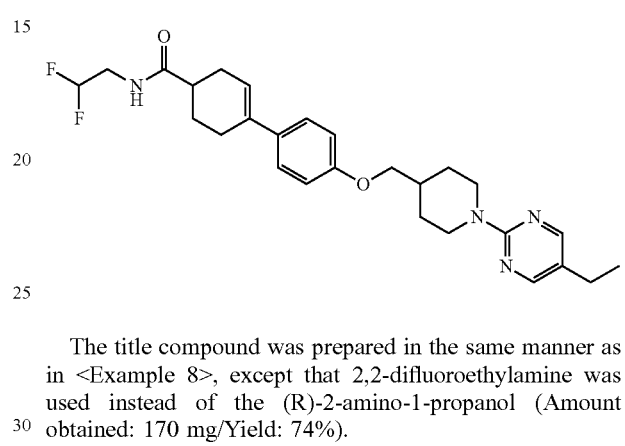

The title compound was prepared in the same manner as in <Example 8>, except that 2,2-difluoroethylamine was used instead of the (R)-2-amino-1-propanol (Amount obtained: 170 mg/Yield: 74%).

$^1$H NMR (400, CDCl$_3$): 8.22 (2H, s), 7.32 (2H, d), 6.87 (2H, d), 6.04 (1H, s), 5.91 (1.5H, m), 5.88 (0.5H, t), 4.80 (2H, d), 3.85 (2H, d), 3.72 (2H, m), 2.98 (2H, t), 2.56 (8H, m), 2.12 (2H, m), 1.94 (3H, m), 1.41 (2H, m), 1.21 (3H, t)

Example 51

Preparation of N-(2,2-difluoroethyl)-4-(4-((1-(3-isopropyl-1,2,4-oxadiazol-5-yl)piperidin-4-yl)methoxy)phenyl)cyclohex-3-enecarboxamide

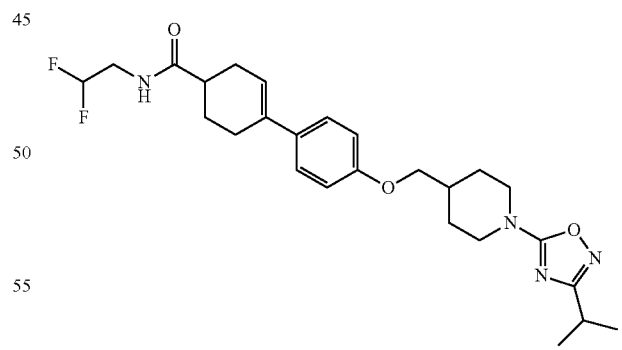

The title compound was prepared in the same manner as in <Example 17>, except that 2,2-difluoroethylamine was used instead of the (R)-3-amino-1,2-propanediol (Amount obtained: 175 mg/Yield: 76%).

$^1$H NMR (400, CDCl$_3$): 7.33 (2H, d), 6.86 (2H, d), 6.04 (1H, m), 5.88 (2H, m), 4.23 (2H, d), 3.84 (2H, d), 3.70 (2H, m), 3.14 (2H, t), 2.91 (1H, m), 2.50 (5H, m), 2.10 (2H, m), 2.05 (3H, m), 1.43 (2H, m), 1.30 (6H, d)

Example 52

Preparation of (4-(4-((1-(3-isopropyl-1,2,4-oxadiazol-5-yl)piperidin-4-yl)methoxy)phenyl)cyclohex-3-enyl)(pyrrolidin-1-yl)methanone

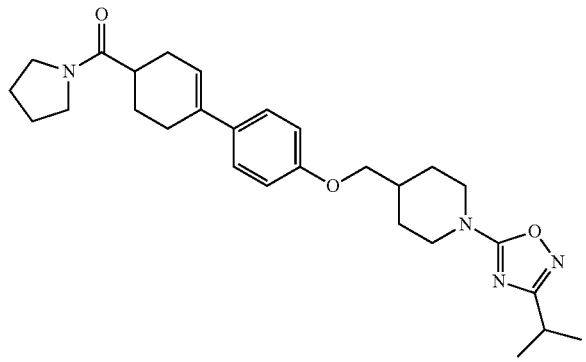 [SMILES: CC(C)c1noc(N2CCC(COc3ccc(C4=CCC(C(=O)N5CCCC5)CC4)cc3)CC2)n1]

The title compound was prepared in the same manner as in <Example 17>, except that pyrrolidine was used instead of the (R)-3-amino-1,2-propanediol (Amount obtained: 200 mg/Yield: 87%).

$^1$H NMR (400, CDCl$_3$): 7.34 (2H, d), 6.86 (2H, d), 6.07 (1H, m), 4.24 (2H, d), 3.84 (2H, d), 3.53 (4H, m), 3.08 (2H, m), 2.91 (1H, m), 2.34 (5H, m), 1.98 (9H, m), 1.47 (2H, m), 1.25 (6H, d)

Example 53

Preparation of ((S)-3-fluoropyrrolidin-1-yl)(4-(4-((1-(3-isopropyl-1,2,4-oxadiazol-5-yl)piperidin-4-yl)methoxy)phenyl)cyclohex-3-enyl)methanone

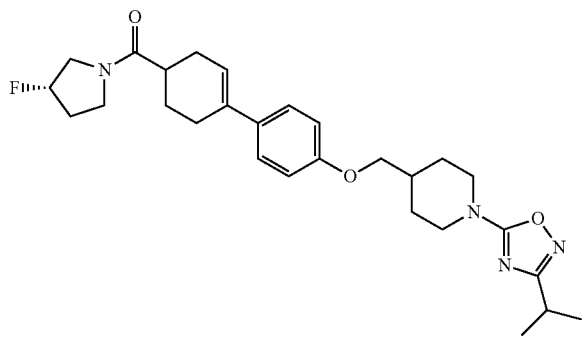 [SMILES: CC(C)c1noc(N2CCC(COc3ccc(C4=CCC(C(=O)N5CC[C@H](F)C5)CC4)cc3)CC2)n1]

The title compound was prepared in the same manner as in <Example 17>, except that (S)-3-fluoropyrrolidine was used instead of the (R)-3-amino-1,2-propanediol (Amount obtained: 175 mg/Yield: 76%).

$^1$H NMR (400, CDCl$_3$): 7.34 (2H, d), 6.87 (2H, d), 5.36 (1H, m), 4.24 (2H, d), 3.75 (6H, m), 3.14 (2H, t), 2.89 (1H, m), 2.50 (7H, m), 2.00 (5H, m), 1.50 (2H, m), 1.30 (6H, d)

Example 54

Preparation of ((R)-3-fluoropyrrolidin-1-yl)(4-(4-((1-(3-isopropyl-1,2,4-oxadiazol-5-yl)piperidin-4-yl)methoxy)phenyl)cyclohex-3-enyl)methanone

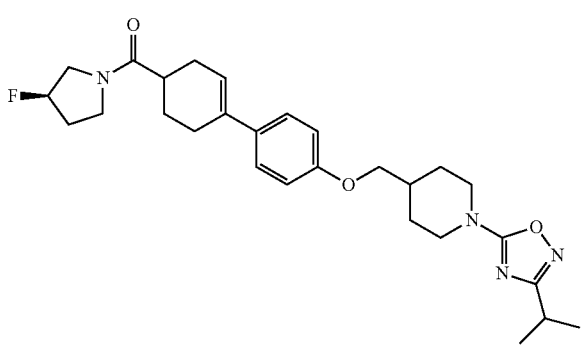 [SMILES: CC(C)c1noc(N2CCC(COc3ccc(C4=CCC(C(=O)N5CC[C@@H](F)C5)CC4)cc3)CC2)n1]

The title compound was prepared in the same manner as in <Example 17>, except that (R)-3-fluoropyrrolidine was used instead of the (R)-3-amino-1,2-propanediol (Amount obtained: 175 mg/Yield: 77%).

$^1$H NMR (400, CDCl$_3$): 7.34 (2H, d), 6.87 (2H, d), 5.36 (1H, m), 4.24 (2H, d), 3.75 (6H, m), 3.14 (2H, t), 2.89 (1H, m), 2.50 (7H, m), 2.00 (5H, m), 1.50 (2H, m), 1.30 (6H, d)

Example 55

Preparation of (4-ethylpiperazin-1-yl)(4-(4-((1-(5-ethylpyrimidin-2-yl)piperidin-4-yl)methoxy)phenyl)cyclohex-3-enyl)methanone

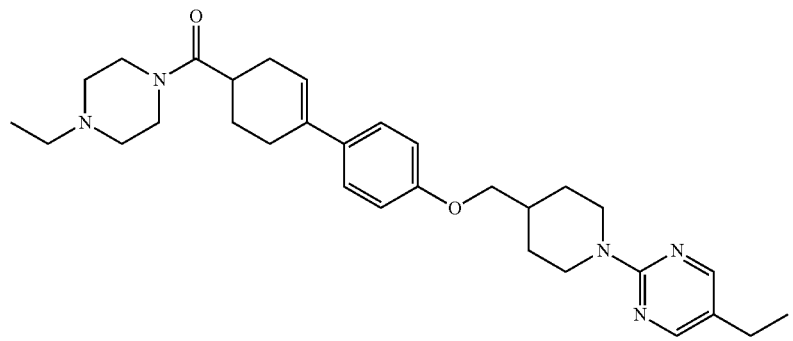 [SMILES: CCc1cnc(N2CCC(COc3ccc(C4=CCC(C(=O)N5CCN(CC)CC5)CC4)cc3)CC2)nc1]

The title compound was prepared in the same manner as in <Example 8>, except that 1-ethyl piperazine was used instead of the (R)-2-amino-1-propanol (Amount obtained: 200 mg/Yield: 87%).

$^1$H NMR (400, CDCl$_3$): 8.19 (2H, s), 7.32 (2H, d), 6.87 (2H, d), 6.05 (1H, s), 4.80 (2H, d), 3.76 (6H, m), 2.50 (13H, m), 1.99 (6H, m), 1.27 (8H, m)

Example 56

Preparation of (4-(4-((1-(3-isopropyl-1,2,4-oxadiazol-5-yl)piperidin-4-yl)methoxy)phenyl)cyclohex-3-enyl)(piperidin-1-yl)methanone

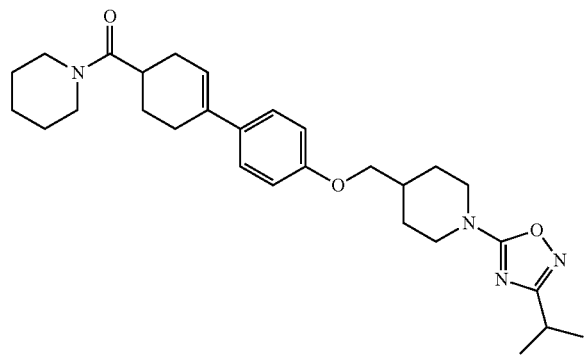 [SMILES: CC(C)c1noc(N2CCC(COc3ccc(C4=CCC(C(=O)N5CCCCC5)CC4)cc3)CC2)n1]

The title compound was prepared in the same manner as in <Example 17>, except that piperidine was used instead of the (R)-3-amino-1,2-propanediol (Amount obtained: 170 mg/Yield: 74%).

$^1$H NMR (400, CDCl$_3$): 7.34 (2H, d), 6.86 (2H, d), 6.07 (1H, m), 4.23 (2H, d), 3.84 (2H, d), 3.59 (4H, m), 3.11 (2H, t), 2.84 (2H, m), 2.49 (3H, m), 2.31 (1H, m), 1.98 (5H, m), 1.67 (6H, m), 1.44 (2H, m), 1.30 (6H, d)

Example 57

Preparation of tert-butyl 4-((2-fluoro-4-(4-((S)-3-fluoropyrrolidine-1-carbonyl)cyclohex-1-enyl)phenoxy)methyl)piperidine-1-carboxylate

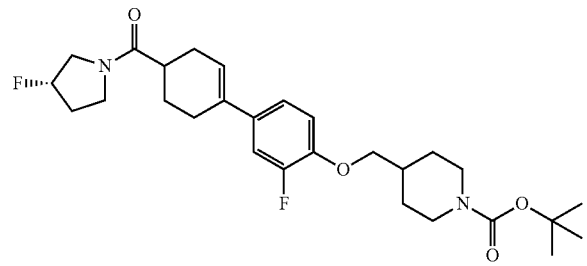 [SMILES: CC(C)(C)OC(=O)N1CCC(COc2ccc(C3=CCC(C(=O)N4CC[C@H](F)C4)CC3)cc2F)CC1]

The title compound was prepared in the same manner as in <Example 44>, except that (S)-3-fluoropyrrolidine was used instead of the (S)-(−)-3-pyrrolidinol (Amount obtained: 175 mg/Yield: 76%).

$^1$H NMR (400, CDCl$_3$): 7.15 (2H, m), 6.92 (1H, t), 6.10 (1H, s), 5.23 (1H, m), 4.17 (2H, m), 3.75 (6H, m), 2.73 (3H, m), 2.39 (5H, m), 2.02 (6H, m), 1.48 (9H, m), 1.27 (2H, m)

Example 58

Preparation of tert-butyl 4-((2-fluoro-4-(4-((R)-3-fluoropyrrolidine-1-carbonyl)cyclohex-1-enyl)phenoxy)methyl)piperidine-1-carboxylate

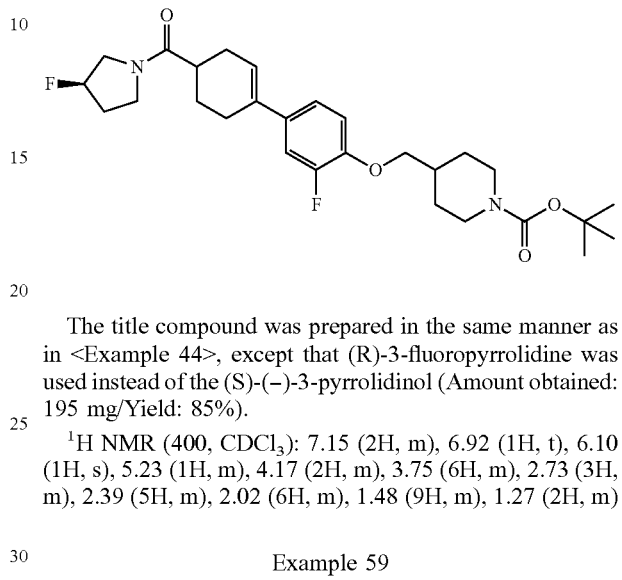

The title compound was prepared in the same manner as in <Example 44>, except that (R)-3-fluoropyrrolidine was used instead of the (S)-(−)-3-pyrrolidinol (Amount obtained: 195 mg/Yield: 85%).

$^1$H NMR (400, CDCl$_3$): 7.15 (2H, m), 6.92 (1H, t), 6.10 (1H, s), 5.23 (1H, m), 4.17 (2H, m), 3.75 (6H, m), 2.73 (3H, m), 2.39 (5H, m), 2.02 (6H, m), 1.48 (9H, m), 1.27 (2H, m)

Example 59

Preparation of tert-butyl 4-((2-fluoro-4-(4-((S)-1-hydroxypropan-2-ylcarbamoyl)cyclohex-1-enyl)phenoxy)methyl)piperidine-1-carboxylate

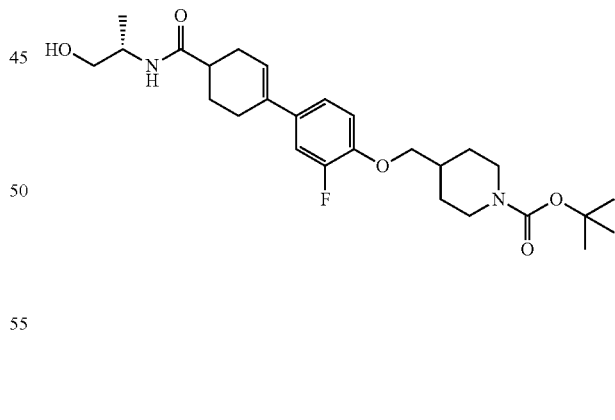

The title compound was prepared in the same manner as in <Example 44>, except that (S)-2-amino-1-propanol was used instead of the (S)-(−)-3-pyrrolidinol (Amount obtained: 200 mg/Yield: 87%).

$^1$H NMR (400, CDCl$_3$): 7.14 (2H, m), 6.89 (1H, t), 6.06 (1H, s), 5.80 (1H, m), 4.16 (3H, m), 3.88 (2H, d), 2.63 (2H, m), 2.76 (2H, m), 2.41 (6H, m), 2.02 (5H, m), 1.48 (9H, m), 1.26 (5H, m)

Example 60

Preparation of tert-butyl 4-((2-fluoro-4-(4-((R)-1-hydroxypropan-2-ylcarbamoyl)cyclohex-1-enyl)phenoxy)methyl)piperidine-1-carboxylate

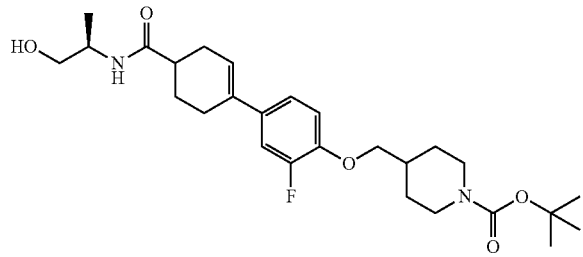 [SMILES: C[C@H](CO)NC(=O)C1CC=C(c2ccc(OCC3CCN(C(=O)OC(C)(C)C)CC3)c(F)c2)CC1]

The title compound was prepared in the same manner as in <Example 44>, except that (R)-2-amino-1-propanol was used instead of the (S)-(−)-3-pyrrolidinol (Amount obtained: 174 mg/Yield: 75%).

$^1$H NMR (400, CDCl$_3$): 7.14 (2H, m), 6.89 (1H, t), 6.06 (1H, s), 5.80 (1H, m), 4.16 (3H, m), 3.88 (2H, d), 2.63 (2H, m), 2.76 (2H, m), 2.41 (6H, m), 2.02 (5H, m), 1.48 (9H, m), 1.26 (5H, m)

Example 61

Preparation of tert-butyl 4-((2-fluoro-4-(4-((S)-2-hydroxypropylcarbamoyl)cyclohex-1-enyl)phenoxy)methyl)piperidine-1-carboxylate

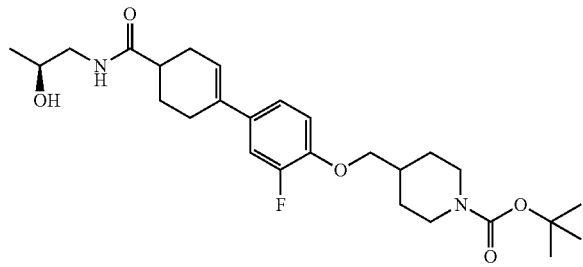 [SMILES: C[C@H](O)CNC(=O)C1CC=C(c2ccc(OCC3CCN(C(=O)OC(C)(C)C)CC3)c(F)c2)CC1]

The title compound was prepared in the same manner as in <Example 44>, except that (S)-1-amino-2-propanol was used instead of the (S)-(−)-3-pyrrolidinol (Amount obtained: 120 mg/Yield: 53%).

$^1$H NMR (400, CDCl$_3$): 7.14 (2H, m), 6.89 (1H, t), 6.07 (1H, s), 4.15 (2H, m), 3.96 (1H, m), 3.86 (2H, d), 3.52 (1H, m), 3.17 (1H, m), 2.76 (2H, m), 2.49 (6H, m), 2.02 (5H, m), 1.48 (9H, m), 1.27 (5H, m)

Example 62

Preparation of tert-butyl 4-((2-fluoro-4-(4-((R)-2-hydroxypropylcarbamoyl)cyclohex-1-enyl)phenoxy)methyl)piperidine-1-carboxylate

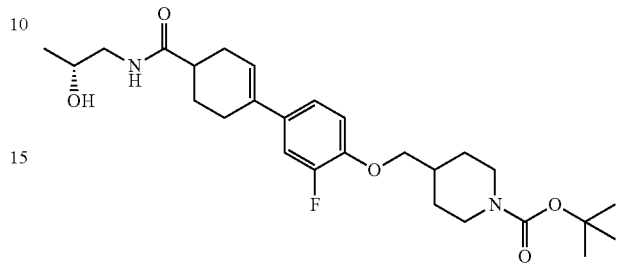

The title compound was prepared in the same manner as in <Example 44>, except that (R)-1-amino-2-propanol was used instead of the (S)-(−)-3-pyrrolidinol (Amount obtained: 139 mg/Yield: 60%).

$^1$H NMR (400, CDCl$_3$): 7.14 (2H, m), 6.89 (1H, t), 6.07 (1H, s), 4.15 (2H, m), 3.96 (1H, m), 3.86 (2H, d), 3.52 (1H, m), 3.17 (1H, m), 2.76 (2H, m), 2.49 (6H, m), 2.02 (5H, m), 1.48 (9H, m), 1.27 (5H, m)

Example 63

Preparation of tert-butyl 4-((4-(4-((S)-2,3-dihydroxypropylcarbamoyl)cyclohex-1-enyl)-2-fluorophenoxy)methyl)piperidine-1-carboxylate

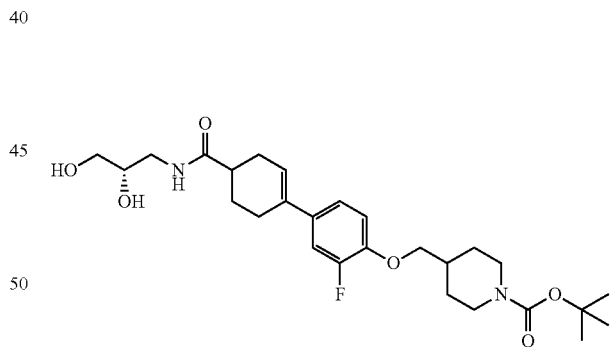

The title compound was prepared in the same manner as in <Example 44>, except that (S)-3-amino-1,2-propanediol was used instead of the (S)-(−)-3-pyrrolidinol (Amount obtained: 185 mg/Yield: 80%).

$^1$H NMR (400, CDCl$_3$): 7.18 (2H, m), 6.93 (1H, t), 6.11 (2H, m), 4.21 (2H, m), 3.91 (3H, m), 3.61 (4H, m), 3.03 (2H, m), 2.83 (2H, m), 2.16 (5H, m), 2.03 (6H, m), 1.50 (9H, m), 1.31 (2H, m)

Example 64

Preparation of tert-butyl 4-((4-(4-((R)-2,3-dihydroxypropylcarbamoyl)cyclohex-1-enyl)-2-fluorophenoxy)methyl)piperidine-1-carboxylate

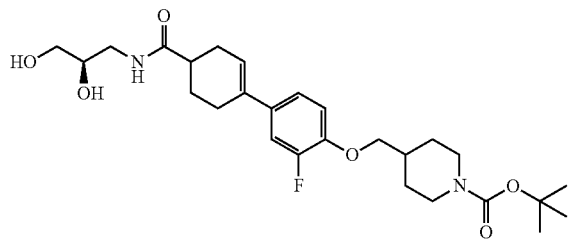 [SMILES: CC(C)(C)OC(=O)N1CCC(COc2ccc(C3=CCC(C(=O)NC[C@@H](O)CO)CC3)cc2F)CC1]

The title compound was prepared in the same manner as in <Example 44>, except that (R)-3-amino-1,2-propanediol was used instead of the (S)-(−)-3-pyrrolidinol (Amount obtained: 177 mg/Yield: 77%).

$^1$H NMR (400, CDCl$_3$): 7.18 (2H, m), 6.93 (1H, t), 6.11 (2H, m), 4.21 (2H, m), 3.91 (3H, m), 3.61 (4H, m), 3.03 (2H, m), 2.83 (2H, m), 2.16 (5H, m), 2.03 (6H, m), 1.50 (9H, m), 1.31 (2H, m)

Example 65

Preparation of azetidin-1-yl(4-(4-((1-(3-isopropyl-1,2,4-oxadiazol-5-yl)piperidin-4-yl)methoxy)phenyl)cyclohex-3-enyl)methanone

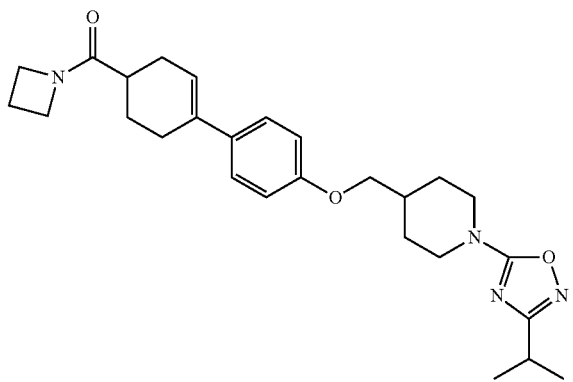 [SMILES: CC(C)c1noc(N2CCC(COc3ccc(C4=CCC(C(=O)N5CCC5)CC4)cc3)CC2)n1]

The title compound was prepared in the same manner as in <Example 17>, except that azetidine was used instead of the (R)-3-amino-1,2-propanediol (Amount obtained: 90 mg/Yield: 40%).

$^1$H NMR (400, CDCl$_3$): 7.34 (2H, d), 6.85 (2H, d), 6.06 (1H, m), 4.24 (4H, m), 4.07 (2H, m), 3.84 (2H, m), 3.11 (2H, t), 2.91 (1H, m), 2.50 (4H, m), 2.31 (3H, m), 1.97 (5H, m), 1.47 (2H, m), 1.31 (6H, m)

Example 66

Preparation of (4-(4-((1-(3-isopropyl-1,2,4-oxadiazol-5-yl)piperidin-4-yl)methoxy)phenyl)cyclohex-3-enyl)(morpholino)methanone

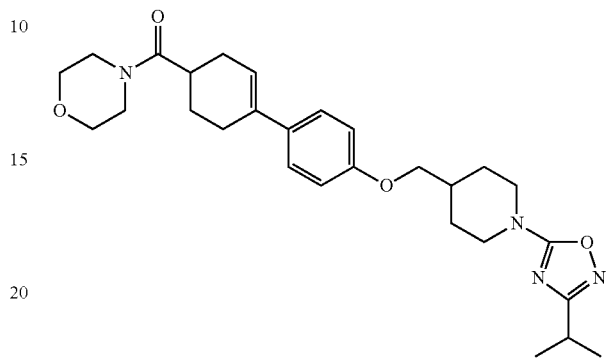

The title compound was prepared in the same manner as in <Example 17>, except that morpholine was used instead of the (R)-3-amino-1,2-propanediol (Amount obtained: 190 mg/Yield: 83%).

$^1$H NMR (400, CDCl$_3$): 7.33 (2H, d), 6.84 (2H, d), 6.06 (1H, m), 4.20 (2H, d), 3.84 (2H, d), 3.72 (8H, m), 3.11 (2H, t), 2.91 (1H, m), 2.77 (1H, m), 2.52 (3H, m), 2.31 (1H, m), 1.98 (5H, m), 1.50 (2H, m), 1.31 (6H, d)

Example 67

Preparation of tert-butyl 4-((4-(4-(1,3-dihydroxypropan-2-ylcarbamoyl)cyclohex-1-enyl)-2-fluorophenoxy)methyl)piperidine-1-carboxylate

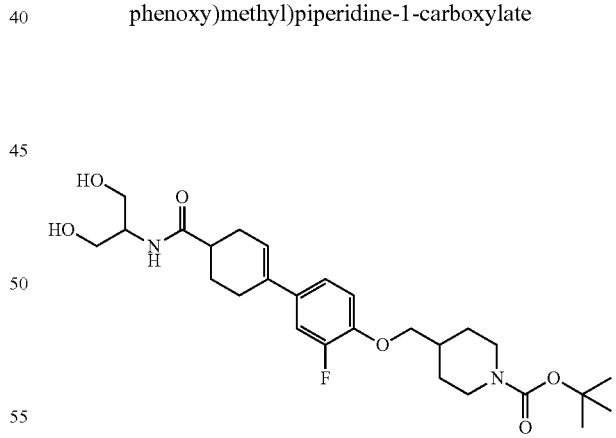

The title compound was prepared in the same manner as in <Example 44>, except that 2-amino-1,3-propanediol was used instead of the (S)-(−)-3-pyrrolidinol (Amount obtained: 115 mg/Yield: 53%).

$^1$H NMR (400, CDCl$_3$): 7.10 (2H, m), 6.88 (1H, t), 6.41 (1H, m), 6.06 (1H, m), 4.15 (2H, m), 3.91 (7H, m), 2.77 (3H, m), 2.45 (6H, m), 2.02 (4H, m), 1.32 (9H, m), 1.26 (2H, m)

Example 68

Preparation of tert-butyl 4-((5-(4-(1,3-dihydroxy-propan-2-ylcarbamoyl)cyclohex-1-enyl)pyridin-2-yloxy)methyl)piperidine-1-carboxylate

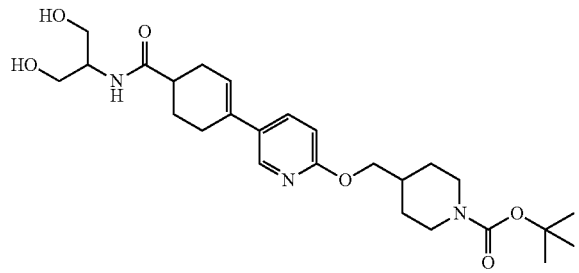 [SMILES: CC(C)(C)OC(=O)N1CCC(COc2ccc(C3=CCC(C(=O)NC(CO)CO)CC3)cn2)CC1]

The title compound was prepared in the same manner as in <Example 24>, except that 2-amino-1,3-propanediol was used instead of the (S)-2-amino-1-propanol (Amount obtained: 142 mg/Yield: 63%).

¹H NMR (400, CDCl₃): 8.14 (1H, s), 7.61 (1H, d), 6.70 (1H, d), 6.40 (1H, d), 6.04 (1H, s), 4.16 (4H, m), 4.01 (1H, m), 3.90 (4H, m), 2.76 (4H, m), 2.12 (1H, m), 1.93 (2H, m), 1.86 (2H, m), 1.48 (9H, m), 1.26 (2H, m).

Example 69

Preparation of tert-butyl 4-((2-fluoro-4-(4-(morpholine-4-carbonyl)cyclohex-1-enyl)phenoxy)methyl)piperidine-1-carboxylate

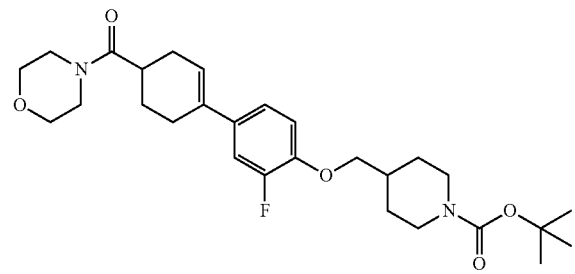 [SMILES: CC(C)(C)OC(=O)N1CCC(COc2ccc(C3=CCC(C(=O)N4CCSCC4)CC3)cc2F)CC1]

The title compound was prepared in the same manner as in <Example 44>, except that morpholine was used instead of the (S)-(−)-3-pyrrolidinol (Amount obtained: 192 mg/Yield: 83%).

¹H NMR (400, CDCl₃): 7.14 (2H, m), 6.89 (1H, t), 6.09 (1H, m), 4.16 (2H, m), 3.88 (2H, d), 3.69 (6H, m), 3.58 (2H, m), 2.78 (3H, m), 2.48 (4H, m), 1.91 (5H, m), 1.48 (9H, s), 1.28 (2H, m)

Example 70

Preparation of tert-butyl 4-((5-(4-(morpholine-4-carbonyl)cyclohex-1-enyl)pyridin-2-yloxy)methyl)piperidine-1-carboxylate

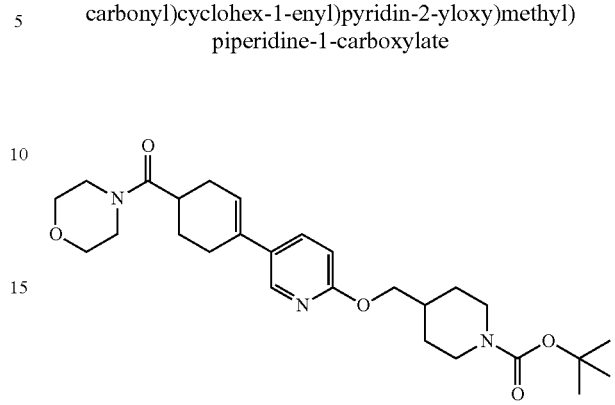

The title compound was prepared in the same manner as in <Example 24>, except that morpholine was used instead of the (S)-2-amino-1-propanol (Amount obtained: 210 mg/Yield: 91%).

¹H NMR (400, CDCl₃): 8.14 (1H, s), 7.63 (1H, d), 6.68 (1H, d), 6.05 (1H, s), 4.15 (4H, m), 3.71 (6H, m), 3.58 (2H, m), 2.77 (3H, m), 2.52 (3H, m), 2.30 (1H, m), 1.98 (3H, m), 1.84 (2H, d), 1.48 (9H, s), 1.27 (2H, m)

Example 71

Preparation of tert-butyl 4-((2-fluoro-4-(4-(thiomorpholine-4-carbonyl)cyclohex-1-enyl)phenoxy)methyl)piperidine-1-carboxylate

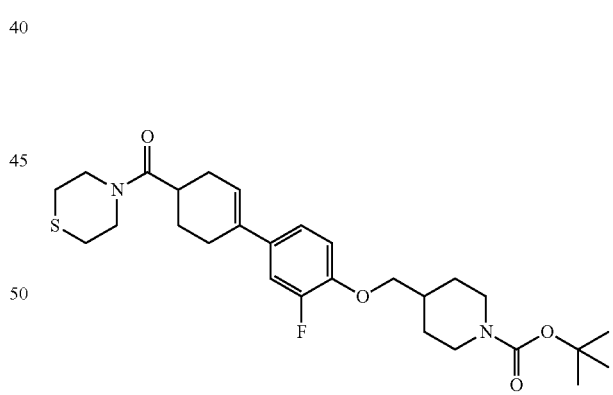

The title compound was prepared in the same manner as in <Example 44>, except that thiomorpholine was used instead of the (S)-(−)-3-pyrrolidinol (Amount obtained: 210 mg/Yield: 87%).

¹H NMR (400, CDCl₃): 7.14 (2H, m), 6.89 (1H, t), 6.07 (1H, m), 4.16 (2H, m), 3.98 (1H, m), 3.88 (5H, d), 2.79 (2H, m), 2.66 (4H, m), 2.31 (3H, m), 2.01 (1H, m), 1.91 (5H, m), 1.48 (9H, s), 1.26 (2H, m)

Example 72

Preparation of tert-butyl 4-((5-(4-(thiomorpholine-4-carbonyl)cyclohex-1-enyl)pyridin-2-yloxy)methyl)piperidine-1-carboxylate

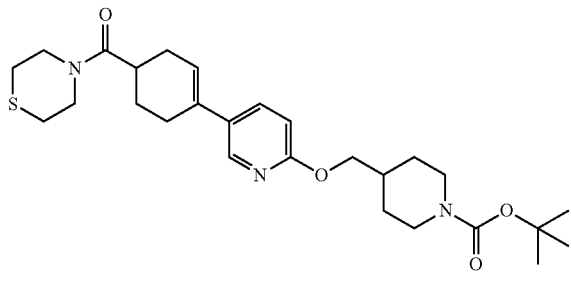 [SMILES: CC(C)(C)OC(=O)N1CCC(COc2ccc(C3=CCC(C(=O)N4CCSCC4)CC3)cn2)CC1]

The title compound was prepared in the same manner as in <Example 24>, except that thiomorpholine was used instead of the (S)-2-amino-1-propanol (Amount obtained: 180 mg/Yield: 79%).

$^1$H NMR (400, CDCl$_3$): 8.14 (1H, s), 7.62 (1H, d), 6.71 (1H, d), 6.06 (1H, s), 4.16 (4H, m), 3.85 (4H, m), 2.78 (2H, m), 2.67 (4H, m), 2.55 (3H, m), 2.31 (1H, m), 1.99 (3H, m), 1.84 (2H, d), 1.48 (9H, s), 1.27 (2H, m)

Example 73

Preparation of tert-butyl 4-((2-fluoro-4-(4-(thiomorpholine-1,1-dioxide-4-carbonyl)cyclohex-1-enyl)phenoxy)methyl)piperidine-1-carboxylate

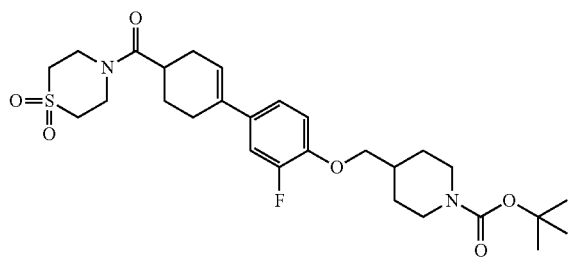 [SMILES: CC(C)(C)OC(=O)N1CCC(COc2ccc(C3=CCC(C(=O)N4CCS(=O)(=O)CC4)CC3)cc2F)CC1]

120 mg of tert-butyl 4-((2-fluoro-4-(4-(thiomorpholine-4-carbonyl)cyclohex-1-enyl)phenoxy)methyl)piperidine-1-carboxylate was dissolved in a THF/water mixture (50 μl/25 μl), and stirred. 360 mg of oxone was added dropwise thereto, and the resulting mixture was stirred for 30 minutes. After the reaction was terminated, the reaction mixture was extracted with 150 μl of ethyl acetate, washed with 100 μl of brine, dried with anhydrous magnesium sulfate, concentrated, and then isolated by silica column chromatography to prepare the title compound (Amount obtained: 100 mg/Yield: 72%).

$^1$H NMR (400, CDCl$_3$): 7.14 (2H, m), 6.90 (1H, t), 6.07 (1H, m), 4.19 (6H, m), 3.89 (2H, d), 3.09 (4H, d), 2.77 (3H, m), 2.54 (3H, m), 2.33 (1H, m), 2.00 (3H, m), 1.87 (2H, m), 1.48 (9H, s), 1.27 (2H, m)

Example 74

Preparation of (4-(4-((1-(3-isopropyl-1,2,4-oxadiazol-5-yl)piperidin-4-yl)methoxy)phenyl)cyclohex-3-enyl)(thiomorpholino)methanone

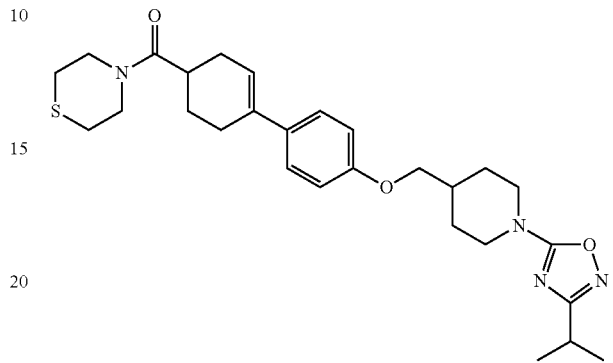

The title compound was prepared in the same manner as in <Example 17>, except that thiomorpholine was used instead of the (R)-3-amino-1,2-propanediol (Amount obtained: 165 mg/Yield: 63%).

$^1$H NMR (400, CDCl$_3$): 7.33 (2H, d), 6.84 (2H, d), 6.05 (1H, s), 4.23 (2H, m), 3.97 (6H, m), 3.08 (2H, t), 2.91 (1H, m), 2.78 (2H, m), 2.66 (4H, m), 2.51 (2H, m), 2.31 (1H, m), 2.03 (5H, m), 1.48 (2H, m), 1.32 (6H, d)

Example 75

Preparation of N-(2-fluoroethyl)-4-(4-((1-(3-isopropyl-1,2,4-oxadiazol-5-yl)piperidin-4-yl)methoxy)phenyl)cyclohex-3-enecarboxamide

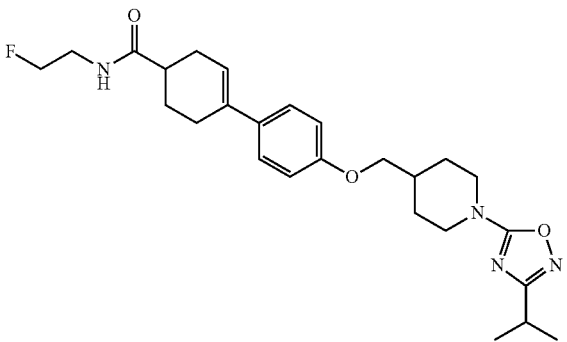 [SMILES: CC(C)c1noc(N2CCC(COc3ccc(C4=CCC(C(=O)NCCF)CC4)cc3)CC2)n1]

The title compound was prepared in the same manner as in <Example 17>, except that 2-fluoroethylamine was used instead of the (R)-3-amino-1,2-propanediol (Amount obtained: 174 mg/Yield: 75%).

$^1$H NMR (400, CDCl$_3$): 7.33 (2H, d), 6.87 (2H, d), 6.04 (2H, m), 4.53 (1H, m), 4.27 (2H, d), 3.86 (2H, d), 3.66 (2H, m), 3.21 (8H, m), 2.01 (5H, m), 1.45 (1H, m), 1.31 (6H, m)

Example 76

Preparation of tert-butyl 3-(4-(4-((1-(3-isopropyl-1,2,4-oxadiazol-5-yl)piperidin-4-yl)methoxy)phenyl)-N-methylcyclohex-3-enecarboxamido)propylcarbamate

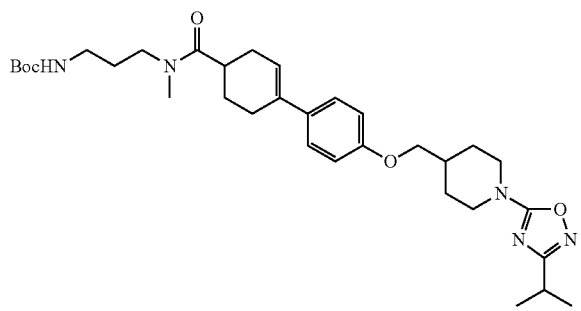 [SMILES: CC(C)c1noc(N2CCC(COc3ccc(C4=CCC(C(=O)N(C)CCCNC(=O)OC(C)(C)C)CC4)cc3)CC2)n1]

The title compound was prepared in the same manner as in <Example 17>, except that tert-butyl 3-(methylamino)propylcarbamate was used instead of the (R)-3-amino-1,2-propanediol (Amount obtained: 160 mg/Yield: 53%).

¹H NMR (400, CDCl₃): 7.34 (2H, d), 6.86 (2H, d), 6.07 (1H, m), 5.01 (1H, m), 4.21 (2H, d), 3.86 (2H, d), 3.56 (2H, m), 3.33 (2H, m), 3.11 (5H, m), 2.93 (1H, m), 2.80 (1H, m), 2.51 (2H, m), 2.98 (1H, m), 2.01 (5H, m), 1.48 (11H, m), 1.32 (6H, d)

Example 77

Preparation of N-(3-aminopropyl)-4-(4-((1-(3-isopropyl-1,2,4-oxadiazol-5-yl)piperidin-4-yl)methoxy)phenyl)-N-methylcyclohex-3-enecarboxamide

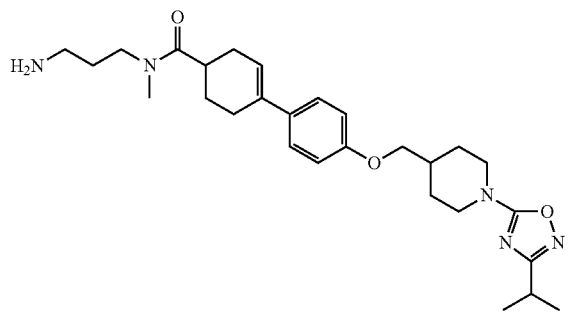 [SMILES: CC(C)c1noc(N2CCC(COc3ccc(C4=CCC(C(=O)N(C)CCCN)CC4)cc3)CC2)n1]

100 mg of tert-butyl 3-(4-(4-((1-(3-isopropyl-1,2,4-oxadiazol-5-yl)piperidin-4-yl)methoxy)phenyl)-N-methylcyclohex-3-enecarboxamido)propylcarbamate was dissolved in 25 μl of DCM, and stirred. 4 N HCl dissolved in 2 μl of dioxane was added dropwise thereto, and the resulting mixture was stirred at room temperature for 3 hours. After the reaction was terminated, the resulting solids were filtered, washed with 50 μl of DCM, and then dried to obtain a desired compound as a white solid (Amount obtained: 30 mg/Yield: 34%).

¹H NMR (400, DMSO): 7.34 (2H, d), 6.86 (2H, d), 6.07 (1H, m), 5.01 (1H, m), 4.21 (2H, d), 3.86 (2H, d), 3.56 (2H, m), 3.33 (2H, m), 3.11 (5H, m), 2.93 (1H, m), 2.80 (1H, m), 2.51 (2H, m), 2.98 (1H, m), 2.01 (5H, m), 1.48 (2H, m), 1.32 (6H, d)

Example 78

Preparation of 4-(4-((1-(3-isopropyl-1,2,4-oxadiazol-5-yl)piperidin-4-yl)methoxy)phenyl)-N-(2,2,2-trifluoroethyl)cyclohex-3-enecarboxamide

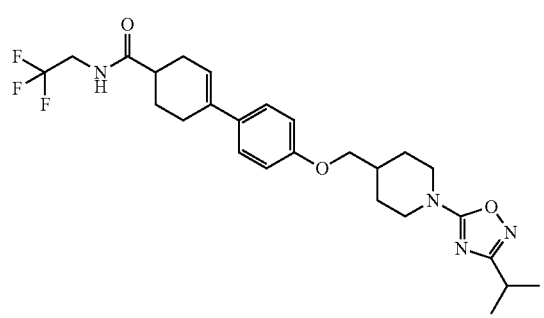 [SMILES: CC(C)c1noc(N2CCC(COc3ccc(C4=CCC(C(=O)NCC(F)(F)F)CC4)cc3)CC2)n1]

The title compound was prepared in the same manner as in <Example 17>, except that 2,2,2-trifluoroethyl amine was used instead of the (R)-3-amino-1,2-propanediol (Amount obtained: 195 mg/Yield: 85%).

¹H NMR (400, CDCl₃): 7.33 (2H, d), 6.86 (2H, d), 6.04 (1H, m), 5.96 (1H, m), 4.23 (2H, d), 3.99 (2H, m), 3.84 (2H, d), 3.12 (2H, m), 2.92 (1H, m), 2.48 (5H, m), 2.01 (5H, m), 1.46 (2H, m), 1.29 (6H, d)

Example 79

Preparation of (4-ethylpiperazin-1-yl)(4-(4-((1-(3-isopropyl-1,2,4-oxadiazol-5-yl)piperidin-4-yl)methoxy)phenyl)cyclohex-3-enyl)methanone

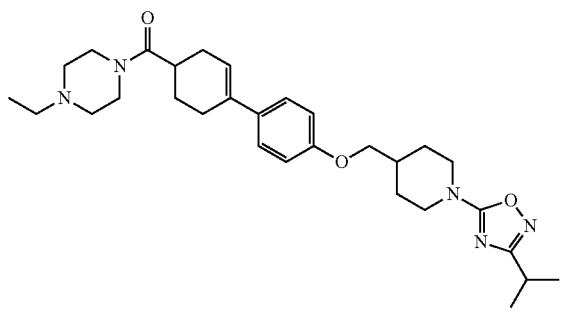 [SMILES: CCN1CCN(C(=O)C2CC=C(c3ccc(OCC4CCN(c5nc(C(C)C)no5)CC4)cc3)CC2)CC1]

The title compound was prepared in the same manner as in <Example 17>, except that N-ethylpiperazine was used instead of the (R)-3-amino-1,2-propanediol (Amount obtained: 150 mg/Yield: 65%).

¹H NMR (400, CDCl₃): 7.33 (2H, d), 6.86 (2H, d), 6.05 (1H, m), 4.23 (2H, d), 3.85 (2H, d), 3.70 (2H, m), 3.59 (2H, m), 3.08 (2H, t), 2.92 (1H, m), 2.89 (1H, m), 2.50 (9H, m), 2.24 (1H, m), 1.98 (5H, m), 1.48 (2H, m), 1.31 (6H, d), 1.11 (3H, t)

Example 80

Preparation of N-(1,3-dihydroxypropan-2-yl)-4-(3-fluoro-4-((1-(3-isopropyl-1,2,4-oxadiazol-5-yl)piperidin-4-yl)methoxy)phenyl)cyclohex-3-enecarboxamide

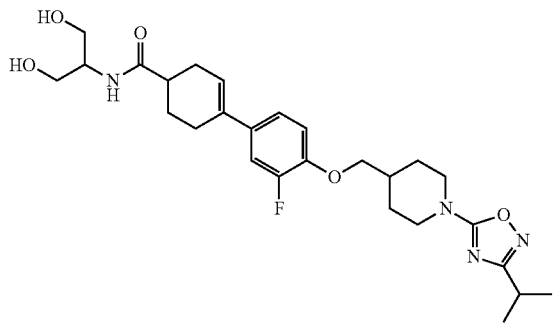 [SMILES: CC(C)c1noc(N2CCC(COc3ccc(C4=CCC(C(=O)NC(CO)CO)CC4)cc3F)CC2)n1]

250 mg of 4-(3-fluoro-4-((1-(3-isopropyl-1,2,4-oxadiazol-5-yl)piperidin-4-yl)methoxy)phenyl)cyclohex-3-enecarboxyilc acid was dissolved in 25 μl of DMF, and stirred. 200 mg of EDCI and 150 mg of HOBt were sequentially added dropwise thereto, and the resulting mixture was then additionally stirred for 10 minutes. 100 mg of 2-amino-1,3-propanediol was added dropwise thereto, and the mixture was stirred at room temperature for 12 hours. After the reaction was terminated, 50 μl of distilled water was slowly added as 0° C., and the resulting solids were filtered, and dried to obtain a desired compound as a white solid (Amount obtained: 210 mg/Yield: 71%).

$^1$H NMR (400, CDCl$_3$): 7.14 (2H, m), 6.91 (1H, t), 6.37 (1H, m), 6.07 (1H, m), 4.24 (2H, d), 4.01 (1H, m), 3.91 (2H, m), 3.81 (4H, m), 3.15 (2H, t), 2.94 (1H, m), 2.64 (2H, m), 2.50 (5H, m), 2.14 (2H, m), 1.92 (2H, d), 1.88 (1H, m), 1.45 (2H, m), 1.30 (6H, d)

Example 81

Preparation of 4-(3-fluoro-4-((1-(3-isopropyl-1,2,4-oxadiazol-5-yl)piperidin-4-yl)methoxy)phenyl)-N-(2-hydroxyethyl)-N-methylcyclohex-3-enecarboxamide

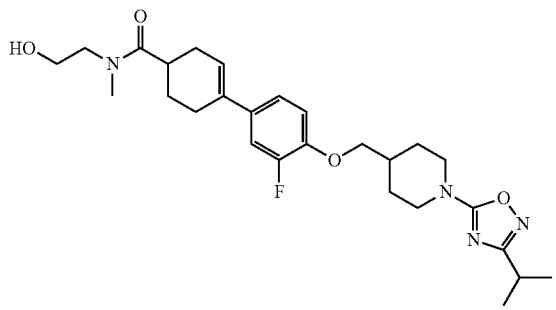

The title compound was prepared in the same manner as in <Example 80>, except that 2-(methylamino)ethanol was used instead of the 2-amino-1,3-propanediol (Amount obtained: 169 mg/Yield: 73%).

$^1$H NMR (400, CDCl$_3$): 7.15 (1H, d), 7.11 (1H, d), 6.91 (1H, m), 6.11 (1H, s), 4.26 (2H, d), 3.94 (2H, d), 3.84 (2H, m), 3.61 (2H, m), 3.21 (3H, s), 3.16 (2H, m), 3.05 (1H, s), 2.91 (1H, m), 2.87 (1H, m), 2.25-2.61 (4H, m), 1.85-2.19 (5H, m), 1.43 (2H, m), 1.30 (6H, d)

Example 82

Preparation of tert-butyl 4-((2-fluoro-4-(4-(3-hydroxy-2,2-dimethylpropylcarbamoyl)cyclohex-1-enyl)phenoxy)methyl)piperidine-1-carboxylate

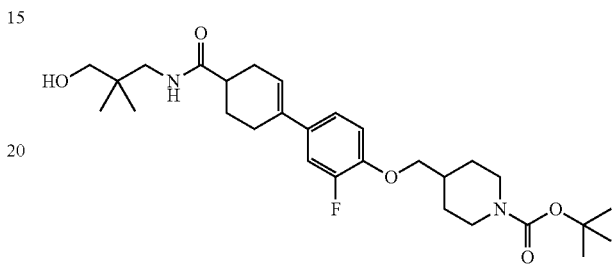

The title compound was prepared in the same manner as in <Example 44>, except that 3-amino-2,2-dimethylpropan-1-ol was used instead of the (S)-(−)-3-pyrrolidinol (Amount obtained: 150 mg/Yield: 65%).

$^1$H NMR (400, CDCl$_3$): 7.15 (1H, d), 7.11 (1H, d), 6.91 (1H, m), 6.11 (1H, s), 6.00 (1H, m), 4.19 (2H, m), 3.89 (3H, m), 3.18 (4H, m), 2.81 (2H, m), 2.45-2.61 (5H, m), 1.85-2.19 (4H, m), 1.48 (9H, s), 1.34 (2H, m), 0.89 (6H, d)

Example 83

Preparation of 4-(3-fluoro-4-((1-(3-isopropyl-1,2,4-oxadiazol-5-yl)piperidin-4-yl)methoxy)phenyl)-N-((S)-1-hydroxypropan-2-yl)cyclohex-3-enecarboxamide

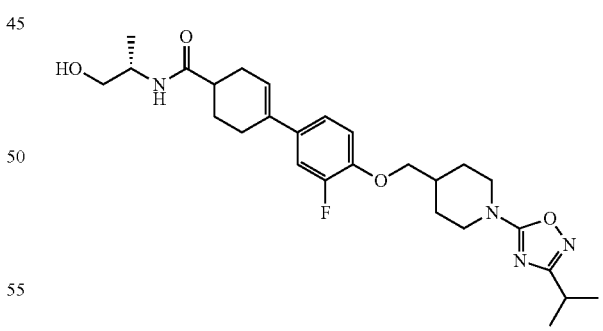

The title compound was prepared in the same manner as in <Example 80>, except that (S)-2-amino-1-propanol was used instead of the 2-amino-1,3-propanediol (Amount obtained: 95 mg/Yield: 48%).

$^1$H NMR (400, CDCl$_3$): 7.15 (1H, d), 7.11 (1H, d), 6.91 (1H, m), 6.11 (1H, s), 5.71 (1H, d), 4.25 (2H, d), 4.16 (1H, m), 3.92 (2H, d), 3.65 (2H, m), 3.16 (2H, m), 2.91 (1H, m), 2.35-2.61 (5H, m), 2.12 (2H, m), 1.98 (2H, d), 1.48 (2H, m), 1.36 (6H, d), 1.21 (3H, d)

Example 84

Preparation of 4-(3-fluoro-4-((1-(3-isopropyl-1,2,4-oxadiazol-5-yl)piperidin-4-yl)methoxy)phenyl)-N-((R)-1-hydroxypropan-2-yl)cyclohex-3-enecarboxamide

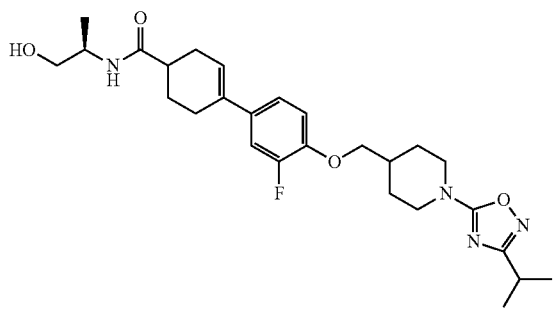 [SMILES: CC(C)c1noc(N2CCC(COc3ccc(C4=CCC(C(=O)N[C@H](C)CO)CC4)cc3F)CC2)n1]

The title compound was prepared in the same manner as in <Example 80>, except that (R)-2-amino-1-propanol was used instead of the 2-amino-1,3-propanediol (Amount obtained: 120 mg/Yield: 53%).

$^1$H NMR (400, CDCl$_3$): 7.15 (1H, d), 7.11 (1H, d), 6.91 (1H, m), 6.11 (1H, s), 5.71 (1H, d), 4.25 (2H, d), 4.16 (1H, m), 3.92 (2H, d), 3.65 (2H, m), 3.16 (2H, m), 2.91 (1H, m), 2.35-2.61 (5H, m), 2.12 (2H, m), 1.98 (2H, d), 1.48 (2H, m), 1.36 (6H, d), 1.21 (3H, d)

Example 85

Preparation of tert-butyl 4-((4-(4-(2,2-difluoroethylcarbamoyl)cyclohex-1-enyl)-2-fluorophenoxy)methyl)piperidine-1-carboxylate

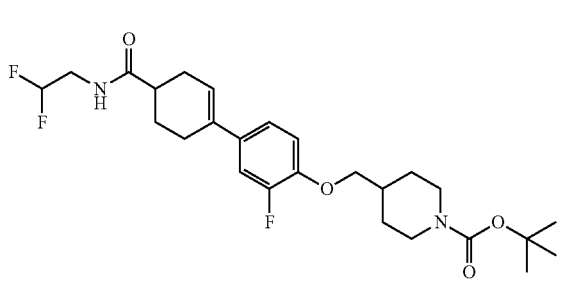 [SMILES: CC(C)(C)OC(=O)N1CCC(COc2ccc(C3=CCC(C(=O)NCC(F)F)CC3)cc2F)CC1]

The title compound was prepared in the same manner as in <Example 44>, except that 2,2-difluoroethylamine was used instead of the (S)-(−)-3-pyrrolidinol (Amount obtained: 150 mg/Yield: 65%).

$^1$H NMR (400, CDCl$_3$): 7.15 (1H, d), 7.11 (1H, d), 6.91 (1H, m), 6.11 (1H, s), 5.88 (1H, m), 5.85 (1H, m), 4.16 (2H, m), 3.87 (2H, d), 3.69 (2H, m), 2.77 (2H, m), 2.35-2.61 (5H, m), 2.12 (2H, m), 2.02 (1H, m), 1.89 (3H, m), 1.46 (9H, s), 1.25 (3H, m)

Example 86

Preparation of tert-butyl 4-((5-(4-(2,2,2-trifluoroethylcarbamoyl)cyclohex-1-enyl)pyridin-2-yloxy)methyl)piperidine-1-carboxylate

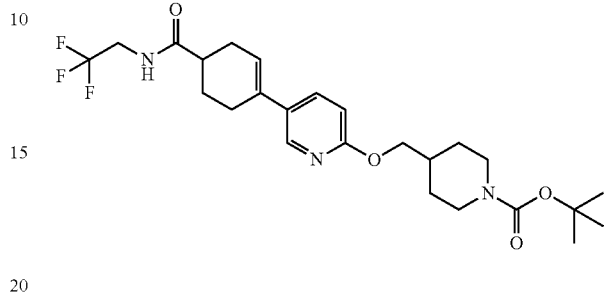

The title compound was prepared in the same manner as in <Example 24>, except that 2,2,2-trifluoroethylamine was used instead of the (S)-2-amino-1-propanol (Amount obtained: 110 mg/Yield: 48%).

$^1$H NMR (400, CDCl$_3$): 8.14 (1H, d), 7.61 (1H, d), 6.70 (1H, d), 6.05 (1H, s), 5.86 (1H, m), 4.16 (4H, d), 3.99 (2H, m), 2.76 (2H, m), 2.35-2.61 (5H, m), 2.12 (1H, m), 1.89 (2H, m), 1.81 (2H, d), 1.48 (9H, s), 1.33 (2H, m)

Example 87

Preparation of tert-butyl 4-((5-(4-(2,2-difluoroethylcarbamoyl)cyclohex-1-enyl)pyridin-2-yloxy)methyl)piperidine-1-carboxylate

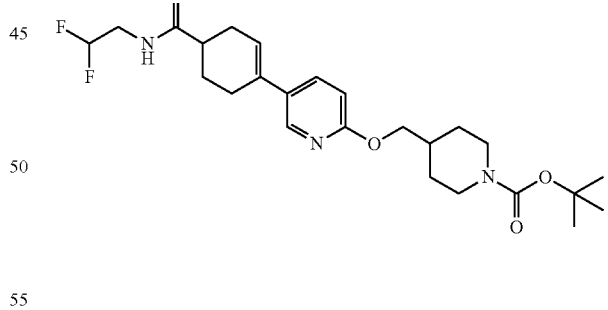

The title compound was prepared in the same manner as in <Example 24>, except that 2,2-difluoroethylamine was used instead of the (S)-2-amino-1-propanol (Amount obtained: 150 mg/Yield: 65%).

$^1$H NMR (400, CDCl$_3$): 8.14 (1H, d), 7.61 (1H, d), 6.70 (1H, d), 6.05 (1H, s), 5.88 (1H, m), 5.85 (1H, m), 4.16 (4H, d), 3.70 (2H, m), 2.76 (2H, m), 2.35-2.61 (5H, m), 2.12 (1H, m), 1.98 (2H, m), 1.82 (2H, d), 1.48 (9H, s), 1.29 (3H, m)

Example 88

Preparation of tert-butyl 4-((5-(4-(2-fluoroethylcarbamoyl)cyclohex-1-enyl)pyridin-2-yloxy)methyl)piperidine-1-carboxylate

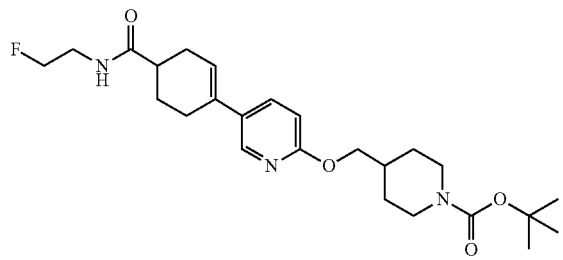 [SMILES: CC(C)(C)OC(=O)N1CCC(COc2ccc(C3=CCC(C(=O)NCCF)CC3)cn2)CC1]

The title compound was prepared in the same manner as in <Example 24>, except that 2-fluoroethylamine was used instead of the (S)-2-amino-1-propanol (Amount obtained: 120 mg/Yield: 52%).

$^1$H NMR (400, CDCl$_3$): 8.14 (1H, d), 7.61 (1H, d), 6.70 (1H, d), 6.05 (1H, s), 5.93 (1H, m), 4.55 (2H, m), 4.16 (4H, d), 3.67 (2H, m), 2.76 (2H, m), 2.35-2.61 (5H, m), 2.12 (1H, m), 1.98 (2H, m), 1.82 (2H, d), 1.48 (9H, s), 1.29 (3H, m)

Example 89

Preparation of (4-cyclopropylpiperazin-1-yl)(4-(4-((1-(3-isopropyl-1,2,4-oxadiazol-5-yl)piperidin-4-yl)methoxy)phenyl)cyclohex-3-enyl)methanone

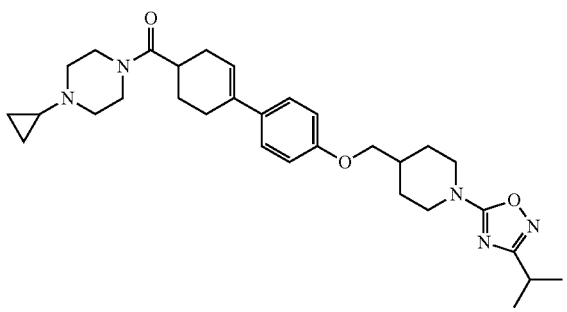 [SMILES: CC(C)c1noc(N2CCC(COc3ccc(C4=CCC(C(=O)N5CCN(C6CC6)CC5)CC4)cc3)CC2)n1]

The title compound was prepared in the same manner as in <Example 17>, except that cyclopropylpiperazine was used instead of the (R)-3-amino-1,2-propanediol (Amount obtained: 210 mg/Yield: 87%).

$^1$H NMR (400, CDCl$_3$): 7.32 (2H, d), 6.85 (2H, d), 6.05 (1H, d), 4.22 (2H, d), 3.85 (2H, d), 3.66 (2H, m), 3.53 (2H, m), 3.12 (3H, m), 2.81 (3H, m), 2.35-2.61 (8H, m), 1.91-2.14 (6H, m), 1.68 (1H, m), 1.48 (2H, m), 1.32 (6H, d), 1.15 (1H, m), 0.48 (4H, m)

Example 90

Preparation of tert-butyl 4-((5-(4-((R)-3-fluoropyrrolidine-1-carbonyl)cyclohex-1-enyl)pyridin-2-yloxy)methyl)piperidine-1-carboxylate

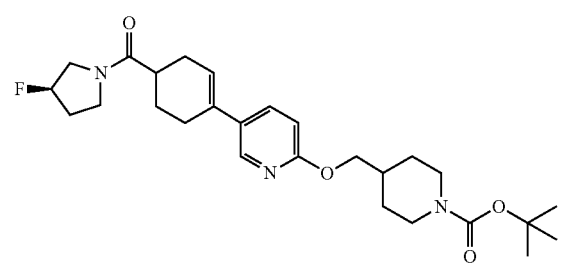 [SMILES: CC(C)(C)OC(=O)N1CCC(COc2ccc(C3=CCC(C(=O)N4CC[C@@H](F)C4)CC3)cn2)CC1]

The title compound was prepared in the same manner as in <Example 24>, except that (R)-3-fluoropyrrolidine was used instead of the (S)-2-amino-1-propanol (Amount obtained: 165 mg/Yield: 72%).

$^1$H NMR (400, CDCl$_3$): 8.15 (1H, s), 7.63 (1H, d), 6.70 (1H, d), 6.08 (1H, s), 5.31 (1H, m), 4.16 (4H, m), 3.53-4.01 (2H, m), 2.76 (2H, m), 2.35-2.61 (5H, m), 1.80-2.16 (6H, m), 1.48 (9H, s), 1.29 (3H, m)

Example 91

Preparation of tert-butyl 4-((5-(4-((S)-3-fluoropyrrolidine-1-carbonyl)cyclohex-1-enyl)pyridin-2-yloxy)methyl)piperidine-1-carboxylate

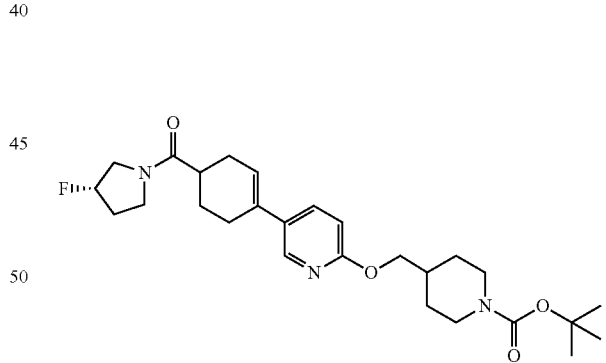

The title compound was prepared in the same manner as in <Example 24>, except that (S)-3-fluoropyrrolidine was used instead of the (S)-2-amino-1-propanol (Amount obtained: 120 mg/Yield: 53%).

$^1$H NMR (400, CDCl$_3$): 8.15 (1H, s), 7.63 (1H, d), 6.70 (1H, d), 6.08 (1H, s), 5.31 (1H, m), 4.16 (4H, m), 3.53-4.01 (2H, m), 2.76 (2H, m), 2.35-2.61 (5H, m), 1.80-2.16 (6H, m), 1.48 (9H, s), 1.29 (3H, m)

Example 92

Preparation of 4-(3-fluoro-4-((1-(3-isopropyl-1,2,4-oxadiazol-5-yl)piperidin-4-yl)methoxy)phenyl)-N-(2,2,2-trifluoroethyl)cyclohex-3-enecarboxamide

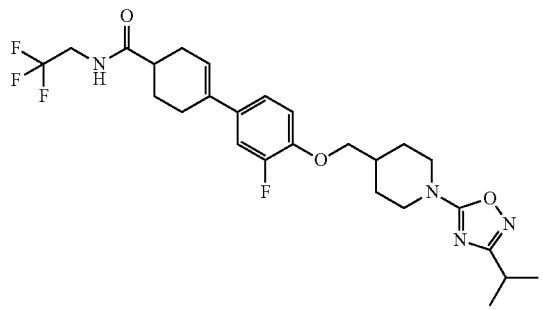

The title compound was prepared in the same manner as in <Example 80>, except that 2,2,2-trifluoroethylamine was used instead of the 2-amino-1,3-propanediol (Amount obtained: 140 mg/Yield: 62%).

$^1$H NMR (400, CDCl$_3$): 7.11 (2H, m), 6.91 (1H, m), 6.07 (1H, d), 5.80 (1H, m), 4.22 (2H, d), 3.99 (1H, m), 3.92 (2H, d), 3.12 (2H, m), 2.92 (1H, m), 2.35-2.61 (5H, m), 1.83-2.21 (5H, m), 1.48 (2H, m), 1.32 (6H, d)

Example 93

Preparation of N-(2,2-difluoroethyl)-4-(3-fluoro-4-((1-(3-isopropyl-1,2,4-oxadiazol-5-yl)piperidin-4-yl)methoxy)phenyl)cyclohex-3-enecarboxamide

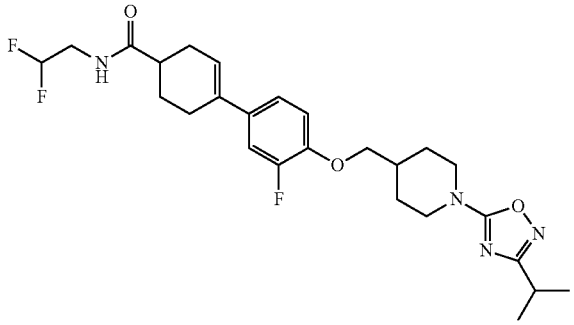

The title compound was prepared in the same manner as in <Example 80>, except that 2,2-difluoroethylamine was used instead of the 2-amino-1,3-propanediol (Amount obtained: 110 mg/Yield: 49%).

$^1$H NMR (400, CDCl$_3$): 7.11 (2H, m), 6.91 (1H, m), 6.07 (1H, d), 5.89 (1H, m), 5.81 (1H, m), 4.22 (2H, d), 3.99 (1H, m), 3.69 (2H, m), 3.12 (2H, m), 2.92 (1H, m), 2.35-2.61 (5H, m), 1.83-2.21 (5H, m), 1.48 (2H, m), 1.32 (6H, d)

Example 94

Preparation of 4-(3-fluoro-4-((1-(3-isopropyl-1,2,4-oxadiazol-5-yl)piperidin-4-yl)methoxy)phenyl)-N-(2-fluoroethyl)cyclohex-3-enecarboxamide

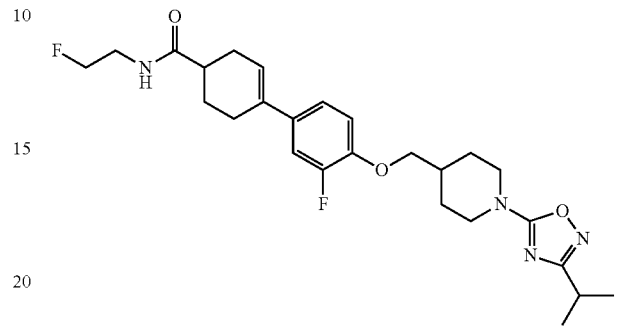

The title compound was prepared in the same manner as in <Example 80>, except that fluoroethylamine was used instead of the 2-amino-1,3-propanediol (Amount obtained: 120 mg/Yield: 53%).

$^1$H NMR (400, CDCl$_3$): 7.11 (2H, m), 6.91 (1H, m), 6.07 (1H, d), 5.94 (1H, s), 4.55 (2H, m), 4.22 (2H, d), 3.99 (1H, m), 3.63 (2H, m), 3.12 (2H, m), 2.92 (1H, m), 2.35-2.61 (5H, m), 1.83-2.21 (5H, m), 1.48 (2H, m), 1.32 (6H, d)

Example 95

Preparation of (4-(3-fluoro-4-((1-(3-isopropyl-1,2,4-oxadiazol-5-yl)piperidin-4-yl)methoxy)phenyl)cyclohex-3-enyl)((S)-3-fluoropyrrolidin-1-yl)methanone

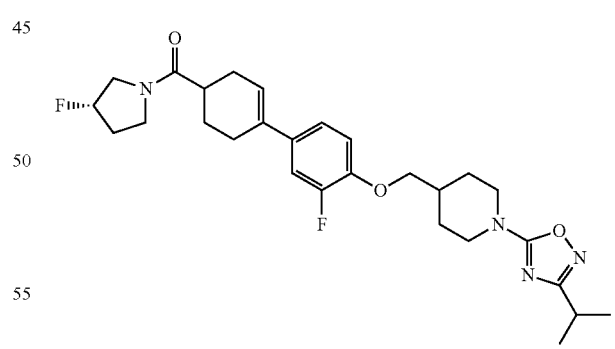

The title compound was prepared in the same manner as in <Example 80>, except that (S)-3-fluoropyrrolidine was used instead of the 2-amino-1,3-propanediol (Amount obtained: 185 mg/Yield: 78%).

$^1$H NMR (400, CDCl$_3$): 7.11 (2H, m), 6.91 (1H, m), 6.10 (1H, s), 5.30 (1H, m), 4.22 (2H, d), 3.95 (2H, d), 3.75 (4H, m), 3.12 (2H, m), 2.92 (1H, m), 2.35-2.61 (5H, m), 1.83-2.21 (5H, m), 1.48 (2H, m), 1.32 (6H, d)

Example 96

Preparation of (4-(3-fluoro-4-((1-(3-isopropyl-1,2,4-oxadiazol-5-yl)piperidin-4-yl)methoxy)phenyl)cyclohex-3-enyl)((R)-3-fluoropyrrolidin-1-yl)methanone

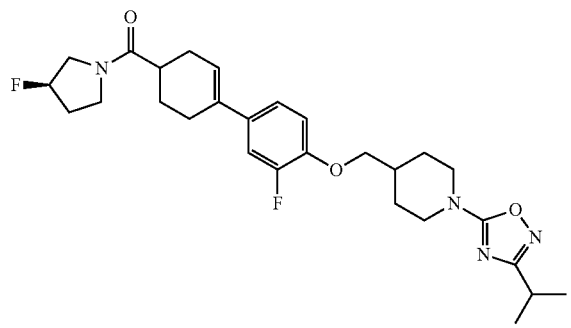

The title compound was prepared in the same manner as in <Example 80>, except that (R)-3-fluoropyrrolidine was used instead of the 2-amino-1,3-propanediol (Amount obtained: 150 mg/Yield: 64%).

$^1$H NMR (400, CDCl$_3$): 7.11 (2H, m), 6.91 (1H, m), 6.10 (1H, s), 5.30 (1H, m), 4.22 (2H, d), 3.95 (2H, d), 3.75 (4H, m), 3.12 (2H, m), 2.92 (1H, m), 2.35-2.61 (5H, m), 1.83-2.21 (5H, m), 1.48 (2H, m), 1.32 (6H, d)

Example 97

Preparation of (4-(3-fluoro-4-((1-(3-isopropyl-1,2,4-oxadiazol-5-yl)piperidin-4-yl)methoxy)phenyl)cyclohex-3-enyl)(morpholino)methanone

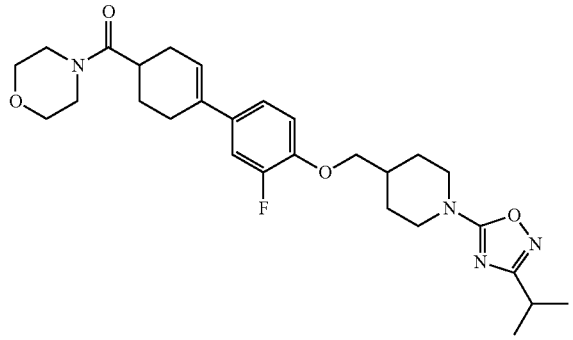 [SMILES: CC(C)c1noc(N2CCC(COc3ccc(C4=CCC(C(=O)N5CCSCC5)CC4)cc3F)CC2)n1]

The title compound was prepared in the same manner as in <Example 80>, except that morpholine was used instead of the 2-amino-1,3-propanediol (Amount obtained: 190 mg/Yield: 83%).

$^1$H NMR (400, CDCl$_3$): 7.11 (2H, m), 6.91 (1H, m), 6.09 (1H, s), 4.21 (2H, d), 3.91 (2H, d), 3.72 (6H, m), 3.59 (2H, m), 3.13 (2H, m), 2.92 (1H, m), 2.78 (1H, m), 2.35-2.61 (3H, m), 2.30 (1H, m), 1.83-2.21 (5H, m), 1.48 (2H, m), 1.32 (6H, d)

Example 98

Preparation of (4-(3-fluoro-4-((1-(3-isopropyl-1,2,4-oxadiazol-5-yl)piperidin-4-yl)methoxy)phenyl)cyclohex-3-enyl)(thiomorpholino)methanone

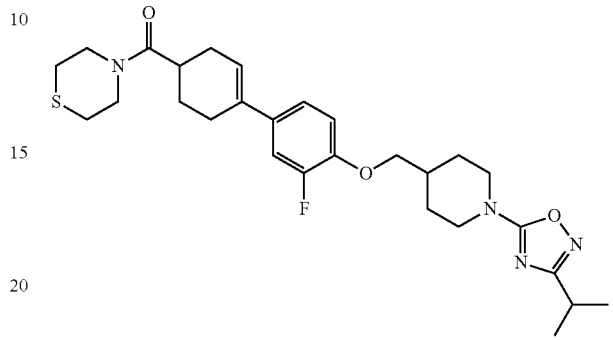

The title compound was prepared in the same manner as in <Example 80>, except that thiomorpholine was used instead of the 2-amino-1,3-propanediol (Amount obtained: 200 mg/Yield: 78%).

$^1$H NMR (400, CDCl$_3$): 7.11 (2H, m), 6.91 (1H, m), 6.09 (1H, s), 4.21 (2H, d), 3.91 (6H, m), 3.13 (2H, m), 2.92 (1H, m), 2.78 (1H, m), 2.65 (4H, m), 2.35-2.61 (5H, m), 1.83-2.21 (5H, m), 1.48 (2H, m), 1.32 (6H, d)

Example 99

Preparation of N-(2,2-difluoroethyl)-4-(5-((1-(3-isopropyl-1,2,4-oxadiazol-5-yl)piperidin-4-yl)methoxy)pyridin-2-yl)cyclohex-3-enecarboxamide

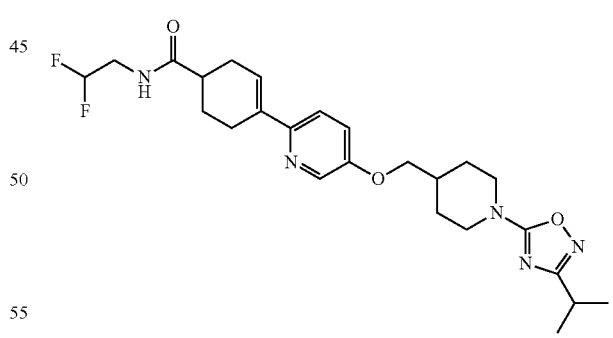

The title compound was prepared in the same manner as in <Example 36>, except that 2,2-difluoroethylamine was used instead of the (R)-2-amino-1-propanol (Amount obtained: 165 mg/Yield: 71%).

$^1$H NMR (400, CDCl$_3$): 8.25 (1H, d), 7.34 (1H, d), 7.16 (1H, d), 6.56 (1H, s), 5.89 (1H, m), 5.83 (1H, m), 4.24 (2H, d), 3.89 (2H, d), 3.71 (2H, m), 3.12 (2H, m), 2.92 (1H, m), 2.75 (1H, m), 2.51 (4H, m), 1.83-2.21 (5H, m), 1.49 (2H, m), 1.32 (6H, d)

Example 100

Preparation of (4-(5-((1-(3-isopropyl-1,2,4-oxadiazol-5-yl)piperidin-4-yl)methoxy)pyridin-2-yl)cyclohex-3-enyl)(morpholino)methanone

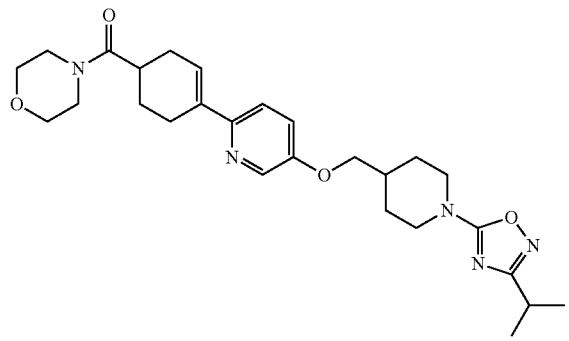 [SMILES: CC(C)c1noc(N2CCC(COc3ccc(C4=CCC(C(=O)N5CCOCC5)CC4)nc3)CC2)n1]

The title compound was prepared in the same manner as in <Example 36>, except that morpholine was used instead of the (R)-2-amino-1-propanol (Amount obtained: 200 mg/Yield: 87%).

$^1$H NMR (400, CDCl$_3$): 8.25 (1H, d), 7.34 (1H, d), 7.16 (1H, d), 6.56 (1H, s), 4.24 (2H, d), 3.90 (2H, d), 3.72 (6H, m), 3.58 (2H, m), 3.12 (2H, m), 2.92 (1H, m), 2.78 (2H, m), 2.57 (2H, m), 2.37 (1H, m), 1.83-2.21 (5H, m), 1.49 (2H, m), 1.32 (6H, d)

Example 101

Preparation of ((R)-3-fluoropyrrolidin-1-yl)(4-(5-((1-(3-isopropyl-1,2,4-oxadiazol-5-yl)piperidin-4-yl)methoxy)pyridin-2-yl)cyclohex-3-enyl)methanone

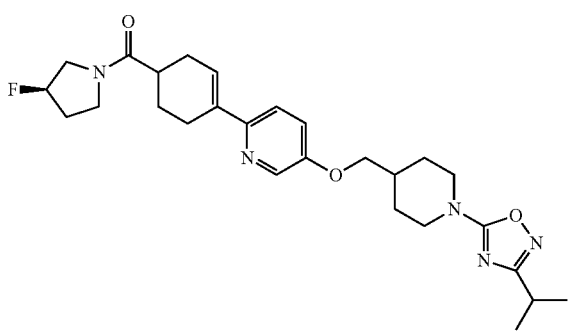 [SMILES: CC(C)c1noc(N2CCC(COc3ccc(C4=CCC(C(=O)N5CC[C@@H](F)C5)CC4)nc3)CC2)n1]

The title compound was prepared in the same manner as in <Example 36>, except that (R)-3-fluoropyrrolidine was used instead of the (R)-2-amino-1-propanol (Amount obtained: 210 mg/Yield: 86%).

$^1$H NMR (400, CDCl$_3$): 8.25 (1H, d), 7.34 (1H, m), 7.16 (1H, m), 6.58 (1H, s), 5.30 (1H, m), 4.23 (2H, d), 3.55-3.99 (6H, m), 3.12 (2H, m), 2.92 (1H, m), 2.25-2.83 (6H, m), 1.83-2.21 (6H, m), 1.49 (2H, m), 1.31 (6H, d)

Example 102

Preparation of ((S)-3-fluoropyrrolidin-1-yl)(4-(5-((1-(3-isopropyl-1,2,4-oxadiazol-5-yl)piperidin-4-yl)methoxy)pyridin-2-yl)cyclohex-3-enyl)methanone

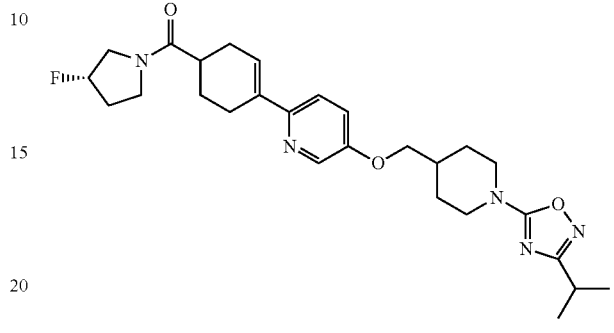

The title compound was prepared in the same manner as in <Example 36>, except that (S)-3-fluoropyrrolidine was used instead of the (R)-2-amino-1-propanol (Amount obtained: 220 mg/Yield: 81%).

$^1$H NMR (400, CDCl$_3$): 8.25 (1H, d), 7.34 (1H, m), 7.16 (1H, m), 6.58 (1H, s), 5.30 (1H, m), 4.23 (2H, d), 3.55-3.99 (6H, m), 3.12 (2H, m), 2.92 (1H, m), 2.25-2.83 (6H, m), 1.83-2.21 (6H, m), 1.49 (2H, m), 1.31 (6H, d)

Example 103

Preparation of 4-(4-((1-(5-ethylpyrimidin-2-yl)piperidin-4-yl)methoxy)phenyl)-N-(2,2,2-trifluoroethyl)cyclohex-3-enecarboxamide

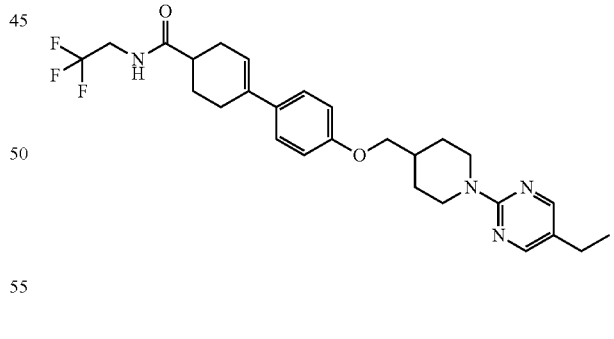

The title compound was prepared in the same manner as in <Example 8>, except that 2,2,2-trifluoroethylamine was used instead of the (R)-2-amino-1-propanol (Amount obtained: 190 mg/Yield: 77%).

$^1$H NMR (400, CDCl$_3$): 8.19 (2H, s), 7.31 (2H, d), 6.86 (2H, d), 6.03 (1H, s), 4.58 (1H, m), 4.79 (2H, d), 3.99 (2H, m), 3.84 (2H, d), 2.96 (2H, m), 2.51 (7H, m), 1.83-2.21 (5H, m), 1.39 (2H, m), 1.21 (3H, m)

Example 104

Preparation of 4-(4-((1-(5-ethylpyrimidin-2-yl)piperidin-4-yl)methoxy)phenyl)-N-(2-fluoroethyl)cyclohex-3-enecarboxamide

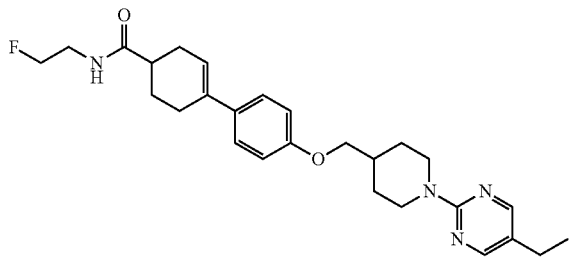 [SMILES: CCc1cnc(N2CCC(COc3ccc(C4=CCC(C(=O)NCCF)CC4)cc3)CC2)nc1]

The title compound was prepared in the same manner as in <Example 8>, except that fluoroethylamine was used instead of the (R)-2-amino-1-propanol (Amount obtained: 180 mg/Yield: 72%).

$^1$H NMR (400, CDCl$_3$): 8.19 (2H, s), 7.31 (2H, d), 6.86 (2H, d), 6.03 (1H, s), 4.58 (1H, m), 4.48 (1H, m), 4.59 (1H, m), 3.85 (2H, d), 3.63 (2H, m), 2.96 (2H, m), 2.51 (7H, m), 1.83-2.21 (5, m), 1.39 (2H, m), 1.21 (3H, m)

Example 105

Preparation of (2S)-1-(4-(4-((1-(5-ethylpyrimidin-2-yl)piperidin-4-yl)methoxy)phenyl)cyclohex-3-enecarbonyl)pyrrolidine-2-carboxamide

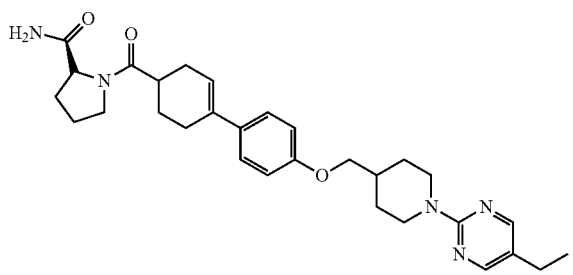

The title compound was prepared in the same manner as in <Example 8>, except that (S)-pyrrolidine-2-carboxamide was used instead of the (R)-2-amino-1-propanol (Amount obtained: 160 mg/Yield: 81%).

$^1$H NMR (400, CDCl$_3$): 8.21 (2H, s), 7.33 (2H, d), 6.86 (2H, d), 6.06 (1H, s), 5.32 (1H, s), 4.79 (2H, d), 4.67 (1H, d), 3.85 (2H, d), 3.68 (1H, m), 3.58 (1H, m), 2.95 (2H, m), 2.74 (1H, m), 2.27-2.62 (7H, m), 1.83-2.21 (10H, m), 1.39 (2H, m), 1.21 (3H, m)

Example 106

Preparation of (2S)-1-(4-(4-((1-(5-ethylpyrimidin-2-yl)piperidin-4-yl)methoxy)phenyl)cyclohex-3-enecarbonyl)pyrrolidine-2-carbonitrile

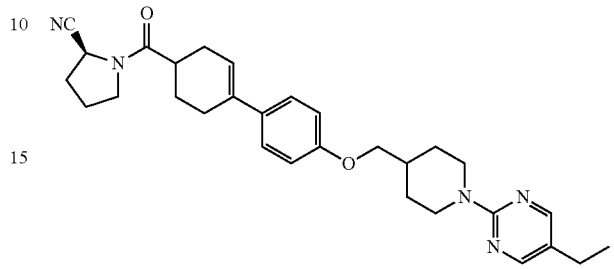

The title compound was prepared in the same manner as in <Example 8>, except that (S)-pyrrolidine-2-carbonitrile hydrochloride was used instead of the (R)-2-amino-1-propanol (Amount obtained: 220 mg/Yield: 83%).

$^1$H NMR (400, CDCl$_3$): 8.23 (2H, s), 7.32 (2H, d), 6.86 (2H, d), 6.06 (1H, s), 4.79 (3H, m), 3.85 (2H, d), 3.75 (1H, m), 3.59 (1H, m), 2.99 (2H, m), 2.4-2.71 (7H, m), 1.83-2.38 (10H, m), 1.39 (2H, m), 1.21 (3H, m)

Example 107

Preparation of tert-butyl 4-((4-(4-((S)-2-carbamoylpyrrolidine-1-carbonyl)cyclohex-1-enyl)-2-fluorophenoxy)methyl)piperidine-1-carboxylate

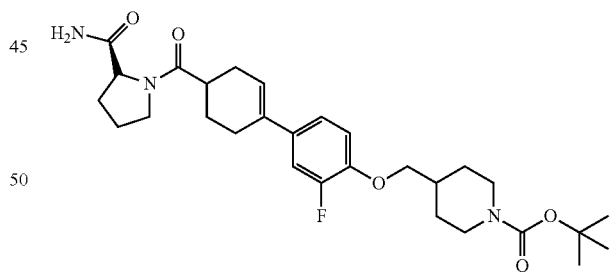

The title compound was prepared in the same manner as in <Example 44>, except that (S)-pyrrolidine-2-carboxamide was used instead of the (S)-(−)-3-pyrrolidinol (Amount obtained: 210 mg/Yield: 82%).

$^1$H NMR (400, CDCl$_3$): 7.11 (3H, m), 6.91 (1H, m), 6.09 (1H, s), 5.32 (1H, s), 4.67 (1H, d), 4.17 (2H, d), 3.88 (2H, d), 3.62 (2H, m), 2.29-2.82 (5H, m), 1.83-2.21 (8H, m), 1.49 (9H, s), 1.29 (2H, m)

Example 108

Preparation of (2S)-1-(4-(3-fluoro-4-((1-(3-isopropyl-1,2,4-oxadiazol-5-yl)piperidin-4-yl)methoxy)phenyl)cyclohex-3-enecarbonyl)pyrrolidine-2-carboxamide

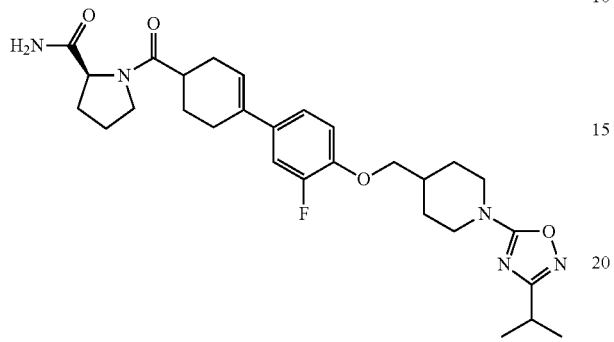

The title compound was prepared in the same manner as in <Example 80>, except that (S)-pyrrolidine-2-carboxamide was used instead of the 2-amino-1,3-propanediol (Amount obtained: 180 mg/Yield: 79%).

$^1$H NMR (400, CDCl$_3$): 7.11 (3H, m), 6.91 (1H, m), 6.10 (1H, s), 5.32 (1H, s), 4.67 (1H, d), 4.22 (2H, d), 3.92 (2H, d), 3.62 (2H, m), 3.12 (2H, m), 2.91 (1H, m), 2.29-2.82 (6H, m), 1.83-2.21 (7H, m), 1.49 (2H, m), 1.31 (6H, d)

Example 109

Preparation of (methyl 2-(4-(3-fluoro-4-((1-(3-isopropyl-1,2,4-oxadiazol-5-yl)piperidin-4-yl)methoxy)phenyl)cyclohex-3-enecarboxamido)acetate

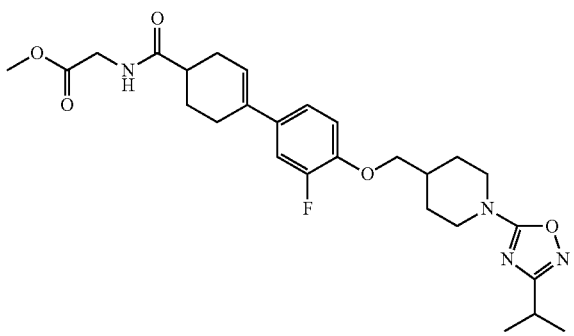 [SMILES: COC(=O)CNC(=O)C1CC=C(c2ccc(OCC3CCN(c4nc(C(C)C)no4)CC3)c(F)c2)CC1]

The title compound was prepared in the same manner as in <Example 80>, except that methyl 2-aminoacetate was used instead of the 2-amino-1,3-propanediol (Amount obtained: 850 mg/Yield: 83%).

$^1$H NMR (400, CDCl$_3$): 7.11 (2H, m), 6.90 (1H, m), 6.08 (1H, s), 4.21 (2H, d), 4.11 (2H, d), 3.91 (2H, d), 3.80 (3H, s), 3.12 (2H, m), 2.91 (1H, m), 2.49 (5H, m), 1.83-2.21 (5H, m), 1.49 (2H, m), 1.31 (6H, d)

Example 110

Preparation of ethyl 3-(4-(3-fluoro-4-((1-(3-isopropyl-1,2,4-oxadiazol-5-yl)piperidin-4-yl)methoxy)phenyl)cyclohex-3-enecarboxamido)propanoate

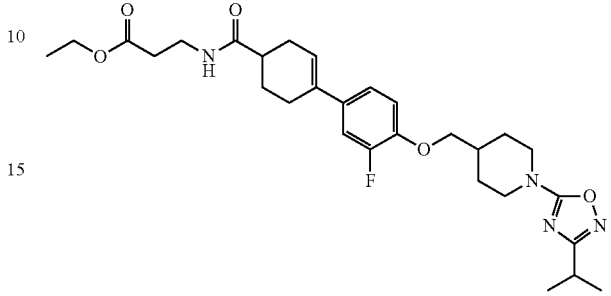

The title compound was prepared in the same manner as in <Example 80>, except that ethyl 3-aminopropanoate was used instead of the 2-amino-1,3-propanediol (Amount obtained: 940 mg/Yield: 86%).

$^1$H NMR (400, CDCl$_3$): 7.11 (2H, m), 6.90 (1H, m), 6.08 (1H, s), 4.21 (4H, m), 3.91 (2H, d), 3.58 (2H, m), 3.12 (2H, m), 2.91 (1H, m), 2.58 (2H, m), 2.49 (5H, m), 1.83-2.21 (5H, m), 1.49 (2H, m), 1.31 (6H, d), 1.29 (3H, m)

Example 111

Preparation of 3-(4-(3-fluoro-4-((1-(3-isopropyl-1,2,4-oxadiazol-5-yl)piperidin-4-yl)methoxy)phenyl)cyclohex-3-enecarboxamido)propanoic acid

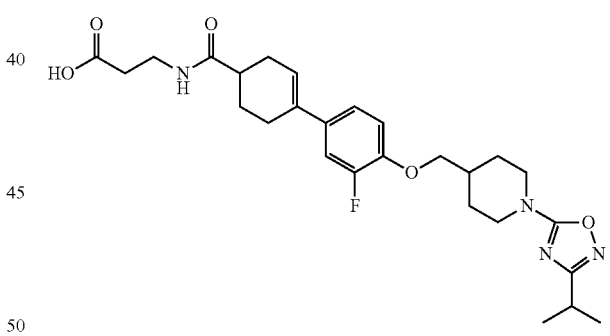

2,000 mg of ethyl 3-(4-(3-fluoro-4-((1-(3-isopropyl-1,2,4-oxadiazol-5-yl)piperidin-4-yl)methoxy)phenyl)cyclohex-3-enecarboxamido)propanoate was dissolved in a THF/water/ethanol mixture (100 μl/50 μl/10 μl) in a 500 μl flask, and stirred under nitrogen. 1.4 g of lithium hydroxide monohydrate was added dropwise thereto, and the resulting mixture was reacted at room temperature for 18 hours. After the reaction was terminated, the pH of the resulting reaction mixture was adjusted to pH 1 to 2 using concentrated HCl. The resulting solids were filtered, and dried to prepare the desired title compound (Amount obtained: 660 mg/Yield: 88%).

$^1$H NMR (400, CDCl$_3$): 7.11 (2H, m), 6.90 (1H, m), 6.08 (1H, s), 4.21 (2H, m), 3.91 (2H, d), 3.58 (2H, m), 3.12 (2H, m), 2.91 (1H, m), 2.58 (2H, m), 2.49 (5H, m), 1.83-2.21 (5H, m), 1.49 (2H, m), 1.31 (6H, d)

Example 112

Preparation of 4-(3-fluoro-4-((1-(3-isopropyl-1,2,4-oxadiazol-5-yl)piperidin-4-yl)methoxy)phenyl)-N-(2-morpholino-2-oxoethyl)cyclohex-3-enecarboxamide

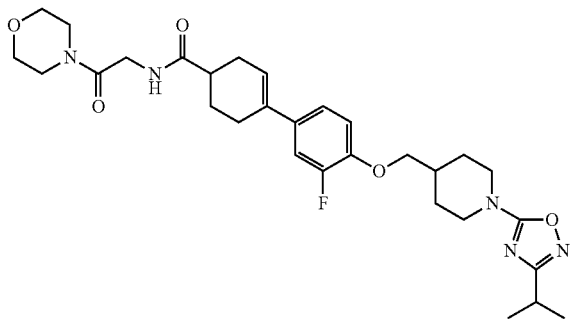 [SMILES: CC(C)c1noc(N2CCC(COc3ccc(C4=CCC(C(=O)NCC(=O)N5CCOCC5)CC4)cc3F)CC2)n1]

250 mg of 2-(4-(3-fluoro-4-((1-(3-isopropyl-1,2,4-oxadiazol-5-yl)piperidin-4-yl)methoxy)phenyl)cyclohex-3-enecarboxamido)acetic acid was dissolved in 20 µl of DMF in a 100 µl flask, and stirred under nitrogen. 140 mg of EDCI and 110 mg of HOBt were sequentially added dropwise thereto, and the resulting mixture was then additionally stirred for 10 minutes. 0.1 µl of morpholine were added dropwise thereof, and the mixture was stirred at room temperature for 5 hours. After the reaction was terminated, 50 µl of distilled water was slowly added at 0° C., and the resulting solids were filtered, and dried to obtain a desired compound as a white solid (Amount obtained: 160 mg/Yield: 72%).

$^1$H NMR (400, CDCl$_3$): 7.11 (2H, m), 6.90 (1H, m), 6.71 (1H, m), 6.07 (1H, s), 4.21 (2H, m), 4.11 (2H, d), 3.91 (2H, d), 3.71 (6H, m), 3.48 (2H, m), 3.12 (2H, m), 2.91 (1H, m), 2.49 (5H, m), 1.83-2.21 (5H, m), 1.49 (2H, m), 1.31 (6H, d)

Example 113

Preparation of 4-(3-fluoro-4-((1-(3-isopropyl-1,2,4-oxadiazol-5-yl)piperidin-4-yl)methoxy)phenyl)-N-(3-morpholino-3-oxopropyl)cyclohex-3-enecarboxamide

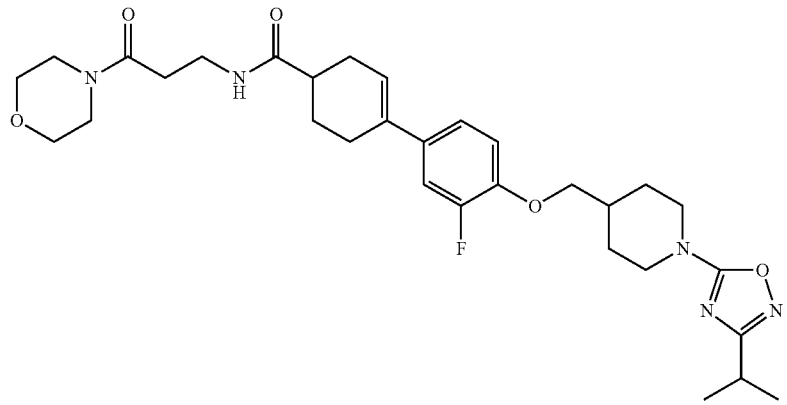 [SMILES: CC(C)c1noc(N2CCC(COc3ccc(C4=CCC(C(=O)NCCC(=O)N5CCOCC5)CC4)cc3F)CC2)n1]

The title compound was prepared in the same manner as in <Example 112>, except that 3-(4-(3-fluoro-4-((1-(3-isopropyl-1,2,4-oxadiazol-5-yl)piperidin-4-yl)methoxy)phenyl)cyclohex-3-enecarboxamido)propanoic acid was used instead of the 2-(4-(3-fluoro-4-((1-(3-isopropyl-1,2,4-oxadiazol-5-yl)piperidin-4-yl)methoxy)phenyl)cyclohex-3-enecarboxamido)acetic acid (Amount obtained: 155 mg/Yield: 74%).

$^1$H NMR (400, CDCl$_3$): 7.11 (2H, m), 6.90 (1H, m), 6.50 (1H, m), 6.06 (1H, s), 4.22 (2H, d), 3.91 (2H, d), 3.71 (6H, m), 3.48 (2H, m), 3.12 (2H, m), 2.91 (1H, m), 2.55 (2H, m), 2.49 (5H, m), 1.83-2.21 (5H, m), 1.49 (2H, m), 1.31 (6H, d)

Example 114

Preparation of tert-butyl 4-((4-(4-((S)-2-cyanopyrrolidine-1-carbonyl)cyclohex-1-enyl)-2-fluorophenoxy)methyl)piperidine-1-carboxylate

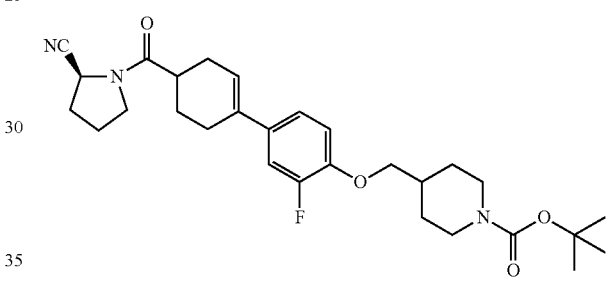

The title compound was prepared in the same manner as in <Example 44>, except that (S)-pyrrolidine-2-carbonitrile hydrochloride was used instead of the (S)-(-)-3-pyrrolidinol (Amount obtained: 180 mg/Yield: 76%).

$^1$H NMR (400, CDCl$_3$): 7.11 (3H, m), 6.91 (1H, m), 6.09 (1H, s), 4.67 (1H, d), 4.17 (2H, d), 3.88 (2H, d), 3.62 (2H, m), 2.29-2.82 (5H, m), 1.83-2.21 (8H, m), 1.49 (9H, s), 1.29 (2H, m).

Example 115

Preparation of (2S)-1-(4-(3-fluoro-4-((1-(3-isopropyl-1,2,4-oxadiazol-5-yl)piperidin-4-yl)methoxy)phenyl)cyclohex-3-enecarbonyl)pyrrolidine-2-carbonitrile

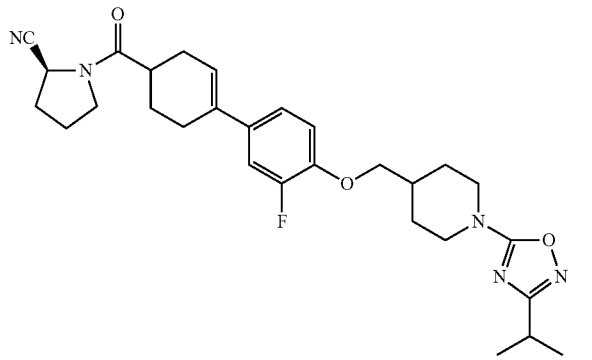 [SMILES: CC(C)c1noc(N2CCC(COc3ccc(C4=CCC(C(=O)N5CCC[C@H]5C#N)CC4)cc3F)CC2)n1]

The title compound was prepared in the same manner as in <Example 80>, except that (S)-pyrrolidine-2-carbonitrile hydrochloride was used instead of the 2-amino-1,3-propanediol (Amount obtained: 190 mg/Yield: 82%).

$^1$H NMR (400, CDCl$_3$): 7.11 (3H, m), 6.91 (1H, m), 6.10 (1H, s), 4.67 (1H, d), 4.22 (2H, d), 3.92 (2H, d), 3.62 (2H, m), 3.12 (2H, m), 2.91 (1H, m), 2.29-2.82 (6H, m), 1.83-2.21 (7H, m), 1.49 (2H, m), 1.31 (6H, d)

Example 116

Preparation of (2R)-1-(4-(3-fluoro-4-((1-(3-isopropyl-1,2,4-oxadiazol-5-yl)piperidin-4-yl)methoxy)phenyl)cyclohex-3-enecarbonyl)pyrrolidine-2-carboxamide

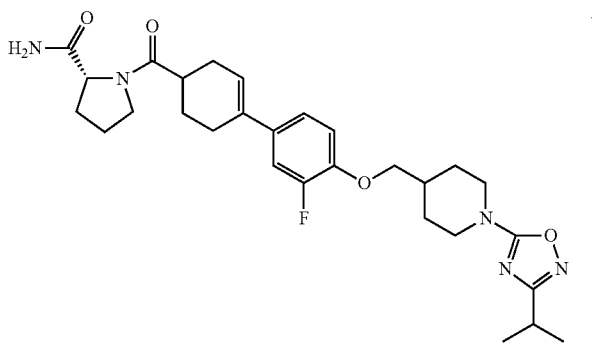

The title compound was prepared in the same manner as in <Example 80>, except that (R)-pyrrolidine-2-carboxamide was used instead of the 2-amino-1,3-propanediol (Amount obtained: 210 mg/Yield: 79%).

$^1$H NMR (400, CDCl$_3$): 7.11 (3H, m), 6.91 (1H, m), 6.10 (1H, s), 5.32 (1H, s), 4.67 (1H, d), 4.22 (2H, d), 3.92 (2H, d), 3.62 (2H, m), 3.12 (2H, m), 2.91 (1H, m), 2.29-2.82 (6H, m), 1.83-2.21 (7H, m), 1.49 (2H, m), 1.31 (6H, d)

Example 117

Preparation of (2R)-1-(4-(3-fluoro-4-((1-(3-isopropyl-1,2,4-oxadiazol-5-yl)piperidin-4-yl)methoxy)phenyl)cyclohex-3-enecarbonyl)pyrrolidine-2-carbonitrile

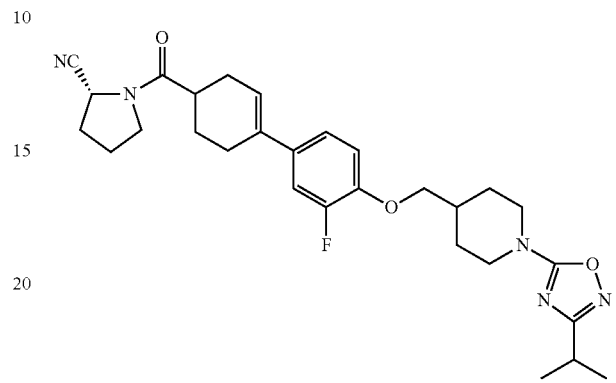

The title compound was prepared in the same manner as in <Example 80>, except that (R)-pyrrolidine-2-carbonitrile hydrochloride was used instead of the 2-amino-1,3-propanediol (Amount obtained: 165 mg/Yield: 73%).

$^1$H NMR (400, CDCl$_3$): 7.11 (3H, m), 6.91 (1H, m), 6.10 (1H, s), 4.67 (1H, d), 4.22 (2H, d), 3.92 (2H, d), 3.62 (2H, m), 3.12 (2H, m), 2.91 (1H, m), 2.29-2.82 (6H, m), 1.83-2.21 (7H, m), 1.49 (2H, m), 1.31 (6H, d)

Example 118

Preparation of (4-(4-((1-(5-ethylpyrimidin-2-yl)piperidin-4-yl)methoxy)phenyl)cyclohex-3-enyl)((R)-2-(hydroxymethyl)pyrrolidin-1-yl)methanone

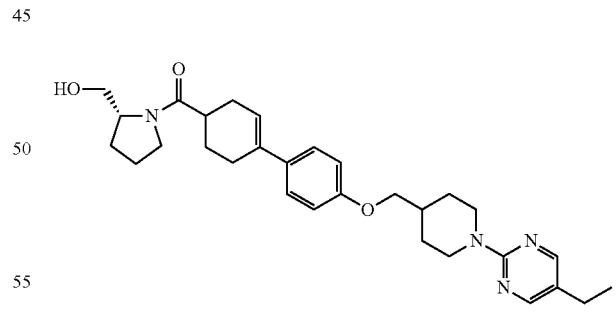

The title compound was prepared in the same manner as in <Example 8>, except that (R)-pyrrolidin-2-yl methanol was used instead of the (R)-2-amino-1-propanol (Amount obtained: 240 mg/Yield: 86%).

$^1$H NMR (400, CDCl$_3$): 8.19 (2H, s), 7.32 (1H, d), 6.86 (1H, d), 6.06 (1H, s), 5.19 (1H, m), 4.88 (2H, d), 4.30 (1H, m), 3.85 (2H, m), 3.62 (4H, m), 2.92 (2H, m), 2.25-2.78 (7H, m), 1.83-2.21 (9H, m), 1.61 (1H, m), 1.31 (2H, m), 1.22 (3H, m)

Example 119

Preparation of (4-(4-((1-(5-ethylpyrimidin-2-yl)piperidin-4-yl)methoxy)phenyl)cyclohex-3-enyl)((S)-2-(hydroxymethyl)pyrrolidin-1-yl)methanone

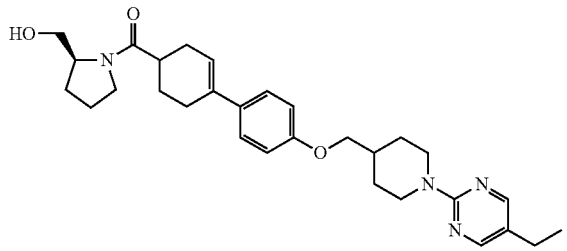 [SMILES: CCc1cnc(N2CCC(COc3ccc(C4=CCC(C(=O)N5CCC[C@H]5CO)CC4)cc3)CC2)nc1]

The title compound was prepared in the same manner as in <Example 8>, except that (S)-pyrrolidin-2-yl methanol was used instead of the (R)-2-amino-1-propanol (Amount obtained: 220 mg/Yield: 83%).

$^1$H NMR (400, CDCl$_3$): 8.19 (2H, s), 7.32 (1H, d), 6.86 (1H, d), 6.06 (1H, s), 5.19 (1H, m), 4.88 (2H, d), 4.30 (1H, m), 3.85 (2H, d), 3.62 (4H, m), 2.92 (2H, m), 2.25-2.78 (7H, m), 1.83-2.21 (9H, m), 1.61 (1H, m), 1.31 (2H, m), 1.22 (3H, m)

Example 120

Preparation of 4-(3-fluoro-4-((1-(3-isopropyl-1,2,4-oxadiazol-5-yl)piperidin-4-yl)methoxy)phenyl)-N-(2-hydroxyethyl)cyclohex-3-enecarboxamide

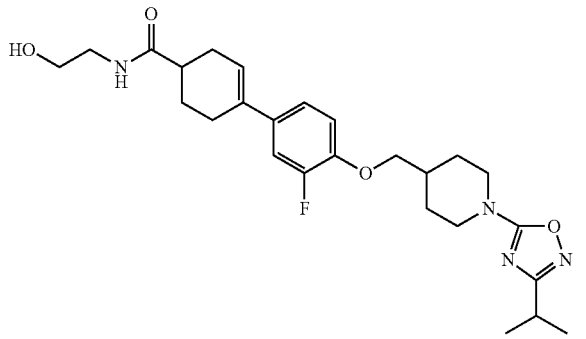 [SMILES: CC(C)c1noc(N2CCC(COc3ccc(C4=CCC(C(=O)NCCO)CC4)cc3F)CC2)n1]

The title compound was prepared in the same manner as in <Example 80>, except that 2-aminoethanol was used instead of the 2-amino-1,3-propanediol (Amount obtained: 180 mg/Yield: 76%).

$^1$H NMR (400, CDCl$_3$): 7.11 (3H, m), 6.91 (1H, m), 6.05 (2H, m), 4.19 (2H, d), 3.91 (2H, d), 3.79 (2H, m), 3.49 (2H, m), 3.12 (2H, m), 2.91 (1H, m), 2.35-2.59 (6H, m), 1.83-2.21 (5H, m), 1.49 (2H, m), 1.31 (6H, d)

Example 121

Preparation of (2R)-1-(2-(4-(3-fluoro-4-((1-(3-isopropyl-1,2,4-oxadiazol-5-yl)piperidin-4-yl)methoxy)phenyl)cyclohex-3-enecarboxamido)acetyl)pyrrolidine-2-carboxamide

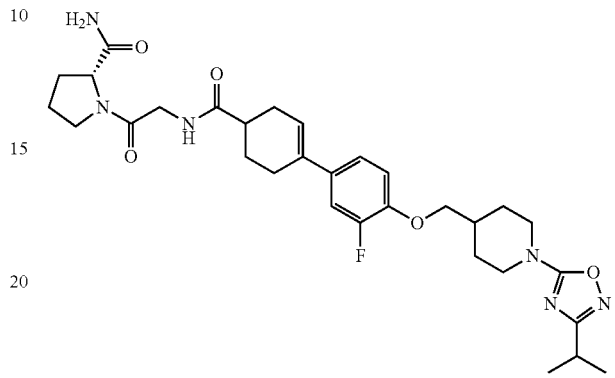

The title compound was prepared in the same manner as in <Example 112>, except that (R)-pyrrolidine-2-carboxamide was used instead of the morpholine (Amount obtained: 160 mg/Yield: 74%).

$^1$H NMR (400, CDCl$_3$): 7.11 (3H, m), 6.91 (1H, m), 6.68 (1H, s), 6.60 (1H, m), 6.07 (2H, m), 5.43 (1H, s), 4.60 (1H, d), 4.22 (2H, d), 4.11 (2H, m), 3.91 (2H, d), 3.65 (1H, m), 3.49 (1H, m), 3.14 (2H, m), 2.91 (1H, m), 2.35-2.59 (6H, m), 1.83-2.21 (8H, m), 1.49 (2H, m), 1.31 (6H, d)

Example 122

Preparation of N-(2-((R)-2-cyanopyrrolidin-1-yl)-2-oxoethyl)-4-(3-fluoro-4-((1-(3-isopropyl-1,2,4-oxadiazol-5-yl)piperidin-4-yl)methoxy)phenyl)cyclohex-3-enecarboxamide

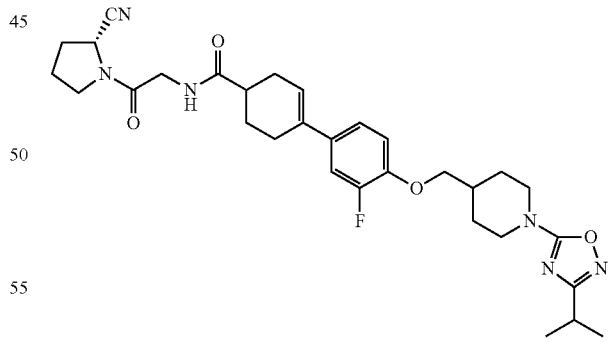

The title compound was prepared in the same manner as in <Example 112>, except that (R)-pyrrolidine-2-carbonitrile hydrochloride was used instead of the morpholine (Amount obtained: 190 mg/Yield: 77%).

$^1$H NMR (400, CDCl$_3$): 7.11 (3H, m), 6.91 (1H, m), 6.60 (1H, m), 6.07 (2H, m), 4.60 (1H, d), 4.22 (2H, d), 4.11 (2H, m), 3.91 (2H, d), 3.65 (1H, m), 3.49 (1H, m), 3.14 (2H, m), 2.91 (1H, m), 2.35-2.59 (6H, m), 1.83-2.21 (8H, m), 1.49 (2H, m), 1.31 (6H, d)

Example 123

Preparation of (4-cyclopropylpiperazin-1-yl)(4-(4-((1-(5-ethylpyrimidin-2-yl)piperidin-4-yl)methoxy)phenyl)cyclohex-3-enyl)methanone

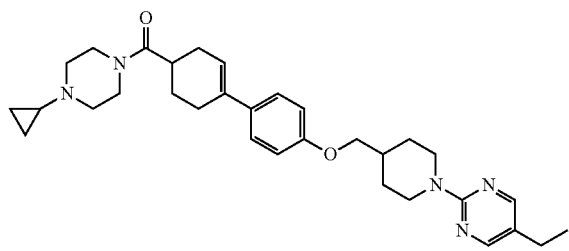 [SMILES: CCc1cnc(N2CCC(COc3ccc(C4=CCC(C(=O)N5CCN(C6CC6)CC5)CC4)cc3)CC2)nc1]

The title compound was prepared in the same manner as in <Example 8>, except that cyclopropylpiperazine was used instead of the (R)-2-amino-1-propanol (Amount obtained: 205 mg/Yield: 79%).

$^1$H NMR (400, CDCl$_3$): 8.19 (2H, s), 7.32 (2H, d), 6.86 (2H, d), 6.05 (1H, m), 4.79 (2H, d), 3.85 (2H, d), 3.64 (2H, m), 3.53 (2H, m), 2.93 (2H, m), 2.80 (1H, m), 2.55 (9H, m), 2.30 (1H, m), 2.01 (5H, m), 1.65 (1H, m), 1.33 (2H, m), 1.20 (3H, m), 0.49 (4H, m)

Example 124

Preparation of (4-(cyclopropylmethyl)piperazin-1-yl)(4-(4-((1-(5-ethylpyrimidin-2-yl)piperidin-4-yl)methoxy)phenyl)cyclohex-3-enyl)methanone

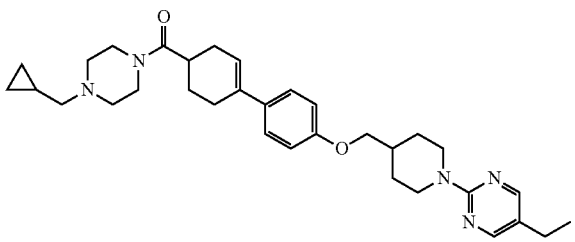 [SMILES: CCc1cnc(N2CCC(COc3ccc(C4=CCC(C(=O)N5CCN(CC6CC6)CC5)CC4)cc3)CC2)nc1]

The title compound was prepared in the same manner as in <Example 8>, except that 1-(cyclopropylmethyl)piperazine was used instead of the (R)-2-amino-1-propanol (Amount obtained: 185 mg/Yield: 77%).

$^1$H NMR (400, CDCl$_3$): 8.19 (2H, s), 7.32 (2H, d), 6.86 (2H, d), 6.05 (1H, m), 4.79 (2H, d), 3.85 (2H, d), 3.64 (2H, m), 3.53 (2H, m), 2.93 (2H, m), 2.80 (1H, m), 2.55 (9H, m), 2.30 (3H, m), 2.01 (5H, m), 1.35 (2H, m), 1.20 (3H, m), 0.89 (1H, m), 0.55 (2H, m), 0.14 (2H, m)

Example 125

Preparation of tert-butyl 4-((3-fluoro-4-(4-((S)-2-hydroxypropylcarbamoyl)cyclohex-1-enyl)phenoxy)methyl)piperidine-1-carboxylate

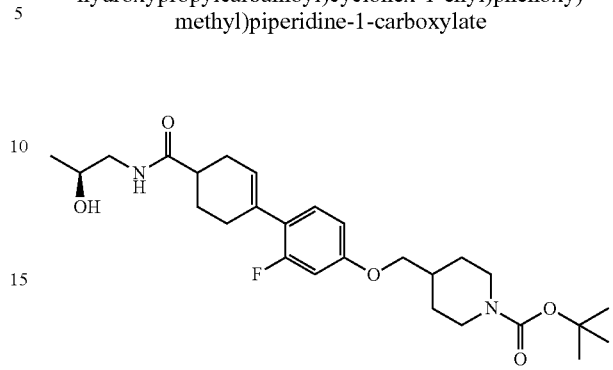

300 mg of 4-(4-((1-(tert-butoxycarbonyl)piperidin-4-yl)methoxy)-2-fluorophenyl)cyclohex-3-enecarboxyilc acid was dissolved in 25 µl of DMF, and stirred. 210 mg of EDCI and 165 mg of HOBt were sequentially added dropwise thereto, and the resulting mixture was then additionally stirred for 10 minutes. 120 mg of (S)-1-amino-2-propanol was added dropwise thereto, and the mixture was stirred at room temperature for 5 hours. After the reaction was terminated, 50 µl of distilled water was slowly added at 0° C., and the resulting solids were filtered, and dried to obtain a desired compound as a white solid (Amount obtained: 230 mg/Yield: 82%).

$^1$H NMR (400, CDCl$_3$): 7.13 (1H, m), 6.60 (2H, m), 6.11 (1H, s), 5.89 (1H, m), 4.17 (2H, s), 3.96 (1H, s), 3.79 (2H, d), 3.51 (1H, m), 3.19 (1H, m), 2.78 (2H, m), 2.63 (1H, s), 2.48 (5H, m), 2.14 (1H, m), 1.96 (2H, m), 1.81 (2H, m), 1.48 (9H, s), 1.28 (2H, m), 1.21 (3H, d)

Example 126

Preparation of tert-butyl 4-((3-fluoro-4-(4-((R)-2-hydroxypropylcarbamoyl)cyclohex-1-enyl)phenoxy)methyl)piperidine-1-carboxylate The title compound was prepared in the same manner as in <Example 125>, except that (R)-1-amino-2-propanol was used instead of the (S)-1-amino-2-propanol (Amount obtained: 210 mg/Yield: 80%).

$^1$H NMR (400, CDCl$_3$): 7.13 (1H, m), 6.60 (2H, m), 6.11 (1H, s), 5.89 (1H, m), 4.17 (2H, s), 3.96 (1H, s), 3.79 (2H, d), 3.51 (1H, m), 3.19 (1H, m), 2.78 (2H, m), 2.63 (1H, s), 2.48 (5H, m), 2.14 (1H, m), 1.96 (2H, m), 1.81 (2H, m), 1.48 (9H, s), 1.28 (2H, m), 1.21 (3H, d)

Example 127

Preparation of 4-(4-((1-(5-ethylpyrimidin-2-yl)piperidin-4-yl)methoxy)phenyl)-N-((S)-1-hydroxypropan-2-yl)cyclohex-3-enecarboxamide

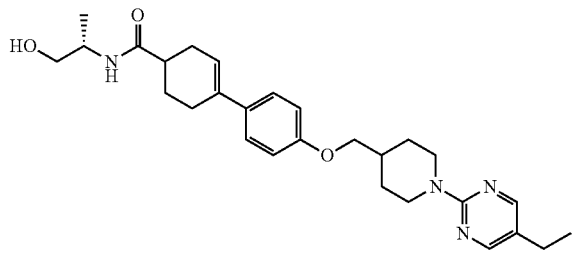 [SMILES: CCc1cnc(N2CCC(COc3ccc(C4=CCC(C(=O)N[C@@H](C)CO)CC4)cc3)CC2)nc1]

The title compound was prepared in the same manner as in <Example 8>, except that (S)-2-amino-1-propanol was used instead of the (R)-2-amino-1-propanol (Amount obtained: 170 mg/Yield: 77%).

$^1$H NMR (400, CDCl$_3$): 8.19 (2H, s), 7.31 (2H, d), 6.86 (2H, d), 6.04 (1H, s), 5.73 (1H, d), 4.79 (2H, d), 4.15 (1H, m), 3.84 (2H, d), 3.72 (1H, m), 3.57 (1H, m), 2.92 (2H, m), 2.80 (1H, s), 2.49 (7H, m), 2.11 (2H, m), 1.91 (3H, m), 1.38 (2H, m), 1.28 (2H, m), 1.21 (3H, d)

Example 128

Preparation of N-((S)-2,3-dihydroxypropyl)-4-(4-((1-(5-ethylpyrimidin-2-yl)piperidin-4-yl)methoxy)phenyl)cyclohex-3-enecarboxamide

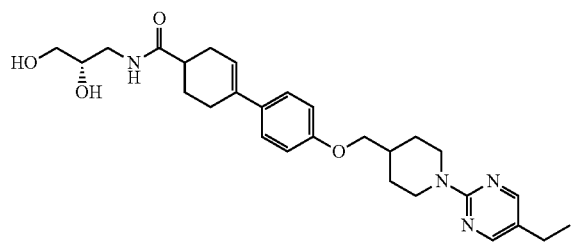 [SMILES: CCc1cnc(N2CCC(COc3ccc(C4=CCC(C(=O)NC[C@H](O)CO)CC4)cc3)CC2)nc1]

The title compound was prepared in the same manner as in <Example 8>, except that (S)-3-amino-1,2-propanediol was used instead of the (R)-2-amino-1-propanol (Amount obtained: 180 mg/Yield: 74%).

$^1$H NMR (400, DMSO-$d_6$): 8.23 (2H, s), 7.85 (1H, t), 7.33 (2H, d), 6.88 (2H, d), 6.05 (1H, s), 4.76 (1H, d), 4.68 (2H, d), 4.53 (1H, t), 3.84 (2H, d), 3.49 (1H, m), 3.34 (2H, m), 3.10 (2H, m), 2.89 (2H, m), 2.21 (7H, m), 1.91 (2H, d), 1.65 (1H, m), 1.18 (5H, m)

Example 129

Preparation of tert-butyl 4-((3-fluoro-4-(4-((R)-1-hydroxypropan-2-ylcarbamoyl)cyclohex-1-enyl)phenoxy)methyl)piperidine-1-carboxylate

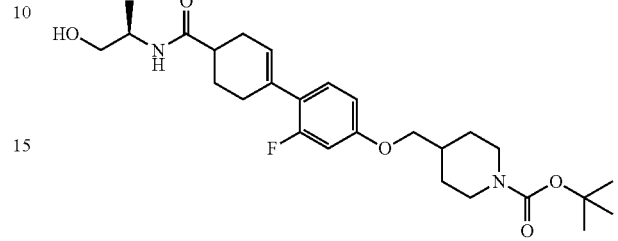

The title compound was prepared in the same manner as in <Example 125>, except that (R)-2-amino-1-propanol was used instead of the (S)-1-amino-2-propanol (Amount obtained: 180 mg/Yield: 80%).

$^1$H NMR (400, CDCl$_3$): 7.15 (1H, t), 6.64 (2H, m), 5.89 (1H, s), 5.80 (1H, s), 4.15 (3H, m), 3.79 (2H, d), 3.59 (1H, d), 3.45 (1H, m), 2.87 (1H, s), 2.75 (2H, m), 2.48 (5H, m), 1.94 (5H, m), 1.48 (9H, s), 1.26 (5H, m)

Example 130

Preparation of tert-butyl 4-((3-fluoro-4-(4-((S)-1-hydroxypropan-2-ylcarbamoyl)cyclohex-1-enyl)phenoxy)methyl)piperidine-1-carboxylate

The title compound was prepared in the same manner as in <Example 125>, except that (S)-2-amino-1-propanol was used instead of the (S)-1-amino-2-propanol (Amount obtained: 170 mg/Yield: 74%).

$^1$H NMR (400, CDCl$_3$): 7.15 (1H, t), 6.62 (2H, m), 5.89 (1H, s), 5.83 (1H, s), 4.16 (3H, m), 3.79 (2H, d), 3.69 (1H, d), 2.95 (1H, m), 2.76 (2H, m), 2.49 (5H, m), 1.98 (5H, m), 1.49 (9H, s), 1.26 (5H, m)

Example 131

Preparation of tert-butyl 4-((4-(4-((R)-2,3-dihydroxypropylcarbamoyl)cyclohex-1-enyl)-3-fluorophenoxy)methyl)piperidine-1-carboxylate

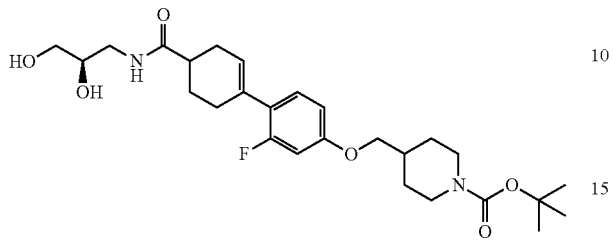

The title compound was prepared in the same manner as in <Example 125>, except that (R)-3-amino-1,2-propanediol was used instead of the (S)-1-amino-2-propanol (Amount obtained: 205 mg/Yield: 81%).

$^1$H NMR (400, CDCl$_3$): 7.13 (1H, t), 6.63 (2H, m), 6.55 (1H, m), 5.88 (1H, s), 4.18 (3H, m), 3.81 (3H, m), 3.61 (4H, m), 2.78 (2H, m), 2.45 (5H, m), 1.82 (7H, m), 1.47 (9H, m), 1.25 (2H, m)

Example 132

Preparation of tert-butyl 4-((4-(4-((S)-2,3-dihydroxypropylcarbamoyl)cyclohex-1-enyl)-3-fluorophenoxy)methyl)piperidine-1-carboxylate

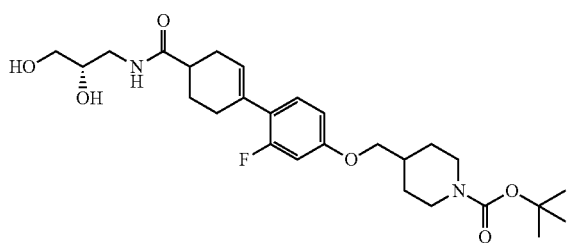 [SMILES: CC(C)(C)OC(=O)N1CCC(COc2ccc(C3=CCC(C(=O)NC[C@H](O)CO)CC3)c(F)c2)CC1]

The title compound was prepared in the same manner as in <Example 125>, except that (S)-3-amino-1,2-propanediol was used instead of the (S)-1-amino-2-propanol (Amount obtained: 165 mg/Yield: 74%).

$^1$H NMR (400, CDCl$_3$): 7.13 (1H, t), 6.63 (2H, m), 6.55 (1H, m), 5.88 (1H, s), 4.18 (3H, m), 3.81 (3H, m), 3.61 (4H, m), 2.78 (2H, m), 2.45 (5H, m), 1.82 (7H, m), 1.47 (9H, m), 1.25 (2H, m)

Example 133

Preparation of (2S)-1-(2-(4-(3-fluoro-4-((1-(3-isopropyl-1,2,4-oxadiazol-5-yl)piperidin-4-yl)methoxy)phenyl)cyclohex-3-enecarboxamido)acetyl)pyrrolidine-2-carboxamide

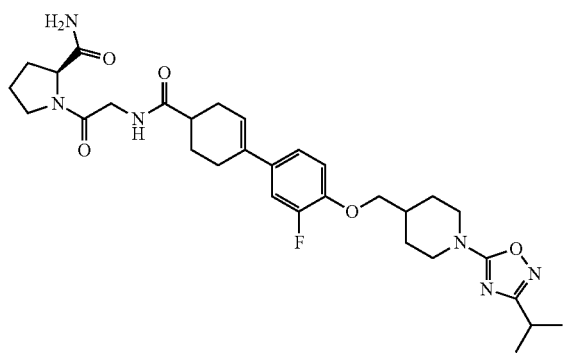 [SMILES: CC(C)c1noc(N2CCC(COc3ccc(C4=CCC(C(=O)NCC(=O)N5CCC[C@H]5C(N)=O)CC4)cc3F)CC2)n1]

The title compound was prepared in the same manner as in <Example 112>, except that (S)-pyrrolidine-2-carboxamide was used instead of the morpholine (Amount obtained: 160 mg/Yield: 71%).

$^1$H NMR (400, CDCl$_3$): 7.15 (1H, t), 6.92 (1H, m), 6.67 (1H, m), 6.07 (1H, s), 5.34 (1H, s), 4.61 (1H, m), 4.24 (2H, d), 4.11 (2H, m), 3.92 (2H, d), 3.64 (1H, m), 3.58 (1H, m), 3.14 (2H, t), 2.91 (1H, m), 2.48 (6H, m), 2.14 (4H, m), 1.91 (3H, m), 1.42 (2H, m), 1.32 (6H, d)

Example 134

Preparation of (2S)-1-(3-(4-(3-fluoro-4-((1-(3-isopropyl-1,2,4-oxadiazol-5-yl)piperidin-4-yl)methoxy)phenyl)cyclohex-3-enecarboxamido)propanoyl)pyrrolidine-2-carboxamide

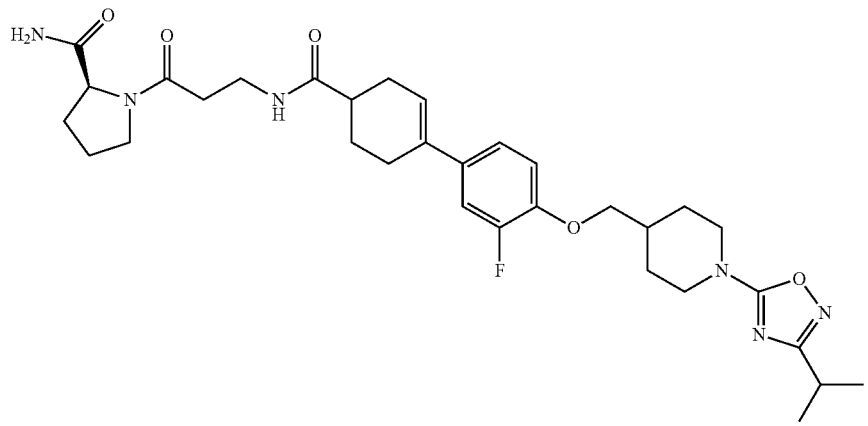 [SMILES: CC(C)c1noc(N2CCC(COc3ccc(C4=CCC(C(=O)NCCC(=O)N5CCC[C@H]5C(N)=O)CC4)cc3F)CC2)n1]

The title compound was prepared in the same manner as in <Example 112> using 3-(4-(3-fluoro-4-((1-(3-isopropyl-1,2,4-oxadiazol-5-yl)piperidin-4-yl)methoxy)phenyl)cyclohex-3-enecarboxamido)propanoic acid and (S)-pyrrolidine-2-carboxamide (Amount obtained: 210 mg/Yield: 80%).

¹H NMR (400, CDCl₃): 7.15 (1H, t), 6.92 (1H, m), 6.67 (1H, m), 6.07 (1H, s), 5.34 (1H, s), 4.61 (1H, m), 4.24 (2H, d), 4.11 (2H, m), 3.92 (2H, d), 3.64 (1H, m), 3.58 (1H, m), 3.14 (2H, t), 2.91 (1H, m), 2.54 (2H, m), 2.48 (6H, m), 2.14 (4H, m), 1.91 (3H, m), 1.42 (2H, m), 1.32 (6H, d)

Example 135

Preparation of (4-(4-((1-(5-ethylpyrimidin-2-yl)piperidin-4-yl)methoxy)phenyl)cyclohex-3-enyl)((S)-3-hydroxypyrrolidin-1-yl)methanone

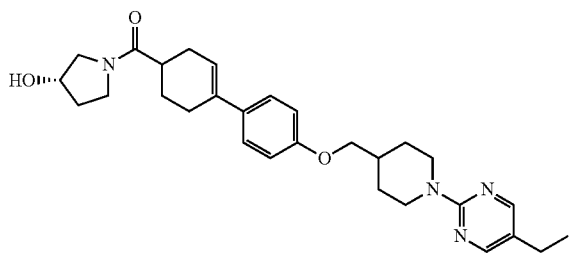 [SMILES: CCc1cnc(N2CCC(COc3ccc(C4=CCC(C(=O)N5CC[C@H](O)C5)CC4)cc3)CC2)nc1]

The title compound was prepared in the same manner as in <Example 8>, except that (S)-(+)-3-pyrrolidinol was used instead of the (R)-2-aminopropan-1-ol (Amount obtained: 220 mg/Yield: 81%).

¹H NMR (400, CDCl₃): 8.19 (2H, s), 7.33 (2H, d), 6.87 (2H, d), 6.07 (1H, s), 4.80 (2H, d), 4.55 (1H, d), 3.85 (2H, d), 3.65 (4H, m), 2.94 (2H, t), 2.48 (7H, m), 2.00 (7H, m), 1.40 (2H, m), 1.18 (3H, m)

Example 136

Preparation of 4-(4-((1-(5-ethylpyrimidin-2-yl)piperidin-4-yl)methoxy)phenyl)-N-((S)-2-hydroxypropyl)cyclohex-3-enecarboxamide

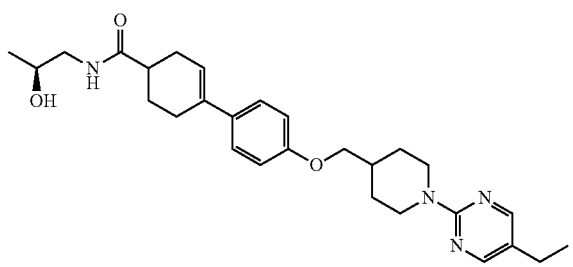 [SMILES: CCc1cnc(N2CCC(COc3ccc(C4=CCC(C(=O)NC[C@H](C)O)CC4)cc3)CC2)nc1]

The title compound was prepared in the same manner as in <Example 8>, except that (S)-1-amino-2-propanol was used instead of the (R)-2-amino-1-propanol (Amount obtained: 215 mg/Yield: 82%).

¹H NMR (400, CDCl₃): 8.19 (2H, s), 7.32 (2H, d), 6.87 (2H, d), 6.04 (2H, s), 4.80 (2H, d), 3.96 (1H, m), 3.85 (2H, d), 3.52 (1H, m), 3.14 (1H, m), 2.96 (2H, t), 2.46 (8H, m), 2.18 (2H, m), 1.96 (3H, m), 1.38 (2H, m), 1.24 (6H, m)

Example 137

Preparation of tert-butyl 4-((4-(4-(cyclopropylcarbamoyl)cyclohex-1-enyl)-3-fluorophenoxy)methyl)piperidine-1-carboxylate

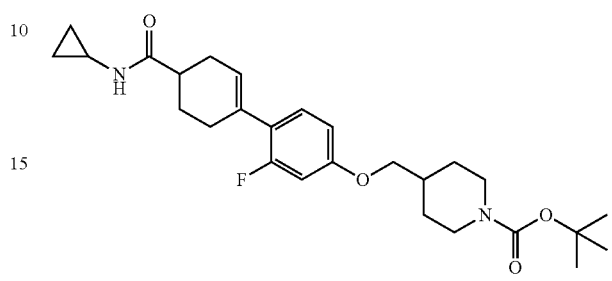

The title compound was prepared in the same manner as in <Example 125>, except that cyclopropylamine was used instead of the (S)-1-amino-2-propanol (Amount obtained: 180 mg/Yield: 74%).

¹H NMR (400, CDCl₃): 7.14 (1H, t), 6.64 (2H, m), 5.88 (1H, s), 5.74 (1H, s), 4.17 (2H, m), 3.79 (2H, d), 2.78 (3H, m), 2.46 (5H, m), 1.87 (5H, m), 1.48 (9H, s), 1.28 (2H, m), 0.78 (2H, m), 0.48 (2H, m)

Example 138

Preparation of tert-butyl 4-((3-fluoro-4-(4-(2-fluoroethylcarbamoyl)cyclohex-1-enyl)phenoxy)methyl)piperidine-1-carboxylate

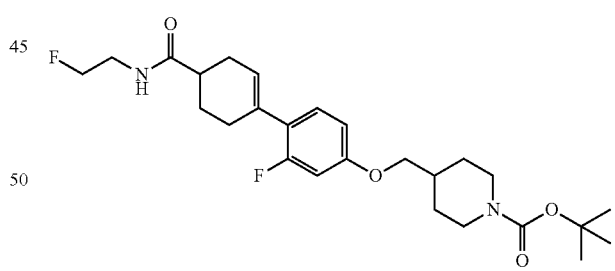

The title compound was prepared in the same manner as in <Example 125>, except that 2-fluoroethylamine was used instead of the (S)-1-amino-2-propanol (Amount obtained: 160 mg/Yield: 71%).

¹H NMR (400, CDCl₃): 7.15 (1H, t), 6.64 (2H, m), 6.04 (1H, m), 5.89 (1H, s), 4.57 (2H, m), 3.79 (2H, d), 3.58 (2H, m), 2.78 (2H, m), 2.54 (5H, m), 1.92 (5H, m), 1.48 (9H, s), 1.28 (2H, m)

Example 139

Preparation of N-(2-((S)-2-cyanopyrrolidin-1-yl)-2-oxoethyl)-4-(3-fluoro-4-((1-(3-isopropyl-1,2,4-oxadiazol-5-yl)piperidin-4-yl)methoxy)phenyl)cyclohex-3-enecarboxamide

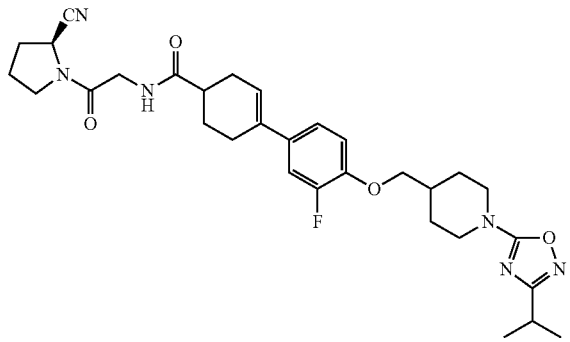 [SMILES: CC(C)c1noc(N2CCC(COc3ccc(C4=CCC(C(=O)NCC(=O)N5CCC[C@H]5C#N)CC4)cc3F)CC2)n1]

The title compound was prepared in the same manner as in <Example 112>, except that (S)-pyrrolidine-2-carbonitrile hydrochloride was used instead of the morpholine (Amount obtained: 190 mg/Yield: 83%).

$^1$H NMR (400, CDCl$_3$): 7.15 (1H, t), 6.92 (1H, m), 6.67 (1H, m), 6.07 (1H, s), 4.61 (1H, m), 4.24 (2H, d), 4.11 (2H, m), 3.92 (2H, d), 3.64 (1H, m), 3.58 (1H, m), 3.14 (2H, t), 2.91 (1H, m), 2.48 (6H, m), 2.14 (4H, m), 1.91 (3H, m), 1.42 (2H, m), 1.32 (6H, d)

Example 140

Preparation of N-(3-((S)-2-cyanopyrrolidin-1-yl)-3-oxopropyl)-4-(3-fluoro-4-((1-(3-isopropyl-1,2,4-oxadiazol-5-yl)piperidin-4-yl)methoxy)phenyl)cyclohex-3-enecarboxamide

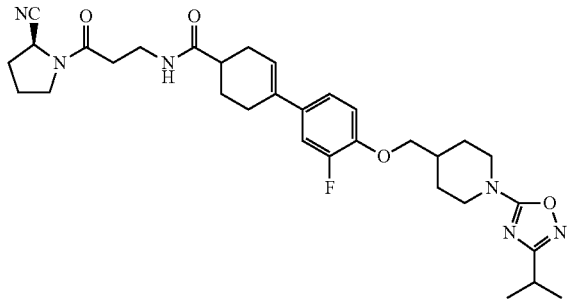 [SMILES: CC(C)c1noc(N2CCC(COc3ccc(C4=CCC(C(=O)NCCC(=O)N5CCC[C@H]5C#N)CC4)cc3F)CC2)n1]

The title compound was prepared in the same manner as in <Example 112> using 3-(4-(3-fluoro-4-((1-(3-isopropyl-1,2,4-oxadiazol-5-yl)piperidin-4-yl)methoxy)phenyl)cyclohex-3-enecarboxamido)propanoic acid and (S)-pyrrolidine-2-carbonitrile hydrochloride (Amount obtained: 145 mg/Yield: 77%).

$^1$H NMR (400, CDCl$_3$): 7.15 (1H, t), 6.92 (1H, m), 6.67 (1H, m), 6.07 (1H, s), 4.61 (1H, m), 4.24 (2H, d), 4.11 (2H, m), 3.92 (2H, d), 3.64 (1H, m), 3.58 (1H, m), 3.14 (2H, t), 2.91 (1H, m), 2.54 (2H, m), 2.48 (6H, m), 2.14 (4H, m), 1.91 (3H, m), 1.42 (2H, m), 1.32 (6H, d)

Example 141

Preparation of tert-butyl 4-((4-(4-(2,2-difluoroethylcarbamoyl)cyclohex-1-enyl)-3-fluorophenoxy)methyl)piperidine-1-carboxylate

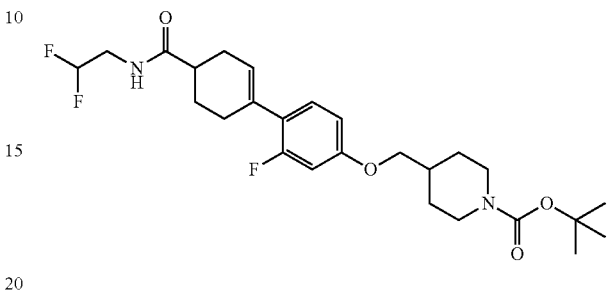

The title compound was prepared in the same manner as in <Example 125>, except that 2,2-difluoroethylamine was used instead of the (S)-1-amino-2-propanol (Amount obtained: 190 mg/Yield: 73%).

$^1$H NMR (400, CDCl$_3$): 7.15 (1H, t), 6.64 (2H, m), 6.04 (1H, m), 5.89 (2H, s), 4.28 (2H, m), 3.79 (2H, d), 3.70 (2H, m), 2.78 (2H, m), 2.54 (5H, m), 1.92 (5H, m), 1.48 (9H, s), 1.28 (2H, m)

Example 142

Preparation of tert-butyl 4-((3-fluoro-4-(4-(2,2,2-trifluoroethylcarbamoyl)cyclohex-1-enyl)phenoxy)methyl)piperidine-1-carboxylate

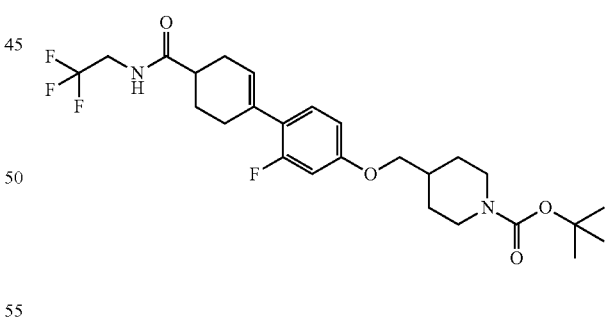

The title compound was prepared in the same manner as in <Example 125>, except that 2,2,2-trifluoroethylamine was used instead of the (S)-1-amino-2-propanol (Amount obtained: 175 mg/Yield: 77%).

$^1$H NMR (400, CDCl$_3$): 7.15 (1H, t), 6.64 (2H, m), 6.04 (1H, m), 5.89 (1H, s), 4.28 (2H, m), 3.99 (1H, m), 3.79 (2H, d), 2.78 (2H, m), 2.54 (5H, m), 1.92 (5H, m), 1.48 (9H, s), 1.28 (2H, m)

Example 143

Preparation of ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone

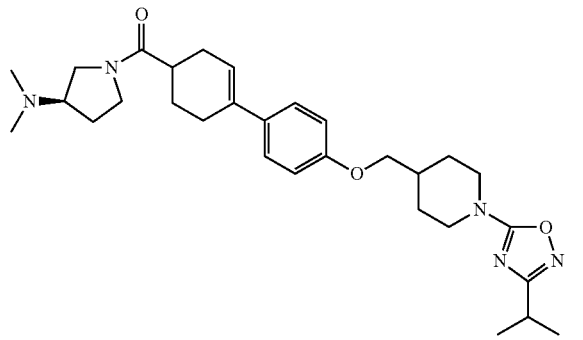 [SMILES: CC(C)c1noc(N2CCC(COc3ccc(C4=CCC(C(=O)N5CC[C@@H](N(C)C)C5)CC4)cc3)CC2)n1]

400 mg of 4-(4-((1-(3-isopropyl-1,2,4-oxadiazol-5-yl)piperidin-4-yl)methoxy)phenyl)cyclohex-3-enecarboxyilc acid was dissolved in 30 ml of DMF in a 100 ml flask, and stirred under a nitrogen atmosphere. 0.4 ml of TEA and 215 mg of (R)-N,N-dimethylpyrrolidine-3-amine hydrochloride were sequentially added dropwise thereto, and the resulting mixture was then additionally stirred for 10 minutes. 400 mg of HATU was added dropwise thereto, and the mixture was stirred at room temperature for an hour. After the reaction was terminated, 50 ml of distilled water was slowly added at 0° C., and the resulting solids were filtered, and dried to prepare the title compound as a white solid (Amount obtained: 450 mg/Yield: 69%).

$^1$H NMR (400, CDCl$_3$): 7.32 (2H, d), 6.85 (2H, d), 6.02 (1H, s), 4.24 (2H, d), 3.86 (4H, m), 3.44 (2H, m), 3.12 (2H, m), 2.85 (2H, m), 2.69-1.85 (19H, m), 1.47 (2H, m), 1.32 (6H, d)

Example 144

Preparation of ((S)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone

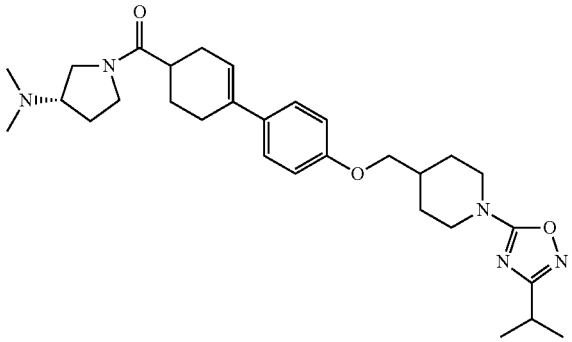 [SMILES: CC(C)c1noc(N2CCC(COc3ccc(C4=CCC(C(=O)N5CC[C@H](N(C)C)C5)CC4)cc3)CC2)n1]

The title compound was prepared in the same manner as in <Example 143>, except that (S)-N,N-dimethylpyrrolidine-3-amine hydrochloride was used instead of the (R)-N,N-dimethylpyrrolidine-3-amine hydrochloride (Amount obtained: 470 mg/Yield: 70%).

$^1$H NMR (400, CDCl$_3$): 7.32 (2H, d), 6.85 (2H, d), 6.02 (1H, s), 4.24 (2H, d), 3.86 (4H, m), 3.44 (2H, m), 3.12 (2H, m), 2.85 (2H, m), 2.69-1.85 (19H, m), 1.47 (2H, m), 1.32 (6H, d)

Example 145

Preparation of ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone hydrochloride

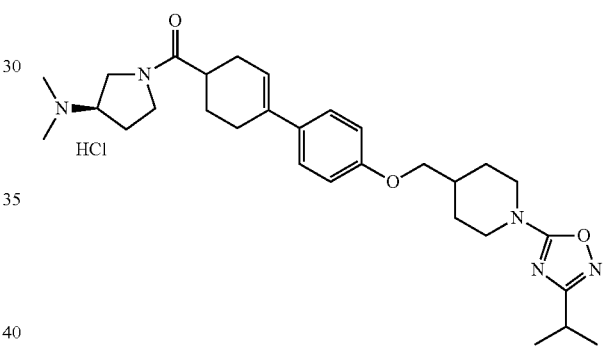

150 mg of ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone was dissolved in 20 ml of dichloromethane in a 100 ml flask, and then stirred under a nitrogen atmosphere. 0.08 ml of 4 N HCl dissolved in dioxane was added dropwise thereto, and the resulting mixture was then stirred at room temperature for 3 hours. After the solvent were removed, 30 ml of acetone was slowly added dropwise. The resulting solids were filtered, washed with 10 ml of ethyl acetate, and then dried to prepare the title compound as a white solid (Amount obtained: 220 mg/Yield: 84%).

$^1$H NMR (400, D$_2$O): 7.07 (2H, d), 6.55 (2H, d), 5.81 (1H, s), 4.12-3.28 (11H, m), 2.93-2.62 (11H, m), 2.44 (2H, m), 2.12 (5H, m), 2.81 (1H, m), 1.52 (4H, m), 1.08 (6H, d), 0.95 (2H, s)

Example 146

Preparation of ((S)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone hydrochloride

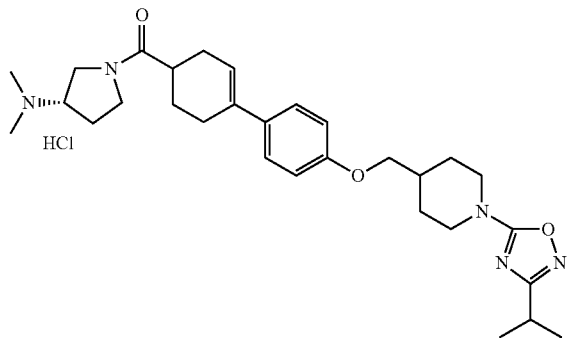 [SMILES: CC(C)c1noc(N2CCC(COc3ccc(C4=CCC(C(=O)N5CC[C@H](N(C)C)C5)CC4)cc3)CC2)n1 ; Cl]

The title compound was prepared in the same manner as in <Example 145>, except that ((S)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone was used instead of the ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone (Amount obtained: 210 mg/Yield: 83%).

$^1$H NMR (400, D$_2$O): 7.07 (2H, d), 6.55 (2H, d), 5.81 (1H, s), 4.12-3.28 (11H, m), 2.93-2.62 (11H, m), 2.44 (2H, m), 2.12 (5H, m), 2.81 (1H, m), 1.52 (4H, m), 1.08 (6H, d), 0.95 (2H, s)

Example 147

Preparation of ((R)-2-(hydroxymethyl)pyrrolidin-1-yl)(4-(4-((1-(3-isopropyl-1,2,4-oxadiazol-5-yl)piperidin-4-yl)methoxy)phenyl)cyclohex-3-enyl)methanone

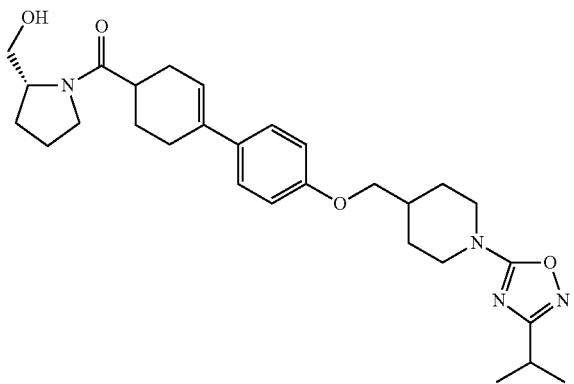 [SMILES: CC(C)c1noc(N2CCC(COc3ccc(C4=CCC(C(=O)N5CCC[C@@H]5CO)CC4)cc3)CC2)n1]

The title compound was prepared in the same manner as in <Example 143>, except that D-prolinol was used instead of the (R)-N,N-dimethylpyrrolidine-3-amine hydrochloride (Amount obtained: 220 mg/Yield: 76%).

$^1$H NMR (400, CDCl$_3$): 7.33 (2H, d), 6.86 (2H, d), 6.06 (1H, s), 5.16 (1H, m), 4.29 (1H, m), 4.22 (2H, d), 3.86 (2H, d), 4.65 (4H, m), 3.13 (2H, m), 2.91 (1H, m), 2.77-2.28 (5H, m), 2.01 (8H, m), 1.61 (1H, m), 1.46 (2H, m), 1.32 (6H, d)

Example 148

Preparation of ((S)-2-(hydroxymethyl)pyrrolidin-1-yl)(4-(4-((1-(3-isopropyl-1,2,4-oxadiazol-5-yl)piperidin-4-yl)methoxy)phenyl)cyclohex-3-enyl)methanone

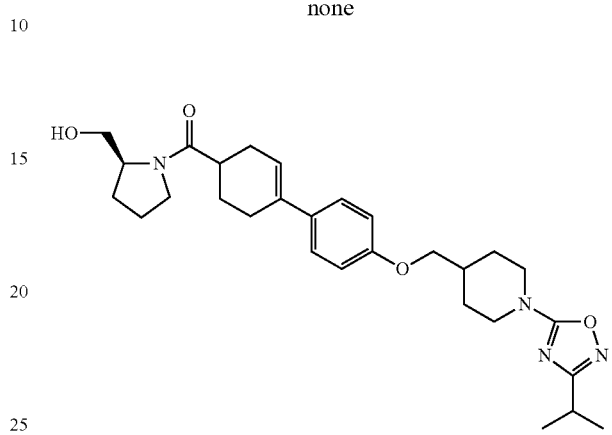

The title compound was prepared in the same manner as in <Example 143>, except that L-prolinol was used instead of the (R)-N,N-dimethylpyrrolidine-3-amine hydrochloride (Amount obtained: 180 mg/Yield: 74%).

$^1$H NMR (400, CDCl$_3$): 7.33 (2H, d), 6.86 (2H, d), 6.06 (1H, s), 5.16 (1H, m), 4.29 (1H, m), 4.22 (2H, d), 3.86 (2H, d), 4.65 (4H, m), 3.13 (2H, m), 2.91 (1H, m), 2.77-2.28 (5H, m), 2.01 (8H, m), 1.61 (1H, m), 1.46 (2H, m), 1.32 (6H, d)

Example 149

Preparation of ((R)-3-(hydroxymethyl)pyrrolidin-1-yl)(4-(4-((1-(3-isopropyl-1,2,4-oxadiazol-5-yl)piperidin-4-yl)methoxy)phenyl)cyclohex-3-enyl)methanone

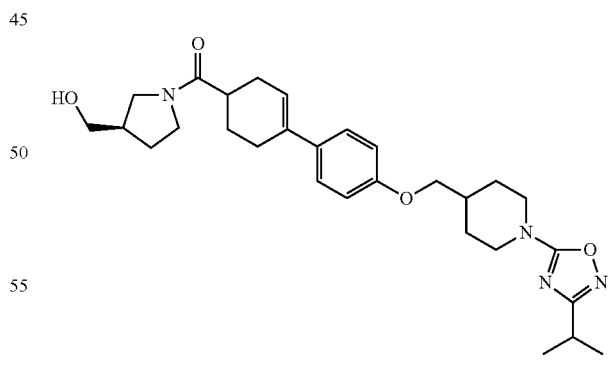

The title compound was prepared in the same manner as in <Example 143>, except that D-β-prolinol was used instead of the (R)-N,N-dimethylpyrrolidine-3-amine hydrochloride (Amount obtained: 175 mg/Yield: 77%).

$^1$H NMR (400, CDCl$_3$): 7.33 (2H, d), 6.86 (2H, d), 6.06 (1H, s), 4.22 (2H, d), 3.86 (2H, d), 3.81-3.24 (6H, m), 3.13 (2H, m), 2.91 (1H, m), 2.77-2.28 (6H, m), 2.01 (6H, m), 1.61 (1H, m), 1.46 (2H, m), 1.32 (6H, d)

Example 150

Preparation of ((S)-3-(hydroxymethyl)pyrrolidin-1-yl)(4-(4-((1-(3-isopropyl-1,2,4-oxadiazol-5-yl)piperidin-4-yl)methoxy)phenyl)cyclohex-3-enyl)methanone

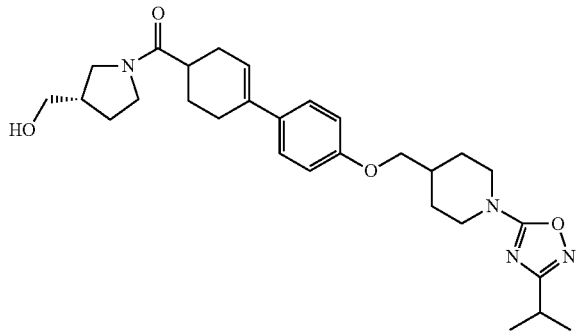 [SMILES: CC(C)c1noc(N2CCC(COc3ccc(C4=CCC(C(=O)N5CC[C@H](CO)C5)CC4)cc3)CC2)n1]

The title compound was prepared in the same manner as in <Example 143>, except that L-β-prolinol was used instead of the (R)-N,N-dimethylpyrrolidine-3-amine hydrochloride (Amount obtained: 210 mg/Yield: 74%).

$^1$H NMR (400, CDCl$_3$): 7.33 (2H, d), 6.86 (2H, d), 6.06 (1H, s), 4.22 (2H, d), 3.86 (2H, d), 3.81-3.24 (6H, m), 3.13 (2H, m), 2.91 (1H, m), 2.77-2.28 (6H, m), 2.01 (6H, m), 1.61 (1H, m), 1.46 (2H, m), 1.32 (6H, d)

Example 151

Preparation of (4-(4-((1-(5-ethylpyrimidin-2-yl)piperidin-4-yl)methoxy)phenyl)cyclohex-3-enyl)((R)-2-(hydroxymethyl)pyrrolidin-1-yl)methanone hydrochloride

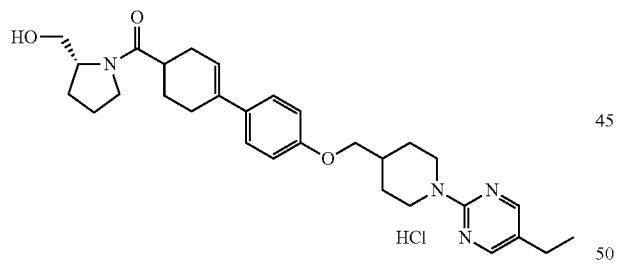

The title compound was prepared in the same manner as in <Example 145>, except that (4-(4-((1-(5-ethylpyrimidin-2-yl)piperidin-4-yl)methoxy)phenyl)cyclohex-3-enyl)((R)-2-(hydroxymethyl)pyrrolidin-1-yl)methanone was used instead of the ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone (Amount obtained: 85 mg/Yield: 72%).

$^1$H NMR (400, CDCl$_3$): 8.41 (2H, s), 7.33 (2H, d), 6.86 (2H, d), 6.06 (1H, s), 5.02 (2H, d), 4.29 (1H, m), 3.86 (2H, d), 3.79-3.24 (6H, m), 2.75-1.89 (17H, m), 1.65 (1H, m), 1.35 (2H, m), 1.21 (3H, m)

Example 152

Preparation of (4-(4-((1-(5-ethylpyrimidin-2-yl)piperidin-4-yl)methoxy)phenyl)cyclohex-3-enyl)((S)-3-(hydroxymethyl)pyrrolidin-1-yl)methanone

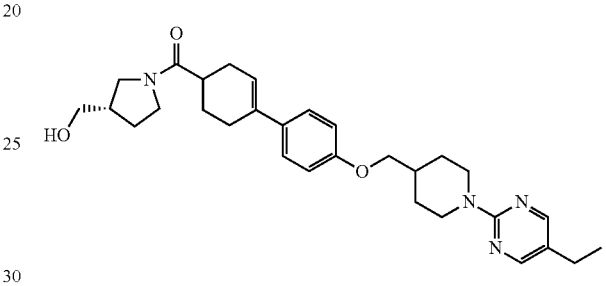

300 mg of 4-(4-((1-(5-ethylpyrimidin-2-yl)piperidin-4-yl)methoxy)phenyl)cyclohex-3-enecarboxyilc acid was dissolved in 30 ml of DMF in a 100 ml flask, and stirred under a nitrogen atmosphere. 0.2 ml of TEA and 110 mg of L-β-prolinol were sequentially added dropwise thereto, and the resulting mixture was then additionally stirred for 10 minutes. 300 mg of HATU was added dropwise thereto, and the mixture was stirred at room temperature for an hour. After the reaction was terminated, 50 ml of distilled water was slowly added at 0° C., and the resulting solids were filtered, and then dried to prepare the title compound (Amount obtained: 230 mg/Yield: 74%).

$^1$H NMR (400, CDCl$_3$): 8.18 (2H, s), 7.33 (2H, d), 6.86 (2H, d), 6.06 (1H, s), 4.78 (2H, d), 3.86 (2H, d), 3.79-3.24 (6H, m), 2.92 (2H, m), 2.77-2.28 (8H, m), 2.19-1.65 (10H, m), 1.35 (2H, m), 1.21 (3H, m)

Example 153

Preparation of (4-(4-((1-(5-ethylpyrimidin-2-yl)piperidin-4-yl)methoxy)phenyl)cyclohex-3-enyl)((R)-3-(hydroxymethyl)pyrrolidin-1-yl)methanone

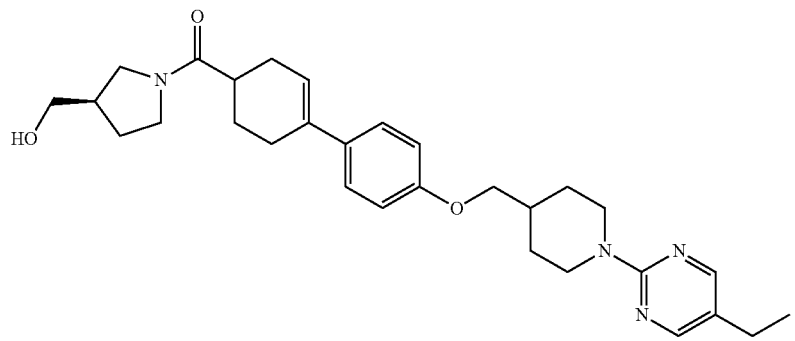 [SMILES: CCc1cnc(N2CCC(COc3ccc(C4=CCC(C(=O)N5CC[C@@H](CO)C5)CC4)cc3)CC2)nc1]

The title compound was prepared in the same manner as in <Example 152>, except that D-β-prolinol was used instead of the L-β-prolinol (Amount obtained: 240 mg/Yield: 82%).

¹H NMR (400, CDCl₃): 8.18 (2H, s), 7.33 (2H, d), 6.86 (2H, d), 6.06 (1H, s), 4.78 (2H, d), 3.86 (2H, d), 3.79-3.24 (6H, m), 2.92 (2H, m), 2.77-2.28 (8H, m), 2.19-1.65 (10H, m), 1.35 (2H, m), 1.21 (3H, m)

Example 154

Preparation of ((S)-3-(dimethylamino)pyrrolidin-1-yl)(4-(4-((1-(5-ethylpyrimidin-2-yl)piperidin-4-yl)methoxy)phenyl)cyclohex-3-enyl)methanone

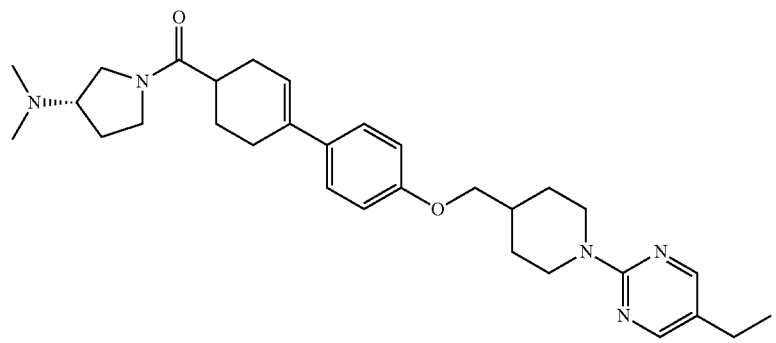 [SMILES: CCc1cnc(N2CCC(COc3ccc(C4=CCC(C(=O)N5CC[C@H](N(C)C)C5)CC4)cc3)CC2)nc1]

The title compound was prepared in the same manner as in <Example 152>, except that (S)-N,N-dimethylpyrrolidine-3-amine hydrochloride was used instead of the L-β-prolinol (Amount obtained: 470 mg/Yield: 80%).

¹H NMR (400, CDCl₃): 8.18 (2H, s), 7.33 (2H, d), 6.86 (2H, d), 6.06 (1H, s), 4.78 (2H, d), 3.93-3.71 (4H, m), 3.59-3.18 (2H, m), 2.92 (2H, m), 2.86-2.41 (7H, m), 2.30 (6H, s), 2.22-1.71 (8H, m), 1.35 (2H, m), 1.21 (3H, m)

Example 155

Preparation of ((R)-3-(dimethylamino)pyrrolidin-1-yl)(4-(4-((1-(5-ethylpyrimidin-2-yl)piperidin-4-yl)methoxy)phenyl)cyclohex-3-enyl)methanone

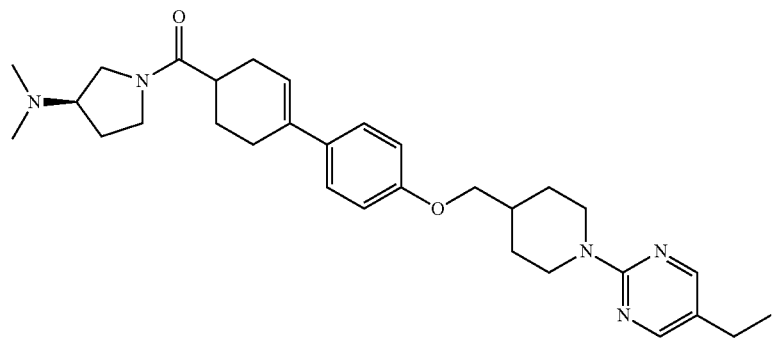 [SMILES: CCc1cnc(N2CCC(COc3ccc(C4=CCC(C(=O)N5CC[C@@H](N(C)C)C5)CC4)cc3)CC2)nc1]

The title compound was prepared in the same manner as in <Example 152>, except that (R)-N,N-dimethylpyrrolidine-3-amine hydrochloride was used instead of the L-β-prolinol (Amount obtained: 440 mg/Yield: 76%).

¹H NMR (400, CDCl₃): 8.18 (2H, s), 7.33 (2H, d), 6.86 (2H, d), 6.06 (1H, s), 4.78 (2H, d), 3.93-3.71 (4H, m), 3.59-3.18 (2H, m), 2.92 (2H, m), 2.86-2.41 (7H, m), 2.30 (6H, s), 2.22-1.71 (8H, m), 1.35 (2H, m), 1.21 (3H, m)

Example 156

Preparation of ((S)-3-(dimethylamino)pyrrolidin-1-yl)(4-(4-((1-(5-ethylpyrimidin-2-yl)piperidin-4-yl)methoxy)phenyl)cyclohex-3-enyl)methanone hydrochloride

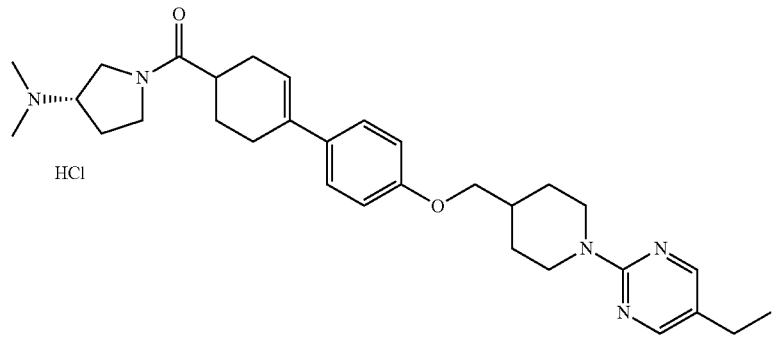 [SMILES: CCc1cnc(N2CCC(COc3ccc(C4=CCC(C(=O)N5CC[C@H](N(C)C)C5)CC4)cc3)CC2)nc1 ; Cl]

The title compound was prepared in the same manner as in <Example 145>, except that ((S)-3-(dimethylamino)pyrrolidin-1-yl)(4-(4-((1-(5-ethylpyrimidin-2-yl)piperidin-4-yl)methoxy)phenyl)cyclohex-3-enyl)methanone was used instead of the ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone (Amount obtained: 180 mg/Yield: 76%).

$^1$H NMR (400, D$_2$O): 8.28 (2H, s), 7.33 (2H, d), 6.86 (2H, d), 6.06 (1H, s), 4.31 (1H, d), 3.95-3.31 (4H, m), 3.14 (2H, m), 2.86 (6H, s), 2.72 (1H, m), 2.53-1.87 (12H, m), 1.63 (1H, m), 1.31 (2H, m), 1.09 (3H, m)

Example 157

Preparation of ((R)-3-(dimethylamino)pyrrolidin-1-yl)(4-(4-((1-(5-ethylpyrimidin-2-yl)piperidin-4-yl)methoxy)phenyl)cyclohex-3-enyl)methanone hydrochloride

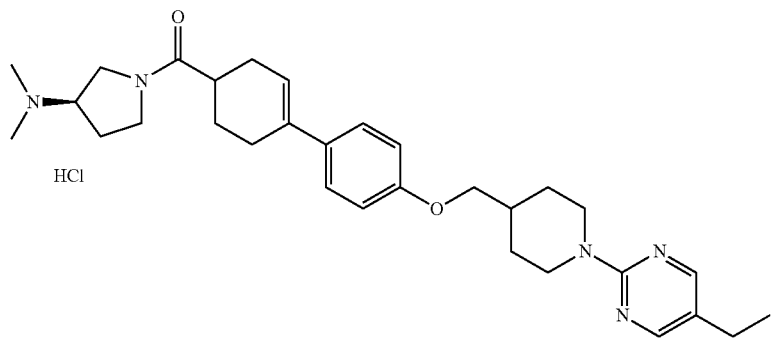 [SMILES: CCc1cnc(N2CCC(COc3ccc(C4=CCC(C(=O)N5CC[C@@H](N(C)C)C5)CC4)cc3)CC2)nc1 ; Cl]

The title compound was prepared in the same manner as in <Example 145>, except that ((R)-3-(dimethylamino)pyrrolidin-1-yl)(4-(4-((1-(5-ethylpyrimidin-2-yl)piperidin-4-yl)methoxy)phenyl)cyclohex-3-enyl)methanone was used instead of the ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone (Amount obtained: 170 mg/Yield: 71%).

$^1$H NMR (400, D$_2$O): 8.28 (2H, s), 7.33 (2H, d), 6.86 (2H, d), 6.06 (1H, s), 4.31 (1H, d), 3.95-3.31 (4H, m), 3.14 (2H, m), 2.86 (6H, s), 2.72 (1H, m), 2.53-1.87 (12H, m), 1.63 (1H, m), 1.31 (2H, m), 1.09 (3H, m)

Example 158

Preparation of (4-(4-((1-(5-ethylpyrimidin-2-yl)piperidin-4-yl)methoxy)phenyl)cyclohex-3-enyl)((S)-3-(hydroxymethyl)pyrrolidin-1-yl)methanone hydrochloride

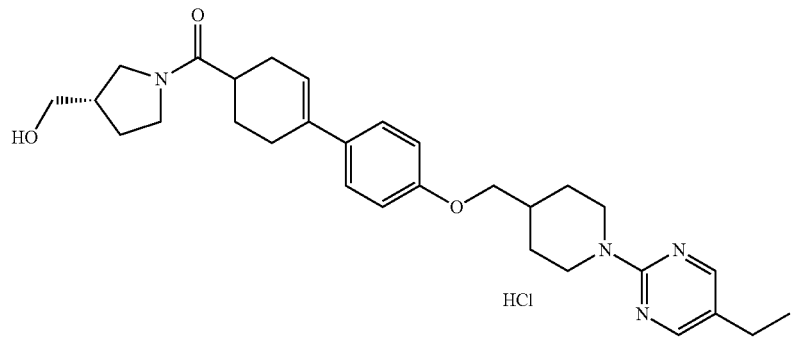 [SMILES: CCc1cnc(N2CCC(COc3ccc(C4=CCC(C(=O)N5CC[C@H](CO)C5)CC4)cc3)CC2)nc1 ; Cl]

The title compound was prepared in the same manner as in <Example 145>, except that (4-(4-((1-(5-ethylpyrimidin-2-yl)piperidin-4-yl)methoxy)phenyl)cyclohex-3-enyl)((S)-3-(hydroxymethyl)pyrrolidin-1-yl)methanone was used instead of the ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone (Amount obtained: 95 mg/Yield: 71%).

$^1$H NMR (400, CDCl$_3$): 8.43 (2H, s), 7.33 (2H, d), 6.86 (2H, d), 6.06 (1H, s), 4.78 (2H, d), 3.86 (2H, d), 3.79-3.24 (6H, m), 2.92 (2H, m), 2.77-2.28 (8H, m), 2.19-1.65 (10H, m), 1.35 (2H, m), 1.21 (3H, m)

Example 159

Preparation of (4-(4-((1-(5-ethylpyrimidin-2-yl)piperidin-4-yl)methoxy)phenyl)cyclohex-3-enyl)((R)-3-(hydroxymethyl)pyrrolidin-1-yl)methanone hydrochloride

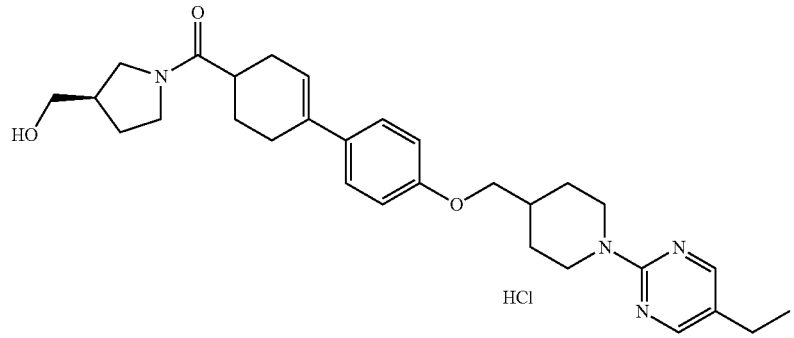 [SMILES: CCc1cnc(N2CCC(COc3ccc(C4=CCC(C(=O)N5CC[C@@H](CO)C5)CC4)cc3)CC2)nc1 ; Cl]

The title compound was prepared in the same manner as in <Example 145>, except that (4-(4-((1-(5-ethylpyrimidin-2-yl)piperidin-4-yl)methoxy)phenyl)cyclohex-3-enyl)((R)-3-(hydroxymethyl)pyrrolidin-1-yl)methanone was used instead of the ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone (Amount obtained: 85 mg/Yield: 73%).

$^1$H NMR (400, CDCl$_3$): 8.43 (2H, s), 7.33 (2H, d), 6.86 (2H, d), 6.06 (1H, s), 4.78 (2H, d), 3.86 (2H, d), 3.79-3.24 (6H, m), 2.92 (2H, m), 2.77-2.28 (8H, m), 2.19-1.65 (10H, m), 1.35 (2H, m), 1.21 (3H, m)

Example 160

Preparation of (4-(4-((1-(5-ethylpyrimidin-2-yl)piperidin-4-yl)methoxy)phenyl)cyclohex-3-enyl)((S)-3-fluoropyrrolidin-1-yl)methanone

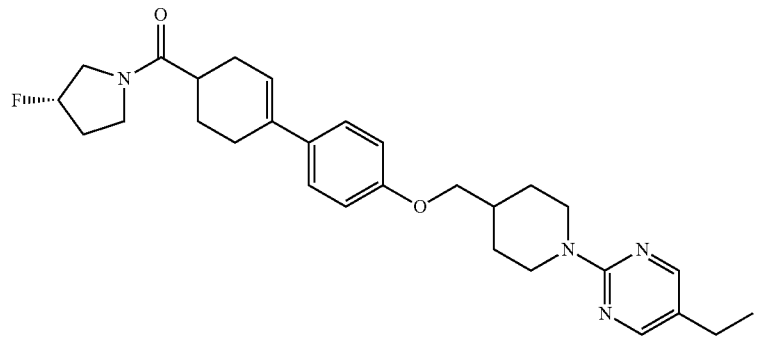 [SMILES: CCc1cnc(N2CCC(COc3ccc(C4=CCC(C(=O)N5CC[C@H](F)C5)CC4)cc3)CC2)nc1]

The title compound was prepared in the same manner as in <Example 152>, except that (S)-3-fluoropyrrolidine was used instead of the L-β-prolinol (Amount obtained: 195 mg/Yield: 76%).

$^1$H NMR (400, CDCl$_3$): 8.19 (2H, s), 7.33 (2H, d), 6.86 (2H, d), 6.06 (1H, s), 5.31 (1H, m), 4.78 (2H, d), 4.01-3.51 (6H, m), 2.92 (2H, m), 2.77-1.87 (14H, m), 1.35 (2H, m), 1.21 (3H, m)

Example 161

Preparation of (4-(4-((1-(5-ethylpyrimidin-2-yl)piperidin-4-yl)methoxy)phenyl)cyclohex-3-enyl)((S)-3-fluoropyrrolidin-1-yl)methanone hydrochloride

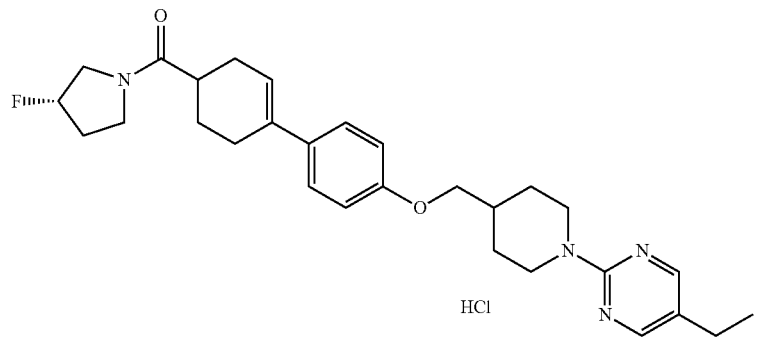 [SMILES: CCc1cnc(N2CCC(COc3ccc(C4=CCC(C(=O)N5CC[C@H](F)C5)CC4)cc3)CC2)nc1 ; Cl]

The title compound was prepared in the same manner as in <Example 145>, except that (4-(4-((1-(5-ethylpyrimidin-2-yl)piperidin-4-yl)methoxy)phenyl)cyclohex-3-enyl)((S)-3-fluoropyrrolidin-1-yl)methanone was used instead of the ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone (Amount obtained: 105 mg/Yield: 73%).

$^1$H NMR (400, CDCl$_3$): 8.41 (2H, s), 7.33 (2H, d), 6.86 (2H, d), 6.06 (1H, s), 5.31 (1H, m), 5.01 (2H, d), 4.01-3.51 (6H, m), 2.92 (2H, m), 2.77-1.87 (14H, m), 1.35 (2H, m), 1.21 (3H, m)

Example 162

Preparation of (4-(4-((1-(5-ethylpyrimidin-2-yl)piperidin-4-yl)methoxy)phenyl)cyclohex-3-enyl)(pyrrolidin-1-yl)methanone

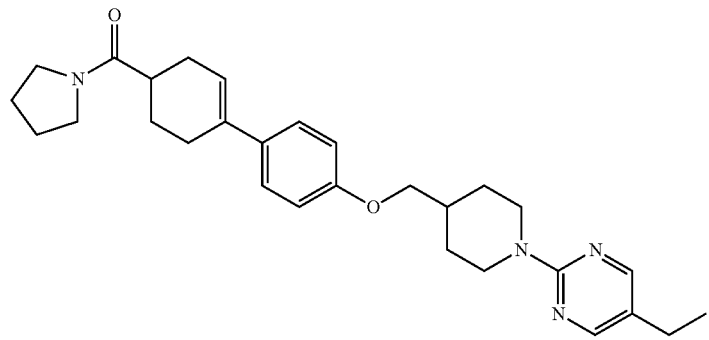 [SMILES: CCc1cnc(N2CCC(COc3ccc(C4=CCC(C(=O)N5CCCC5)CC4)cc3)CC2)nc1]

The title compound was prepared in the same manner as in <Example 152>, except that pyrrolidine was used instead of the L-β-prolinol (Amount obtained: 250 mg/Yield: 84%).

$^1$H NMR (400, CDCl$_3$): 8.19 (2H, s), 7.33 (2H, d), 6.86 (2H, d), 6.06 (1H, s), 4.78 (2H, d), 3.85 (2H, d), 3.52 (4H, m), 2.92 (2H, m), 2.71-2.28 (7H, m), 2.17-1.85 (9H, m), 1.35 (2H, m), 1.21 (3H, m)

Example 163

Preparation of (4-(4-((1-(5-ethylpyrimidin-2-yl)piperidin-4-yl)methoxy)phenyl)cyclohex-3-enyl)(piperidin-1-yl)methanone

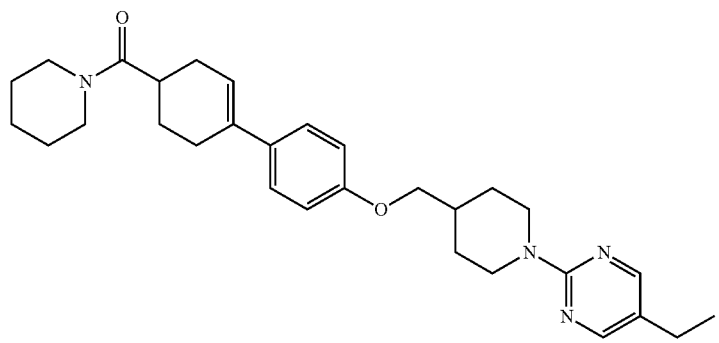 [SMILES: CCc1cnc(N2CCC(COc3ccc(C4=CCC(C(=O)N5CCCCC5)CC4)cc3)CC2)nc1]

The title compound was prepared in the same manner as in <Example 152>, except that piperidine was used instead of the L-β-prolinol (Amount obtained: 250 mg/Yield: 83%).

$^1$H NMR (400, CDCl$_3$): 8.19 (2H, s), 7.33 (2H, d), 6.86 (2H, d), 6.06 (1H, s), 4.78 (2H, d), 3.85 (2H, d), 3.67-3.52 (4H, m), 2.92 (2H, m), 2.80 (1H, m), 2.61-1.85 (11H, m), 1.74-1.54 (6H, m), 1.35 (2H, m), 1.21 (3H, m)

Example 164

Preparation of (4-(4-((1-(5-ethylpyrimidin-2-yl)piperidin-4-yl)methoxy)phenyl)cyclohex-3-enyl)(4-hydroxypiperidin-1-yl)methanone

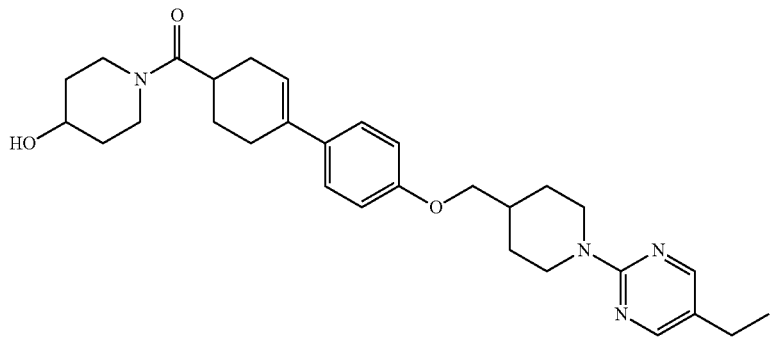

The title compound was prepared in the same manner as in <Example 152>, except that 4-hydroxy piperidine was used instead of the L-β-prolinol (Amount obtained: 215 mg/Yield: 77%).

$^1$H NMR (400, CDCl$_3$): 8.19 (2H, s), 7.33 (2H, d), 6.86 (2H, d), 6.06 (1H, s), 4.78 (2H, d), 4.18 (1H, m), 3.89 (2H, m), 3.85 (2H, d), 3.28 (2H, m), 2.92 (2H, m), 2.80 (1H, m), 2.61-2.28 (6H, m), 2.09 (1H, m), 1.98 (6H, m), 1.55 (2H, m), 1.35 (2H, m), 1.21 (3H, m)

Example 165

Preparation of (4-(4-((1-(5-ethylpyrimidin-2-yl)piperidin-4-yl)methoxy)phenyl)cyclohex-3-enyl)(4-(hydroxymethyl)piperidin-1-yl)methanone

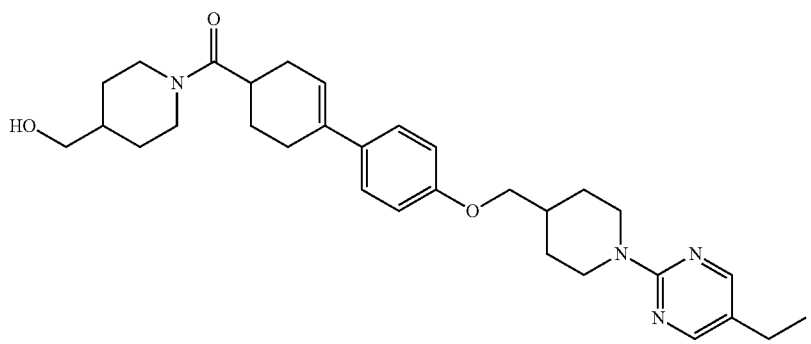

The title compound was prepared in the same manner as in <Example 152>, except that 4-piperidinemethanol was used instead of the L-β-prolinol (Amount obtained: 225 mg/Yield: 75%).

¹H NMR (400, CDCl₃): 8.19 (2H, s), 7.33 (2H, d), 6.86 (2H, d), 6.06 (1H, s), 4.78 (3H, m), 4.08 (1H, d), 3.85 (2H, d), 3.55 (2H, m), 3.09 (1H, m), 2.92 (2H, m), 2.81 (1H, m), 2.65-2.28 (7H, m), 2.11 (1H, m), 2.04-1.75 (7H, m), 1.35 (2H, m), 1.21 (3H, m)

Example 166

Preparation of (4-(4-((1-(5-ethylpyrimidin-2-yl)piperidin-4-yl)methoxy)phenyl)cyclohex-3-enyl)(pyrrolidin-1-yl)methanone hydrochloride

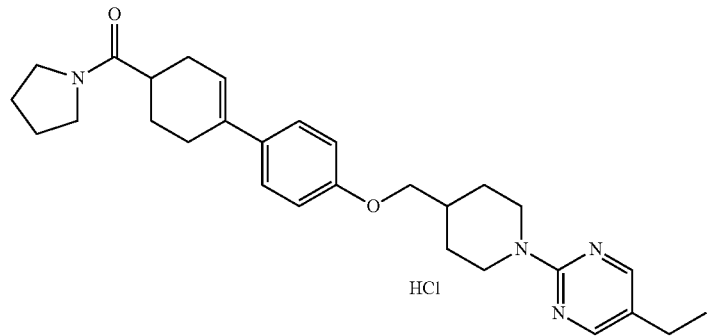 [SMILES: CCc1cnc(N2CCC(COc3ccc(C4=CCC(C(=O)N5CCCC5)CC4)cc3)CC2)nc1 ; Cl]

The title compound was prepared in the same manner as in <Example 145>, except that (4-(4-((1-(5-ethylpyrimidin-2-yl)piperidin-4-yl)methoxy)phenyl)cyclohex-3-enyl)(pyrrolidin-1-yl)methanone was used instead of the ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone (Amount obtained: 100 mg/Yield: 74%).

¹H NMR (400, CDCl₃): 8.41 (2H, s), 7.33 (2H, d), 6.86 (2H, d), 6.06 (1H, s), 5.03 (2H, d), 3.85 (2H, d), 3.52 (4H, m), 2.92 (2H, m), 2.71-2.28 (7H, m), 2.17-1.85 (9H, m), 1.35 (2H, m), 1.21 (3H, m)

Example 167

Preparation of (4-(4-((1-(5-ethylpyrimidin-2-yl)piperidin-4-yl)methoxy)phenyl)cyclohex-3-enyl)(piperidin-1-yl)methanone hydrochloride

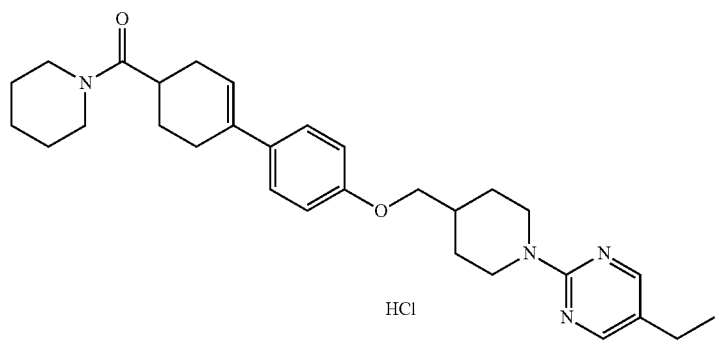 [SMILES: CCc1cnc(N2CCC(COc3ccc(C4=CCC(C(=O)N5CCCCC5)CC4)cc3)CC2)nc1 ; Cl]

The title compound was prepared in the same manner as in <Example 145>, except that (4-(4-((1-(5-ethylpyrimidin-2-yl)piperidin-4-yl)methoxy)phenyl)cyclohex-3-enyl)(piperidin-1-yl)methanone was used instead of the ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone (Amount obtained: 85 mg/Yield: 71%).

$^1$H NMR (400, CDCl$_3$): 8.41 (2H, s), 7.33 (2H, d), 6.86 (2H, d), 6.06 (1H, s), 5.03 (2H, d), 3.85 (2H, d), 3.67-3.52 (4H, m), 2.92 (2H, m), 2.80 (1H, m), 2.61-1.85 (11H, m), 1.74-1.54 (6H, m), 1.35 (2H, m), 1.21 (3H, m)

Example 168

Preparation of (4-(4-((1-(5-ethylpyrimidin-2-yl)piperidin-4-yl)methoxy)phenyl)cyclohex-3-enyl)(4-hydroxypiperidin-1-yl)methanone hydrochloride

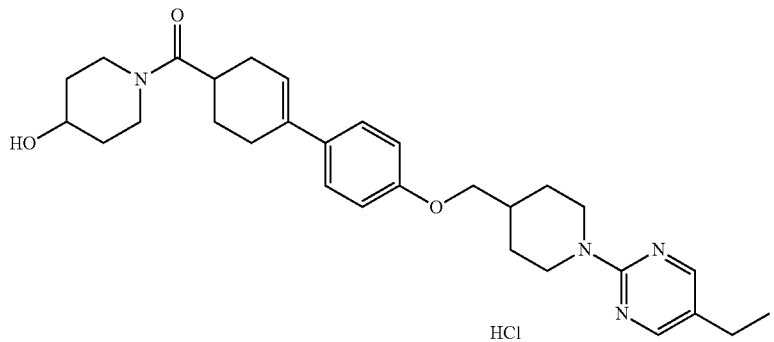 [SMILES: CCc1cnc(N2CCC(COc3ccc(C4=CCC(C(=O)N5CCC(O)CC5)CC4)cc3)CC2)nc1 ; Cl]

The title compound was prepared in the same manner as in <Example 145>, except that (4-(4-((1-(5-ethylpyrimidin-2-yl)piperidin-4-yl)methoxy)phenyl)cyclohex-3-enyl)(4-hydroxypiperidin-1-yl)methanone was used instead of the ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone (Amount obtained: 85 mg/Yield: 77%).

$^1$H NMR (400, CDCl$_3$): 8.41 (2H, s), 7.33 (2H, d), 6.86 (2H, d), 6.06 (1H, s), 5.03 (2H, d), 4.18 (1H, m), 3.89 (2H, m), 3.85 (2H, d), 3.28 (2H, m), 2.92 (2H, m), 2.80 (1H, m), 2.61-2.28 (6H, m), 2.09 (1H, m), 1.98 (6H, m), 1.55 (2H, m), 1.35 (2H, m), 1.21 (3H, m)

Example 169

Preparation of (4-(4-((1-(5-ethylpyrimidin-2-yl)piperidin-4-yl)methoxy)phenyl)cyclohex-3-enyl)(4-(hydroxymethyl)piperidin-1-yl)methanone hydrochloride

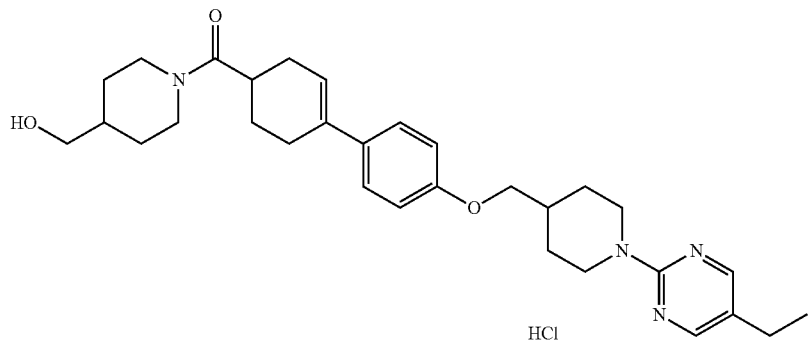 [SMILES: CCc1cnc(N2CCC(COc3ccc(C4=CCC(C(=O)N5CCC(CO)CC5)CC4)cc3)CC2)nc1 ; Cl]

The title compound was prepared in the same manner as in <Example 145>, except that (4-(4-((1-(5-ethylpyrimidin-2-yl)piperidin-4-yl)methoxy)phenyl)cyclohex-3-enyl)(4-(hydroxymethyl)piperidin-1-yl)methanone was used instead of the ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone (Amount obtained: 95 mg/Yield: 76%).

$^1$H NMR (400, CDCl$_3$): 8.41 (2H, s), 7.33 (2H, d), 6.86 (2H, d), 6.06 (1H, s), 5.03 (2H, m), 4.72 (1H, d), 4.08 (1H, d), 3.85 (2H, d), 3.55 (2H, m), 3.09 (1H, m), 2.92 (2H, m), 2.81 (1H, m), 2.65-2.28 (7H, m), 2.11 (1H, m), 2.04-1.75 (7H, m), 1.35 (2H, m), 1.21 (3H, m)

Example 170

Preparation of azetidin-1-yl(4-(4-((1-(5-ethylpyrimidin-2-yl)piperidin-4-yl)methoxy)phenyl)cyclohex-3-enyl)methanone

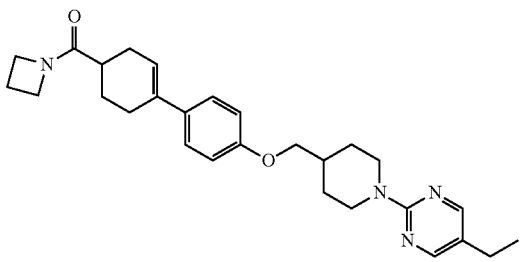 [SMILES: CCc1cnc(N2CCC(COc3ccc(C4=CCC(C(=O)N5CCC5)CC4)cc3)CC2)nc1]

The title compound was prepared in the same manner as in <Example 152>, except that azetidine was used instead of the L-β-prolinol (Amount obtained: 180 mg/Yield: 76%).

$^1$H NMR (400, CDCl$_3$): 8.19 (2H, s), 7.33 (2H, d), 6.86 (2H, d), 6.06 (1H, s), 4.78 (3H, m), 4.15 (4H, m), 3.85 (2H, d), 2.91 (2H, m), 2.61-1.81 (14H, m), 1.35 (2H, m), 1.21 (3H, m)

Example 171

Preparation of (4-(4-((1-(5-ethylpyrimidin-2-yl)piperidin-4-yl)methoxy)phenyl)cyclohex-3-enyl)(3-hydroxyazetidin-1-yl)methanone

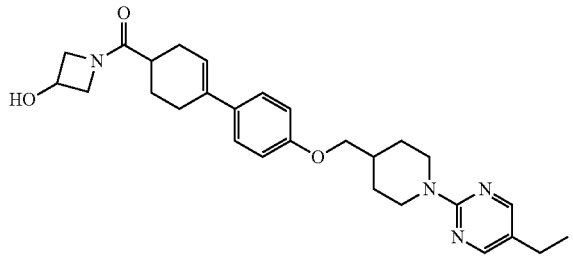 [SMILES: CCc1cnc(N2CCC(COc3ccc(C4=CCC(C(=O)N5CC(O)C5)CC4)cc3)CC2)nc1]

The title compound was prepared in the same manner as in <Example 152>, except that azetidine was used instead of the L-β-prolinol (Amount obtained: 200 mg/Yield: 81%).

$^1$H NMR (400, CDCl$_3$): 8.19 (2H, s), 7.33 (2H, d), 6.86 (2H, d), 6.06 (1H, s), 4.78 (2H, m), 4.35 (4H, m), 3.85 (2H, d), 2.91 (2H, m), 2.71-1.81 (13H, m), 1.35 (2H, m), 1.21 (3H, m)

Example 172

Preparation of (4-(4-((1-(5-ethylpyrimidin-2-yl)piperidin-4-yl)methoxy)phenyl)cyclohex-3-enyl)(4-(2-hydroxyethyl)piperazin-1-yl)methanone

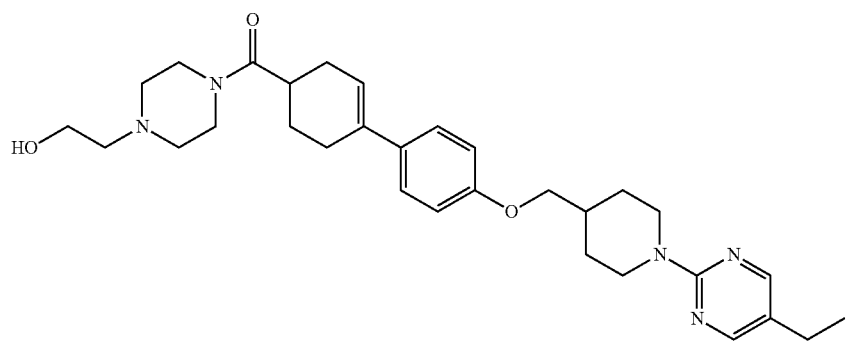 [SMILES: CCc1cnc(N2CCC(COc3ccc(C4=CCC(C(=O)N5CCN(CCO)CC5)CC4)cc3)CC2)nc1]

The title compound was prepared in the same manner as in <Example 152>, except that 4-hydroxyethylpiperazine was used instead of the L-β-prolinol (Amount obtained: 220 mg/Yield: 79%).

$^1$H NMR (400, CDCl$_3$): 8.19 (2H, s), 7.33 (2H, d), 6.86 (2H, d), 6.06 (1H, s), 4.78 (2H, m), 3.85 (2H, d), 3.65 (6H, m), 2.91 (2H, m), 2.86-1.81 (12H, m), 1.35 (2H, m), 1.21 (3H, m)

Example 173

Preparation of (4-(4-((1-(5-ethylpyrimidin-2-yl)piperidin-4-yl)methoxy)phenyl)cyclohex-3-enyl)(4-(2-hydroxyethyl)piperidin-1-yl)methanone

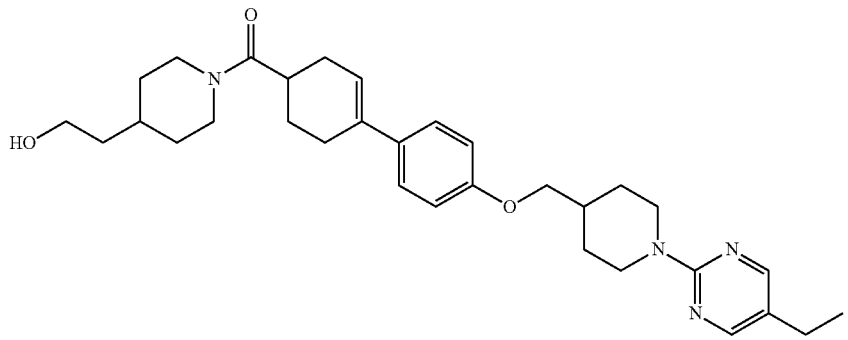 [SMILES: CCc1cnc(N2CCC(COc3ccc(C4=CCC(C(=O)N5CCC(CCO)CC5)CC4)cc3)CC2)nc1]

The title compound was prepared in the same manner as in <Example 152>, except that 4-piperidine ethanol was used instead of the L-β-prolinol (Amount obtained: 230 mg/Yield: 77%).

$^1$H NMR (400, CDCl$_3$): 8.19 (2H, s), 7.33 (2H, d), 6.86 (2H, d), 6.06 (1H, s), 4.78 (2H, m), 3.69 (1H, d), 3.99 (1H, d), 3.85 (2H, d), 3.75 (2H, m), 3.09 (1H, m), 2.91 (2H, m), 2.86-1.41 (17H, m), 1.35 (2H, m), 1.21 (3H, m)

Example 174

Preparation of N-ethoxy-4-(4-((1-(5-ethylpyrimidin-2-yl)piperidin-4-yl)methoxy)phenyl)cyclohex-3-enecarboxamide

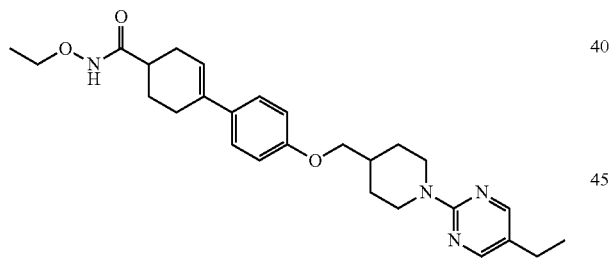

The title compound was prepared in the same manner as in <Example 152>, except that O-ethylhydroxylamine hydrochloride was used instead of the L-β-prolinol (Amount obtained: 230 mg/Yield: 81%).

$^1$H NMR (400, CDCl$_3$): 8.19 (2H, s), 7.33 (2H, d), 6.86 (2H, d), 6.06 (1H, s), 4.78 (2H, m), 4.01 (2H, m), 3.85 (2H, d), 2.91 (2H, m), 2.71-1.81 (12H, m), 1.35 (5H, m), 1.21 (3H, m)

Example 175

Preparation of N-ethyl-4-(4-((1-(5-ethylpyrimidin-2-yl)piperidin-4-yl)methoxy)phenyl)-N-(2-hydroxyethyl)cyclohex-3-enecarboxamide

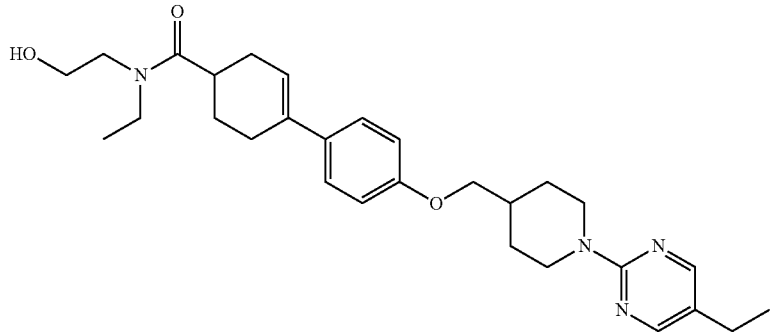 [SMILES: CCc1cnc(N2CCC(COc3ccc(C4=CCC(C(=O)N(CC)CCO)CC4)cc3)CC2)nc1]

The title compound was prepared in the same manner as in <Example 152>, except that 2-(ethylamino)ethanol was used instead of the L-β-prolinol (Amount obtained: 205 mg/Yield: 82%).

$^1$H NMR (400, CDCl$_3$): 8.19 (2H, s), 7.33 (2H, d), 6.86 (2H, d), 6.06 (1H, s), 4.78 (2H, m), 3.85 (4H, m), 3.71 (1H, s), 3.52 (4H, m), 2.91 (2H, m), 2.81-1.81 (12H, m), 1.35 (2H, m), 1.21 (6H, m)

Example 176

Preparation of 4-(4-((1-(5-ethylpyrimidin-2-yl)piperidin-4-yl)methoxy)phenyl)-N-(2-hydroxyethyl)cyclohex-3-enecarboxamide

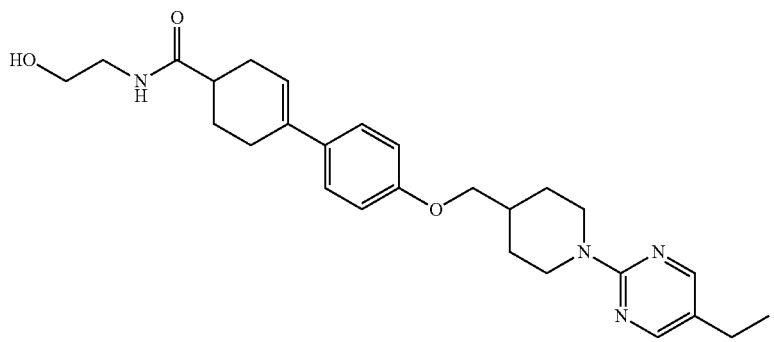 [SMILES: CCc1cnc(N2CCC(COc3ccc(C4=CCC(C(=O)NCCO)CC4)cc3)CC2)nc1]

The title compound was prepared in the same manner as in <Example 152>, except that 2-aminoethanol was used instead of the L-β-prolinol (Amount obtained: 260 mg/Yield: 85%).

$^1$H NMR (400, CDCl$_3$): 8.19 (2H, s), 7.33 (2H, d), 6.86 (2H, d), 6.06 (2H, m), 4.78 (2H, m), 3.85 (2H, d), 3.78 (2H, m), 3.51 (2H, m), 2.91 (2H, m), 2.48 (7H, m), 2.21-1.81 (5H, m), 1.35 (2H, m), 1.21 (3H, m)

Example 177

Preparation of 4-(4-((1-(5-ethylpyrimidin-2-yl)piperidin-4-yl)methoxy)phenyl)-N-(3-hydroxy-2,2-dimethylpropyl)cyclohex-3-enecarboxamide

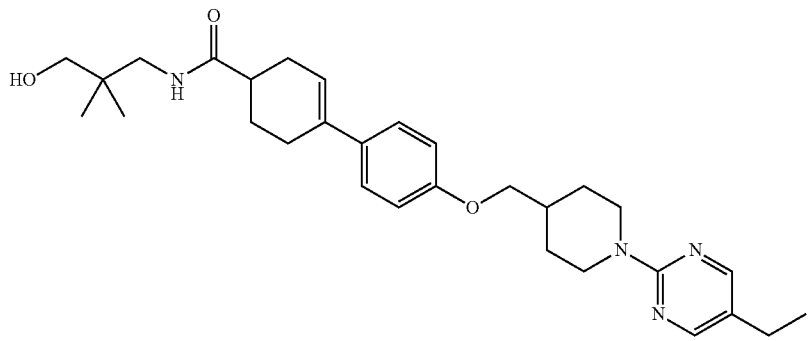 [SMILES: CCc1cnc(N2CCC(COc3ccc(C4=CCC(C(=O)NCC(C)(C)CO)CC4)cc3)CC2)nc1]

The title compound was prepared in the same manner as in <Example 152>, except that 3-amino-2,2-dimethylpropanol was used instead of the L-β-prolinol (Amount obtained: 265 mg/Yield: 85%).

¹H NMR (400, CDCl₃): 8.19 (2H, s), 7.33 (2H, d), 6.86 (2H, d), 6.06 (1H, s), 5.98 (1H, m), 4.78 (2H, m), 3.85 (2H, d), 3.49 (2H, m), 3.16 (4H, m), 2.91 (2H, m), 2.48 (7H, m), 2.21-1.81 (5H, m), 1.35 (2H, m), 1.21 (3H, m), 0.89 (6H, d)

Example 178

Preparation of 1-(4-(4-((1-(5-ethylpyrimidin-2-yl)piperidin-4-yl)methoxy)phenyl)cyclohex-3-enecarbonyl)piperidine-4-carboxamide

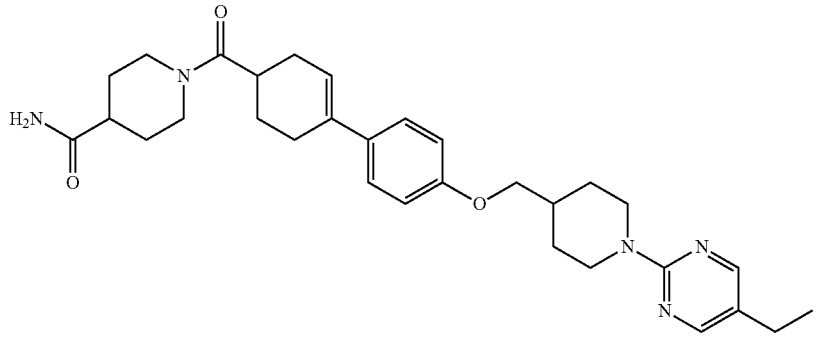

The title compound was prepared in the same manner as in <Example 152>, except that isonipecotamide was used instead of the L-β-prolinol (Amount obtained: 240 mg/Yield: 79%).

¹H NMR (400, CDCl₃): 8.19 (2H, s), 7.33 (2H, d), 6.86 (2H, d), 6.06 (1H, s), 5.39 (2H, m), 4.78 (2H, m), 4.68 (1H, m), 4.02 (1H, d), 3.85 (2H, d), 3.65 (6H, m), 3.14 (1H, m), 2.91 (2H, m), 2.86-2.18 (9H, m), 2.15-1.59 (13H, m), 1.35 (2H, m), 1.21 (3H, m)

Example 179

Preparation of 4-(4-((1-(5-ethylpyrimidin-2-yl)piperidin-4-yl)methoxy)phenyl)-N-(3-methoxypropyl)cyclohex-3-enecarboxamide

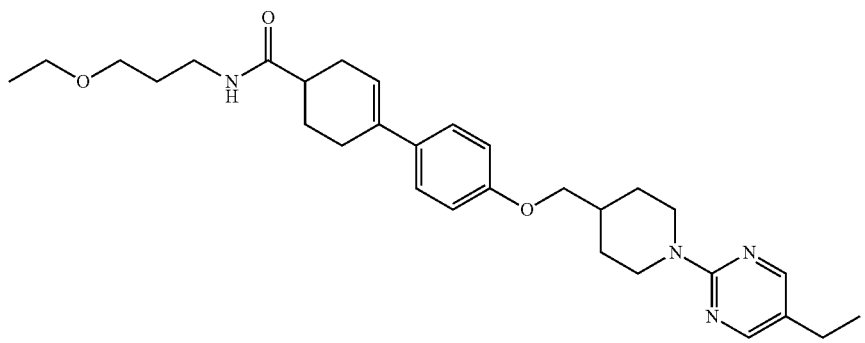 [SMILES: CCOCCCNC(=O)C1CC=C(c2ccc(OCC3CCN(c4ncc(CC)cn4)CC3)cc2)CC1]

The title compound was prepared in the same manner as in <Example 152>, except that 3-ethoxypropylamine was used instead of the L-β-prolinol (Amount obtained: 240 mg/Yield: 78%).

¹H NMR (400, CDCl₃): 8.19 (2H, s), 7.33 (2H, d), 6.86 (2H, d), 6.31 (1H, m), 6.06 (1H, s), 4.78 (2H, m), 3.85 (2H, d), 3.48 (6H, m), 2.91 (2H, m), 2.86-1.79 (14H, m), 1.35 (2H, m), 1.21 (6H, m)

Example 180

Preparation of 4-(4-((1-(5-ethylpyrimidin-2-yl)piperidin-4-yl)methoxy)phenyl)-N-(furan-2-ylmethyl)cyclohex-3-enecarboxamide

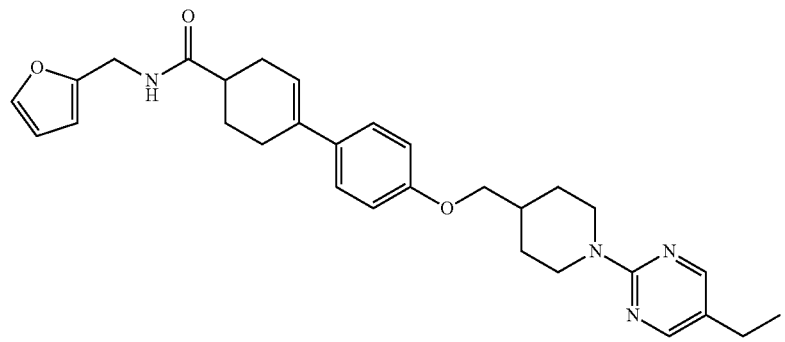 [SMILES: CCc1cnc(N2CCC(COc3ccc(C4=CCC(C(=O)NCc5ccco5)CC4)cc3)CC2)nc1]

The title compound was prepared in the same manner as in <Example 152>, except that furfurylamine was used instead of the L-β-prolinol (Amount obtained: 180 mg/Yield: 76%).

$^1$H NMR (400, CDCl$_3$): 8.19 (2H, s), 7.37 (1H, s), 7.33 (2H, d), 6.86 (2H, d), 6.31 (2H, m), 6.06 (1H, s), 5.89 (1H, m), 4.78 (2H, m), 4.51 (2H, d), 3.85 (2H, d), 2.91 (2H, m), 2.59-1.81 (12H, m), 1.35 (2H, m), 1.21 (3H, m)

Example 181

Preparation of 4-(4-((1-(5-ethylpyrimidin-2-yl)piperidin-4-yl)methoxy)phenyl)-N,N-bis(2-hydroxyethyl)cyclohex-3-enecarboxamide

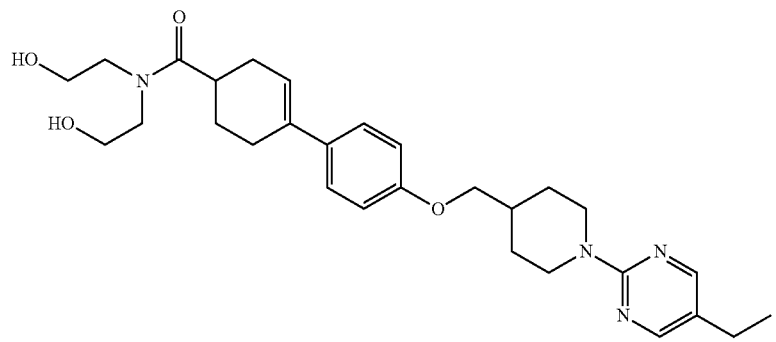 [SMILES: CCc1cnc(N2CCC(COc3ccc(C4=CCC(C(=O)N(CCO)CCO)CC4)cc3)CC2)nc1]

The title compound was prepared in the same manner as in <Example 152>, except that diethanolamine was used instead of the L-β-prolinol (Amount obtained: 185 mg/Yield: 77%).

$^1$H NMR (400, CDCl$_3$): 8.19 (2H, s), 7.33 (2H, d), 6.86 (2H, d), 6.06 (1H, s), 4.78 (2H, m), 3.88 (6H, m), 3.69 (4H, m), 3.15 (2H, d), 2.91 (3H, m), 2.59-1.83 (11H, m), 1.35 (2H, m), 1.21 (3H, m)

Example 182

Preparation of (4-hydroxypiperidin-1-yl)(4-(4-((1-(3-isopropyl-1,2,4-oxadiazol-5-yl)piperidin-4-yl)methoxy)phenyl)cyclohex-3-enyl)methanone

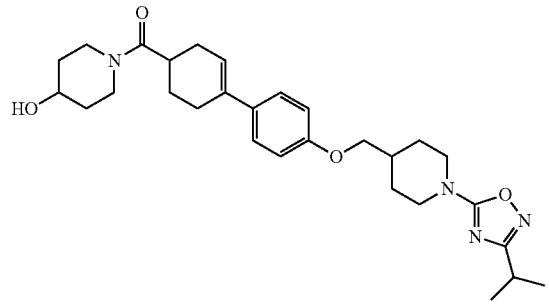

The title compound was prepared in the same manner as in <Example 143>, except that 4-hydroxypiperidine was used instead of the (R)-N,N-dimethylpyrrolidine-3-amine hydrochloride (Amount obtained: 230 mg/Yield: 80%).

$^1$H NMR (400, CDCl$_3$): 7.33 (2H, d), 6.86 (2H, d), 6.06 (1H, s), 5.16 (1H, m), 4.19 (3H, m), 3.98 (1H, s), 3.85 (3H, m), 3.21 (4H, m), 2.88 (2H, m), 2.62-1.85 (11H, m), 1.59 (6H, m), 1.32 (6H, d)

Example 183

Preparation of (4-(hydroxymethyl)piperidin-1-yl)(4-(4-((1-(3-isopropyl-1,2,4-oxadiazol-5-yl)piperidin-4-yl)methoxy)phenyl)cyclohex-3-enyl)methanone

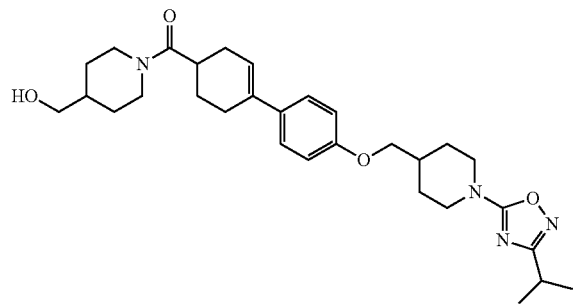

The title compound was prepared in the same manner as in <Example 143>, except that 4-piperidine methanol was used instead of the (R)-N,N-dimethylpyrrolidine-3-amine hydrochloride (Amount obtained: 240 mg/Yield: 82%).

$^1$H NMR (400, CDCl$_3$): 7.33 (2H, d), 6.86 (2H, d), 6.06 (1H, s), 4.72 (1H, s), 4.22 (2H, d), 4.04 (1H, d), 3.85 (2H, d), 3.56 (2H, m), 3.11 (3H, m), 2.88 (2H, m), 2.62-1.75 (13H, m), 1.45 (3H, m), 1.32 (6H, d)

Example 184

Preparation of N-cyclopropyl-4-(4-((1-(3-isopropyl-1,2,4-oxadiazol-5-yl)piperidin-4-yl)methoxy)phenyl)cyclohex-3-enecarboxamide

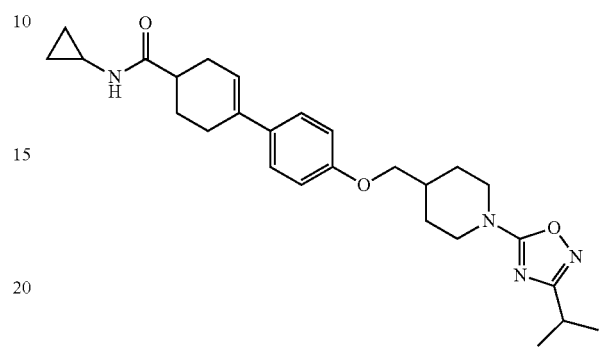

The title compound was prepared in the same manner as in <Example 143>, except that cyclopropylamine was used instead of the (R)-N,N-dimethylpyrrolidine-3-amine hydrochloride (Amount obtained: 235 mg/Yield: 81%).

$^1$H NMR (400, CDCl$_3$): 7.33 (2H, d), 6.86 (2H, d), 6.06 (1H, s), 5.70 (1H, s), 4.21 (2H, d), 3.85 (2H, d), 3.11 (2H, m), 2.91 (1H, m), 2.76 (1H, m), 2.42 (5H, m), 1.98 (5H, m), 1.59 (6H, m), 1.32 (6H, d), 0.81 (2H, m), 0.51 (2H, m)

Example 185

Preparation of N-(3-hydroxypropyl)-4-(4-((1-(3-isopropyl-1,2,4-oxadiazol-5-yl)piperidin-4-yl)methoxy)phenyl)cyclohex-3-enecarboxamide

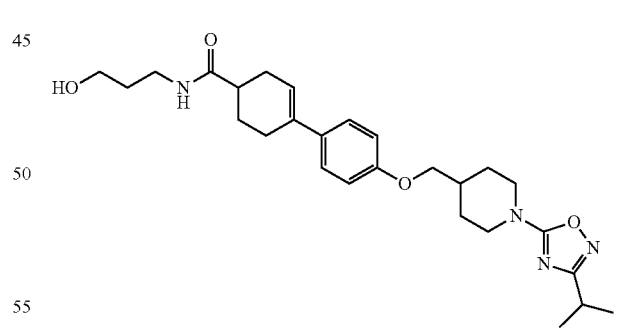

The title compound was prepared in the same manner as in <Example 143>, except that 3-aminopropanol was used instead of the (R)-N,N-dimethylpyrrolidine-3-amine hydrochloride (Amount obtained: 220 mg/Yield: 79%).

$^1$H NMR (400, CDCl$_3$): 7.33 (2H, d), 6.86 (2H, d), 6.06 (1H, s), 5.96 (1H, m), 4.21 (2H, m), 3.85 (2H, m), 3.66 (2H, m), 3.48 (2H, m), 3.20 (1H, m), 3.11 (2H, m) 2.89 (1H, m), 2.48 (5H, m), 2.01 (5H, m), 1.71 (2H, m), 1.59 (6H, m), 1.32 (6H, d)

Example 186

Preparation of (4-(2-hydroxyethyl)piperidin-1-yl)(4-(4-((1-(3-isopropyl-1,2,4-oxadiazol-5-yl)piperidin-4-yl)methoxy)phenyl)cyclohex-3-enyl)methanone

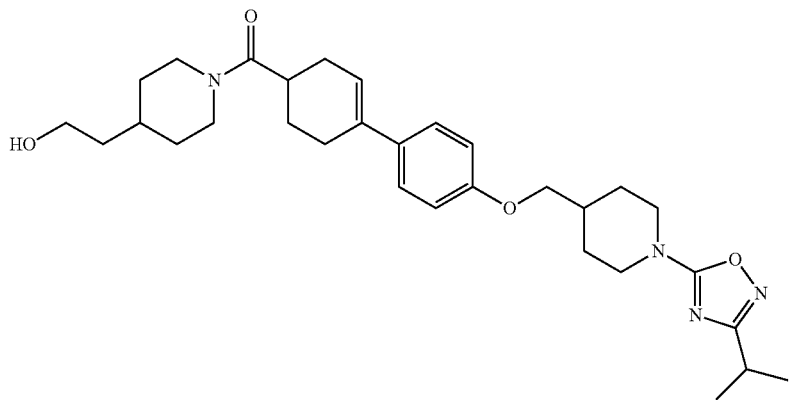

The title compound was prepared in the same manner as in <Example 143>, except that 4-piperidine ethanol was used instead of the (R)-N,N-dimethylpyrrolidine-3-amine hydrochloride (Amount obtained: 205 mg/Yield: 77%).

$^1$H NMR (400, CDCl$_3$): 7.33 (2H, d), 6.86 (2H, d), 6.06 (1H, s), 4.69 (1H, d), 4.21 (2H, m), 3.99 (1H, d), 3.85 (2H, d), 3.74 (2H, m), 3.20 (3H, m), 2.89 (1H, m), 2.81 (1H, m), 2.64-2.24 (5H, m), 2.12-1.69 (8H, m), 1.66 (2H, m), 1.46 (2H, m), 1.32 (6H, d), 1.19 (2H, m)

Example 187

Preparation of (4-(2-hydroxyethyl)piperazin-1-yl)(4-(4-((1-(3-isopropyl-1,2,4-oxadiazol-5-yl)piperidin-4-yl)methoxy)phenyl)cyclohex-3-enyl)methanone

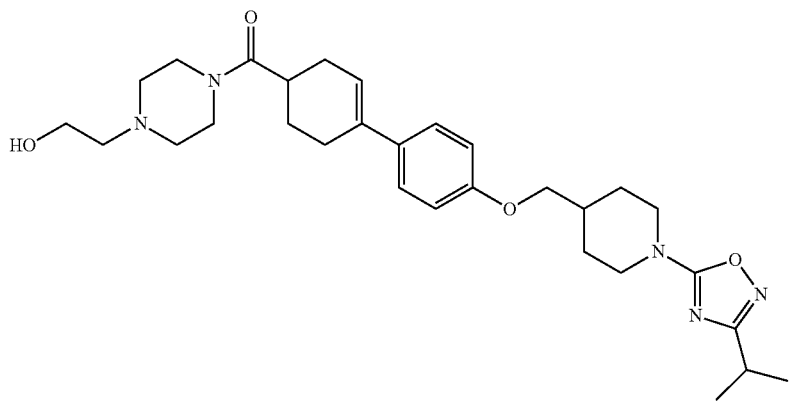 [SMILES: CC(C)c1noc(N2CCC(COc3ccc(C4=CCC(C(=O)N5CCN(CCO)CC5)CC4)cc3)CC2)n1]

The title compound was prepared in the same manner as in <Example 143>, except that 4-hydroxyethyl piperazine was used instead of the (R)-N,N-dimethylpyrrolidine-3-amine hydrochloride (Amount obtained: 180 mg/Yield: 72%).

$^1$H NMR (400, CDCl$_3$): 7.33 (2H, d), 6.86 (2H, d), 6.06 (1H, s), 4.21 (2H, m), 3.85 (2H, d), 3.71 (6H, m), 3.12 (2H, m), 2.89 (1H, m), 2.81-2.24 (12H, m), 2.12-1.85 (5H, m), 1.46 (2H, m), 1.32 (6H, d)

Example 188

Preparation of 4-(4-((1-(3-isopropyl-1,2,4-oxadiazol-5-yl)piperidin-4-yl)methoxy)phenyl)-N-(methoxymethyl)cyclohex-3-enecarboxamide

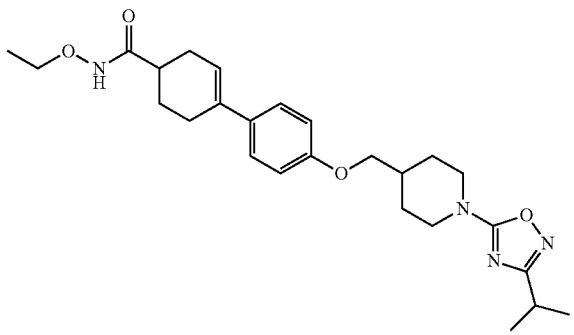 [SMILES: CCONC(=O)C1CC=C(c2ccc(OCC3CCN(c4nc(C(C)C)no4)CC3)cc2)CC1]

The title compound was prepared in the same manner as in <Example 143>, except that O-ethylhydroxylamine hydrochloride was used instead of the (R)-N,N-dimethylpyrrolidine-3-amine hydrochloride (Amount obtained: 170 mg/Yield: 71%).

$^1$H NMR (400, CDCl$_3$): 8.14 (1H, s), 7.33 (2H, d), 6.86 (2H, d), 6.06 (1H, s), 4.21 (2H, m), 3.99 (2H, m), 3.85 (2H, d), 3.12 (2H, m), 2.89 (1H, m), 2.62-2.28 (5H, m), 2.14-1.87 (5H, m), 1.46 (2H, m), 1.32 (6H, d)

Example 189

Preparation of N-cyclopropyl-4-(4-((1-(5-ethylpyrimidin-2-yl)piperidin-4-yl)methoxy)phenyl)cyclohex-3-enecarboxamide

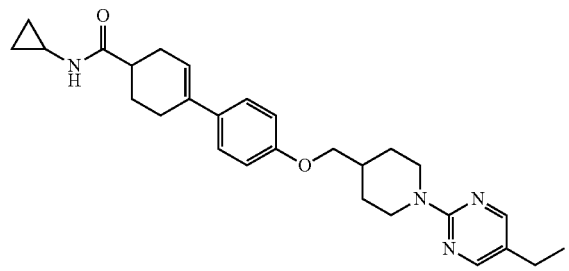 [SMILES: CCc1cnc(N2CCC(COc3ccc(C4=CCC(C(=O)NC5CC5)CC4)cc3)CC2)nc1]

The title compound was prepared in the same manner as in <Example 152>, except that cyclopropylamine was used instead of the L-β-prolinol (Amount obtained: 180 mg/Yield: 76%).

$^1$H NMR (400, CDCl$_3$): 8.19 (2H, s), 7.33 (2H, d), 6.86 (2H, d), 6.06 (1H, s), 5.66 (1H, s), 4.78 (3H, m), 3.85 (2H, d), 2.91 (2H, m), 2.76 (1H, s), 2.61-2.30 (7H, m), 2.09 (2H, m), 1.91 (3H, m), 1.35 (2H, m), 1.21 (3H, m), 0.81 (2H, m), 0.50 (2H, m)

Example 190

Preparation of tert-butyl 4-((4-(4-(2-hydroxyethylcarbamoyl)cyclohex-1-enyl)phenoxy)methyl)piperidine-1-carboxylate

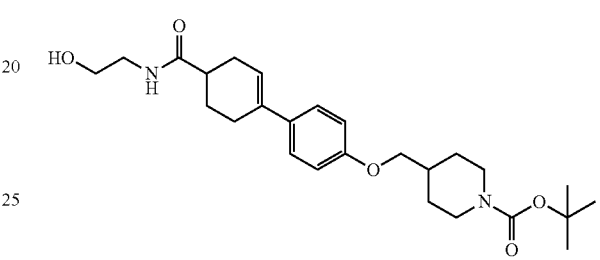

400 mg of 4-(4-((1-(tert-butoxycarbonyl)piperidin-4-yl)methoxy)phenyl)cyclohex-3-enecarboxyilc acid was dissolved in 30 ml of DMF in a 100 ml flask, and then stirred under a nitrogen atmosphere. 0.3 ml of TEA was added dropwise thereto, 90 mg of 2-aminoethanol was in turn added dropwise, and the resulting mixture was additionally stirred for 10 minutes. 400 mg of HATU was added dropwise thereto, and the mixture was stirred at room temperature for an hour. After the reaction was terminated, 50 ml of distilled water was slowly added at 0° C., and the resulting solids were filtered, and then dried to prepare the title compound as a white solid (Amount obtained: 190 mg/Yield: 77%).

$^1$H NMR (400, CDCl$_3$): 7.33 (2H, d), 6.86 (2H, d), 6.14 (1H, m), 6.04 (1H, s), 4.18 (2H, s), 3.79 (4H, m), 3.48 (2H, m), 2.75 (3H, m), 2.48 (5H, m), 2.11 (1H, m), 1.89 (4H, m), 1.48 (9H, s), 1.29 (2H, m)

Example 191

Preparation of tert-butyl 4-((4-(4-(3-hydroxy-2,2-dimethylpropylcarbamoyl)cyclohex-1-enyl)phenoxy)methyl)piperidine-1-carboxylate

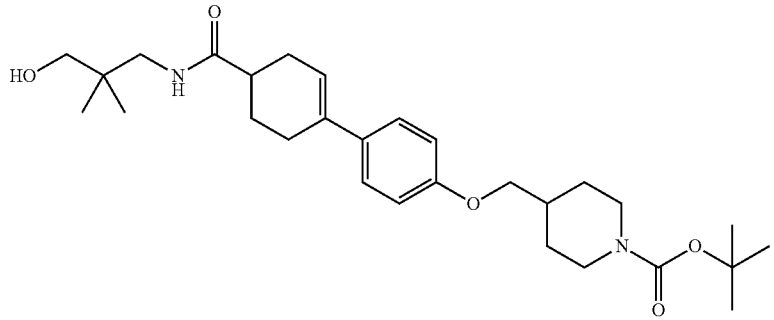 [SMILES: CC(C)(CO)CNC(=O)C1CC=C(c2ccc(OCC3CCN(C(=O)OC(C)(C)C)CC3)cc2)CC1]

The title compound was prepared in the same manner as in <Example 190>, except that 3-amino-2,2-dimethylpropanol was used instead of the 2-aminoethanol (Amount obtained: 230 mg/Yield: 84%).

$^1$H NMR (400, CDCl$_3$): 7.33 (2H, d), 6.86 (2H, d), 6.04 (1H, s), 5.99 (1H, m), 4.18 (2H, s), 4.01 (1H, m), 3.80 (2H, d), 3.16 (4H, m), 2.75 (2H, m), 2.48 (5H, m), 2.11 (1H, m), 1.89 (4H, m), 1.48 (9H, s), 1.29 (2H, m), 0.89 (6H, d)

Example 192

Preparation of tert-butyl 4-((4-(4-(methoxymethylcarbamoyl)cyclohex-1-enyl)phenoxy)methyl)piperidine-1-carboxylate

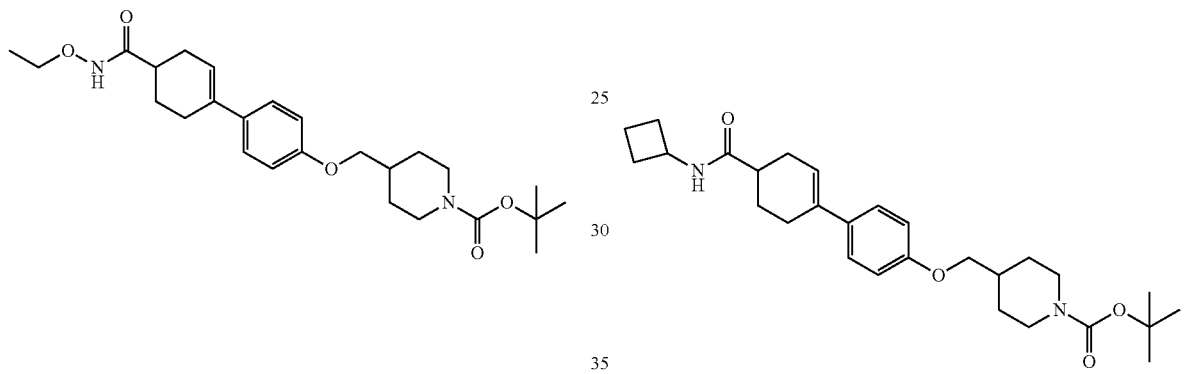

The title compound was prepared in the same manner as in <Example 190>, except that O-ethylhydroxylamine hydrochloride was used instead of the 2-aminoethanol (Amount obtained: 220 mg/Yield: 81%).

$^1$H NMR (400, CDCl$_3$): 8.15 (1H, s), 7.33 (2H, d), 6.86 (2H, d), 6.04 (1H, s), 4.18 (2H, s), 4.00 (2H, m), 3.81 (2H, m), 3.48 (2H, m), 2.75 (2H, m), 2.48 (5H, m), 2.11 (1H, m), 1.89 (4H, m), 1.48 (9H, s), 1.29 (5H, m)

Example 193

Preparation of tert-butyl 4-((4-(4-(4-(pyrrolidin-1-yl)piperidine-1-carbonyl)cyclohex-1-enyl)phenoxy)methyl)piperidine-1-carboxylate

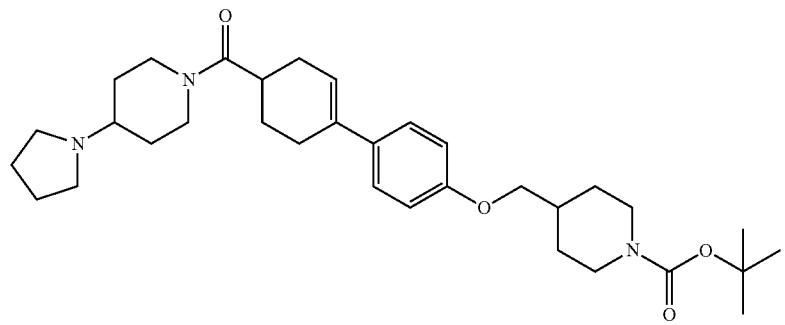 [SMILES: CC(C)(C)OC(=O)N1CCC(COc2ccc(C3=CCC(C(=O)N4CCC(N5CCCC5)CC4)CC3)cc2)CC1]

The title compound was prepared in the same manner as in <Example 190>, except that 4-(pyrrolidin-1-yl)piperidine was used instead of the 2-aminoethanol (Amount obtained: 180 mg/Yield: 76%).

$^1$H NMR (400, CDCl$_3$): 7.31 (3H, d), 6.82 (2H, d), 6.04 (1H, s), 4.59 (1H, s), 4.15 (2H, s), 3.95 (1H, d), 3.81 (1H, s), 3.09 (1H, m), 2.75-2.48 (11H, m), 2.29 (2H, d), 2.05-1.82 (11H, m), 1.47 (11H, s), 1.31 (2H, m)

Example 194

Preparation of tert-butyl 4-((4-(4-(cyclobutylcarbamoyl)cyclohex-1-enyl)phenoxy)methyl)piperidine-1-carboxylate The title compound was prepared in the same manner as in <Example 190>, except that cyclobutylamine hydrochloride was used instead of the 2-aminoethanol (Amount obtained: 170 mg/Yield: 71%).

$^1$H NMR (400, CDCl$_3$): 7.32 (2H, d), 6.85 (2H, d), 6.04 (1H, m), 5.69 (1H, d), 4.46 (1H, m), 4.18 (2H, s), 3.82 (2H, d), 2.75 (2H, t), 2.44-2.34 (7H, m), 2.12-1.71 (9H, m), 1.48 (9H, s), 1.29 (2H, m)

Example 195

Preparation of tert-butyl 4-((4-(4-(cyclopentylcarbamoyl)cyclohex-1-enyl)phenoxy)methyl)piperidine-1-carboxylate

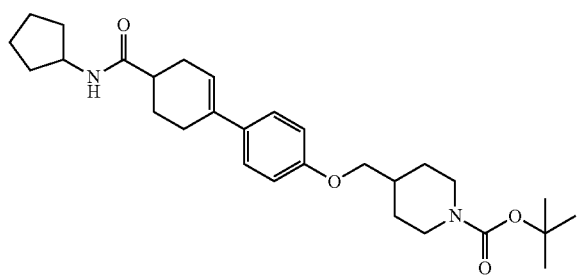 [SMILES: CC(C)(C)OC(=O)N1CCC(COc2ccc(C3=CCC(C(=O)NC4CCCC4)CC3)cc2)CC1]

The title compound was prepared in the same manner as in <Example 190>, except that cyclopentylamine was used instead of the 2-aminoethanol (Amount obtained: 195 mg/Yield: 79%).

$^1$H NMR (400, CDCl$_3$): 7.31 (2H, d), 6.85 (2H, d), 6.04 (1H, m), 5.54 (1H, m), 4.30-4.18 (3H, m), 3.81 (2H, d), 2.81 (2H, m), 2.56-2.32 (5H, m), 2.10-1.58 (12H, m), 1.48 (9H, s), 1.41-1.22 (4H, m)

Example 196

Preparation of tert-butyl 4-((4-(4-(4-morpholinopiperidine-1-carbonyl)cyclohex-1-enyl)phenoxy)methyl)piperidine-1-carboxylate

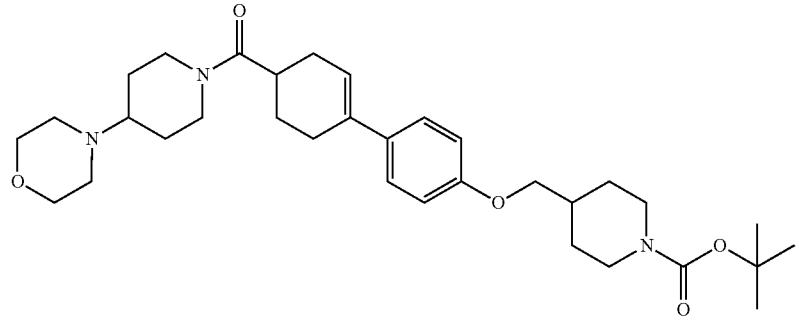 [SMILES: CC(C)(C)OC(=O)N1CCC(COc2ccc(C3=CCC(C(=O)N4CCC(N5CCOCC5)CC4)CC3)cc2)CC1]

The title compound was prepared in the same manner as in <Example 190>, except that 4-morpholinopiperidine was used instead of the 2-aminoethanol (Amount obtained: 805 mg/Yield: 77%).

$^1$H NMR (400, CDCl$_3$): 7.33 (2H, m), 6.86 (2H, m), 6.05 (1H, m), 4.72 (1H, m), 4.16-4.02 (3H, m), 4.16-4.02 (3H, m), 3.82-3.74 (6H, m), 3.12 (1H, m), 2.83-2.26 (13H, m), 1.98-1.82 (7H, m), 1.48 (9H, s), 1.33 (2H, m)

Example 197

Preparation of 4-(4-((1-(5-ethylpyrimidin-2-yl)piperidin-4-yl)methoxy)phenyl)-N-methoxy-N-methylcyclohex-3-enecarboxamide

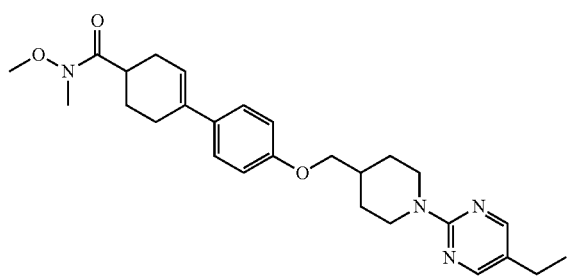 [SMILES: CCc1cnc(N2CCC(COc3ccc(C4=CCC(C(=O)N(C)OC)CC4)cc3)CC2)nc1]

The title compound was prepared in the same manner as in <Example 152>, except that N,O-dimethylhydroxylamine hydrochloride was used instead of the L-β-prolinol (Amount obtained: 220 mg/Yield: 79%).

$^1$H NMR (400, CDCl$_3$): 8.19 (2H, s), 7.34 (2H, m), 6.88 (2H, m), 6.07 (1H, m), 4.80 (2H, m), 3.85 (2H, d), 3.74 (3H, s), 3.24 (3H, s), 2.99-2.88 (3H, m), 2.54-2.33 (6H, m), 2.13-1.83 (5H, m), 1.41 (2H, m), 1.22 (3H, m)

Example 198

Preparation of 4-(4-((1-(5-ethylpyrimidin-2-yl)piperidin-4-yl)methoxy)phenyl)-N-methoxycyclohex-3-enecarboxamide

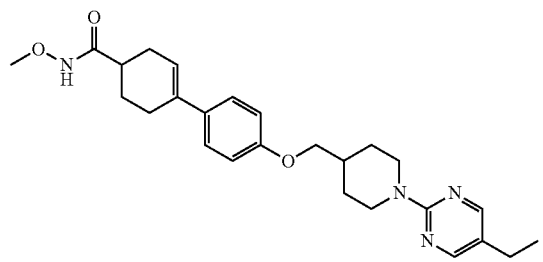

The title compound was prepared in the same manner as in <Example 152>, except that O-methylhydroxylamine hydrochloride was used instead of the L-β-prolinol (Amount obtained: 240 mg/Yield: 83%).

¹H NMR (400, CDCl₃): 8.24 (2H, s), 7.33 (2H, m), 6.87 (2H, m), 6.03 (1H, s), 4.80 (2H, m), 3.84 (5H, m), 2.96 (2H, m), 2.57-1.93 (13H, m), 1.41 (2H, m), 1.20 (3H, m)

Example 199

Preparation of tert-butyl 4-((4-(4-(ethyl(2-hydroxyethyl)carbamoyl)cyclohex-1-enyl)phenoxy)methyl)piperidine-1-carboxylate

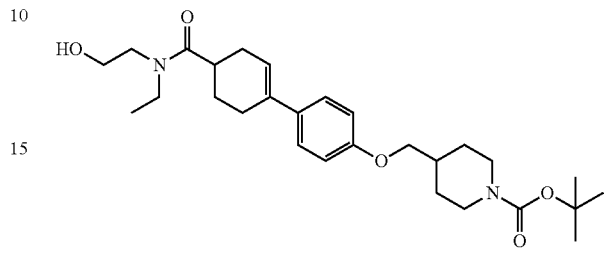

The title compound was prepared in the same manner as in <Example 190>, except that 2-(ethylamino)ethanol was used instead of the 2-aminoethanol (Amount obtained: 170 mg/Yield: 72%).

¹H NMR (400, CDCl₃): 7.32 (2H, m), 6.85 (2H, m), 6.05 (1H, s), 4.16 (2H, s), 3.80 (3H, m), 3.73 (1H, m), 3.57-3.44 (4H, m), 2.87-1.71 (12H, m), 1.47 (9H, s), 1.31-1.13 (5H, m)

Example 200

Preparation of tert-butyl 4-((4-(4-(4-(2-hydroxyethyl)piperidine-1-carbonyl)cyclohex-1-enyl)phenoxy)methyl)piperidine-1-carboxylate

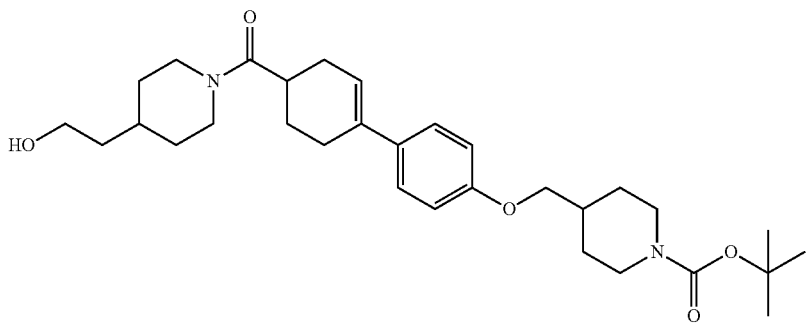 [SMILES: CC(C)(C)OC(=O)N1CCC(COc2ccc(C3=CCC(C(=O)N4CCC(CCO)CC4)CC3)cc2)CC1]

The title compound was prepared in the same manner as in <Example 190>, except that 4-hydroxyethylpiperidine was used instead of the 2-aminoethanol (Amount obtained: 343 mg/Yield: 71%).

¹H NMR (400, CDCl₃): 7.32 (2H, m), 6.84 (2H, m), 6.04 (1H, m), 4.68 (1H, m), 4.16 (2H, s), 3.99 (1H, m), 3.81 (4H, m), 3.09 (1H, m), 2.78 (3H, m), 2.60 (4H, m), 2.29 (1H, m), 1.97-1.47 (20H, m), 2.31 (4H, m)

Example 201

Preparation of tert-butyl 4-((4-(4-(4-(2-hydroxyethyl)piperazine-1-carbonyl)cyclohex-1-enyl)phenoxy)methyl)piperidine-1-carboxylate

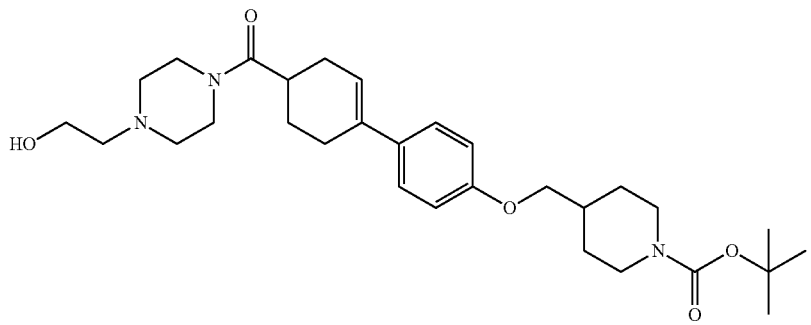 [SMILES: CC(C)(C)OC(=O)N1CCC(COc2ccc(C3=CCC(C(=O)N4CCN(CCO)CC4)CC3)cc2)CC1]

The title compound was prepared in the same manner as in <Example 190>, except that 1-hydroxyethylpiperazine was used instead of the 2-aminoethanol (Amount obtained: 331 mg/Yield: 68%).

$^1$H NMR (400, CDCl$_3$): 7.32 (2H, m), 6.85 (2H, m), 6.04 (1H, m), 4.16 (2H, s), 3.81-3.59 (8H, m), 2.78-2.49 (14H, m), 1.98-1.84 (5H, m), 1.47 (9H, s), 1.28 (2H, m)

Example 202

Preparation of tert-butyl 4-((4-(4-(pyrrolidine-1-carbonyl)cyclohex-1-enyl)phenoxy)methyl)piperidine-1-carboxylate

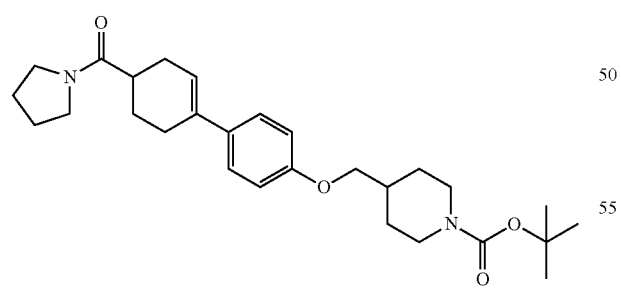

The title compound was prepared in the same manner as in <Example 190>, except that pyrrolidine was used instead of the 2-aminoethanol (Amount obtained: 357 mg/Yield: 74%).

$^1$H NMR (400, CDCl$_3$): 7.32 (2H, m), 6.85 (2H, m), 6.06 (1H, m), 4.16 (2H, s), 3.81 (2H, m), 3.54 (4H, m), 2.75-2.28 (7H, m), 2.00-1.81 (8H, m), 1.48 (9H, s), 1.31 (2H, m)

Example 203

Preparation of tert-butyl 4-((4-(4-(4-ethylpiperazine-1-carbonyl)cyclohex-1-enyl)phenoxy)methyl)piperidine-1-carboxylate

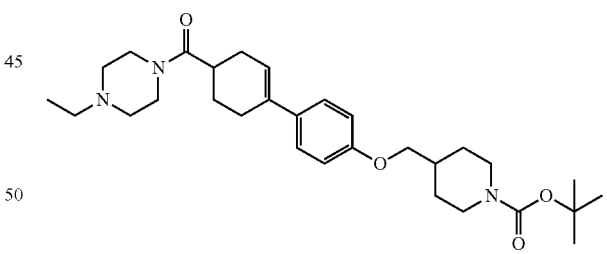

The title compound was prepared in the same manner as in <Example 190>, except that 1-ethylpiperazine was used instead of the 2-aminoethanol (Amount obtained: 330 mg/Yield: 59%).

$^1$H NMR (400, CDCl$_3$): 7.32 (2H, m), 6.85 (2H, m), 6.04 (1H, m), 4.16 (2H, s), 3.81-3.59 (6H, m), 2.78 (3H, m), 2.52-2.26 (10H, m), 1.98-1.81 (6H, m), 1.47 (9H, s), 1.31 (2H, m), 1.141 (3H, m)

Example 204

Preparation of tert-butyl 4-((4-(4-(piperidine-1-carbonyl)cyclohex-1-enyl)phenoxy)methyl)piperidine-1-carboxylate

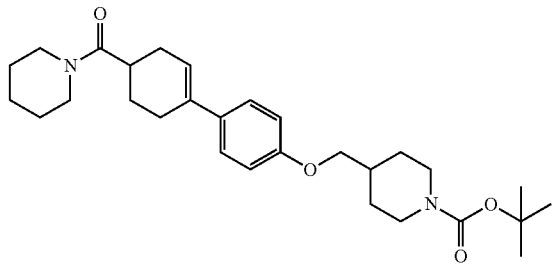 [SMILES: CC(C)(C)OC(=O)N1CCC(COc2ccc(C3=CCC(C(=O)N4CCCCC4)CC3)cc2)CC1]

The title compound was prepared in the same manner as in <Example 190>, except that piperidine was used instead of the 2-aminoethanol (Amount obtained: 345 mg/Yield: 67%).

$^1$H NMR (400, CDCl$_3$): 7.32 (2H, m), 6.85 (2H, m), 6.05 (1H, m), 4.15 (2H, s), 3.81 (2H, m), 3.62-3.49 (4H, m), 2.79 (3H, m), 2.52 (3H, m), 2.31 (1H, m), 1.98-1.58 (11H, m), 1.47 (9H, m), 1.28 (2H, m)

Example 205

Preparation of tert-butyl 4-((4-(4-(3-ethoxypropylcarbamoyl)cyclohex-1-enyl)phenoxy)methyl)piperidine-1-carboxylate

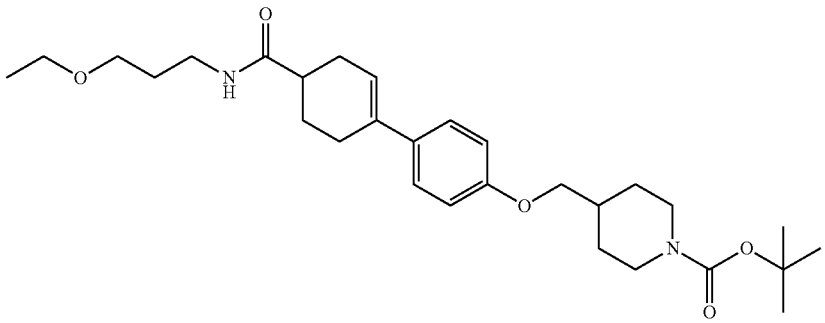 [SMILES: CCOCCCNC(=O)C1CC=C(c2ccc(OCC3CCN(C(=O)OC(C)(C)C)CC3)cc2)CC1]

The title compound was prepared in the same manner as in <Example 190>, except that 3-ethoxypropane-1-amine was used instead of the 2-aminoethanol (Amount obtained: 339 mg/Yield: 64%).

$^1$H NMR (400, CDCl$_3$): 7.33 (2H, m), 6.86 (2H, m), 6.36 (1H, m), 6.04 (1H, m), 4.17 (2H, s), 3.81 (2H, d), 3.57-3.40 (6H, m), 2.78 (2H, m), 2.52-2.36 (5H, m), 2.13 (1H, m), 1.97 (1H, m), 1.85-1.77 (5H, m), 1.47 (9H, s), 1.31-1.21 (5H, m)

Example 206

Preparation of tert-butyl 4-((4-(4-(bis(2-hydroxyethyl)carbamoyl)cyclohex-1-enyl)phenoxy)methyl)piperidine-1-carboxylate

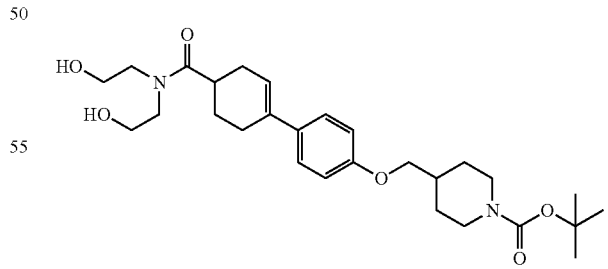

The title compound was prepared in the same manner as in <Example 190>, except that diethanolamine was used instead of the 2-aminoethanol (Amount obtained: 351 mg/Yield: 70%).

$^1$H NMR (400, CDCl$_3$): 7.32 (2H, m), 6.86 (2H, m), 6.05 (1H, m), 4.16 (2H, m), 3.91 (2H, m), 3.84 (4H, m), 3.63 (4H, m), 3.31 (2H, s), 2.90-2.30 (7H, m), 2.04-1.82 (5H, m), 1.48 (9H, s), 1.32 (2H, m)

Example 207

Preparation of 1-(4-(4-((1-(3-isopropyl-1,2,4-oxadiazol-5-yl)piperidin-4-yl)methoxy)phenyl)cyclohex-3-enecarbonyl)piperidine-4-carboxamide

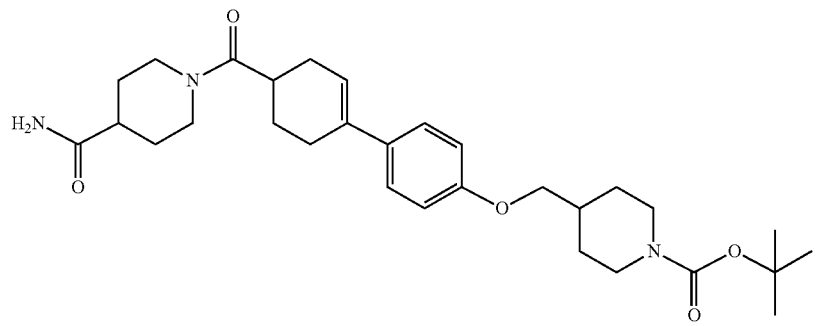 [SMILES: CC(C)(C)OC(=O)N1CCC(COc2ccc(C3=CCC(C(=O)N4CCC(C(N)=O)CC4)CC3)cc2)CC1]

The title compound was prepared in the same manner as in <Example 143>, except that isonipecotamide was used instead of the (R)-N,N-dimethylpyrrolidine-3-amine hydrochloride (Amount obtained: 142 mg/Yield: 53%).

$^1$H NMR (400, CDCl$_3$): 7.32 (2H, m), 6.86 (2H, m), 6.05 (1H, m), 5.68 (2H, m), 4.67 (1H, m), 4.16-3.98 (3H, m), 3.81 (2H, m), 3.17 (1H, m), 2.89-2.40 (8H, m), 1.99-1.63 (10H, m), 1.47 (9H, m), 1.29 (2H, m)

Example 208

Preparation of (4-(4-((1-(3-isopropyl-1,2,4-oxadiazol-5-yl)piperidin-4-yl)methoxy)phenyl)cyclohex-3-enyl)(4-(pyrrolidin-1-yl)piperidin-1-yl)methanone

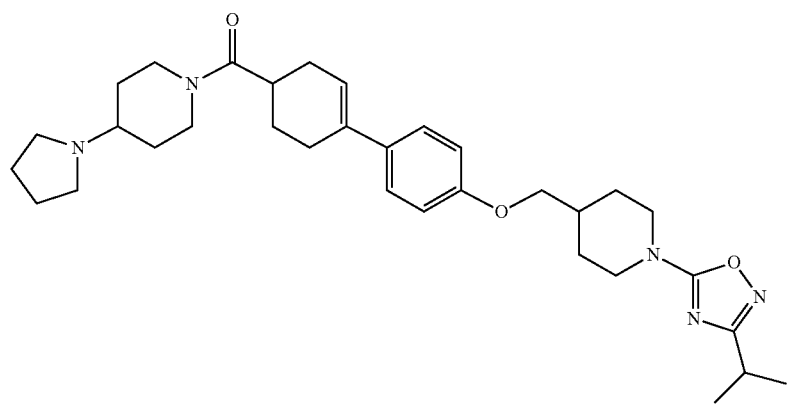 [SMILES: CC(C)c1noc(N2CCC(COc3ccc(C4=CCC(C(=O)N5CCC(N6CCCC6)CC5)CC4)cc3)CC2)n1]

The title compound was prepared in the same manner as in <Example 143>, except that 4-(pyrrolidin-1-yl)piperidine was used instead of the (R)-N,N-dimethylpyrrolidine-3-amine hydrochloride (Amount obtained: 159 mg/Yield: 51%).

$^1$H NMR (400, CDCl$_3$): 7.54 (2H, m), 6.86 (2H, m), 6.05 (1H, m) 4.67 (1H, m), 4.23 (2H, m), 4.05 (2H, m), 3.85 (2H, m), 3.14 (3H, m), 2.94-2.46 (12H, m), 2.30 (1H, m), 2.10-1.94 (12H, m), 1.62-1.51 (4H, m), 1.31 (6H, d)

Example 209

Preparation of (4-(4-((1-(3-isopropyl-1,2,4-oxadiazol-5-yl)piperidin-4-yl)methoxy)phenyl)cyclohex-3-enyl)(4-morpholinopiperidin-1-yl)methanone

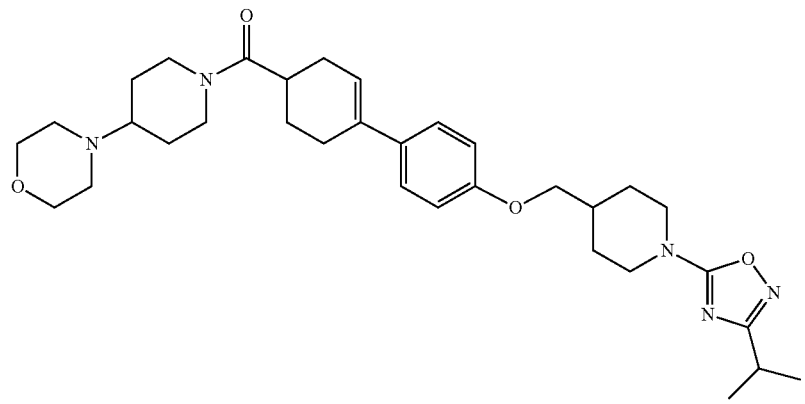 [SMILES: CC(C)c1noc(N2CCC(COc3ccc(C4=CCC(C(=O)N5CCC(N6CCOCC6)CC5)CC4)cc3)CC2)n1]

The title compound was prepared in the same manner as in <Example 143>, except that 4-morpholinopiperidine was used instead of the (R)-N,N-dimethylpyrrolidine-3-amine hydrochloride (Amount obtained: 155 mg/Yield: 58%).

¹H NMR (400, CDCl₃): 7.33 (2H, m), 6.86 (2H, m), 6.05 (1H, m), 4.75 (1H, m), 4.23 (2H, m), 4.02 (1H, m), 3.85 (2H, d), 3.52 (4H, m), 3.14 (3H, m), 2.97 (1H, s), 2.94-2.80 (3H, m), 2.59-2.47 (9H, m), 2.30 (1H, m), 2.07-1.91 (7H, m), 1.50 (4H, m), 1.29 (6H, d)

Example 210

Preparation of N-cyclopentyl-4-(4-((1-(3-isopropyl-1,2,4-oxadiazol-5-yl)piperidin-4-yl)methoxy)phenyl)cyclohex-3-enecarboxamide

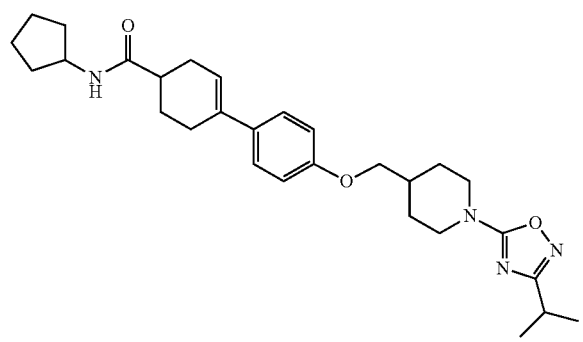 [SMILES: CC(C)c1noc(N2CCC(COc3ccc(C4=CCC(C(=O)NC5CCCC5)CC4)cc3)CC2)n1]

The title compound was prepared in the same manner as in <Example 143>, except that cyclopentylamine was used instead of the (R)-N,N-dimethylpyrrolidine-3-amine hydrochloride (Amount obtained: 171 mg/Yield: 65%).

¹H NMR (400, CDCl₃): 7.33 (2H, m), 6.86 (2H, m), 6.04 (1H, m), 5.51 (1H, m), 4.26-4.20 (3H, m), 3.85 (2H, d), 3.14 (2H, m), 2.92 (1H, m), 2.46-2.37 (5H, m), 2.06-1.94 (7H, m), 1.68-1.61 (5H, m), 1.47-1.36 (4H, m), 1.32 (6H, d)

Example 211

Preparation of N-cyclobutyl-4-(4-((1-(3-isopropyl-1,2,4-oxadiazol-5-yl)piperidin-4-yl)methoxy)phenyl)cyclohex-3-enecarboxamide The title compound was prepared in the same manner as in <Example 143>, except that cyclobutylamine hydrochloride was used instead of the (R)-N,N-dimethylpyrrolidine-3-amine hydrochloride (Amount obtained: 170 mg/Yield: 63%).

¹H NMR (400, CDCl₃): 7.33 (2H, m), 6.68 (2H, m), 6.04 (1H, m), 5.71 (1H, m), 4.45 (1H, m), 4.23 (2H, m), 3.85 (2H, m), 3.13 (2H, m), 2.92 (1H, m), 2.42-2.34 (7H, m), 2.07-1.72 (9H, m), 1.47 (2H, m), 1.31 (6H, d)

Example 212

Preparation of (3,4-dihydroisoquinolin-2(1H)-yl)(4-(4-((1-(3-isopropyl-1,2,4-oxadiazol-5-yl)piperidin-4-yl)methoxy)phenyl)cyclohex-3-enyl)methanone

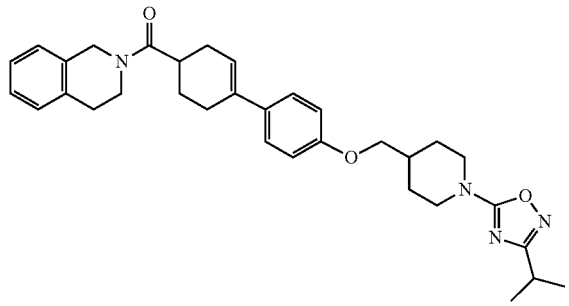 [SMILES: CC(C)c1noc(N2CCC(COc3ccc(C4=CCC(C(=O)N5CCc6ccccc6C5)CC4)cc3)CC2)n1]

The title compound was prepared in the same manner as in <Example 143>, except that 1,2,3,4-tetrahydroisoquinoline was used instead of the (R)-N,N-dimethylpyrrolidine-3-amine hydrochloride (Amount obtained: 183 mg/Yield: 65%).

$^1$H NMR (400, CDCl3): 7.32 (2H, m), 7.23-7.12 (4H, m), 6.87 (2H, m), 6.08 (1H, m), 4.80-4.74 (2H, m), 4.23 (2H, m), 3.91-3.78 (4H, m), 3.15 (2H, m), 3.08-2.87 (4H, m), 2.60 (3H, m), 2.36 (1H, m), 2.08-1.91 (5H, m), 1.60 (2H, m), 1.31 (6H, d)

Example 213

Preparation of (4-(4-((1-(3-isopropyl-1,2,4-oxadiazol-5-yl)piperidin-4-yl)methoxy)phenyl)cyclohex-3-enyl)(1-methyl-3,4-dihydroisoquinolin-2(1H)-yl)methanone

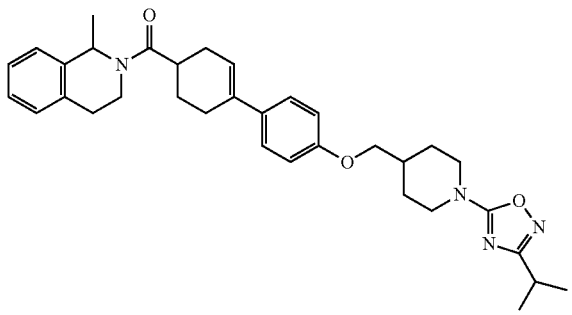 [SMILES: CC(C)c1noc(N2CCC(COc3ccc(C4=CCC(C(=O)N5CCc6ccccc6C5C)CC4)cc3)CC2)n1]

The title compound was prepared in the same manner as in <Example 143>, except that 1-methyl-1,2,3,4-tetrahydroisoquinoline was used instead of the (R)-N,N-dimethylpyrrolidine-3-amine hydrochloride (Amount obtained: 174 mg/Yield: 60%).

$^1$H NMR (400, CDCl$_3$): 7.35 (2H, m), 7.24-7.12 (4H, m), 6.89 (2H, m), 6.12 (1H, m), 5.74-5.16 (1H, m), 4.79-3.56 (6H, m), 3.15-1.90 (15H, m), 1.62 (2H, m), 1.51-1.40 (4H, m), 1.31 (6H, d)

Example 214

Preparation of isoindolin-2-yl(4-(4-((1-(3-isopropyl-1,2,4-oxadiazol-5-yl)piperidin-4-yl)methoxy)phenyl)cyclohex-3-enyl)methanone

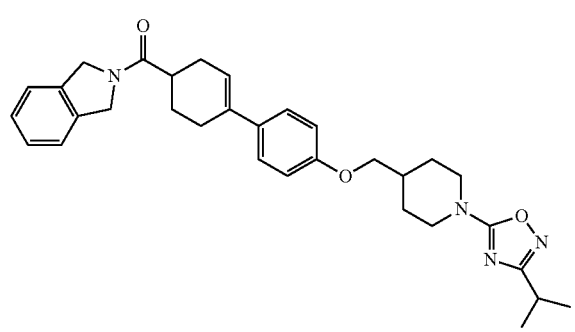 [SMILES: CC(C)c1noc(N2CCC(COc3ccc(C4=CCC(C(=O)N5Cc6ccccc6C5)CC4)cc3)CC2)n1]

The title compound was prepared in the same manner as in <Example 143>, except that isoindoline was used instead of the (R)-N,N-dimethylpyrrolidine-3-amine hydrochloride (Amount obtained: 170 mg/Yield: 69%).

$^1$H NMR (400, CDCl$_3$): 7.33-7.28 (7H, m), 6.88 (2H, m), 6.10 (1H, m), 4.95 (4H, d), 4.24 (2H, m), 3.92 (2H, m), 3.15 (2H, m), 2.94 (1H, m), 2.79 (1H, m), 2.64-2.37 (4H, m), 2.12-1.93 (5H, m), 1.51 (2H, m), 1.31 (6H, d)

Example 215

Preparation of 1,4'-bipiperidin-1'-yl(4-(4-((1-(3-isopropyl-1,2,4-oxadiazol-5-yl)piperidin-4-yl)methoxy)phenyl)cyclohex-3-enyl)methanone

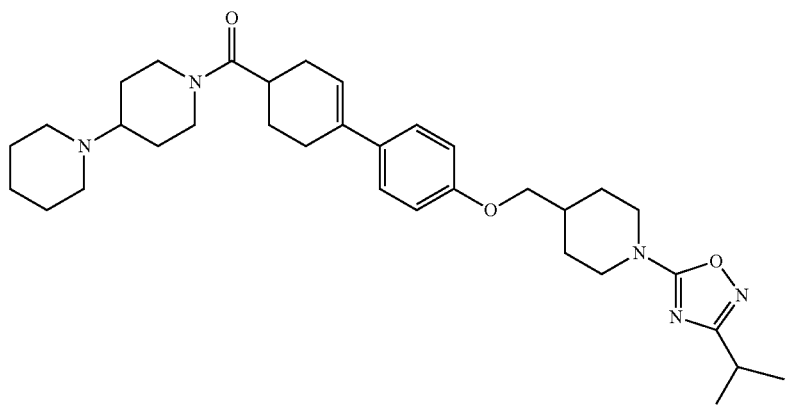 [SMILES: CC(C)c1noc(N2CCC(COc3ccc(C4=CCC(C(=O)N5CCC(N6CCCCC6)CC5)CC4)cc3)CC2)n1]

The title compound was prepared in the same manner as in <Example 143>, except that 1,4'-bipiperidine was used instead of the (R)-N,N-dimethylpyrrolidine-3-amine hydrochloride (Amount obtained: 165 mg/Yield: 71%).

$^1$H NMR (400, CDCl$_3$): 7.33 (2H, m), 6.87 (2H, m), 6.05 (1H, m), 4.78 (1H, m), 4.23 (2H, m), 4.07 (1H, m), 3.85 (2H, m), 3.14 (3H, m), 2.94 (1H, m), 2.79 (1H, m), 2.56-2.25 (9H, m), 2.07-1.40 (18H, m), 1.31 (6H, d)

Example 216

Preparation of tert-butyl 4-((4-(4-(1,4'-bipiperidine-1'-carbonyl)cyclohex-1-enyl)phenoxy)methyl)piperidine-1-carboxylate

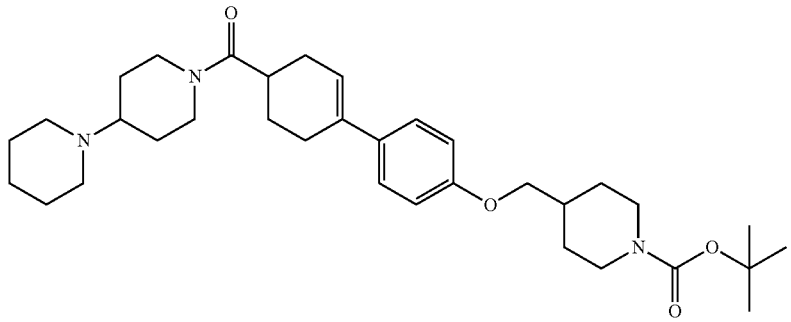 [SMILES: CC(C)(C)OC(=O)N1CCC(COc2ccc(C3=CCC(C(=O)N4CCC(N5CCCCC5)CC4)CC3)cc2)CC1]

The title compound was prepared in the same manner as in <Example 190>, except that 1,4'-bipiperidine was used instead of the 2-aminoethanol (Amount obtained: 169 mg/Yield: 75%).

$^1$H NMR (400, CDCl$_3$): 7.33 (2H, m), 6.86 (2H, m), 6.05 (1H, m), 4.76 (1H, m), 4.16-4.05 (3H, m), 3.81 (2H, m), 3.08 (1H, m), 2.83 (3H, m), 2.57-2.51 (9H, m), 2.30 (1H, m), 2.00-1.82 (7H, m), 1.63 (4H, m), 1.45 (13H, m), 1.31 (2H, m)

Example 217

Preparation of (4-(4-((1-(5-ethylpyrimidin-2-yl)piperidin-4-yl)methoxy)phenyl)cyclohex-3-enyl)(3-(hydroxyimino)pyrrolidin-1-yl)methanone

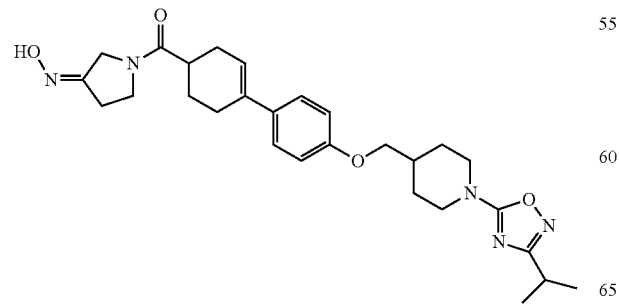

600 mg of 1-(4-(4-((1-(3-isopropyl-1,2,4-oxadiazol-5-yl)piperidin-4-yl)methoxy)phenyl)cyclohex-3-enecarbonyl)piperidine-4-carboxamide was dissolved in a THF/water mixture (30 ml/10 ml) in a 100 ml flask, and stirred under nitrogen. 200 mg of sodium bicarbonate was added dropwise thereto, 170 mg of hydroxylamine hydrochloride was in turn added dropwise, and the resulting mixture was stirred at room temperature for 3 hours. After the reaction was terminated, the reaction mixture was distilled under reduced pressure to remove the solvent. Then, 50 ml of distilled water was slowly added thereto at 0° C., and the resulting solids were filtered to obtain a mixture including E and Z forms at a ratio of 3:1 (Amount obtained: 485 mg/Yield: 68%).

Example 218

Preparation of (4-(4-((1-(5-ethylpyrimidin-2-yl)piperidin-4-yl)methoxy)phenyl)cyclohex-3-enyl)(4-(pyrrolidin-1-yl)piperidin-1-yl)methanone

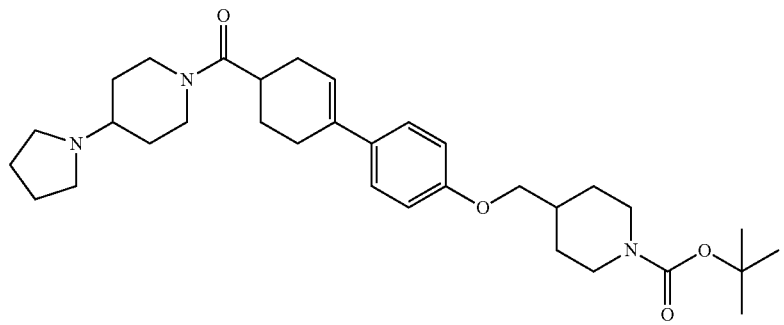 [SMILES: CC(C)(C)OC(=O)N1CCC(COc2ccc(C3=CCC(C(=O)N4CCC(N5CCCC5)CC4)CC3)cc2)CC1]

The title compound was prepared in the same manner as in <Example 152>, except that 4-(pyrrolidin-1-yl)piperidine was used instead of the L-β-prolinol (Amount obtained: 171 mg/Yield: 69%).
$^1$H NMR (400, CDCl$_3$): 8.23 (2H, s), 7.32 (2H, m), 6.87 (2H, m), 6.05 (1H, m), 4.79 (2H, m), 4.59 (1H, m), 4.02 (1H, m), 3.84 (2H, d), 3.16 (1H, m), 2.95 (2H, m), 2.82-2.94 (11H, m), 2.29 (2H, m), 2.12-1.82 (11H, m), 1.51 (2H, m), 1.40 (2H, m), 1.31 (3H, m)

Example 219

Preparation of 1,4'-bipiperidin-1'-yl(4-(4-((1-(5-ethylpyrimidin-2-yl)piperidin-4-yl)methoxy)phenyl)cyclohex-3-enyl)methanone

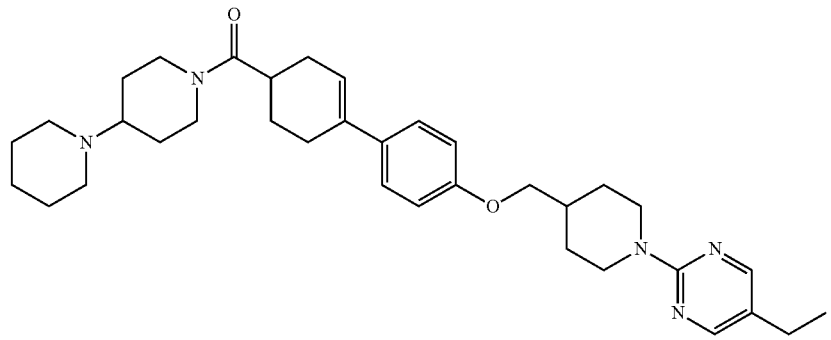 [SMILES: CCc1cnc(N2CCC(COc3ccc(C4=CCC(C(=O)N5CCC(N6CCCCC6)CC5)CC4)cc3)CC2)nc1]

The title compound was prepared in the same manner as in <Example 152>, except that 1,4'-bipiperidine was used instead of the L-β-prolinol (Amount obtained: 180 mg/Yield: 77%).
$^1$H NMR (400, CDCl$_3$): 8.18 (2H, s), 7.33 (2H, m), 6.87 (2H, m), 6.05 (1H, m), 4.79 (3H, m), 4.05 (1H, m), 3.84 (2H, d), 3.08 (1H, m), 2.95 (2H, m), 2.83 (1H, m), 2.58-2.44 (11H, m), 2.30 (1H, m), 2.12-1.87 (7H, m), 1.61 (4H, m), 1.52-1.30 (6H, m), 1.22 (3H, m)

Example 220

Preparation of (4-(4-((1-(5-ethylpyrimidin-2-yl)piperidin-4-yl)methoxy)phenyl)cyclohex-3-enyl)(4-morpholinopiperidin-1-yl)methanone

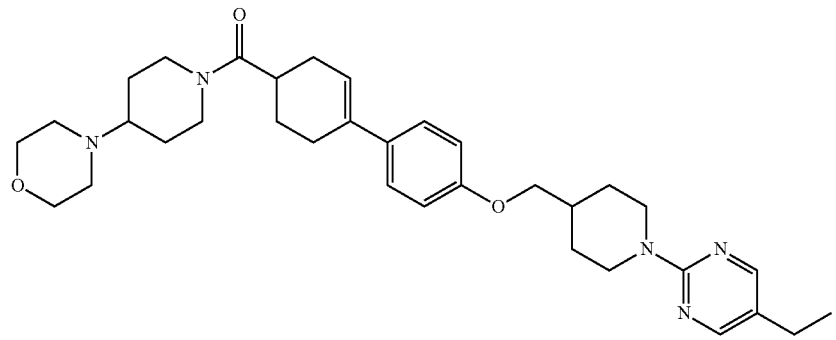 [SMILES: CCc1cnc(N2CCC(COc3ccc(C4=CCC(C(=O)N5CCC(N6CCOCC6)CC5)CC4)cc3)CC2)nc1]

The title compound was prepared in the same manner as in <Example 152>, except that 4-morpholinopiperidine was used instead of the L-β-prolinol (Amount obtained: 162 mg/Yield: 58%).

¹H NMR (400, CDCl₃): 8.18 (2H, s), 7.33 (2H, m), 6.87 (2H, m), 6.05 (1H, m), 4.80-4.69 (3H, m), 4.05 (1H, m), 3.84 (2H, d), 3.76 (4H, m), 3.12 (1H, m), 2.95 (2H, m), 2.82 (1H, m), 2.65-2.44 (11H, m), 2.30 (1H, m), 2.13 (1H, m), 1.96-1.93 (7H, m), 1.48-1.30 (4H, m), 1.22 (3H, m)

Example 221

Preparation of tert-butyl 4-((4-(4-(furan-2-ylmethylcarbamoyl)cyclohex-1-enyl)phenoxy)methyl)piperidine-1-carboxylate

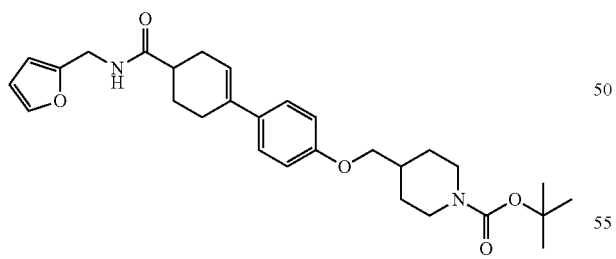

The title compound was prepared in the same manner as in <Example 190>, except that furfurylamine was used instead of the 2-aminoethanol (Amount obtained: 169 mg/Yield: 70%).

¹H NMR (400, CDCl₃): 7.36 (1H, m), 7.31 (2H, m), 6.85 (2H, m), 6.34 (1H, m), 6.24 (1H, m), 6.03 (1H, m), 5.97 (1H, m), 4.49 (2H, m), 4.16 (2H, s), 3.81 (2H, m), 2.97 (1H, m), 2.78 (2H, m), 2.55-2.39 (5H, m), 2.12 (1H, m), 1.99-1.81 (4H, m), 1.47 (9H, s), 2.31 (2H, m)

Example 222

Preparation of tert-butyl 4-((4-(4-(methoxycarbamoyl)cyclohex-1-enyl)phenoxy)methyl)piperidine-1-carboxylate

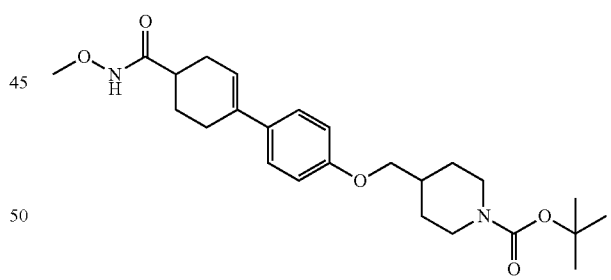

The title compound was prepared in the same manner as in <Example 190>, except that O-methylhydroxylamine hydrochloride was used instead of the 2-aminoethanol (Amount obtained: 166 mg/Yield: 72%).

¹H NMR (400, CDCl₃): 8.24 (1H, m), 7.33 (2H, m), 6.86 (2H, m), 6.03 (1H, m), 4.17 (2H, m), 3.85-3.80 (5H, m), 2.79 (2H, m), 2.57-2.35 (5H, m), 2.09 (1H, m), 2.01-1.82 (4H, m), 1.59 (1H, m), 1.47 (9H, s), 1.32 (2H, m)

Example 223

Preparation of tert-butyl 4-((4-(4-(methoxy(methyl)carbamoyl)cyclohex-1-enyl)phenoxy)methyl)piperidine-1-carboxylate

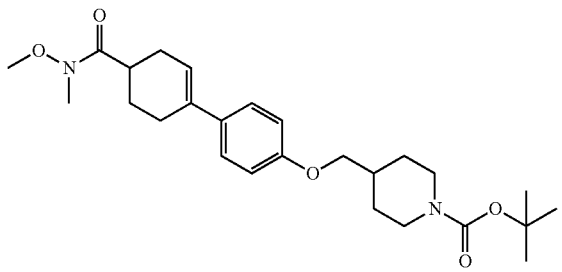 [SMILES: CON(C)C(=O)C1CC=C(c2ccc(OCC3CCN(C(=O)OC(C)(C)C)CC3)cc2)CC1]

The title compound was prepared in the same manner as in <Example 190>, except that N,O-dimethylhydroxylamine hydrochloride was used instead of the 2-aminoethanol (Amount obtained: 171 mg/Yield: 74%).

$^1$H NMR (400, CDCl$_3$): 7.34 (2H, m), 6.86 (2H, m), 6.07 (1H, m), 4.16 (2H, s), 3.82 (2H, m), 3.74 (3H, s), 3.24 (3H, s), 2.99-2.73 (4H, m), 2.52-2.33 (4H, m), 2.07-1.82 (5H, m), 1.47 (9H, s), 2.33 (2H, m)

Example 224

Preparation of tert-butyl 4-((4-(4-(2,5-dihydro-1H-pyrrole-1-carbonyl)cyclohex-1-enyl)phenoxy)methyl)piperidine-1-carboxylate

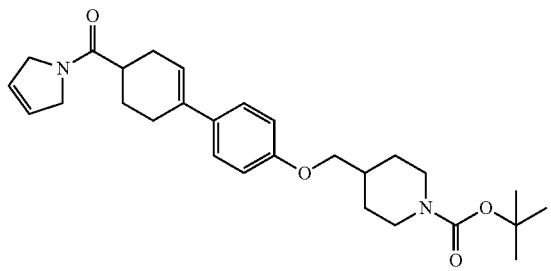 [SMILES: CC(C)(C)OC(=O)N1CCC(COc2ccc(C3=CCC(C(=O)N4CC=CC4)CC3)cc2)CC1]

The title compound was prepared in the same manner as in <Example 190>, except that 2,5-dihydro-1H-pyrrole was used instead of the 2-aminoethanol (Amount obtained: 167 mg/Yield: 63%).

$^1$H NMR (400, CDCl$_3$): 7.34 (2H, m), 6.87 (2H, m), 6.08 (1H, m), 5.93 (1H, m), 5.85 (1H, m), 4.37 (2H, m), 4.60 (2H, m), 4.17 (2H, s), 3.82 (2H, d), 3.53 (1H, m), 2.79 (2H, m), 2.66-2.47 (4H, m), 2.36 (1H, m), 2.05-1.82 (6H, m), 1.47 (9H, s), 1.32 (2H, m)

Example 225

Preparation of tert-butyl 4-((4-(4-(4-hydroxypiperidine-1-carbonyl)cyclohex-1-enyl)phenoxy)methyl)piperidine-1-carboxylate

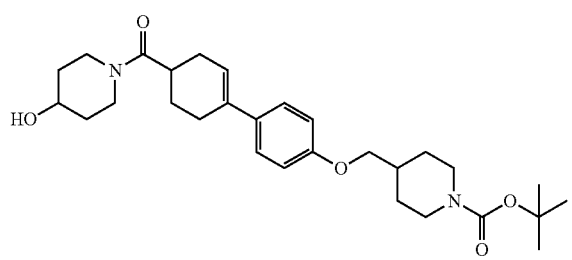

The title compound was prepared in the same manner as in <Example 190>, except that 4-hydroxypiperidine was used instead of the 2-aminoethanol (Amount obtained: 174 mg/Yield: 70%).

$^1$H NMR (400, CDCl$_3$): 7.33 (2H, m), 6.86 (2H, m), 6.05 (1H, m), 4.16 (3H, m), 3.97 (1H, m), 3.87-3.80 (3H, m), 3.32-3.20 (2H, m), 2.97-2.72 (4H, m), 2.54-2.47 (3H, m), 2.31 (1H, m), 2.01-2.56 (8H, m), 1.56-1.51 (2H, m), 1.47 (9H, s), 1.32 (2H, m)

Example 226

Preparation of tert-butyl 4-((4-(4-(4-(hydroxymethyl)piperidine-1-carbonyl)cyclohex-1-enyl)phenoxy)methyl)piperidine-1-carboxylate

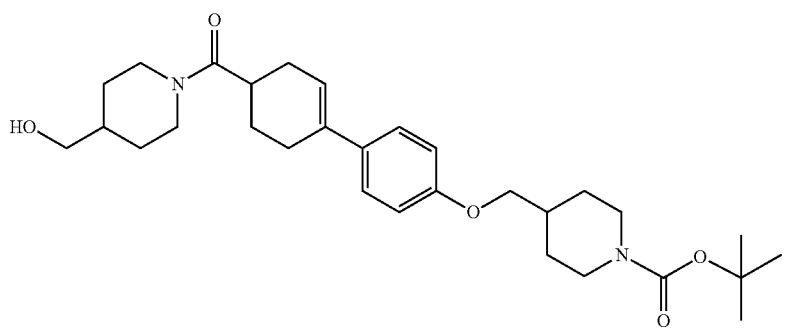 [SMILES: CC(C)(C)OC(=O)N1CCC(COc2ccc(C3=CCC(C(=O)N4CCC(CO)CC4)CC3)cc2)CC1]

The title compound was prepared in the same manner as in <Example 190>, except that piperidinemethanol was used instead of the 2-aminoethanol (Amount obtained: 167 mg/Yield: 65%).

$^1$H NMR (400, CDCl$_3$): 7.33 (2H, m), 6.86 (2H, m), 6.05 (1H, m), 4.73 (1H, m), 4.16 (2H, s), 4.04 (1H, m), 3.81 (2H, d), 3.54 (2H, m), 3.07 (1H, m), 2.80 (3H, m), 2.59-2.46 (4H, m), 2.30 (1H, m), 2.00-1.70 (10H, m), 1.47 (9H, m), 1.31 (4H, m)

Example 227

Preparation of 1-(4-(4-((1-(5-ethylpyrimidin-2-yl)piperidin-4-yl)methoxy)phenyl)cyclohex-3-enecarbonyl)piperidine-4-carbonitrile

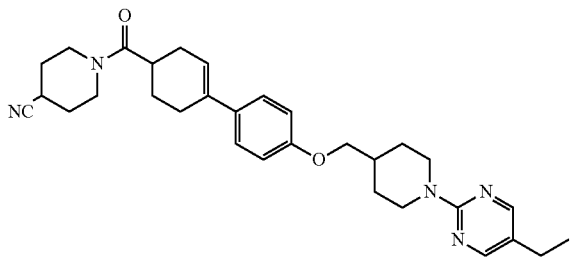

The title compound was prepared in the same manner as in <Example 152>, except that piperidine-4-carbonitrile was used instead of the L-β-prolinol (Amount obtained: 165 mg/Yield: 62%).

$^1$H NMR (400, CDCl$_3$): 8.19 (2H, s), 7.32 (2H, m), 6.87 (2H, m), 6.04 (1H, m), 4.80 (2H, m), 3.85-3.55 (6H, m), 2.95 (3H, m), 2.82 (1H, m), 2.58-2.44 (5H, m), 2.28 (1H, m), 2.11-1.89 (9H, m), 1.41 (2H, m), 1.22 (3H, m)

Example 228

Preparation of (4-(4-((1-(5-ethylpyrimidin-2-yl)piperidin-4-yl)methoxy)phenyl)cyclohex-3-enyl)(spiro[indene-1,4'-piperidin]-1'-yl)methanone

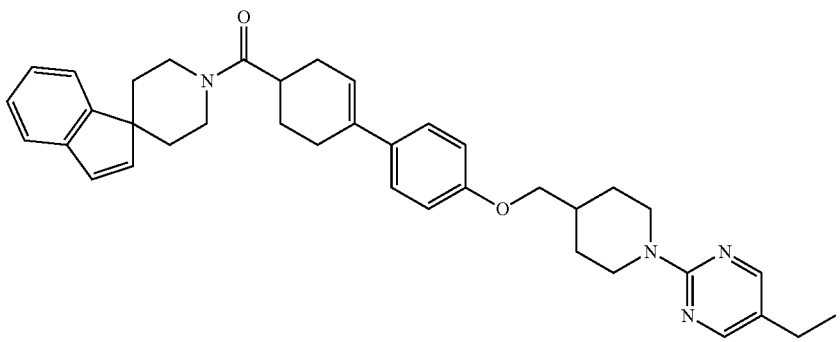 [SMILES: CCc1cnc(N2CCC(COc3ccc(C4=CCC(C(=O)N5CCC6(C=Cc7ccccc76)CC5)CC4)cc3)CC2)nc1]

The title compound was prepared in the same manner as in <Example 152>, except that 4-spiroindene-piperidine hydrochloride was used instead of the L-β-prolinol (Amount obtained: 183 mg/Yield: 74%).

$^1$H NMR (400, CDCl$_3$): 8.19 (2H, s), 7.37-7.22 (7H, m), 6.91-6.83 (4H, m), 6.08 (1H, m), 4.80 (3H, m), 4.13 (1H, m), 3.85 (2H, d), 3.50 (1H, m), 3.19-2.87 (4H, m), 2.62-2.37 (6H, m), 2.10-1.93 (7H, m), 1.48-1.31 (4H, m), 1.23 (3H, m)

Example 229

Preparation of (4-(4-((1-(5-ethylpyrimidin-2-yl)piperidin-4-yl)methoxy)phenyl)cyclohex-3-enyl)(1,4-dioxa-8-azaspiro[4.5]decan-8-yl)methanone

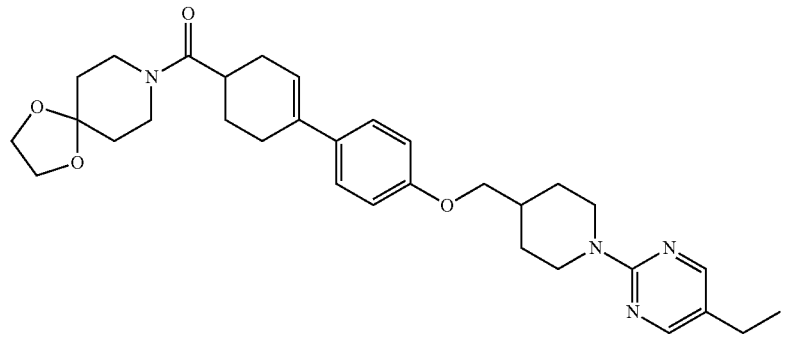 [SMILES: CCc1cnc(N2CCC(COc3ccc(C4=CCC(C(=O)N5CCC6(CC5)OCCO6)CC4)cc3)CC2)nc1]

The title compound was prepared in the same manner as in <Example 152>, except that 1,4-dioxa-8-azaspiro[4.5]decane was used instead of the L-β-prolinol (Amount obtained: 175 mg/Yield: 69%).

¹H NMR (400, CDCl₃): 8.19 (2H, s), 7.32 (2H, m), 6.87 (2H, m), 6.05 (1H, m), 4.80 (2H, m), 4.01 (4H, s), 3.84-3.63 (6H, m), 2.95-2.82 (3H, m), 2.58-2.46 (5H, m), 2.31 (1H, m), 2.11-1.88 (5H, m), 1.75-1.70 (5H, m), 1.40 (2H, m), 1.22 (3H, m)

Example 230

Preparation of N-cyclopentyl-4-(4-((1-(5-ethylpyrimidin-2-yl)piperidin-4-yl)methoxy)phenyl)cyclohex-3-enecarboxamide

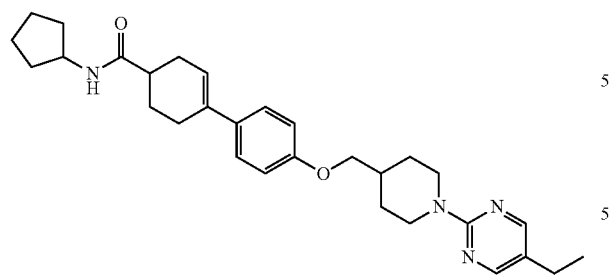

The title compound was prepared in the same manner as in <Example 152>, except that pentylamine was used instead of the L-β-prolinol (Amount obtained: 153 mg/Yield: 58%).

¹H NMR (400, CDCl₃): 8.23 (2H, s), 7.33 (2H, m), 6.87 (2H, m), 6.03 (1H, m), 5.55 (2H, m), 4.79 (2H, d), 4.26 (1H, m), 3.84 (2H, d), 2.95 (2H, m), 2.50-2.36 (7H, m), 2.09-1.92 (7H, m), 1.68-1.61 (4H, m), 1.40-1.33 (4H, m), 2.12 (3H, m)

Example 231

Preparation of N-cyclobutyl-4-(4-((1-(5-ethylpyrimidin-2-yl)piperidin-4-yl)methoxy)phenyl)cyclohex-3-enecarboxamide

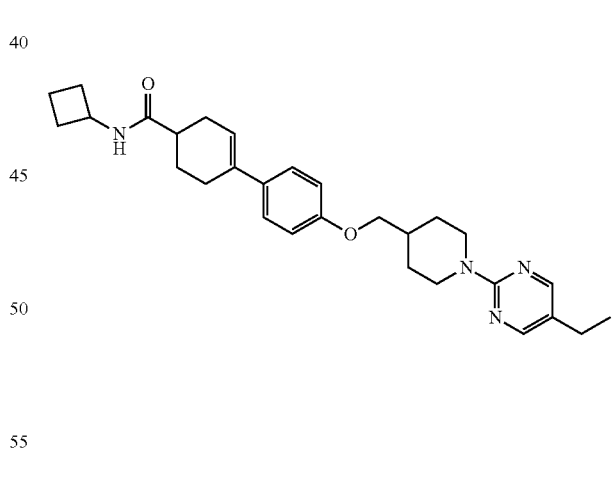

The title compound was prepared in the same manner as in <Example 152>, except that cyclobutylamine hydrochloride was used instead of the L-β-prolinol (Amount obtained: 165 mg/Yield: 68%).

¹H NMR (400, CDCl₃): 8.18 (2H, m), 7.31 (2H, m), 6.86 (2H, m), 6.04 (1H, m), 5.74 (1H, m), 4.79 (2H, d), 4.47 (1H, m), 3.84 (2H, d), 2.95 (2H, m), 2.51-2.35 (9H, m), 2.09-2.06 (2H, m), 1.96-1.80 (5H, m), 1.75-1.69 (2H, m), 1.39 (2H, m), 1.22 (3H, m)

Example 232

Preparation of (3,4-dihydroisoquinolin-2(1H)-yl)(4-(4-((1-(5-ethylpyrimidin-2-yl)piperidin-4-yl)methoxy)phenyl)cyclohex-3-enyl)methanone

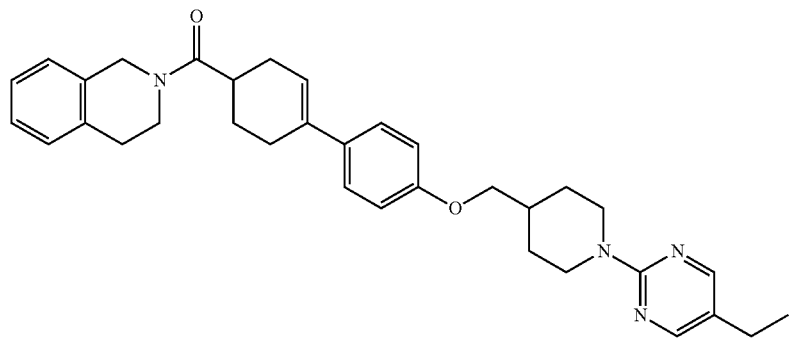 [SMILES: CCc1cnc(N2CCC(COc3ccc(C4=CCC(C(=O)N5CCc6ccccc6C5)CC4)cc3)CC2)nc1]

The title compound was prepared in the same manner as in <Example 152>, except that 1,2,3,4-tetrahydroisoquinoline was used instead of the L-β-prolinol (Amount obtained: 173 mg/Yield: 69%).

$^1$H NMR (400, CDCl$_3$): 8.19 (2H, m), 7.34 (2H, m), 7.24-7.12 (4H, m), 6.87 (2H, m), 6.07 (1H, m), 4.74-4.73 (4H, m), 3.91-3.78 (4H, m), 2.97-2.89 (5H, m), 2.60-2.44 (5H, m), 2.36 (1H, m), 2.13-1.93 (5H, m), 1.41 (2H, m), 1.24 (3H, m)

Example 233

Preparation of tert-butyl 4-((4-(4-(5-hydroxypentylcarbamoyl)cyclohex-1-enyl)phenoxy)methyl)piperidine-1-carboxylate

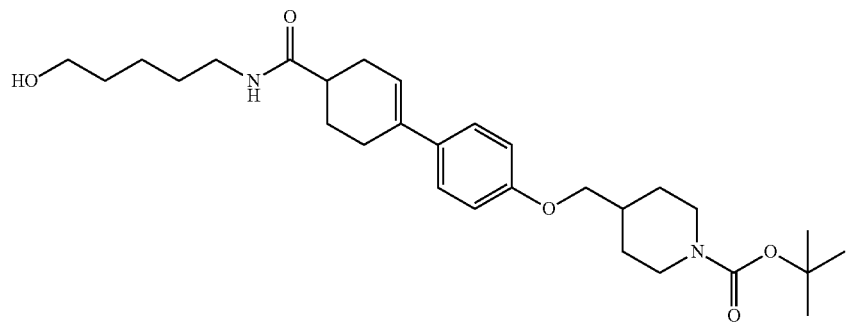 [SMILES: CC(C)(C)OC(=O)N1CCC(COc2ccc(C3=CCC(C(=O)NCCCCCO)CC3)cc2)CC1]

The title compound was prepared in the same manner as in <Example 190>, except that 5-aminopentanol was used instead of the 2-aminoethanol (Amount obtained: 166 mg/Yield: 67%).

$^1$H NMR (400, CDCl$_3$): 7.31 (2H, m), 6.84 (2H, m), 6.03 (1H, m), 5.73 (1H, m), 4.15 (2H, s), 3.81 (2H, d), 3.66 (2H, m), 3.32 (2H, m), 2.97 (2H, d), 2.78 (2H, m), 2.50-2.38 (5H, m), 2.09 (1H, m), 1.96-1.73 (5H, m), 1.58-1.52 (5H, m), 1.47 (9H, s), 1.44-1.22 (5H, m)

Example 234

Preparation of 4-(4-((1-(5-ethylpyrimidin-2-yl)piperidin-4-yl)methoxy)phenyl)-N-(5-hydroxypentyl)cyclohex-3-enecarboxamide

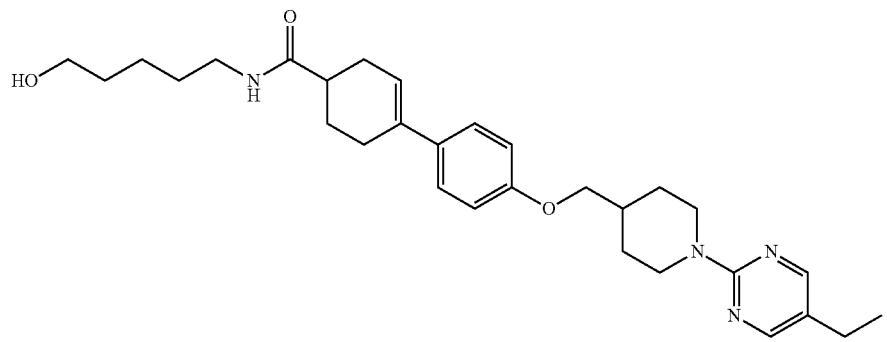 [SMILES: CCc1cnc(N2CCC(COc3ccc(C4=CCC(C(=O)NCCCCCO)CC4)cc3)CC2)nc1]

The title compound was prepared in the same manner as in <Example 152>, except that 5-aminopentanol was used instead of the L-β-prolinol (Amount obtained: 172 mg/Yield: 71%).

$^1$H NMR (400, CDCl$_3$): 8.18 (2H, s), 7.32 (2H, m), 6.86 (2H, m), 6.03 (1H, m), 5.66 (1H, m), 4.79 (2H, d), 3.84 (2H, d), 3.67 (2H, m), 3.33 (2H, m), 2.95 (2H, m), 2.50-2.38 (7H, m), 2.09-1.87 (5H, m), 1.69-1.30 (10H, m), 1.22 (3H, m)

Example 235

Preparation of (2,5-dihydro-1H-pyrrol-1-yl)(4-(4-((1-(5-ethylpyrimidin-2-yl)piperidin-4-yl)methoxy)phenyl)cyclohex-3-enyl)methanone

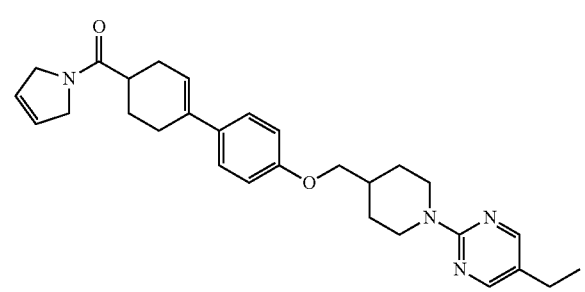 [SMILES: CCc1cnc(N2CCC(COc3ccc(C4=CCC(C(=O)N5CC=CC5)CC4)cc3)CC2)nc1]

The title compound was prepared in the same manner as in <Example 152>, except that 2,5-dihydro-1H-pyrrole was used instead of the L-β-prolinol (Amount obtained: 184 mg/Yield: 85%).

$^1$H NMR (400, CDCl$_3$): 8.18 (2H, s), 7.34 (2H, m), 6.88 (2H, m), 6.08 (1H, m), 5.93-5.84 (2H, m), 4.80 (2H, d), 4.37 (3H, m), 3.85 (2H, d), 3.53 (1H, m), 2.95 (2H, m), 2.65-2.32 (7H, m), 2.10-1.88 (6H, m), 1.37 (2H, m), 1.22 (3H, m)

Example 236

Preparation of tert-butyl 4-((4-(4-((2-hydroxyethyl)(methyl)carbamoyl)cyclohex-1-enyl)phenoxy)methyl)piperidine-1-carboxylate The title compound was prepared in the same manner as in <Example 190>, except that 2-(methylamino)ethanol was used instead of the 2-aminoethanol (Amount obtained: 162 mg/Yield: 64%).

$^1$H NMR (400, CDCl$_3$): 7.33 (2H, m), 6.86 (2H, m), 6.07 (1H, m), 4.16 (2H, s), 3.84 (4H, m), 3.63-3.57 (2H, m), 3.18 (3H, s), 2.83-2.73 (3H, m), 2.54-2.46 (3H, m), 2.36 (1H, m), 2.03-1.82 (5H, m), 1.48 (9H, s), 1.32 (2H, m)

Example 237

Preparation of tert-butyl 4-((4-(4-(1,3-dihydroxy-propan-2-ylcarbamoyl)cyclohex-1-enyl)phenoxy)methyl)piperidine-1-carboxylate

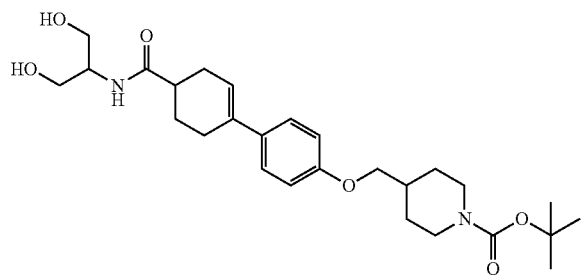 [SMILES: CC(C)(C)OC(=O)N1CCC(COc2ccc(C3=CCC(C(=O)NC(CO)CO)CC3)cc2)CC1]

The title compound was prepared in the same manner as in <Example 190>, except that 2-amino-1,3-propanediol was used instead of the 2-aminoethanol (Amount obtained: 166 mg/Yield: 68%).

$^1$H NMR (400, DMSO-$_{d6}$): 7.50 (1H, d), 7.35 (2H, m), 6.88 (2H, m), 6.04 (1H, m), 4.61 (2H, m), 4.03 (2H, m), 3.97 (2H, m), 3.82 (2H, d), 3.74 (1H, m), 3.41 (4H, m), 2.72 (2H, m), 2.44-2.19 (5H, m), 1.92-1.89 (2H, m), 1.74 (2H, m), 1.66 (1H, m), 1.39 (9H, s), 1.23 (2H, m)

Example 238

Preparation of tert-butyl 4-((4-(4-(3-hydroxypropyl-carbamoyl)cyclohex-1-enyl)phenoxy)methyl)piperidine-1-carboxylate

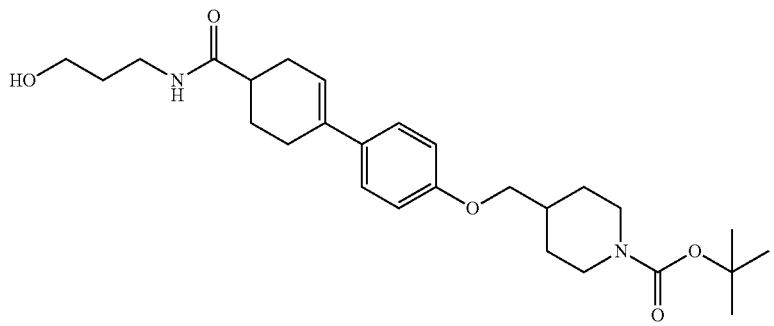 [SMILES: CC(C)(C)OC(=O)N1CCC(COc2ccc(C3=CCC(C(=O)NCCCO)CC3)cc2)CC1]

The title compound was prepared in the same manner as in <Example 190>, except that 3-aminopropanol was used instead of the 2-aminoethanol (Amount obtained: 172 mg/Yield: 69%).

$^1$H NMR (400, CDCl$_3$): 7.32 (2H, m), 6.85 (2H, m), 6.03 (2H, m), 4.16 (2H, s), 3.81 (2H, d), 3.67 (2H, m), 3.50 (2H, m), 3.27 (1H, m), 2.78 (2H, m), 2.53-2.41 (5H, m), 2.12 (1H, m), 1.98-1.82 (4H, m), 1.73 (2H, m), 1.48 (9H, s), 1.31 (2H, m)

Example 239

Preparation of tert-butyl 4-((4-(4-(1,2,3,4-tetrahydroisoquinoline-2-carbonyl)cyclohex-1-enyl)phenoxy)methyl)piperidine-1-carboxylate

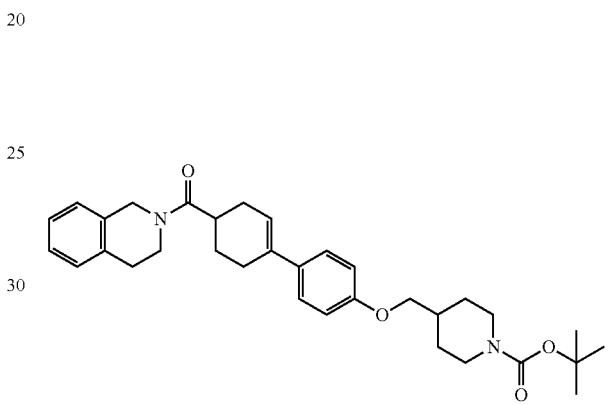

The title compound was prepared in the same manner as in <Example 190>, except that 1,2,3,4-tetrahydroisoquinoline was used instead of the 2-aminoethanol (Amount obtained: 185 mg/Yield: 81%).

$^1$H NMR (400, CDCl$_3$): 7.35 (2H, m), 7.25-7.12 (4H, m), 6.86 (2H, m), 6.07 (1H, m), 4.84 (2H, m), 4.18 (2H, s), 3.91-3.78 (4H, m), 2.97-2.88 (3H, m), 2.79 (2H, m), 2.60-2.50 (3H, m), 2.33 (1H, m), 2.06-1.93 (3H, m), 1.86 (2H, m), 1.59 (1H, s), 1.48 (9H, s), 1.33 (2H, m)

Example 240

Preparation of tert-butyl 4-((4-(4-(isoindoline-2-carbonyl)cyclohex-1-enyl)phenoxy)methyl)piperidine-1-carboxylate

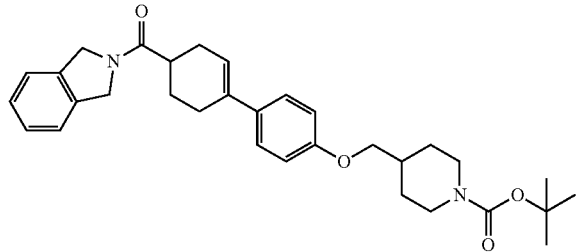 [SMILES: CC(C)(C)OC(=O)N1CCC(COc2ccc(C3=CCC(C(=O)N4Cc5ccccc5C4)CC3)cc2)CC1]

The title compound was prepared in the same manner as in <Example 190>, except that isoindoline was used instead of the 2-aminoethanol (Amount obtained: 181 mg/Yield: 77%).

$^1$H NMR (400, CDCl$_3$): 7.36-7.29 (6H, m), 6.88 (2H, m), 6.10 (1H, m), 4.95 (2H, s), 4.86 (2H, s), 4.17 (2H, s), 3.83 (2H, d), 2.82-2.73 (3H, m), 2.63-2.37 (4H, m), 2.12 (1H, m), 2.02 (2H, m), 1.86 (2H, m), 1.64 (1H, s), 1.48 (9H, s), 1.33 (2H, m)

Example 241

Preparation of (4-(4-((1-(5-ethylpyrimidin-2-yl)piperidin-4-yl)methoxy)phenyl)cyclohex-3-enyl)(isoindolin-2-yl)methanone

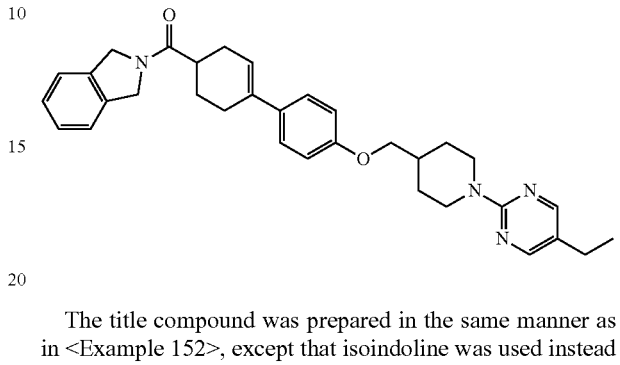

The title compound was prepared in the same manner as in <Example 152>, except that isoindoline was used instead of the L-β-prolinol (Amount obtained: 180 mg/Yield: 76%).

$^1$H NMR (400, CDCl$_3$): 8.19 (2H, s), 7.64-7.23 (6H, m), 6.89 (2H, m), 6.10 (1H, m), 4.95 (2H, s), 4.86 (2H, s), 4.80 (2H, d), 3.86 (2H, d), 2.96 (2H, m), 2.82 (1H, m), 2.63-2.36 (6H, m), 2.12-2.09 (2H, m), 2.02-1.93 (3H, m), 1.42-4.31 (2H, m), 1.22 (3H, m)

Example 242

Preparation of 4-(4-((1-(5-ethylpyrimidin-2-yl)piperidin-4-yl)methoxy)phenyl)-N-(3-hydroxypropyl)-N-methylcyclohex-3-enecarboxamide

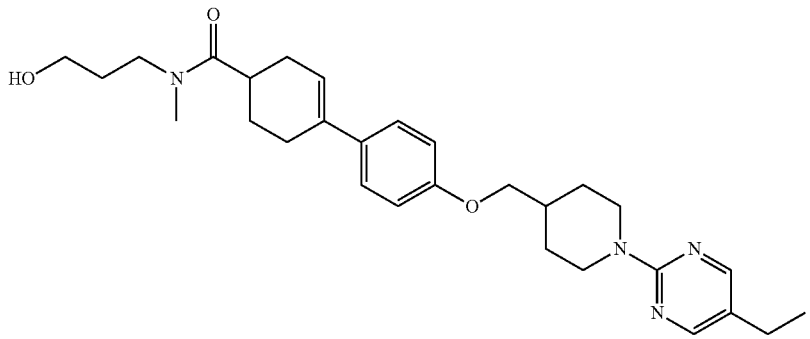

The title compound was prepared in the same manner as in <Example 152>, except that 3-methylaminopropanol was used instead of the L-β-prolinol (Amount obtained: 175 mg/Yield: 73%).

$^1$H NMR (400, CDCl$_3$): 8.18 (2H, s), 7.31 (2H, d), 6.86 (2H, d), 6.05 (1H, d), 4.76 (2H, d), 4.03 (1H, s), 3.84 (2H, d), 3.58 (2H, t), 3.50 (2H, s), 3.09 (3H, s), 2.96-2.80 (4H, m), 2.88-2.82 (5H, m), 2.55-2.44 (1H, m), 2.10-2.00 (2H, m), 1.99-1.89 (3H, m), 1.75 (2H, m), 1.38-1.31 (2H, m), 1.22 (3H, t)

Example 243

Preparation of N-(3-hydroxypropyl)-4-(4-((1-(3-isopropyl-1,2,4-oxadiazol-5-yl)piperidin-4-yl)methoxy)phenyl)-N-methylcyclohex-3-enecarboxamide

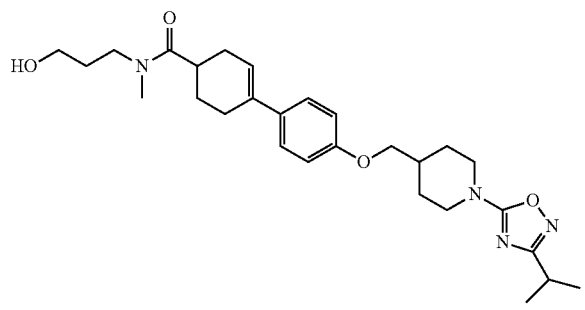 [SMILES: CC(C)c1noc(N2CCC(COc3ccc(C4=CCC(C(=O)N(C)CCCO)CC4)cc3)CC2)n1]

The title compound was prepared in the same manner as in <Example 143>, except that 3-methylaminopropanol was used instead of the (R)-N,N-dimethylpyrrolidine-3-amine hydrochloride (Amount obtained: 174 mg/Yield: 71%).

$^1$H NMR (400, CDCl$_3$): 7.31 (2H, d), 6.84 (2H, d), 6.05 (1H, m), 4.21 (2H, d), 4.01 (1H, t), 3.84 (2H, d), 3.52 (2H, t), 3.50 (2H, m), 3.11 (5H, m), 2.90 (2H, m), 2.55-2.48 (3H, m), 2.34 (1H, m), 2.06-1.90 (5H, m), 1.73 (2H, m), 1.47 (2H, m), 1.31 (6H, d)

Example 244

Preparation of N-(furan-2-ylmethyl)-4-(4-((1-(3-isopropyl-1,2,4-oxadiazol-5-yl)piperidin-4-yl)methoxy)phenyl)cyclohex-3-enecarboxamide The title compound was prepared in the same manner as in <Example 143>, except that furfurylamine was used instead of the (R)-N,N-dimethylpyrrolidine-3-amine hydrochloride (Amount obtained: 159 mg/Yield: 62%).

$^1$H NMR (400, CDCl$_3$): 7.37 (1H, s), 7.30 (2H, d), 6.83 (2H, d), 6.34 (1H, t), 6.25 (1H, d), 6.03 (1H, s), 5.88 (1H, t), 4.48 (2H, d), 4.21 (2H, d), 3.84 (2H, d), 3.10 (2H, t), 2.90 (1H, m), 2.46 (2H, m), 2.06 (2H, m), 1.89 (3H, m), 1.49 (2H, m), 1.31 (6H, d)

Example 245

Preparation of N-(3-ethoxypropyl)-4-(4-((1-(3-isopropyl-1,2,4-oxadiazol-5-yl)piperidin-4-yl)methoxy)phenyl)cyclohex-3-enecarboxamide

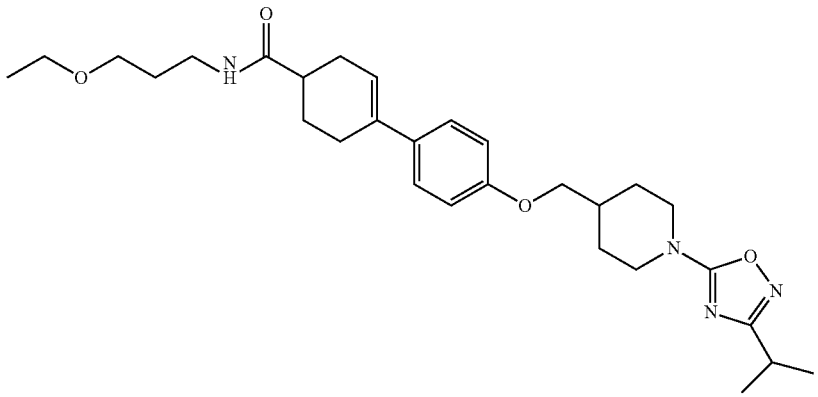 [SMILES: CCOCCCNC(=O)C1CC=C(c2ccc(OCC3CCN(c4nc(C(C)C)no4)CC3)cc2)CC1]

The title compound was prepared in the same manner as in <Example 143>, except that 3-ethoxypropylamine was used instead of the (R)-N,N-dimethylpyrrolidine-3-amine hydrochloride (Amount obtained: 167 mg/Yield: 64%).

$^1$H NMR (400, CDCl$_3$): 7.32 (2H, d), 6.84 (2H, d), 6.33 (1H, t), 6.04 (1H, s), 4.21 (2H, d), 3.84 (2H, d), 3.55 (2H, t), 3.47 (2H, q), 3.40 (2H, q), 3.11 (2H, m), 2.90 (1H, m), 2.52-2.36 (5H, m), 2.13-2.05 (2H, m), 1.97 (2H, d), 1.85-1.77 (3H, m), 1.47 (2H, m), 1.31 (6H, d), 1.23 (3H, t)

Example 246

Preparation of 4-(4-((1-(3-isopropyl-1,2,4-oxadiazol-5-yl)piperidin-4-yl)methoxy)phenyl)-N-methoxycyclohex-3-enecarboxamide

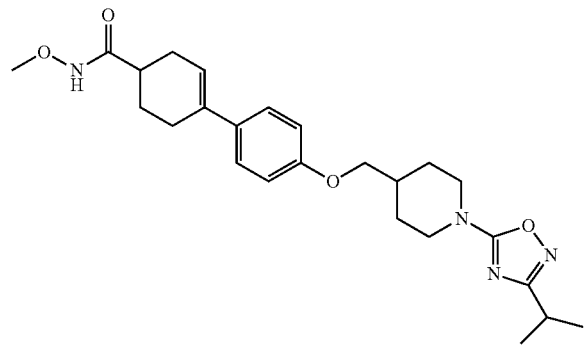 [SMILES: CONC(=O)C1CC=C(c2ccc(OCC3CCN(c4nc(C(C)C)no4)CC3)cc2)CC1]

The title compound was prepared in the same manner as in <Example 143>, except that O-methylhydroxylamine hydrochloride was used instead of the (R)-N,N-dimethylpyrrolidine-3-amine hydrochloride (Amount obtained: 170 mg/Yield: 67%).

$^1$H NMR (400, CDCl$_3$): 8.39 (1H, s), 7.30 (2H, d), 6.83 (2H, d), 6.03 (1H, s), 4.22 (2H, d), 3.84 (2H, d), 3.80 (3H, s), 3.10 (2H, t), 2.90 (1H, m), 2.56-2.35 (5H, m), 2.05 (2H, m), 1.93 (2H, d), 1.43 (2H, m), 1.31 (6H, d)

Example 247

Preparation of 4-(4-((1-(3-isopropyl-1,2,4-oxadiazol-5-yl)piperidin-4-yl)methoxy)phenyl)-N-methoxy-N-methylcyclohex-3-enecarboxamide

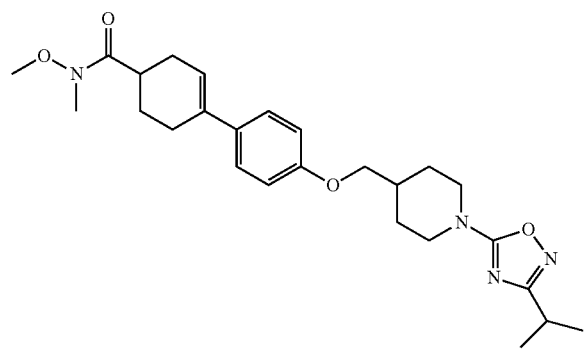 [SMILES: CON(C)C(=O)C1CC=C(c2ccc(OCC3CCN(c4nc(C(C)C)no4)CC3)cc2)CC1]

The title compound was prepared in the same manner as in <Example 143>, except that N,O-dimethylhydroxylamine was used instead of the (R)-N,N-dimethylpyrrolidine-3-amine hydrochloride (Amount obtained: 176 mg/Yield: 73%).

$^1$H NMR (400, CDCl$_3$): 7.33 (2H, d), 6.85 (2H, d), 6.07 (1H, d), 4.21 (2H, d), 3.84 (2H, d), 3.74 (3H, s), 3.24 (3H, s), 3.07 (2H, m), 2.89 (1H, m), 2.52-2.33 (4H, m), 2.04 (4H, m), 1.97 (2H, d), 1.83 (1H, m), 1.46 (2H, m), 1.30 (6H, s)

Example 248

Preparation of N,N-bis(2-hydroxyethyl)-4-(4-((1-(3-isopropyl-1,2,4-oxadiazol-5-yl)piperidin-4-yl)methoxy)phenyl)cyclohex-3-enecarboxamide

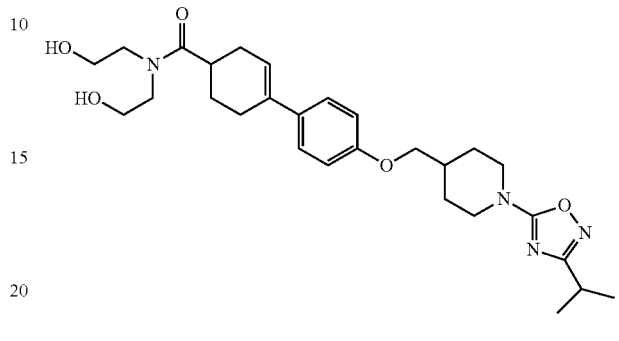

The title compound was prepared in the same manner as in <Example 143>, except that diethanolamine was used instead of the (R)-N,N-dimethylpyrrolidine-3-amine hydrochloride (Amount obtained: 157 mg/Yield: 55%).

$^1$H NMR (400, CDCl$_3$): 7.31 (2H, d), 6.84 (2H, d), 6.05 (1H, d), 4.20 (2H, d), 3.90 (2H, s), 3.84 (4H, m), 3.60 (4H, m), 3.27 (2H, s), 3.10 (4H, m), 2.92 (2H, m), 2.50 (2H, m), 2.30 (2H, m), 2.05-1.87 (5H, m), 1.44 (2H, m), 1.30 (6H, d)

Example 249

Preparation of 1-(4-(4-((1-(3-isopropyl-1,2,4-oxadiazol-5-yl)piperidin-4-yl)methoxy)phenyl)cyclohex-3-enecarbonyl)piperidine-4-carboxamide

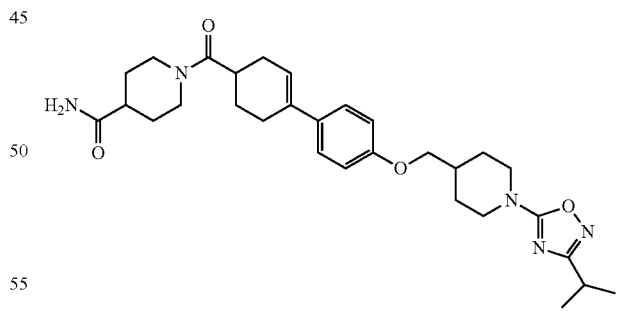

The title compound was prepared in the same manner as in <Example 143>, except that isonipecotamide was used instead of the (R)-N,N-dimethylpyrrolidine-3-amine hydrochloride (Amount obtained: 167 mg/Yield: 65%).

$^1$H NMR (400, CDCl$_3$): 7.32 (2H, d), 6.85 (2H, d), 6.05 (1H, d), 5.49 (1H, s), 5.36 (1H, s), 4.67 (1H, m), 4.21 (2H, d), 4.04 (1H, m), 3.85 (2H, d), 3.11 (2H, m), 2.89 (1H, m), 2.77-2.53 (2H, m), 2.50-2.31 (4H, m), 2.27 (1H, m), 2.06-1.94 (7H, m), 1.66 (2H, m), 1.41 (2H, m), 1.23 (6H, d)

Example 250

Preparation of 1-(4-(4-((1-(5-ethylpyrimidin-2-yl)piperidin-4-yl)methoxy)phenyl)cyclohex-3-enecarbonyl)pyrrolidin-3-one

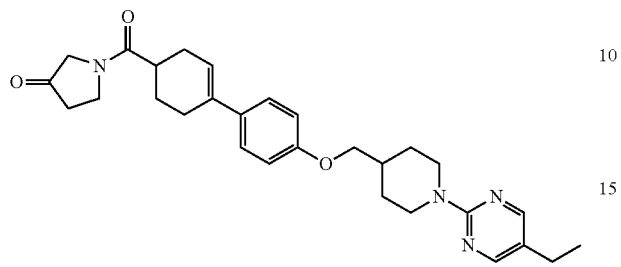

The title compound was prepared in the same manner as in <Example 152>, except that pyrrolidin-3-one hydrochloride was used instead of the L-β-prolinol (Amount obtained: 189 mg/Yield: 81%).

$^1$H NMR (400, CDCl$_3$): 8.19 (2H, s), 7.31 (2H, m), 6.86 (2H, d), 6.04 (1H, t), 4.77 (2H, d), 3.99 (4H, m), 3.83 (2H, d), 2.92 (2H, t), 2.75 (2H, t), 2.66 (2H, t), 2.57 (2H, m), 2.48 (2H, q), 2.36 (1H, m), 2.10 (2H, m), 1.95 (2H, d), 1.40 (2H, m), 1.28 (6H, d)

Example 251

Preparation of 1-(4-(4-((1-(3-isopropyl-1,2,4-oxadiazol-5-yl)piperidin-4-yl)methoxy)phenyl)cyclohex-3-enecarbonyl)piperidine-4-carboxamide

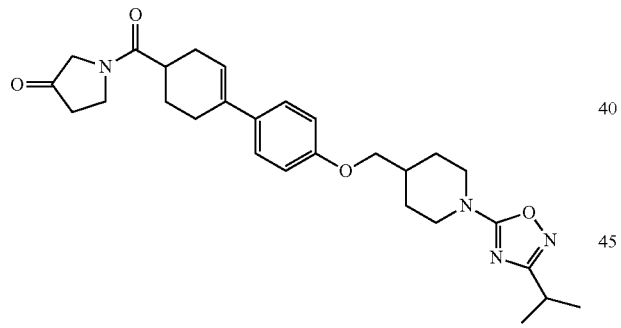

The title compound was prepared in the same manner as in <Example 143>, except that pyrrolidin-3-one hydrochloride was used instead of the (R)-N,N-dimethylpyrrolidine-3-amine hydrochloride (Amount obtained: 177 mg/Yield: 65%).

$^1$H NMR (400, CDCl$_3$): 7.32 (2H, m), 6.85 (2H, d), 6.33 (1H, t), 6.05 (1H, t), 4.21 (2H, d), 4.04-3.95 (4H, m), 3.84 (2H, d), 3.14 (2H, t), 2.89 (1H, q), 2.77 (2H, t), 2.68 (2H, t), 2.55 (3H, t), 2.60-2.33 (3H, m), 2.06 (3H, m), 1.94 (2H, d), 1.44 (2H, m), 1.35 (6H, s)

Example 252

Preparation of 1-(4-(4-((1-(3-isopropyl-1,2,4-oxadiazol-5-yl)piperidin-4-yl)methoxy)phenyl)cyclohex-3-enecarbonyl)piperidine-4-carboxamide

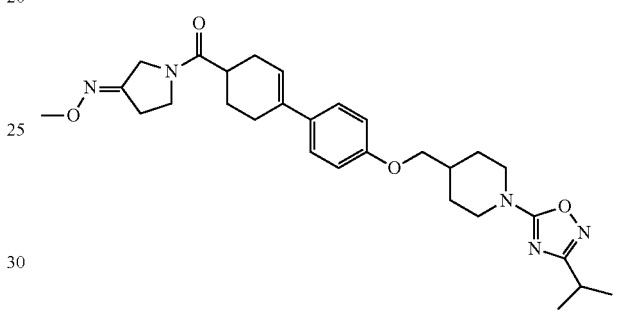

The title compound was prepared in the same manner as in <Example 217>, except that O-methylhydroxylamine hydrochloride was used instead of the hydroxylamine hydrochloride (Amount obtained: 170 mg/Yield: 56%).

$^1$H NMR (400, CDCl$_3$): 7.32 (2H, d), 6.86 (2H, d), 6.05 (1H, s), 4.23 (4H, m), 3.91 (3H, s), 3.82-3.77 (4H, m), 3.11 (2H, t), 2.94 (2H, q), 2.89-2.45 (5H, m), 2.30 (1H, m), 2.05-1.90 (5H, m), 1.46 (2H, m), 1.30 (6H, s)

Example 253

Preparation of (Z)-(3,3-bis(hydroxymethyl)-4-(methoxyimino)pyrrolidin-1-yl)(4-(4-((1-(5-ethylpyrimidin-2-yl)piperidin-4-yl)methoxy)phenyl)cyclohex-3-enyl)methanone

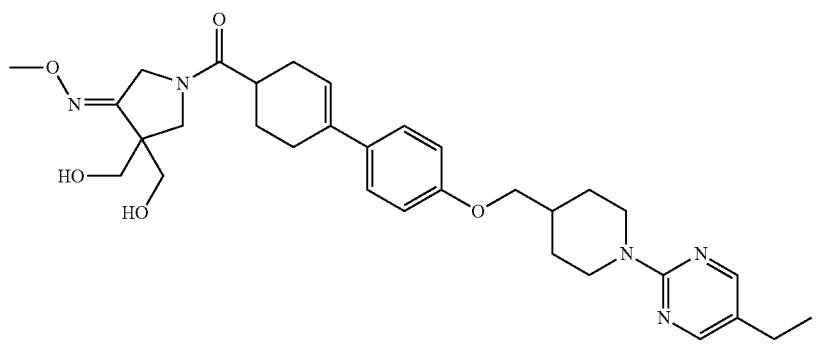 [SMILES: CCc1cnc(N2CCC(COc3ccc(C4=CCC(C(=O)N5C/C(=N\OC)C(CO)(CO)C5)CC4)cc3)CC2)nc1]

The title compound was prepared in the same manner as in <Example 152>, except that (Z)-4,4-bis(hydroxymethyl)pyrrolidin-3-one O-methyl oxime was used instead of the L-β-prolinol (Amount obtained: 190 mg/Yield: 79%).

$^1$H NMR (400, CDCl$_3$): 8.18 (2H, s) 7.30 (2H, d), 6.85 (2H, d), 6.03 (1H, s), 4.77 (2H, d), 4.32 (2H, d), 3.92-3.67 (11H, m), 2.91 (2H, t), 2.80 (1H, s), 2.70-2.46 (7H, m), 2.32 (1H, m), 2.09-1.88 (3H, m), 1.36 (2H, m), 1.19 (2H, t)

Example 254

Preparation of (Z)-tert-butyl 6-(4-(4-((1-(5-ethylpyrimidin-2-yl)piperidin-4-yl)methoxy)phenyl)cyclohex-3-enecarbonyl)-8-(methoxyimino)-2,6-diazaspiro[3.4]octane-2-carboxylate

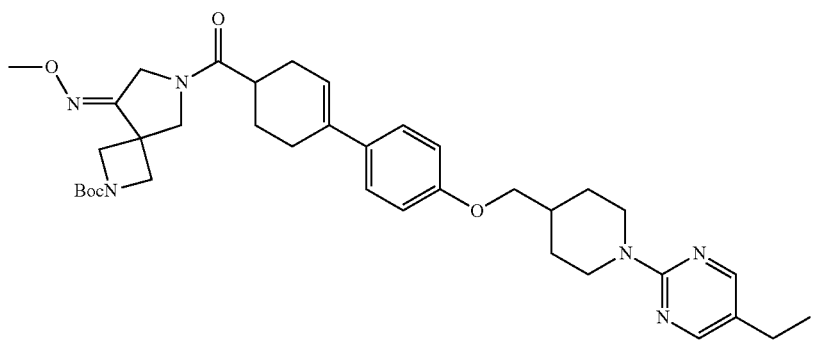 [SMILES: CCc1cnc(N2CCC(COc3ccc(C4=CCC(C(=O)N5C/C(=N\OC)C6(CN(C(=O)OC(C)(C)C)C6)C5)CC4)cc3)CC2)nc1]

The title compound was prepared in the same manner as in <Example 152>, except that (Z)-tert-butyl 8-(methoxyimino)-2,6-diazaspiro[3.4]octane-2-carboxylate was used instead of the L-β-prolinol (Amount obtained: 177 mg/Yield: 68%).

$^1$H NMR (400, CDCl$_3$): 8.18 (2H, s) 7.29 (2H, d), 6.85 (2H, d), 6.03 (1H, s), 4.77 (2H, d), 4.32 (2H, d), 4.20 (2H, m), 3.95-3.89 (7H, m), 3.83 (2H, d), 2.92 (2H, t), 2.59-2.44 (6H, m), 2.32 (1H, d), 2.10 (1H, s), 1.96 (4H, m), 1.47 (9H, s), 1.36-1.28 (4H, m))

Example 255

Preparation of (Z)-(4-(4-((1-(5-ethylpyrimidin-2-yl)piperidin-4-yl)methoxy)phenyl)cyclohex-3-enyl)(8-(methoxyimino)-2,6-diazaspiro[3.4]octan-6-yl)methanone hydrochloride

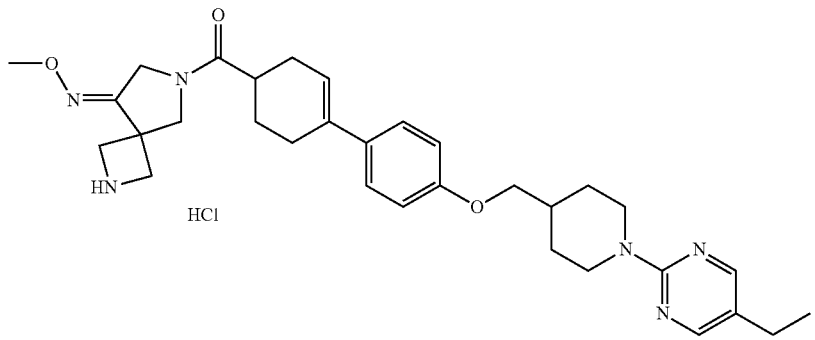 [SMILES: CCc1cnc(N2CCC(COc3ccc(C4=CCC(C(=O)N5C/C(=N\OC)C6(CNC6)C5)CC4)cc3)CC2)nc1 ; Cl]

150 mg of the compound (Z)-tert-butyl 6-(4-(4-((1-(5-ethylpyrimidin-2-yl)piperidin-4-yl)methoxy)phenyl)cyclohex-3-enecarbonyl)-8-(methoxyimino)-2,6-diazaspiro[3.4]octane-2-carboxylate prepared in <Example 254> was dissolved in 20 ml of ethyl acetate in a 100 ml flask, and then stirred under a nitrogen atmosphere. 0.08 ml of 4 N HCl dissolved in dioxane was added dropwise thereto, and the resulting mixture was then stirred at room temperature for 3 hours. The resulting solids were filtered, washed with 10 ml of ethyl acetate, and then dried to prepare the title compound as a white solid (Amount obtained: 130 mg/Yield: 73%).

$^1$H NMR (400, MeOD): 8.50 (2H, s), 7.34 (2H, d), 6.87 (2H, d), 6.06 (1H, s), 4.61 (2H, d), 3.99 (3H, s), 3.63 (8H, s), 3.49 (2H, m), 2.67 (2H, q), 2.54 (1H, s), 2.43 (1H, s), 2.16 (3H, m), 1.79 (1H, m), 1.52 (2H, q), 1.30 (4H, m)

Example 256

Preparation of tert-butyl 4-((4-(4-(4-(cyclopropylmethyl)piperazine-1-carbonyl)cyclohex-1-enyl)phenoxy)methyl)piperidine-1-carboxylate

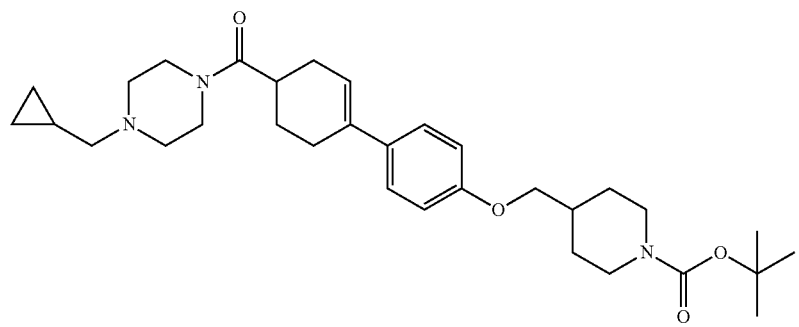 [SMILES: CC(C)(C)OC(=O)N1CCC(COc2ccc(C3=CCC(C(=O)N4CCN(CC5CC5)CC4)CC3)cc2)CC1]

The title compound was prepared in the same manner as in <Example 190>, except that 1-cyclopropylmethyl piperazine was used instead of the 2-aminoethanol (Amount obtained: 169 mg/Yield: 71%).

$^1$H NMR (400, CDCl$_3$): 7.32 (2H, d), 6.84 (2H, d), 6.05 (1H, d), 4.17 (2H, s), 3.82 (2H, d), 3.72 (2H, s), 3.61 (2H, s), 2.77 (3H, m), 2.57-2.46 (7H, m), 2.28 (3H, m), 2.00-1.82 (5H, m), 1.48 (9H, s), 1.28 (2H, m), 0.89 (1H, m), 0.55 (2H, q), 0.12 (2H, q)

Example 257

Preparation of tert-butyl 4-((4-(4-(3,3-difluoropyrrolidine-1-carbonyl)cyclohex-1-enyl)phenoxy)methyl)piperidine-1-carboxylate

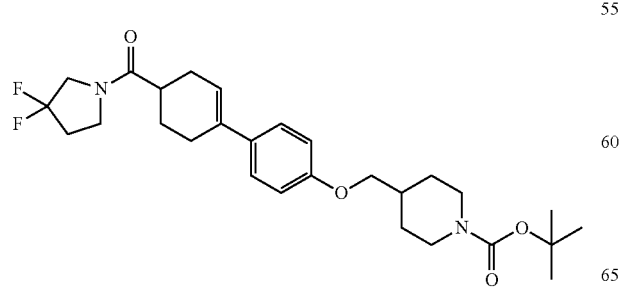

The title compound was prepared in the same manner as in <Example 190>, except that 3,3-difluoropyrrolidine hydrochloride was used instead of the 2-aminoethanol (Amount obtained: 174 mg/Yield: 76%).

$^1$H NMR (400, CDCl$_3$): 7.30 (2H, d), 6.84 (2H, d), 6.05 (1H, d), 4.16 (2H, s), 3.92-3.73 (2H, m), 2.78 (2H, t), 2.56 (1H, m), 2.49-2.29 (6H, m), 2.04-1.97 (3H, m), 1.82 (2H, d), 1.47 (9H, s), 1.25 (2H, m)

Example 258

Preparation of (3,3-difluoropyrrolidin-1-yl)(4-(4-((1-(5-ethylpyrimidin-2-yl)piperidin-4-yl)methoxy)phenyl)cyclohex-3-enyl)methanone

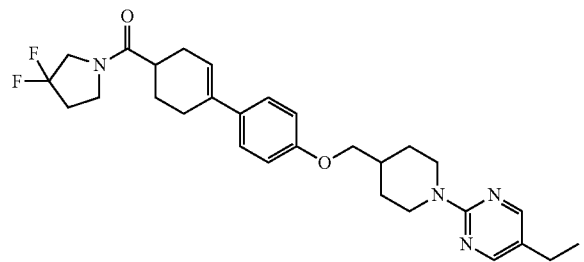 [SMILES: CCc1cnc(N2CCC(COc3ccc(C4=CCC(C(=O)N5CCC(F)(F)C5)CC4)cc3)CC2)nc1]

The title compound was prepared in the same manner as in <Example 152>, except that 3,3-difluoropyrrolidine hydrochloride was used instead of the L-β-prolinol (Amount obtained: 175 mg/Yield: 73%).

$^1$H NMR (400, CDCl$_3$): 8.19 (2H, s), 7.32 (2H, d), 6.85 (2H, d), 6.05 (1H, d), 4.77 (2H, d), 3.92-3.74 (6H, m), 2.92 (2H, m), 2.56-2.32 (9H, m), 2.11-1.88 (5H, m), 1.37 (2H, m), 1.22 (3H, t)

Example 259

Preparation of (3,3-difluoropyrrolidin-1-yl)(4-(4-((1-(3-isopropyl-1,2,4-oxadiazol-5-yl)piperidin-4-yl)methoxy)phenyl)cyclohex-3-enyl)methanone

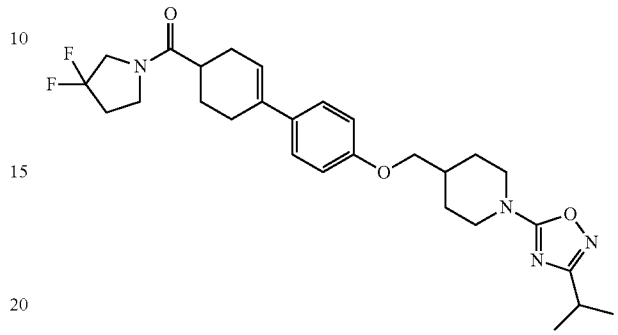

The title compound was prepared in the same manner as in <Example 143>, except that 3,3-difluoropyrrolidine hydrochloride was used instead of the (R)-N,N-dimethylpyrrolidine-3-amine hydrochloride (Amount obtained: 182 mg/Yield: 77%).

$^1$H NMR (400, CDCl$_3$): 7.32 (2H, d), 6.84 (2H, d), 6.05 (1H, d), 4.21 (2H, d), 3.92-3.74 (6H, m), 3.11 (2H, m), 2.94 (1H, m), 2.56-2.33 (7H, m), 2.06-1.94 (5H, m), 1.47 (2H, m), 1.31 (6H, d)

Example 260

Preparation of N-(5-hydroxypentyl)-4-(4-((1-(3-isopropyl-1,2,4-oxadiazol-5-yl)piperidin-4-yl)methoxy)phenyl)cyclohex-3-enecarboxamide

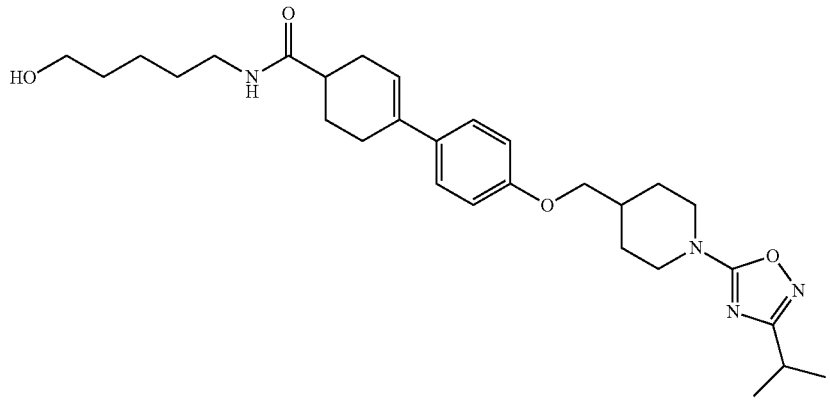 [SMILES: CC(C)c1noc(N2CCC(COc3ccc(C4=CCC(C(=O)NCCCCCO)CC4)cc3)CC2)n1]

The title compound was prepared in the same manner as in <Example 143>, except that 5-aminopentanol was used instead of the (R)-N,N-dimethylpyrrolidine-3-amine hydrochloride (Amount obtained: 185 mg/Yield: 78%).

$^1$H NMR (400, CDCl$_3$): 7.30 (2H, d), 6.84 (2H, d), 6.04 (1H, d), 5.67 (1H, t), 4.19 (2H, d), 3.85 (2H, d), 3.65 (2H, t), 3.31 (2H, q), 3.07 (2H, m), 2.90 (1H, m), 2.51-2.38 (5H, m), 2.03 (2H, m), 1.85 (3H, m), 1.58 (5H, m), 1.43 (5H, m), 1.30 (6H, d)

Example 261

Preparation of tert-butyl 4-((4-(4-(2,2,2-trifluoroethylcarbamoyl)cyclohex-1-enyl)phenoxy)methyl)piperidine-1-carboxylate

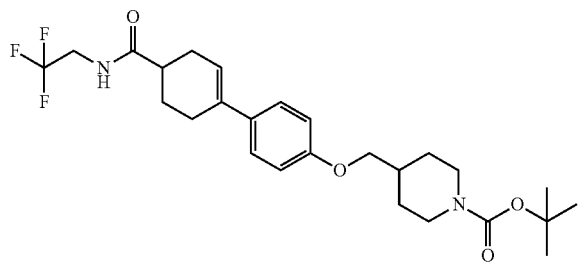 [SMILES: CC(C)(C)OC(=O)N1CCC(COc2ccc(C3=CCC(C(=O)NCC(F)(F)F)CC3)cc2)CC1]

The title compound was prepared in the same manner as in <Example 190>, except that 2,2,2-trifluoroethylamine was used instead of the 2-aminoethanol (Amount obtained: 164 mg/Yield: 70%).

$^1$H NMR (400, CDCl$_3$): 7.31 (2H, d), 6.84 (2H, d), 6.03 (1H, d), 5.90 (1H, t), 4.17 (2H, s), 3.97 (2H, m), 3.81 (2H, d), 2.76 (2H, t), 2.57-2.42 (5H, m), 2.13-2.09 (1H, m), 1.99-1.85 (2H, m), 1.84 (2H, d), 1.47 (9H, s), 1.24 (2H, m)

Example 262

Preparation of tert-butyl 4-((4-(4-(4-cyanocyclohexanecarbonyl)cyclohex-1-enyl)phenoxy)methyl)piperidine-1-carboxylate

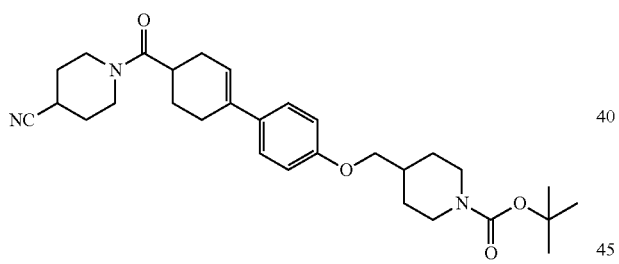

The title compound was prepared in the same manner as in <Example 190>, except that 2,2,2-trifluoroethylamine was used instead of the 2-aminoethanol (Amount obtained: 165 mg/Yield: 67%).

$^1$H NMR (400, CDCl$_3$): 7.30 (2H, d), 6.84 (2H, d), 6.04 (1H, s), 4.17 (2H, s), 3.87-3.76 (4H, m), 3.63-3.50 (2H, m), 2.93 (1H, m), 2.82-2.73 (3H, m), 2.73-2.47 (3H, m), 2.28 (1H, m), 1.97-1.82 (9H, m), 1.47 (9H, s), 1.23 (2H, m)

Example 263

Preparation of tert-butyl 4-((4-(4-(1,4-dioxa-8-azaspiro[4.5]decane-8-carbonyl)cyclohex-1-enyl)phenoxy)methyl)piperidine-1-carboxylate

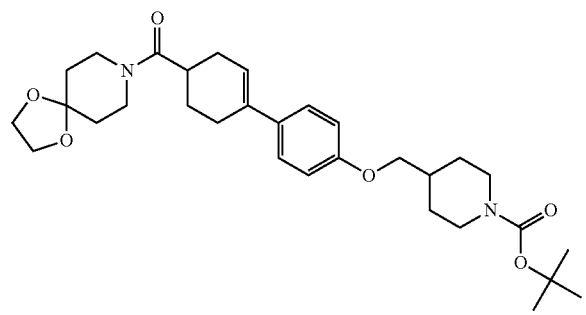 [SMILES: CC(C)(C)OC(=O)N1CCC(COc2ccc(C3=CCC(C(=O)N4CCC5(CC4)OCCO5)CC3)cc2)CC1]

The title compound was prepared in the same manner as in <Example 190>, except that 1,4-dioxa-8-azaspiro[4.5]decane was used instead of the 2-aminoethanol (Amount obtained: 177 mg/Yield: 74%).

$^1$H NMR (400, CDCl$_3$): 7.32 (2H, d), 6.84 (2H, d), 6.05 (1H, d), 4.17 (2H, s), 4.01 (4H, s), 3.82-3.70 (4H, m), 3.63 (2H, t), 2.83-2.76 (3H, m), 2.53-2.47 (2H, m), 2.31 (1H, m), 2.02-1.90 (3H, m), 1.81 (2H, d), 1.73 (4H, m), 1.48 (9H, s), 1.25 (2H, m)

Example 264

Preparation of tert-butyl 4-((4-(4-(spiro[indene-1,4'-piperidin]-1'-ylcarbonyl)cyclohex-1-enyl)phenoxy)methyl)piperidine-1-carboxylate

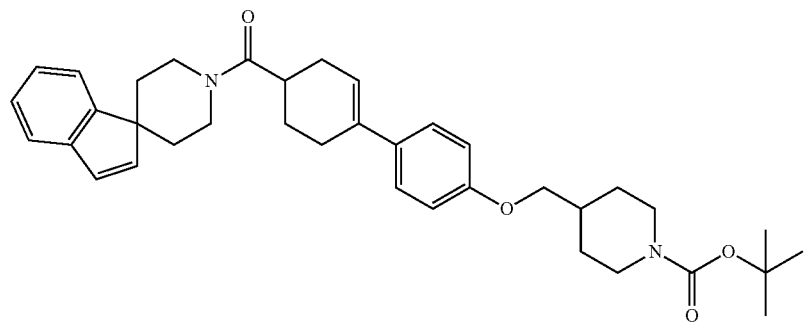

The title compound was prepared in the same manner as in <Example 190>, except that 2,3-dihydrospiro[indene-1,4'-piperidine] was used instead of the 2-aminoethanol (Amount obtained: 183 mg/Yield: 75%).

¹H NMR (400, CDCl₃): 7.37-7.31 (4H, m), 7.29-7.22 (2H, m), 6.91 (1H, dd), 6.87-6.83 (3H, m), 6.08 (1H, t), 4.76 (2H, d), 4.10 (3H, m), 3.81 (2H, d), 3.47 (2H, t), 3.05 (1H, t), 2.89 (1H, m), 2.79 (2H, m), 2.73-2.52 (3H, m), 2.37 (1H, m), 2.11-1.93 (5H, m), 1.83 (2H, d), 1.47-1.32 (11H, m), 1.23 (2H, m)

Example 265

Preparation of tert-butyl 4-((4-(4-(3-oxopyrrolidine-1-carbonyl)cyclohex-1-enyl)phenoxy)methyl)piperidine-1-carboxylate

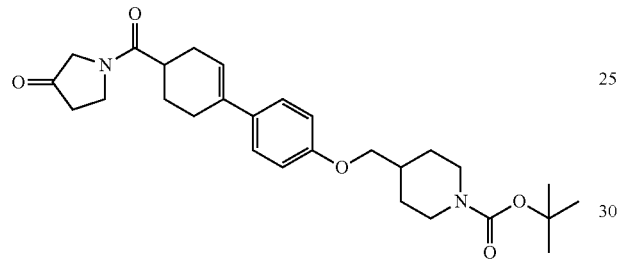

The title compound was prepared in the same manner as in <Example 190>, except that pyrrolidin-3-one hydrochloride was used instead of the 2-aminoethanol (Amount obtained: 159 mg/Yield: 64%).

¹H NMR (400, CDCl₃): 7.32 (2H, d), 6.84 (2H, d), 6.06 (1H, d), 4.17 (2H, s), 3.99 (4H, m), 3.81 (2H, d), 2.75 (5H, m), 2.60-2.42 (5H, m), 2.33-2.30 (1H, m), 2.06-1.94 (33H, m), 1.89 (2H, d), 1.48 (9H, s), 1.27 (2H, m)

Example 266

Preparation of 1-(4-(4-((1-(3-isopropyl-1,2,4-oxadiazol-5-yl)piperidin-4-yl)methoxy)phenyl)cyclohex-3-enecarbonyl)piperidine-4-carbonitrile

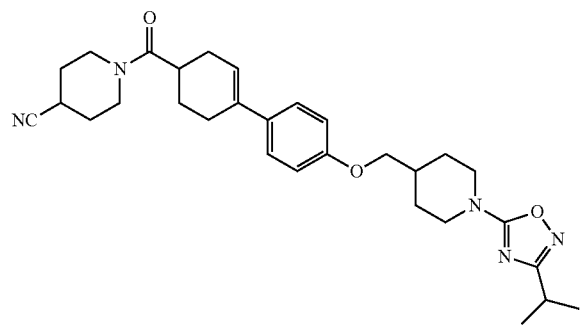 [SMILES: CC(C)c1noc(N2CCC(COc3ccc(C4=CCC(C(=O)N5CCC(C#N)CC5)CC4)cc3)CC2)n1]

The title compound was prepared in the same manner as in <Example 143>, except that piperidine-4-carbonitrile was used instead of the (R)-N,N-dimethylpyrrolidine-3-amine hydrochloride (Amount obtained: 174 mg/Yield: 70%).

¹H NMR (400, CDCl₃): 7.31 (2H, d), 6.86 (2H, d), 6.05 (1H, d), 4.20 (2H, d), 3.84-3.50 (6H, m), 2.11 (2H, m), 2.93 (2H, m), 2.78 (1H, m), 2.52 (3H, m), 2.28 (1H, m), 2.05-1.89 (9H, m), 1.43 (2H, m), 1.29 (9H, s)

Example 267

Preparation of (4-(4-((1-(3-isopropyl-1,2,4-oxadiazol-5-yl)piperidin-4-yl)methoxy)phenyl)cyclohex-3-enyl)(1,4-dioxa-8-azaspiro[4.5]decan-8-yl)methanone

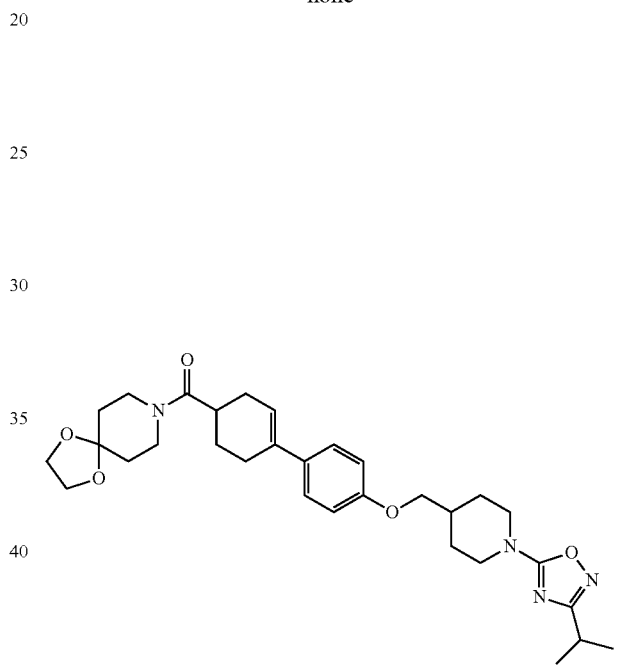

The title compound was prepared in the same manner as in <Example 143>, except that 1,4-dioxa-8-azaspiro[4.5]decane was used instead of the (R)-N,N-dimethylpyrrolidine-3-amine hydrochloride (Amount obtained: 180 mg/Yield: 76%).

¹H NMR (400, CDCl₃): 7.32 (2H, d), 6.84 (2H, d), 6.05 (1H, d), 4.20 (2H, d), 4.01 (4H, s), 3.85 (2H, d), 3.75 (2H, m), 3.63 (2H, t), 3.11 (2H, m), 2.94-2.83 (2H, m), 2.51 (3H, m), 2.31 (1H, m), 2.06-1.90 (5H, m), 1.73 (4H, m), 1.44 (2H, m), 1.31 (6H, d)

Example 268

Preparation of (2,3-dihydrospiro[indene-1,4'-piperidin]-1'-yl)(4-(4-((1-(3-isopropyl-1,2,4-oxadiazol-5-yl)piperidin-4-yl)methoxy)phenyl)cyclohex-3-enyl)methanone

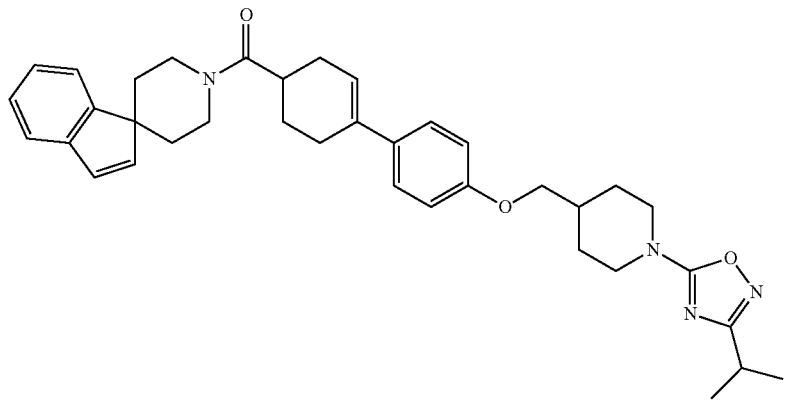 [SMILES: CC(C)c1noc(N2CCC(COc3ccc(C4=CCC(C(=O)N5CCC6(C=Cc7ccccc76)CC5)CC4)cc3)CC2)n1]

The title compound was prepared in the same manner as in <Example 143>, except that 3-dihydrospiro[indene-1,4'-piperidine] was used instead of the (R)-N,N-dimethylpyrrolidine-3-amine hydrochloride (Amount obtained: 194 mg/Yield: 82%).

$^1$H NMR (400, CDCl$_3$): 7.35-7.22 (8H, m), 6.91-6.84 (4H, m), 6.09 (1H, t), 4.75 (1H, d), 4.20 (2H, d), 4.10 (1H, d), 3.84 (2H, d), 3.49 (1H, m), 3.08 (3H, m), 2.89 (2H, m), 2.62-2.34 (4H, m), 2.19-1.94 (7H, m), 1.46 (4H, m), 1.31 (6H, d)

Example 269

Preparation of (3-(ethoxyimino)pyrrolidin-1-yl)(4-(4-((1-(5-ethylpyrimidin-2-yl)piperidin-4-yl)methoxy)phenyl)cyclohex-3-enyl)methanone

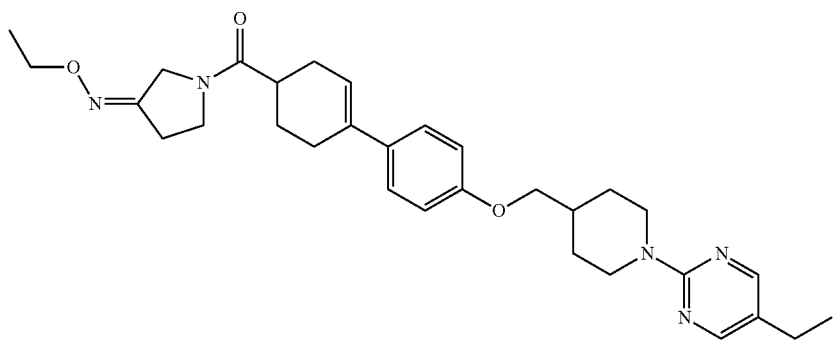 [SMILES: CCO/N=C1/CCN(C(=O)C2CC=C(c3ccc(OCC4CCN(c5ncc(CC)cn5)CC4)cc3)CC2)C1]

The title compound was prepared in the same manner as in <Example 217>, except that O-ethylhydroxylamine hydrochloride was used instead of the hydroxylamine hydrochloride (Amount obtained: 177 mg/Yield: 71%).

$^1$H NMR (400, CDCl$_3$): 8.19 (2H, s), 7.32 (2H, d), 6.86 (2H, d), 6.05 (1H, d), 4.77 (2H, d), 4.24 (2H, d), 4.12 (2H, m), 3.85-3.77 (4H, m), 2.95 (3H, m), 2.78-2.45 (7H, m), 2.34 (1H, m), 2.10-1.90 (5H, m), 1.36 (2H, m), 1.29 (3H, t), 1.20 (3H, t)

Example 270

Preparation of tert-butyl 4-((4-(4-(4-(methoxyimino)piperidine-1-carbonyl)cyclohex-1-enyl)phenoxy)methyl)piperidine-1-carboxylate

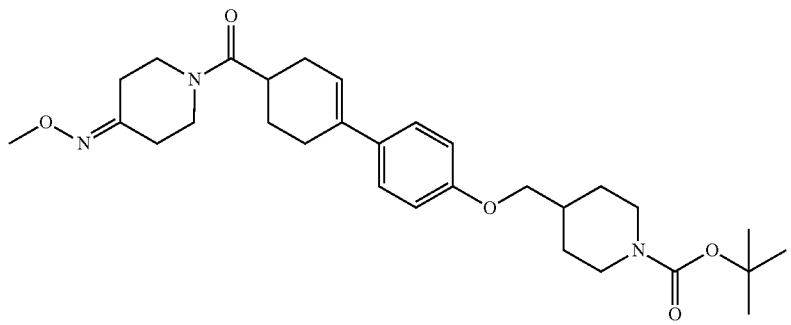 [SMILES: CON=C1CCN(C(=O)C2CC=C(c3ccc(OCC4CCN(C(=O)OC(C)(C)C)CC4)cc3)CC2)CC1]

The title compound was prepared in the same manner as in <Example 217>, except that O-methylhydroxylamine hydrochloride was used instead of the hydroxylamine hydrochloride (Amount obtained: 173 mg/Yield: 75%).

$^1$H NMR (400, CDCl$_3$): 7.30 (2H, d), 6.84 (2H, d), 6.05 (1H, d), 4.17 (2H, s), 3.86 (3H, s), 3.80-3.70 (6H, m), 2.82-2.48 (10H, m), 2.30 (1H, m), 2.02-1.91 (3H, m), 1.82 (2H, d), 1.48 (9H, s), 1.25 (2H, m)

Example 271

Preparation of tert-butyl 4-((4-(4-(4-(hydroxyimino)piperidine-1-carbonyl)cyclohex-1-enyl)phenoxy)methyl)piperidine-1-carboxylate

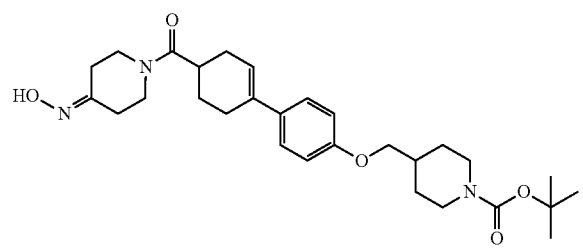 [SMILES: CC(C)(C)OC(=O)N1CCC(COc2ccc(C3=CCC(C(=O)N4CCC(=NO)CC4)CC3)cc2)CC1]

The title compound was prepared in the same manner as in <Example 217>, except that tert-butyl 4-((4-(4-(4-oxopiperidine-1-carbonyl)cyclohex-1-enyl)phenoxy)methyl)piperidine-1-carboxylate was used instead of the 1-(4-(4-((1-(3-isopropyl-1,2,4-oxadiazol-5-yl)piperidin-4-yl)methoxy)phenyl)cyclohex-3-enecarbonyl)piperidine-4-carboxamide (Amount obtained: 161 mg/Yield: 66%).

$^1$H NMR (400, CDCl$_3$): 7.32 (2H, d), 6.84 (2H, d), 6.05 (1H, d), 4.16 (2H, s), 3.93-3.76 (6H, m), 2.83-2.73 (5H, m), 2.66-2.41 (5H, m), 2.30 (1H, m), 2.04-1.91 (3H, m), 1.82 (2H, d), 1.48 (9H, s), 1.22 (2H, m)

Example 272

Preparation of tert-butyl 4-((4-(4-(4-oxopiperidine-1-carbonyl)cyclohex-1-enyl)phenoxy)methyl)piperidine-1-carboxylate

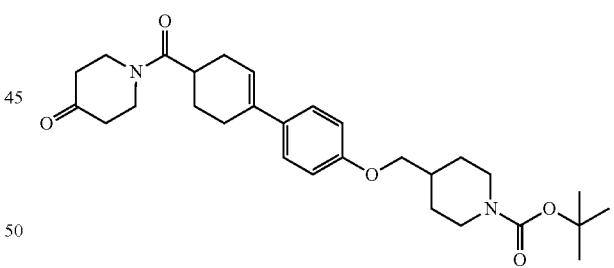

The title compound was prepared in the same manner as in <Example 190>, except that piperidin-4-one hydrochloride was used instead of the 2-aminoethanol (Amount obtained: 172 mg/Yield: 75%).

$^1$H NMR (400, CDCl$_3$): 7.32 (2H, d), 6.84 (2H, d), 6.06 (1H, d), 4.16 (2H, s), 3.99-3.87 (6H, m), 2.89 (1H, m), 2.85 (2H, m), 2.61-2.56 (7H, m), 2.35 (1H, m), 2.07-1.98 (3H, m), 1.84 (2H, d), 1.48 (9H, s), 1.24 (2H, m)

Example 273

Preparation of tert-butyl 4-((4-(4-(3-(methoxyimino)pyrrolidine-1-carbonyl)cyclohex-1-enyl)phenoxy)methyl)piperidine-1-carboxylate

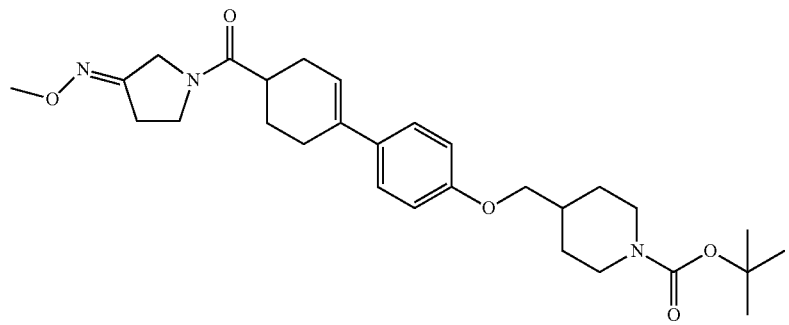 [SMILES: CO/N=C1\CCN(C(=O)C2CC=C(c3ccc(OCC4CCN(C(=O)OC(C)(C)C)CC4)cc3)CC2)C1]

The title compound was prepared in the same manner as in <Example 217>, except that O-methylhydroxylamine hydrochloride was used instead of the hydroxylamine hydrochloride (Amount obtained: 169 mg/Yield: 69%).

¹H NMR (400, CDCl₃): 7.32 (2H, d), 6.84 (2H, d), 6.06 (1H, d), 4.26 (2H, d), 4.16 (2H, s), 3.90 (3H, s), 3.77 (4H, m), 2.86-2.49 (8H, m), 2.32 (1H, m), 2.04-1.85 (5H, m), 1.48 (9H, s), 1.23 (2H, m)

Example 274

Preparation of 1-(4-(4-((1-(5-ethylpyrimidin-2-yl)piperidin-4-yl)methoxy)phenyl)cyclohex-3-enecarbonyl)piperidin-4-one

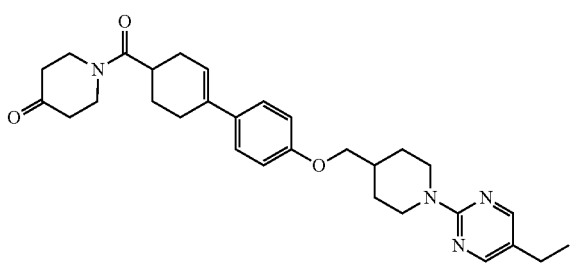 [SMILES: CCc1cnc(N2CCC(COc3ccc(C4=CCC(C(=O)N5CCC(=O)CC5)CC4)cc3)CC2)nc1]

The title compound was prepared in the same manner as in <Example 152>, except that piperidin-4-one hydrochloride was used instead of the L-β-prolinol (Amount obtained: 180 mg/Yield: 77%).

¹H NMR (400, CDCl₃): 8.19 (2H, s), 7.31 (2H, d), 6.86 (2H, d), 6.06 (1H, d), 4.76 (2H, d), 3.96-3.83 (6H, m), 2.96-2.89 (3H, m), 2.61-2.45 (9H, m), 2.36 (1H, m), 2.11-2.03 (2H, m), 1.95 (2H, d), 1.34 (2H, m), 1.21 (3H, t)

Example 275

Preparation of 1-(4-(4-((1-(3-isopropyl-1,2,4-oxadiazol-5-yl)piperidin-4-yl)methoxy)phenyl)cyclohex-3-enecarbonyl)piperidin-4-one

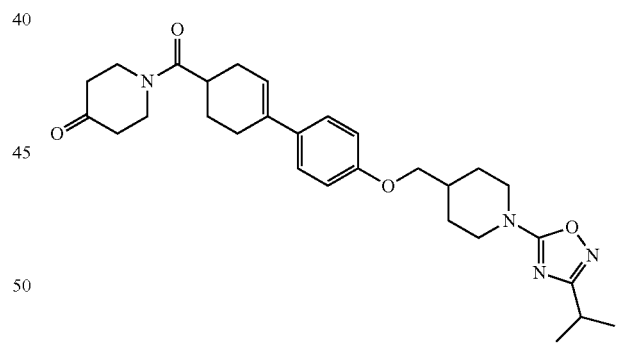

The title compound was prepared in the same manner as in <Example 143>, except that piperidin-4-one hydrochloride was used instead of the (R)-N,N-dimethylpyrrolidine-3-amine hydrochloride (Amount obtained: 184 mg/Yield: 77%).

¹H NMR (400, CDCl₃): 7.32 (2H, d), 6.85 (2H, d), 6.06 (1H, d), 4.21 (2H, d), 3.98-3.84 (6H, m), 3.14 (2H, m), 2.90 (2H, m), 2.61-2.53 (7H, m), 2.35 (1H, m), 2.07-1.92 (5H, m), 1.51 (2H, m), 1.41 (6H, d)

Example 276

Preparation of (4-(hydroxyimino)piperidin-1-yl)(4-(4-((1-(3-isopropyl-1,2,4-oxadiazol-5-yl)piperidin-4-yl)methoxy)phenyl)cyclohex-3-enyl)methanone

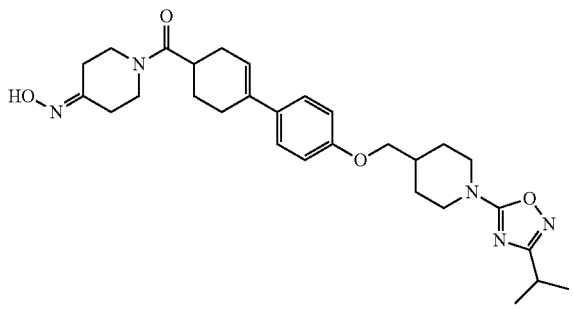 [SMILES: CC(C)c1noc(N2CCC(COc3ccc(C4=CCC(C(=O)N5CCC(=NO)CC5)CC4)cc3)CC2)n1]

The title compound was prepared in the same manner as in <Example 217>, except that 1-(4-(4-((1-(3-isopropyl-1,2,4-oxadiazol-5-yl)piperidin-4-yl)methoxy)phenyl)cyclohex-3-enecarbonyl)piperidin-4-one was used instead of the 1-(4-(4-((1-(3-isopropyl-1,2,4-oxadiazol-5-yl)piperidin-4-yl)methoxy)phenyl)cyclohex-3-enecarbonyl)piperidine-4-carboxamide (Amount obtained: 183 mg/Yield: 76%).

$^1$H NMR (400, CDCl$_3$): 7.51 (1H, m), 7.31 (2H, d), 6.86 (2H, d), 6.06 (1H, d), 4.51 (2H, s), 3.84 (2H, d), 3.79-3.66 (4H, m), 3.11 (2H, m), 2.92 (2H, m), 2.87 (2H, m), 2.58-2.42 (5H, m), 2.33 (1H, m), 2.05 (2H, m), 1.94 (3H, m), 1.45 (2H, m), 1.43 (9H, s)

Example 277

Preparation of (4-(4-((1-(5-ethylpyrimidin-2-yl)piperidin-4-yl)methoxy)phenyl)cyclohex-3-enyl)(4-(hydroxyimino)piperidin-1-yl)methanone

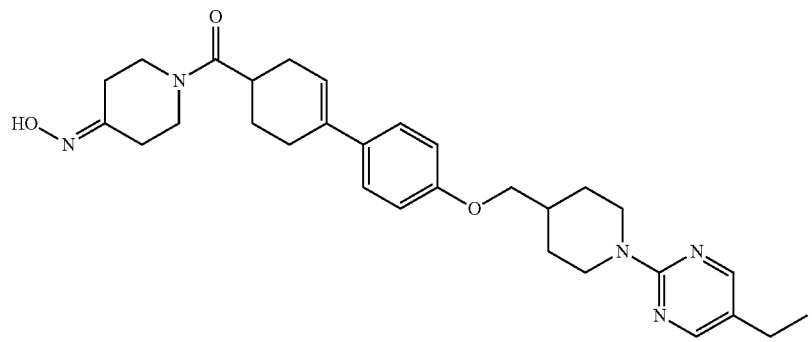 [SMILES: CCc1cnc(N2CCC(COc3ccc(C4=CCC(C(=O)N5CCC(=NO)CC5)CC4)cc3)CC2)nc1]

The title compound was prepared in the same manner as in <Example 217>, except that 1-(4-(4-((1-(5-ethylpyrimidin-2-yl)piperidin-4-yl)methoxy)phenyl)cyclohex-3-enecarbonyl)piperidin-4-one was used instead of the 1-(4-(4-((1-(3-isopropyl-1,2,4-oxadiazol-5-yl)piperidin-4-yl)methoxy)phenyl)cyclohex-3-enecarbonyl)piperidine-4-carboxamide (Amount obtained: 166 mg/Yield: 65%).

$^1$H NMR (400, CDCl$_3$): 8.19 (2H, s), 8.14 (1H, d), 7.31 (2H, d), 6.85 (2H, d), 6.05 (1H, d), 4.76 (2H, d), 3.84-3.70 (6H, m), 2.95 (2H, m), 2.84 (1H, m), 2.70 (2H, m), 2.67-2.42 (7H, m), 2.33 (1H, m), 2.10-1.91 (5H, m), 1.34 (2H, m), 1.20 (3H, t)

Example 278

Preparation of (4-(4-((1-(3-isopropyl-1,2,4-oxadiazol-5-yl)piperidin-4-yl)methoxy)phenyl)cyclohex-3-enyl)(4-(methoxyimino)piperidin-1-yl)methanone

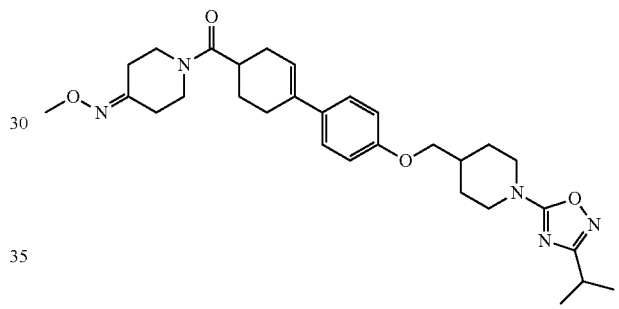

The title compound was prepared in the same manner as in <Example 217>, except that O-methylhydroxylamine hydrochloride was used instead of the hydroxylamine hydrochloride (Amount obtained: 179 mg/Yield: 73%).

$^1$H NMR (400, CDCl$_3$): 7.32 (2H, d), 6.85 (2H, d), 6.05 (1H, d), 4.21 (2H, d), 3.86 (3H, s), 3.83-3.70 (5H, m), 3.63 (1H, m), 3.11 (2H, m), 2.92 (2H, m), 2.62-2.45 (7H, m), 2.40 (1H, m), 2.05-1.93 (5H, m), 1.44 (2H, m), 1.29 (6H, d)

Example 279

Preparation of (4-(4-((1-(3-isopropyl-1,2,4-oxadiazol-5-yl)piperidin-4-yl)methoxy)phenyl)cyclohex-3-enyl)(4-(methoxyimino)piperidin-1-yl)methanone

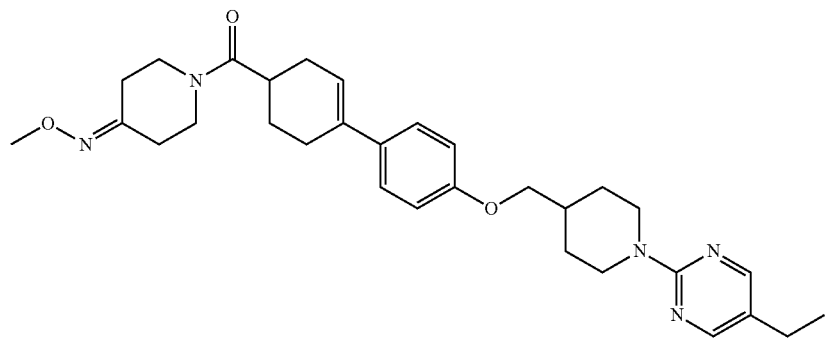 [SMILES: CCc1cnc(N2CCC(COc3ccc(C4=CCC(C(=O)N5CCC(=NOC)CC5)CC4)cc3)CC2)nc1]

The title compound was prepared in the same manner as in <Example 217>, except that O-methylhydroxylamine hydrochloride was used instead of the hydroxylamine hydrochloride (Amount obtained: 173 mg/Yield: 69%).

$^1$H NMR (400, CDCl$_3$): 8.19 (2H, s), 7.31 (2H, d), 6.85 (2H, d), 6.05 (1H, d), 4.77 (2H, d), 3.87 (3H, s), 3.85-3.70 (5H, m), 3.63 (1H, m), 2.95 (2H, m), 2.88 (1H, m), 2.65-2.39 (9H, m), 2.40 (1H, m), 2.00-1.93 (5H, m), 1.33 (2H, m), 1.18 (3H, t)

Example 280

Preparation of tert-butyl 4-((4-(4-(3-oxoazetidine-1-carbonyl)cyclohex-1-enyl)phenoxy)methyl)piperidine-1-carboxylate

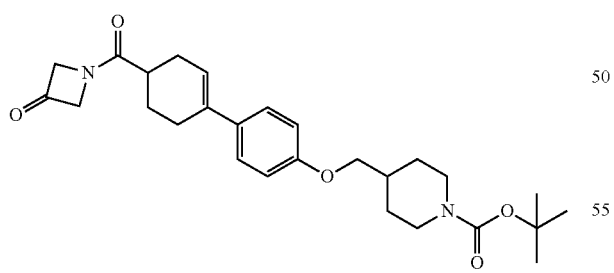

The title compound was prepared in the same manner as in <Example 190>, except that azetidin-3-one hydrochloride was used instead of the 2-aminoethanol (Amount obtained: 172 mg/Yield: 75%).

$^1$H NMR (400, CDCl$_3$): 7.32 (2H, d), 6.84 (2H, d), 6.05 (1H, d), 4.85 (4H, d), 4.16 (2H, s), 3.81 (2H, d), 2.78 (2H, t), 2.63-2.37 (5H, m), 2.10-1.82 (5H, m), 1.48 (9H, s), 1.24 (2H, m)

Example 281

Preparation of tert-butyl 4-((4-(4-(3-(hydroxyimino)azetidine-1-carbonyl)cyclohex-1-enyl)phenoxy)methyl)piperidine-1-carboxylate

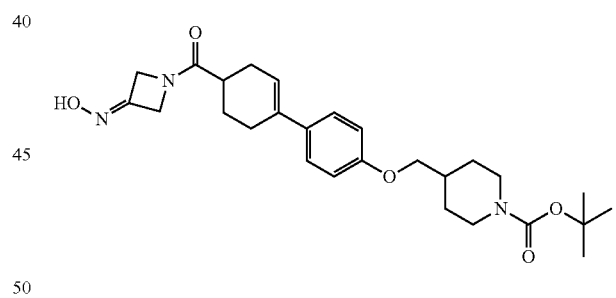

The title compound was prepared in the same manner as in <Example 217>, except that tert-butyl 4-((4-(4-(3-oxoazetidine-1-carbonyl)cyclohex-1-enyl)phenoxy)methyl)piperidine-1-carboxylate was used instead of the 1-(4-(4-((1-(3-isopropyl-1,2,4-oxadiazol-5-yl)piperidin-4-yl)methoxy)phenyl)cyclohex-3-enecarbonyl)piperidine-4-carboxamide (Amount obtained: 167 mg/Yield: 66%).

$^1$H NMR (400, CDCl$_3$): 7.80 (1H, s), 7.31 (2H, d), 6.84 (2H, d), 6.04 (1H, d), 4.89 (2H, d), 4.74 (2H, d), 4.15 (2H, s), 3.87 (2H, d), 2.76 (2H, t), 2.58-2.29 (5H, m), 2.06-1.82 (6H, m), 1.48 (9H, s), 1.27 (2H, m)

Example 282

Preparation of tert-butyl 4-((4-(4-(3-(methoxyimino) azetidine-1-carbonyl)cyclohex-1-enyl)phenoxy) methyl)piperidine-1-carboxylate

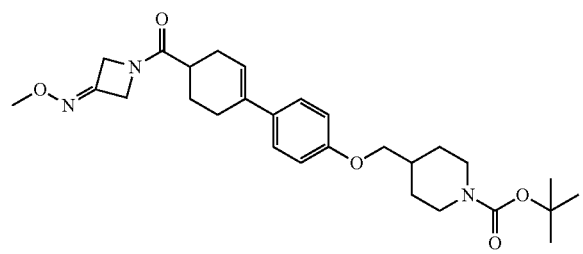 [SMILES: CON=C1CN(C(=O)C2CC=C(c3ccc(OCC4CCN(C(=O)OC(C)(C)C)CC4)cc3)CC2)C1]

The title compound was prepared in the same manner as in <Example 217>, except that O-methylhydroxylamine hydrochloride was used instead of the hydroxylamine hydrochloride (Amount obtained: 175 mg/Yield: 73%).

$^1$H NMR (400, CDCl3): 7.32 (2H, d), 6.84 (2H, d), 6.04 (1H, d), 4.85 (2H, m), 4.69 (2H, d), 4.17 (2H, s), 3.91 (3H, s), 3.82 (2H, d), 2.76 (3H, m), 2.53-2.47 (5H, m), 2.29 (2H, m), 2.09-1.82 (9H, m), 1.48 (9H, s), 1.27 (2H, m)

Example 283

Preparation of 1-(4-(4-((1-(5-ethylpyrimidin-2-yl) piperidin-4-yl)methoxy)phenyl)cyclohex-3-enecarbonyl)azetidin-3-one

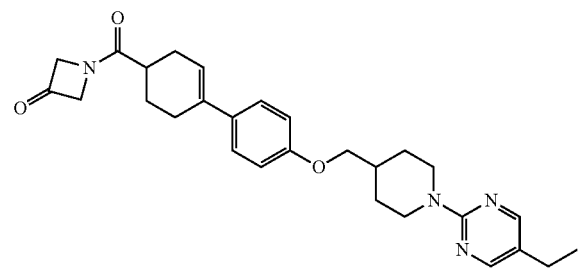 [SMILES: CCc1cnc(N2CCC(COc3ccc(C4=CCC(C(=O)N5CC(=O)C5)CC4)cc3)CC2)nc1]

The title compound was prepared in the same manner as in <Example 152>, except that azetidin-3-one hydrochloride was used instead of the L-β-prolinol (Amount obtained: 175 mg/Yield: 77%).

$^1$H NMR (400, CDCl3): 8.19 (2H, s), 7.32 (2H, d), 6.85 (2H, d), 6.05 (1H, d), 5.02-4.76 (2H, m), 3.85 (2H, d), 2.95 (2H, m), 2.63-2.59 (3H, m), 2.58-2.48 (3H, m), 2.36 (1H, m), 2.11-2.06 (2H, m), 1.98-1.91 (3H, m), 1.34 (2H, m), 1.20 (3H, t)

Example 284

Preparation of 1-(4-(4-((1-(3-isopropyl-1,2,4-oxadiazol-5-yl)piperidin-4-yl)methoxy)phenyl)cyclohex-3-enecarbonyl)azetidin-3-one

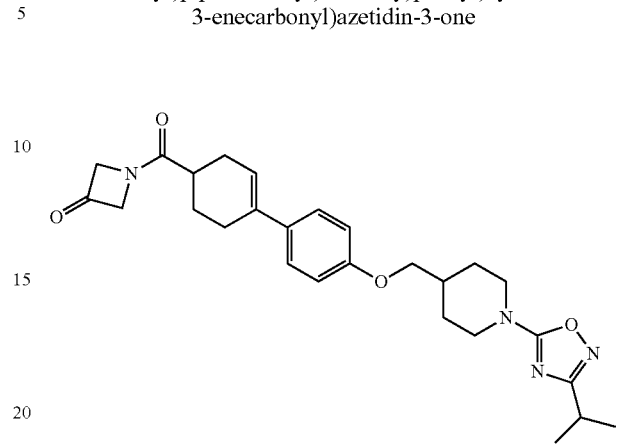

The title compound was prepared in the same manner as in <Example 143>, except that azetidin-3-one hydrochloride was used instead of the (R)-N,N-dimethylpyrrolidine-3-amine hydrochloride (Amount obtained: 180 mg/Yield: 75%).

$^1$H NMR (400, CDCl$_3$): 7.32 (2H, d), 6.85 (2H, d), 6.06 (1H, d), 4.88 (2H, s), 4.83 (2H, s), 4.21 (2H, d), 3.84 (2H, d), 3.12 (2H, m), 2.92 (1H, m), 2.63-2.53 (4H, m), 2.38 (1H, m), 2.07 (2H, m), 1.97-2.91 (3H, m), 1.44 (2H, m), 1.41 (9H, d)

Example 285

Preparation of (3-(hydroxyimino)azetidin-1-yl)(4-(4-((1-(3-isopropyl-1,2,4-oxadiazol-5-yl)piperidin-4-yl)methoxy)phenyl)cyclohex-3-enyl)methanone

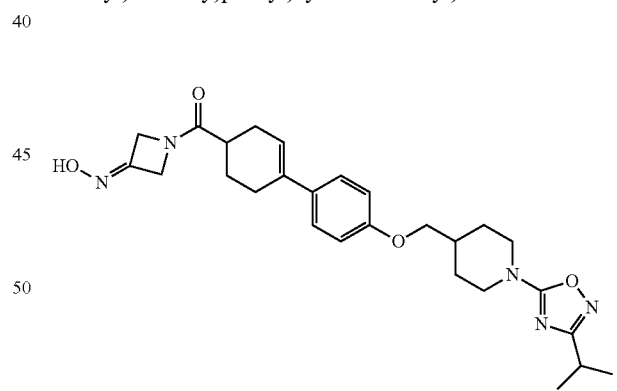

The title compound was prepared in the same manner as in <Example 217>, except that 1-(4-(4-((1-(3-isopropyl-1,2,4-oxadiazol-5-yl)piperidin-4-yl)methoxy)phenyl)cyclohex-3-enecarbonyl)azetidin-3-one was used instead of the 1-(4-(4-((1-(3-isopropyl-1,2,4-oxadiazol-5-yl)piperidin-4-yl)methoxy)phenyl)cyclohex-3-enecarbonyl)piperidine-4-carboxamide (Amount obtained: 184 mg/Yield: 78%).

$^1$H NMR (400, CDCl$_3$): 8.11 (1H, s), 7.32 (2H, d), 6.84 (2H, d), 6.04 (1H, d), 4.87 (2H, d), 4.75 (2H, d), 4.21 (2H, d), 3.84 (2H, d), 3.11 (2H, m), 2.93 (1H, m), 2.58-2.42 (4H, m), 2.30 (1H, m), 2.09-2.02 (2H, m), 1.97-1.89 (3H, m), 1.43 (2H, m), 1.30 (6H, d)

Example 286

Preparation of (4-(4-((1-(3-isopropyl-1,2,4-oxadiazol-5-yl)piperidin-4-yl)methoxy)phenyl)cyclohex-3-enyl)(3-(methoxyimino)azetidin-1-yl)methanone

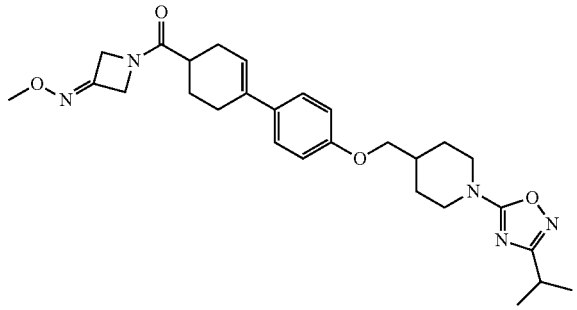 [SMILES: CON=C1CN(C(=O)C2CC=C(c3ccc(OCC4CCN(c5nc(C(C)C)no5)CC4)cc3)CC2)C1]

The title compound was prepared in the same manner as in <Example 217>, except that O-methylhydroxylamine hydrochloride was used instead of the hydroxylamine hydrochloride (Amount obtained: 179 mg/Yield: 71%).

$^1$H NMR (400, CDCl$_3$): 7.32 (2H, d), 6.84 (2H, d), 4.85 (2H, m), 4.69 (2H, m), 4.21 (2H, d), 3.96 (3H, s), 3.84 (2H, d), 3.11 (2H, m), 2.89 (1H, m), 2.59-5.47 (4H, m), 2.29 (1H, m), 2.07-1.89 (5H, m), 1.46 (2H, m), 1.36 (6H, d)

Example 287

Preparation of (4-(4-((1-(5-ethylpyrimidin-2-yl)piperidin-4-yl)methoxy)phenyl)cyclohex-3-enyl)(3-(methoxyimino)azetidin-1-yl)methanone

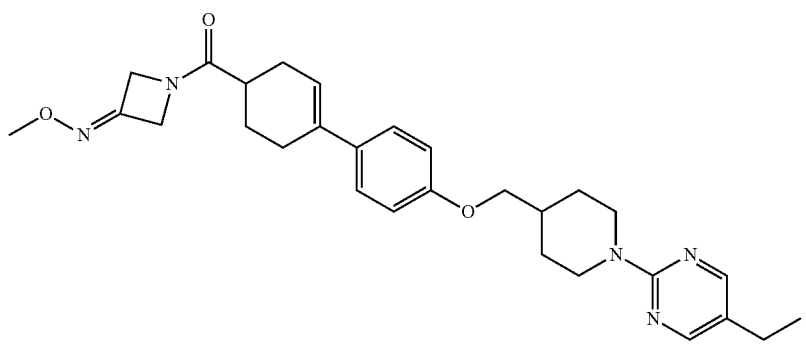 [SMILES: CCc1cnc(N2CCC(COc3ccc(C4=CCC(C(=O)N5CC(=NOC)C5)CC4)cc3)CC2)nc1]

The title compound was prepared in the same manner as in <Example 217>, except that O-methylhydroxylamine hydrochloride was used instead of the hydroxylamine hydrochloride (Amount obtained: 177 mg/Yield: 73%).

$^1$H NMR (400, CDCl$_3$): 8.20 (2H, s), 7.29 (2H, d), 6.85 (2H, d), 6.04 (1H, s), 4.85 (2H, d), 4.79 (2H, d), 4.72 (2H, d), 3.96 (3H, s), 3.84 (2H, d), 2.92 (2H, m), 2.55-2.41 (6H, m), 2.28 (1H, m), 2.14-1.92 (5H, m), 1.39 (2H, m), 1.20 (3H, t)

Example 288

Preparation of tert-butyl 4-((4-(4-(3-hydroxyazetidine-1-carbonyl)cyclohex-1-enyl)phenoxy)methyl)piperidine-1-carboxylate

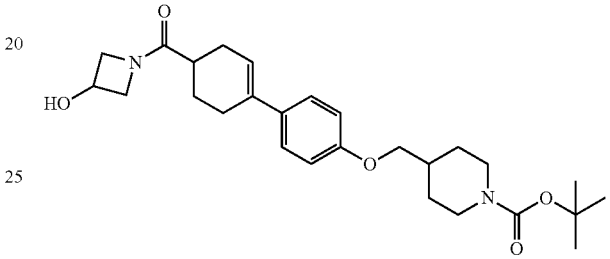

470 mg of tert-butyl 4-((4-(4-(3-oxoazetidine-1-carbonyl)cyclohex-1-enyl)phenoxy)methyl)piperidine-1-carboxylate was dissolved in 100 ml of THF in a 1,000 ml flask while stirring under nitrogen. After the resulting mixture was cooled to a temperature of 5° C., 80 mg of sodium borohydride was slowly added dropwise, and the mixture was then stirred for 5 minutes. After the reaction was terminated, 300 ml of distilled water was slowly added thereto, and the mixture was extracted with 500 ml of ethyl acetate, washed with 100 ml of brine, dried with anhydrous magnesium sulfate, concentrated, and then isolated by silica column chromatography to prepare the title compound (Amount obtained: 432 mg/Yield: 71%).

$^1$H NMR (400, CDCl$_3$): 7.30 (2H, d), 6.84 (2H, d), 6.03 (1H, d), 4.71 (1H, m), 4.42 (1H, t), 4.28-4.07 (4H, m), 3.92 (1H, dd), 3.81 (2H, d), 2.76 (2H, t), 2.63 (1H, d), 2.52-2.43 (4H, m), 2.27 (1H, m), 2.01-1.82 (5H, m), 1.48 (9H, s), 1.26 (2H, m)

Example 289

Preparation of (3-hydroxyazetidin-1-yl)(4-(4-((1-(3-isopropyl-1,2,4-oxadiazol-5-yl)piperidin-4-yl)methoxy)phenyl)cyclohex-3-enyl)methanone

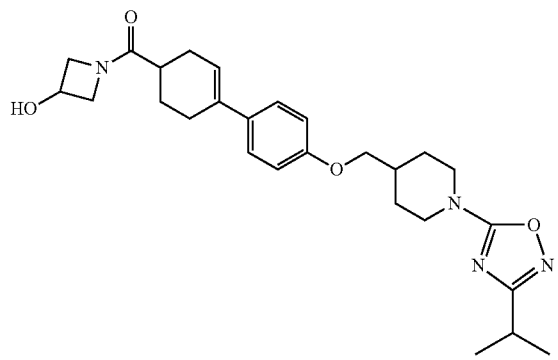 [SMILES: CC(C)c1noc(N2CCC(COc3ccc(C4=CCC(C(=O)N5CC(O)C5)CC4)cc3)CC2)n1]

The title compound was prepared in the same manner as in <Example 288>, except that 1-(4-(4-((1-(3-isopropyl-1,2,4-oxadiazol-5-yl)piperidin-4-yl)methoxy)phenyl)cyclohex-3-enecarbonyl)azetidin-3-one was used instead of the tert-butyl 4-((4-(4-(3-oxoazetidine-1-carbonyl)cyclohex-1-enyl)phenoxy)methyl)piperidine-1-carboxylate (Amount obtained: 402 mg/Yield: 66%).

$^1$H NMR (400, CDCl$_3$): 7.30 (2H, d), 6.84 (2H, d), 6.04 (1H, d), 4.70 (1H, m), 4.43 (1H, t), 4.30 (1H, dd), 4.23 (2H, d), 4.09 (1H, m), 3.92 (1H, dd), 3.84 (2H, m), 3.14 (2H, m), 2.97 (2H, d), 2.88 (1H, m), 2.55 (1H, m), 2.53-2.43 (3H, m), 2.27 (1H, m), 2.07-2.02 (1H, m), 1.94 (3H, m), 1.84 (1H, m), 1.44 (2H, m), 1.31 (6H, d)

Comparative Example 1

Preparation of N-(2-fluoro-4-methylsulfonylphenyl)-5-nitro-6-[4-(3-propan-2-yl-1,2,4-oxadiazol-5-yl)piperidin-1-yl]pyrimidine-4-amine

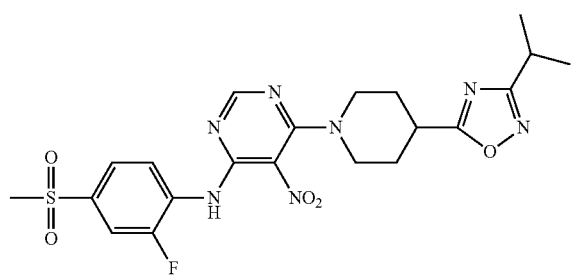 [SMILES: CC(C)c1noc(C2CCN(c3ncnc(Nc4ccc(S(C)(=O)=O)cc4F)c3[N+](=O)[O-])CC2)n1]

N-(2-fluoro-4-methyl sulfonylphenyl)-5-nitro-6-[4-(3-propan-2-yl-1,2,4-oxadiazol-5-yl)piperidin-1-yl]pyrimidine-4-amine was prepared using a method known in International Publication No. WO 2004/065380.

Comparative Example 2

Preparation of 2-(4-methanesulfonylphenyl)-5-({1-[3-(propan-2-yl)-1,2,4-oxadiazol-5-yl]piperidin-4-yl}methoxy)pyridine

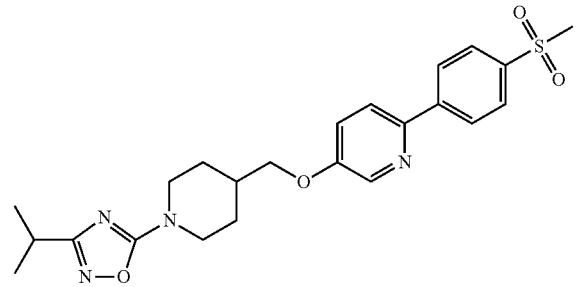 [SMILES: CC(C)c1noc(N2CCC(COc3ccc(-c4ccc(S(C)(=O)=O)cc4)nc3)CC2)n1]

2-(4-Methanesulfonylphenyl)-5-({1-[3-(propan-2-yl)-1,2,4-oxadiazol-5-yl]piperidin-4-yl}methoxy)pyridine was prepared using a method known in International Publication No. WO 2008/070692.

Comparative Example 3

Preparation of Metformin

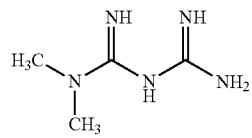

Metformin was prepared using a method known in International Publication No. WO 2010/146604 A2.

Comparative Example 4

Preparation of Sibutramine

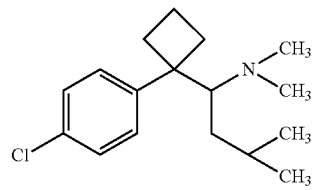 [SMILES: CC(C)CC(N(C)C)C1(c2ccc(Cl)cc2)CCC1]

Sibutramine was prepared using a method known in International Publication No. WO 2002/083631 A1.

Comparative Example 5
Preparation of Forskolin
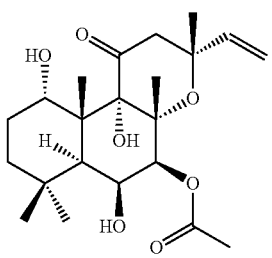
Forskolin was prepared using a method known in International Publication No. WO 1991/017154 A1.
The chemical structures of the compounds prepared in Examples 1 to 466 are summarized and listed in the following Table 1. In Table 1, the group '-Boc' is
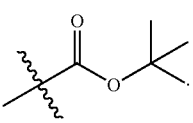
TABLE 1
| Examples | Chemical structures |
|---|---|
| 1 | 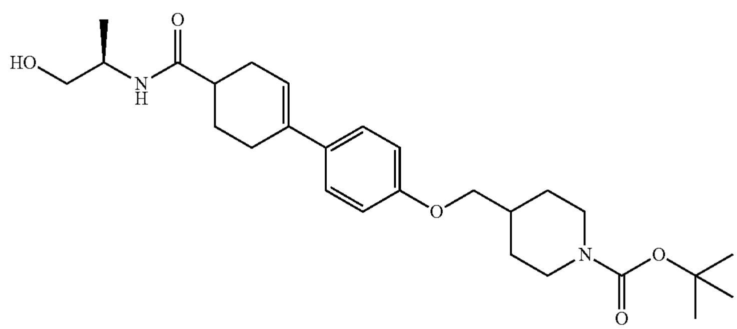 [SMILES: C[C@H](CO)NC(=O)C1CC=C(c2ccc(OCC3CCN(C(=O)OC(C)(C)C)CC3)cc2)CC1] |
| 2 | 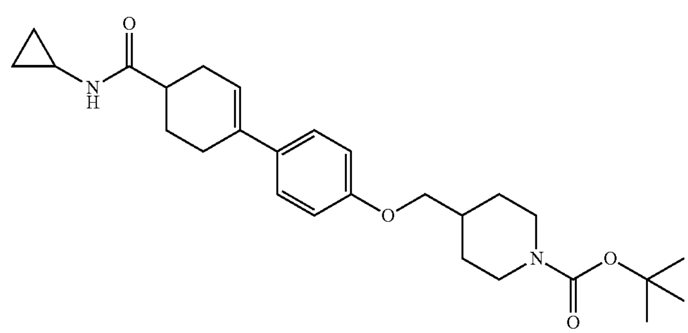 [SMILES: CC(C)(C)OC(=O)N1CCC(COc2ccc(C3=CCC(C(=O)NC4CC4)CC3)cc2)CC1] |
| 3 | 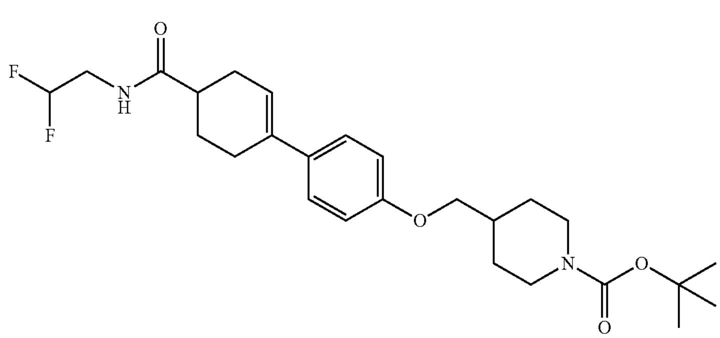 [SMILES: CC(C)(C)OC(=O)N1CCC(COc2ccc(C3=CCC(C(=O)NCC(F)F)CC3)cc2)CC1] |

TABLE 1-continued
| Examples | Chemical structures |
|---|---|
| 4 | 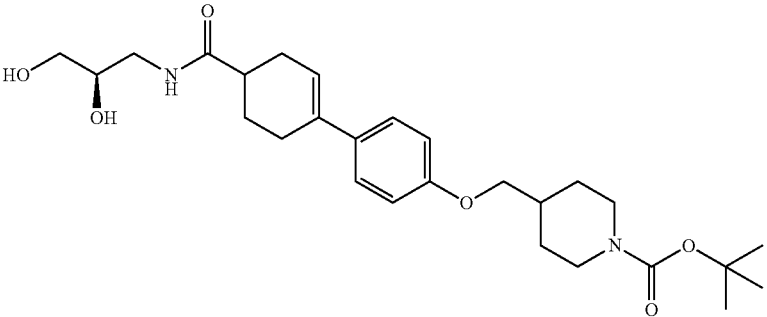 |
| 5 | 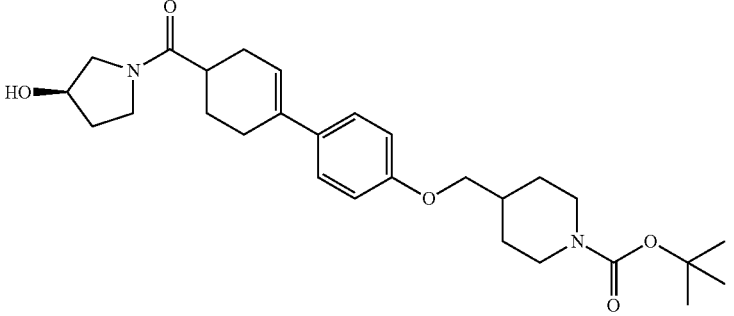 [SMILES: CC(C)(C)OC(=O)N1CCC(COc2ccc(C3=CCC(C(=O)N4CC[C@@H](O)C4)CC3)cc2)CC1] |
| 6 | 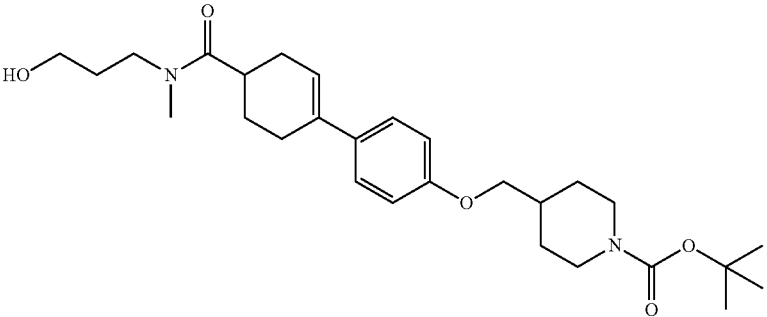 [SMILES: CN(CCCO)C(=O)C1CC=C(c2ccc(OCC3CCN(C(=O)OC(C)(C)C)CC3)cc2)CC1] |
| 7 | 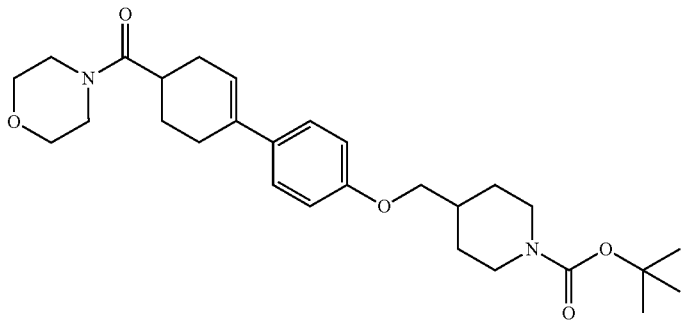 [SMILES: CC(C)(C)OC(=O)N1CCC(COc2ccc(C3=CCC(C(=O)N4CCOCC4)CC3)cc2)CC1] |

TABLE 1-continued
| Examples | Chemical structures |
|---|---|
| 8 | 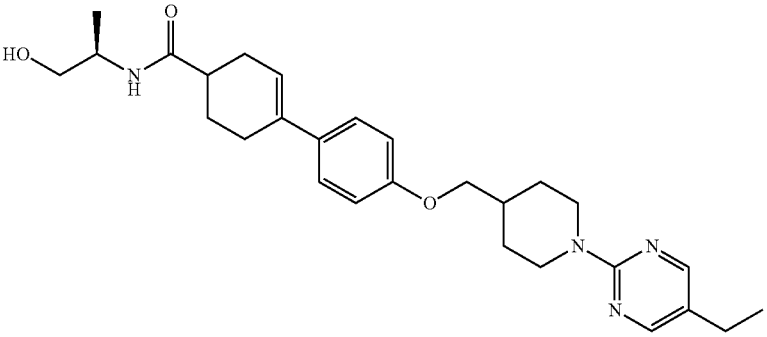 [SMILES: CCc1cnc(N2CCC(COc3ccc(C4=CCC(C(=O)N[C@H](C)CO)CC4)cc3)CC2)nc1] |
| 9 | 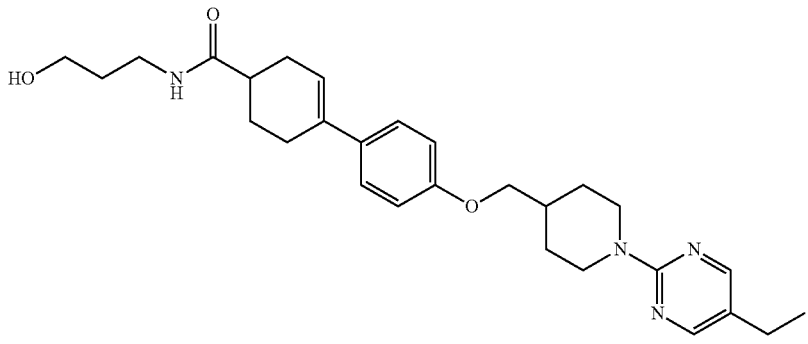 [SMILES: CCc1cnc(N2CCC(COc3ccc(C4=CCC(C(=O)NCCCO)CC4)cc3)CC2)nc1] |
| 10 | 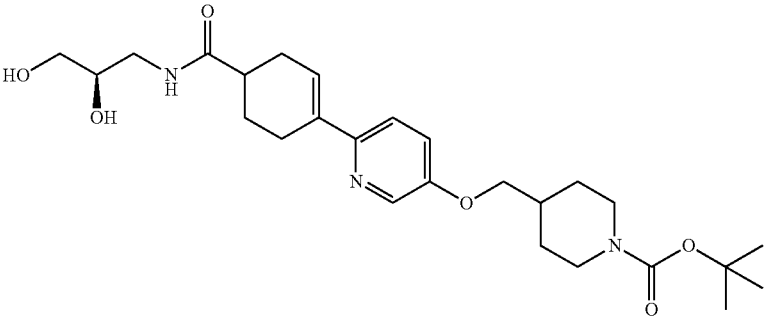 [SMILES: CC(C)(C)OC(=O)N1CCC(COc2ccc(C3=CCC(C(=O)NC[C@@H](O)CO)CC3)nc2)CC1] |
| 11 | 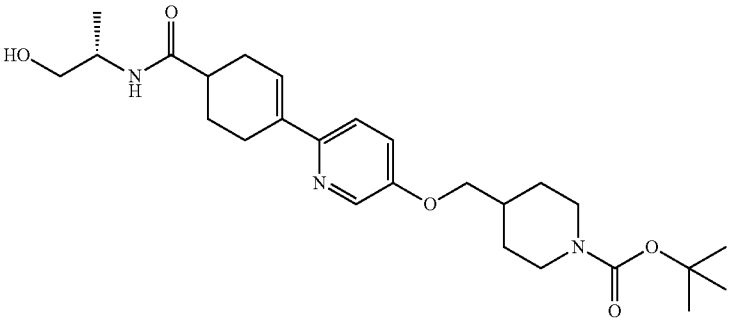 [SMILES: C[C@@H](CO)NC(=O)C1CC=C(c2ccc(OCC3CCN(C(=O)OC(C)(C)C)CC3)cn2)CC1] |

TABLE 1-continued
| Examples | Chemical structures |
|---|---|
| 12 | 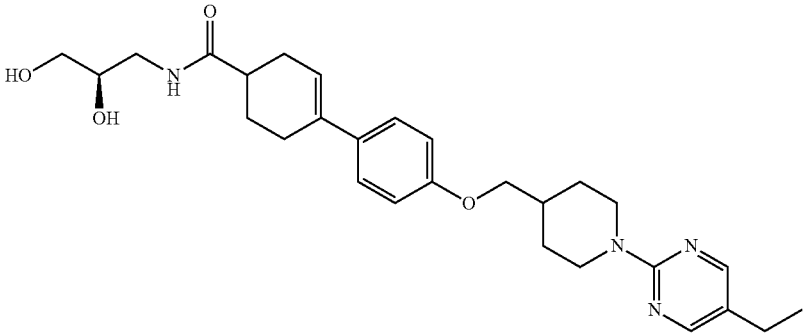 [SMILES: CCc1cnc(N2CCC(COc3ccc(C4=CCC(C(=O)NC[C@@H](O)CO)CC4)cc3)CC2)nc1] |
| 13 | 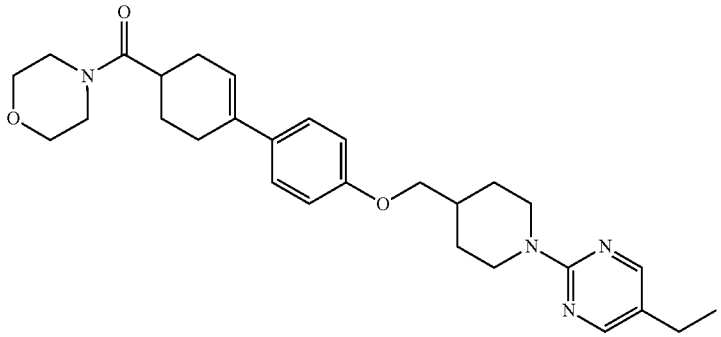 [SMILES: CCc1cnc(N2CCC(COc3ccc(C4=CCC(C(=O)N5CCOCC5)CC4)cc3)CC2)nc1] |
| 14 | 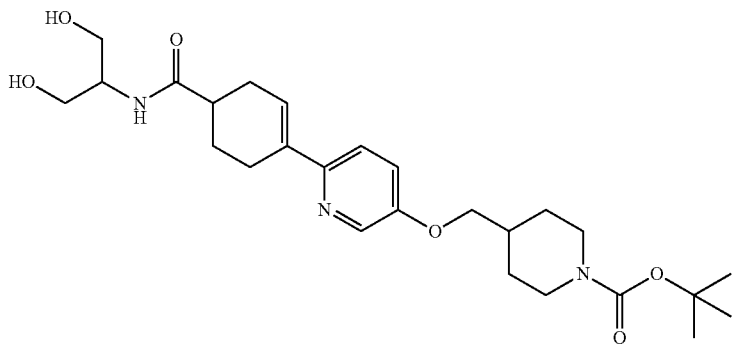 [SMILES: CC(C)(C)OC(=O)N1CCC(COc2ccc(C3=CCC(C(=O)NC(CO)CO)CC3)nc2)CC1] |
| 15 | 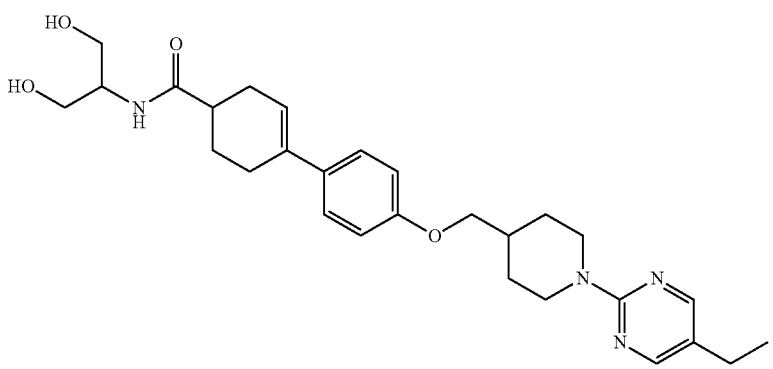 [SMILES: CCc1cnc(N2CCC(COc3ccc(C4=CCC(C(=O)NC(CO)CO)CC4)cc3)CC2)nc1] |

TABLE 1-continued

| Examples | Chemical structures |
|---|---|
| 16 | 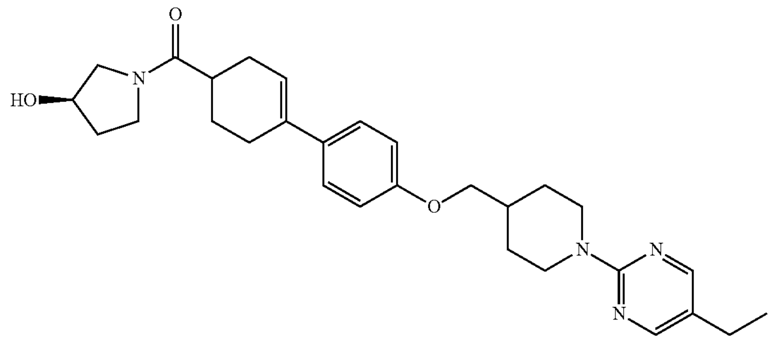 [SMILES: CCc1cnc(N2CCC(COc3ccc(C4=CCC(C(=O)N5CC[C@@H](O)C5)CC4)cc3)CC2)nc1] |
| 17 | 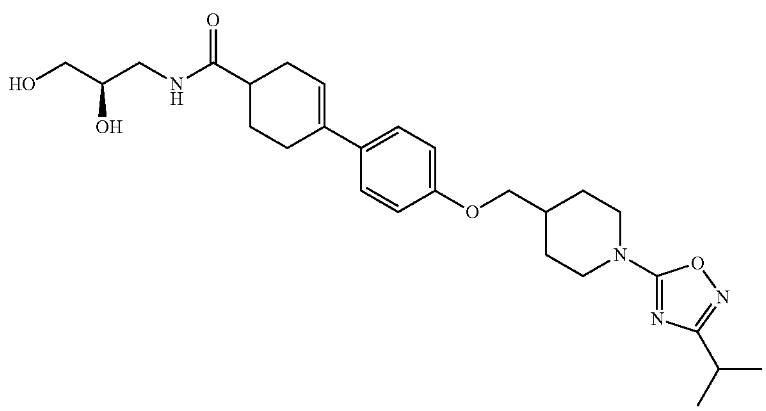 |
| 18 | 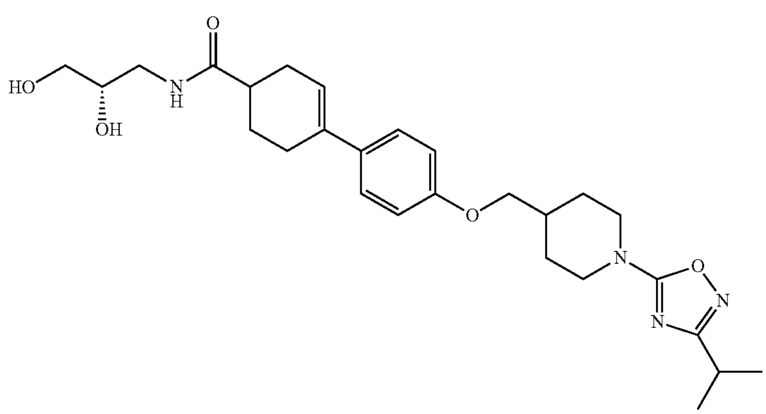 |
| 19 | 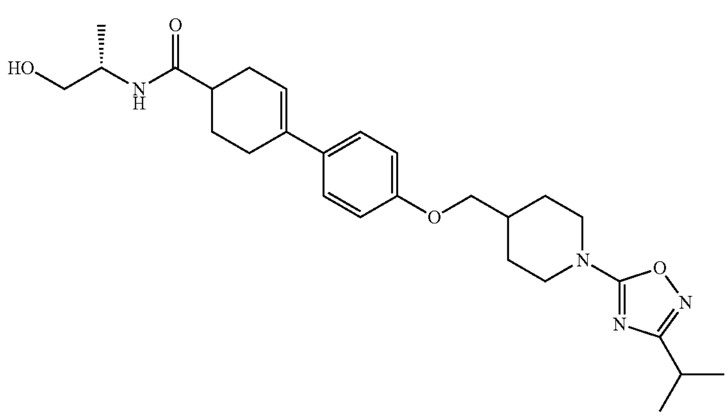 [SMILES: CC(C)c1noc(N2CCC(COc3ccc(C4=CCC(C(=O)N[C@@H](C)CO)CC4)cc3)CC2)n1] |

TABLE 1-continued
| Examples | Chemical structures |
|---|---|
| 20 | 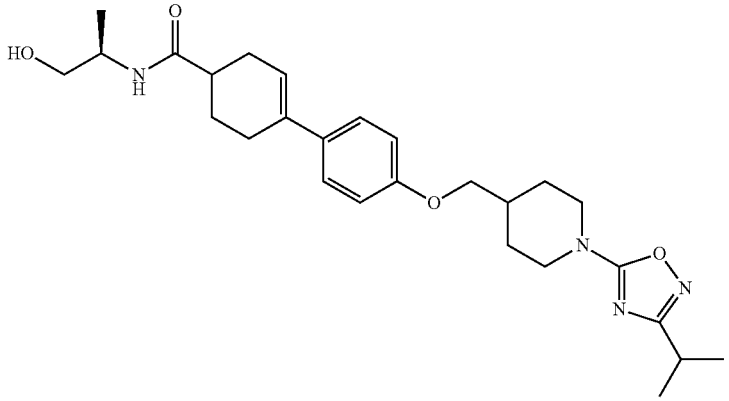 [SMILES: CC(C)c1noc(N2CCC(COc3ccc(C4=CCC(C(=O)N[C@H](C)CO)CC4)cc3)CC2)n1] |
| 21 | 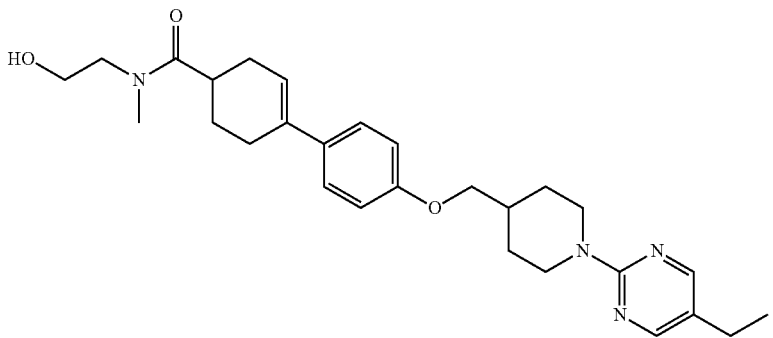 [SMILES: CCc1cnc(N2CCC(COc3ccc(C4=CCC(C(=O)N(C)CCO)CC4)cc3)CC2)nc1] |
| 22 | 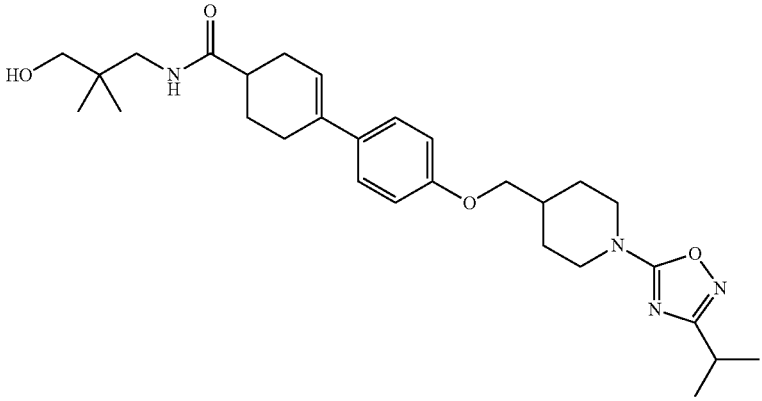 [SMILES: CC(C)c1noc(N2CCC(COc3ccc(C4=CCC(C(=O)NCC(C)(C)CO)CC4)cc3)CC2)n1] |
| 23 | 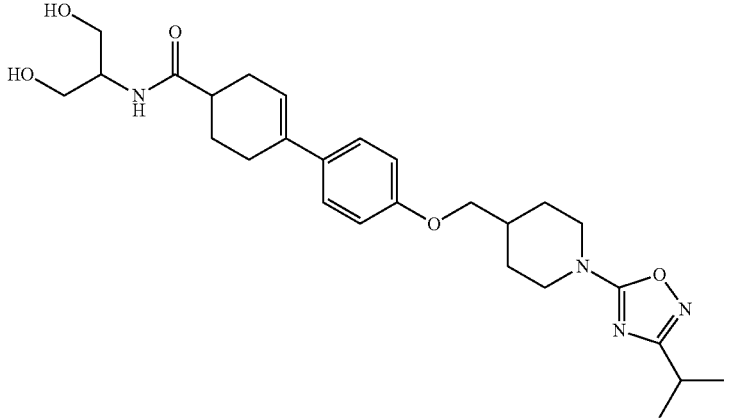 |

TABLE 1-continued
| Examples | Chemical structures |
|---|---|
| 24 | 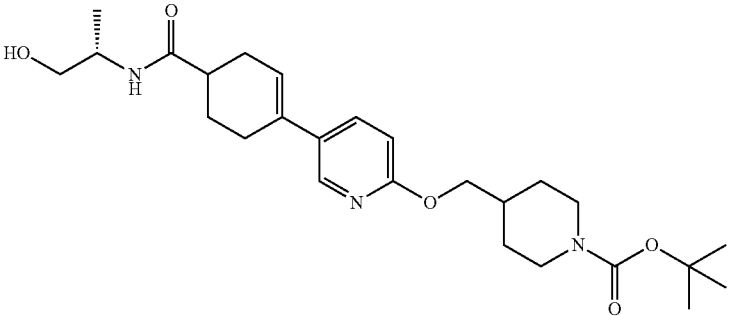 [SMILES: C[C@@H](CO)NC(=O)C1CC=C(c2ccc(OCC3CCN(C(=O)OC(C)(C)C)CC3)nc2)CC1] |
| 25 | 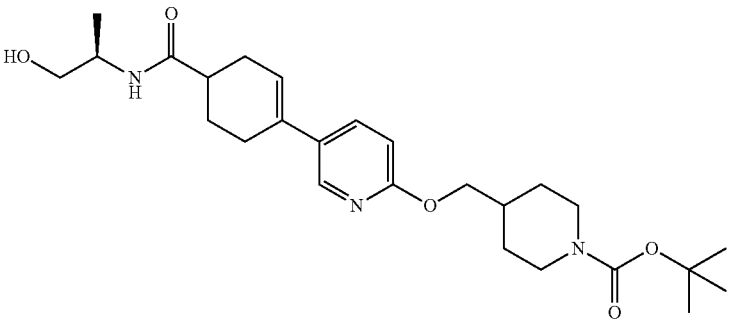 [SMILES: C[C@H](CO)NC(=O)C1CC=C(c2ccc(OCC3CCN(C(=O)OC(C)(C)C)CC3)nc2)CC1] |
| 26 | 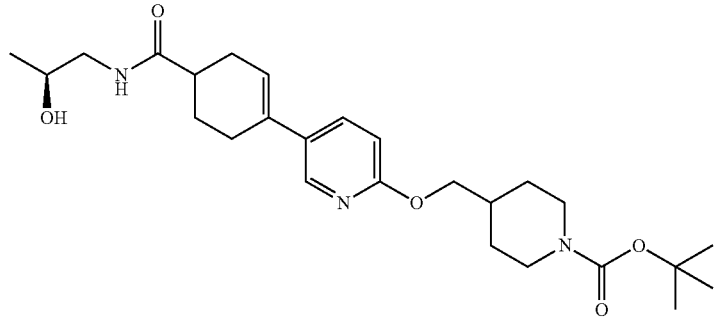 [SMILES: C[C@H](O)CNC(=O)C1CC=C(c2ccc(OCC3CCN(C(=O)OC(C)(C)C)CC3)nc2)CC1] |
| 27 | 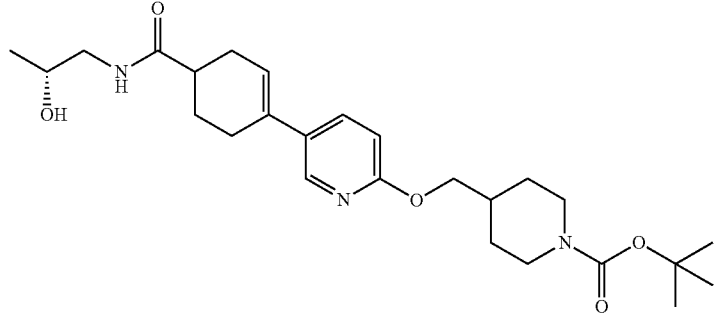 [SMILES: C[C@@H](O)CNC(=O)C1CC=C(c2ccc(OCC3CCN(C(=O)OC(C)(C)C)CC3)nc2)CC1] |

TABLE 1-continued

| Examples | Chemical structures |
|---|---|
| 28 | (S)-N-(2-hydroxypropyl)-4'-((1-(3-isopropyl-1,2,4-oxadiazol-5-yl)piperidin-4-yl)methoxy)-2,3,4,5-tetrahydro-[1,1'-biphenyl]-4-carboxamide |
| 29 | (R)-N-(2-hydroxypropyl)-4'-((1-(3-isopropyl-1,2,4-oxadiazol-5-yl)piperidin-4-yl)methoxy)-2,3,4,5-tetrahydro-[1,1'-biphenyl]-4-carboxamide |
| 30 | (R)-4'-((1-(5-ethylpyrimidin-2-yl)piperidin-4-yl)methoxy)-N-(2-hydroxypropyl)-2,3,4,5-tetrahydro-[1,1'-biphenyl]-4-carboxamide |
| 31 | N-(2-hydroxyethyl)-4'-((1-(3-isopropyl-1,2,4-oxadiazol-5-yl)piperidin-4-yl)methoxy)-2,3,4,5-tetrahydro-[1,1'-biphenyl]-4-carboxamide |

TABLE 1-continued

| Examples | Chemical structures |
|---|---|
| 32 | 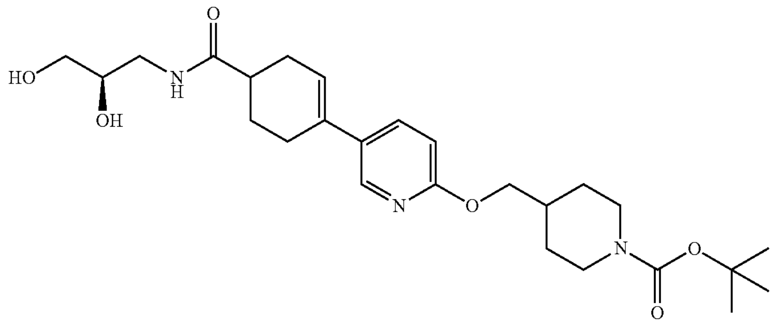 [SMILES: CC(C)(C)OC(=O)N1CCC(COc2ccc(C3=CCC(C(=O)NC[C@@H](O)CO)CC3)cn2)CC1] |
| 33 | 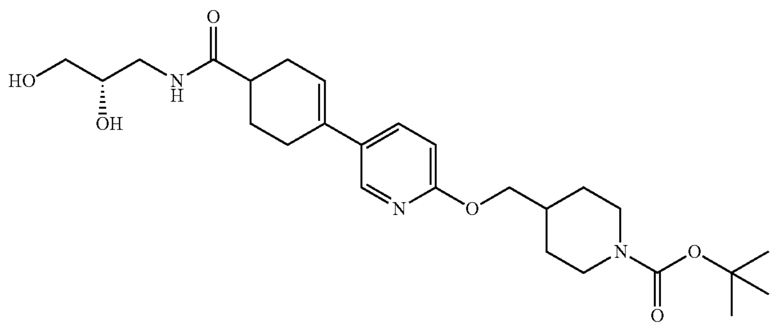 [SMILES: CC(C)(C)OC(=O)N1CCC(COc2ccc(C3=CCC(C(=O)NC[C@H](O)CO)CC3)cn2)CC1] |
| 34 | 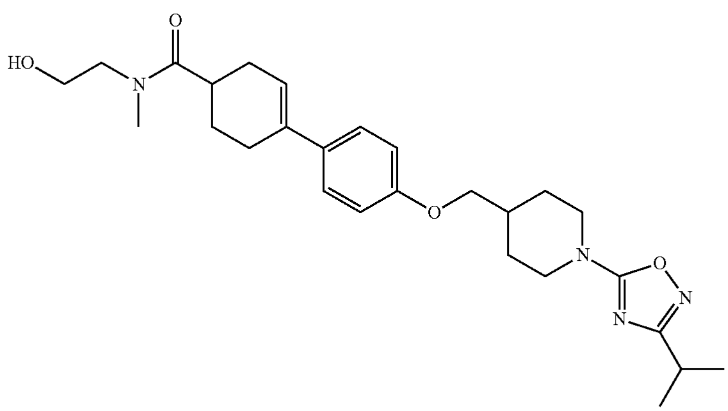 [SMILES: CC(C)c1noc(N2CCC(COc3ccc(C4=CCC(C(=O)N(C)CCO)CC4)cc3)CC2)n1] |
| 35 | 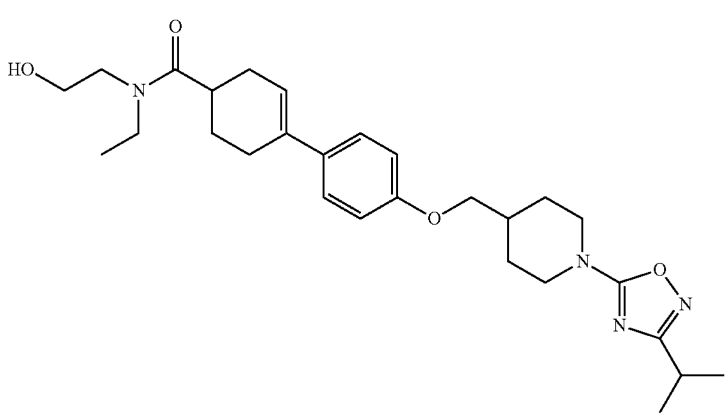 [SMILES: CCN(CCO)C(=O)C1CC=C(c2ccc(OCC3CCN(c4nc(C(C)C)no4)CC3)cc2)CC1] |

TABLE 1-continued

| Examples | Chemical structures |
|---|---|
| 36 | 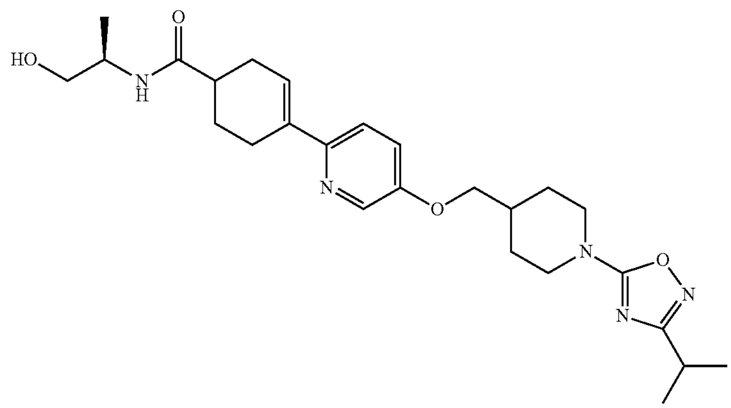 [SMILES: CC(C)c1noc(N2CCC(COc3ccc(C4=CCC(C(=O)N[C@H](C)CO)CC4)nc3)CC2)n1] |
| 37 | 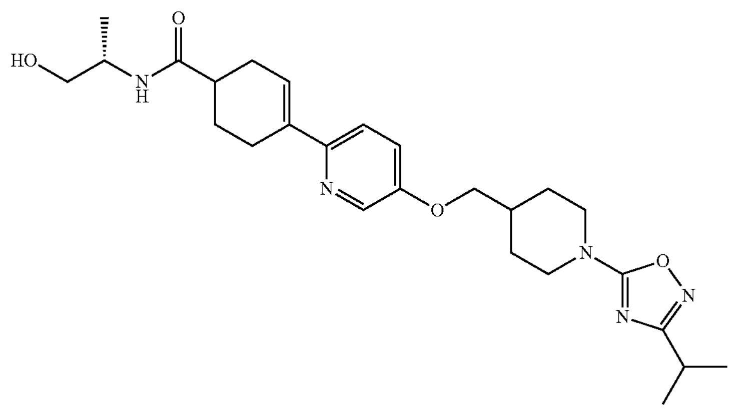 [SMILES: CC(C)c1noc(N2CCC(COc3ccc(C4=CCC(C(=O)N[C@@H](C)CO)CC4)nc3)CC2)n1] |
| 38 | 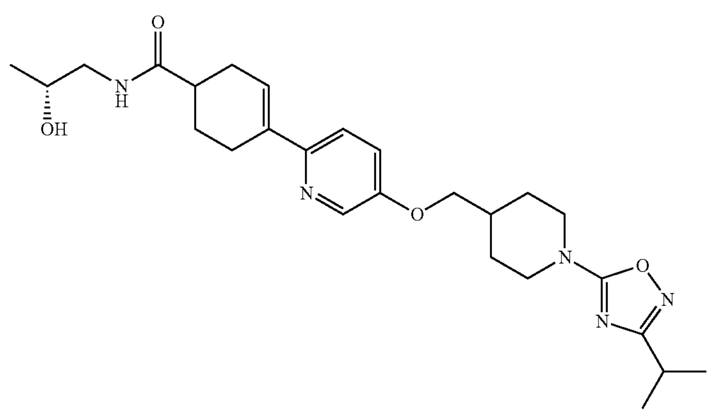 |
| 39 | 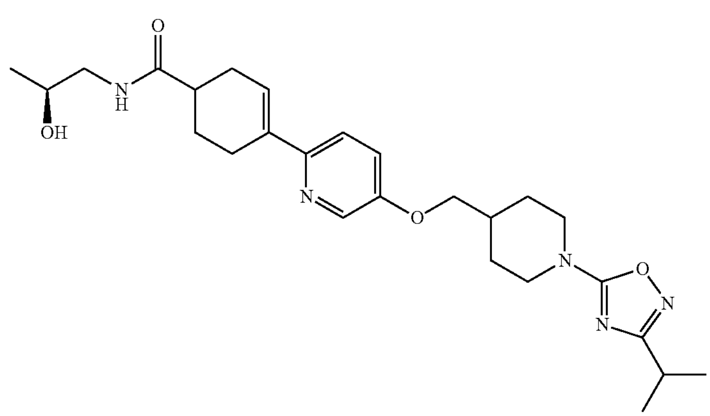 |

TABLE 1-continued

| Examples | Chemical structures |
|---|---|
| 40 | 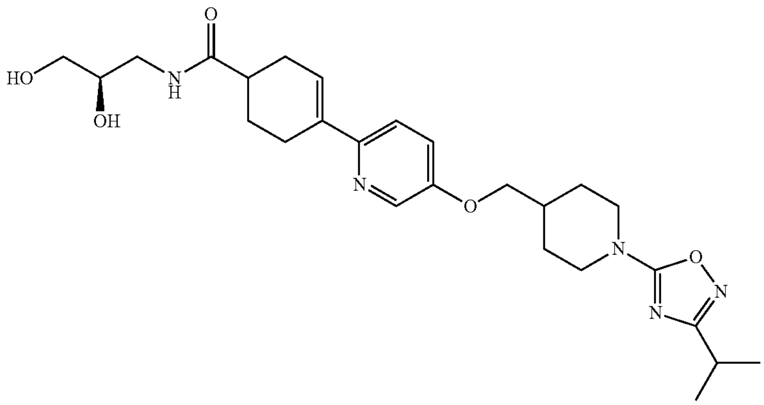 [SMILES: CC(C)c1noc(N2CCC(COc3ccc(C4=CCC(C(=O)NC[C@@H](O)CO)CC4)nc3)CC2)n1] |
| 41 | 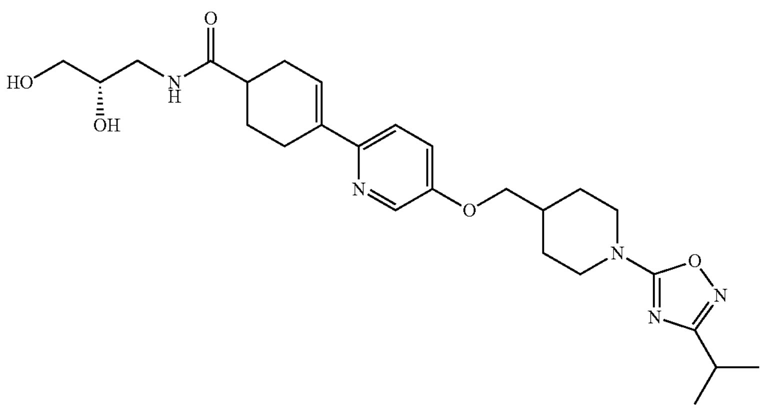 [SMILES: CC(C)c1noc(N2CCC(COc3ccc(C4=CCC(C(=O)NC[C@H](O)CO)CC4)nc3)CC2)n1] |
| 42 | 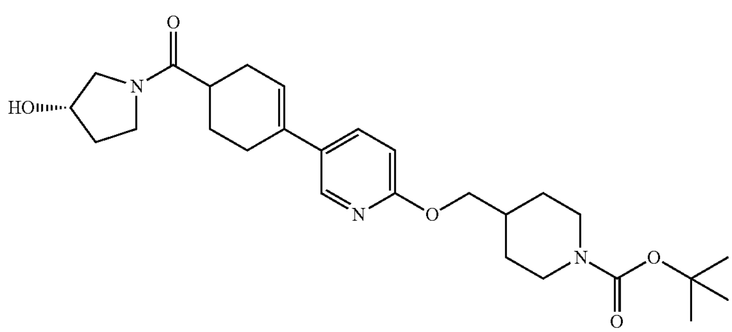 [SMILES: CC(C)(C)OC(=O)N1CCC(COc2ccc(C3=CCC(C(=O)N4CC[C@H](O)C4)CC3)cn2)CC1] |
| 43 | 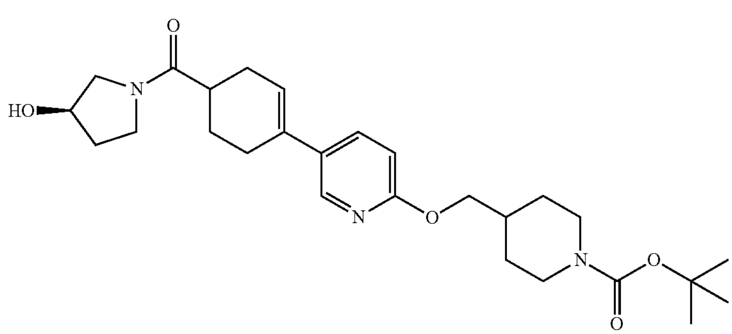 [SMILES: CC(C)(C)OC(=O)N1CCC(COc2ccc(C3=CCC(C(=O)N4CC[C@@H](O)C4)CC3)cn2)CC1] |

TABLE 1-continued

| Examples | Chemical structures |
|---|---|
| 44 | 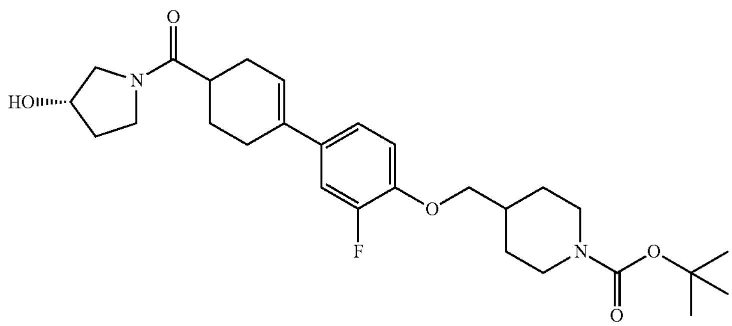 [SMILES: CC(C)(C)OC(=O)N1CCC(COc2ccc(C3=CCC(C(=O)N4CC[C@H](O)C4)CC3)cc2F)CC1] |
| 45 | 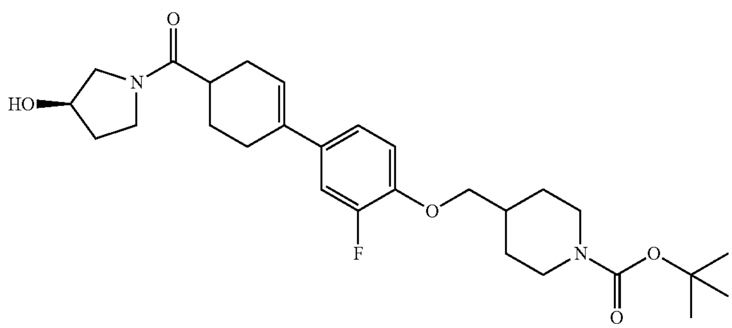 [SMILES: CC(C)(C)OC(=O)N1CCC(COc2ccc(C3=CCC(C(=O)N4CC[C@@H](O)C4)CC3)cc2F)CC1] |
| 46 | 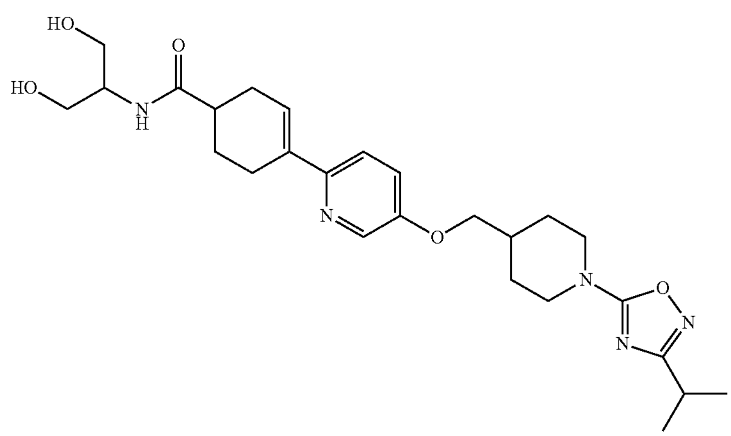 [SMILES: CC(C)c1noc(N2CCC(COc3ccc(C4=CCC(C(=O)NC(CO)CO)CC4)nc3)CC2)n1] |
| 47 | 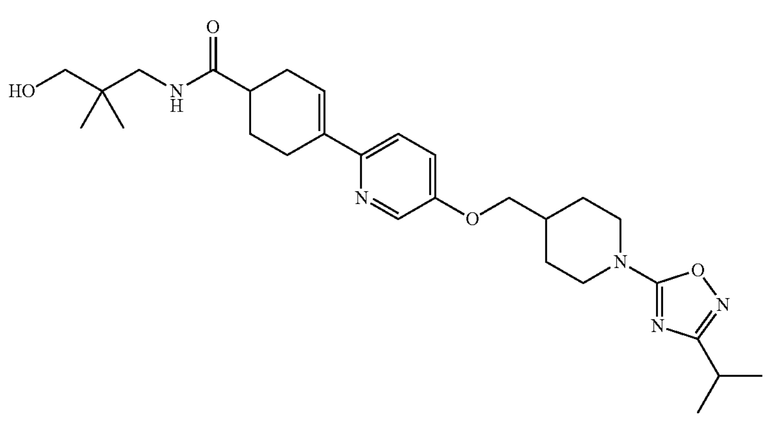 |

TABLE 1-continued
| Examples | Chemical structures |
|---|---|
| 48 | 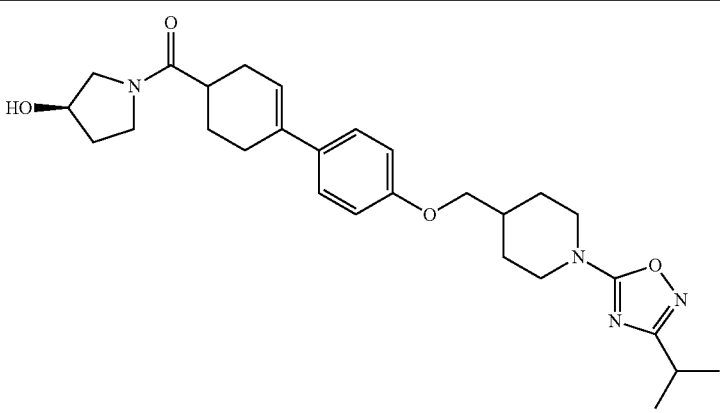 |
| 49 | 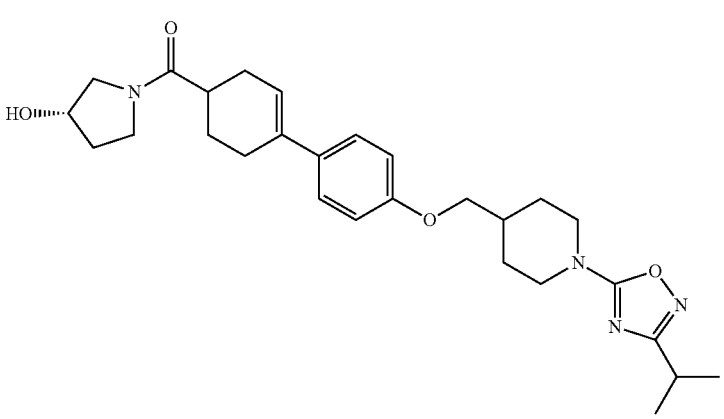 [SMILES: CC(C)c1noc(N2CCC(COc3ccc(C4=CCC(C(=O)N5CC[C@H](O)C5)CC4)cc3)CC2)n1] |
| 50 | 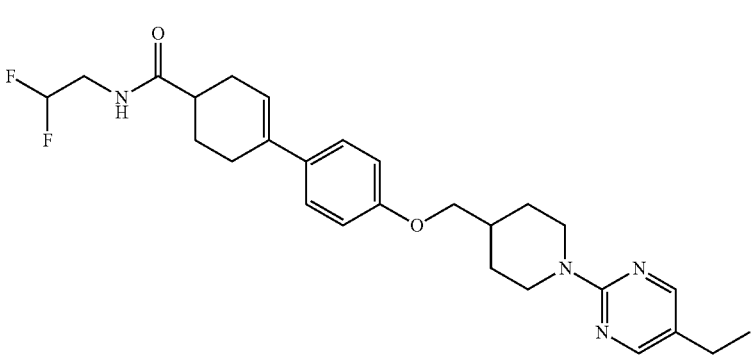 [SMILES: CCc1cnc(N2CCC(COc3ccc(C4=CCC(C(=O)NCC(F)F)CC4)cc3)CC2)nc1] |
| 51 | 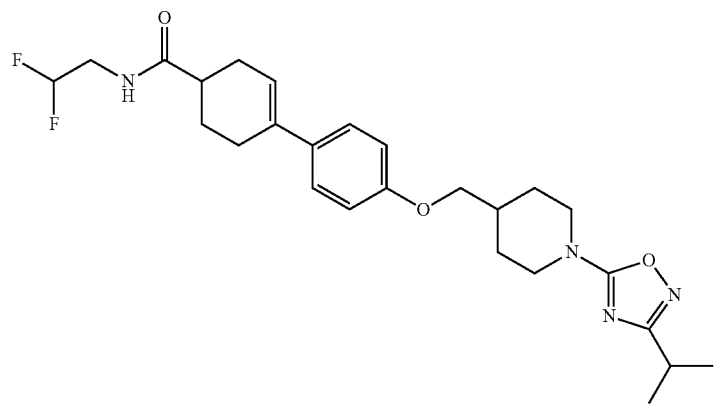 |

TABLE 1-continued

| Examples | Chemical structures |
| --- | --- |
| 52 | 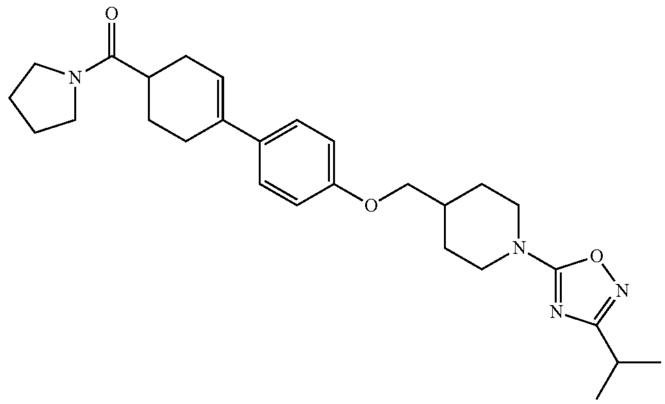 [SMILES: CC(C)c1noc(N2CCC(COc3ccc(C4=CCC(C(=O)N5CCCC5)CC4)cc3)CC2)n1] |
| 53 | 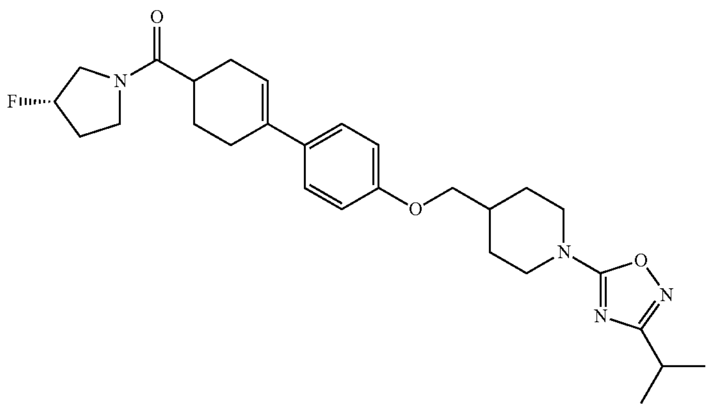 [SMILES: CC(C)c1noc(N2CCC(COc3ccc(C4=CCC(C(=O)N5CC[C@H](F)C5)CC4)cc3)CC2)n1] |
| 54 | 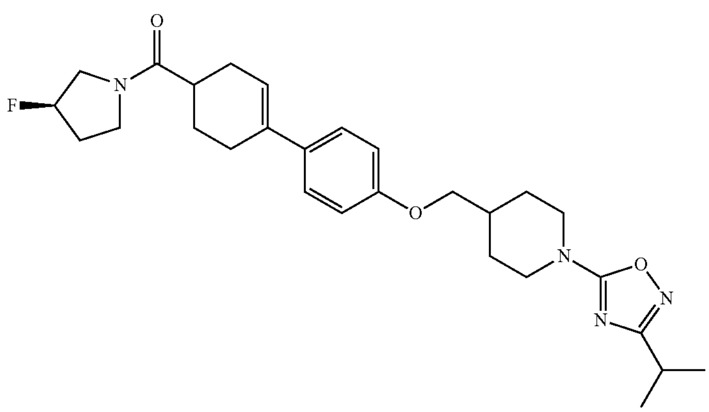 [SMILES: CC(C)c1noc(N2CCC(COc3ccc(C4=CCC(C(=O)N5CC[C@@H](F)C5)CC4)cc3)CC2)n1] |
| 55 | 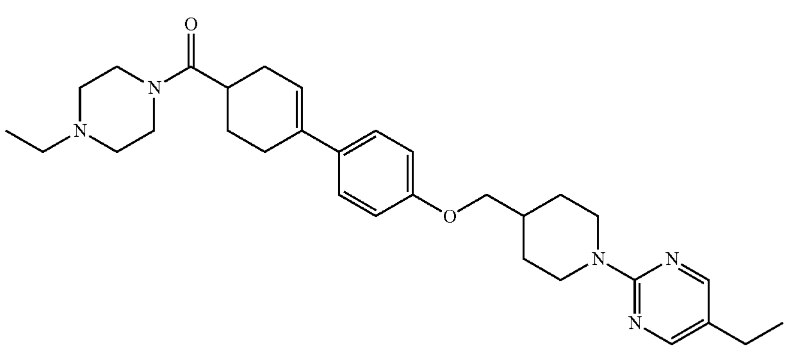 [SMILES: CCc1cnc(N2CCC(COc3ccc(C4=CCC(C(=O)N5CCN(CC)CC5)CC4)cc3)CC2)nc1] |

TABLE 1-continued
| Examples | Chemical structures |
|---|---|
| 56 | 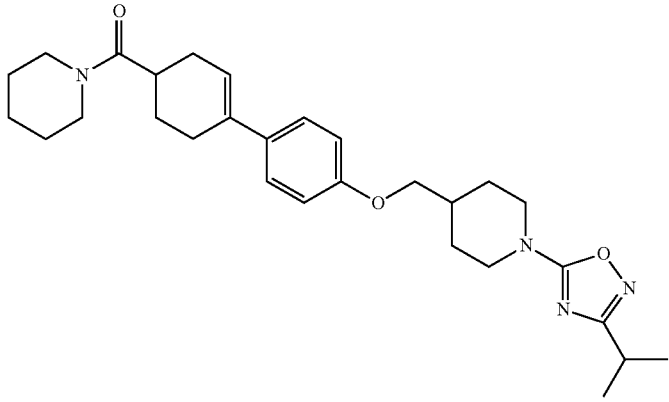 [SMILES: CC(C)c1noc(N2CCC(COc3ccc(C4=CCC(C(=O)N5CCCCC5)CC4)cc3)CC2)n1] |
| 57 | 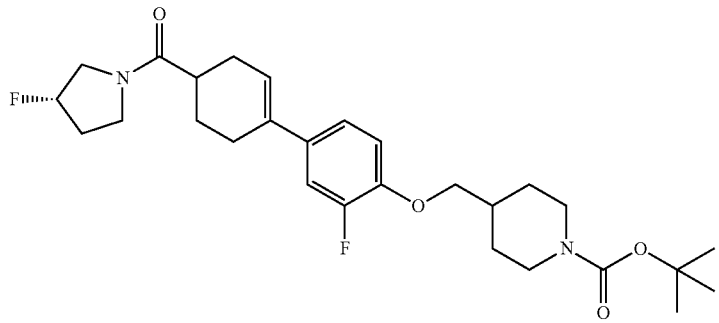 [SMILES: CC(C)(C)OC(=O)N1CCC(COc2ccc(C3=CCC(C(=O)N4CC[C@H](F)C4)CC3)cc2F)CC1] |
| 58 | 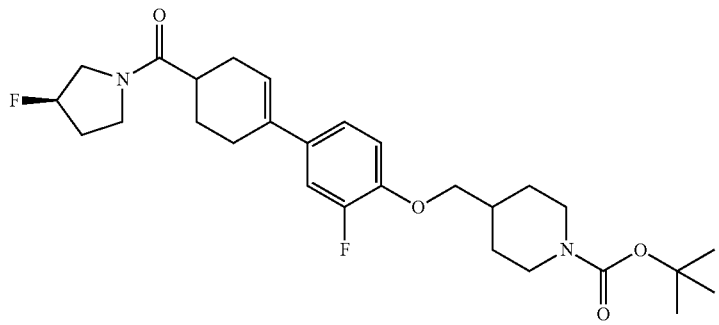 [SMILES: CC(C)(C)OC(=O)N1CCC(COc2ccc(C3=CCC(C(=O)N4CC[C@@H](F)C4)CC3)cc2F)CC1] |
| 59 | 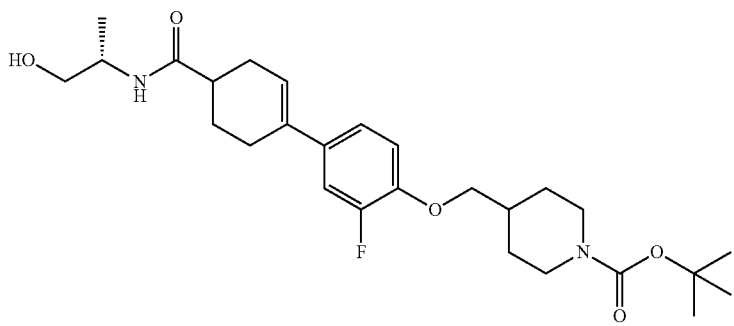 [SMILES: C[C@@H](CO)NC(=O)C1CC=C(c2ccc(OCC3CCN(C(=O)OC(C)(C)C)CC3)c(F)c2)CC1] |

TABLE 1-continued
| Examples | Chemical structures |
|---|---|
| 60 | 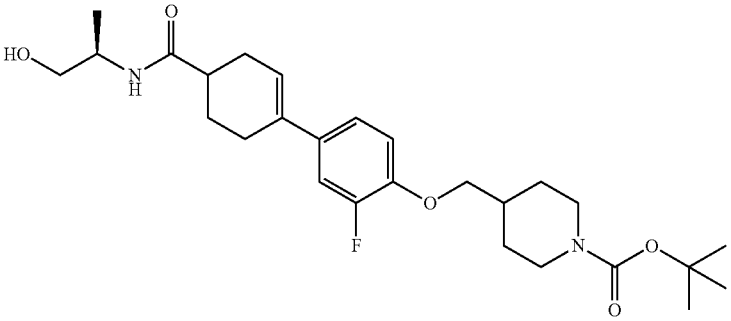 [SMILES: C[C@H](CO)NC(=O)C1CC=C(c2ccc(OCC3CCN(C(=O)OC(C)(C)C)CC3)c(F)c2)CC1] |
| 61 | 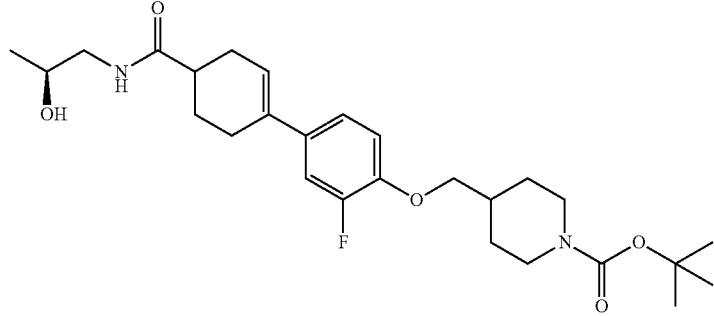 [SMILES: C[C@H](O)CNC(=O)C1CC=C(c2ccc(OCC3CCN(C(=O)OC(C)(C)C)CC3)c(F)c2)CC1] |
| 62 | 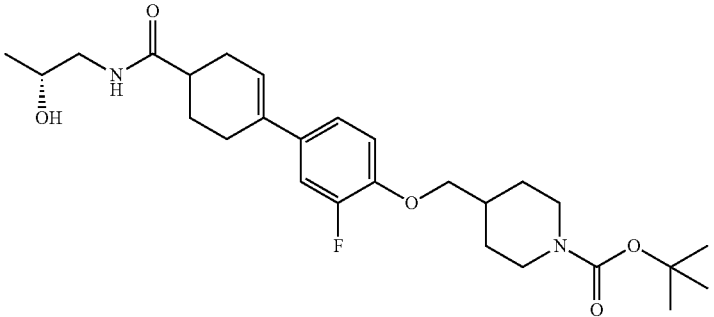 [SMILES: C[C@@H](O)CNC(=O)C1CC=C(c2ccc(OCC3CCN(C(=O)OC(C)(C)C)CC3)c(F)c2)CC1] |
| 63 | 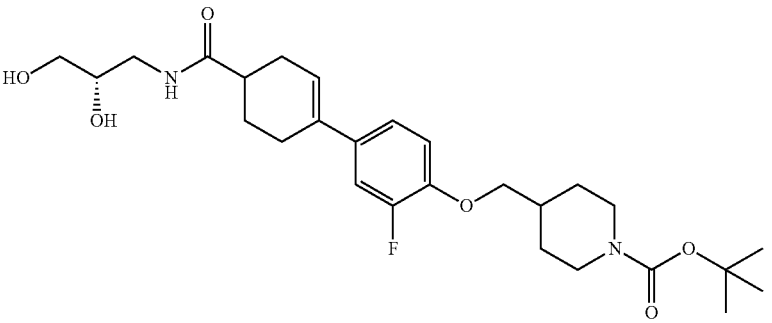 [SMILES: CC(C)(C)OC(=O)N1CCC(COc2ccc(C3=CCC(C(=O)NC[C@H](O)CO)CC3)cc2F)CC1] |

TABLE 1-continued

| Examples | Chemical structures |
|---|---|
| 64 | 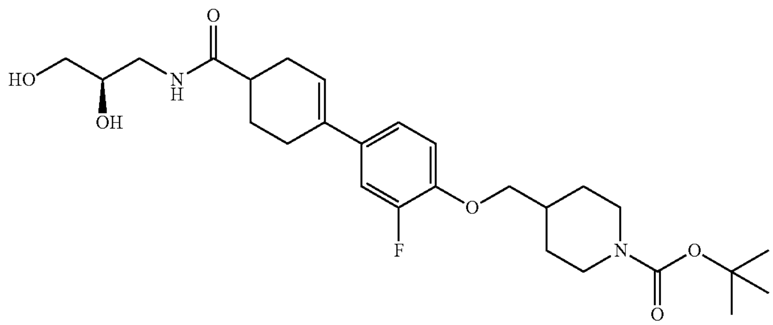 [SMILES: CC(C)(C)OC(=O)N1CCC(COc2ccc(C3=CCC(C(=O)NC[C@@H](O)CO)CC3)cc2F)CC1] |
| 65 | 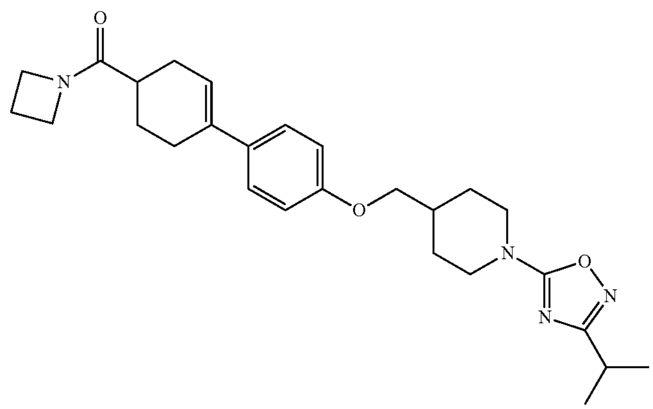 [SMILES: CC(C)c1noc(N2CCC(COc3ccc(C4=CCC(C(=O)N5CCC5)CC4)cc3)CC2)n1] |
| 66 | 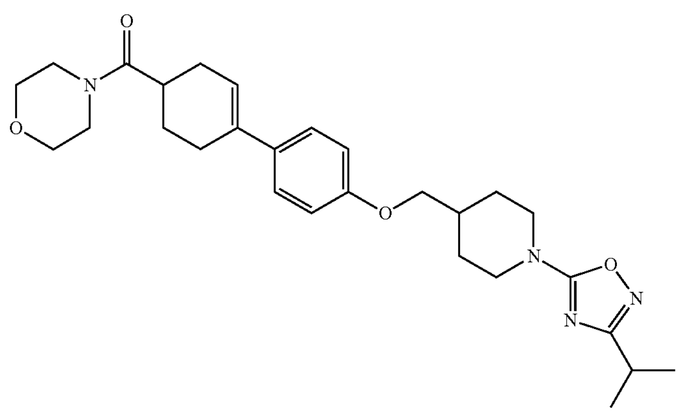 |
| 67 | 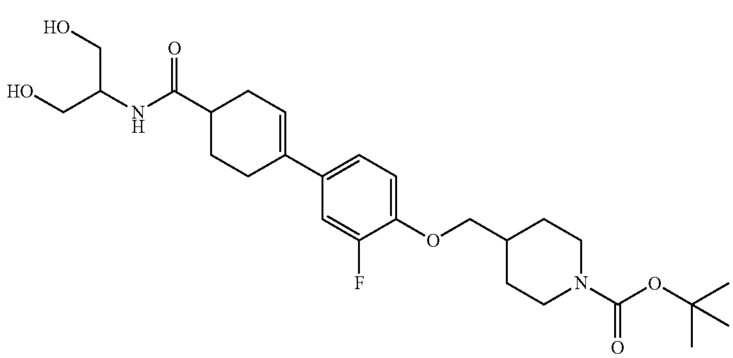 [SMILES: CC(C)(C)OC(=O)N1CCC(COc2ccc(C3=CCC(C(=O)NC(CO)CO)CC3)cc2F)CC1] |

TABLE 1-continued

| Examples | Chemical structures |
|---|---|
| 68 | *(chemical structure: 4-(6-((1-Boc-piperidin-4-yl)methoxy)pyridin-3-yl)-N-(1,3-dihydroxypropan-2-yl)cyclohex-3-ene-1-carboxamide)* |
| 69 | *(chemical structure: tert-butyl 4-((2-fluoro-4-(4-(morpholine-4-carbonyl)cyclohex-1-en-1-yl)phenoxy)methyl)piperidine-1-carboxylate)* |
| 70 | *(chemical structure: tert-butyl 4-(((5-(4-(morpholine-4-carbonyl)cyclohex-1-en-1-yl)pyridin-2-yl)oxy)methyl)piperidine-1-carboxylate)* |
| 71 | *(chemical structure: tert-butyl 4-((2-fluoro-4-(4-(thiomorpholine-4-carbonyl)cyclohex-1-en-1-yl)phenoxy)methyl)piperidine-1-carboxylate)* |

TABLE 1-continued

| Examples | Chemical structures |
|---|---|
| 72 | 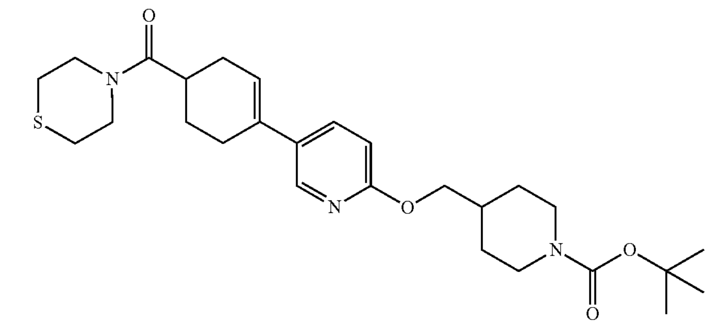 [SMILES: CC(C)(C)OC(=O)N1CCC(COc2ccc(C3=CCC(C(=O)N4CCSCC4)CC3)cn2)CC1] |
| 73 | 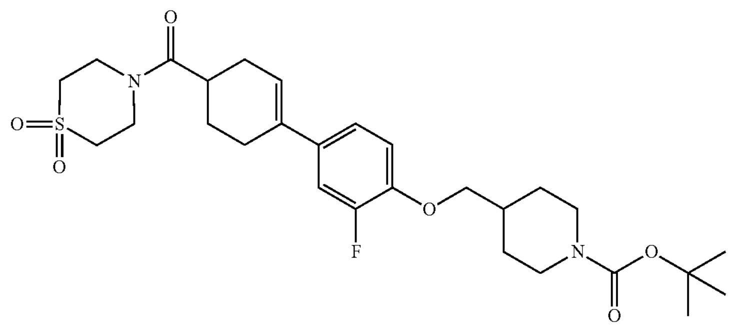 [SMILES: CC(C)(C)OC(=O)N1CCC(COc2ccc(C3=CCC(C(=O)N4CCS(=O)(=O)CC4)CC3)cc2F)CC1] |
| 74 | 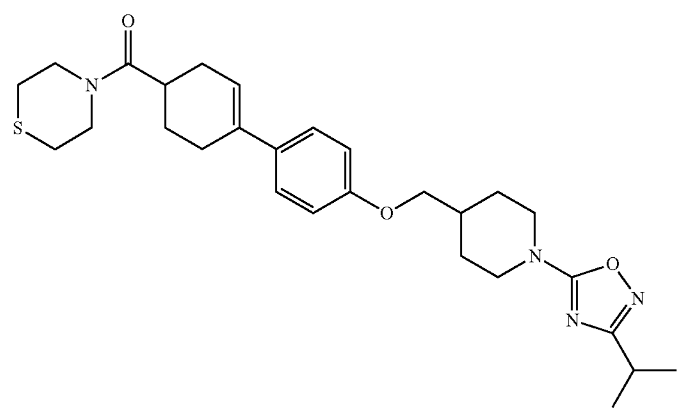 [SMILES: CC(C)c1noc(N2CCC(COc3ccc(C4=CCC(C(=O)N5CCSCC5)CC4)cc3)CC2)n1] |
| 75 | 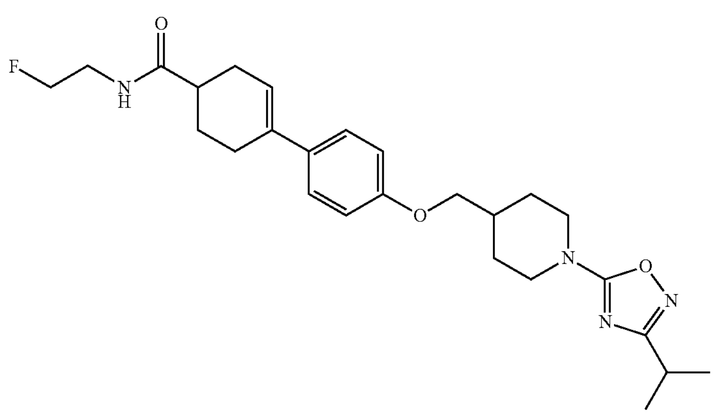 [SMILES: CC(C)c1noc(N2CCC(COc3ccc(C4=CCC(C(=O)NCCF)CC4)cc3)CC2)n1] |

TABLE 1-continued
| Examples | Chemical structures |
|---|---|
| 76 | 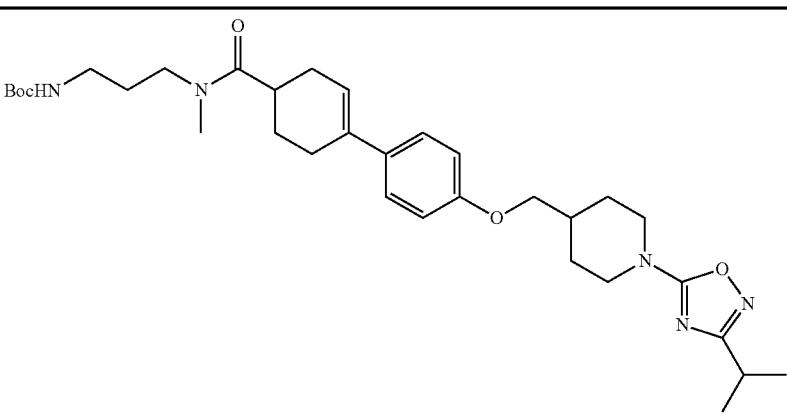 |
| 77 | 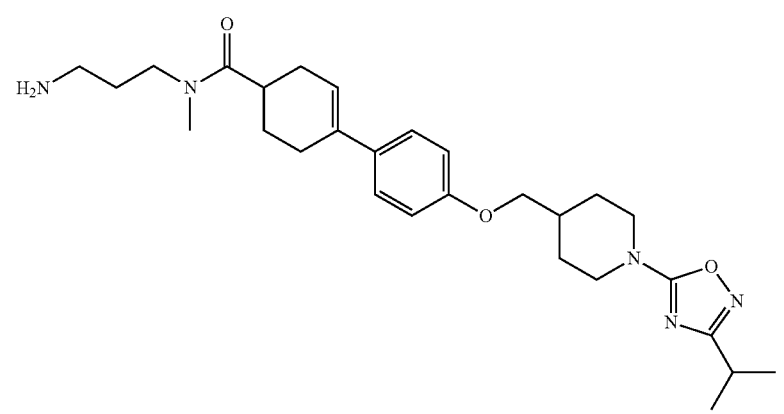 [SMILES: CC(C)c1noc(N2CCC(COc3ccc(C4=CCC(C(=O)N(C)CCCN)CC4)cc3)CC2)n1] |
| 78 | 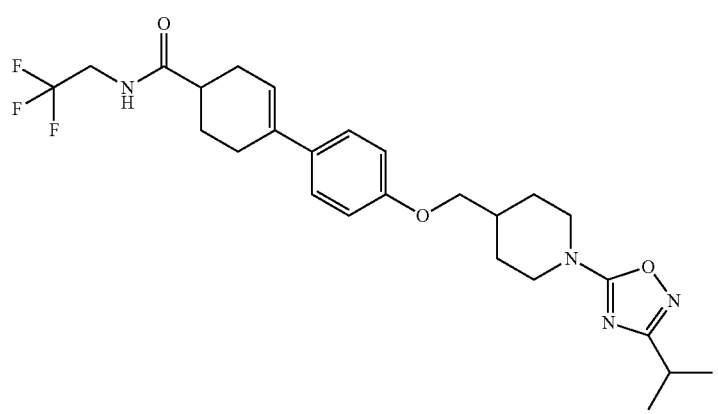 [SMILES: CC(C)c1noc(N2CCC(COc3ccc(C4=CCC(C(=O)NCC(F)(F)F)CC4)cc3)CC2)n1] |
| 79 | 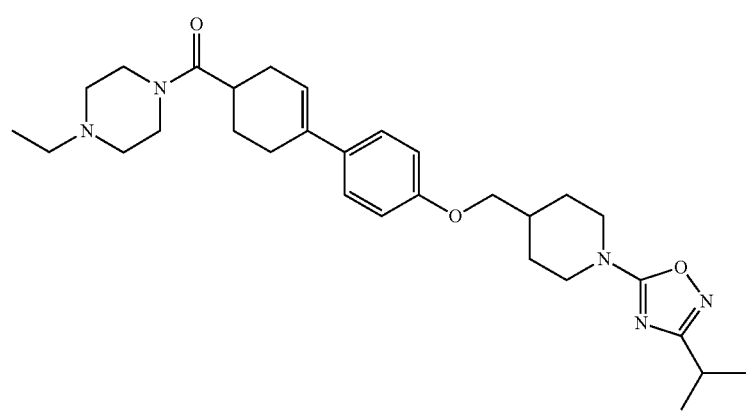 [SMILES: CCN1CCN(C(=O)C2CC=C(c3ccc(OCC4CCN(c5nc(C(C)C)no5)CC4)cc3)CC2)CC1] |

TABLE 1-continued
| Examples | Chemical structures |
|---|---|
| 80 | 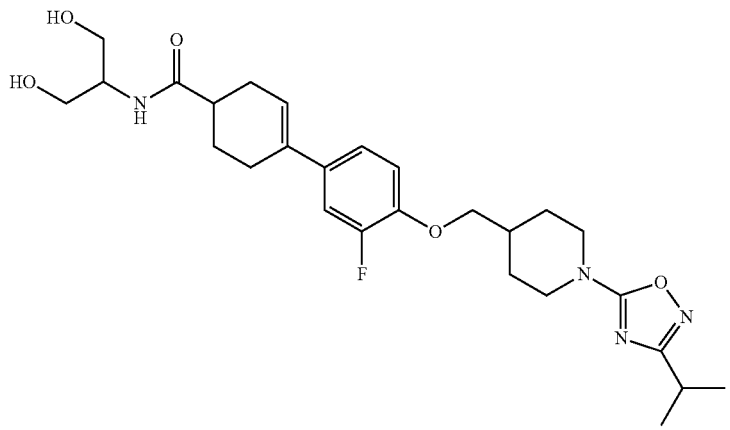 [SMILES: CC(C)c1noc(N2CCC(COc3ccc(C4=CCC(C(=O)NC(CO)CO)CC4)cc3F)CC2)n1] |
| 81 | 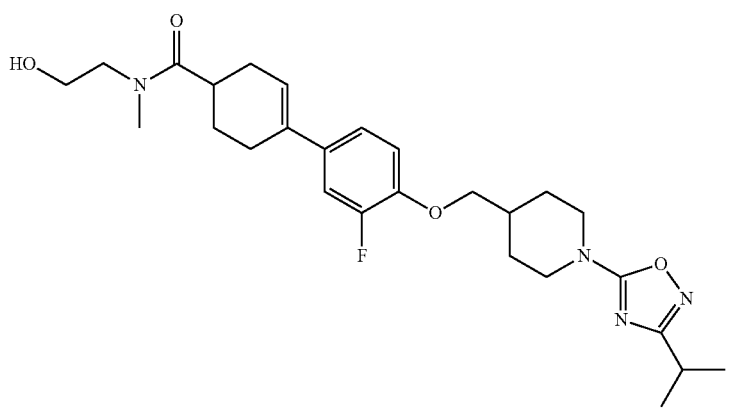 [SMILES: CC(C)c1noc(N2CCC(COc3ccc(C4=CCC(C(=O)N(C)CCO)CC4)cc3F)CC2)n1] |
| 82 | 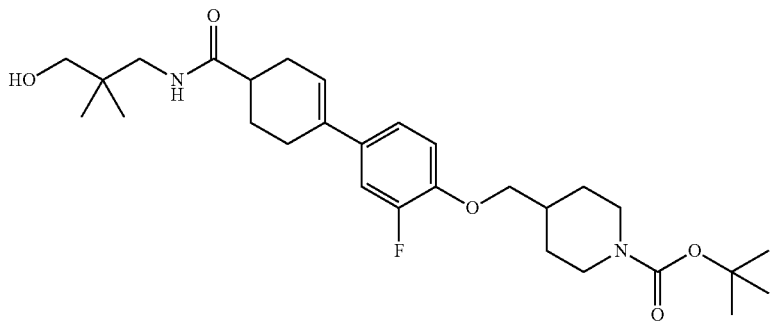 [SMILES: CC(C)(CO)CNC(=O)C1CC=C(c2ccc(OCC3CCN(C(=O)OC(C)(C)C)CC3)c(F)c2)CC1] |
| 83 | 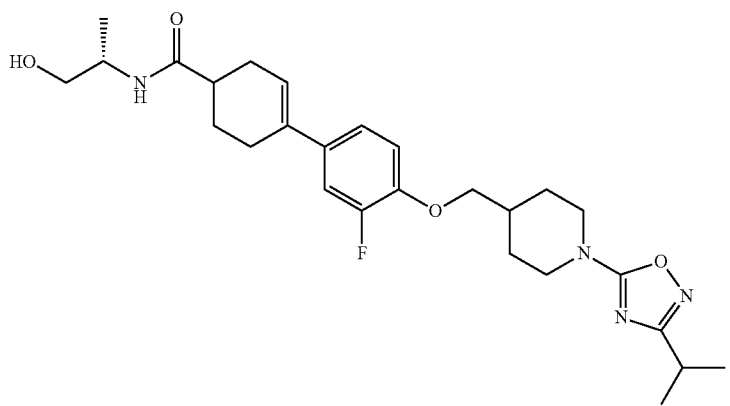 [SMILES: CC(C)c1noc(N2CCC(COc3ccc(C4=CCC(C(=O)N[C@@H](C)CO)CC4)cc3F)CC2)n1] |

TABLE 1-continued
| Examples | Chemical structures |
|---|---|
| 84 | 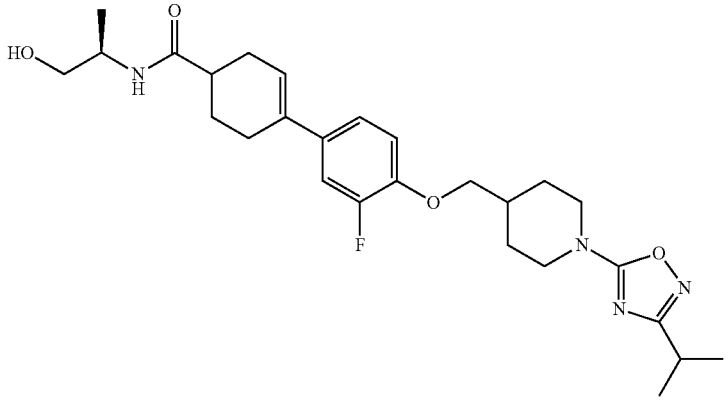 [SMILES: CC(C)c1noc(N2CCC(COc3ccc(C4=CCC(C(=O)N[C@H](C)CO)CC4)cc3F)CC2)n1] |
| 85 | 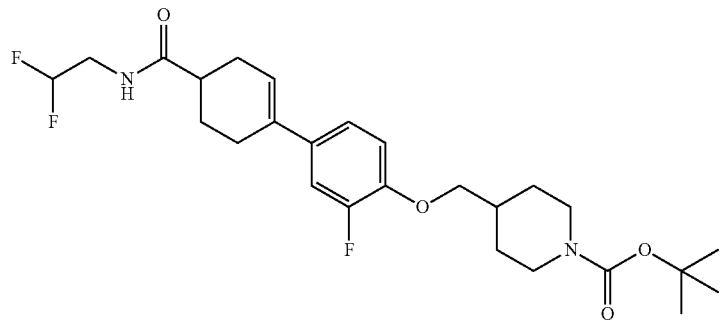 [SMILES: CC(C)(C)OC(=O)N1CCC(COc2ccc(C3=CCC(C(=O)NCC(F)F)CC3)cc2F)CC1] |
| 86 | 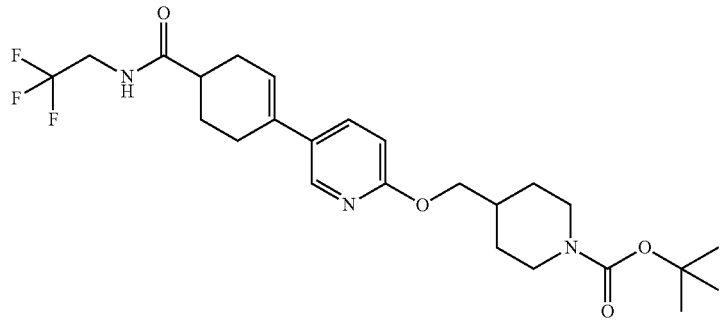 [SMILES: CC(C)(C)OC(=O)N1CCC(COc2ccc(C3=CCC(C(=O)NCC(F)(F)F)CC3)cn2)CC1] |
| 87 | 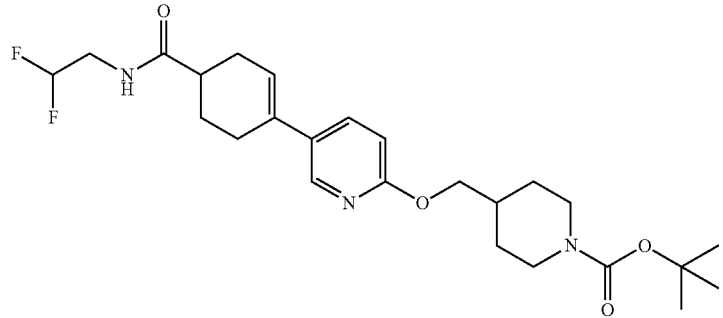 [SMILES: CC(C)(C)OC(=O)N1CCC(COc2ccc(C3=CCC(C(=O)NCC(F)F)CC3)cn2)CC1] |

TABLE 1-continued
| Examples | Chemical structures |
|---|---|
| 88 | 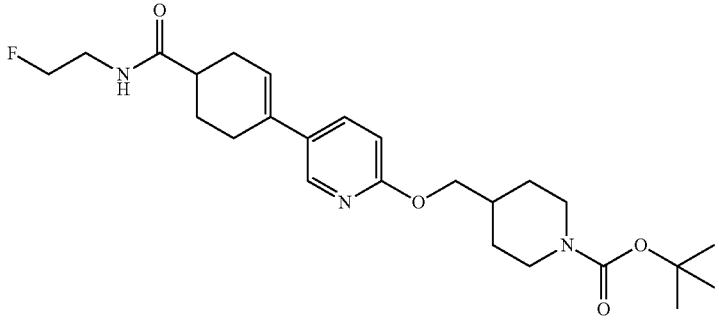 [SMILES: CC(C)(C)OC(=O)N1CCC(COc2ccc(C3=CCC(C(=O)NCCF)CC3)cn2)CC1] |
| 89 | 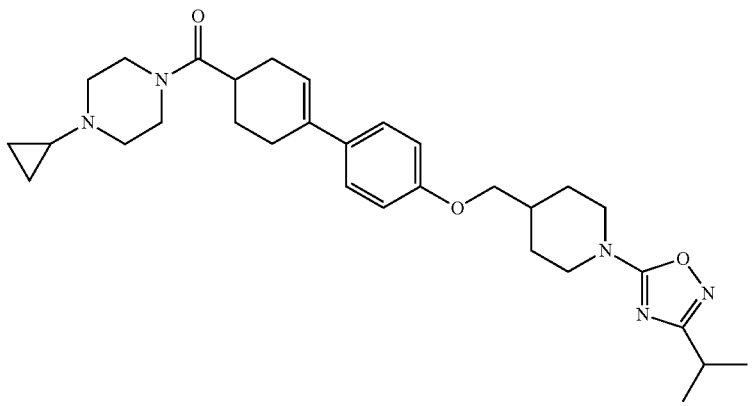 [SMILES: CC(C)c1noc(N2CCC(COc3ccc(C4=CCC(C(=O)N5CCN(C6CC6)CC5)CC4)cc3)CC2)n1] |
| 90 | 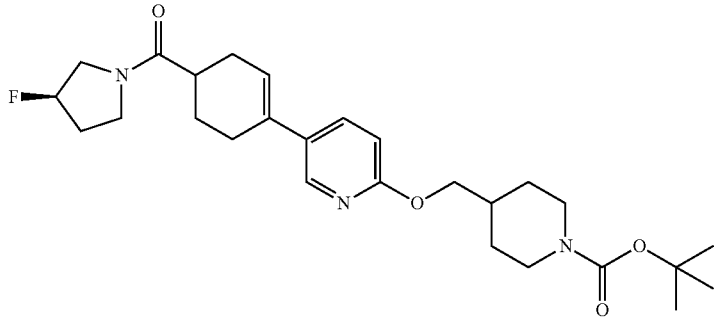 [SMILES: CC(C)(C)OC(=O)N1CCC(COc2ccc(C3=CCC(C(=O)N4CC[C@@H](F)C4)CC3)cn2)CC1] |
| 91 | 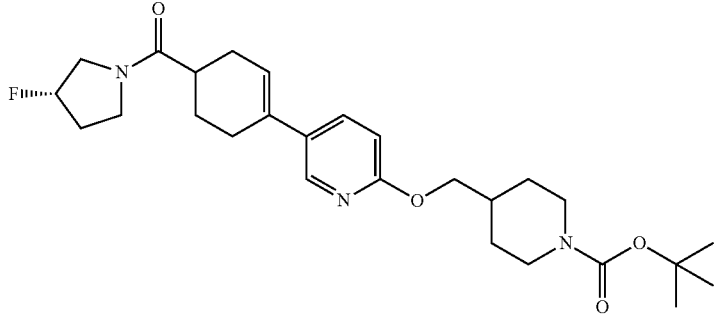 [SMILES: CC(C)(C)OC(=O)N1CCC(COc2ccc(C3=CCC(C(=O)N4CC[C@H](F)C4)CC3)cn2)CC1] |

TABLE 1-continued
| Examples | Chemical structures |
|---|---|
| 92 | 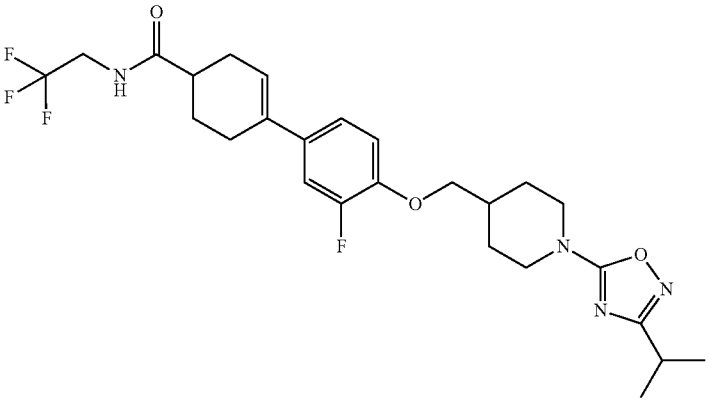 [SMILES: CC(C)c1noc(N2CCC(COc3ccc(C4=CCC(C(=O)NCC(F)(F)F)CC4)cc3F)CC2)n1] |
| 93 | 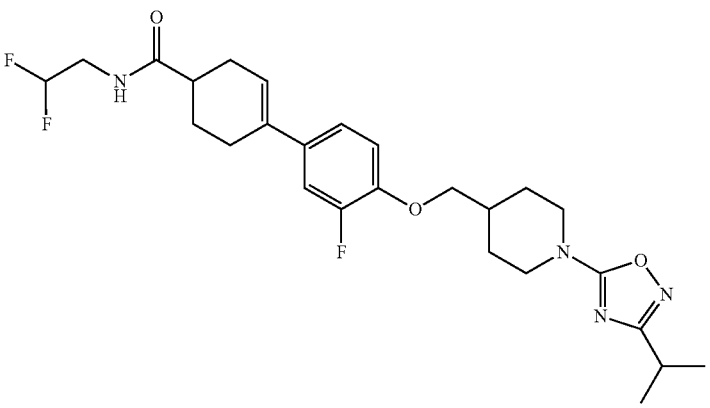 [SMILES: CC(C)c1noc(N2CCC(COc3ccc(C4=CCC(C(=O)NCC(F)F)CC4)cc3F)CC2)n1] |
| 94 | 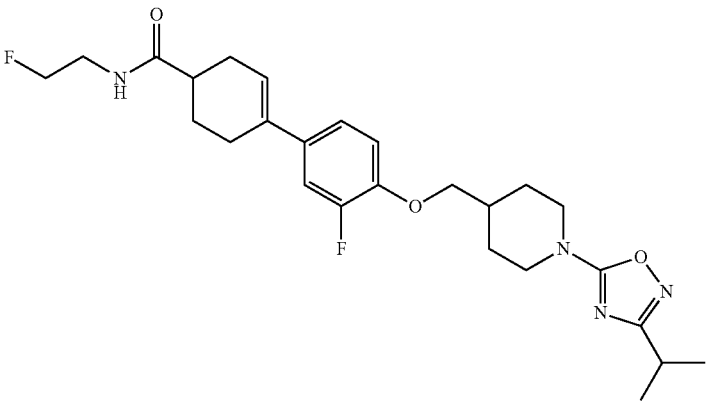 [SMILES: CC(C)c1noc(N2CCC(COc3ccc(C4=CCC(C(=O)NCCF)CC4)cc3F)CC2)n1] |

TABLE 1-continued
| Examples | Chemical structures |
|---|---|
| 95 | 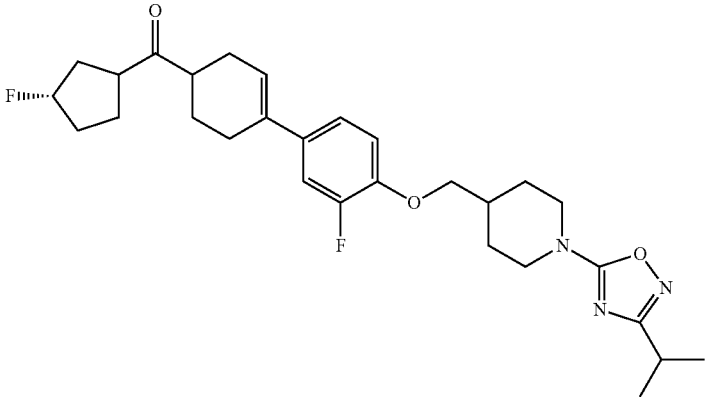 [SMILES: CC(C)c1noc(N2CCC(COc3ccc(C4=CCC(C(=O)C5CC[C@H](F)C5)CC4)cc3F)CC2)n1] |
| 96 | 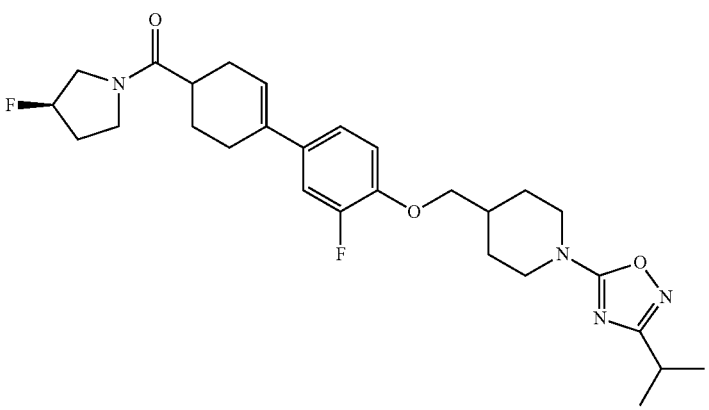 [SMILES: CC(C)c1noc(N2CCC(COc3ccc(C4=CCC(C(=O)N5CC[C@@H](F)C5)CC4)cc3F)CC2)n1] |
| 97 | 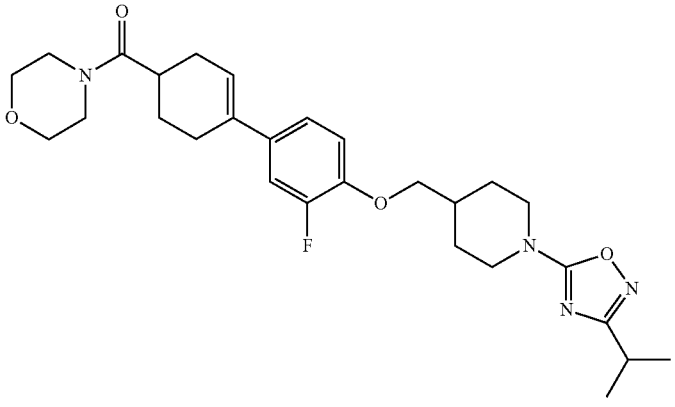 [SMILES: CC(C)c1noc(N2CCC(COc3ccc(C4=CCC(C(=O)N5CCOCC5)CC4)cc3F)CC2)n1] |

TABLE 1-continued
| Examples | Chemical structures |
| --- | --- |
| 98 | 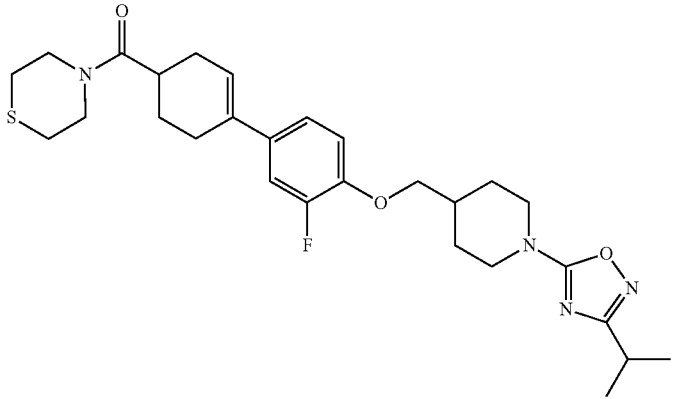 [SMILES: CC(C)c1noc(N2CCC(COc3ccc(C4=CCC(C(=O)N5CCSCC5)CC4)cc3F)CC2)n1] |
| 99 | 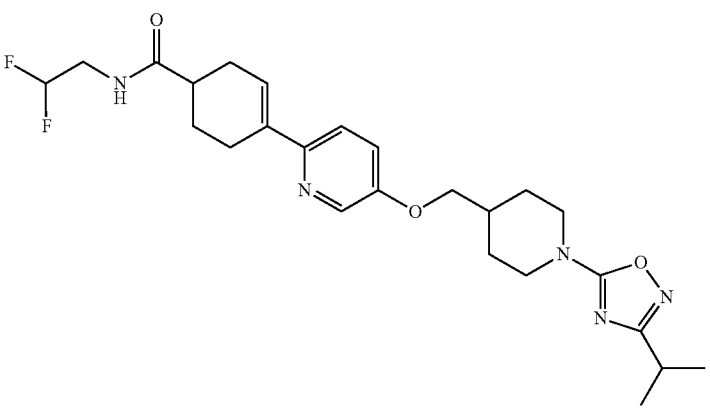 [SMILES: CC(C)c1noc(N2CCC(COc3ccc(C4=CCC(C(=O)NCC(F)F)CC4)nc3)CC2)n1] |
| 100 | 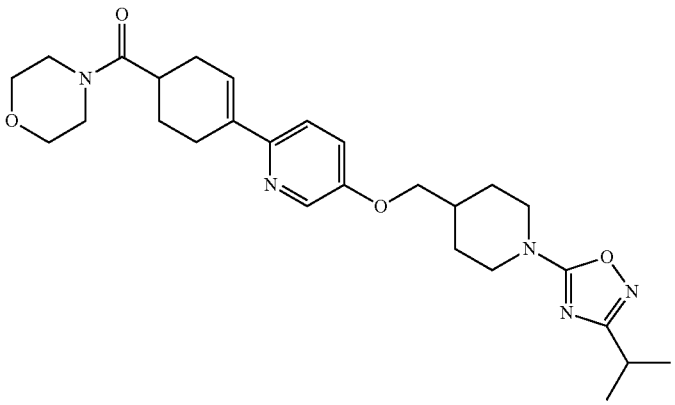 [SMILES: CC(C)c1noc(N2CCC(COc3ccc(C4=CCC(C(=O)N5CCOCC5)CC4)nc3)CC2)n1] |

TABLE 1-continued
| Examples | Chemical structures |
|---|---|
| 101 | 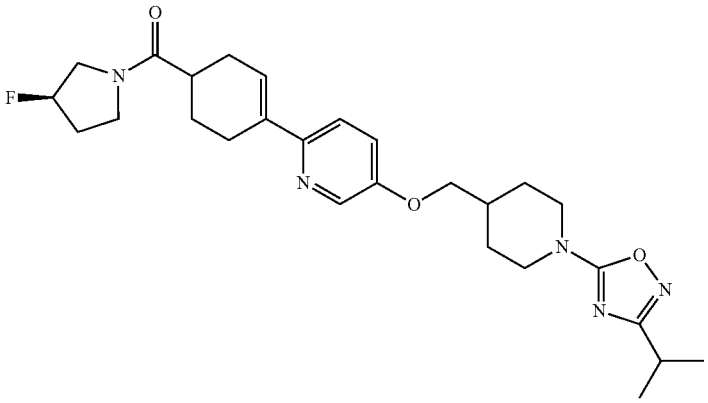 |
| 102 | 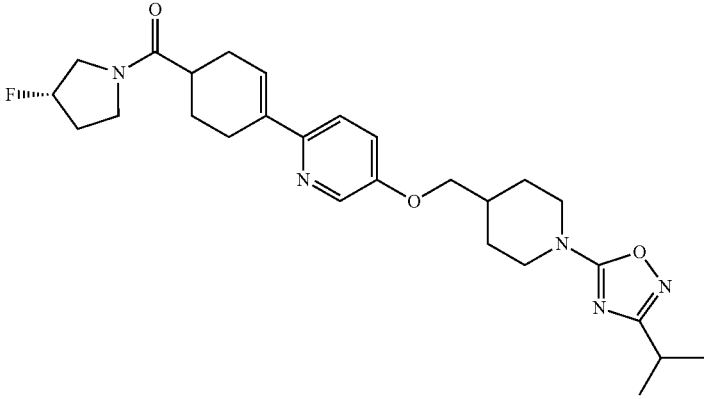 |
| 103 | 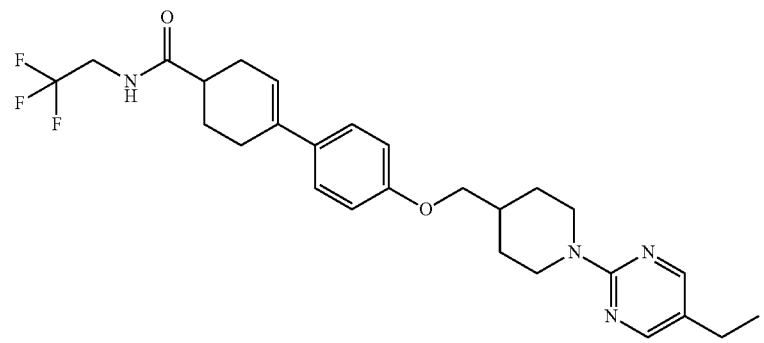 [SMILES: CCc1cnc(N2CCC(COc3ccc(C4=CCC(C(=O)NCC(F)(F)F)CC4)cc3)CC2)nc1] |
| 104 | 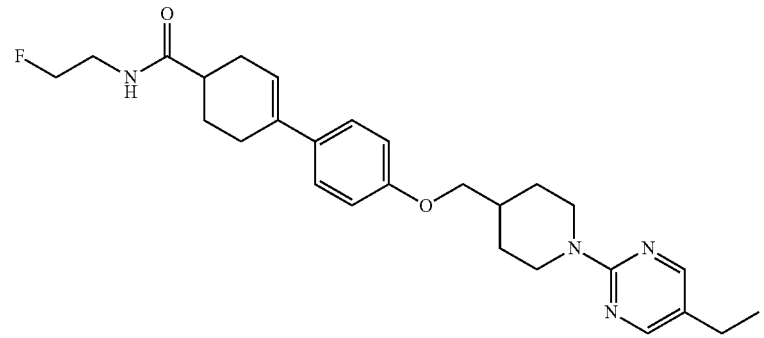 [SMILES: CCc1cnc(N2CCC(COc3ccc(C4=CCC(C(=O)NCCF)CC4)cc3)CC2)nc1] |

TABLE 1-continued

| Examples | Chemical structures |
|---|---|
| 105 | 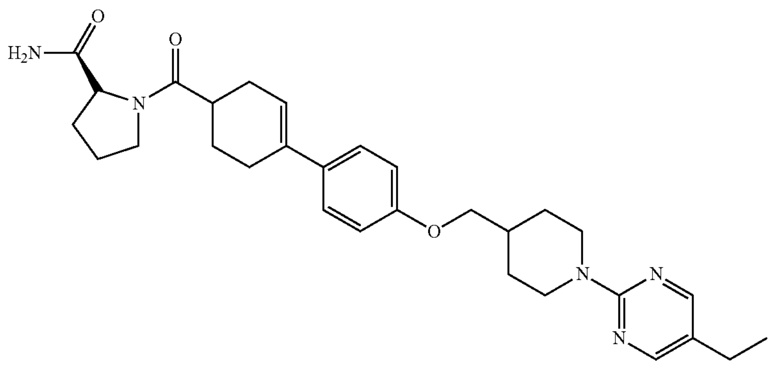 |
| 106 | 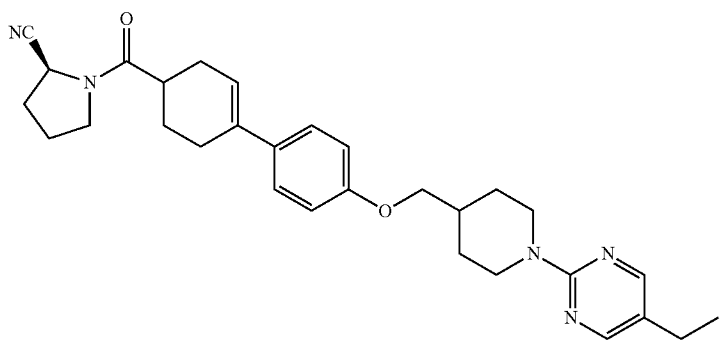 [SMILES: CCc1cnc(N2CCC(COc3ccc(C4=CCC(C(=O)N5CCC[C@H]5C#N)CC4)cc3)CC2)nc1] |
| 107 | 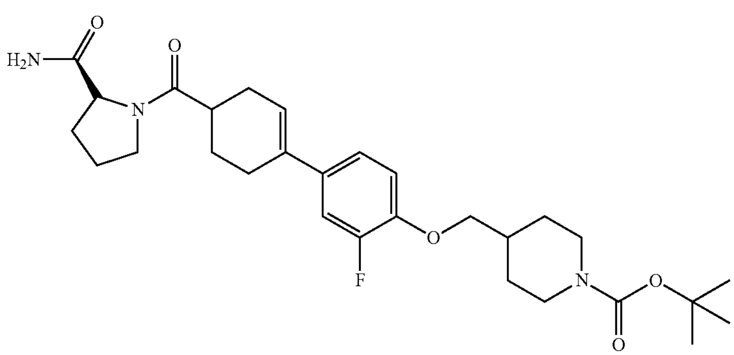 |
| 108 | 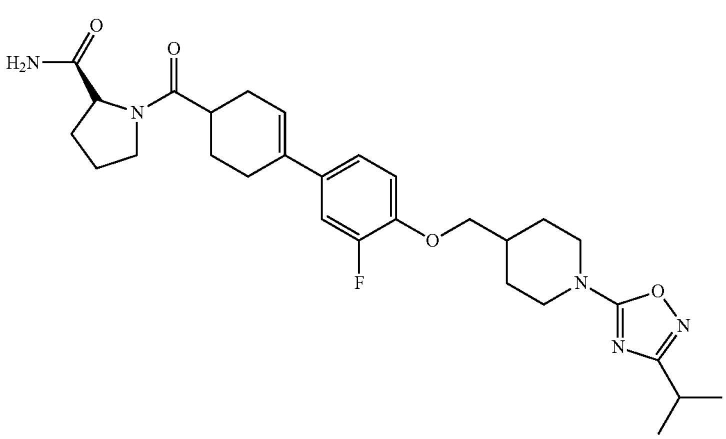 |

TABLE 1-continued
| Examples | Chemical structures |
| --- | --- |
| 109 | 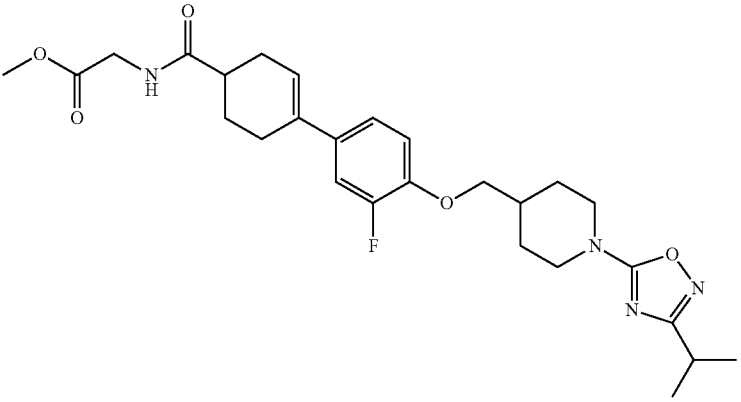 [SMILES: COC(=O)CNC(=O)C1CC=C(c2ccc(OCC3CCN(c4nc(C(C)C)no4)CC3)c(F)c2)CC1] |
| 110 | 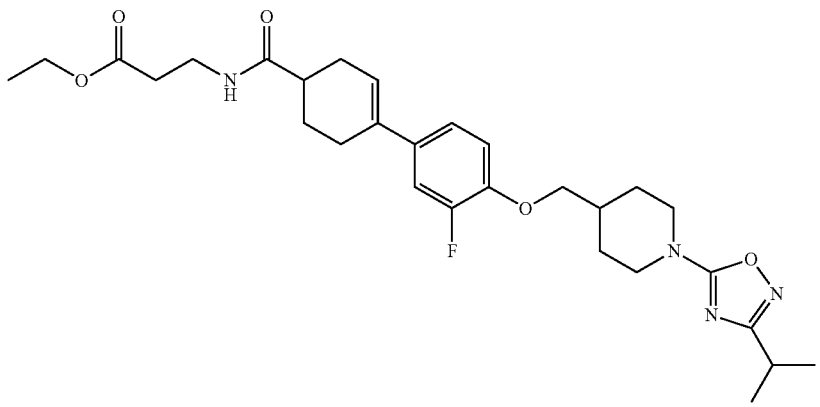 [SMILES: CCOC(=O)CCNC(=O)C1CC=C(c2ccc(OCC3CCN(c4nc(C(C)C)no4)CC3)c(F)c2)CC1] |
| 111 | 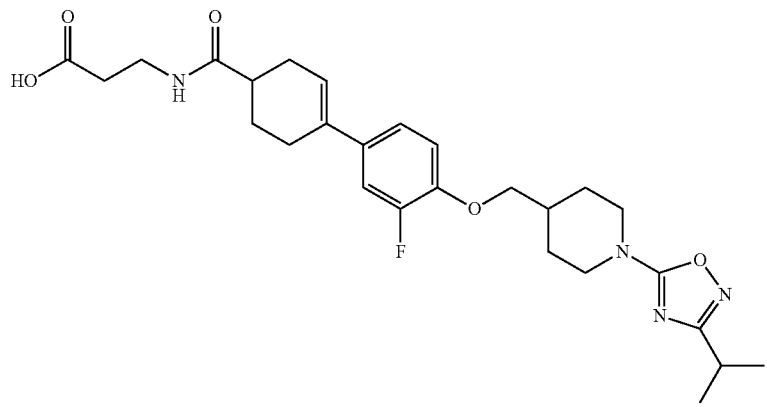 [SMILES: CC(C)c1noc(N2CCC(COc3ccc(C4=CCC(C(=O)NCCC(=O)O)CC4)cc3F)CC2)n1] |

TABLE 1-continued

| Examples | Chemical structures |
| --- | --- |
| 112 | 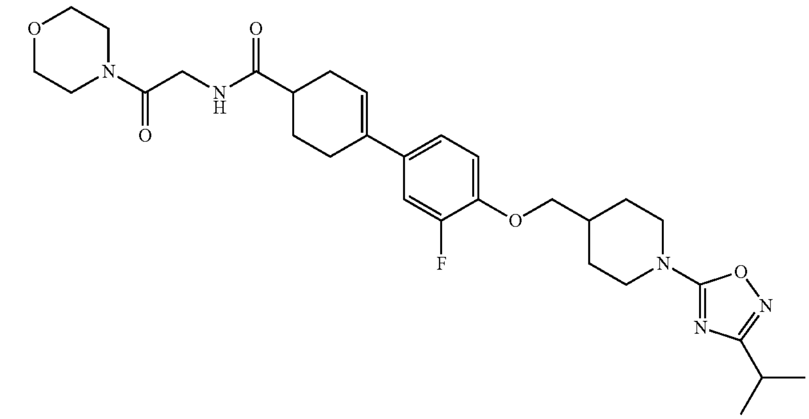 [SMILES: CC(C)c1noc(N2CCC(COc3ccc(C4=CCC(C(=O)NCC(=O)N5CCOCC5)CC4)cc3F)CC2)n1] |
| 113 | 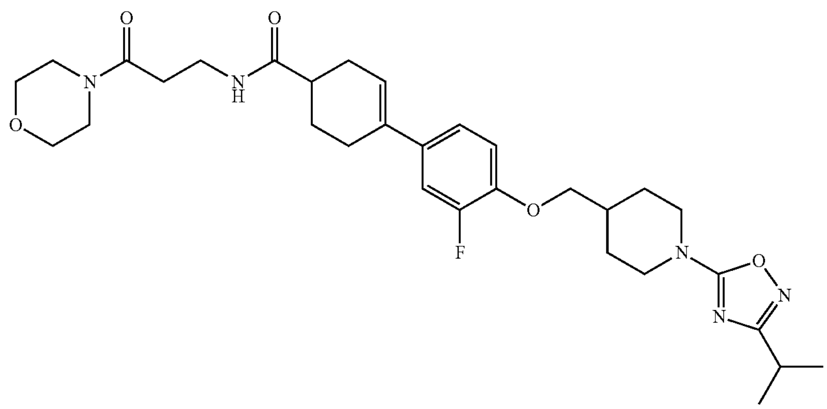 [SMILES: CC(C)c1noc(N2CCC(COc3ccc(C4=CCC(C(=O)NCCC(=O)N5CCOCC5)CC4)cc3F)CC2)n1] |
| 114 | 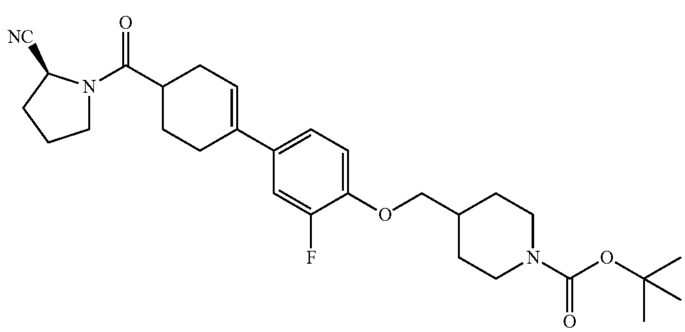 [SMILES: CC(C)(C)OC(=O)N1CCC(COc2ccc(C3=CCC(C(=O)N4CCC[C@H]4C#N)CC3)cc2F)CC1] |
| 115 | 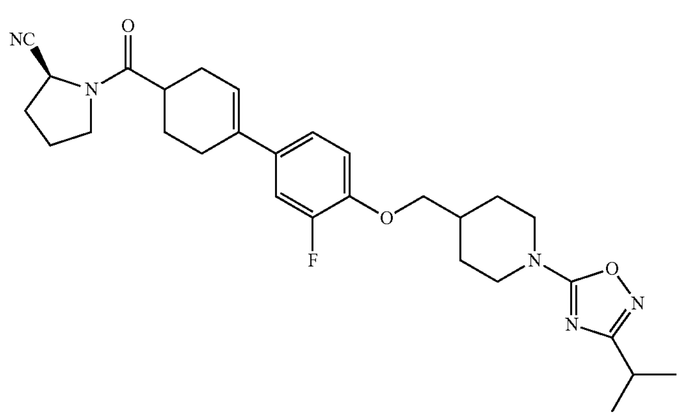 [SMILES: CC(C)c1noc(N2CCC(COc3ccc(C4=CCC(C(=O)N5CCC[C@H]5C#N)CC4)cc3F)CC2)n1] |

TABLE 1-continued
| Examples | Chemical structures |
|---|---|
| 116 | 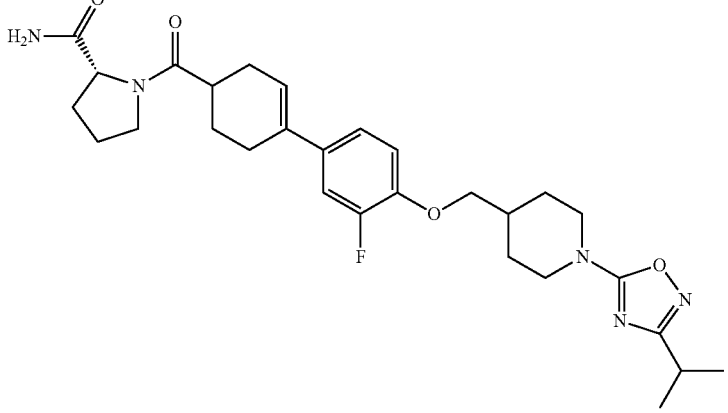 |
| 117 | 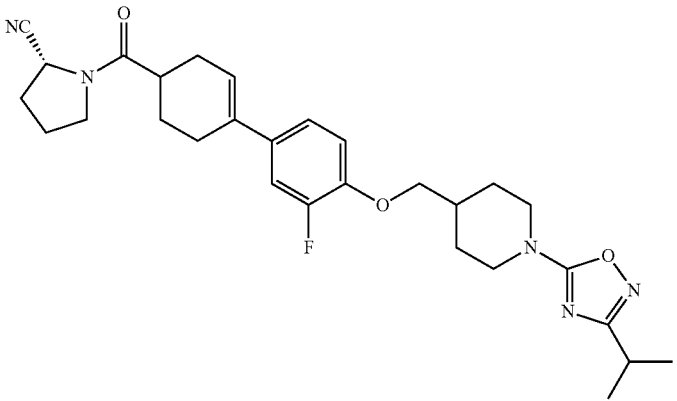 [SMILES: CC(C)c1noc(N2CCC(COc3ccc(C4=CCC(C(=O)N5CCC[C@@H]5C#N)CC4)cc3F)CC2)n1] |
| 118 | 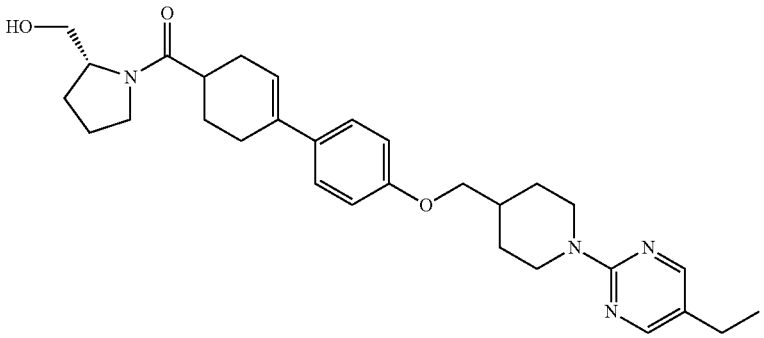 [SMILES: CCc1cnc(N2CCC(COc3ccc(C4=CCC(C(=O)N5CCC[C@@H]5CO)CC4)cc3)CC2)nc1] |
| 119 | 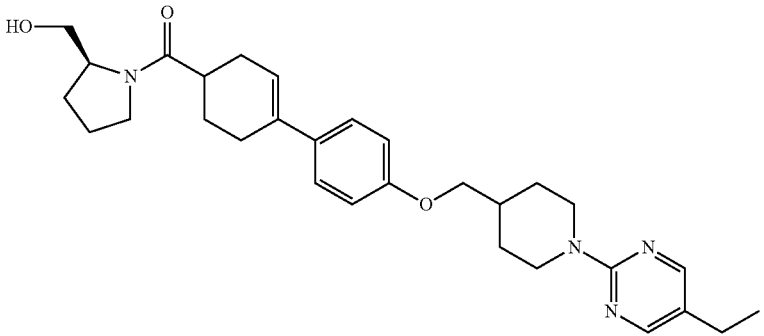 [SMILES: CCc1cnc(N2CCC(COc3ccc(C4=CCC(C(=O)N5CCC[C@H]5CO)CC4)cc3)CC2)nc1] |

TABLE 1-continued
| Examples | Chemical structures |
|---|---|
| 120 | 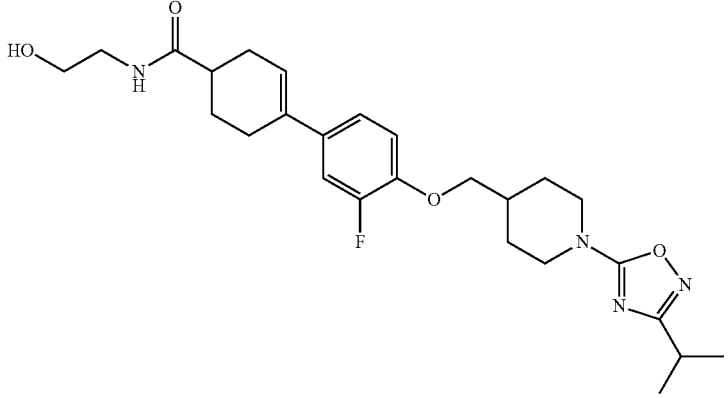 |
| 121 | 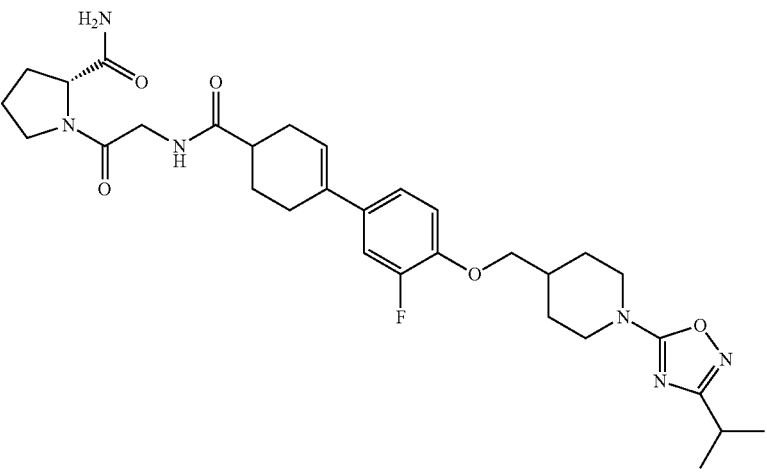 [SMILES: CC(C)c1noc(N2CCC(COc3ccc(C4=CCC(C(=O)NCC(=O)N5CCC[C@@H]5C(N)=O)CC4)cc3F)CC2)n1] |
| 122 | 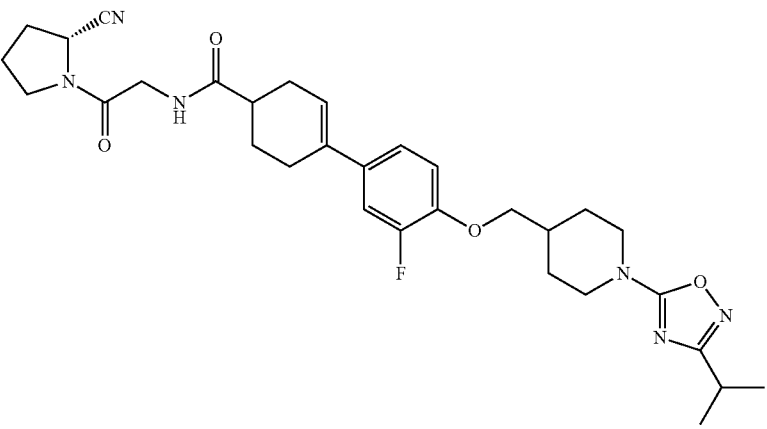 [SMILES: CC(C)c1noc(N2CCC(COc3ccc(C4=CCC(C(=O)NCC(=O)N5CCC[C@@H]5C#N)CC4)cc3F)CC2)n1] |

TABLE 1-continued
| Examples | Chemical structures |
|---|---|
| 123 | 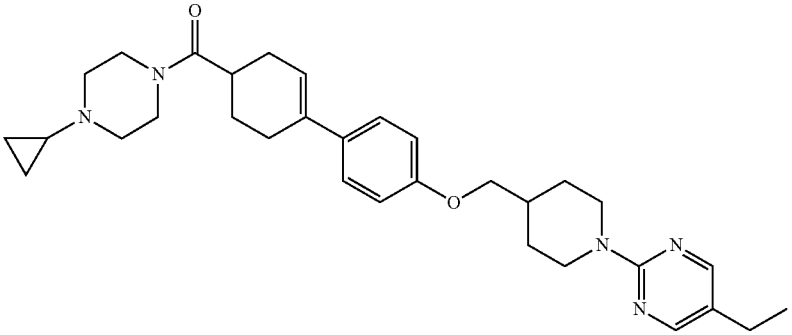 [SMILES: CCc1cnc(N2CCC(COc3ccc(C4=CCC(C(=O)N5CCN(C6CC6)CC5)CC4)cc3)CC2)nc1] |
| 124 | 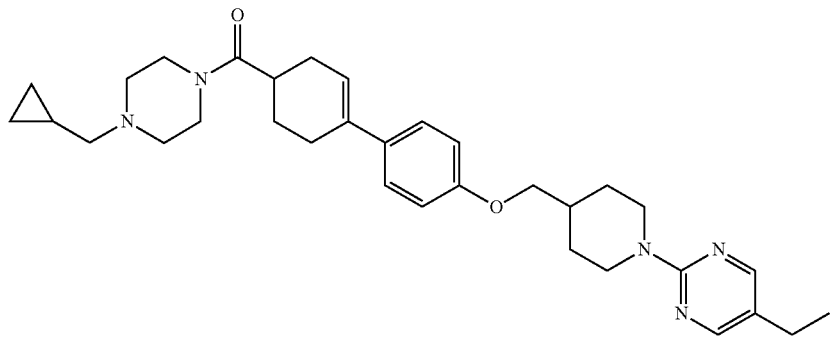 [SMILES: CCc1cnc(N2CCC(COc3ccc(C4=CCC(C(=O)N5CCN(CC6CC6)CC5)CC4)cc3)CC2)nc1] |
| 125 | 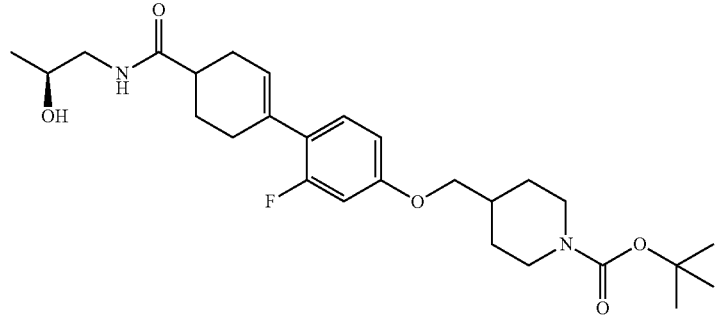 [SMILES: C[C@H](O)CNC(=O)C1CC=C(c2ccc(OCC3CCN(C(=O)OC(C)(C)C)CC3)cc2F)CC1] |
| 126 | 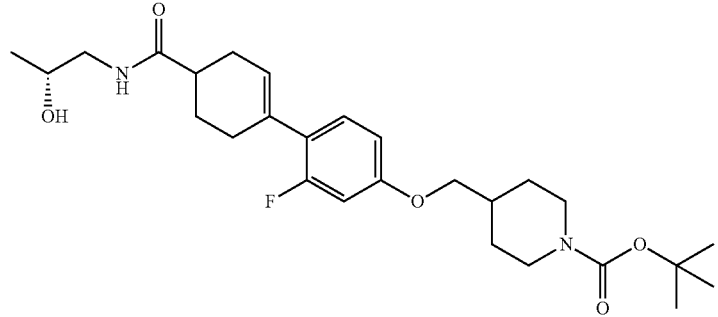 [SMILES: C[C@@H](O)CNC(=O)C1CC=C(c2ccc(OCC3CCN(C(=O)OC(C)(C)C)CC3)cc2F)CC1] |

TABLE 1-continued
| Examples | Chemical structures |
|---|---|
| 127 | 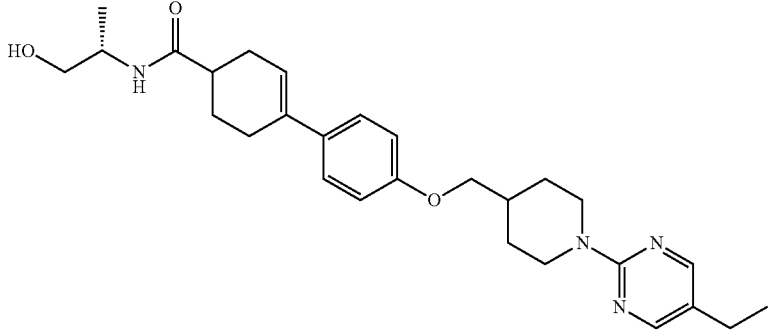 [SMILES: CCc1cnc(N2CCC(COc3ccc(C4=CCC(C(=O)N[C@@H](C)CO)CC4)cc3)CC2)nc1] |
| 128 | 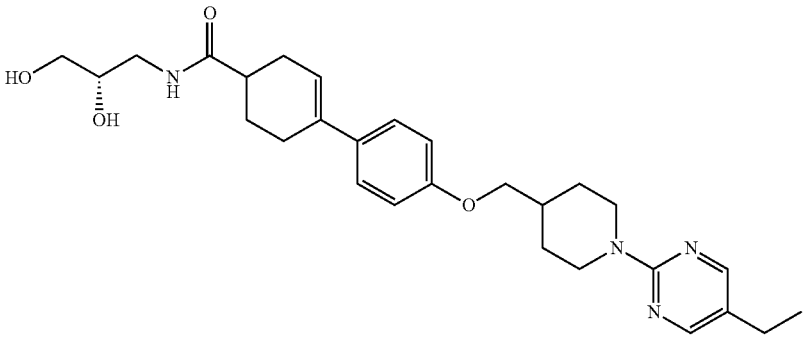 [SMILES: CCc1cnc(N2CCC(COc3ccc(C4=CCC(C(=O)NC[C@H](O)CO)CC4)cc3)CC2)nc1] |
| 129 | 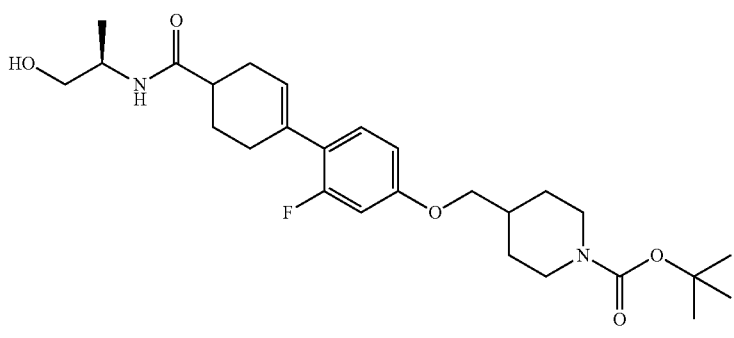 [SMILES: C[C@H](CO)NC(=O)C1CC=C(c2ccc(OCC3CCN(C(=O)OC(C)(C)C)CC3)cc2F)CC1] |
| 130 | 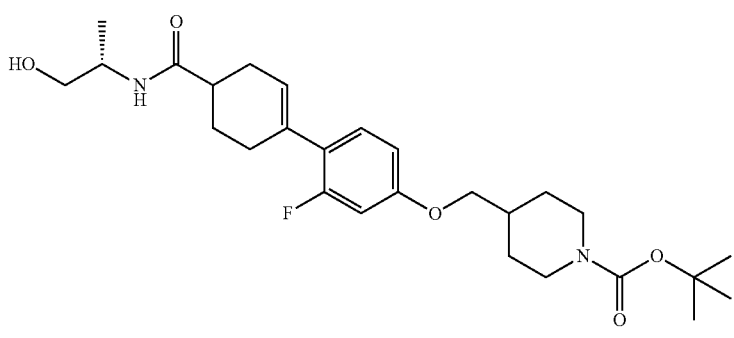 [SMILES: C[C@@H](CO)NC(=O)C1CC=C(c2ccc(OCC3CCN(C(=O)OC(C)(C)C)CC3)cc2F)CC1] |

TABLE 1-continued
| Examples | Chemical structures |
|---|---|
| 131 | 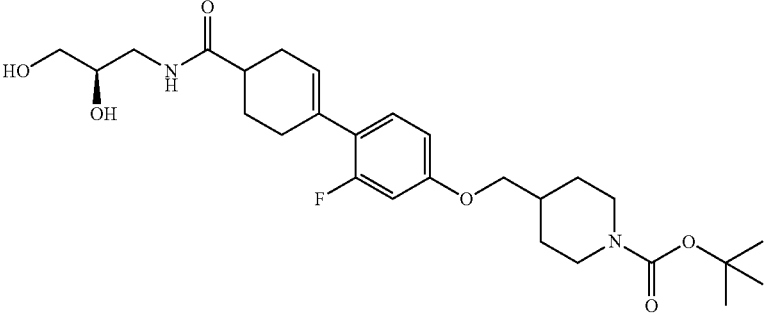 [SMILES: CC(C)(C)OC(=O)N1CCC(COc2ccc(C3=CCC(C(=O)NC[C@@H](O)CO)CC3)c(F)c2)CC1] |
| 132 | 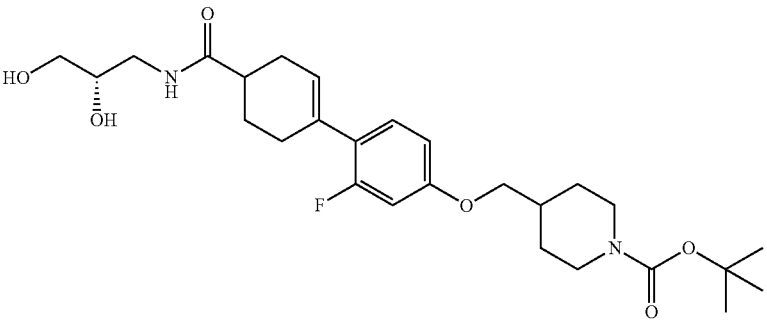 [SMILES: CC(C)(C)OC(=O)N1CCC(COc2ccc(C3=CCC(C(=O)NC[C@H](O)CO)CC3)c(F)c2)CC1] |
| 133 | 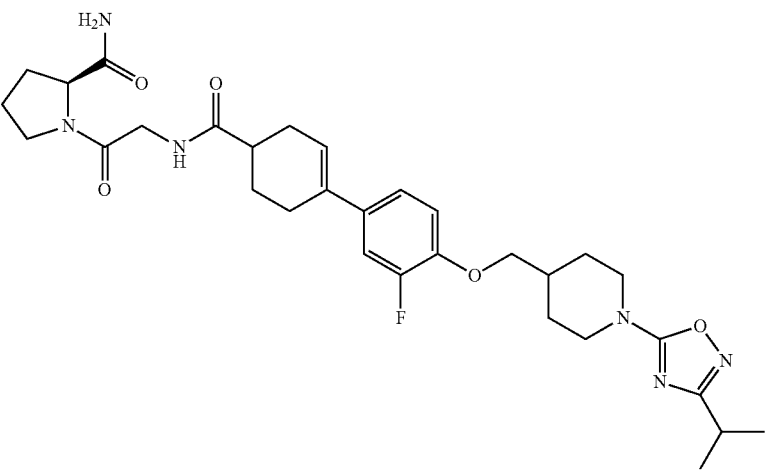 [SMILES: CC(C)c1noc(N2CCC(COc3ccc(C4=CCC(C(=O)NCC(=O)N5CCC[C@H]5C(N)=O)CC4)cc3F)CC2)n1] |
| 134 | 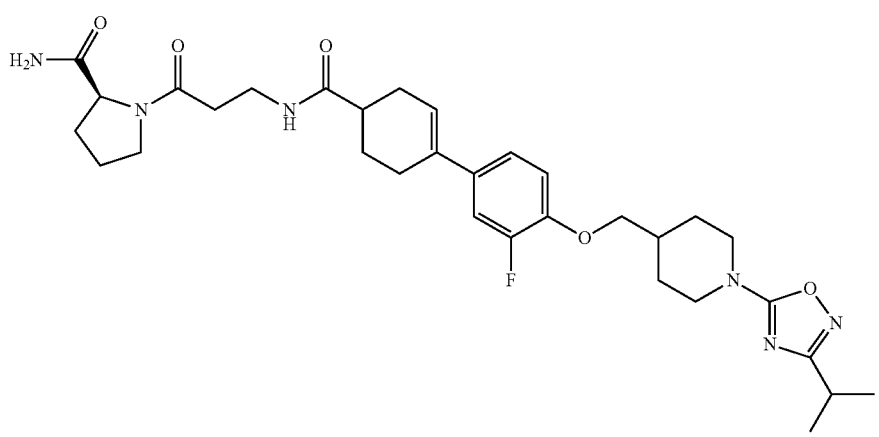 [SMILES: CC(C)c1noc(N2CCC(COc3ccc(C4=CCC(C(=O)NCCC(=O)N5CCC[C@H]5C(N)=O)CC4)cc3F)CC2)n1] |

TABLE 1-continued
| Examples | Chemical structures |
|---|---|
| 135 | 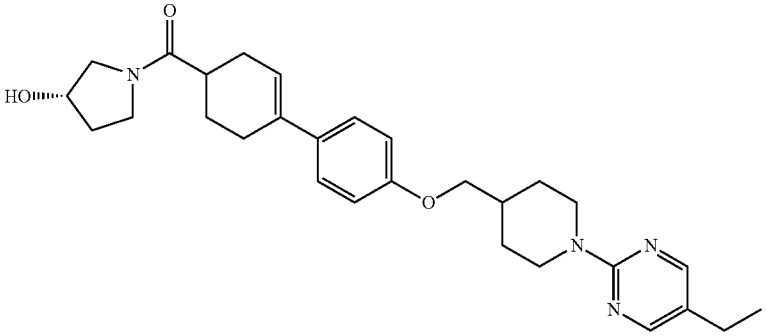 [SMILES: CCc1cnc(N2CCC(COc3ccc(C4=CCC(C(=O)N5CC[C@H](O)C5)CC4)cc3)CC2)nc1] |
| 136 | 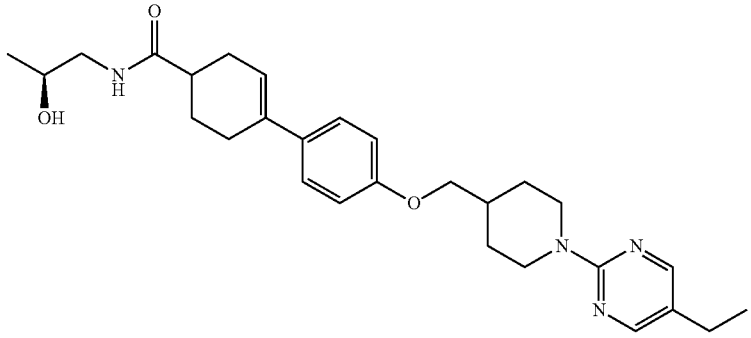 [SMILES: CCc1cnc(N2CCC(COc3ccc(C4=CCC(C(=O)NC[C@H](C)O)CC4)cc3)CC2)nc1] |
| 137 | 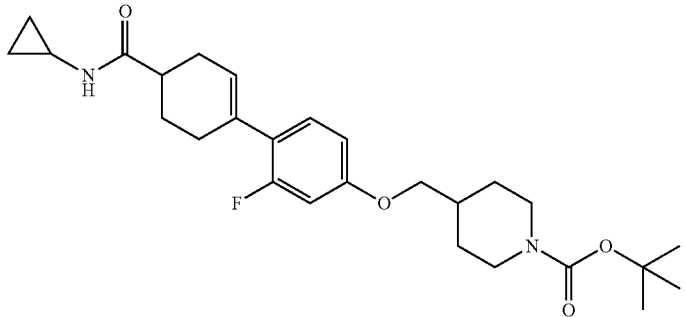 [SMILES: CC(C)(C)OC(=O)N1CCC(COc2ccc(C3=CCC(C(=O)NC4CC4)CC3)c(F)c2)CC1] |
| 138 | 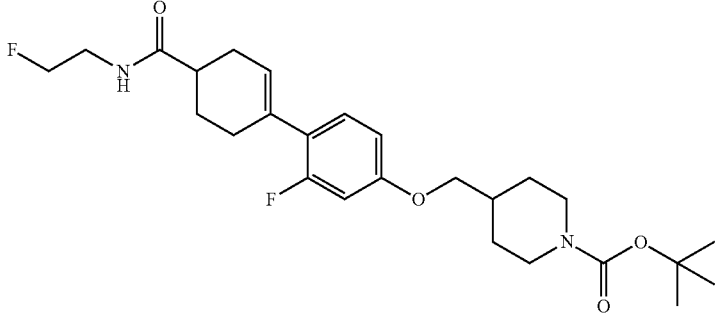 [SMILES: CC(C)(C)OC(=O)N1CCC(COc2ccc(C3=CCC(C(=O)NCCF)CC3)c(F)c2)CC1] |

TABLE 1-continued
| Examples | Chemical structures |
|---|---|
| 139 | 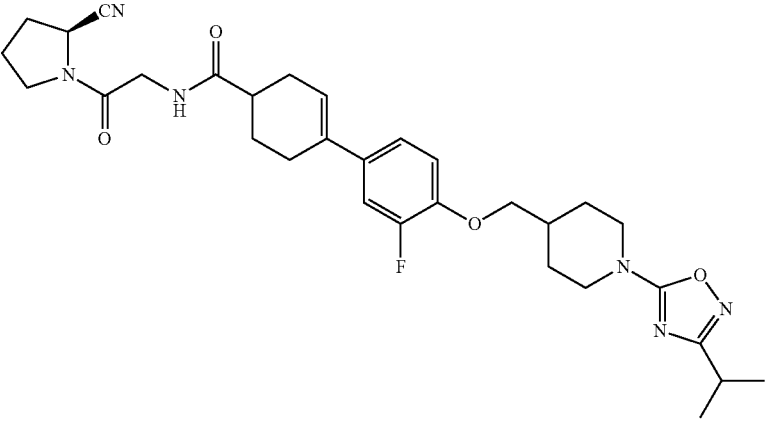 [SMILES: CC(C)c1noc(N2CCC(COc3ccc(C4=CCC(C(=O)NCC(=O)N5CCC[C@H]5C#N)CC4)cc3F)CC2)n1] |
| 140 | 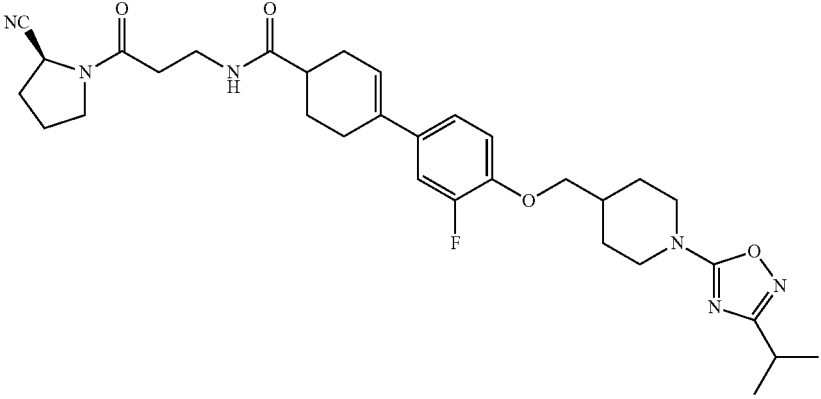 [SMILES: CC(C)c1noc(N2CCC(COc3ccc(C4=CCC(C(=O)NCCC(=O)N5CCC[C@H]5C#N)CC4)cc3F)CC2)n1] |
| 141 | 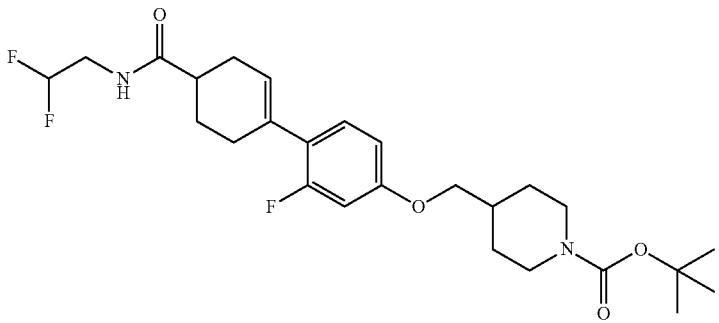 [SMILES: CC(C)(C)OC(=O)N1CCC(COc2ccc(C3=CCC(C(=O)NCC(F)F)CC3)c(F)c2)CC1] |
| 142 | 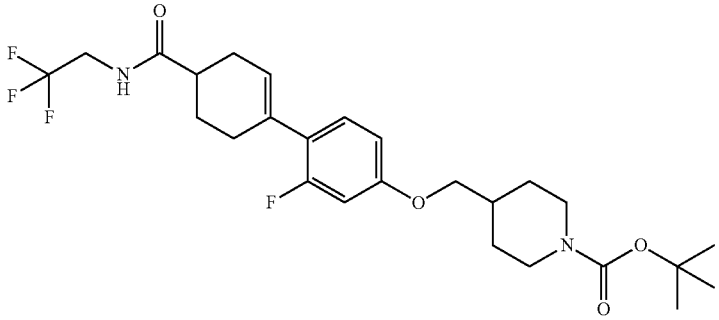 [SMILES: CC(C)(C)OC(=O)N1CCC(COc2ccc(C3=CCC(C(=O)NCC(F)(F)F)CC3)c(F)c2)CC1] |

TABLE 1-continued

| Examples | Chemical structures |
| --- | --- |
| 143 | 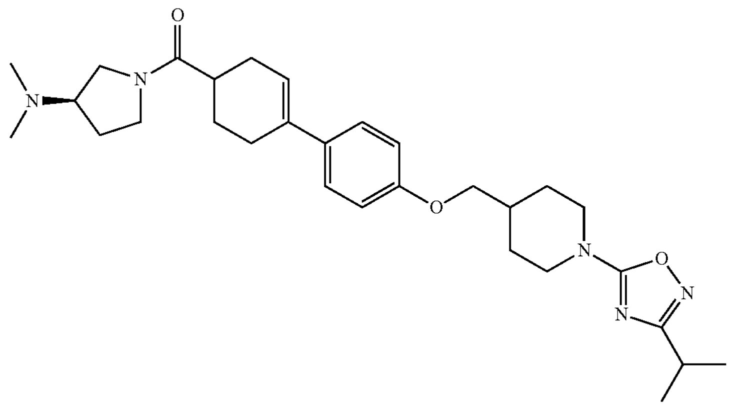 [SMILES: CC(C)c1noc(N2CCC(COc3ccc(C4=CCC(C(=O)N5CC[C@@H](N(C)C)C5)CC4)cc3)CC2)n1] |
| 144 | 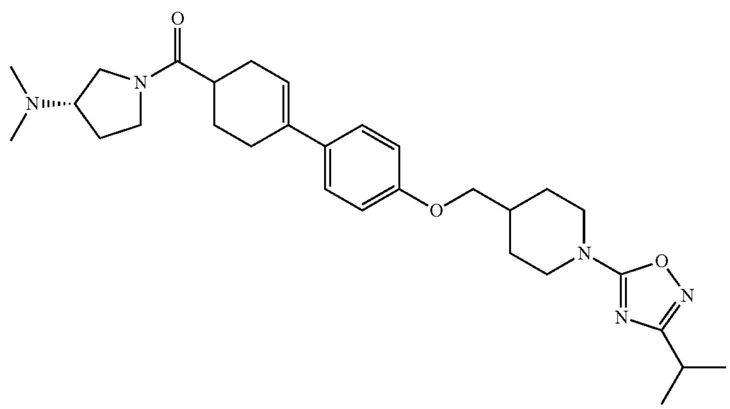 [SMILES: CC(C)c1noc(N2CCC(COc3ccc(C4=CCC(C(=O)N5CC[C@H](N(C)C)C5)CC4)cc3)CC2)n1] |
| 145 | HCl |
| 146 | HCl |

TABLE 1-continued
| Examples | Chemical structures |
|---|---|
| 147 | 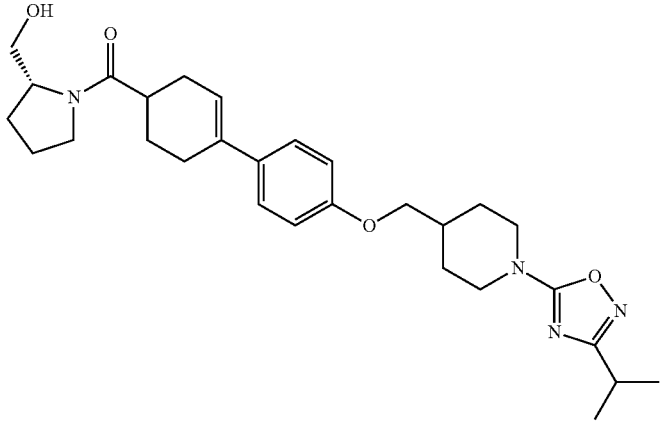 [SMILES: CC(C)c1noc(N2CCC(COc3ccc(C4=CCC(C(=O)N5CCC[C@@H]5CO)CC4)cc3)CC2)n1] |
| 148 | 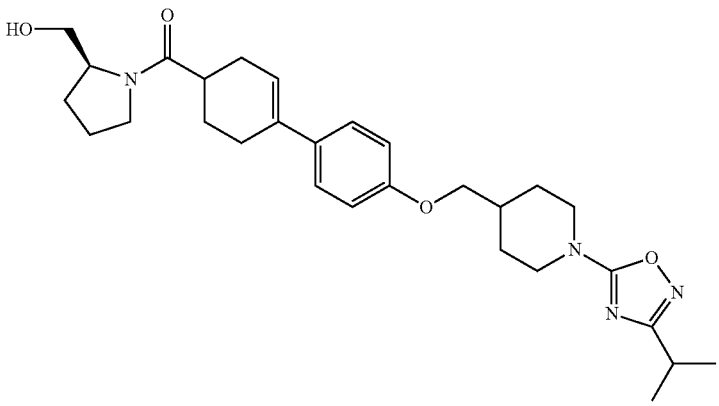 [SMILES: CC(C)c1noc(N2CCC(COc3ccc(C4=CCC(C(=O)N5CCC[C@H]5CO)CC4)cc3)CC2)n1] |
| 149 | 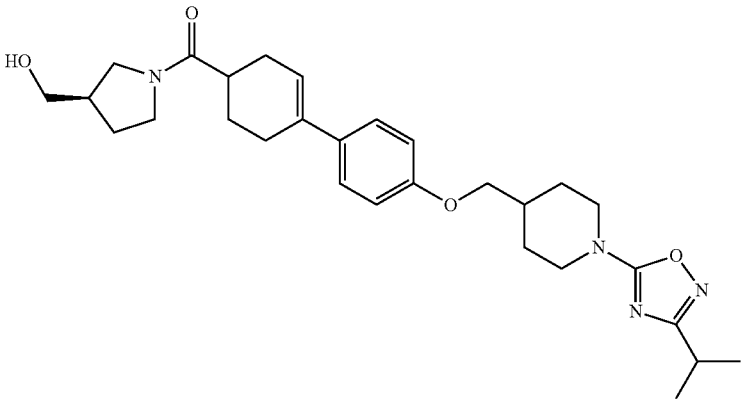 [SMILES: CC(C)c1noc(N2CCC(COc3ccc(C4=CCC(C(=O)N5CC[C@@H](CO)C5)CC4)cc3)CC2)n1] |

TABLE 1-continued
| Examples | Chemical structures |
|---|---|
| 150 | 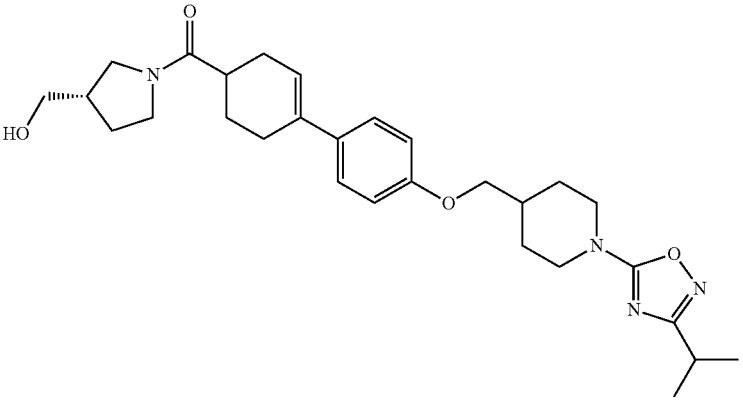 [SMILES: CC(C)c1noc(N2CCC(COc3ccc(C4=CCC(C(=O)N5CC[C@H](CO)C5)CC4)cc3)CC2)n1] |
| 151 | 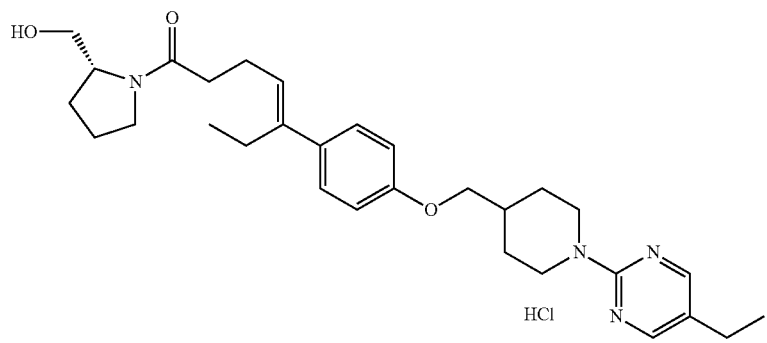 [SMILES: CC/C(=C\CCC(=O)N1CCC[C@@H]1CO)c1ccc(OCC2CCN(c3ncc(CC)cn3)CC2)cc1 ; Cl] |
| 152 | 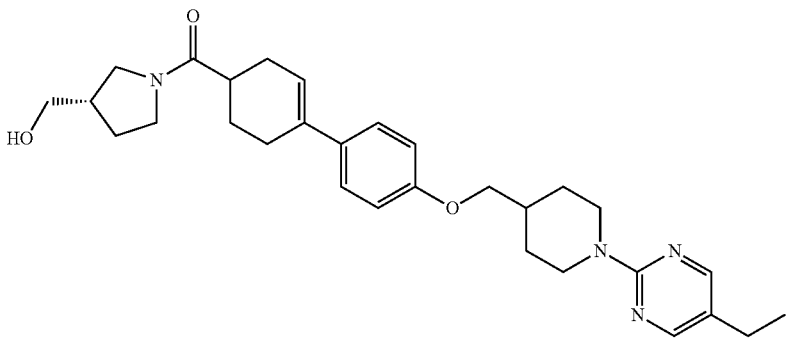 [SMILES: CCc1cnc(N2CCC(COc3ccc(C4=CCC(C(=O)N5CC[C@H](CO)C5)CC4)cc3)CC2)nc1] |
| 153 | 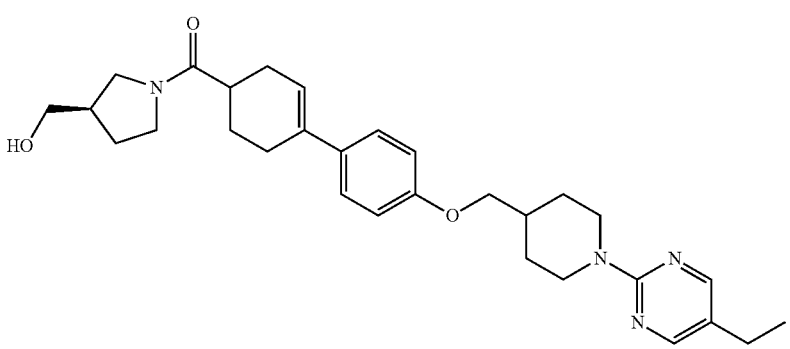 [SMILES: CCc1cnc(N2CCC(COc3ccc(C4=CCC(C(=O)N5CC[C@@H](CO)C5)CC4)cc3)CC2)nc1] |

TABLE 1-continued
| Examples | Chemical structures |
|---|---|
| 154 | 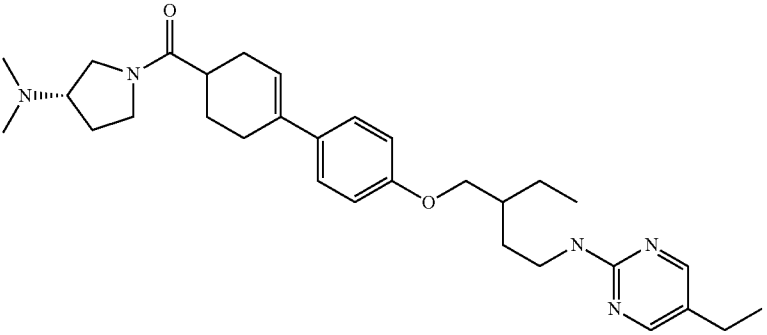 |
| 155 | 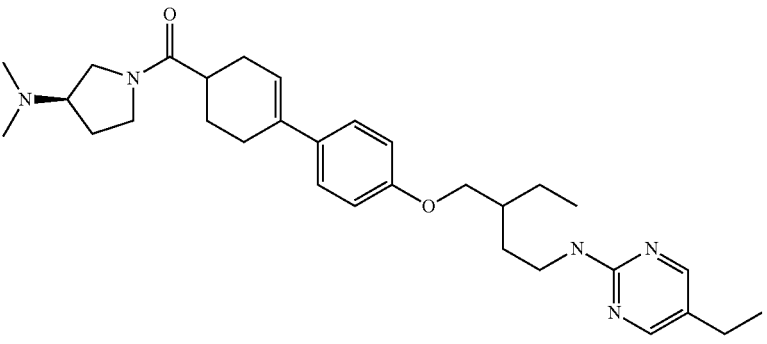 |
| 156 | 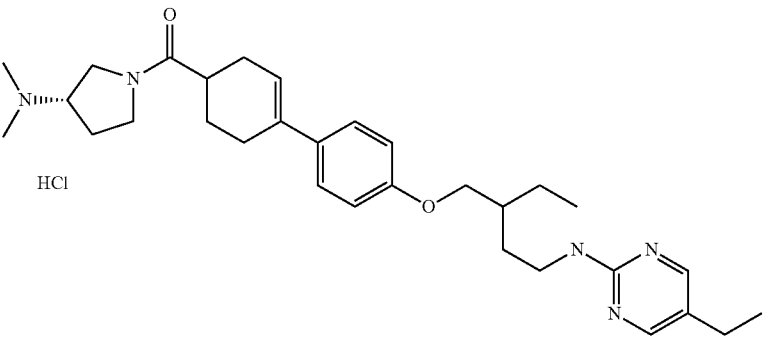 [SMILES: CCc1cnc(NCCC(CC)COc2ccc(C3=CCC(C(=O)N4CC[C@H](N(C)C)C4)CC3)cc2)nc1 ; Cl]
HCl |
| 157 | 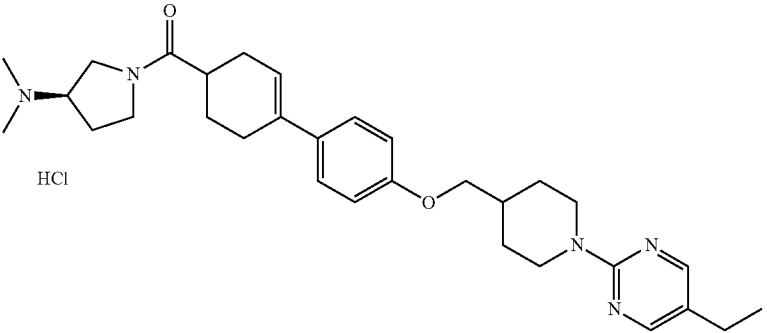 [SMILES: CCc1cnc(N2CCC(COc3ccc(C4=CCC(C(=O)N5CC[C@@H](N(C)C)C5)CC4)cc3)CC2)nc1 ; Cl]
HCl |

TABLE 1-continued
| Examples | Chemical structures |
|---|---|
| 158 | 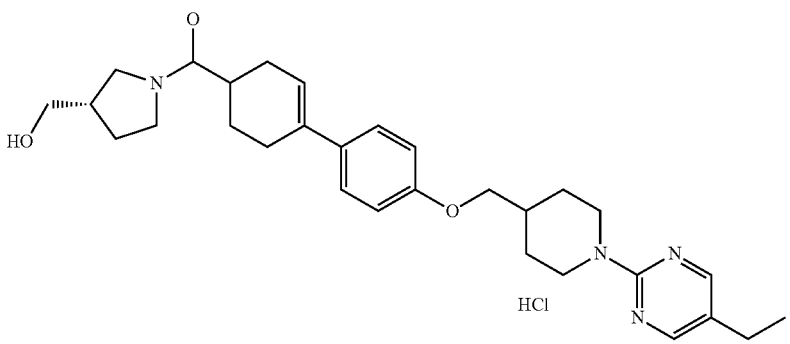 [SMILES: CCc1cnc(N2CCC(COc3ccc(C4=CCC(C(O)N5CC[C@H](CO)C5)CC4)cc3)CC2)nc1 ; Cl] |
| 159 | 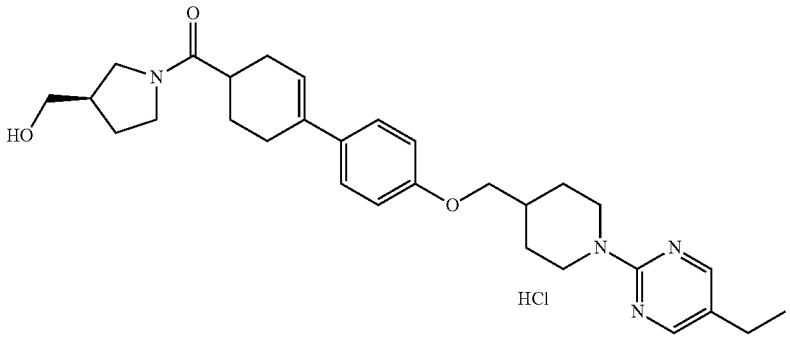 [SMILES: CCc1cnc(N2CCC(COc3ccc(C4=CCC(C(=O)N5CC[C@@H](CO)C5)CC4)cc3)CC2)nc1 ; Cl] |
| 160 | 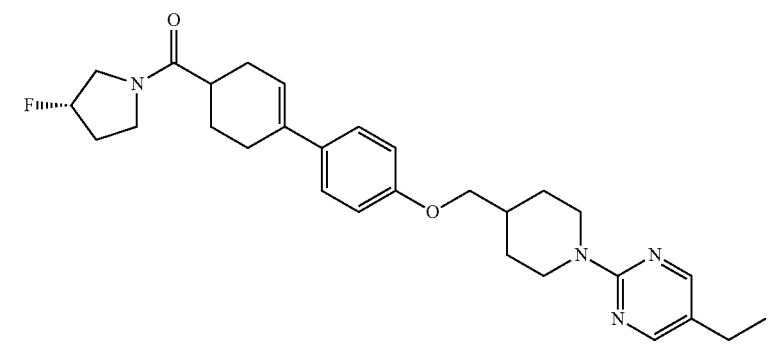 [SMILES: CCc1cnc(N2CCC(COc3ccc(C4=CCC(C(=O)N5CC[C@H](F)C5)CC4)cc3)CC2)nc1] |
| 161 | 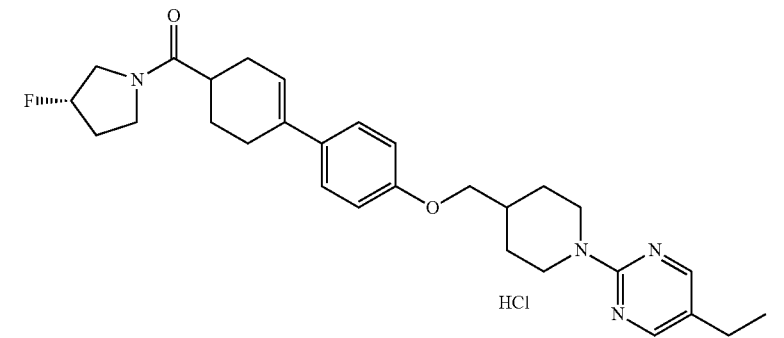 [SMILES: CCc1cnc(N2CCC(COc3ccc(C4=CCC(C(=O)N5CC[C@H](F)C5)CC4)cc3)CC2)nc1 ; Cl] |

TABLE 1-continued
| Examples | Chemical structures |
|---|---|
| 162 | 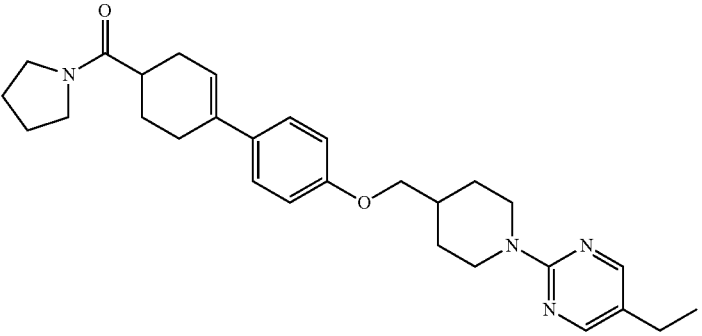 [SMILES: CCc1cnc(N2CCC(COc3ccc(C4=CCC(C(=O)N5CCCC5)CC4)cc3)CC2)nc1] |
| 163 | 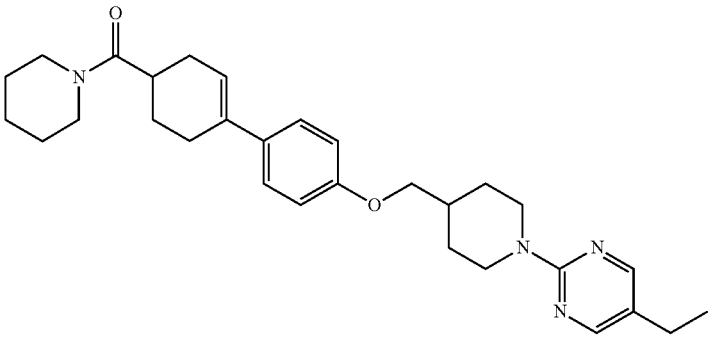 [SMILES: CCc1cnc(N2CCC(COc3ccc(C4=CCC(C(=O)N5CCCCC5)CC4)cc3)CC2)nc1] |
| 164 | 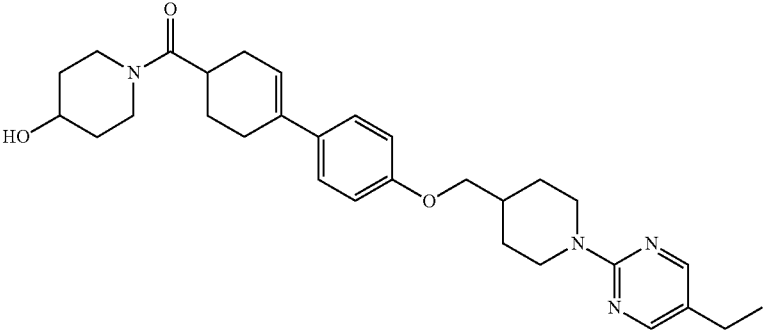 [SMILES: CCc1cnc(N2CCC(COc3ccc(C4=CCC(C(=O)N5CCC(O)CC5)CC4)cc3)CC2)nc1] |
| 165 | 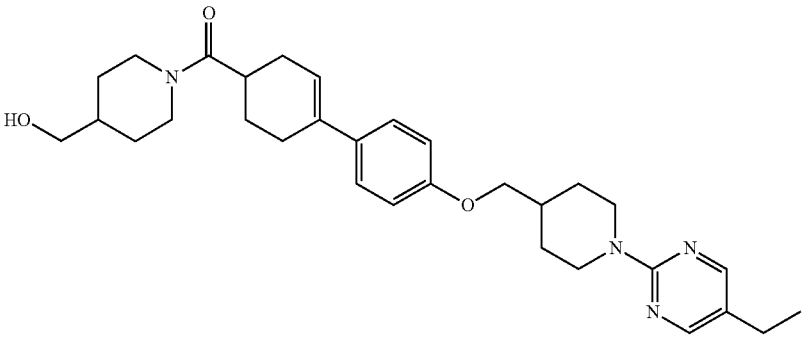 [SMILES: CCc1cnc(N2CCC(COc3ccc(C4=CCC(C(=O)N5CCC(CO)CC5)CC4)cc3)CC2)nc1] |

TABLE 1-continued
| Examples | Chemical structures |
|---|---|
| 166 | 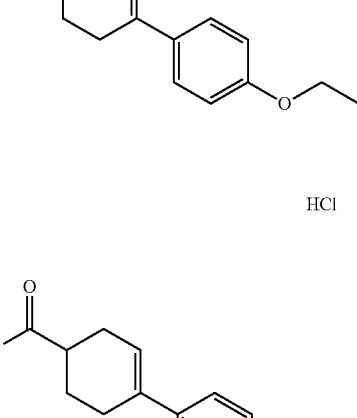 HCl |
| 167 | 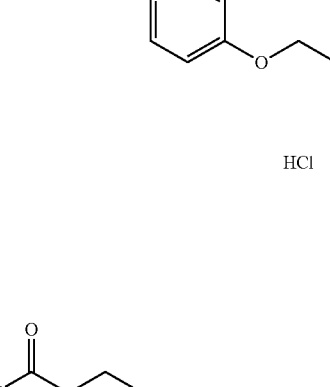 HCl |
| 168 | 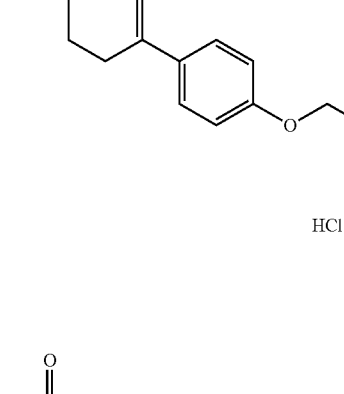 HCl |
| 169 | 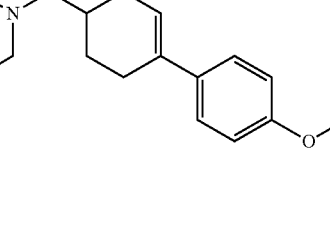 HCl |

TABLE 1-continued
| Examples | Chemical structures |
|---|---|
| 170 | 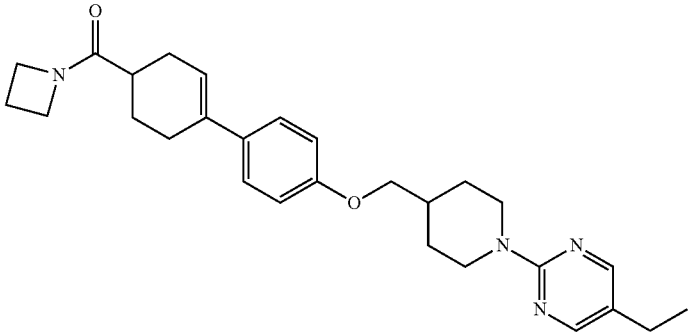 [SMILES: CCc1cnc(N2CCC(COc3ccc(C4=CCC(C(=O)N5CCC5)CC4)cc3)CC2)nc1] |
| 171 | 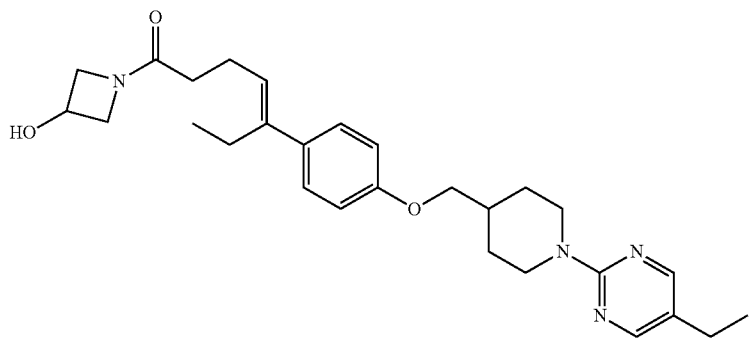 [SMILES: CC/C(=C\CCC(=O)N1CC(O)C1)c1ccc(OCC2CCN(c3ncc(CC)cn3)CC2)cc1] |
| 172 | 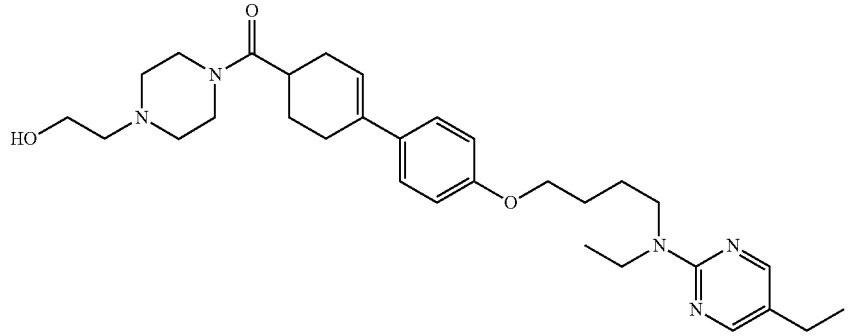 [SMILES: CCc1cnc(N(CC)CCCCOc2ccc(C3=CCC(C(=O)N4CCN(CCO)CC4)CC3)cc2)nc1] |
| 173 | 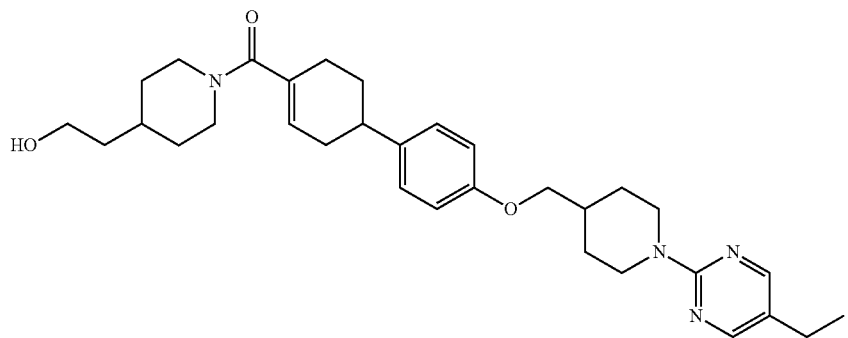 |

TABLE 1-continued
| Examples | Chemical structures |
|---|---|
| 174 | 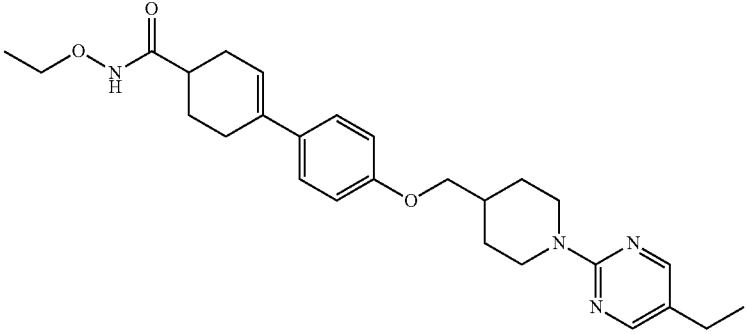 [SMILES: CCONC(=O)C1CC=C(c2ccc(OCC3CCN(c4ncc(CC)cn4)CC3)cc2)CC1] |
| 175 | 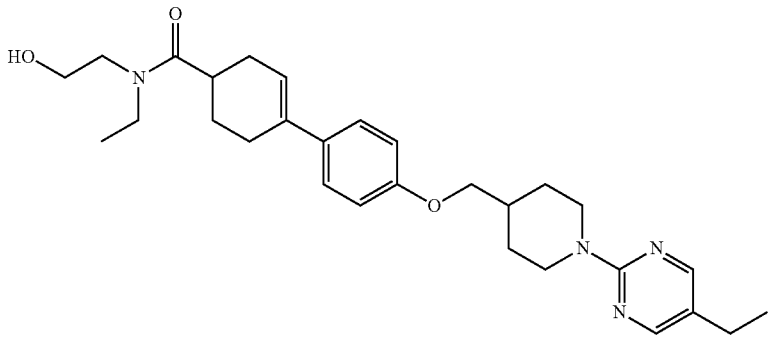 [SMILES: CCc1cnc(N2CCC(COc3ccc(C4=CCC(C(=O)N(CC)CCO)CC4)cc3)CC2)nc1] |
| 176 | 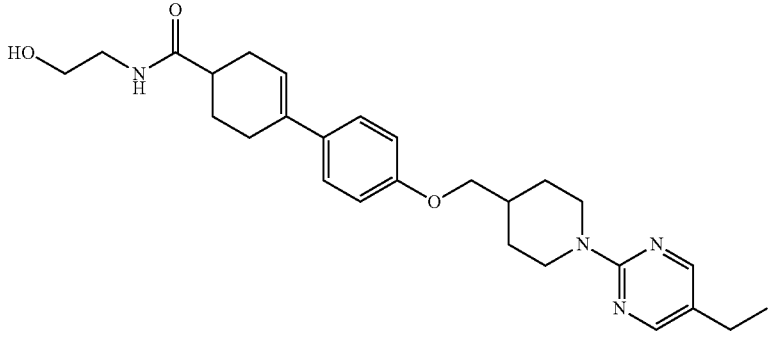 [SMILES: CCc1cnc(N2CCC(COc3ccc(C4=CCC(C(=O)NCCO)CC4)cc3)CC2)nc1] |
| 177 | 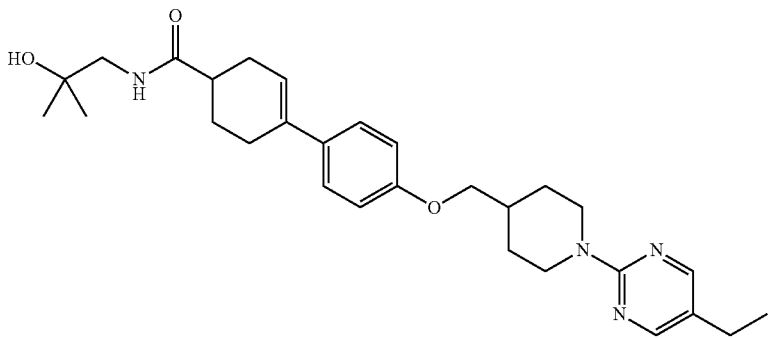 [SMILES: CCc1cnc(N2CCC(COc3ccc(C4=CCC(C(=O)NCC(C)(C)O)CC4)cc3)CC2)nc1] |

TABLE 1-continued
| Examples | Chemical structures |
|---|---|
| 178 | 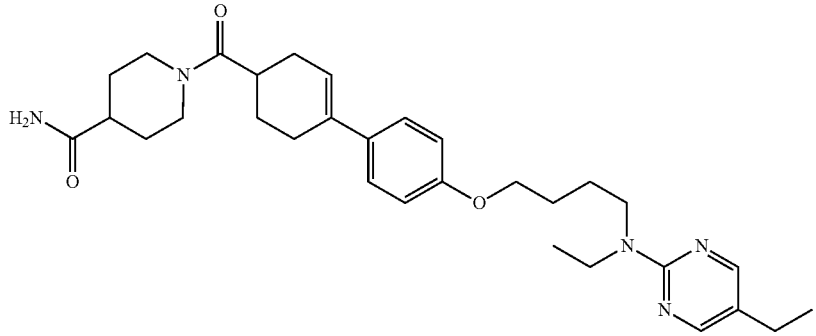 [SMILES: CCc1cnc(N(CC)CCCCOc2ccc(C3=CCC(C(=O)N4CCC(C(N)=O)CC4)CC3)cc2)nc1] |
| 179 | 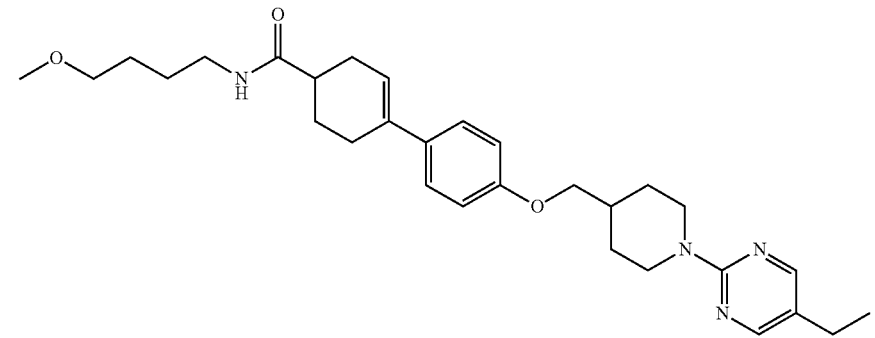 [SMILES: CCc1cnc(N2CCC(COc3ccc(C4=CCC(C(=O)NCCCCOC)CC4)cc3)CC2)nc1] |
| 180 | 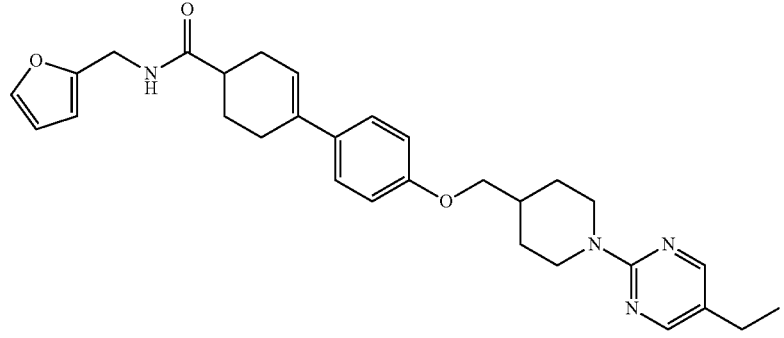 [SMILES: CCc1cnc(N2CCC(COc3ccc(C4=CCC(C(=O)NCc5ccco5)CC4)cc3)CC2)nc1] |
| 181 | 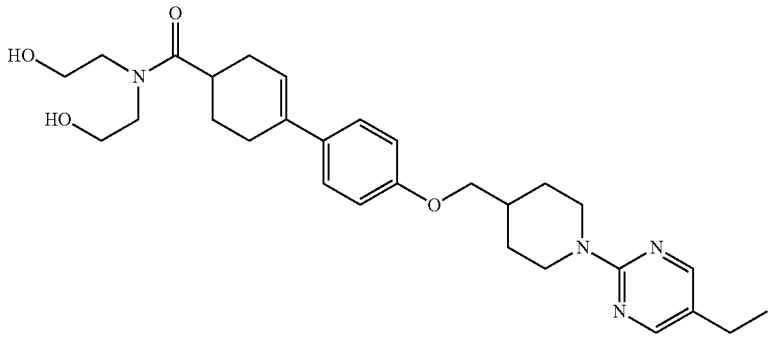 [SMILES: CCc1cnc(N2CCC(COc3ccc(C4=CCC(C(=O)N(CCO)CCO)CC4)cc3)CC2)nc1] |

TABLE 1-continued
| Examples | Chemical structures |
|---|---|
| 182 | 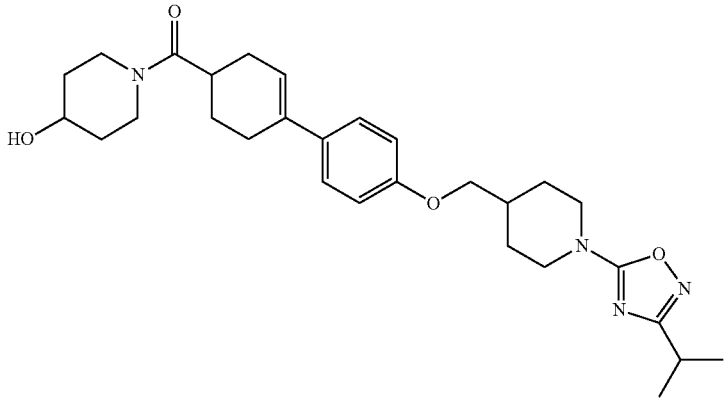 [SMILES: CC(C)c1noc(N2CCC(COc3ccc(C4=CCC(C(=O)N5CCC(O)CC5)CC4)cc3)CC2)n1] |
| 183 | 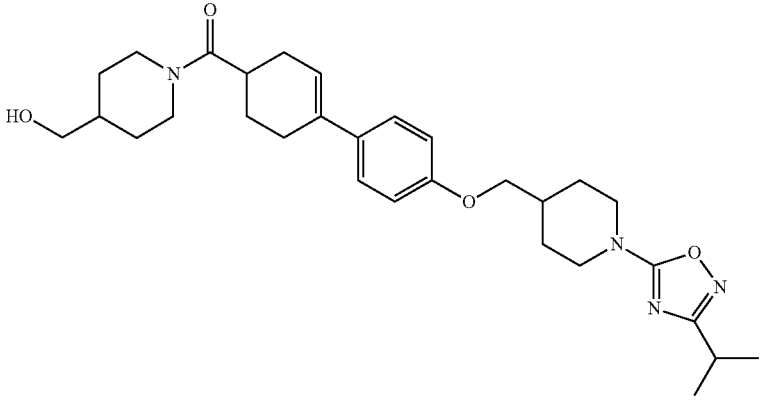 [SMILES: CC(C)c1noc(N2CCC(COc3ccc(C4=CCC(C(=O)N5CCC(CO)CC5)CC4)cc3)CC2)n1] |
| 184 | 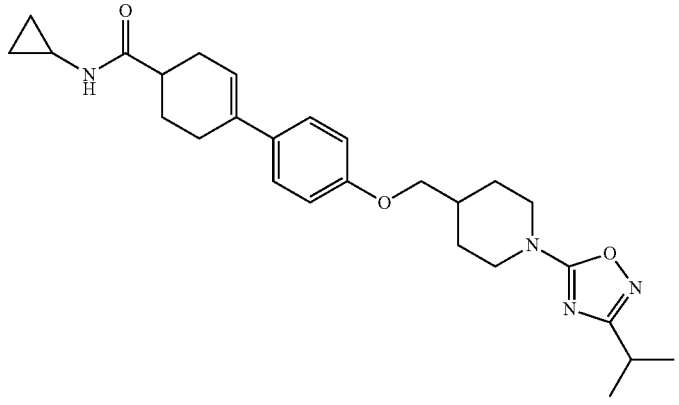 [SMILES: CC(C)c1noc(N2CCC(COc3ccc(C4=CCC(C(=O)NC5CC5)CC4)cc3)CC2)n1] |
| 185 | 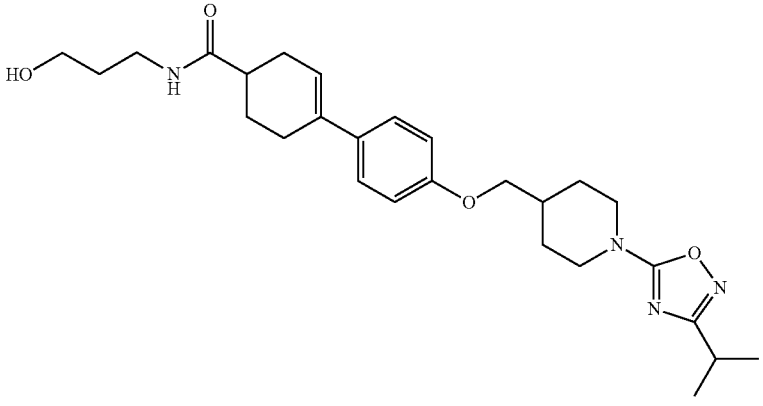 [SMILES: CC(C)c1noc(N2CCC(COc3ccc(C4=CCC(C(=O)NCCCO)CC4)cc3)CC2)n1] |

TABLE 1-continued
| Examples | Chemical structures |
|---|---|
| 186 | 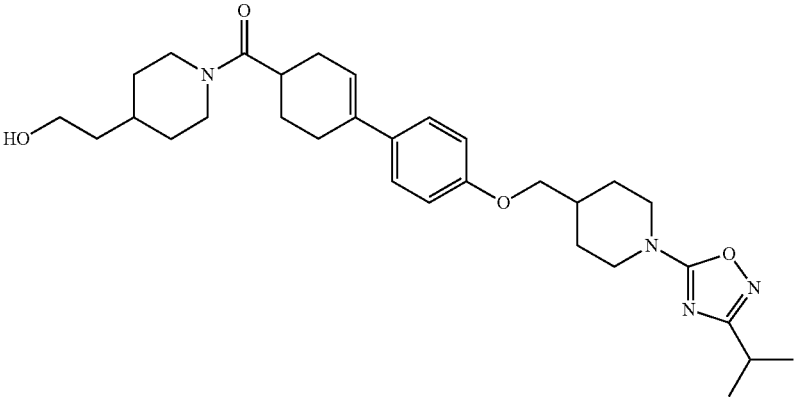 [SMILES: CC(C)c1noc(N2CCC(COc3ccc(C4=CCC(C(=O)N5CCN(CCO)CC5)CC4)cc3)CC2)n1] |
| 187 | 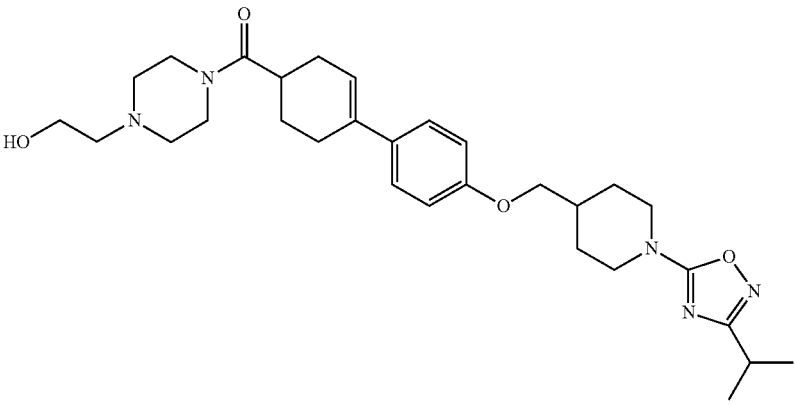 |
| 188 | 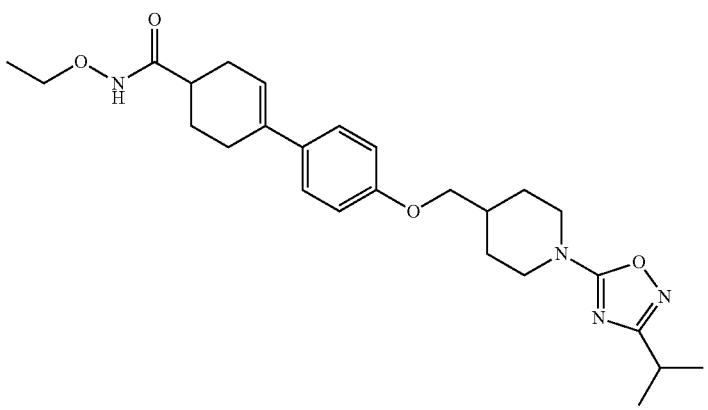 [SMILES: CCONC(=O)C1CC=C(c2ccc(OCC3CCN(c4nc(C(C)C)no4)CC3)cc2)CC1] |
| 189 | 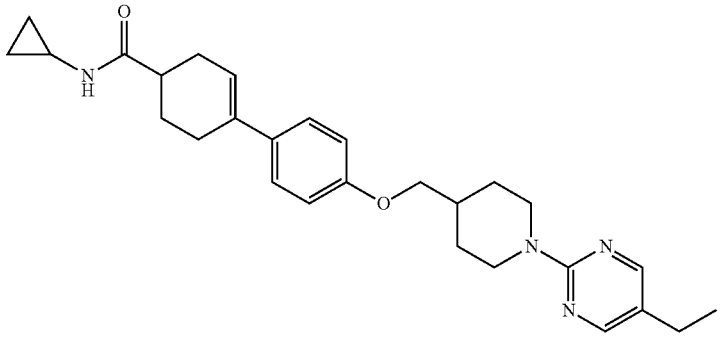 [SMILES: CCc1cnc(N2CCC(COc3ccc(C4=CCC(C(=O)NC5CC5)CC4)cc3)CC2)nc1] |

TABLE 1-continued
| Examples | Chemical structures |
|---|---|
| 190 | 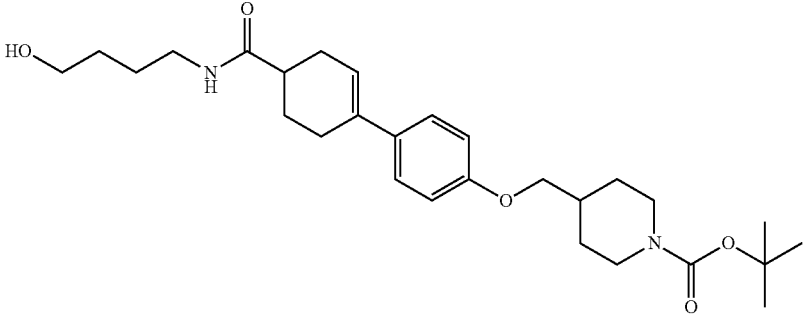 [SMILES: CC(C)(C)OC(=O)N1CCC(COc2ccc(C3=CCC(C(=O)NCCCCO)CC3)cc2)CC1] |
| 191 | 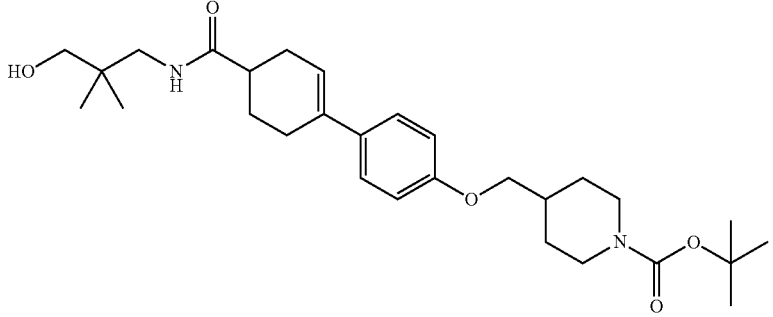 [SMILES: CC(C)(CO)CNC(=O)C1CC=C(c2ccc(OCC3CCN(C(=O)OC(C)(C)C)CC3)cc2)CC1] |
| 192 | 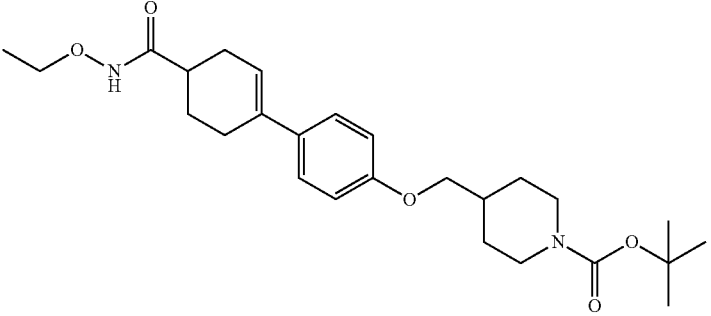 [SMILES: CCONC(=O)C1CC=C(c2ccc(OCC3CCN(C(=O)OC(C)(C)C)CC3)cc2)CC1] |
| 193 | 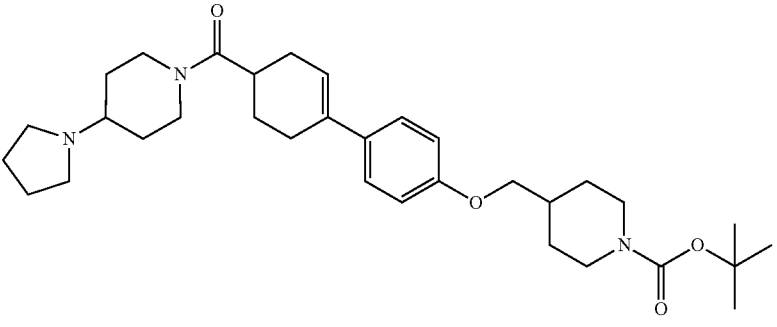 [SMILES: CC(C)(C)OC(=O)N1CCC(COc2ccc(C3=CCC(C(=O)N4CCC(N5CCCC5)CC4)CC3)cc2)CC1] |

TABLE 1-continued

| Examples | Chemical structures |
|---|---|
| 194 | 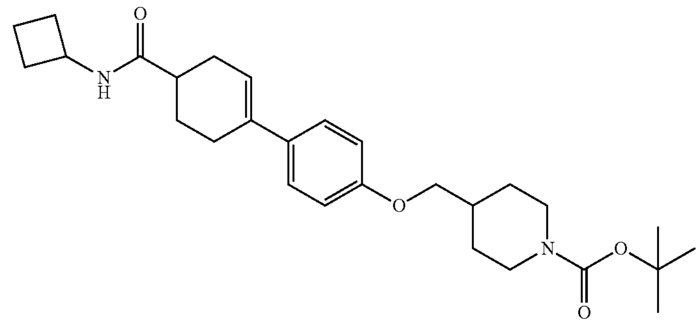 [SMILES: CC(C)(C)OC(=O)N1CCC(COc2ccc(C3=CCC(C(=O)NC4CCC4)CC3)cc2)CC1] |
| 195 | 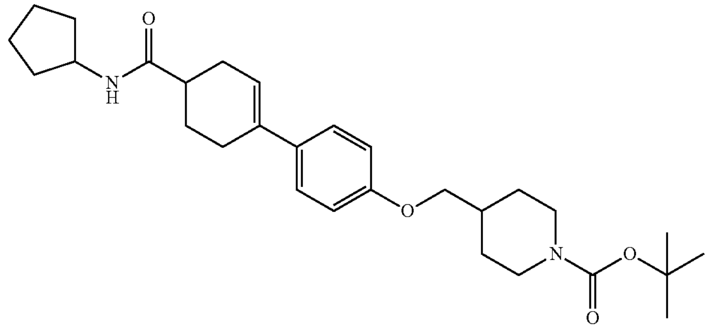 [SMILES: CC(C)(C)OC(=O)N1CCC(COc2ccc(C3=CCC(C(=O)NC4CCCC4)CC3)cc2)CC1] |
| 196 | 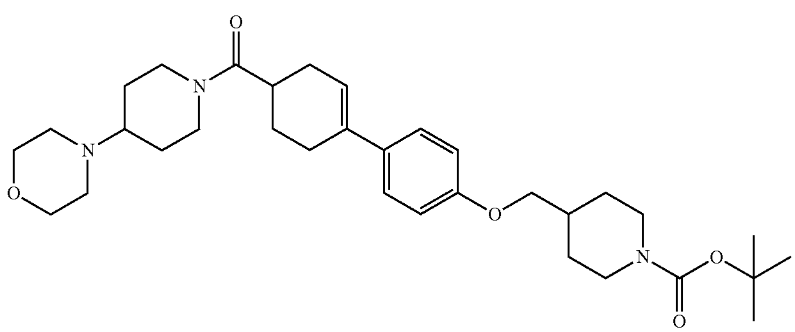 [SMILES: CC(C)(C)OC(=O)N1CCC(COc2ccc(C3=CCC(C(=O)N4CCC(N5CCOCC5)CC4)CC3)cc2)CC1] |
| 197 | 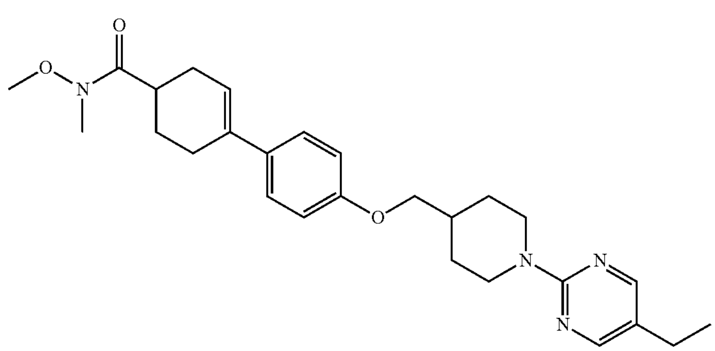 [SMILES: CCc1cnc(N2CCC(COc3ccc(C4=CCC(C(=O)N(C)OC)CC4)cc3)CC2)nc1] |

333
334
TABLE 1-continued
| Examples | Chemical structures |
|---|---|
| 198 | 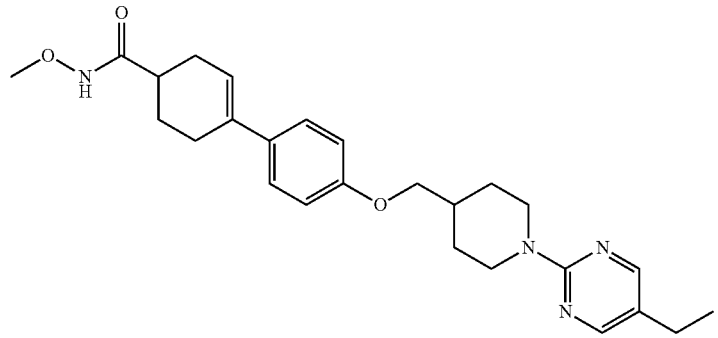 [SMILES: CCc1cnc(N2CCC(COc3ccc(C4=CCC(C(=O)NOC)CC4)cc3)CC2)nc1] |
| 199 | 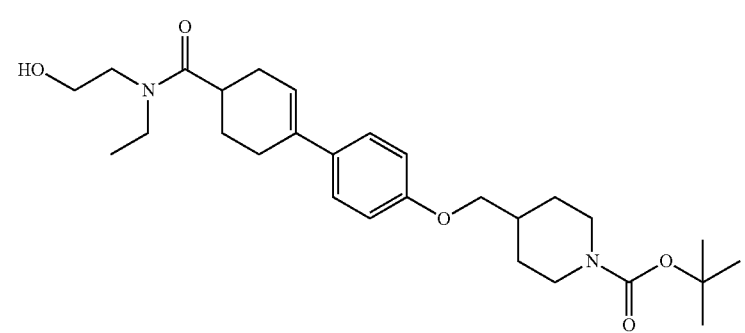 [SMILES: CCN(CCO)C(=O)C1CC=C(c2ccc(OCC3CCN(C(=O)OC(C)(C)C)CC3)cc2)CC1] |
| 200 | 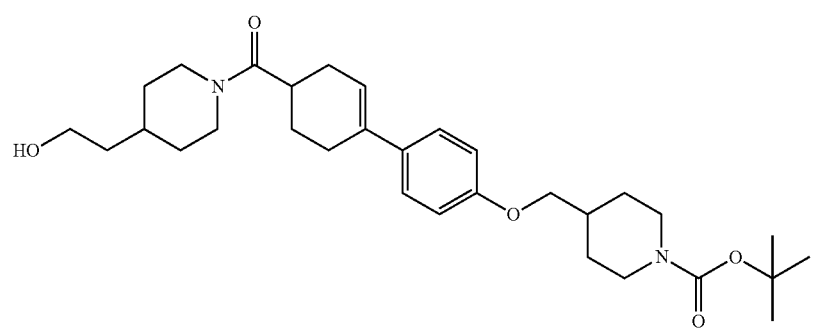 |
| 201 | 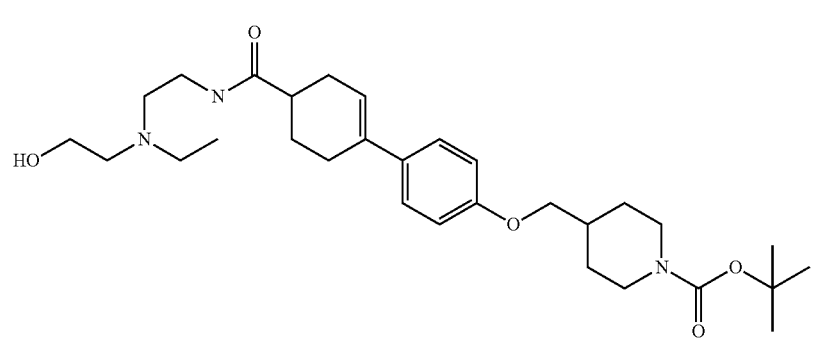 [SMILES: CCN(CCO)CCNC(=O)C1CC=C(c2ccc(OCC3CCN(C(=O)OC(C)(C)C)CC3)cc2)CC1] |

TABLE 1-continued
| Examples | Chemical structures |
|---|---|
| 202 | 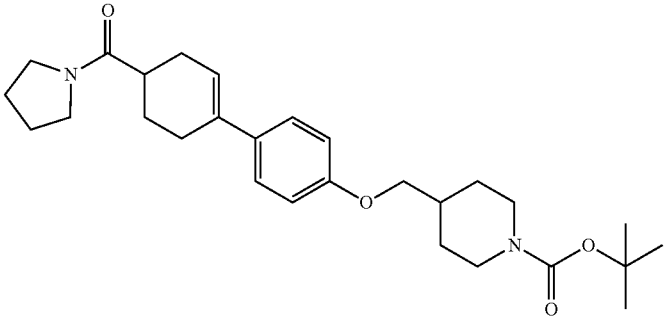 [SMILES: CC(C)(C)OC(=O)N1CCC(COc2ccc(C3=CCC(C(=O)N4CCCC4)CC3)cc2)CC1] |
| 203 | 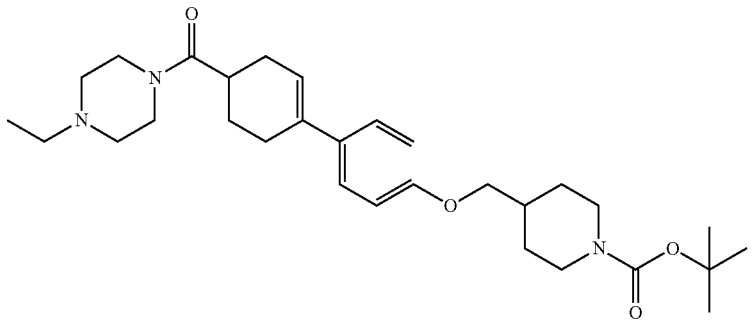 [SMILES: C=C/C(=C\C=C\OCC1CCN(C(=O)OC(C)(C)C)CC1)C1=CCC(C(=O)N2CCN(CC)CC2)CC1] |
| 204 | 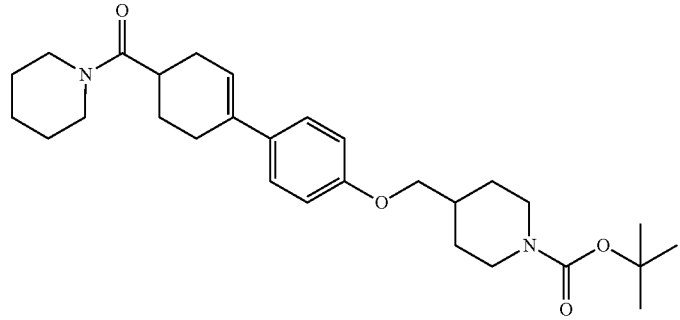 [SMILES: CC(C)(C)OC(=O)N1CCC(COc2ccc(C3=CCC(C(=O)N4CCCCC4)CC3)cc2)CC1] |
| 205 | 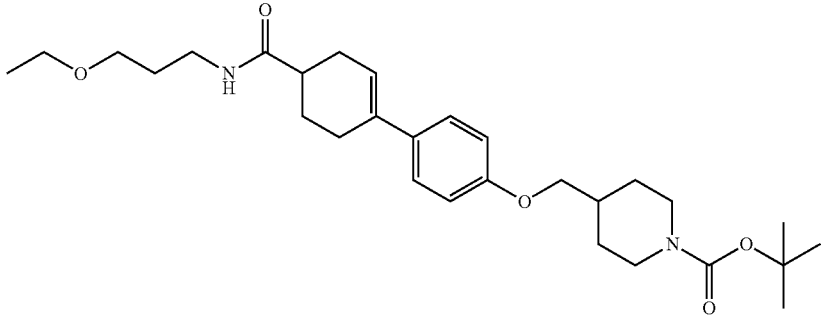 [SMILES: CCOCCCNC(=O)C1CC=C(c2ccc(OCC3CCN(C(=O)OC(C)(C)C)CC3)cc2)CC1] |

TABLE 1-continued
| Examples | Chemical structures |
|---|---|
| 206 | 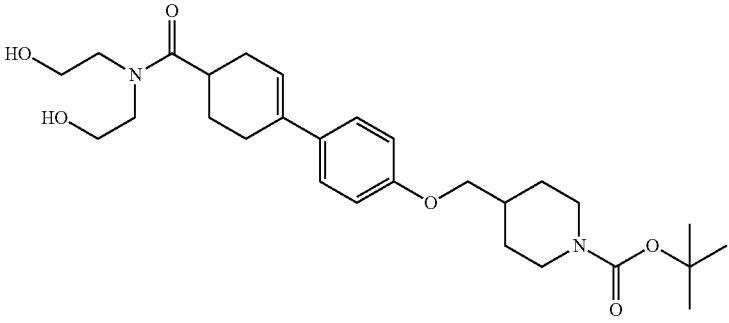 [SMILES: CC(C)(C)OC(=O)N1CCC(COc2ccc(C3=CCC(C(=O)N(CCO)CCO)CC3)cc2)CC1] |
| 207 | 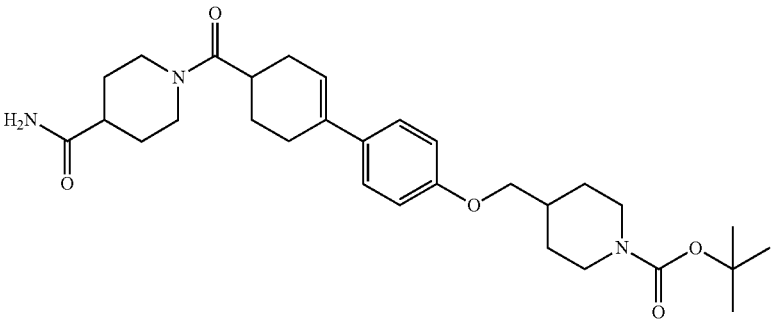 [SMILES: CC(C)(C)OC(=O)N1CCC(COc2ccc(C3=CCC(C(=O)N4CCC(C(N)=O)CC4)CC3)cc2)CC1] |
| 208 | 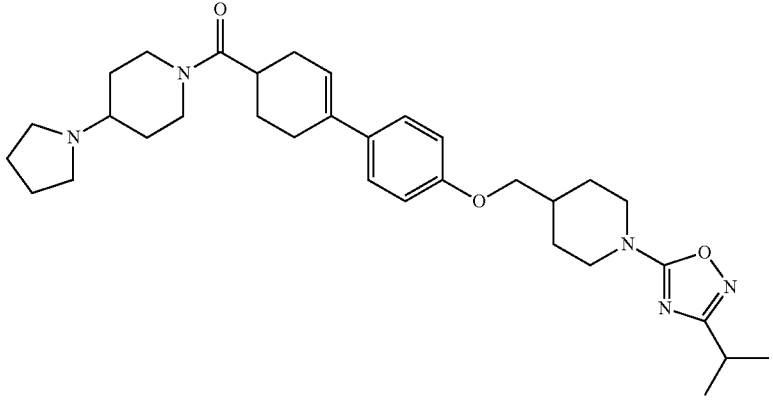 [SMILES: CC(C)c1noc(N2CCC(COc3ccc(C4=CCC(C(=O)N5CCC(N6CCCC6)CC5)CC4)cc3)CC2)n1] |
| 209 | 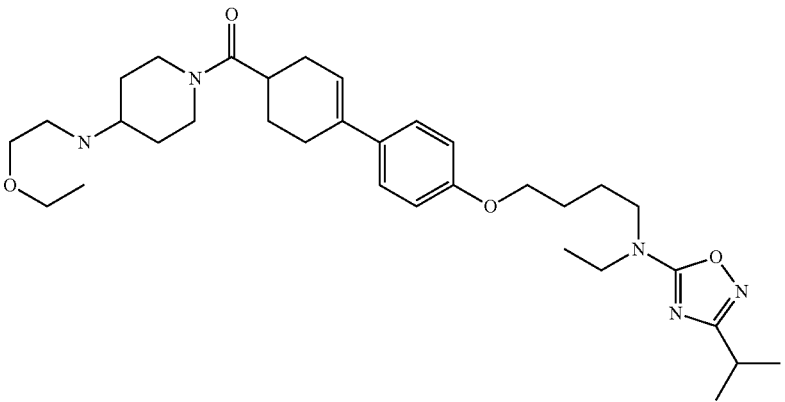 [SMILES: CCOCCNC1CCN(C(=O)C2CC=C(c3ccc(OCCCCN(CC)c4nc(C(C)C)no4)cc3)CC2)CC1] |

TABLE 1-continued
| Examples | Chemical structures |
|---|---|
| 210 | 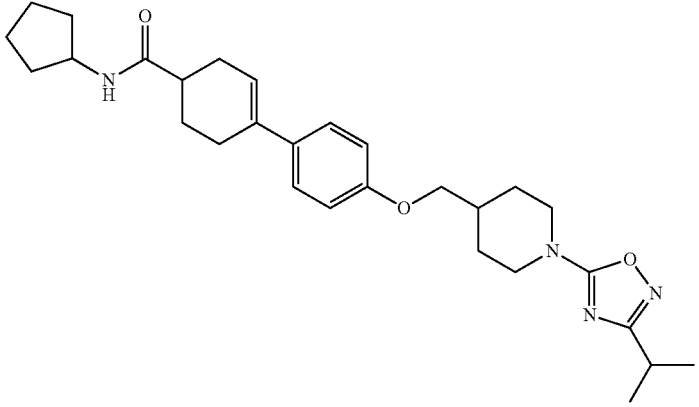 [SMILES: CC(C)c1noc(N2CCC(COc3ccc(C4=CCC(C(=O)NC5CCCC5)CC4)cc3)CC2)n1] |
| 212 | 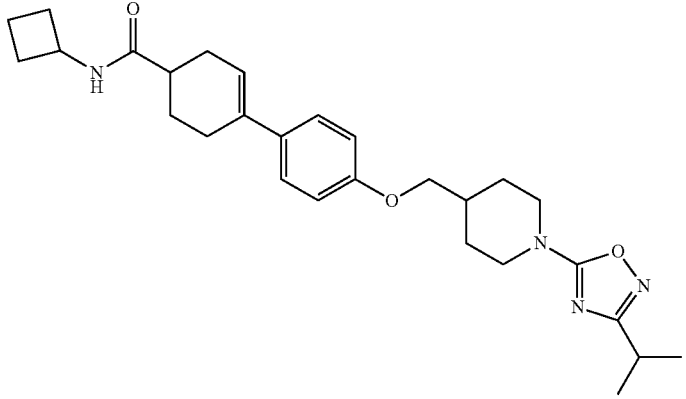 [SMILES: CC(C)c1noc(N2CCC(COc3ccc(C4=CCC(C(=O)NC5CCC5)CC4)cc3)CC2)n1] |
| 212 | 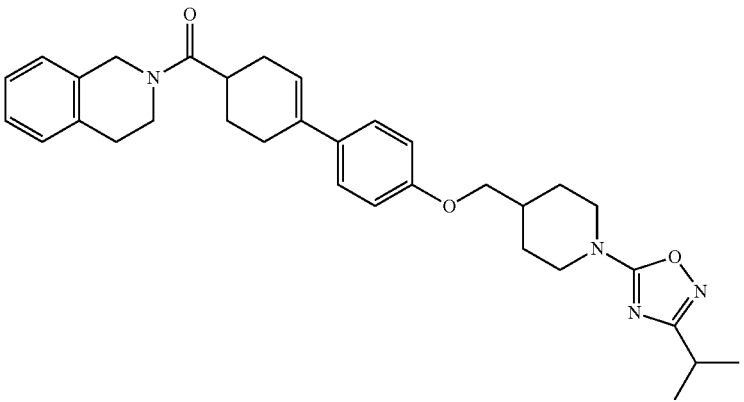 [SMILES: CC(C)c1noc(N2CCC(COc3ccc(C4=CCC(C(=O)N5CCc6ccccc6C5)CC4)cc3)CC2)n1] |

TABLE 1-continued
| Examples | Chemical structures |
|---|---|
| 213 | 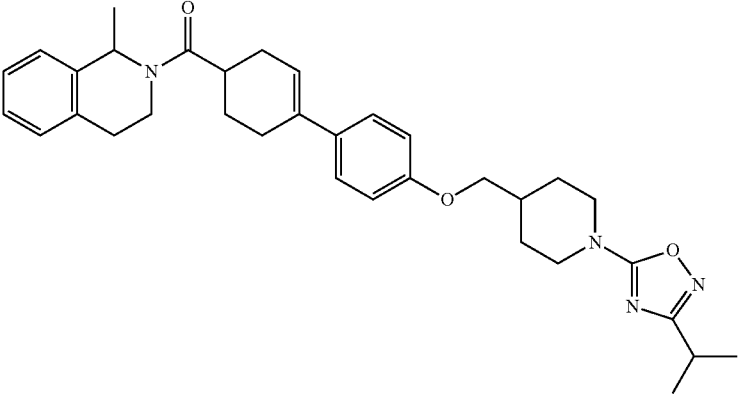 [SMILES: CC(C)c1noc(N2CCC(COc3ccc(C4=CCC(C(=O)N5CCc6ccccc6C5C)CC4)cc3)CC2)n1] |
| 214 | 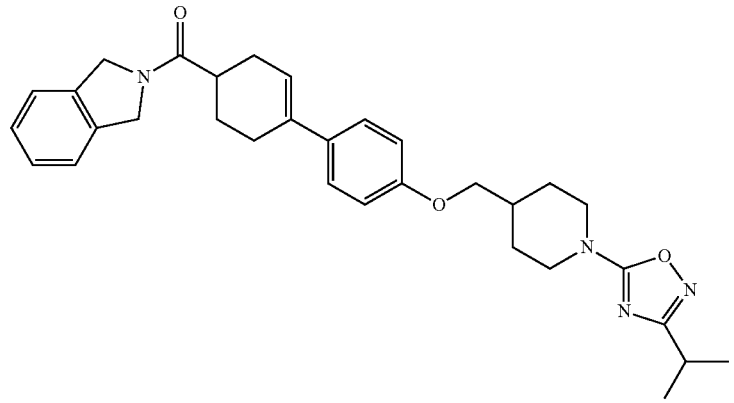 [SMILES: CC(C)c1noc(N2CCC(COc3ccc(C4=CCC(C(=O)N5Cc6ccccc6C5)CC4)cc3)CC2)n1] |
| 215 | 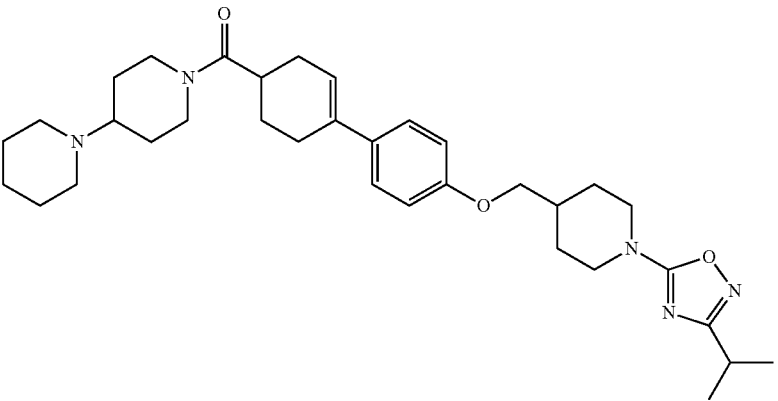 [SMILES: CC(C)c1noc(N2CCC(COc3ccc(C4=CCC(C(=O)N5CCC(N6CCCCC6)CC5)CC4)cc3)CC2)n1] |
| 216 | 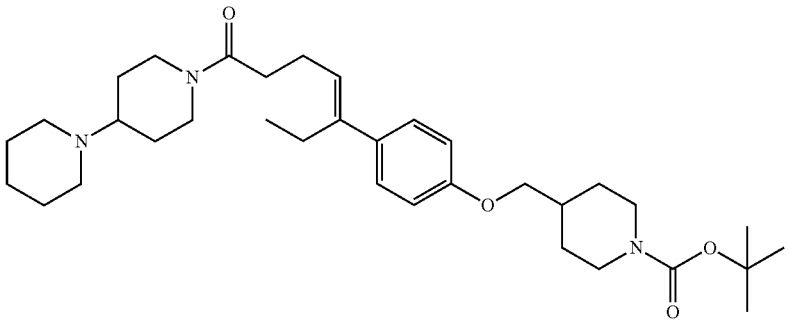 [SMILES: CC/C(=C\CCC(=O)N1CCC(N2CCCCC2)CC1)c1ccc(OCC2CCN(C(=O)OC(C)(C)C)CC2)cc1] |

TABLE 1-continued
| Examples | Chemical structures |
|---|---|
| 217 | 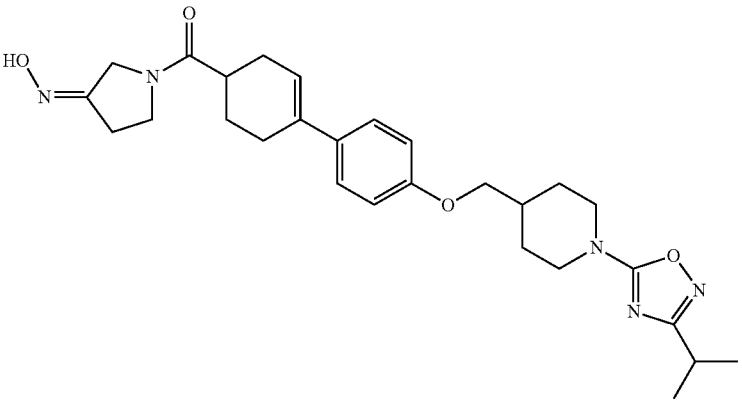 [SMILES: CC(C)c1noc(N2CCC(COc3ccc(C4=CCC(C(=O)N5CC/C(=N/O)C5)CC4)cc3)CC2)n1] |
| 218 | 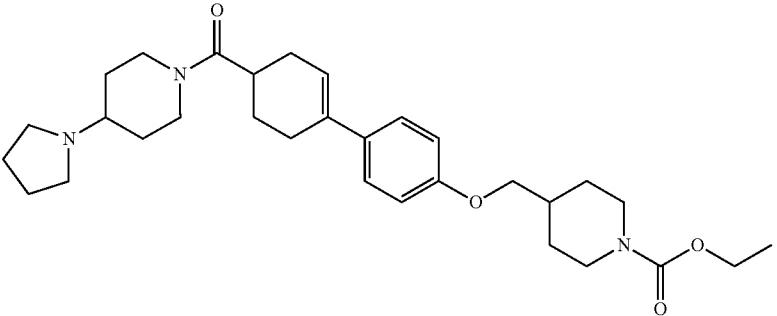 [SMILES: CCOC(=O)N1CCC(COc2ccc(C3=CCC(C(=O)N4CCC(N5CCCC5)CC4)CC3)cc2)CC1] |
| 219 | 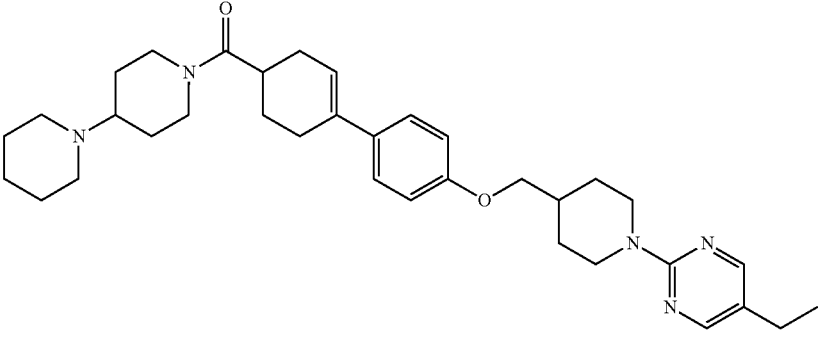 [SMILES: CCc1cnc(N2CCC(COc3ccc(C4=CCC(C(=O)N5CCC(N6CCCCC6)CC5)CC4)cc3)CC2)nc1] |
| 220 | 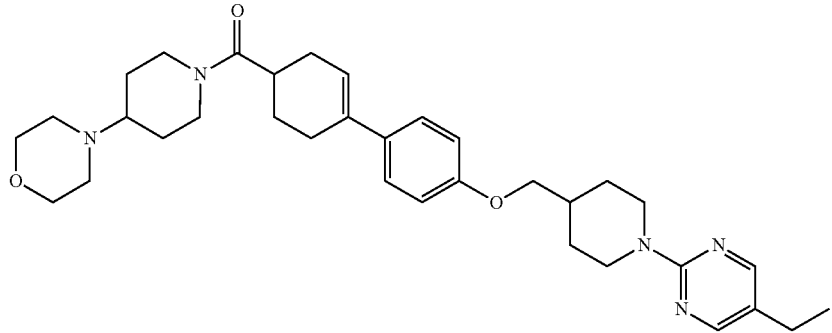 [SMILES: CCc1cnc(N2CCC(COc3ccc(C4=CCC(C(=O)N5CCC(N6CCOCC6)CC5)CC4)cc3)CC2)nc1] |

TABLE 1-continued
| Examples | Chemical structures |
|---|---|
| 221 | 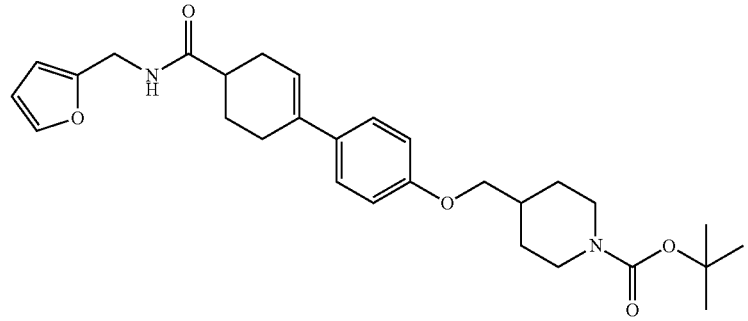 [SMILES: CC(C)(C)OC(=O)N1CCC(COc2ccc(C3=CCC(C(=O)NCc4ccco4)CC3)cc2)CC1] |
| 222 | 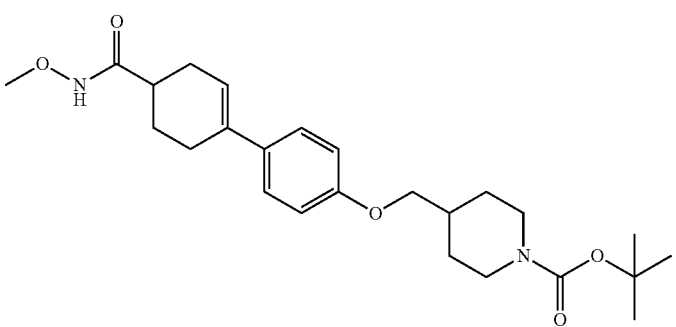 [SMILES: CONC(=O)C1CC=C(c2ccc(OCC3CCN(C(=O)OC(C)(C)C)CC3)cc2)CC1] |
| 223 | 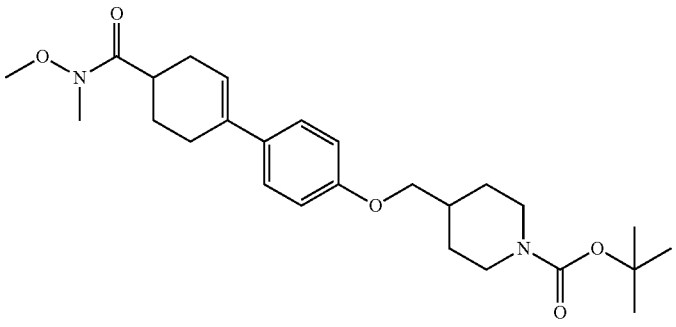 [SMILES: CON(C)C(=O)C1CC=C(c2ccc(OCC3CCN(C(=O)OC(C)(C)C)CC3)cc2)CC1] |
| 224 | 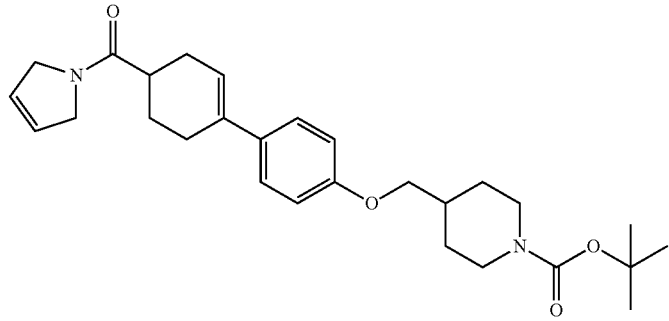 [SMILES: CC(C)(C)OC(=O)N1CCC(COc2ccc(C3=CCC(C(=O)N4CC=CC4)CC3)cc2)CC1] |

TABLE 1-continued
| Examples | Chemical structures |
|---|---|
| 225 | 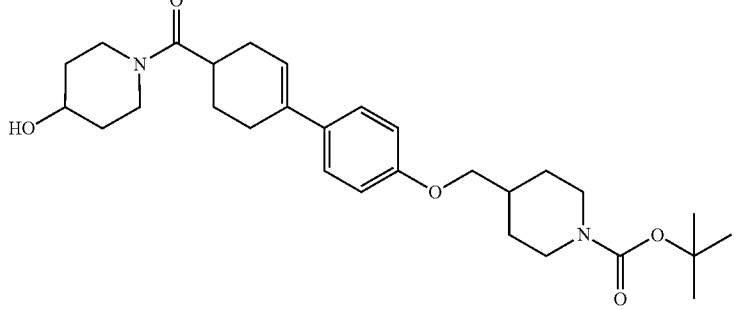 |
| 226 | 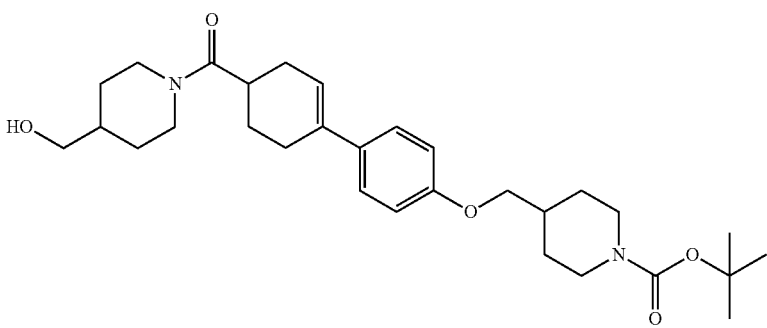 [SMILES: CC(C)(C)OC(=O)N1CCC(COc2ccc(C3=CCC(C(=O)N4CCC(CO)CC4)CC3)cc2)CC1] |
| 227 | 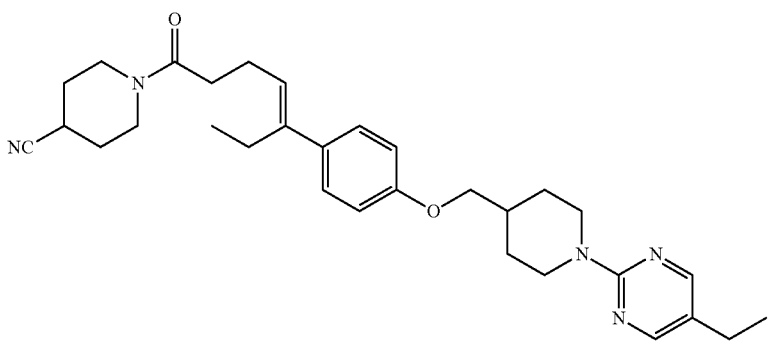 [SMILES: CC/C(=C\CCC(=O)N1CCC(C#N)CC1)c1ccc(OCC2CCN(c3ncc(CC)cn3)CC2)cc1] |
| 228 | 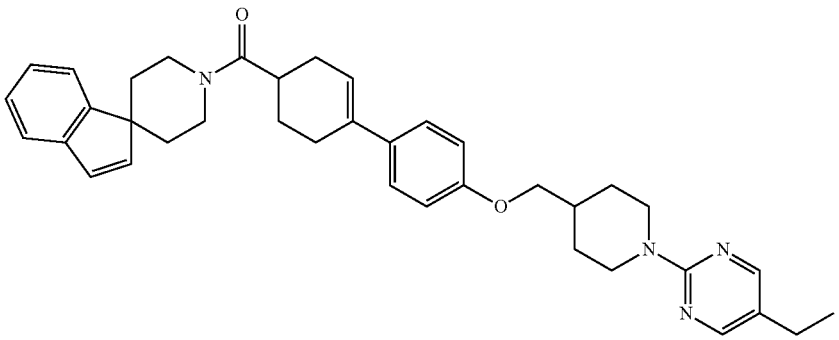 [SMILES: CCc1cnc(N2CCC(COc3ccc(C4=CCC(C(=O)N5CCC6(C=Cc7ccccc76)CC5)CC4)cc3)CC2)nc1] |

TABLE 1-continued
| Examples | Chemical structures |
|---|---|
| 229 | 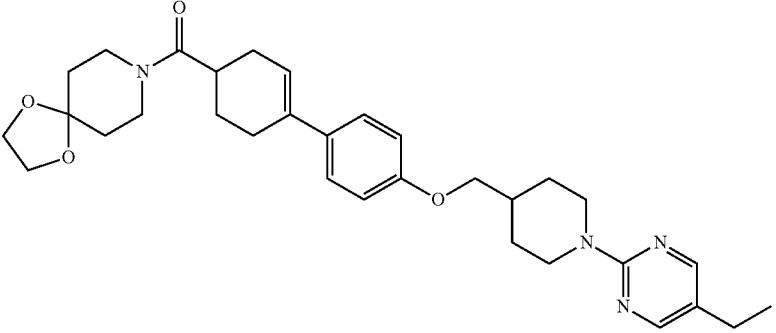 [SMILES: CCc1cnc(N2CCC(COc3ccc(C4=CCC(C(=O)N5CCC6(CC5)OCCO6)CC4)cc3)CC2)nc1] |
| 230 | 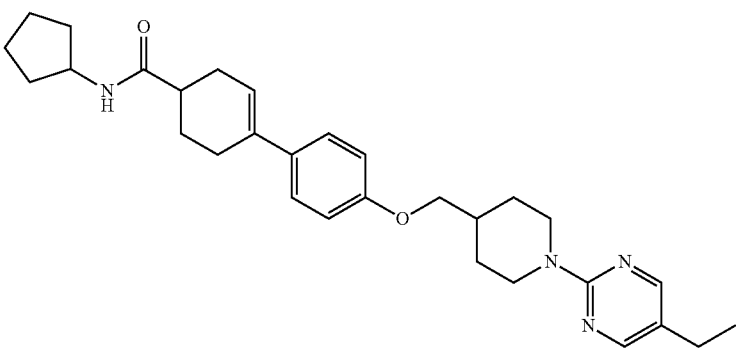 [SMILES: CCc1cnc(N2CCC(COc3ccc(C4=CCC(C(=O)NC5CCCC5)CC4)cc3)CC2)nc1] |
| 231 | 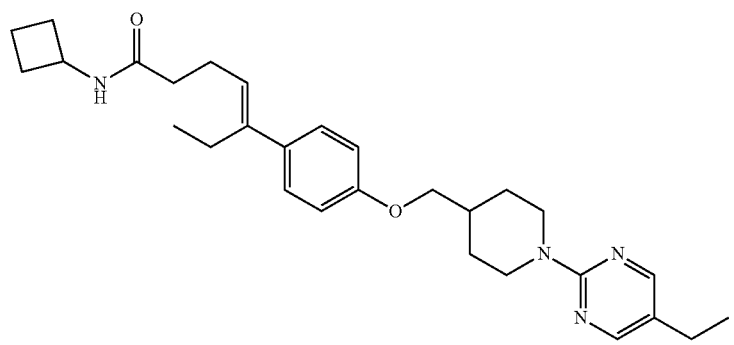 [SMILES: CC/C(=C\CCC(=O)NC1CCC1)c1ccc(OCC2CCN(c3ncc(CC)cn3)CC2)cc1] |
| 232 | 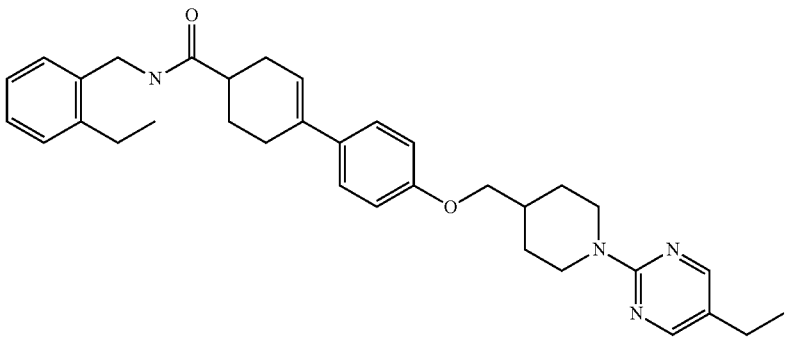 [SMILES: CCc1cnc(N2CCC(COc3ccc(C4=CCC(C(=O)NCc5ccccc5CC)CC4)cc3)CC2)nc1] |

TABLE 1-continued
| Examples | Chemical structures |
|---|---|
| 233 | 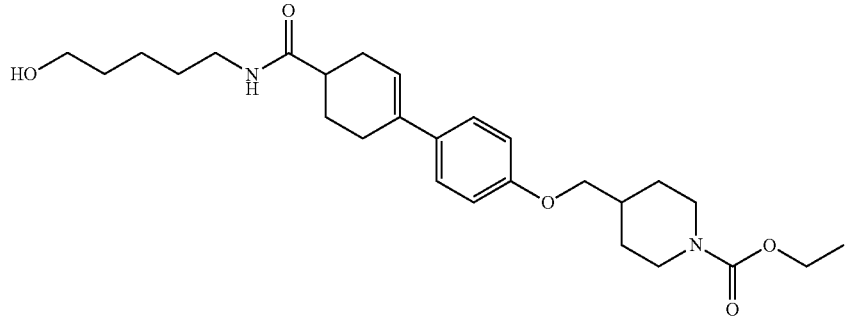 [SMILES: CCOC(=O)N1CCC(COc2ccc(C3=CCC(C(=O)NCCCCCO)CC3)cc2)CC1] |
| 234 | 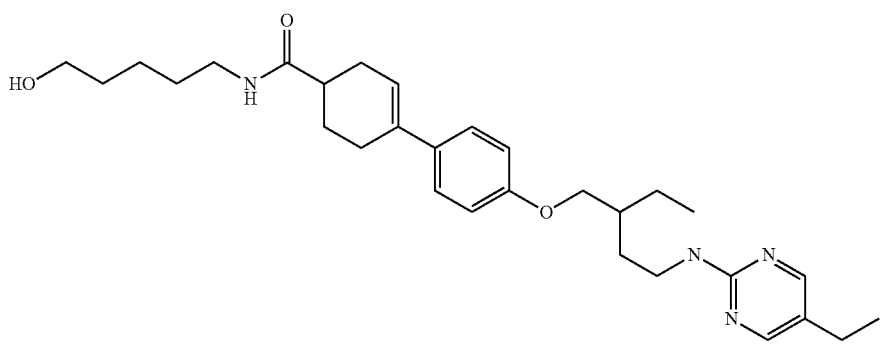 [SMILES: CCc1cnc(NCCC(CC)COc2ccc(C3=CCC(C(=O)NCCCCCO)CC3)cc2)nc1] |
| 235 | 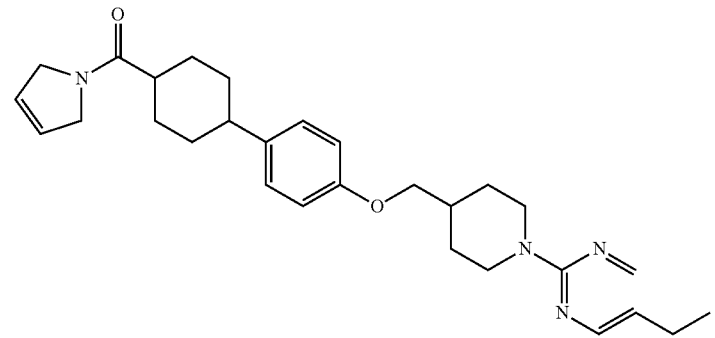 [SMILES: C=N/C(=N\C=C\CC)N1CCC(COc2ccc(C3CCC(C(=O)N4CC=CC4)CC3)cc2)CC1] |
| 236 | 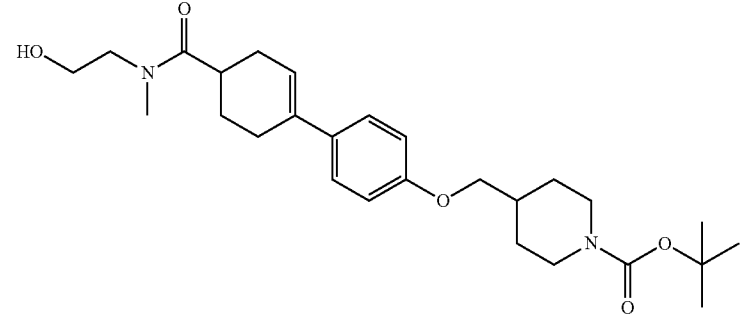 [SMILES: CN(CCO)C(=O)C1CC=C(c2ccc(OCC3CCN(C(=O)OC(C)(C)C)CC3)cc2)CC1] |

TABLE 1-continued
| Examples | Chemical structures |
|---|---|
| 237 | 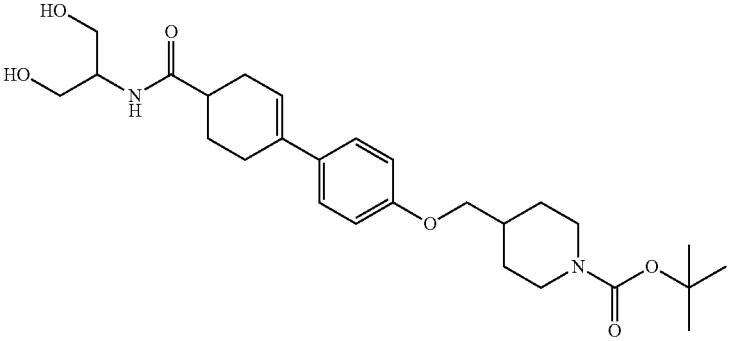 [SMILES: CC(C)(C)OC(=O)N1CCC(COc2ccc(C3=CCC(C(=O)NC(CO)CO)CC3)cc2)CC1] |
| 238 | 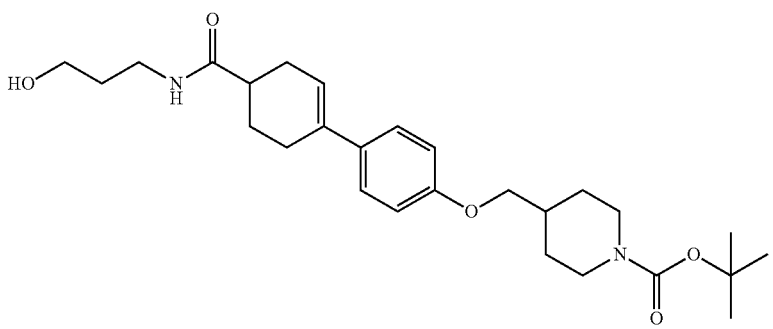 [SMILES: CC(C)(C)OC(=O)N1CCC(COc2ccc(C3=CCC(C(=O)NCCCO)CC3)cc2)CC1] |
| 239 | 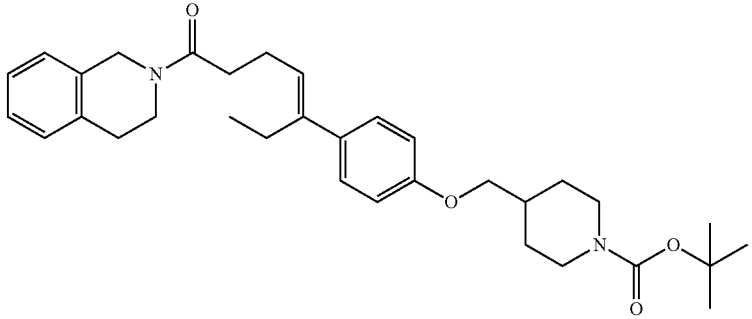 [SMILES: CC/C(=C\CCC(=O)N1CCc2ccccc2C1)c1ccc(OCC2CCN(C(=O)OC(C)(C)C)CC2)cc1] |
| 240 | 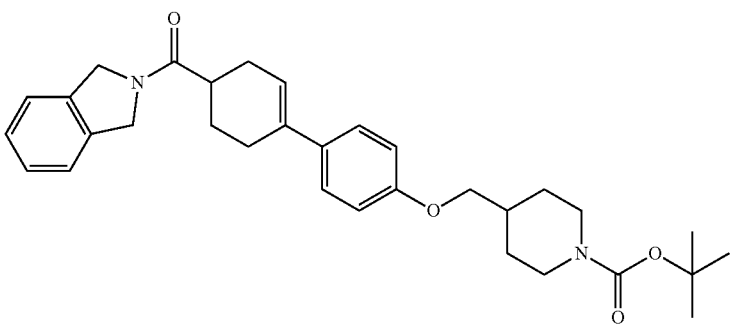 [SMILES: CC(C)(C)OC(=O)N1CCC(COc2ccc(C3=CCC(C(=O)N4Cc5ccccc5C4)CC3)cc2)CC1] |

TABLE 1-continued
| Examples | Chemical structures |
|---|---|
| 241 | 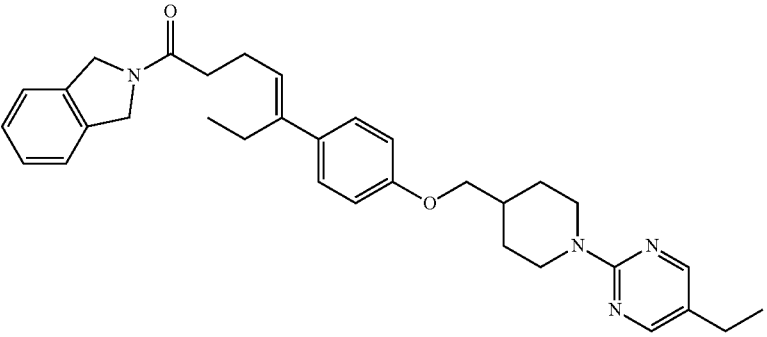 [SMILES: CC/C(=C\CCC(=O)N1Cc2ccccc2C1)c1ccc(OCC2CCN(c3ncc(CC)cn3)CC2)cc1] |
| 242 | 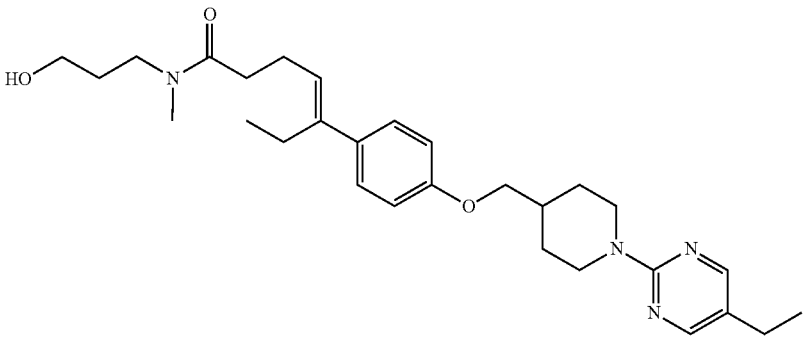 [SMILES: CC/C(=C\CCC(=O)N(C)CCCO)c1ccc(OCC2CCN(c3ncc(CC)cn3)CC2)cc1] |
| 243 | 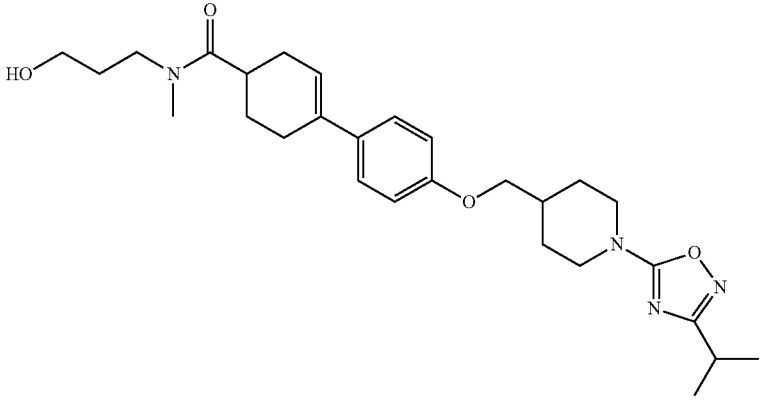 [SMILES: CC(C)c1noc(N2CCC(COc3ccc(C4=CCC(C(=O)N(C)CCCO)CC4)cc3)CC2)n1] |
| 244 | 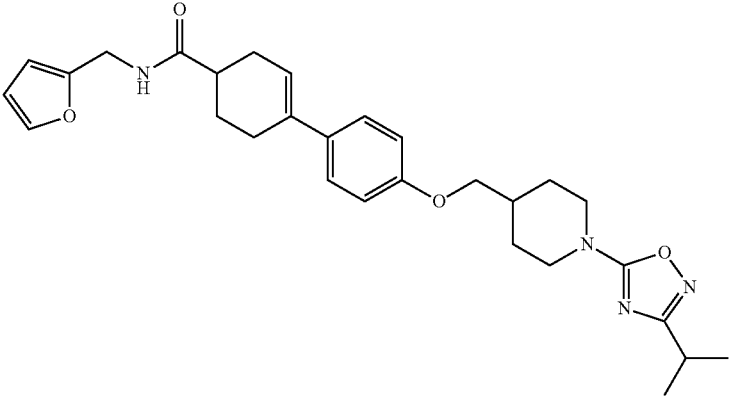 [SMILES: CC(C)c1noc(N2CCC(COc3ccc(C4=CCC(C(=O)NCc5ccco5)CC4)cc3)CC2)n1] |

TABLE 1-continued
| Examples | Chemical structures |
|---|---|
| 245 | 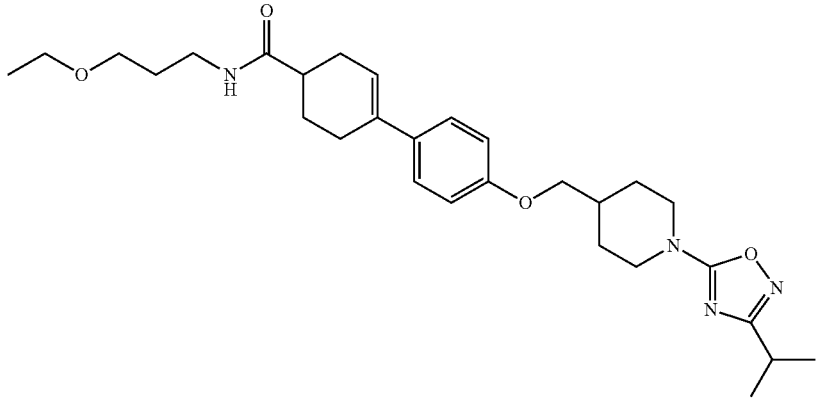 [SMILES: CCOCCCNC(=O)C1CC=C(c2ccc(OCC3CCN(c4nc(C(C)C)no4)CC3)cc2)CC1] |
| 246 | 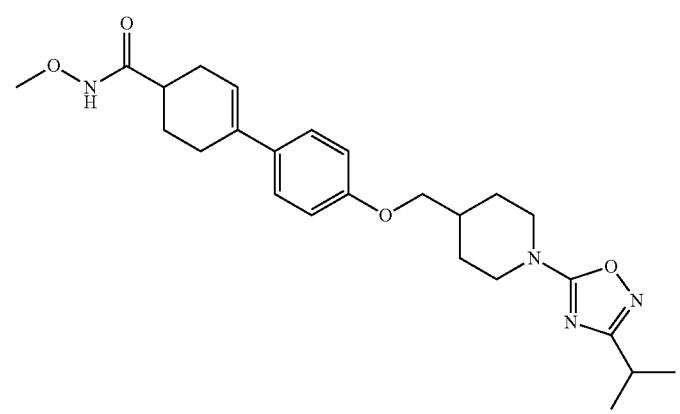 [SMILES: CONC(=O)C1CC=C(c2ccc(OCC3CCN(c4nc(C(C)C)no4)CC3)cc2)CC1] |
| 247 | 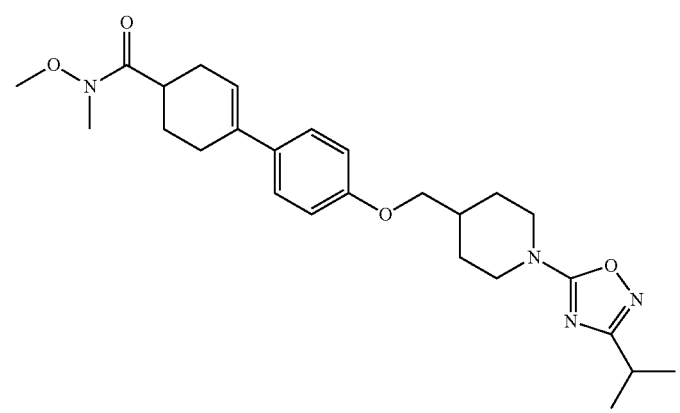 [SMILES: CON(C)C(=O)C1CC=C(c2ccc(OCC3CCN(c4nc(C(C)C)no4)CC3)cc2)CC1] |
| 248 | 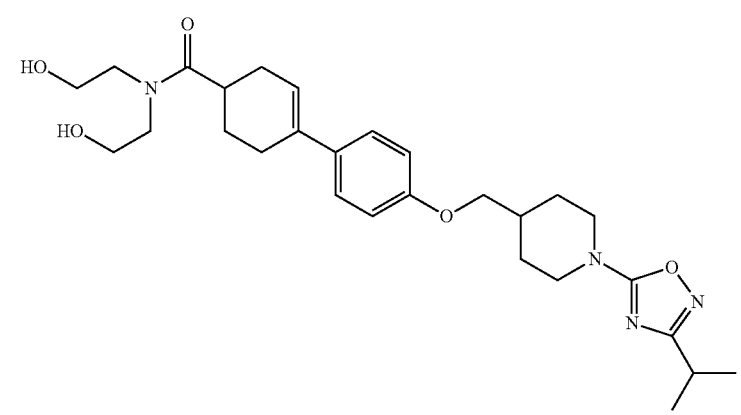 [SMILES: CC(C)c1noc(N2CCC(COc3ccc(C4=CCC(C(=O)N(CCO)CCO)CC4)cc3)CC2)n1] |

TABLE 1-continued
| Examples | Chemical structures |
| --- | --- |
| 249 | 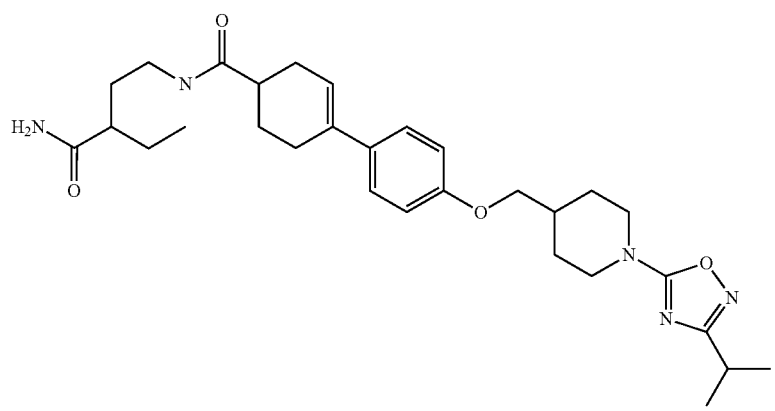 [SMILES: CCC(CCNC(=O)C1CC=C(c2ccc(OCC3CCN(c4nc(C(C)C)no4)CC3)cc2)CC1)C(N)=O] |
| 250 | 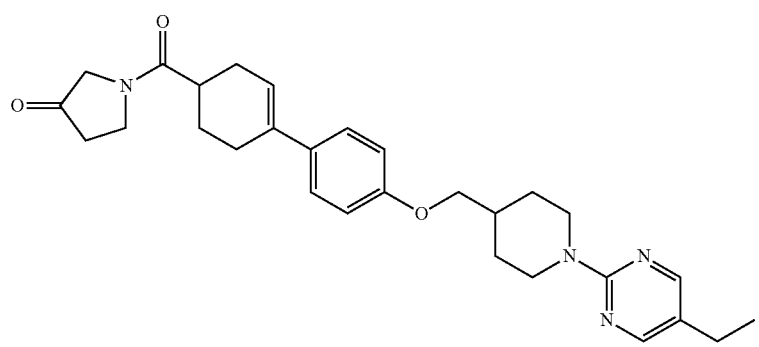 |
| 251 | 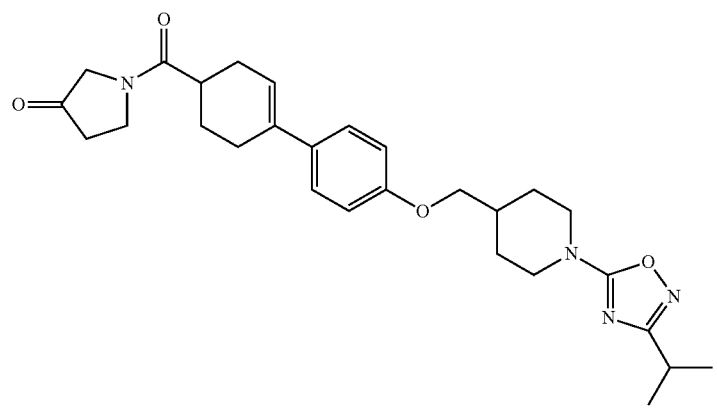 [SMILES: CC(C)c1noc(N2CCC(COc3ccc(C4=CCC(C(=O)N5CCC(=O)C5)CC4)cc3)CC2)n1] |
| 252 | 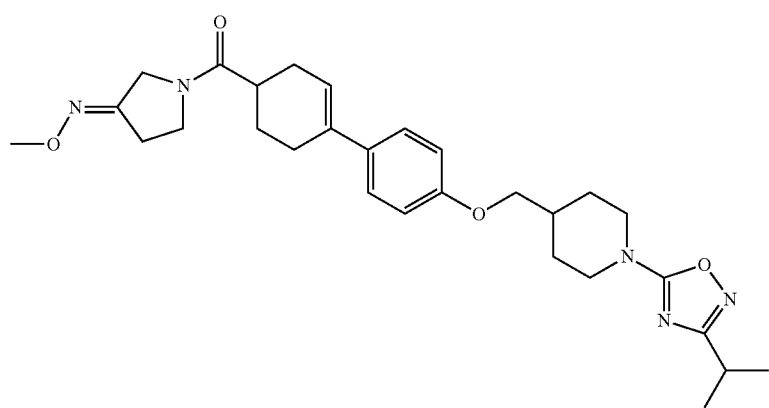 [SMILES: CO/N=C1\CCN(C(=O)C2CC=C(c3ccc(OCC4CCN(c5nc(C(C)C)no5)CC4)cc3)CC2)C1] |

TABLE 1-continued
| Examples | Chemical structures |
|---|---|
| 253 | 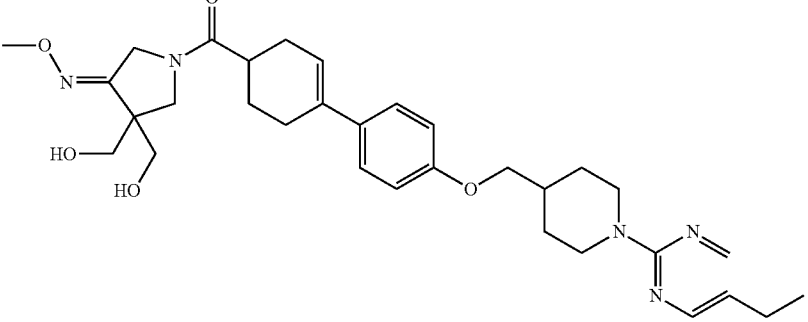 |
| 254 | 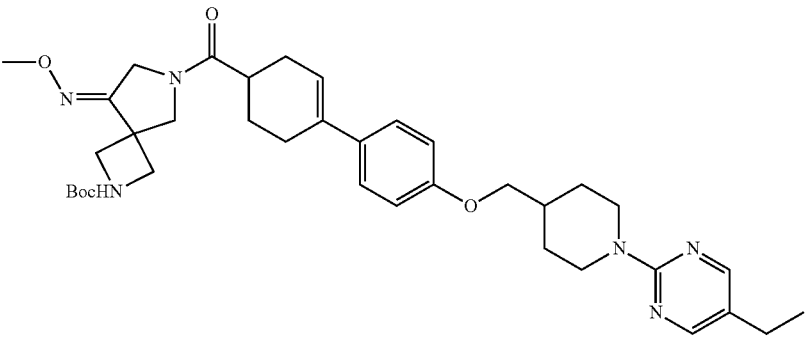 |
| 255 | 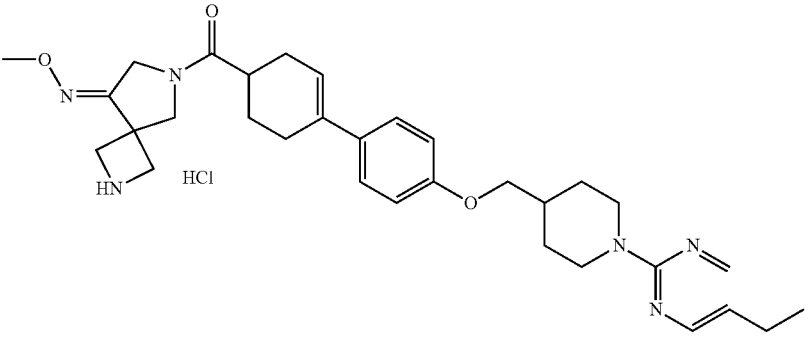 [SMILES: C=N/C(=N\C=C\CC)N1CCC(COc2ccc(C3=CCC(C(=O)N4C/C(=N\OC)C5(CNC5)C4)CC3)cc2)CC1 ; Cl] |
| 256 | 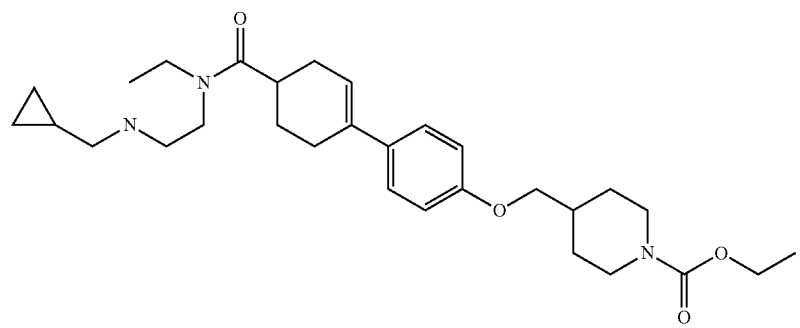 [SMILES: CCOC(=O)N1CCC(COc2ccc(C3=CCC(C(=O)N(CC)CCNCC4CC4)CC3)cc2)CC1] |

TABLE 1-continued
| Examples | Chemical structures |
|---|---|
| 257 | 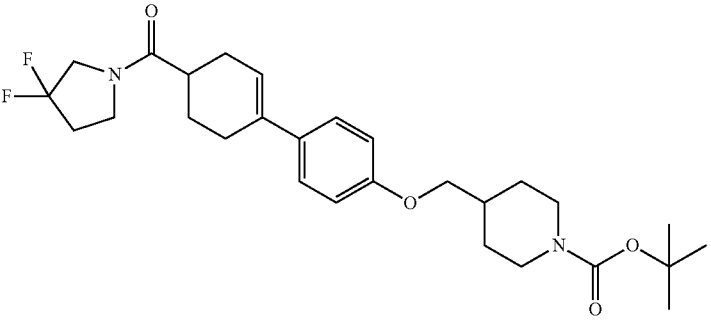 [SMILES: CC(C)(C)OC(=O)N1CCC(COc2ccc(C3=CCC(C(=O)N4CCC(F)(F)C4)CC3)cc2)CC1] |
| 258 | 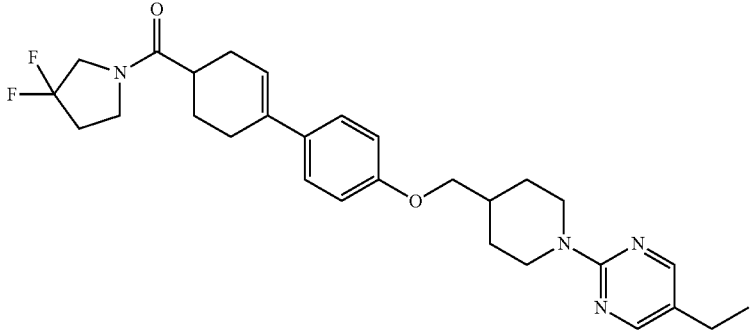 [SMILES: CCc1cnc(N2CCC(COc3ccc(C4=CCC(C(=O)N5CCC(F)(F)C5)CC4)cc3)CC2)nc1] |
| 259 | 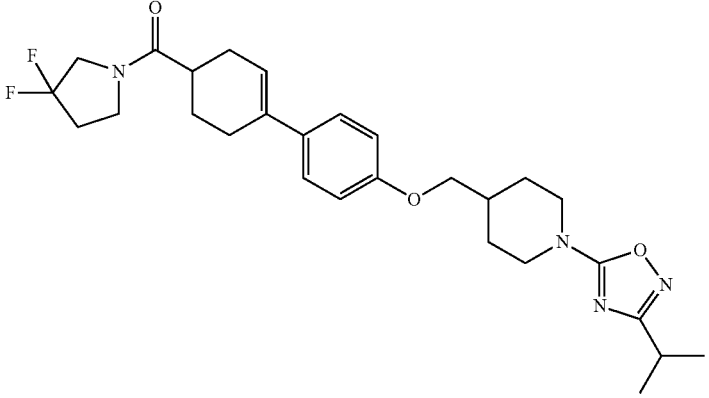 [SMILES: CC(C)c1noc(N2CCC(COc3ccc(C4=CCC(C(=O)N5CCC(F)(F)C5)CC4)cc3)CC2)n1] |
| 260 | 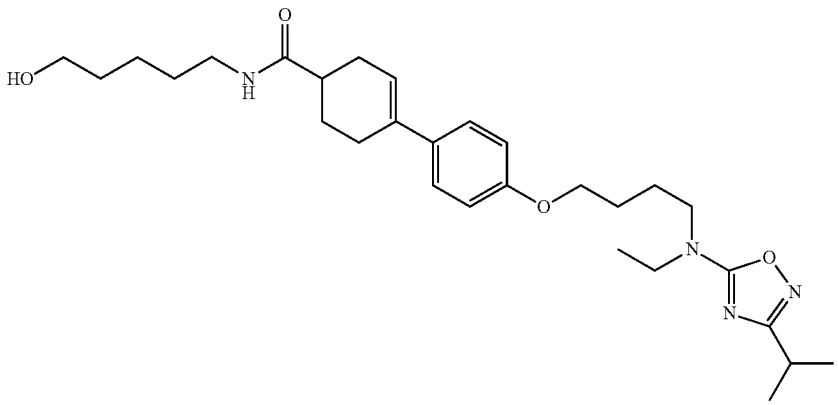 [SMILES: CCN(CCCCOc1ccc(C2=CCC(C(=O)NCCCCCO)CC2)cc1)c1nc(C(C)C)no1] |

TABLE 1-continued

| Examples | Chemical structures |
| --- | --- |
| 261 | 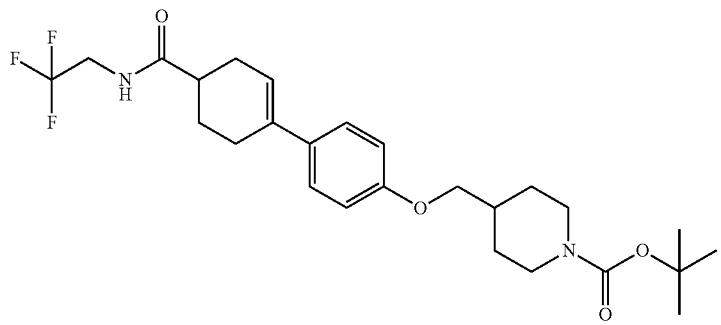 [SMILES: CC(C)(C)OC(=O)N1CCC(COc2ccc(C3=CCC(C(=O)NCC(F)(F)F)CC3)cc2)CC1] |
| 262 | 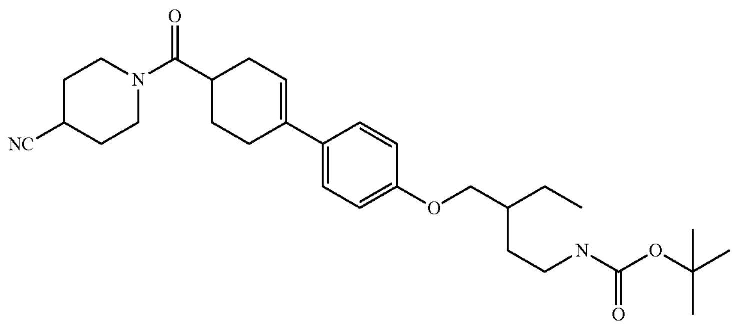 [SMILES: CCC(CCNC(=O)OC(C)(C)C)COc1ccc(C2=CCC(C(=O)N3CCC(C#N)CC3)CC2)cc1] |
| 263 | 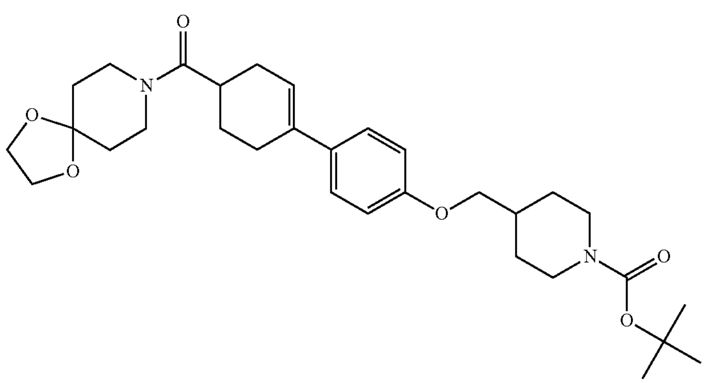 [SMILES: CC(C)(C)OC(=O)N1CCC(COc2ccc(C3=CCC(C(=O)N4CCC5(CC4)OCCO5)CC3)cc2)CC1] |
| 264 | 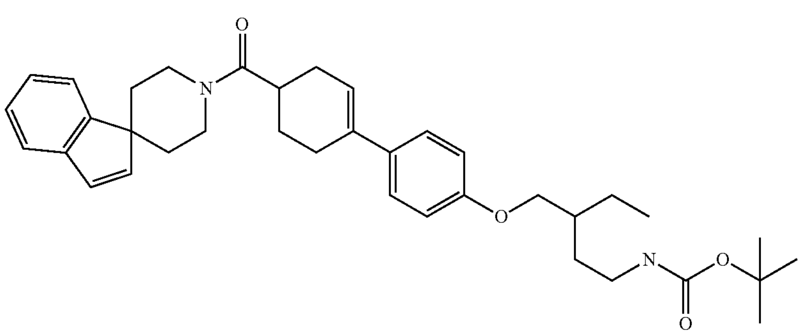 [SMILES: CCC(CCNC(=O)OC(C)(C)C)COc1ccc(C2=CCC(C(=O)N3CCC4(C=Cc5ccccc54)CC3)CC2)cc1] |

TABLE 1-continued
| Examples | Chemical structures |
|---|---|
| 265 | 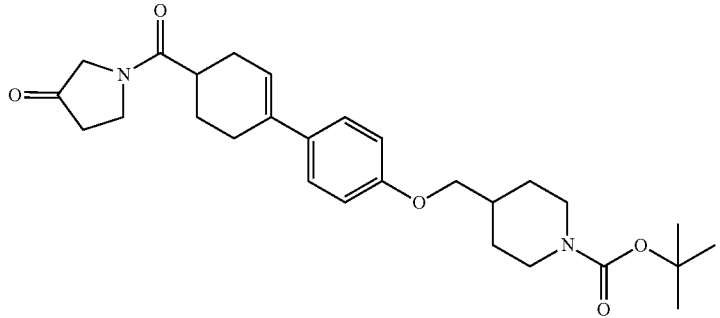 [SMILES: CC(C)(C)OC(=O)N1CCC(COc2ccc(C3=CCC(C(=O)N4CCC(=O)C4)CC3)cc2)CC1] |
| 266 | 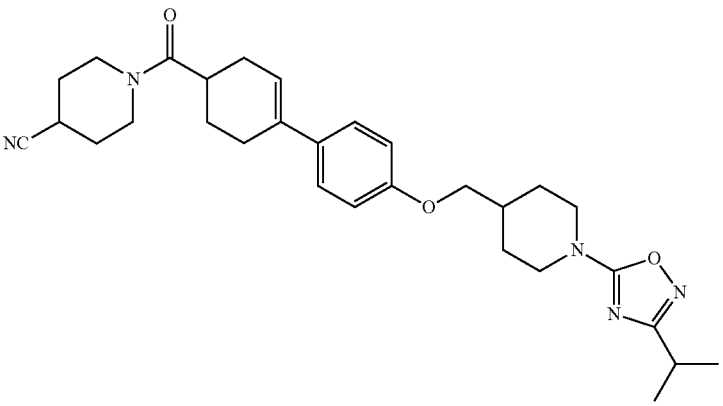 [SMILES: CC(C)c1noc(N2CCC(COc3ccc(C4=CCC(C(=O)N5CCC(C#N)CC5)CC4)cc3)CC2)n1] |
| 267 | 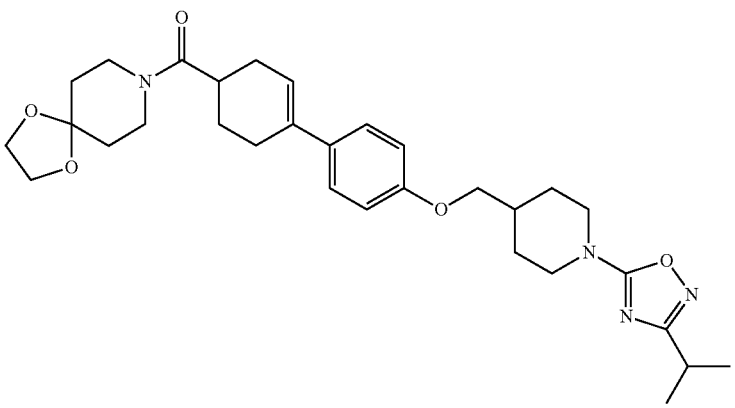 [SMILES: CC(C)c1noc(N2CCC(COc3ccc(C4=CCC(C(=O)N5CCC6(CC5)OCCO6)CC4)cc3)CC2)n1] |
| 268 | 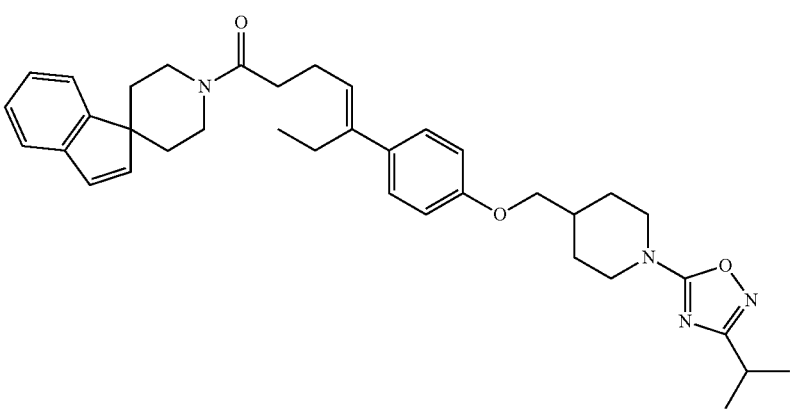 [SMILES: CC/C(=C\CCC(=O)N1CCC2(C=Cc3ccccc32)CC1)c1ccc(OCC2CCN(c3nc(C(C)C)no3)CC2)cc1] |

TABLE 1-continued

| Examples | Chemical structures |
|---|---|
| 269 | 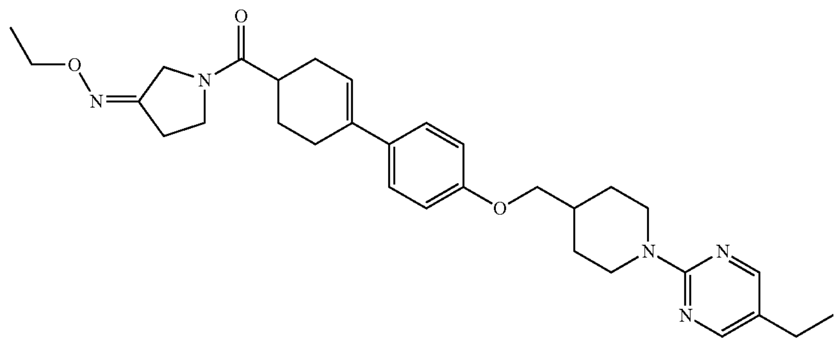 [SMILES: CCO/N=C1/CCN(C(=O)C2CC=C(c3ccc(OCC4CCN(c5ncc(CC)cn5)CC4)cc3)CC2)C1] |
| 270 | 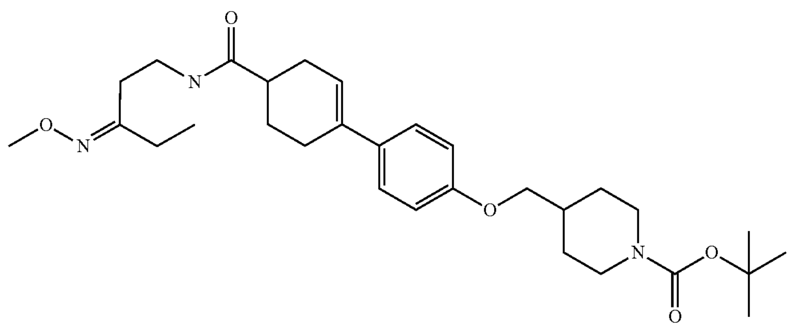 |
| 271 | 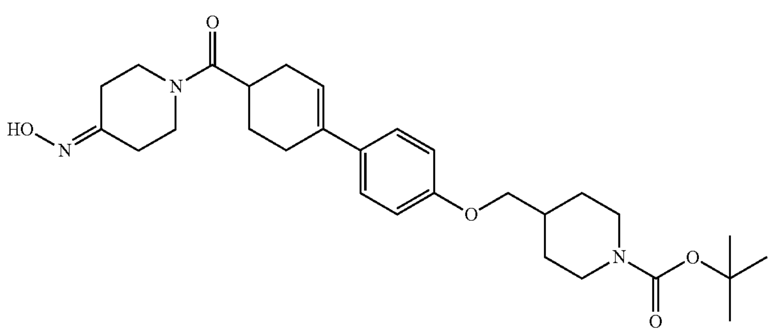 [SMILES: CC(C)(C)OC(=O)N1CCC(COc2ccc(C3=CCC(C(=O)N4CCC(=NO)CC4)CC3)cc2)CC1] |
| 272 | 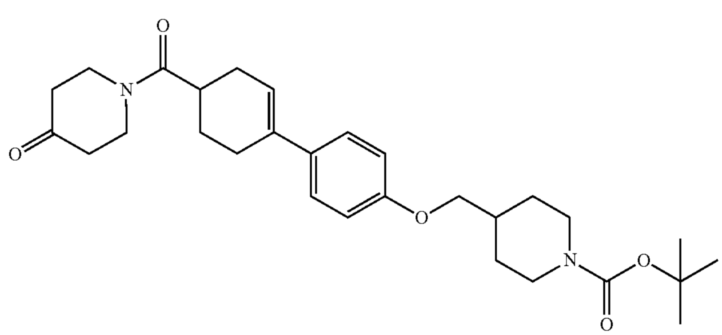 [SMILES: CC(C)(C)OC(=O)N1CCC(COc2ccc(C3=CCC(C(=O)N4CCC(=O)CC4)CC3)cc2)CC1] |

TABLE 1-continued
| Examples | Chemical structures |
|---|---|
| 273 | 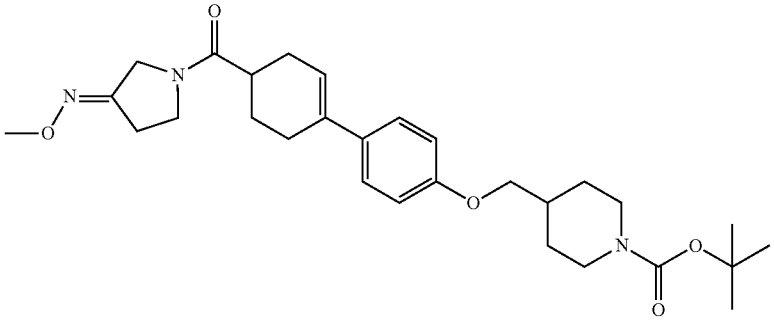 [SMILES: CO/N=C1\CCN(C(=O)C2CC=C(c3ccc(OCC4CCN(C(=O)OC(C)(C)C)CC4)cc3)CC2)C1] |
| 274 | 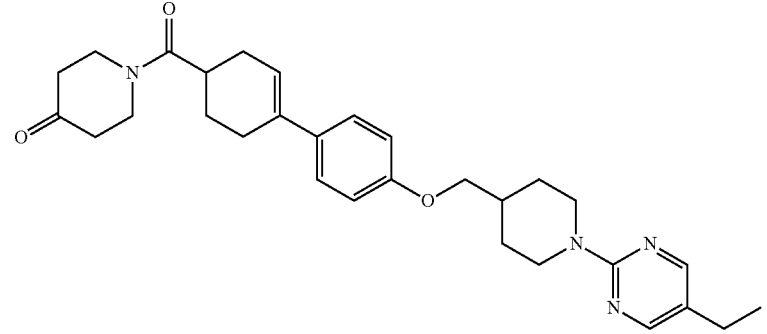 [SMILES: CCc1cnc(N2CCC(COc3ccc(C4=CCC(C(=O)N5CCC(=O)CC5)CC4)cc3)CC2)nc1] |
| 275 | 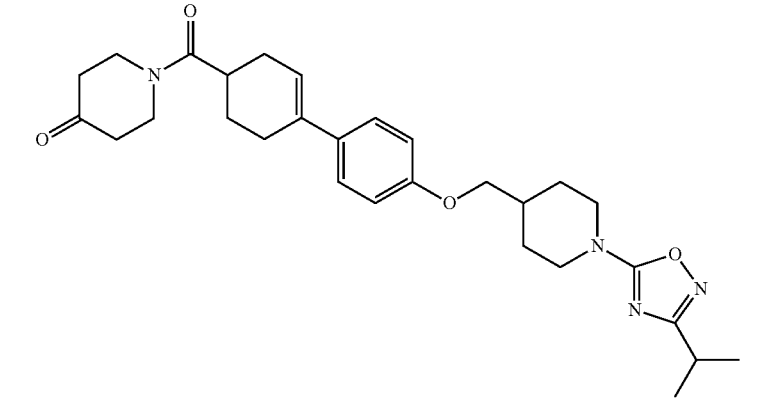 [SMILES: CC(C)c1noc(N2CCC(COc3ccc(C4=CCC(C(=O)N5CCC(=O)CC5)CC4)cc3)CC2)n1] |
| 276 | 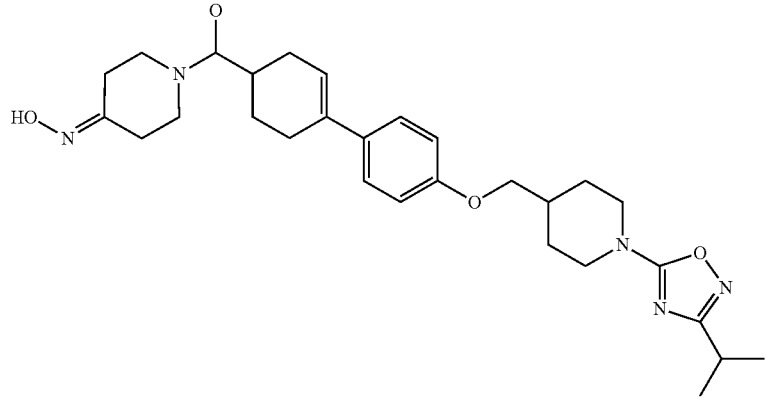 [SMILES: CC(C)c1noc(N2CCC(COc3ccc(C4=CCC(C(O)N5CCC(=NO)CC5)CC4)cc3)CC2)n1] |

TABLE 1-continued
| Examples | Chemical structures |
|---|---|
| 277 | 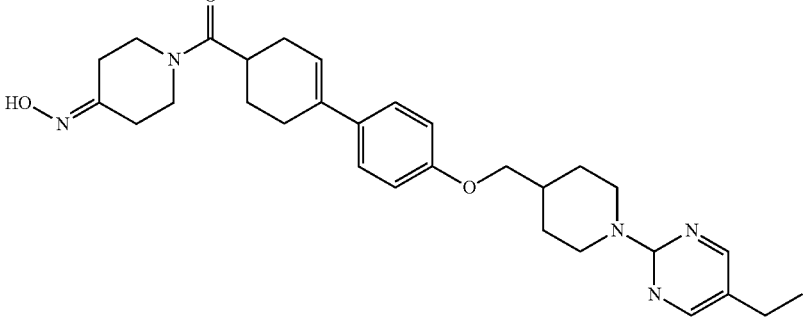 |
| 278 | 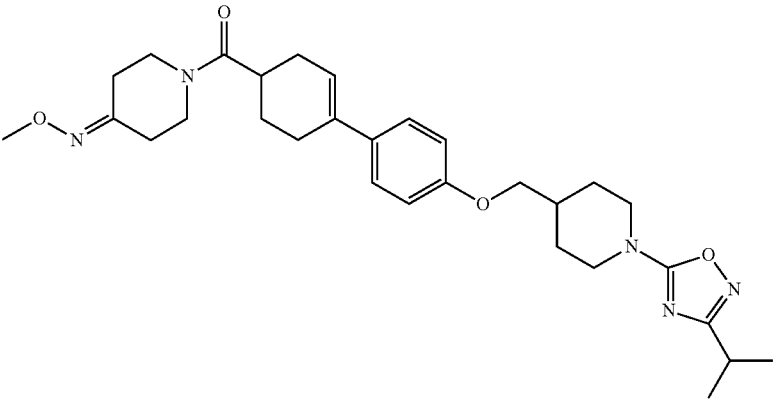 [SMILES: CON=C1CCN(C(=O)C2CC=C(c3ccc(OCC4CCN(c5nc(C(C)C)no5)CC4)cc3)CC2)CC1] |
| 279 | 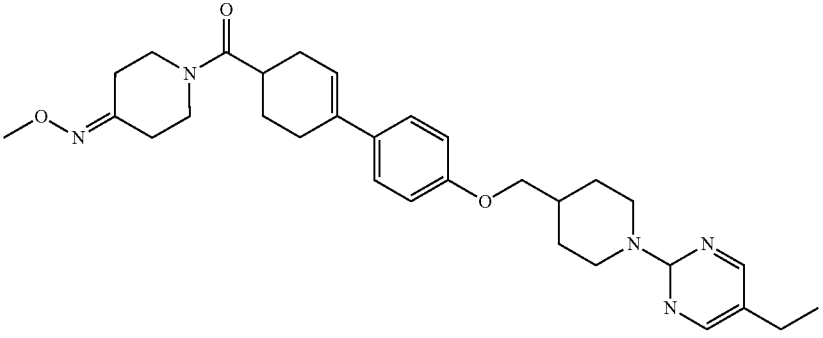 [SMILES: CCC1=CNC(N2CCC(COc3ccc(C4=CCC(C(=O)N5CCC(=NOC)CC5)CC4)cc3)CC2)N=C1] |
| 280 | 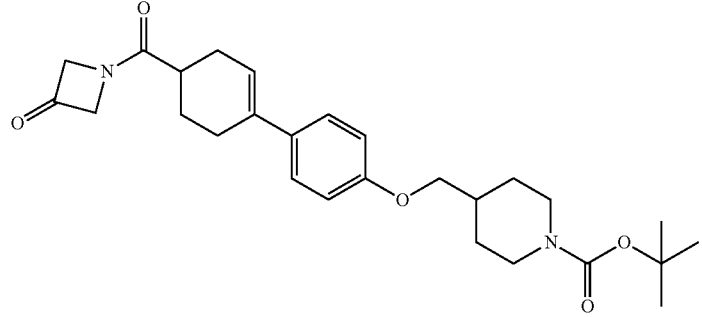 [SMILES: CC(C)(C)OC(=O)N1CCC(COc2ccc(C3=CCC(C(=O)N4CC(=O)C4)CC3)cc2)CC1] |

TABLE 1-continued
| Examples | Chemical structures |
|---|---|
| 281 | 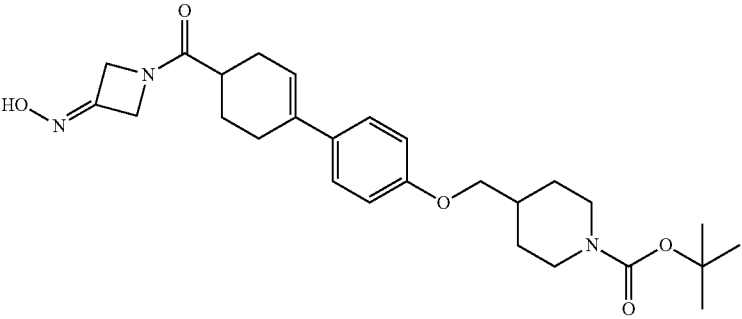 [SMILES: CC(C)(C)OC(=O)N1CCC(COc2ccc(C3=CCC(C(=O)N4CC(=NO)C4)CC3)cc2)CC1] |
| 282 | 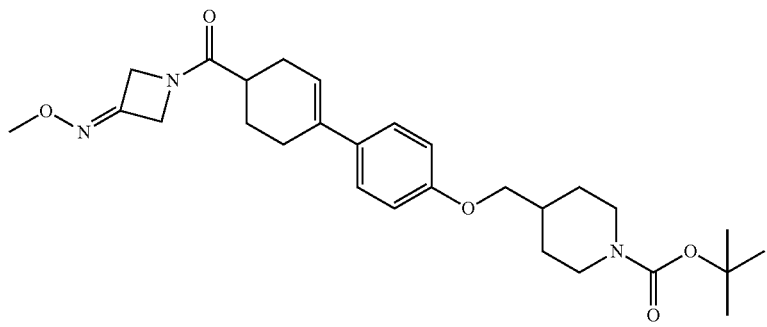 [SMILES: CON=C1CN(C(=O)C2CC=C(c3ccc(OCC4CCN(C(=O)OC(C)(C)C)CC4)cc3)CC2)C1] |
| 283 | 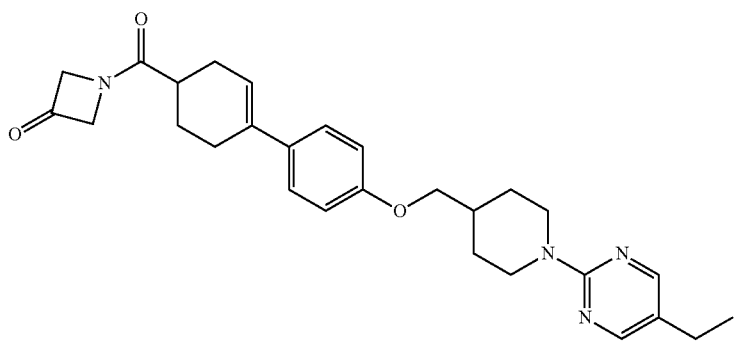 [SMILES: CCc1cnc(N2CCC(COc3ccc(C4=CCC(C(=O)N5CC(=O)C5)CC4)cc3)CC2)nc1] |
| 284 | 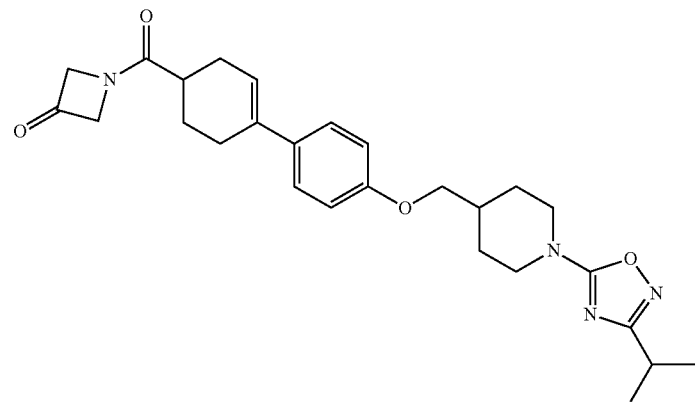 [SMILES: CC(C)c1noc(N2CCC(COc3ccc(C4=CCC(C(=O)N5CC(=O)C5)CC4)cc3)CC2)n1] |

TABLE 1-continued

| Examples | Chemical structures |
| --- | --- |
| 285 | 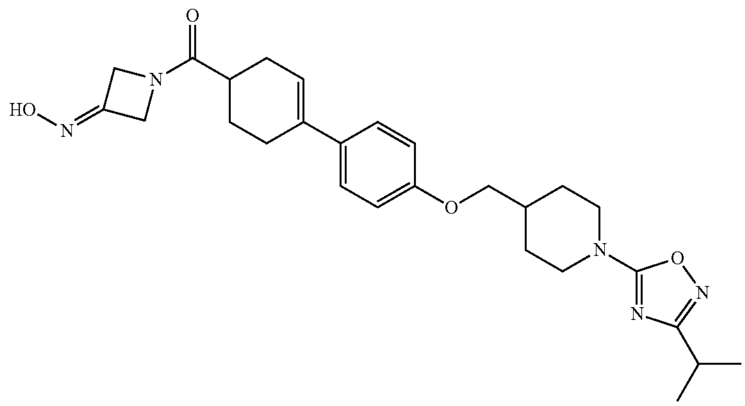 [SMILES: CC(C)c1noc(N2CCC(COc3ccc(C4=CCC(C(=O)N5CC(=NO)C5)CC4)cc3)CC2)n1] |
| 286 | 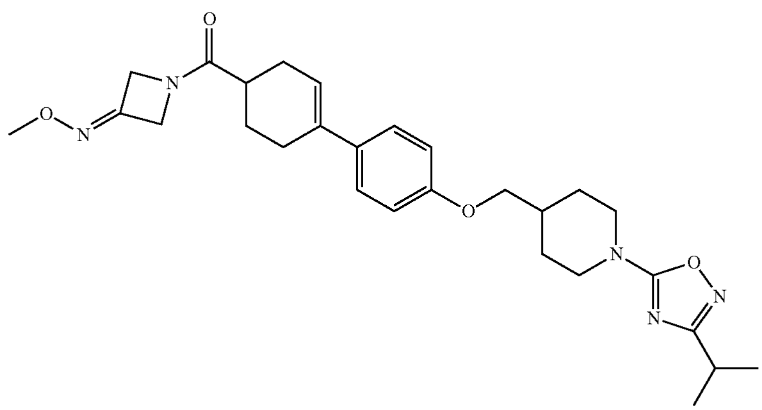 [SMILES: CON=C1CN(C(=O)C2CC=C(c3ccc(OCC4CCN(c5nc(C(C)C)no5)CC4)cc3)CC2)C1] |
| 287 | 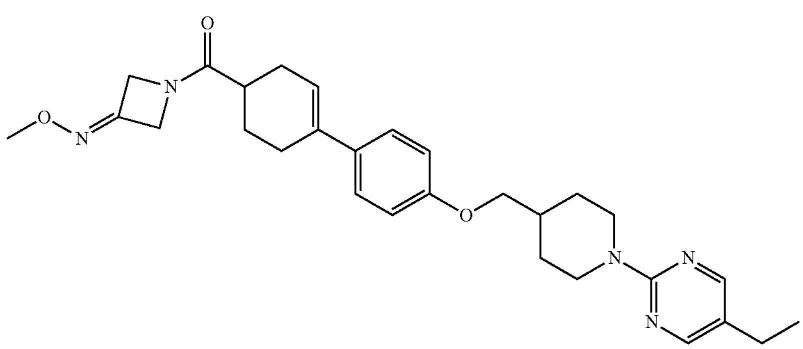 [SMILES: CCc1cnc(N2CCC(COc3ccc(C4=CCC(C(=O)N5CC(=NOC)C5)CC4)cc3)CC2)nc1] |
| 288 | 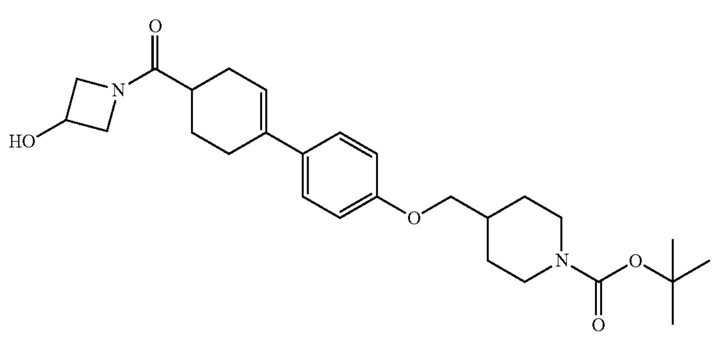 [SMILES: CC(C)(C)OC(=O)N1CCC(COc2ccc(C3=CCC(C(=O)N4CC(O)C4)CC3)cc2)CC1] |

TABLE 1-continued

| Examples | Chemical structures |
|---|---|
| 289 | (structure shown) |

Experimental Example 1

Evaluation of cAMP Activity

To check whether the cyclohexene derivatives according to the present invention activate cyclic adenosine monophosphate (cAMP), experiments were carried out, as follows.

Specifically, as hamster-derived β-cells containing G protein-coupled receptor 119 (GPR-119), HIT-T15 cells (Korean Cell Line Bank) were used to determine intracellular activation of cAMP in response to the stimulation of the GPR-119. The HIT-T15 cells were plated on a 96-well plate at 60,000 cells per well. On the next day of plating, the cells were treated with a varying concentration of each of the example compounds according to the present invention, and incubated at 37° C. for an hour. In this case, each of the treated compounds was used at six concentrations, ranging from 0.0032 to 10 M, to treat the cells.

The cyclic adenosine monophosphate (cAMP) activity was measured according to the manufacturer's instruction using a cAMP dynamic kit commercially available from Cis Bio Inc. (Bedford, Mass.). The cells were lysed, and a level of cAMP was determined by a competitive immunoassay using D2-labeled cAMP and a cryptate-labeled anti-cAMP antibody. Fluorescence was read in Flex Station (Molecular Devices). Fluorescence resonance energy transfer (FRET) was observed when D2 and cryptate were in close proximity, and then measured as a fluorescence ratio of 665 nm/620 nm. Unlabeled cAMP in the cell lysate competed with the D2-labeled cAMP against the cryptate-labeled antibody. Since a decrease in the measured intensity of the FRET signals represents a level of cAMP in the cells, the cAMP activities of the compounds are calculated as a change in FRET signals by adjusting an amount of dimethyl sulfoxide (DMSO). The calculated $EC_{50}$ values are listed in the following Table 2.

TABLE 2

| Examples | $EC_{50}$ (nM) |
|---|---|
| 1 | 65 |
| 2 | 40 |
| 3 | 34 |
| 4 | 150 |

TABLE 2-continued

| Examples | $EC_{50}$ (nM) |
|---|---|
| 5 | 29 |
| 6 | 38 |
| 7 | 13 |
| 8 | 90 |
| 9 | 75 |
| 10 | 500 |
| 11 | 110 |
| 12 | 80 |
| 13 | 13 |
| 14 | 650 |
| 15 | 370 |
| 16 | 13 |
| 17 | 85 |
| 18 | 170 |
| 19 | 110 |
| 20 | 90 |
| 21 | 16 |
| 22 | 41 |
| 23 | 160 |
| 24 | 260 |
| 25 | 210 |
| 26 | 250 |
| 27 | 310 |
| 28 | 110 |
| 29 | 95 |
| 30 | 105 |
| 31 | 260 |
| 32 | 650 |
| 33 | 600 |
| 34 | 21 |
| 35 | 22 |
| 36 | 170 |
| 37 | 300 |
| 38 | 450 |
| 39 | 350 |
| 40 | 500 |
| 41 | 650 |
| 42 | 82 |
| 43 | 85 |
| 44 | 13 |
| 45 | 25 |
| 46 | 500 |
| 47 | 150 |
| 48 | 35 |
| 49 | 26 |
| 50 | 95 |
| 51 | 66 |
| 52 | 55 |
| 53 | 21 |
| 54 | 42 |
| 55 | 100 |
| 56 | 30 |

TABLE 2-continued

| Examples | EC$_{50}$ (nM) |
|---|---|
| 57 | 8 |
| 58 | 17 |
| 59 | 78 |
| 60 | 40 |
| 61 | 45 |
| 62 | 70 |
| 63 | 110 |
| 64 | 50 |
| 65 | 41 |
| 66 | 18 |
| 67 | 60 |
| 68 | 300 |
| 69 | 7 |
| 70 | 45 |
| 71 | 5.4 |
| 72 | 25 |
| 73 | 11 |
| 74 | 6.2 |
| 75 | 210 |
| 76 | 12 |
| 77 | 12 |
| 78 | 100 |
| 79 | 49 |
| 80 | 89 |
| 81 | 9 |
| 82 | 9 |
| 83 | 75 |
| 84 | 30 |
| 85 | 18 |
| 86 | 130 |
| 87 | 70 |
| 88 | 130 |
| 89 | 21 |
| 90 | 24 |
| 91 | 28 |
| 92 | 64 |
| 93 | 50 |
| 94 | 68 |
| 95 | 16 |
| 96 | 27 |
| 97 | 8.4 |
| 98 | 6.1 |
| 99 | 160 |
| 100 | 95 |
| 101 | 110 |
| 102 | 52 |
| 103 | 75 |
| 104 | 70 |
| 105 | 43 |
| 106 | 22 |
| 107 | 35 |
| 108 | 55 |
| 109 | 190 |
| 110 | 110 |
| 111 | 1,500 |
| 112 | 70 |
| 113 | 68 |
| 114 | 14 |
| 115 | 15 |
| 116 | 28 |
| 117 | 11 |
| 118 | 31 |
| 119 | 6.8 |
| 120 | 80 |
| 121 | 500 |
| 122 | 130 |
| 123 | 35 |
| 124 | 100 |
| 125 | 70 |
| 126 | 130 |
| 127 | 83 |
| 128 | 200 |
| 129 | 140 |
| 130 | 90 |
| 131 | 150 |
| 132 | 210 |
| 133 | 400 |
| 134 | 350 |

TABLE 2-continued

| Examples | EC$_{50}$ (nM) |
|---|---|
| 135 | 30 |
| 136 | 62 |
| 137 | 60 |
| 138 | 100 |
| 139 | 130 |
| 140 | 120 |
| 141 | 75 |
| 142 | 85 |
| 147 | 6.9 |
| 148 | 13 |
| 149 | 23 |
| 150 | 19 |
| 152 | 36 |
| 158 | 25 |
| 159 | 20 |
| 160 | 14 |
| 161 | 6 |
| 162 | 27 |
| 163 | 7 |
| 164 | 16 |
| 165 | 7 |
| 166 | 22 |
| 167 | 14 |
| 168 | 17 |
| 169 | 9 |
| 172 | 38 |
| 173 | 18 |
| 175 | 7 |
| 177 | 38 |
| 181 | 24 |
| 182 | 27 |
| 183 | 12 |
| 186 | 17 |
| 195 | 28 |
| 197 | 18 |
| 199 | 8 |
| 200 | 23 |
| 202 | 24 |
| 203 | 37 |
| 204 | 9 |
| 213 | 24 |
| 217 | 30 |
| 220 | 40 |
| 223 | 25 |
| 224 | 38 |
| 225 | 22 |
| 226 | 14 |
| 227 | 6 |
| 228 | 8 |
| 229 | 11 |
| 235 | 24 |
| 236 | 14 |
| 239 | 22 |
| 242 | 21 |
| 243 | 30 |
| 247 | 16 |
| 250 | 12 |
| 251 | 22 |
| 252 | 17 |
| 253 | 9 |
| 254 | 10 |
| 256 | 32 |
| 257 | 8 |
| 258 | 10 |
| 259 | 10 |
| 262 | 7 |
| 263 | 9 |
| 264 | 18 |
| 265 | 32 |
| 266 | 12 |
| 267 | 21 |
| 268 | 17 |
| 269 | 35 |
| 270 | 12 |
| 271 | 13 |
| 272 | 33 |
| 273 | 11 |
| 274 | 27 |

TABLE 2-continued

| Examples | EC$_{50}$ (nM) |
| --- | --- |
| 275 | 28 |
| 276 | 29 |
| 277 | 20 |
| 278 | 18 |
| 279 | 29 |
| 286 | 37 |
| 289 | 32 |
| Comparative Example 2 | 49 |

As listed in Table 2, it was revealed that the compounds according to the present invention activated cAMP even at a very low concentration. It was revealed that most of the compounds according to the present invention had an EC$_{50}$ value of 200 nM or less. More specifically, it was revealed that the compounds of Examples 2, 3, 5 to 7, 13, 16, 21, 22, 34, 35, 44, 45, 48, 49, 53, 54, 56 to 58, 60, 61, 64 to 66, 69 to 74, 76, 77, 79, 81, 82, 84, 85, 89 to 91, 93, 95 to 98, 105 to 107, 114 to 119, 123, 135, 147 to 150, 152, 158 to 169, 172, 173, 175, 177, 181-183, 186, 195, 197, 199, 200, 202 to 204, 213, 217, 220, 223 to 229, 235, 236, 239, 242, 243, 247, 250 to 254, 256 to 259, 262 to 279, 286 and 289 had a high EC$_{50}$ value of 50 nM or less. From these results, it could be seen that the cyclohexene derivative according to the present invention had an excellent effect of activating cAMP by stimulating the GPR-119 receptor.

Therefore, the cyclohexene derivative according to the present invention activated GPR-119 since the cyclohexene derivative had an excellent effect of activating cAMP, and thus was able to be useful for pharmaceutical compositions for preventing or treating metabolic diseases such as obesity, type 1 diabetes, type 2 diabetes, inadequate glucose tolerance, insulin resistance, hyperglycemia, hyperlipidemia, hypertriglyceridemia, hypercholesterolemia, dyslipidemia, and syndrome X.

Experimental Example 2

Oral Glucose Tolerance Test (OGTT)

To evaluate in vivo effective effects of the cyclohexene derivatives according to the present invention, experiments were carried out, as follows.

Specifically, male C57BL/6J (C57 black 6) rats (8 to 10 weeks old) in a high-fat diet model were acclimated for at least 7 days, and only healthy rat populations were selected and subjected to an oral glucose tolerance test (OGTT). The rats were fasted for 12 to 15 hours, and then randomly divided into groups with five rats per group. Thereafter, each of the compounds of Examples 1, 14, 48, 69, 80, 118, 139, 147, 148, 169, 190, 199, 200, 204, 227, and Comparative Examples 1 and 2 according to the present invention was administered to the rats at a dose of 20 mg/kg. In this case, a vehicle (0.5%, carboxymethyl cellulose (CMC)) was administered as an untreated group, and the dose of the compound administered together with the vehicle was orally administered at 10 ml/kg. After 30 minutes of administration, glucose (2 g/kg) was orally administered at a dose of 10 ml/kg. A blood glucose level was measured using an Accu-Chek Active Strip (Rosche Diagnostic Co.). In this case, the glucose level in blood collected via caudal venipuncture was measured at time points of −30, 0, 20, 40, 60, and 120 minutes after glucose administration. The results are listed in the following Table 3.

TABLE 3

| Examples | % AUC |
| --- | --- |
| 1 | 28.5 |
| 14 | 21.9 |
| 48 | 21.2 |
| 69 | 19.1 |
| 80 | 19.7 |
| 118 | 23.5 |
| 139 | 25.4 |
| 147 | 23.3 |
| 148 | 22.6 |
| 169 | 21.7 |
| 190 | 20.9 |
| 199 | 20.9 |
| 200 | 24.0 |
| 204 | 24.0 |
| 227 | 26.8 |
| 277 | 19.8 |
| Comparative Example 1 | 13.5 |
| Comparative Example 2 | 15.3 |

In Table 3, the unit "% AUC (area under the curve)" represents a hypoglycemic level.

As listed in Table 3, it could be seen that the example compounds according to the present invention had 20% of a hypoglycemic effect on average and a high in vivo effective effect, compared to those in the untreated group. Also, it was revealed that the compounds of Comparative Examples 1 and 2 known as the GPR-119 protein activator in the art had a hypoglycemic effect of 13.5% and 15.3%, respectively, but that the example compounds according to the present invention had a superior hypoglycemic effect (over 19.1%) to the compounds of Comparative Examples 1 and 2.

Therefore, the cyclohexene derivative according to the present invention derivative had a very excellent hypoglycemic effect since the cyclohexene derivative had an excellent effect of activating a GPR-119 protein, thereby exhibiting an excellent effect of promoting insulin secretion. Accordingly, a pharmaceutical composition including the cyclohexene derivative as an active ingredient was able to be useful as a pharmaceutical composition for preventing or treating metabolic diseases such as obesity, type 1 diabetes, type 2 diabetes, inadequate glucose tolerance, insulin resistance, hyperglycemia, hyperlipidemia, hypertriglyceridemia, hypercholesterolemia, dyslipidemia, syndrome X, etc.

Experimental Example 3

Simultaneous Evaluation of Both Weight-loss and Hypoglycemic Effects in Diet-induced Obesity (DIO) Model To simultaneously evaluate both the weight-loss and hypoglycemic effects of the cyclohexene derivative according to the present invention, experiments were carried out, as follows.

Specifically, male Sprague Dawley (SD) rats (approximately 4 weeks old) in a diet-induced obesity model were fed with a high-fat diet (Lab. Diet Co.) for approximately 10 weeks to induce high-fat diet-induced obesity (DIO). The rats undergoing the high-fat diet were randomly selected, and divided into groups (n=8) for respective administrations. The compounds of Comparative Examples 3 and 4 and Examples 48 and 119 were administered to the divided DIO rats each group for 4 weeks.

The weights of the DIO rats were measured twice a week during a period of administration of 4 weeks to record a change in the weights. The results are shown in FIG. 1. At the end of the 4-week period of administration, a hypoglycemic effect was evaluated using an oral glucose tolerance test (OGTT), as follows.

Specifically, each of the compounds of Comparative Example 3 (300 mg/kg) and Examples 48 and 119 (10, 20, 50 mg/kg) was administered, and 2 g/kg of glucose was orally administered after 30 minutes of the administration. A blood glucose level was determined using an Accu-Chek Active Strip (Roche diagnostic Co.). In this case, the glucose level in blood collected via caudal venipuncture was measured at time points of −30, 0, 20, 40, 60, and 120 minutes after glucose administration. Area-under-curve (AUC) values (%) of the respective groups were calculated from the results based on the blood glucose levels measured at the respective time points so as to evaluate the hypoglycemic effect. The results are shown in FIGS. 2A and 2B [FIG. 2A: Example 48, and FIG. 2B: Example 119].

FIG. 1 is a graph determining the changes in weights of rats after compounds of Example 48 and Comparative Examples 3 and 4 according to the present invention are administered to a diet-induced obesity (DIO) rat model for 4 weeks (In FIG. 1, the term "untreated group (Vehicle)" represents an untreated group in a high-fat DIO rat model; and the term "Lean" represents an untreated group in a normal SD rat model rather than a disease model).

FIG. 2A is a graph for evaluating hypoglycemic effects over time when glucose is administered at the end of the 4-week period of administration of the compounds of Example 48 and Comparative Example 3 according to the present invention in the DIO rat model, and after 30 minutes of administration of the compounds of Example 48 and Comparative Example 3.

FIG. 2B is a graph for evaluating hypoglycemic effects over time when glucose is administered at the end of the 4-week period of administration of the compound of Example 119 according to the present invention in the DIO rat model, and after 30 minutes of administration of the compound of Example 119.

As shown in FIG. 1, it was confirmed that the compound of Example 48 according to the present invention had a higher weight-loss effect when administered at a dose of 10, 20, and 50 mg/kg, compared to when the compounds of Comparative Examples 3 and 4 were administered at a dose of 300 mg/kg and 5 mg/kg, respectively. More specifically, it was revealed that the weight loss was observed for 2 weeks after oral administration of the compounds of Comparative Examples 3 and 4 (300 mg/kg and 5 mg/kg, respectively), but the weight rather increased after 2 weeks of the oral administration. On the other hand, it was revealed that the persistent weight loss was observed for 4 weeks after oral administration of the compound of Example 48 (10, 20, and 50 mg/kg) according to the present invention.

As shown in FIG. 2A, it was confirmed that the compound of Example 48 according to the present invention had a hypoglycemic effect of approximately 18 to 25% when administered at a dose of 10, 20, and 50 mg/kg. More specifically, it was revealed that the compound of Comparative Example 3 had a hypoglycemic effect of approximately 22% when orally administered at a dose of 300 mg/kg, and the compound of Example 48 according to the present invention had a hypoglycemic effect of approximately 25% when orally administered at a dose of 50 mg/kg, indicating that the compound of Example 48 had a remarkably superior hypoglycemic effect to that of Comparative Example 3. Also, as shown in FIG. 2B, when it was assumed that the hypoglycemic effect in the untreated group was 0, it was confirmed that the compound of Example 119 according to the present invention had a hypoglycemic effect of approximately 10 to 15% when administered at a dose of 10, 20, and 50 mg/kg.

Therefore, the cyclohexene derivative according to the present invention had excellent weight-loss and hypoglycemic effects during a period of oral administration, and these effects were also expressed at the same time. Accordingly, a pharmaceutical composition including the cyclohexene derivative as an active ingredient was able to be useful as a pharmaceutical composition for treating metabolic diseases such as obesity, type 1 diabetes, type 2 diabetes, inadequate glucose tolerance, insulin resistance, hyperglycemia, hyperlipidemia, hypertriglyceridemia, hypercholesterolemia, dyslipidemia, syndrome X, etc.

Experimental Example 4

Evaluation of Promotion of Glucagon-like Peptide-1 (GLP-1) Secretion

To evaluate an effect of the cyclohexene derivative according to the present invention on promotion of glucagon-like peptide-1 (GLP-1) secretion, experiments were carried out, as follows.

NCI-H716 cells that were human enterocytes were plated on 12 wells at $1 \times 10^6$ cells per well. After 48 hours, the cells were starved in serum-free media for 2 hours, and treated with a varying concentration of siptagliptin that was a dipeptidyl peptidase-IV (DPP-IV) inhibitor, and the compounds of Comparative Example 1 (1, 10, 30 μM), Comparative Example 5 (10 μM), Example 48 (1, 10, 30 μM), and Example 291 (1, 10, 30 μM). After an hour, supernatants are recovered to determine an amount of the secreted GLP-1 peptide. The GLP-1 measurement was performed using an enzyme-linked immunosorbent assay (ELISA; Millipore, EGLP-35K), and the amount of the secreted GLP-1 peptide was indicated by the unit "pM". The results are shown in FIG. 3.

FIG. 3 is graph plotted for amounts of secreted GLP-1 when NCI-H716 cells that are human enterocytes are treated with the compounds of Comparative Examples 1 and 5 and Example 48 according to the present invention.

As shown in FIG. 3, it was confirmed that the GLP-1 was secreted at approximately 340 to 470 pM when the cells were treated with an increasing concentration (1, 10, and 30 μM) of the compound of Example 48 according to the present invention. More specifically, it was revealed that the compound of Example 48 induced GLP-1 secretion to a higher level than that of Comparative Example 1 in all the 1, 10 and 30 μM-treated groups when comparing the amounts of the GLP-1 secreted in response to the concentrations of the treated compounds of Comparative Example 1 and Example 48.

Therefore, the cyclohexene derivative according to the present invention had an excellent effect of inducing the GLP-1 secretion through activation of GPR-119. Accordingly, a pharmaceutical composition including the cyclohexene derivative as an active ingredient was able to be useful as a pharmaceutical composition for treating metabolic diseases such as obesity, type 1 diabetes, type 2 diabetes, inadequate glucose tolerance, insulin resistance, hyperglycemia, hyperlipidemia, hypertriglyceridemia, hypercholesterolemia, dyslipidemia, syndrome X, etc.

Experimental Example 5

Acute Toxicity Test

To evaluate acute toxicity of the cyclohexene derivative according to the present invention, experiments were carried out, as follows.

Five 7-week-old female Ihara's cataract rats (ICRs) were supplied by Nara Biotech Co. Ltd., housed in a breeding farm, and acclimated to new environments while being fed with general solid feeds and water. When the rats were 8 weeks old, experiments were carried out. Environmental conditions were maintained constant: a set temperature of 23±3° C., a humidity of 55±15%, an illuminance of 150 to 300 Lux, a ventilation rate of 10 to 20 times/hour, and a lighting time of 12 hours (light-dark cycle: lighting at 8 a.m. and lights-out at 8 p.m.). As the feeds, solid feeds for laboratory animals (5L79 Lab Diet, Purina Mills, Richmond, Ind., USA), which had been sterilized by exposure to radiation, were provided by Orientbio Inc. so that rats were allowed to freely consume the solid feeds. As the water, running water was disinfected using a UV sterilizer and an ultra-filtration system, and then provided o that rats were allowed to freely drink the water in a water bottle. Analyses of contaminants in the water and feeds were carried out according to the ChemOn Inc.'s standard operating procedure (SOP). Each of the compounds prepared in Examples 48 and 119 of the present invention was diluted to a concentration of 2,000 mg/kg in a vehicle (1% PEG), and the test chemicals were intragastrically administered once daily to each group of five rats using an oral zonde for rats, and the general conditions, toxic symptoms, and mortality of animals were observed twice a day during a test period.

As a result, it was confirmed that the lethal dose 50 percent ($LD_{50}$) values of the female ICR rats were greater than or equal to 2 g/kg. From these result, it could be seen that the cyclohexene derivative according to the present invention had very low toxicity.

Therefore, the cyclohexene derivative according to the present invention had an excellent effect of promoting cAMP by activating GPR-119, and also exhibited very high safety to human bodies due to low cytotoxicity. Accordingly, the cyclohexene derivative according to the present invention activated the GPR-119, and thus was able to be useful for a pharmaceutical composition for preventing or treating metabolic diseases such as obesity, type 1 diabetes, type 2 diabetes, inadequate glucose tolerance, insulin resistance, hyperglycemia, hyperlipidemia, hypertriglyceridemia, hypercholesterolemia, dyslipidemia, syndrome X, etc.

Meanwhile, the compound represented by formula 1 according to the present invention can be formulated into several types depending on the desired purposes. The followings are representative preparative examples comprising the compound represented by formula 1 according to the present invention as an active ingredient, but the present invention is not limited thereto.

Preparative Examples 1

Preparation of Pharmaceutical Formulations

1-1: Preparation of Powder

| | |
|---|---|
| Compound of Formula 1 | 500 mg |
| Lactose | 100 mg |
| Talc | 10 mg |

The components are mixed, and filled in an airtight pack to prepare a powder.

1-2: Preparation of Tablet

| | |
|---|---|
| Compound of Formula 1 | 500 mg |
| Corn starch | 100 mg |
| Lactose | 100 mg |
| Magnesium stearate | 2 mg |

The components were mixed, and tablet-pressed to prepare a tablet according to a conventional method of preparing a tablet.

1-3: Preparation of Capsule

| | |
|---|---|
| Compound of Formula 1 | 500 mg |
| Corn starch | 100 mg |
| Lactose | 100 mg |
| Magnesium stearate | 2 mg |

The components were mixed, and filled in a gelatin capsule to prepare a capsule according to a conventional method of preparing a capsule.

1-4: Preparation of Injectable Solution

| | |
|---|---|
| Compound of Formula 1 | 500 mg |
| Sterile distilled water for injection | Proper amount |
| pH regulating agent | Proper amount |

An injectable solution was prepared, according to a conventional method of preparing an injectable solution, so that one ampule (2 ml) contains the above-mentioned contents of the components.

1-5: Preparation of Solution

| | |
|---|---|
| Compound of Formula 1 | 100 mg |
| Isomerized sugar | 10 g |
| Mannitol | 5 g |
| Purified water | Proper amount |

A solution was prepared according to a conventional method of preparing a solution by dissolving the respective components in purified water, adding a proper amount of a lemon flavor thereto, mixing all the components, adding purified water to the resulting mixture so that a final amount of the mixture was adjusted to 100 ml, putting the mixture into a brown vial, and sterilizing the mixture.

INDUSTRIAL APPLICABILITY

The cyclohexene derivative according to the present invention, or the optical isomer or pharmaceutically acceptable salt thereof activates G protein-coupled receptor 119 (GPR-119) to enhance the intracellular activity of cyclic adenosine monophosphate (cAMP), and simultaneously induces the release of glucagon-like peptide-1 (GLP-1), which is a neuroendocrine protein, to simultaneously exhibit weight-loss and hypoglycemic effects, and thus can be useful for pharmaceutical compositions for preventing or treating metabolic diseases such as obesity, type 1 diabetes, type 2 diabetes, inadequate glucose tolerance, insulin resistance, hyperglycemia, hyperlipidemia, hypertriglyceridemia, hypercholesterolemia, dyslipidemia, syndrome X, etc.

The invention claimed is:
1. A compound represented by the following Formula 1, or an isomer or pharmaceutically acceptable salt thereof:

[Formula 1]

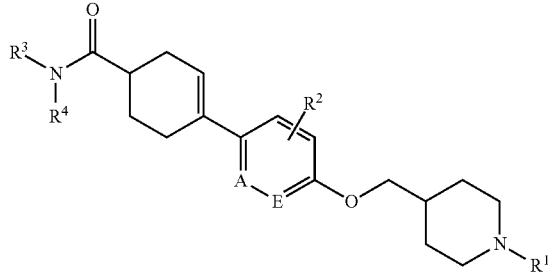

wherein R$^1$ is —H, —OH, a C$_{1-10}$ linear or branched alkyl, a C$_{1-10}$ linear or branched alkoxy, a C$_{1-10}$ linear or branched alkoxycarbonyl, or an unsubstituted or substituted 5- to 10-membered heteroaryl containing one or more heteroatoms selected from the group consisting of N, O, and S, wherein:
the substituted 5- to 10-membered heteroaryl is a 5- to 10-membered heteroaryl substituted with one or more C$_{1-10}$ linear or branched alkyl;
R$^2$ is —H, —OH, a halogen, a C$_{1-10}$ linear or branched alkyl, or a C$_{1-10}$ linear or branched alkoxy;
R$^3$ is —H, a C$_{1-10}$ linear or branched alkyl which is not substituted or substituted with one or more —OH or a halogen, a C$_{1-10}$ linear or branched alkoxy, a C$_{1-10}$ linear or branched alkoxy C$_{1-10}$ linear or branched alkyl, an unsubstituted C$_{3-10}$ cycloalkyl, an unsubstituted 5- to 10-membered heteroaryl C$_{1-10}$ linear or branched alkyl containing one or more heteroatoms selected from the group consisting of N, O, and S, —(CH$_2$)$_n$NR$^5$R$^6$, —(CH$_2$)$_m$C(=O)OR$^7$, or —(CH$_2$)$_p$C(=O)NR$^8$R$^9$, wherein:
R$^5$ and R$^6$ are each independently —H, -Boc

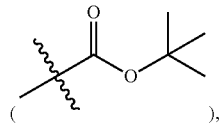

or a C$_{1-5}$ linear or branched alkyl,
R$^7$ is —H, or a C$_{1-5}$ linear or branched alkyl, and
R$^8$ and R$^9$ may be taken together with a nitrogen atom to which they are attached to form an unsubstituted or substituted 5- to 10-membered heterocycloalkyl containing one or more heteroatoms selected from the group consisting of N, O, and S, wherein:
the substituted 5- to 10-membered heterocycloalkyl is a 5- to 10-membered heterocycloalkyl substituted with one or more substituents selected from the group consisting of —CN, a C$_{1-5}$ linear or branched alkyl, a C$_{1-5}$ linear or branched alkoxy, and —C(=O)NR$^{10}$R$^{11}$, wherein R$^{10}$ and R$^{11}$ are each independently —H, or a C$_{1-5}$ linear or branched alkyl;
n, m, and p are each independently an integer ranging from 1 to 10;
R$^4$ is —H, a C$_{1-10}$ linear or branched alkyl which is not substituted or substituted with one or more —OH, or a C$_{1-10}$ linear or branched alkoxy;

provided that R$^3$ and R$^4$ may be taken together with a nitrogen atom to which they are attached to form an unsubstituted 3- to 10-membered heterocycloakenyl containing one or more heteroatoms selected from the group consisting of N, O, and S, or an unsubstituted, substituted or fused 3- to 10-membered heterocycloalkyl containing one or more heteroatoms selected from the group consisting of N, O, and S, wherein:
the substituted 3- to 10-membered heterocycloalkyl is a 3- to 10-membered heterocycloalkyl substituted with one or more substituents selected from the group consisting of —OH, —CN, =O, a halogen, a C$_{1-5}$ linear or branched alkyl which is not substituted or substituted with one or more —OH, a C$_{1-5}$ linear or branched alkoxy, an unsubstituted C$_{3-10}$ cycloalkyl C$_{1-5}$ linear or branched alkyl, an unsubstituted C$_{3-10}$ cycloalkyl, an unsubstituted 3- to 10-membered heterocycloalkyl containing one or more heteroatoms selected from the group consisting of N, O, and S, —C(=O)NR$^{12}$R$^{13}$, —NR$^{14}$R$^{15}$, and =NR$^{16}$; or substituted in a spiro fashion with a C$_{5-10}$ cycloakenyl fused with an unsubstituted C$_{6-10}$ aryl, or a 3- to 10-membered heterocycloalkyl which is not substituted or substituted with one or more -Boc

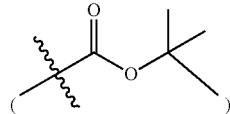 [SMILES: *C(=O)OC(C)(C)C]

and contains one or more heteroatoms selected from the group consisting of N, O, and S,
R$^{12}$, R$^{13}$, R$^{14}$, and R$^{15}$ are each independently —H, or a C$_{1-5}$ linear or branched alkyl, and R$^{16}$ is —H, —OH, or a C$_{1-5}$ linear or branched alkoxy,
provided that the fused 3- to 10-membered heterocycloalkyl is a 3- to 10-membered heterocycloalkyl fused with an unsubstituted C$_{6-10}$ aryl, and
the substitution and fusion may occur at the same time in the case of the unsubstituted, substituted or fused 3- to 10-membered heterocycloalkyl; and
A and E are each independently —CH=, or —N=.

2. The compound of Formula 1 or the isomer or pharmaceutically acceptable salt thereof according to claim 1, wherein R$^1$ is a C$_{1-10}$ linear or branched alkoxycarbonyl, or an unsubstituted or substituted 5- to 10-membered heteroaryl containing one or more heteroatoms selected from the group consisting of N, O, and S, wherein:
the substituted 5- to 10-membered heteroaryl is a 5- to 10-membered heteroaryl substituted with one or more C$_{1-10}$ linear or branched alkyl;
R$^2$ is —H or a halogen;
R$^3$ is a C$_{1-10}$ linear or branched alkyl which is not substituted or substituted with one or more —OH or a halogen, a C$_{1-10}$ linear or branched alkoxy, a C$_{1-10}$ linear or branched alkoxy C$_{1-10}$ linear or branched alkyl, an unsubstituted C$_{3-10}$ cycloalkyl, an unsubstituted 5- to 10-membered heteroaryl C$_{1-10}$ linear or branched alkyl containing one or more heteroatoms selected from the group consisting of N, O, and S, —(CH$_2$)$_n$NR$^5$R$^6$, —(CH$_2$)$_m$C(=O)OR$^7$, or —(CH$_2$)$_p$C(=O)NR$^8$R$^9$, wherein:

$R^5$ and $R^6$ are each independently —H or -Boc

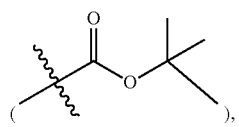 [SMILES: *C(=O)OC(C)(C)C]

$R^7$ is —H, or a $C_{1-5}$ linear or branched alkyl, and
$R^8$ and $R^9$ may be taken together with a nitrogen atom to which they are attached to form an unsubstituted or substituted 5- to 10-membered heterocycloalkyl containing one or more heteroatoms selected from the group consisting of N, O, and S, wherein:
the substituted 5- to 10-membered heterocycloalkyl is a 5- to 10-membered heterocycloalkyl substituted with one or more substituents selected from the group consisting of —CN and —C(=O)NR$^{10}$R$^{11}$, and R$^{10}$ and R$^{11}$ are each independently —H,
n, m, and p is each independently an integer ranging from 1 to 5;
$R^4$ is —H, or a $C_{1-10}$ linear or branched alkyl which is not substituted or substituted with one or more —OH;
provided that $R^3$ and $R^4$ may be taken together with a nitrogen atom to which they are attached to form an unsubstituted 3- to 10-membered heterocycloakenyl containing one or more heteroatoms selected from the group consisting of N, O, and S, or an unsubstituted, substituted or fused 3- to 10-membered heterocycloalkyl containing one or more heteroatoms selected from the group consisting of N, O, and S, wherein:
the substituted 3- to 10-membered heterocycloalkyl is a 3- to 10-membered heterocycloalkyl substituted with one or more substituents selected from the group consisting of —OH, —CN, =O, a halogen, a $C_{1-5}$ linear or branched alkyl which is not substituted or substituted with one or more —OH, an unsubstituted $C_{3-10}$ cycloalkyl $C_{1-5}$ linear or branched alkyl, an unsubstituted $C_{3-10}$ cycloalkyl, an unsubstituted 3- to 10-membered heterocycloalkyl containing one or more heteroatoms selected from the group consisting of N, O, and S, —C(=O)NR$^{12}$R$^{13}$, —NR$^{14}$R$^{15}$, and =NR$^{16}$; or substituted in a spiro fashion with a $C_{5-10}$ cycloakenyl fused with an unsubstituted $C_{6-10}$ aryl, or a 3- to 10-membered heterocycloalkyl which is not substituted or substituted with one or more -Boc

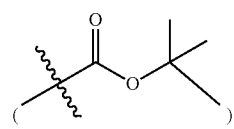 [SMILES: *C(=O)OC(C)(C)C]

and contains one or more heteroatoms selected from the group consisting of N, O, and S,
R$^{12}$, R$^{13}$, R$^{14}$, and R$^{15}$ are each independently —H, or a $C_{1-5}$ linear or branched alkyl, and R$^{16}$ is —OH, or a $C_{1-5}$ linear or branched alkoxy,
provided that the fused 3- to 10-membered heterocycloalkyl is a 3- to 10-membered heterocycloalkyl fused with an unsubstituted $C_{6-10}$ aryl, and the substitution and fusion may occur at the same time in the case of the unsubstituted, substituted or fused 3- to 10-membered heterocycloalkyl; and
A and E are each independently —CH=, or —N=.

3. The compound of Formula 1 or the isomer or pharmaceutically acceptable salt thereof according to claim 1, wherein $R^1$ is

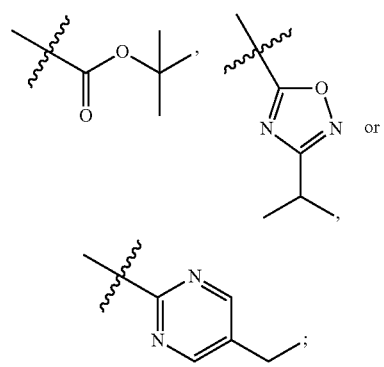

$R^2$ is —H or —F;
$R^3$ is

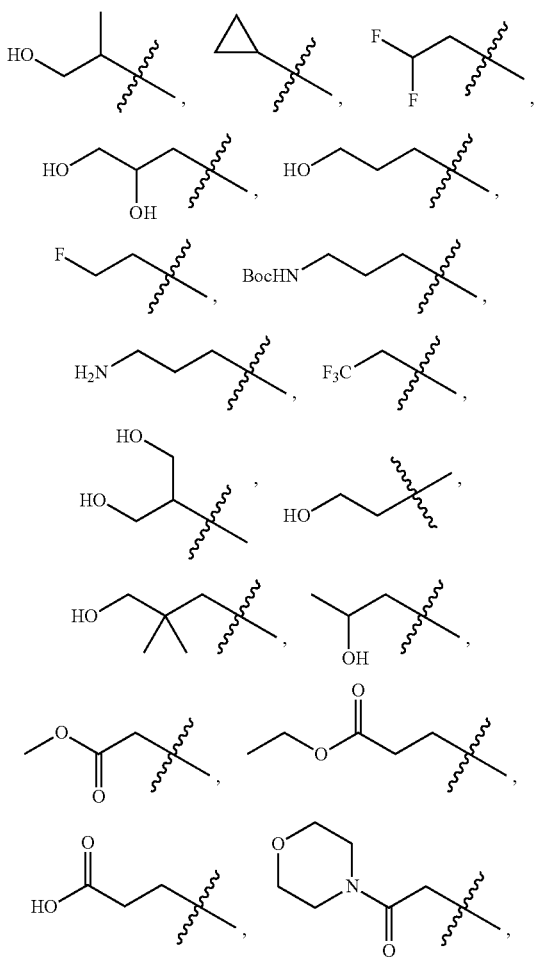

-continued
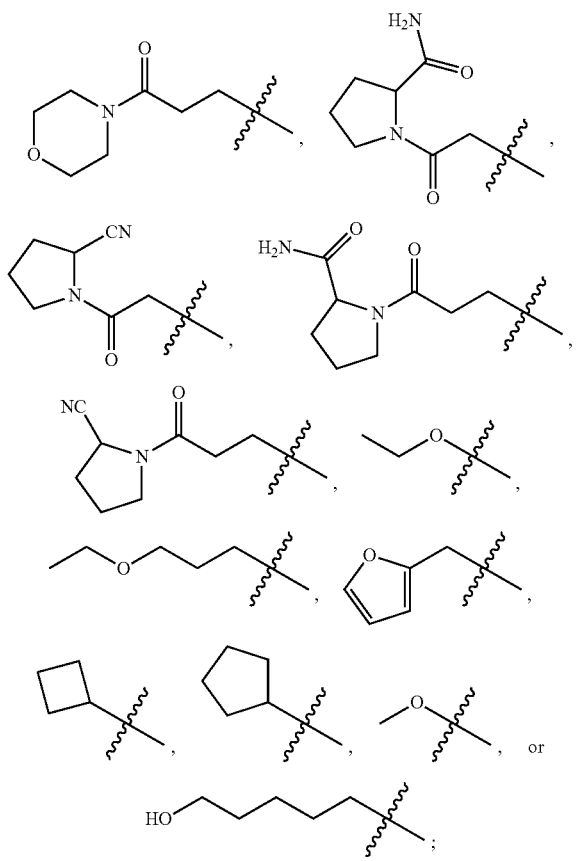
$R^4$ is —H, methyl, ethyl, or
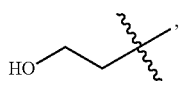
provided that $R^3$ and $R^4$ may be taken together with a nitrogen atom to which they are attached to form
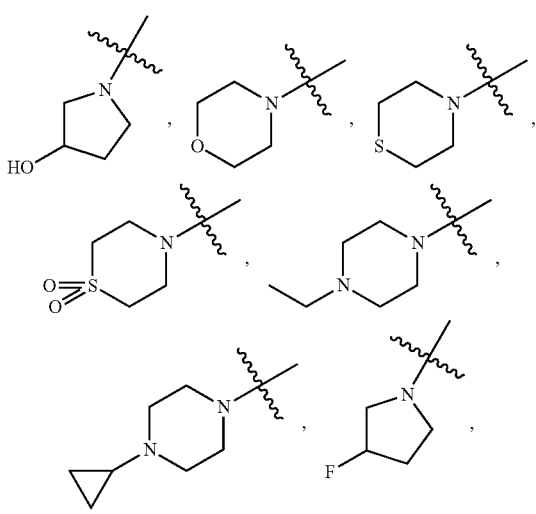
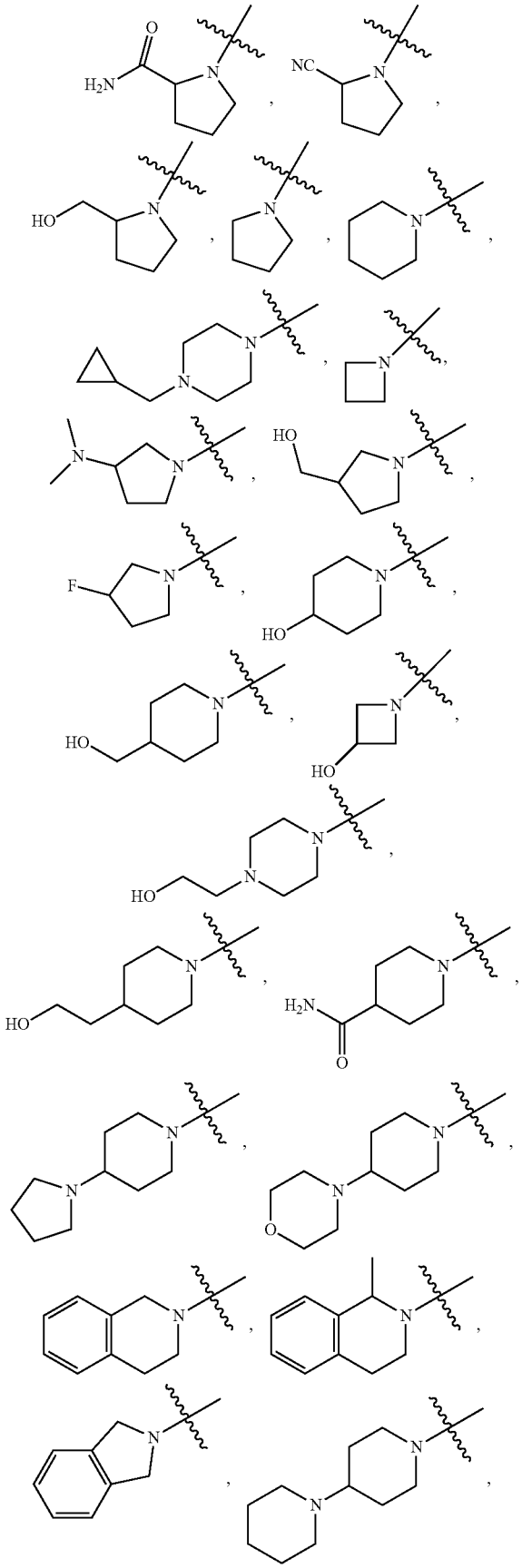

-continued

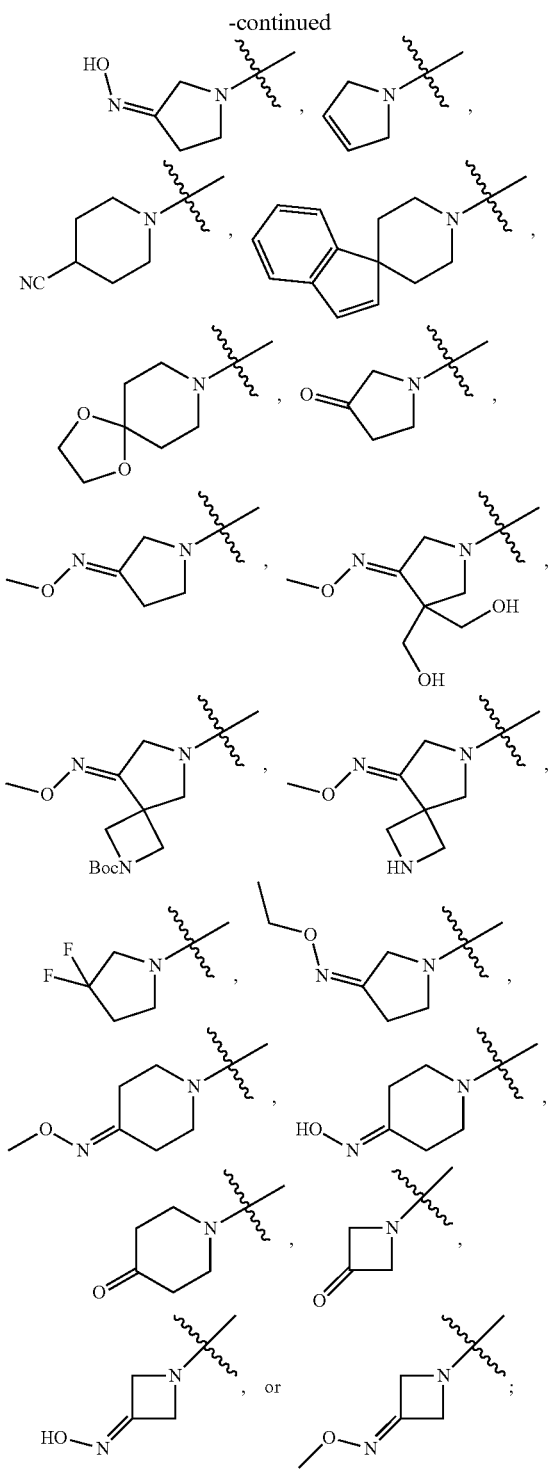

and

A and E are each independently —CH=, or —N=.

4. The compound of Formula 1 or the isomer or pharmaceutically acceptable salt thereof according to claim 1, wherein the compound represented by Formula 1 is the compound selected from the group consisting of:

(1) tert-butyl 4-((4-(4-((R)-1-hydroxypropan-2-ylcarbamoyl)cyclohex-1-enyl)phenoxy)methyl)piperidine-1-carboxylate;
(2) tert-butyl 4-((4-(4-(cyclopropylcarbamoyl)cyclohex-1-enyl)phenoxy)methyl)piperidine-1-carboxylate;
(3) tert-butyl 4-((4-(4-(2,2-difluoroethylcarbamoyl)cyclohex-1-enyl)phenoxy)methyl)piperidine-1-carboxylate;
(4) tert-butyl 4-((4-(4-((R)-2,3-dihydroxypropylcarbamoyl)cyclohex-1-enyl)phenoxy)methyl)piperidine-1-carboxylate;
(5) tert-butyl 4-((4-(4-((R)-3-hydroxypyrrolidine-1-carbonyl)cyclohex-1-enyl)phenoxy)methyl)piperidine-1-carboxylate;
(6) tert-butyl 4-((4-(4-((3-hydroxypropyl)(methyl)carbamoyl)cyclohex-1-enyl)phenoxy)methyl)piperidine-1-carboxylate;
(7) tert-butyl 4-((4-(4-(morpholine-4-carbonyl)cyclohex-1-enyl)phenoxy)methyl)piperidine-1-carboxylate;
(8) 4-(4-((1-(5-ethylpyrimidin-2-yl)piperidin-4-yl)methoxy)phenyl)-N-((R)-1-hydroxypropan-2-yl)cyclohex-3-enecarboxamide;
(9) 4-(4-((1-(5-ethylpyrimidin-2-yl)piperidin-4-yl)methoxy)phenyl)-N-(3-hydroxypropyl)cyclohex-3-enecarboxamide;
(10) tert-butyl 4-((6-(4-((R)-2,3-dihydroxypropylcarbamoyl)cyclohex-1-enyl)pyridin-3-yloxy)methyl)piperidine-1-carboxylate;
(11) tert-butyl 4-((6-(4-((S)-1-hydroxypropan-2-ylcarbamoyl)cyclohex-1-enyl)pyridin-3-yloxy)methyl)piperidine-1-carboxylate;
(12) N-((R)-2,3-dihydroxypropyl)-4-(4-((1-(5-ethylpyrimidin-2-yl)piperidin-4-yl)methoxy)phenyl)cyclohex-3-enecarboxamide;
(13) (4-(4-((1-(5-ethylpyrimidin-2-yl)piperidin-4-yl)methoxy)phenyl)cyclohex-3-enyl)(morpholino)methanone;
(14) tert-butyl 4-((6-(4-(1,3-dihydroxypropan-2-ylcarbamoyl)cyclohex-1-enyl)pyridin-3-yloxy)methyl)piperidine-1-carboxylate;
(15) N-(1,3-dihydroxypropan-2-yl)-4-(4-((1-(5-ethylpyrimidin-2-yl)piperidin-4-yl)methoxy)phenyl)cyclohex-3-enecarboxamide;
(16) (4-(4-((1-(5-ethylpyrimidin-2-yl)piperidin-4-yl)methoxy)phenyl)cyclohex-3-enyl)((R)-3-hydroxypyrrolidin-1-yl)methanone;
(17) N-((R)-2,3-dihydroxypropyl)-4-(4-((1-(3-isopropyl-1,2,4-oxadiazol-5-yl)piperidin-4-yl)methoxy)phenyl)cyclohex-3-enecarboxamide;
(18) N-((S)-2,3-dihydroxypropyl)-4-(4-((1-(3-isopropyl-1,2,4-oxadiazol-5-yl)piperidin-4-yl)methoxy)phenyl)cyclohex-3-enecarboxamide;
(19) N-((S)-1-hydroxypropan-2-yl)-4-(4-((1-(3-isopropyl-1,2,4-oxadiazol-5-yl)piperidin-4-yl)methoxy)phenyl)cyclohex-3-enecarboxamide;
(20) N-((R)-1-hydroxypropan-2-yl)-4-(4-((1-(3-isopropyl-1,2,4-oxadiazol-5-yl)piperidin-4-yl)methoxy)phenyl)cyclohex-3-enecarboxamide;
(21) 4-(4-((1-(5-ethylpyrimidin-2-yl)piperidin-4-yl)methoxy)phenyl)-N-(2-hydroxyethyl)-N-methylcyclohex-3-enecarboxamide;
(22) N-(3-hydroxy-2,2-dimethylpropyl)-4-(4-((1-(3-isopropyl-1,2,4-oxadiazol-5-yl)piperidin-4-yl)methoxy)phenyl)cyclohex-3-enecarboxamide;
(23) N-(1,3-dihydroxypropan-2-yl)-4-(4-((1-(3-isopropyl-1,2,4-oxadiazol-5-yl)piperidin-4-yl)methoxy)phenyl)cyclohex-3-enecarboxamide;
(24) tert-butyl 4-((5-(4-((S)-1-hydroxypropan-2-ylcarbamoyl)cyclohex-1-enyl)pyridin-2-yloxy)methyl)piperidine-1-carboxylate;

(25) tert-butyl 4-((5-(4-((R)-1-hydroxypropan-2-ylcarbamoyl)cyclohex-1-enyl)pyridin-2-yloxy)methyl)piperidine-1-carboxylate;
(26) tert-butyl 4-((5-(4-((S)-2-hydroxypropylcarbamoyl)cyclohex-1-enyl)pyridin-2-yloxy)methyl)piperidine-1-carboxylate;
(27) tert-butyl 4-((5-(4-((R)-2-hydroxypropylcarbamoyl)cyclohex-1-enyl)pyridin-2-yloxy)methyl)piperidine-1-carboxylate;
(28) N-((R)-2-hydroxypropyl)-4-(4-((1-(3-isopropyl-1,2,4-oxadiazol-5-yl)piperidin-4-yl)methoxy)phenyl)cyclohex-3-enecarboxamide;
(29) N-((S)-2-hydroxypropyl)-4-(4-((1-(3-isopropyl-1,2,4-oxadiazol-5-yl)piperidin-4-yl)methoxy)phenyl)cyclohex-3-enecarboxamide;
(30) 4-(4-((1-(5-ethylpyrimidin-2-yl)piperidin-4-yl)methoxy)phenyl)-N-((R)-2-hydroxypropyl)cyclohex-3-enecarboxamide;
(31) N-(2-hydroxyethyl)-4-(4-((1-(3-isopropyl-1,2,4-oxadiazol-5-yl)piperidin-4-yl)methoxy)phenyl)cyclohex-3-enecarboxamide;
(32) tert-butyl 4-((5-(4-((R)-2,3-dihydroxypropylcarbamoyl)cyclohex-1-enyl)pyridin-2-yloxy)methyl)piperidine-1-carboxylate;
(33) tert-butyl 4-((5-(4-((S)-2,3-dihydroxypropylcarbamoyl)cyclohex-1-enyl)pyridin-2-yloxy)methyl)piperidine-1-carboxylate;
(34) N-(2-hydroxyethyl)-4-(4-((1-(3-isopropyl-1,2,4-oxadiazol-5-yl)piperidin-4-yl)methoxy)phenyl)-N-methylcyclohex-3-enecarboxamide;
(35) N-ethyl-N-(2-hydroxyethyl)-4-(4-((1-(3-isopropyl-1,2,4-oxadiazol-5-yl)piperidin-4-yl)methoxy)phenyl)cyclohex-3-enecarboxamide;
(36) N-((R)-1-hydroxypropan-2-yl)-4-(5-((1-(3-isopropyl-1,2,4-oxadiazol-5-yl)piperidin-4-yl)methoxy)pyridin-2-yl)cyclohex-3-enecarboxamide;
(37) N-((S)-1-hydroxypropan-2-yl)-4-(5-((1-(3-isopropyl-1,2,4-oxadiazol-5-yl)piperidin-4-yl)methoxy)pyridin-2-yl)cyclohex-3-enecarboxamide;
(38) N-((R)-2-hydroxypropyl)-4-(5-((1-(3-isopropyl-1,2,4-oxadiazol-5-yl)piperidin-4-yl)methoxy)pyridin-2-yl)cyclohex-3-enecarboxamide;
(39) N-((S)-2-hydroxypropyl)-4-(5-((1-(3-isopropyl-1,2,4-oxadiazol-5-yl)piperidin-4-yl)methoxy)pyridin-2-yl)cyclohex-3-enecarboxamide;
(40) N-((R)-2,3-dihydroxypropyl)-4-(5-((1-(3-isopropyl-1,2,4-oxadiazol-5-yl)piperidin-4-yl)methoxy)pyridin-2-yl)cyclohex-3-enecarboxamide;
(41) N-((S)-2,3-dihydroxypropyl)-4-(5-((1-(3-isopropyl-1,2,4-oxadiazol-5-yl)piperidin-4-yl)methoxy)pyridin-2-yl)cyclohex-3-enecarboxamide;
(42) tert-butyl 4-((5-(4-((S)-3-hydroxypyrrolidine-1-carbonyl)cyclohex-1-enyl)pyridin-2-yloxy)methyl)piperidine-1-carboxylate;
(43) tert-butyl 4-((5-(4-((R)-3-hydroxypyrrolidine-1-carbonyl)cyclohex-1-enyl)pyridin-2-yloxy)methyl)piperidine-1-carboxylate;
(44) tert-butyl 4-((2-fluoro-4-(4-((S)-3-hydroxypyrrolidine-1-carbonyl)cyclohex-1-enyl)phenoxy)methyl)piperidine-1-carboxylate;
(45) tert-butyl 4-((2-fluoro-4-(4-((R)-3-hydroxypyrrolidine-1-carbonyl)cyclohex-1-enyl)phenoxy)methyl)piperidine-1-carboxylate;
(46) N-(1,3-dihydroxypropan-2-yl)-4-(5-((1-(3-isopropyl-1,2,4-oxadiazol-5-yl)piperidin-4-yl)methoxy)pyridin-2-yl)cyclohex-3-enecarboxamide;
(47) N-(3-hydroxy-2,2-dimethylpropyl)-4-(5-((1-(3-isopropyl-1,2,4-oxadiazol-5-yl)piperidin-4-yl)methoxy)pyridin-2-yl)cyclohex-3-enecarboxamide;
(48) ((R)-3-hydroxypyrrolidin-1-yl)(4-(4-((1-(3-isopropyl-1,2,4-oxadiazol-5-yl)piperidin-4-yl)methoxy)phenyl)cyclohex-3-enyl)methanone;
(49) ((S)-3-hydroxypyrrolidin-1-yl)(4-(4-((1-(3-isopropyl-1,2,4-oxadiazol-5-yl)piperidin-4-yl)methoxy)phenyl)cyclohex-3-enyl)methanone;
(50) N-(2,2-difluoroethyl)-4-(4-((1-(5-ethylpyrimidin-2-yl)piperidin-4-yl)methoxy)phenyl)cyclohex-3-enecarboxamide;
(51) N-(2,2-difluoroethyl)-4-(4-((1-(3-isopropyl-1,2,4-oxadiazol-5-yl)piperidin-4-yl)methoxy)phenyl)cyclohex-3-enecarboxamide;
(52) (4-(4-((1-(3-isopropyl-1,2,4-oxadiazol-5-yl)piperidin-4-yl)methoxy)phenyl)cyclohex-3-enyl)(pyrrolidin-1-yl)methanone;
(53) ((S)-3-fluoropyrrolidin-1-yl)(4-(4-((1-(3-isopropyl-1,2,4-oxadiazol-5-yl)piperidin-4-yl)methoxy)phenyl)cyclohex-3-enyl)methanone;
(54) ((R)-3-fluoropyrrolidin-1-yl)(4-(4-((1-(3-isopropyl-1,2,4-oxadiazol-5-yl)piperidin-4-yl)methoxy)phenyl)cyclohex-3-enyl)methanone;
(55) (4-ethylpiperazin-1-yl)(4-(4-((1-(5-ethylpyrimidin-2-yl)piperidin-4-yl)methoxy)phenyl)cyclohex-3-enyl)methanone;
(56) (4-(4-((1-(3-isopropyl-1,2,4-oxadiazol-5-yl)piperidin-4-yl)methoxy)phenyl)cyclohex-3-enyl)(piperidin-1-yl)methanone;
(57) tert-butyl 4-((2-fluoro-4-(4-((S)-3-fluoropyrrolidine-1-carbonyl)cyclohex-1-enyl)phenoxy)methyl)piperidine-1-carboxylate;
(58) tert-butyl 4-((2-fluoro-4-(4-((R)-3-fluoropyrrolidine-1-carbonyl)cyclohex-1-enyl)phenoxy)methyl)piperidine-1-carboxylate;
(59) tert-butyl 4-((2-fluoro-4-(4-((S)-1-hydroxypropan-2-ylcarbamoyl)cyclohex-1-enyl)phenoxy)methyl)piperidine-1-carboxylate;
(60) tert-butyl 4-((2-fluoro-4-(4-((R)-1-hydroxypropan-2-ylcarbamoyl)cyclohex-1-enyl)phenoxy)methyl)piperidine-1-carboxylate;
(61) tert-butyl 4-((2-fluoro-4-(4-((S)-2-hydroxypropylcarbamoyl)cyclohex-1-enyl)phenoxy)methyl)piperidine-1-carboxylate;
(62) tert-butyl 4-((2-fluoro-4-(4-((R)-2-hydroxypropylcarbamoyl)cyclohex-1-enyl)phenoxy)methyl)piperidine-1-carboxylate;
(63) tert-butyl 4-((4-(4-((S)-2,3-dihydroxypropylcarbamoyl)cyclohex-1-enyl)-2-fluorophenoxy)methyl)piperidine-1-carboxylate;
(64) tert-butyl 4-((4-(4-((R)-2,3-dihydroxypropylcarbamoyl)cyclohex-1-enyl)-2-fluorophenoxy)methyl)piperidine-1-carboxylate;
(65) azetidin-1-yl(4-(4-((1-(3-isopropyl-1,2,4-oxadiazol-5-yl)piperidin-4-yl)methoxy)phenyl)cyclohex-3-enyl)methanone;
(66) (4-(4-((1-(3-isopropyl-1,2,4-oxadiazol-5-yl)piperidin-4-yl)methoxy)phenyl)cyclohex-3-enyl)(morpholino)methanone;
(67) tert-butyl 4-((4-(4-(1,3-dihydroxypropan-2-ylcarbamoyl)cyclohex-1-enyl)-2-fluorophenoxy)methyl)piperidine-1-carboxylate;
(68) tert-butyl 4-((5-(4-(1,3-dihydroxypropan-2-ylcarbamoyl)cyclohex-1-enyl)pyridin-2-yloxy)methyl)piperidine-1-carboxylate;

(69) tert-butyl 4-((2-fluoro-4-(4-(morpholine-4-carbonyl)cyclohex-1-enyl)phenoxy)methyl)piperidine-1-carboxylate;

(70) tert-butyl 4-((5-(4-(morpholine-4-carbonyl)cyclohex-1-enyl)pyridin-2-yloxy)methyl)piperidine-1-carboxylate;

(71) tert-butyl 4-((2-fluoro-4-(4-(thiomorpholine-4-carbonyl)cyclohex-1-enyl)phenoxy)methyl)piperidine-1-carboxylate;

(72) tert-butyl 4-((5-(4-(thiomorpholine-4-carbonyl)cyclohex-1-enyl)pyridin-2-yloxy)methyl)piperidine-1-carboxylate;

(73) tert-butyl 4-((2-fluoro-4-(4-(thiomorpholine-1,1-dioxide-4-carbonyl)cyclohex-1-enyl)phenoxy)methyl)piperidine-1-carboxylate;

(74) (4-(4-((1-(3-isopropyl-1,2,4-oxadiazol-5-yl)piperidin-4-yl)methoxy)phenyl)cyclohex-3-enyl)(thiomorpholino)methanone;

(75) N-(2-fluoroethyl)-4-(4-((1-(3-isopropyl-1,2,4-oxadiazol-5-yl)piperidin-4-yl)methoxy)phenyl)cyclohex-3-enecarboxamide;

(76) tert-butyl 3-(4-(4-((1-(3-isopropyl-1,2,4-oxadiazol-5-yl)piperidin-4-yl)methoxy)phenyl)-N-methylcyclohex-3-enecarboxamido)propylcarbamate;

(77) N-(3-aminopropyl)-4-(4-((1-(3-isopropyl-1,2,4-oxadiazol-5-yl)piperidin-4-yl)methoxy)phenyl)-N-methylcyclohex-3-enecarboxamide;

(78) 4-(4-((1-(3-isopropyl-1,2,4-oxadiazol-5-yl)piperidin-4-yl)methoxy)phenyl)-N-(2,2,2-trifluoroethyl)cyclohex-3-enecarboxamide;

(79) (4-ethylpiperazin-1-yl)(4-(4-((1-(3-isopropyl-1,2,4-oxadiazol-5-yl)piperidin-4-yl)methoxy)phenyl)cyclohex-3-enyl)methanone;

(80) N-(1,3-dihydroxypropan-2-yl)-4-(3-fluoro-4-((1-(3-isopropyl-1,2,4-oxadiazol-5-yl)piperidin-4-yl)methoxy)phenyl)cyclohex-3-enecarboxamide;

(81) 4-(3-fluoro-4-((1-(3-isopropyl-1,2,4-oxadiazol-5-yl)piperidin-4-yl)methoxy)phenyl)-N-(2-hydroxyethyl)-N-methylcyclohex-3-enecarboxamide;

(82) tert-butyl 4-((2-fluoro-4-(4-(3-hydroxy-2,2-dimethylpropylcarbamoyl)cyclohex-1-enyl)phenoxy)methyl)piperidine-1-carboxylate;

(83) 4-(3-fluoro-4-((1-(3-isopropyl-1,2,4-oxadiazol-5-yl)piperidin-4-yl)methoxy)phenyl)-N-((S)-1-hydroxypropan-2-yl)cyclohex-3-enecarboxamide;

(84) 4-(3-fluoro-4-((1-(3-isopropyl-1,2,4-oxadiazol-5-yl)piperidin-4-yl)methoxy)phenyl)-N-((R)-1-hydroxypropan-2-yl)cyclohex-3-enecarboxamide;

(85) tert-butyl 4-((4-(4-(2,2-difluoroethylcarbamoyl)cyclohex-1-enyl)-2-fluorophenoxy)methyl)piperidine-1-carboxylate;

(86) tert-butyl 4-((5-(4-(2,2,2-trifluoroethylcarbamoyl)cyclohex-1-enyl)pyridin-2-yloxy)methyl)piperidine-1-carboxylate;

(87) tert-butyl 4-((5-(4-(2,2-difluoroethylcarbamoyl)cyclohex-1-enyl)pyridin-2-yloxy)methyl)piperidine-1-carboxylate;

(88) tert-butyl 4-((5-(4-(2-fluoroethylcarbamoyl)cyclohex-1-enyl)pyridin-2-yloxy)methyl)piperidine-1-carboxylate;

(89) (4-cyclopropylpiperazin-1-yl)(4-(4-((1-(3-isopropyl-1,2,4-oxadiazol-5-yl)piperidin-4-yl)methoxy)phenyl)cyclohex-3-enyl)methanone;

(90) tert-butyl 4-((5-(4-((R)-3-fluoropyrrolidine-1-carbonyl)cyclohex-1-enyl)pyridin-2-yloxy)methyl)piperidine-1-carboxylate;

(91) tert-butyl 4-((5-(4-((S)-3-fluoropyrrolidine-1-carbonyl)cyclohex-1-enyl)pyridin-2-yloxy)methyl)piperidine-1-carboxylate;

(92) 4-(3-fluoro-4-((1-(3-isopropyl-1,2,4-oxadiazol-5-yl)piperidin-4-yl)methoxy)phenyl)-N-(2,2,2-trifluoroethyl)cyclohex-3-enecarboxamide;

(93) N-(2,2-difluoroethyl)-4-(3-fluoro-4-((1-(3-isopropyl-1,2,4-oxadiazol-5-yl)piperidin-4-yl)methoxy)phenyl)cyclohex-3-enecarboxamide;

(94) 4-(3-fluoro-4-((1-(3-isopropyl-1,2,4-oxadiazol-5-yl)piperidin-4-yl)methoxy)phenyl)-N-(2-fluoroethyl)cyclohex-3-enecarboxamide;

(95) (4-(3-fluoro-4-((1-(3-isopropyl-1,2,4-oxadiazol-5-yl)piperidin-4-yl)methoxy)phenyl)cyclohex-3-enyl)((S)-3-fluoropyrrolidin-1-yl)methanone;

(96) (4-(3-fluoro-4-((1-(3-isopropyl-1,2,4-oxadiazol-5-yl)piperidin-4-yl)methoxy)phenyl)cyclohex-3-enyl)((R)-3-fluoropyrrolidin-1-yl)methanone;

(97) (4-(3-fluoro-4-((1-(3-isopropyl-1,2,4-oxadiazol-5-yl)piperidin-4-yl)methoxy)phenyl)cyclohex-3-enyl)(morpholino)methanone;

(98) (4-(3-fluoro-4-((1-(3-isopropyl-1,2,4-oxadiazol-5-yl)piperidin-4-yl)methoxy)phenyl)cyclohex-3-enyl)(thiomorpholino)methanone;

(99) N-(2,2-difluoroethyl)-4-(5-((1-(3-isopropyl-1,2,4-oxadiazol-5-yl)piperidin-4-yl)methoxy)pyridin-2-yl)cyclohex-3-enecarboxamide;

(100) (4-(5-((1-(3-isopropyl-1,2,4-oxadiazol-5-yl)piperidin-4-yl)methoxy)pyridin-2-yl)cyclohex-3-enyl)(morpholino)methanone;

(101) ((R)-3-fluoropyrrolidin-1-yl)(4-(5-((1-(3-isopropyl-1,2,4-oxadiazol-5-yl)piperidin-4-yl)methoxy)pyridin-2-yl)cyclohex-3-enyl)methanone;

(102) ((S)-3-fluoropyrrolidin-1-yl)(4-(5-((1-(3-isopropyl-1,2,4-oxadiazol-5-yl)piperidin-4-yl)methoxy)pyridin-2-yl)cyclohex-3-enyl)methanone;

(103) 4-(4-((1-(5-ethylpyrimidin-2-yl)piperidin-4-yl)methoxy)phenyl)-N-(2,2,2-trifluoroethyl)cyclohex-3-enecarboxamide;

(104) 4-(4-((1-(5-ethylpyrimidin-2-yl)piperidin-4-yl)methoxy)phenyl)-N-(2-fluoroethyl)cyclohex-3-enecarboxamide;

(105) (2 S)-1-(4-(4-((1-(5-ethylpyrimidin-2-yl)piperidin-4-yl)methoxy)phenyl)cyclohex-3-enecarbonyl)pyrrolidine-2-carboxamide;

(106) (2 S)-1-(4-(4-((1-(5-ethylpyrimidin-2-yl)piperidin-4-yl)methoxy)phenyl)cyclohex-3-enecarbonyl)pyrrolidine-2-carbonitrile;

(107) tert-butyl 4-((4-(4-((S)-2-carbamoylpyrrolidine-1-carbonyl)cyclohex-1-enyl)-2-fluorophenoxy)methyl)piperidine-1-carboxylate;

(108) (2S)-1-(4-(3-fluoro-4-((1-(3-isopropyl-1,2,4-oxadiazol-5-yl)piperidin-4-yl)methoxy)phenyl)cyclohex-3-enecarbonyl)pyrrolidine-2-carboxamide;

(109) (methyl 2-(4-(3-fluoro-4-((1-(3-isopropyl-1,2,4-oxadiazol-5-yl)piperidin-4-yl)methoxy)phenyl)cyclohex-3-enecarboxamido)acetate;

(110) ethyl 3-(4-(3-fluoro-4-((1-(3-isopropyl-1,2,4-oxadiazol-5-yl)piperidin-4-yl)methoxy)phenyl)cyclohex-3-enecarboxamido)propanoate;

(111) 3-(4-(3-fluoro-4-((1-(3-isopropyl-1,2,4-oxadiazol-5-yl)piperidin-4-yl)methoxy)phenyl)cyclohex-3-enecarboxamido)propanoic acid;

(112) 4-(3-fluoro-4-((1-(3-isopropyl-1,2,4-oxadiazol-5-yl)piperidin-4-yl)methoxy)phenyl)-N-(2-morpholino-2-oxoethyl)cyclohex-3-enecarboxamide;

(113) 4-(3-fluoro-4-((1-(3-isopropyl-1,2,4-oxadiazol-5-yl)piperidin-4-yl)methoxy)phenyl)-N-(3-morpholino-3-oxopropyl)cyclohex-3-enecarboxamide;

(114) tert-butyl 4-((4-(4-((S)-2-cyanopyrrolidine-1-carbonyl)cyclohex-1-enyl)-2-fluorophenoxy)methyl)piperidine-1-carboxylate;

(115) (2S)-1-(4-(3-fluoro-4-((1-(3-isopropyl-1,2,4-oxadiazol-5-yl)piperidin-4-yl)methoxy)phenyl)cyclohex-3-enecarbonyl)pyrrolidine-2-carbonitrile;

(116) (2R)-1-(4-(3-fluoro-4-((1-(3-isopropyl-1,2,4-oxadiazol-5-yl)piperidin-4-yl)methoxy)phenyl)cyclohex-3-enecarbonyl)pyrrolidine-2-carboxamide;

(117) (2R)-1-(4-(3-fluoro-4-((1-(3-isopropyl-1,2,4-oxadiazol-5-yl)piperidin-4-yl)methoxy)phenyl)cyclohex-3-enecarbonyl)pyrrolidine-2-carbonitrile;

(118) (4-(4-((1-(5-ethylpyrimidin-2-yl)piperidin-4-yl)methoxy)phenyl)cyclohex-3-enyl)((R)-2-(hydroxymethyl)pyrrolidin-1-yl)methanone;

(119) (4-(4-((1-(5-ethylpyrimidin-2-yl)piperidin-4-yl)methoxy)phenyl)cyclohex-3-enyl)((S)-2-(hydroxymethyl)pyrrolidin-1-yl)methanone;

(120) 4-(3-fluoro-4-((1-(3-isopropyl-1,2,4-oxadiazol-5-yl)piperidin-4-yl)methoxy)phenyl)-N-(2-hydroxyethyl)cyclohex-3-enecarboxamide;

(121) (2R)-1-(2-(4-(3-fluoro-4-((1-(3-isopropyl-1,2,4-oxadiazol-5-yl)piperidin-4-yl)methoxy)phenyl)cyclohex-3-enecarboxamido)acetyl)pyrrolidine-2-carboxamide;

(122) N-(2-((R)-2-cyanopyrrolidin-1-yl)-2-oxoethyl)-4-(3-fluoro-4-((1-(3-isopropyl-1,2,4-oxadiazol-5-yl)piperidin-4-yl)methoxy)phenyl)cyclohex-3-enecarboxamide;

(123) (4-cyclopropylpiperazin-1-yl)(4-(4-((1-(5-ethylpyrimidin-2-yl)piperidin-4-yl)methoxy)phenyl)cyclohex-3-enyl)methanone;

(124) (4-(cyclopropylmethyl)piperazin-1-yl)(4-(4-((1-(5-ethylpyrimidin-2-yl)piperidin-4-yl)methoxy)phenyl)cyclohex-3-enyl)methanone;

(125) tert-butyl 4-((3-fluoro-4-(4-((S)-2-hydroxypropylcarbamoyl)cyclohex-1-enyl)phenoxy)methyl)piperidine-1-carboxylate;

(126) tert-butyl 4-((3-fluoro-4-(4-((R)-2-hydroxypropylcarbamoyl)cyclohex-1-enyl)phenoxy)methyl)piperidine-1-carboxylate;

(127) 4-(4-((1-(5-ethylpyrimidin-2-yl)piperidin-4-yl)methoxy)phenyl)-N-((S)-1-hydroxypropan-2-yl)cyclohex-3-enecarboxamide;

(128) N-((S)-2,3-dihydroxypropyl)-4-(4-((1-(5-ethylpyrimidin-2-yl)piperidin-4-yl)methoxy)phenyl)cyclohex-3-enecarboxamide;

(129) tert-butyl 4-((3-fluoro-4-(4-((R)-1-hydroxypropan-2-ylcarbamoyl)cyclohex-1-enyl)phenoxy)methyl)piperidine-1-carboxylate;

(130) tert-butyl 4-((3-fluoro-4-(4-((S)-1-hydroxypropan-2-ylcarbamoyl)cyclohex-1-enyl)phenoxy)methyl)piperidine-1-carboxylate;

(131) tert-butyl 4-((4-(4-((R)-2,3-dihydroxypropylcarbamoyl)cyclohex-1-enyl)-3-fluorophenoxy)methyl)piperidine-1-carboxylate;

(132) tert-butyl 4-((4-(4-((S)-2,3-dihydroxypropylcarbamoyl)cyclohex-1-enyl)-3-fluorophenoxy)methyl)piperidine-1-carboxylate;

(133) (2S)-1-(2-(4-(3-fluoro-4-((1-(3-isopropyl-1,2,4-oxadiazol-5-yl)piperidin-4-yl)methoxy)phenyl)cyclohex-3-enecarboxamido)acetyl)pyrrolidine-2-carboxamide;

(134) (2S)-1-(3-(4-(3-fluoro-4-((1-(3-isopropyl-1,2,4-oxadiazol-5-yl)piperidin-4-yl)methoxy)phenyl)cyclohex-3-enecarboxamido)propanoyl)pyrrolidine-2-carboxamide;

(135) (4-(4-((1-(5-ethylpyrimidin-2-yl)piperidin-4-yl)methoxy)phenyl)cyclohex-3-enyl)((S)-3-hydroxypyrrolidin-1-yl)methanone;

(136) 4-(4-((1-(5-ethylpyrimidin-2-yl)piperidin-4-yl)methoxy)phenyl)-N-((S)-2-hydroxypropyl)cyclohex-3-enecarboxamide;

(137) tert-butyl 4-((4-(4-(cyclopropylcarbamoyl)cyclohex-1-enyl)-3-fluorophenoxy)methyl)piperidine-1-carboxylate;

(138) tert-butyl 4-((3-fluoro-4-(4-(2-fluoroethylcarbamoyl)cyclohex-1-enyl)phenoxy)methyl)piperidine-1-carboxylate;

(139) N-(2-((S)-2-cyanopyrrolidin-1-yl)-2-oxoethyl)-4-(3-fluoro-4-((1-(3-isopropyl-1,2,4-oxadiazol-5-yl)piperidin-4-yl)methoxy)phenyl)cyclohex-3-enecarboxamide;

(140) N-(3-((S)-2-cyanopyrrolidin-1-yl)-3-oxopropyl)-4-(3-fluoro-4-((1-(3-isopropyl-1,2,4-oxadiazol-5-yl)piperidin-4-yl)methoxy)phenyl)cyclohex-3-enecarboxamide;

(141) tert-butyl 4-((4-(4-(2,2-difluoroethylcarbamoyl)cyclohex-1-enyl)-3-fluorophenoxy)methyl)piperidine-1-carboxylate;

(142) tert-butyl 4-((3-fluoro-4-(4-(2,2,2-trifluoroethylcarbamoyl)cyclohex-1-enyl)phenoxy)methyl)piperidine-1-carboxylate;

(143) ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone;

(144) ((S)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone;

(145) ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone hydrochloride;

(146) ((S)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone hydrochloride;

(147) ((R)-2-(hydroxymethyl)pyrrolidin-1-yl)(4-(4-((1-(3-isopropyl-1,2,4-oxadiazol-5-yl)piperidin-4-yl)methoxy)phenyl)cyclohex-3-enyl)methanone;

(148) ((S)-2-(hydroxymethyl)pyrrolidin-1-yl)(4-(4-((1-(3-isopropyl-1,2,4-oxadiazol-5-yl)piperidin-4-yl)methoxy)phenyl)cyclohex-3-enyl)methanone;

(149) ((R)-3-(hydroxymethyl)pyrrolidin-1-yl)(4-(4-((1-(3-isopropyl-1,2,4-oxadiazol-5-yl)piperidin-4-yl)methoxy)phenyl)cyclohex-3-enyl)methanone;

(150) ((S)-3-(hydroxymethyl)pyrrolidin-1-yl)(4-(4-((1-(3-isopropyl-1,2,4-oxadiazol-5-yl)piperidin-4-yl)methoxy)phenyl)cyclohex-3-enyl)methanone;

(151) (4-(4-((1-(5-ethylpyrimidin-2-yl)piperidin-4-yl)methoxy)phenyl)cyclohex-3-enyl)((R)-2-(hydroxymethyl)pyrrolidin-1-yl)methanone hydrochloride;

(152) (4-(4-((1-(5-ethylpyrimidin-2-yl)piperidin-4-yl)methoxy)phenyl)cyclohex-3-enyl)((S)-3-(hydroxymethyl)pyrrolidin-1-yl)methanone;

(153) (4-(4-((1-(5-ethylpyrimidin-2-yl)piperidin-4-yl)methoxy)phenyl)cyclohex-3-enyl)((R)-3-(hydroxymethyl)pyrrolidin-1-yl)methanone;

(154) ((S)-3-(dimethylamino)pyrrolidin-1-yl)(4-(4-((1-(5-ethylpyrimidin-2-yl)piperidin-4-yl)methoxy)phenyl)cyclohex-3-enyl)methanone;

(155) ((R)-3-(dimethylamino)pyrrolidin-1-yl)(4-(4-((1-(5-ethylpyrimidin-2-yl)piperidin-4-yl)methoxy)phenyl)cyclohex-3-enyl)methanone;

(156) ((S)-3-(dimethylamino)pyrrolidin-1-yl)(4-(4-((1-(5-ethylpyrimidin-2-yl)piperidin-4-yl)methoxy)phenyl)cyclohex-3-enyl)methanone hydrochloride;

(157) ((R)-3-(dimethylamino)pyrrolidin-1-yl)(4-(4-((1-(5-ethylpyrimidin-2-yl)piperidin-4-yl)methoxy)phenyl)cyclohex-3-enyl)methanone hydrochloride;

(158) (4-(4-((1-(5-ethylpyrimidin-2-yl)piperidin-4-yl)methoxy)phenyl)cyclohex-3-enyl)((S)-3-(hydroxymethyl)pyrrolidin-1-yl)methanone hydrochloride;

(159) (4-(4-((1-(5-ethylpyrimidin-2-yl)piperidin-4-yl)methoxy)phenyl)cyclohex-3-enyl)((R)-3-(hydroxymethyl)pyrrolidin-1-yl)methanone hydrochloride;

(160) (4-(4-((1-(5-ethylpyrimidin-2-yl)piperidin-4-yl)methoxy)phenyl)cyclohex-3-enyl)((S)-3-fluoropyrrolidin-1-yl)methanone;

(161) (4-(4-((1-(5-ethylpyrimidin-2-yl)piperidin-4-yl)methoxy)phenyl)cyclohex-3-enyl)((S)-3-fluoropyrrolidin-1-yl)methanone hydrochloride;

(162) (4-(4-((1-(5-ethylpyrimidin-2-yl)piperidin-4-yl)methoxy)phenyl)cyclohex-3-enyl)(pyrrolidin-1-yl)methanone;

(163) (4-(4-((1-(5-ethylpyrimidin-2-yl)piperidin-4-yl)methoxy)phenyl)cyclohex-3-enyl)(piperidin-1-yl)methanone;

(164) (4-(4-((1-(5-ethylpyrimidin-2-yl)piperidin-4-yl)methoxy)phenyl)cyclohex-3-enyl)(4-hydroxypiperidin-1-yl)methanone;

(165) (4-(4-((1-(5-ethylpyrimidin-2-yl)piperidin-4-yl)methoxy)phenyl)cyclohex-3-enyl)(4-(hydroxymethyl)piperidin-1-yl)methanone;

(166) (4-(4-((1-(5-ethylpyrimidin-2-yl)piperidin-4-yl)methoxy)phenyl)cyclohex-3-enyl)(pyrrolidin-1-yl)methanone hydrochloride;

(167) (4-(4-((1-(5-ethylpyrimidin-2-yl)piperidin-4-yl)methoxy)phenyl)cyclohex-3-enyl)(piperidin-1-yl)methanone hydrochloride;

(168) (4-(4-((1-(5-ethylpyrimidin-2-yl)piperidin-4-yl)methoxy)phenyl)cyclohex-3-enyl)(4-hydroxypiperidin-1-yl)methanone hydrochloride;

(169) (4-(4-((1-(5-ethylpyrimidin-2-yl)piperidin-4-yl)methoxy)phenyl)cyclohex-3-enyl)(4-(hydroxymethyl)piperidin-1-yl)methanone hydrochloride;

(170) azetidin-1-yl(4-(4-((1-(5-ethylpyrimidin-2-yl)piperidin-4-yl)methoxy)phenyl)cyclohex-3-enyl)methanone;

(171) (4-(4-((1-(5-ethylpyrimidin-2-yl)piperidin-4-yl)methoxy)phenyl)cyclohex-3-enyl)(3-hydroxyazetidin-1-yl)methanone;

(172) (4-(4-((1-(5-ethylpyrimidin-2-yl)piperidin-4-yl)methoxy)phenyl)cyclohex-3-enyl)(4-(2-hydroxyethyl)piperazin-1-yl)methanone;

(173) (4-(4-((1-(5-ethylpyrimidin-2-yl)piperidin-4-yl)methoxy)phenyl)cyclohex-3-enyl)(4-(2-hydroxyethyl)piperidin-1-yl)methanone;

(174) N-ethoxy-4-(4-((1-(5-ethylpyrimidin-2-yl)piperidin-4-yl)methoxy)phenyl)cyclohex-3-enecarboxamide;

(175) N-ethyl-4-(4-((1-(5-ethylpyrimidin-2-yl)piperidin-4-yl)methoxy)phenyl)-N-(2-hydroxyethyl)cyclohex-3-enecarboxamide;

(176) 4-(4-((1-(5-ethylpyrimidin-2-yl)piperidin-4-yl)methoxy)phenyl)-N-(2-hydroxyethyl)cyclohex-3-enecarboxamide;

(177) 4-(4-((1-(5-ethylpyrimidin-2-yl)piperidin-4-yl)methoxy)phenyl)-N-(3-hydroxy-2,2-dimethylpropyl)cyclohex-3-enecarboxamide;

(178) 1-(4-(4-((1-(5-ethylpyrimidin-2-yl)piperidin-4-yl)methoxy)phenyl)cyclohex-3-enecarbonyl)piperidine-4-carboxamide;

(179) 4-(4-((1-(5-ethylpyrimidin-2-yl)piperidin-4-yl)methoxy)phenyl)-N-(3-methoxypropyl)cyclohex-3-enecarboxamide;

(180) 4-(4-((1-(5-ethylpyrimidin-2-yl)piperidin-4-yl)methoxy)phenyl)-N-(furan-2-ylmethyl)cyclohex-3-enecarboxamide;

(181) 4-(4-((1-(5-ethylpyrimidin-2-yl)piperidin-4-yl)methoxy)phenyl)-N,N-bis(2-hydroxyethyl)cyclohex-3-enecarboxamide;

(182) (4-hydroxypiperidin-1-yl)(4-(4-((1-(3-isopropyl-1,2,4-oxadiazol-5-yl)piperidin-4-yl)methoxy)phenyl)cyclohex-3-enyl)methanone;

(183) (4-(hydroxymethyl)piperidin-1-yl)(4-(4-((1-(3-isopropyl-1,2,4-oxadiazol-5-yl)piperidin-4-yl)methoxy)phenyl)cyclohex-3-enyl)methanone;

(184) N-cyclopropyl-4-(4-((1-(3-isopropyl-1,2,4-oxadiazol-5-yl)piperidin-4-yl)methoxy)phenyl)cyclohex-3-enecarboxamide;

(185) N-(3-hydroxypropyl)-4-(4-((1-(3-isopropyl-1,2,4-oxadiazol-5-yl)piperidin-4-yl)methoxy)phenyl)cyclohex-3-enecarboxamide;

(186) (4-(2-hydroxyethyl)piperidin-1-yl)(4-(4-((1-(3-isopropyl-1,2,4-oxadiazol-5-yl)piperidin-4-yl)methoxy)phenyl)cyclohex-3-enyl)methanone;

(187) (4-(2-hydroxyethyl)piperazin-1-yl)(4-(4-((1-(3-isopropyl-1,2,4-oxadiazol-5-yl)piperidin-4-yl)methoxy)phenyl)cyclohex-3-enyl)methanone;

(188) 4-(4-((1-(3-isopropyl-1,2,4-oxadiazol-5-yl)piperidin-4-yl)methoxy)phenyl)-N-(methoxymethyl)cyclohex-3-enecarboxamide;

(189) N-cyclopropyl-4-(4-((1-(5-ethylpyrimidin-2-yl)piperidin-4-yl)methoxy)phenyl)cyclohex-3-enecarboxamide;

(190) tert-butyl 4-((4-(4-(2-hydroxyethylcarbamoyl)cyclohex-1-enyl)phenoxy)methyl)piperidine-1-carboxylate;

(191) tert-butyl 4-((4-(4-(3-hydroxy-2,2-dimethylpropylcarbamoyl)cyclohex-1-enyl)phenoxy)methyl)piperidine-1-carboxylate;

(192) tert-butyl 4-((4-(4-(methoxymethylcarbamoyl)cyclohex-1-enyl)phenoxy)methyl)piperidine-1-carboxylate;

(193) tert-butyl 4-((4-(4-(4-(pyrrolidin-1-yl)piperidine-1-carbonyl)cyclohex-1-enyl)phenoxy)methyl)piperidine-1-carboxylate;

(194) tert-butyl 4-((4-(4-(cyclobutylcarbamoyl)cyclohex-1-enyl)phenoxy)methyl)piperidine-1-carboxylate;

(195) tert-butyl 4-((4-(4-(cyclopentylcarbamoyl)cyclohex-1-enyl)phenoxy)methyl)piperidine-1-carboxylate;

(196) tert-butyl 4-((4-(4-(4-morpholinopiperidine-1-carbonyl)cyclohex-1-enyl)phenoxy)methyl)piperidine-1-carboxylate;

(197) 4-(4-((1-(5-ethylpyrimidin-2-yl)piperidin-4-yl)methoxy)phenyl)-N-methoxy-N-methylcyclohex-3-enecarboxamide;

(198) 4-(4-((1-(5-ethylpyrimidin-2-yl)piperidin-4-yl)methoxy)phenyl)-N-methoxycyclohex-3-enecarboxamide;

(199) tert-butyl 4-((4-(4-(ethyl(2-hydroxyethyl)carbamoyl)cyclohex-1-enyl)phenoxy)methyl)piperidine-1-carboxylate;
(200) tert-butyl 4-((4-(4-(4-(2-hydroxyethyl)piperidine-1-carbonyl)cyclohex-1-enyl)phenoxy)methyl)piperidine-1-carboxylate;
(201) tert-butyl 4-((4-(4-(4-(2-hydroxyethyl)piperazine-1-carbonyl)cyclohex-1-enyl)phenoxy)methyl)piperidine-1-carboxylate;
(202) tert-butyl 4-((4-(4-(pyrrolidine-1-carbonyl)cyclohex-1-enyl)phenoxy)methyl)piperidine-1-carboxylate;
(203) tert-butyl 4-((4-(4-(4-ethylpiperazine-1-carbonyl)cyclohex-1-enyl)phenoxy)methyl)piperidine-1-carboxylate;
(204) tert-butyl 4-((4-(4-(piperidine-1-carbonyl)cyclohex-1-enyl)phenoxy)methyl)piperidine-1-carboxylate;
(205) tert-butyl 4-((4-(4-(3-ethoxypropylcarbamoyl)cyclohex-1-enyl)phenoxy)methyl)piperidine-1-carboxylate;
(206) tert-butyl 4-((4-(4-(bis(2-hydroxyethyl)carbamoyl)cyclohex-1-enyl)phenoxy)methyl)piperidine-1-carboxylate;
(207) 1-(4-(4-((1-(3-isopropyl-1,2,4-oxadiazol-5-yl)piperidin-4-yl)methoxy)phenyl)cyclohex-3-enecarbonyl)piperidine-4-carboxamide;
(208) (4-(4-((1-(3-isopropyl-1,2,4-oxadiazol-5-yl)piperidin-4-yl)methoxy)phenyl)cyclohex-3-enyl)(4-(pyrrolidin-1-yl)piperidin-1-yl)methanone;
(209) (4-(4-((1-(3-isopropyl-1,2,4-oxadiazol-5-yl)piperidin-4-yl)methoxy)phenyl)cyclohex-3-enyl)(4-morpholinopiperidin-1-yl)methanone;
(210) N-cyclopentyl-4-(4-((1-(3-isopropyl-1,2,4-oxadiazol-5-yl)piperidin-4-yl)methoxy)phenyl)cyclohex-3-enecarboxamide;
(211) N-cyclobutyl-4-(4-((1-(3-isopropyl-1,2,4-oxadiazol-5-yl)piperidin-4-yl)methoxy)phenyl)cyclohex-3-enecarboxamide;
(212) (3,4-dihydroisoquinolin-2(1H)-yl)(4-(4-((1-(3-isopropyl-1,2,4-oxadiazol-5-yl)piperidin-4-yl)methoxy)phenyl)cyclohex-3-enyl)methanone;
(213) (4-(4-((1-(3-isopropyl-1,2,4-oxadiazol-5-yl)piperidin-4-yl)methoxy)phenyl)cyclohex-3-enyl)(1-methyl-3,4-dihydroisoquinolin-2(1H)-yl)methanone;
(214) isoindolin-2-yl(4-(4-((1-(3-isopropyl-1,2,4-oxadiazol-5-yl)piperidin-4-yl)methoxy)phenyl)cyclohex-3-enyl)methanone;
(215) 1,4'-bipiperidin-1'-yl(4-(4-((1-(3-isopropyl-1,2,4-oxadiazol-5-yl)piperidin-4-yl)methoxy)phenyl)cyclohex-3-enyl)methanone;
(216) tert-butyl 4-((4-(4-(1,4'-bipiperidine-1'-carbonyl)cyclohex-1-enyl)phenoxy)methyl)piperidine-1-carboxylate;
(217) (4-(4-((1-(5-ethylpyrimidin-2-yl)piperidin-4-yl)methoxy)phenyl)cyclohex-3-enyl)(3-(hydroxyimino)pyrrolidin-1-yl)methanone;
(218) (4-(4-((1-(5-ethylpyrimidin-2-yl)piperidin-4-yl)methoxy)phenyl)cyclohex-3-enyl)(4-(pyrrolidin-1-yl)piperidin-1-yl)methanone;
(219) 1,4'-bipiperidin-1'-yl(4-(4-((1-(5-ethylpyrimidin-2-yl)piperidin-4-yl)methoxy)phenyl)cyclohex-3-enyl)methanone;
(220) (4-(4-((1-(5-ethylpyrimidin-2-yl)piperidin-4-yl)methoxy)phenyl)cyclohex-3-enyl)(4-morpholinopiperidin-1-yl)methanone;
(221) tert-butyl 4-((4-(4-(furan-2-ylmethylcarbamoyl)cyclohex-1-enyl)phenoxy)methyl)piperidine-1-carboxylate;
(222) tert-butyl 4-((4-(4-(methoxycarbamoyl)cyclohex-1-enyl)phenoxy)methyl)piperidine-1-carboxylate;
(223) tert-butyl 4-((4-(4-(methoxy(methyl)carbamoyl)cyclohex-1-enyl)phenoxy)methyl)piperidine-1-carboxylate;
(224) tert-butyl 4-((4-(4-(2, 5-dihydro-1H-pyrrole-1-carbonyl)cyclohex-1-enyl)phenoxy)methyl)piperidine-1-carboxylate;
(225) tert-butyl 4-((4-(4-(4-hydroxypiperidine-1-carbonyl)cyclohex-1-enyl)phenoxy)methyl)piperidine-1-carboxylate;
(226) tert-butyl 4-((4-(4-(4-(hydroxymethyl)piperidine-1-carbonyl)cyclohex-1-enyl)phenoxy)methyl)piperidine-1-carboxylate;
(227) 1-(4-(4-((1-(5-ethylpyrimidin-2-yl)piperidin-4-yl)methoxy)phenyl)cyclohex-3-enecarbonyl)piperidine-4-carbonitrile;
(228) (4-(4-((1-(5-ethylpyrimidin-2-yl)piperidin-4-yl)methoxy)phenyl)cyclohex-3-enyl)(spiro[indene-1,4'-piperidin]-1'-yl)methanone;
(229) (4-(4-((1-(5-ethylpyrimidin-2-yl)piperidin-4-yl)methoxy)phenyl)cyclohex-3-enyl)(1,4-dioxa-8-azaspiro[4.5]decan-8-yl)methanone;
(230) N-cyclopentyl-4-(4-((1-(5-ethylpyrimidin-2-yl)piperidin-4-yl)methoxy)phenyl)cyclohex-3-enecarboxamide;
(231) N-cyclobutyl-4-(4-((1-(5-ethylpyrimidin-2-yl)piperidin-4-yl)methoxy)phenyl)cyclohex-3-enecarboxamide;
(232) (3,4-dihydroisoquinolin-2(1H)-yl)(4-(4-((1-(5-ethylpyrimidin-2-yl)piperidin-4-yl)methoxy)phenyl)cyclohex-3-enyl)methanone;
(233) tert-butyl 4-((4-(4-(5-hydroxypentylcarbamoyl)cyclohex-1-enyl)phenoxy)methyl)piperidine-1-carboxylate;
(234) 4-(4-((1-(5-ethylpyrimidin-2-yl)piperidin-4-yl)methoxy)phenyl)-N-(5-hydroxypentyl)cyclohex-3-enecarboxamide;
(235) (2,5-dihydro-1H-pyrrol-1-yl)(4-(4-((1-(5-ethylpyrimidin-2-yl)piperidin-4-yl)methoxy)phenyl)cyclohex-3-enyl)methanone;
(236) tert-butyl 4-((4-(4-((2-hydroxyethyl)(methyl)carbamoyl)cyclohex-1-enyl)phenoxy)methyl)piperidine-1-carboxylate;
(237) tert-butyl 4-((4-(4-(1,3-dihydroxypropan-2-ylcarbamoyl)cyclohex-1-enyl)phenoxy)methyl)piperidine-1-carboxylate;
(238) tert-butyl 4-((4-(4-(3-hydroxypropylcarbamoyl)cyclohex-1-enyl)phenoxy)methyl)piperidine-1-carboxylate;
(239) tert-butyl 4-((4-(4-(1,2,3,4-tetrahydroisoquinoline-2-carbonyl)cyclohex-1-enyl)phenoxy)methyl)piperidine-1-carboxylate;
(240) tert-butyl 4-((4-(4-(isoindoline-2-carbonyl)cyclohex-1-enyl)phenoxy)methyl)piperidine-1-carboxylate;
(241) (4-(4-((1-(5-ethylpyrimidin-2-yl)piperidin-4-yl)methoxy)phenyl)cyclohex-3-enyl)(isoindolin-2-yl)methanone;
(242) 4-(4-((1-(5-ethylpyrimidin-2-yl)piperidin-4-yl)methoxy)phenyl)-N-(3-hydroxypropyl)-N-methylcyclohex-3-enecarboxamide;
(243) N-(3-hydroxypropyl)-4-(4-((1-(3-isopropyl-1,2,4-oxadiazol-5-yl)piperidin-4-yl)methoxy)phenyl)-N-methylcyclohex-3-enecarboxamide;
(244) N-(furan-2-ylmethyl)-4-(4-((1-(3-isopropyl-1,2,4-oxadiazol-5-yl)piperidin-4-yl)methoxy)phenyl)cyclohex-3-enecarboxamide;

(245) N-(3-ethoxypropyl)-4-(4-((1-(3-isopropyl-1,2,4-oxadiazol-5-yl)piperidin-4-yl)methoxy)phenyl)cyclohex-3-enecarboxamide;

(246) 4-(4-((1-(3-isopropyl-1,2,4-oxadiazol-5-yl)piperidin-4-yl)methoxy)phenyl)-N-methoxycyclohex-3-enecarboxamide;

(247) 4-(4-((1-(3-isopropyl-1,2,4-oxadiazol-5-yl)piperidin-4-yl)methoxy)phenyl)-N-methoxy-N-methylcyclohex-3-enecarboxamide;

(248) N,N-bis(2-hydroxyethyl)-4-(4-((1-(3-isopropyl-1,2,4-oxadiazol-5-yl)piperidin-4-yl)methoxy)phenyl)cyclohex-3-enecarboxamide;

(249) 1-(4-(4-((1-(3-isopropyl-1,2,4-oxadiazol-5-yl)piperidin-4-yl)methoxy)phenyl)cyclohex-3-enecarbonyl)piperidine-4-carboxamide;

(250) 1-(4-(4-((1-(5-ethylpyrimidin-2-yl)piperidin-4-yl)methoxy)phenyl)cyclohex-3-enecarbonyl)pyrrolidin-3-one;

(251) 1-(4-(4-((1-(3-isopropyl-1,2,4-oxadiazol-5-yl)piperidin-4-yl)methoxy)phenyl)cyclohex-3-enecarbonyl)piperidine-4-carboxamide;

(252) 1-(4-(4-((1-(3-isopropyl-1,2,4-oxadiazol-5-yl)piperidin-4-yl)methoxy)phenyl)cyclohex-3-enecarbonyl)piperidine-4-carboxamide;

(253) (Z)-(3,3-bis(hydroxymethyl)-4-(methoxyimino)pyrrolidin-1-yl)(4-(4-((1-(5-ethylpyrimidin-2-yl)piperidin-4-yl)methoxy)phenyl)cyclohex-3-enyl)methanone;

(254) (Z)-tert-butyl 6-(4-(4-((1-(5-ethylpyrimidin-2-yl)piperidin-4-yl)methoxy)phenyl)cyclohex-3-enecarbonyl)-8-(methoxyimino)-2,6-diazaspiro[3.4]octane-2-carboxylate;

(255) (Z)-(4-(4-((1-(5-ethylpyrimidin-2-yl)piperidin-4-yl)methoxy)phenyl)cyclohex-3-enyl)(8-(methoxyimino)-2,6-diazaspiro[3.4]octan-6-yl)methanone hydrochloride;

(256) tert-butyl 4-((4-(4-(4-(cyclopropylmethyl)piperazine-1-carbonyl)cyclohex-1-enyl)phenoxy)methyl)piperidine-1-carboxylate;

(257) tert-butyl 4-((4-(4-(3,3-difluoropyrrolidine-1-carbonyl)cyclohex-1-enyl)phenoxy)methyl)piperidine-1-carboxylate;

(258) (3,3-difluoropyrrolidin-1-yl)(4-(4-((1-(5-ethylpyrimidin-2-yl)piperidin-4-yl)methoxy)phenyl)cyclohex-3-enyl)methanone;

(259) (3,3-difluoropyrrolidin-1-yl)(4-(4-((1-(3-isopropyl-1,2,4-oxadiazol-5-yl)piperidin-4-yl)methoxy)phenyl)cyclohex-3-enyl)methanone;

(260) N-(5-hydroxypentyl)-4-(4-((1-(3-isopropyl-1,2,4-oxadiazol-5-yl)piperidin-4-yl)methoxy)phenyl)cyclohex-3-enecarboxamide;

(261) tert-butyl 4-((4-(4-(2,2,2-trifluoroethylcarbamoyl)cyclohex-1-enyl)phenoxy)methyl)piperidine-1-carboxylate;

(262) tert-butyl 4-((4-(4-(4-cyanocyclohexanecarbonyl)cyclohex-1-enyl)phenoxy)methyl)piperidine-1-carboxylate;

(263) tert-butyl 4-((4-(4-(1,4-dioxa-8-azaspiro[4.5]decane-8-carbonyl)cyclohex-1-enyl)phenoxy)methyl)piperidine-1-carboxylate;

(264) tert-butyl 4-((4-(4-(spiro[indene-1,4'-piperidin]-1'-ylcarbonyl)cyclohex-1-enyl)phenoxy)methyl)piperidine-1-carboxylate;

(265) tert-butyl 4-((4-(4-(3-oxopyrrolidine-1-carbonyl)cyclohex-1-enyl)phenoxy)methyl)piperidine-1-carboxylate;

(266) 1-(4-(4-((1-(3-isopropyl-1,2,4-oxadiazol-5-yl)piperidin-4-yl)methoxy)phenyl)cyclohex-3-enecarbonyl)piperidine-4-carbonitrile;

(267) (4-(4-((1-(3-isopropyl-1,2,4-oxadiazol-5-yl)piperidin-4-yl)methoxy)phenyl)cyclohex-3-enyl)(1,4-dioxa-8-azaspiro[4.5]decan-8-yl)methanone;

(268) (2,3-dihydrospiro[indene-1,4'-piperidin]-1'-yl)(4-(4-((1-(3-isopropyl-1,2,4-oxadiazol-5-yl)piperidin-4-yl)methoxy)phenyl)cyclohex-3-enyl)methanone;

(269) (3-(ethoxyimino)pyrrolidin-1-yl)(4-(4-((1-(5-ethylpyrimidin-2-yl)piperidin-4-yl)methoxy)phenyl)cyclohex-3-enyl)methanone;

(270) tert-butyl 4-((4-(4-(4-(methoxyimino)piperidine-1-carbonyl)cyclohex-1-enyl)phenoxy)methyl)piperidine-1-carboxylate;

(271) tert-butyl 4-((4-(4-(4-(hydroxyimino)piperidine-1-carbonyl)cyclohex-1-enyl)phenoxy)methyl)piperidine-1-carboxylate;

(272) tert-butyl 4-((4-(4-(4-oxopiperidine-1-carbonyl)cyclohex-1-enyl)phenoxy)methyl)piperidine-1-carboxylate;

(273) tert-butyl 4-((4-(4-(3-(methoxyimino)pyrrolidine-1-carbonyl)cyclohex-1-enyl)phenoxy)methyl)piperidine-1-carboxylate;

(274) 1-(4-(4-((1-(5-ethylpyrimidin-2-yl)piperidin-4-yl)methoxy)phenyl)cyclohex-3-enecarbonyl)piperidin-4-one;

(275) 1-(4-(4-((1-(3-isopropyl-1,2,4-oxadiazol-5-yl)piperidin-4-yl)methoxy)phenyl)cyclohex-3-enecarbonyl)piperidin-4-one;

(276) (4-(hydroxyimino)piperidin-1-yl)(4-(4-((1-(3-isopropyl-1,2,4-oxadiazol-5-yl)piperidin-4-yl)methoxy)phenyl)cyclohex-3-enyl)methanone;

(277) (4-(4-((1-(5-ethylpyrimidin-2-yl)piperidin-4-yl)methoxy)phenyl)cyclohex-3-enyl)(4-(hydroxyimino)piperidin-1-yl)methanone;

(278) (4-(4-((1-(3-isopropyl-1,2,4-oxadiazol-5-yl)piperidin-4-yl)methoxy)phenyl)cyclohex-3-enyl)(4-(methoxyimino)piperidin-1-yl)methanone;

(279) (4-(4-((1-(3-isopropyl-1,2,4-oxadiazol-5-yl)piperidin-4-yl)methoxy)phenyl)cyclohex-3-enyl)(4-(methoxyimino)piperidin-1-yl)methanone;

(280) tert-butyl 4-((4-(4-(3-oxoazetidine-1-carbonyl)cyclohex-1-enyl)phenoxy)methyl)piperidine-1-carboxylate;

(281) tert-butyl 4-((4-(4-(3-(hydroxyimino)azetidine-1-carbonyl)cyclohex-1-enyl)phenoxy)methyl)piperidine-1-carboxylate;

(282) tert-butyl 4-((4-(4-(3-(methoxyimino)azetidine-1-carbonyl)cyclohex-1-enyl)phenoxy)methyl)piperidine-1-carboxylate;

(283) 1-(4-(4-((1-(5-ethylpyrimidin-2-yl)piperidin-4-yl)methoxy)phenyl)cyclohex-3-enecarbonyl)azetidin-3-one;

(284) 1-(4-(4-((1-(3-isopropyl-1,2,4-oxadiazol-5-yl)piperidin-4-yl)methoxy)phenyl)cyclohex-3-enecarbonyl)azetidin-3-one;

(285) (3-(hydroxyimino)azetidin-1-yl)(4-(4-((1-(3-isopropyl-1,2,4-oxadiazol-5-yl)piperidin-4-yl)methoxy)phenyl)cyclohex-3-enyl)methanone;

(286) (4-(4-((1-(3-isopropyl-1,2,4-oxadiazol-5-yl)piperidin-4-yl)methoxy)phenyl)cyclohex-3-enyl)(3-(methoxyimino)azetidin-1-yl)methanone;

(287) (4-(4-((1-(5-ethylpyrimidin-2-yl)piperidin-4-yl)methoxy)phenyl)cyclohex-3-enyl)(3-(methoxyimino)azetidin-1-yl)methanone;

(288) tert-butyl 4-((4-(4-(3-hydroxyazetidine-1-carbonyl)cyclohex-1-enyl)phenoxy)methyl)piperidine-1-carboxylate; and
(289) (3-hydroxyazetidin-1-yl)(4-(4-((1-(3-isopropyl-1,2,4-oxadiazol-5-yl)piperidin-4-yl)methoxy)phenyl)cyclohex-3-enyl)methanone.

5. A method for preparing the compound represented by Formula 1 defined in claim 1, which comprises, as shown in the following Scheme 1:

reacting a compound represented by Formula 2 with a compound represented by Formula 3 to prepare a compound represented by Formula 4 (Step 1);

reacting the compound represented by Formula 4 prepared in Step 1 with a compound represented by Formula 5 to prepare a compound represented by Formula 6 (Step 2);

reacting the compound represented by Formula 6 prepared in Step 2 with a base to prepare a compound represented by Formula 7 (Step 3); and reacting the compound represented by Formula 7 prepared in Step 3 with a compound represented by Formula 8 to obtain the compound represented by Formula 1 (Step 4):

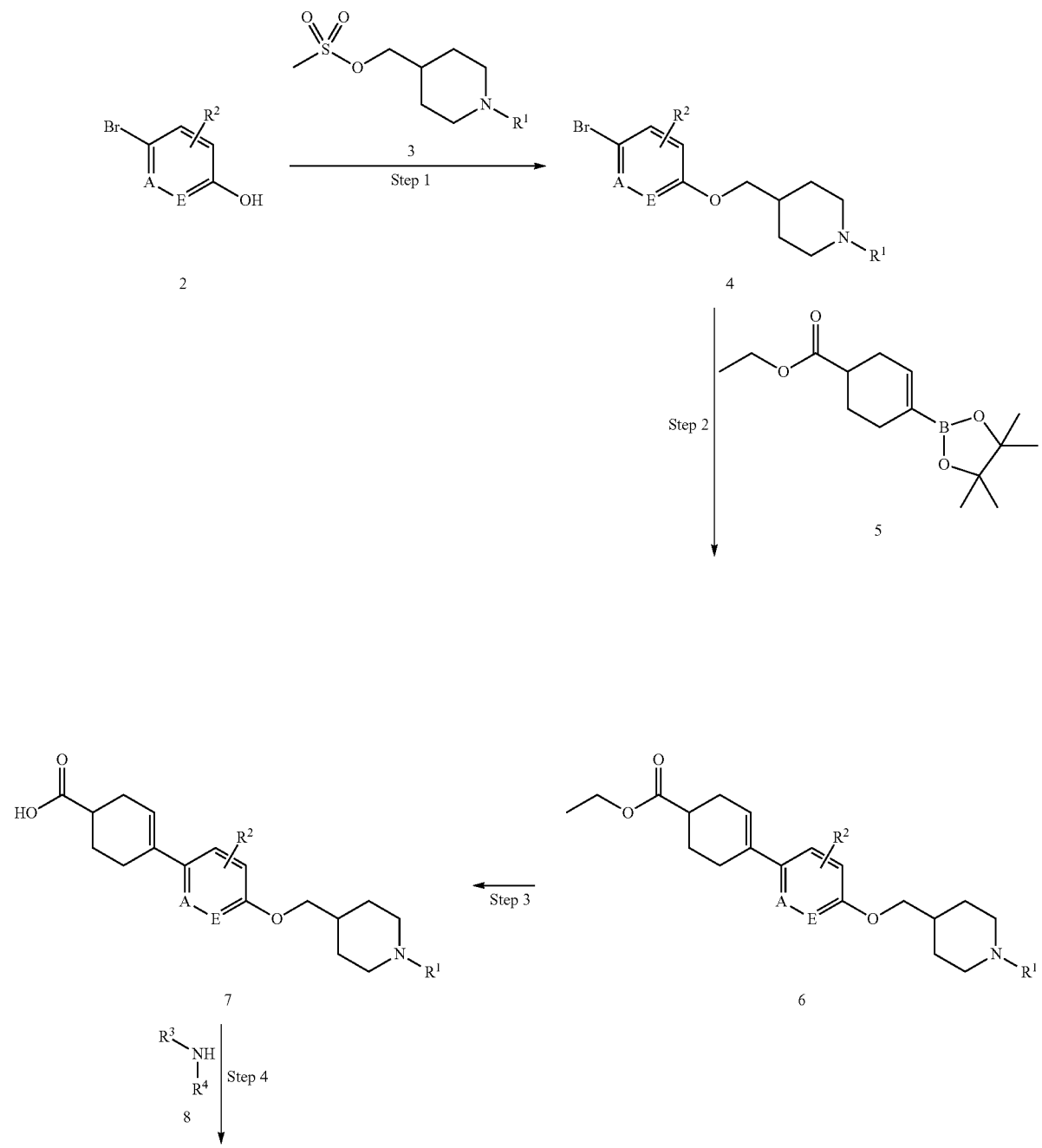

-continued

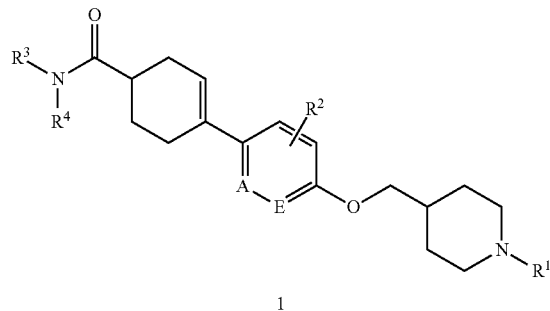

1 wherein $R^1$, $R^2$, $R^3$, $R^4$, A, and E are as defined in Formula 1 defined in claim 1.

6. The method according to claim 5, wherein the base in Step 3 is the one selected from the group consisting of cesium carbonate ($Cs_2CO_3$), potassium hydroxide (KOH), sodium hydroxide (NaOH), and lithium hydroxide (LiOH).

7. A pharmaceutical composition comprising the compound of claim 1, or the isomer or pharmaceutically acceptable salt thereof as an active ingredient.

8. A method of treating a metabolic disease comprising administering a therapeutically effective amount of the pharmaceutical composition according to claim 7 to a patient in need thereof, wherein the metabolic disease is selected from the group consisting of obesity, type 1 diabetes, type 2 diabetes, inadequate glucose tolerance, insulin resistance, hyperglycemia, hyperlipidemia, hypertriglyceridemia, hypercholesterolemia, dyslipidemia, and syndrome X.

* * * * *